United States Patent
Velazquez et al.

(10) Patent No.: US 12,365,869 B2
(45) Date of Patent: Jul. 22, 2025

(54) SYSTEMS FOR PRODUCTION OF PRODUCTS TO PROMOTE NITROGEN USE EFFICIENCY IN PLANTS

(71) Applicant: Tenfold Technologies, LLC, Pilot Point, TX (US)

(72) Inventors: Luis Francisco Velazquez, Grand Prairie, TX (US); Allana Kay Welsh, Denton, TX (US); Neissa Maryann Pinzon, Frisco, TX (US); Maud Ann Wrightson Hinchee, Little Elm, TX (US); Robert D Chisholm, Mckinney, TX (US); Mohammad Kamrul Hassan, Aubrey, TX (US); Leslie Michelle Perry, Fort Worth, TX (US); Shashi S Rajbanshi, Frisco, TX (US); Katherine McElhany Williams, Corinth, TX (US)

(73) Assignee: TENFOLD TECHNOLOGIES, LLC, Pilot Point, TX (US)

( * ) Notice: Subject to any disclaimer, the term of this patent is extended or adjusted under 35 U.S.C. 154(b) by 0 days.

(21) Appl. No.: 18/541,917

(22) Filed: Dec. 15, 2023

(65) Prior Publication Data
US 2024/0425789 A1    Dec. 26, 2024

Related U.S. Application Data

(60) Provisional application No. 63/610,535, filed on Dec. 15, 2023, provisional application No. 63/510,615, (Continued)

(51) Int. Cl.
C12M 1/00    (2006.01)
A01N 63/22   (2020.01)
(Continued)

(52) U.S. Cl.
CPC ............ *C12N 1/20* (2013.01); *A01N 63/22* (2020.01); *A01N 63/25* (2020.01); *A01P 21/00* (2021.08);
(Continued)

(58) Field of Classification Search
CPC ...... C12M 23/58; C12M 27/00; C12M 29/18; C12M 47/02
See application file for complete search history.

(56) References Cited

U.S. PATENT DOCUMENTS

| 4,245,432 A | 1/1981 | Dannelly |
| 4,339,456 A | 7/1982 | Rushing |

(Continued)

FOREIGN PATENT DOCUMENTS

| EP | 2674411 A1 * 12/2013 | ............ C05B 17/00 |
| KR | 20130123276 A * 11/2013 | |

(Continued)

OTHER PUBLICATIONS

Achouak, W. et al., Comparative phylogeny of rrs and nifH genes in the Bacillaceae, International Journal of Systematic Bacteriology, vol. 49, (1999):961-967.

(Continued)

*Primary Examiner* — Liban M Hassan
(74) *Attorney, Agent, or Firm* — WILSON SONSINI GOODRICH & ROSATI

(57) ABSTRACT

The present disclosure provides methods and systems for production of biostimulants that promote nitrogen use efficiency in plants. Embodiments described include methods of making a biostimulant composition in a bioreactor system that includes two or more containers arranged in series. The bioreactor system may include an established population of a nitrogen use efficiency-promoting microbial strain. The method may include operating the bioreactor system by
(Continued)

transferring into the system an aqueous feedstock that comprises a microbial consortium, transferring working fluid between containers of the system, and collecting a product. The method may further include maintaining a concentration of a nitrogen use efficiency-promoting microbial strain in the system.

43 Claims, 132 Drawing Sheets

Specification includes a Sequence Listing.

Related U.S. Application Data filed on Jun. 27, 2023, provisional application No. 63/509,263, filed on Jun. 20, 2023.

(51) Int. Cl.
| | | |
|---|---|---|
| *A01N 63/25* | (2020.01) | |
| *A01P 21/00* | (2006.01) | |
| *C05F 11/08* | (2006.01) | |
| *C12M 1/02* | (2006.01) | |
| *C12N 1/20* | (2006.01) | |

(52) U.S. Cl.
CPC ............. *C05F 11/08* (2013.01); *C12M 23/58* (2013.01); *C12M 27/00* (2013.01); *C12M 29/18* (2013.01); *C12M 47/02* (2013.01)

(56) References Cited

U.S. PATENT DOCUMENTS

| | | | |
|---|---|---|---|
| 4,372,080 A | 2/1983 | Rushing | |
| 4,465,017 A | 8/1984 | Simmons | |
| 4,634,587 A | 1/1987 | Hsiao | |
| 4,735,015 A | 4/1988 | Schmolka | |
| 4,759,945 A | 7/1988 | Nemecek et al. | |
| 5,328,942 A | 7/1994 | Akhtar et al. | |
| 5,389,399 A | 2/1995 | Bazin et al. | |
| 5,554,445 A | 9/1996 | Struszczyk et al. | |
| 5,580,544 A | 12/1996 | Dao et al. | |
| 5,661,103 A | 8/1997 | Harms et al. | |
| 5,791,084 A | 8/1998 | Kohno et al. | |
| 5,821,112 A | 10/1998 | Botto et al. | |
| 5,849,320 A | 12/1998 | Turnblad et al. | |
| 5,876,739 A | 3/1999 | Turnblad et al. | |
| 5,918,413 A | 7/1999 | Otani et al. | |
| 5,939,356 A | 8/1999 | Wellinghoff | |
| 6,054,044 A * | 4/2000 | Hoffland | C02F 3/006 210/139 |
| 9,187,381 B1 | 11/2015 | Lanz | |
| 10,577,358 B2 | 3/2020 | Davidson et al. | |
| 10,793,484 B2 | 10/2020 | Dent et al. | |
| 11,357,233 B2 | 6/2022 | Verstraete et al. | |
| 11,565,979 B2 | 1/2023 | Temme et al. | |
| 11,618,720 B2 | 4/2023 | Dent et al. | |
| 11,866,698 B2 | 1/2024 | Wigley et al. | |
| 11,871,752 B2 | 1/2024 | Wigley et al. | |
| 2009/0318292 A1 | 12/2009 | Kang | |
| 2010/0154299 A1 | 6/2010 | Kobayashi et al. | |
| 2012/0297846 A1 | 11/2012 | Lanciault et al. | |
| 2013/0244061 A1 | 9/2013 | Dhar et al. | |
| 2013/0324406 A1 * | 12/2013 | Chisholm | C12M 47/06 435/252.4 |
| 2018/0072633 A1 | 3/2018 | Dent et al. | |
| 2019/0039964 A1 | 2/2019 | Temme et al. | |
| 2020/0131096 A1 * | 4/2020 | Kanagalingam | C05F 17/20 |
| 2022/0033868 A1 | 2/2022 | Danquah et al. | |
| 2022/0151241 A1 | 5/2022 | Reisinger et al. | |
| 2023/0234898 A1 | 7/2023 | Dent et al. | |
| 2023/0292764 A1 | 9/2023 | Santiago-Ortiz et al. | |

FOREIGN PATENT DOCUMENTS

| | | | | |
|---|---|---|---|---|
| WO | WO-2013056084 A2 | 4/2013 | | |
| WO | WO-2020245675 A1 | 12/2020 | | |
| WO | WO-2021150993 A1 * | 7/2021 | ............. | C05F 17/20 |
| WO | WO-2024263793 | 12/2024 | | |

OTHER PUBLICATIONS

Ali, A. et al., Functional analysis and genome mining reveal high potential of biocontrol and plant growth promotion in nodule-inhabiting bacteria within Paenibacillus polymyxa complex, Frontiers in Microbiology, vol. 11, (2021):618601.

Ambrosini, A. et al., Diazotrophic bacilli isolated from the sunflower rhizosphere and the potential of Bacillus mycoides B38V as biofertiliser, Annals of Applied Biology, vol. 168, (2016):93-110.

Ambrosini, A. et al., Genome sequence of Bacillus mycoides B38V, a growth-promoting bacterium of sunflower, Genome Announcements, vol. 3, 2 (2015):1-2.

Amicucci, M.J. et al., Strategy for structural elucidation of polysaccharides: elucidation of a maize mucilage that harbors diazotrophic bacteria, Analytical Chem., vol. 91, (2019):7254-7265.

Anand, R. et al., Detection of GFP-labeled Peanibacillus polymyxa in autofluorescing pine seedling tissues, Biol. Fertil. Soils, vol. 49, (2013):111-118.

Aslam, S. et al., Dual action of chromium-reducing and nitrogen-fixing Bacillus megaterium-ASNF3 for improved agro-rehabilitation of chromium-stressed soils, Biotech, vol. 6, (2016):125.

Barber, L.E. et al., Acetylene reduction (nitrogen fixation) associated with corn inoculated with Spirillum, Applied and Environmental Microbiology, vol. 32, 2 (1976):108-113.

Bastida, F. et al., Soil microbial diversity-biomass relationships are driven by soil carbon content across global biomes, The ISME Journal, vol. 15, 7 (2021):2081-2091.

Benedetto, N.A.D. et al., The role of plant growth promoting bacteria in improving nitrogen use efficiency for sustainable crop production: a focus on wheat, AIMS Microbiology, vol. 3, 3 (2017):413-434.

Bennett, A.E. et al., Plant lignin content altered by soil microbial community, New Phytologist, vol. 206, (2015):166-174.

Berge, O. et al., Paenibacillus graminis sp. nov. and Paenibacillus odorifer sp. nov. isolated from plant roots, soil and food, International Journal of Systematic and Evolutionary Microbiology, vol. 52, (2002):607-616.

Bloch, S.E. et al., Biological nitrogen fixation in maize: optimizing nitrogenase expression in a root-associated diazotroph, Journal of experimental botany, vol. 71, 15 (2020):4591-4603.

Carvalho, T.L.G. et al., Nitrogen signalling in plant interaction with associative and endophytic diazotrophic bacteria, vol. 65, 19 (2014):5631-5642.

Chakraborty, S. et al., Quantifying nitrogen fixation by heterotrophic bacteria in sinking marine particles, vol. 12, 4085 (2021).

Chakraborty, S. et al., Scripting a new dialogue between diazotrophs and crops, Trends in Microbiology, (2023).

Chauhan, H. et al., Inoculation with selected microbial consortia not only enhances growth and yield of French bean but also reduces fertilizer application under field condition, Scientia Horticulture, vol. 197, (2015):441-446.

Choo, Q. et al., Phylogeny and characterization of three nifH-Homologous genes from Paenibacillus azotofixans, Applied and Environmental Microbiology, vol. 69, 6 (2003):3658-3662.

Clark, A., The merit of corn biological products used in-furrow, B.S. University of Missouri, (2012).

Combes-Meynet, E. et al., The Pseudomonas secondary metabolite 2,4-diacetylphloroglucinol is a signal inducing rhizoplane expression of Azospirillum genes involved in plant-growth promotion, MPMI e-Xtra, vol. 24, 2 (2011):271-284.

Davis, W.G., Nitrogen use in cereal crops with Pivot Bio Proven inoculant, B.S., Kansa State University, 2017.

Delavaux, C.S. et al., Beyond nutrients: a meta-analysis of the diverse effects of arbuscular mycorrhizal fungi on plants and soils, Ecology, vol. 98, 8 (2017):2111-2119.

(56) References Cited

OTHER PUBLICATIONS

Diaz-Garcia, L. et al., Dilution-to-Stimulation/Extinction Method: a combination enrichment strategy to develop a minimal and versatile lignocellulolytic bacterial consortium, Applied and Environmental Microbiology, vol. 87, 2 (2021).
Ding, Y. et al., Isolation and identification of nitrogen-fixing bacilli from plant rhizospheres in Beijing region, Journal of Applied Microbiology, vol. 99, (2005):1271-1281.
Domeignoz-Horta, L.A. et al., Direct evidence for the role of microbial community composition in the formation of soil organic matter composition and persistence, Nature, vol. 1, 1 (2021).
Domeignoz-Horta, L.A. et al., Microbial diversity drives carbon use efficiency in a model soil, Nature Communications, vol. 11, (2020):3684.
Dudeja, S.S. et al., Interaction of endophytic microbes with legumes, Journal of Basic Microbiology, vol. 52, (2012):248-260.
Elo, S. et al., Humus bacteria of Norway spruce stands: plant growth promoting properties and birch, red fescue and alder colonizing capacity, FEMS Microbiology Ecology, vol. 31, (2000):143-152.
Elo, S. et al., Paenibacillus borealis sp. nov., a nitrogen fixing species isolated from spruce forest humus in Finland, vol. 51, (2001):535-545.
Farzadfar, S. et al., Soil organic nitrogen: an overlooked but potentially significant contribution to crop nutrition, Plant Soil, vol. 462, (2021):7-23.
Fernandes, G.D.C. et al., Alternative nitrogenase and pseudogenes: unique features of the Paenibacillus riograndensis nitrogen fixation system, Research in Microbiology, vol. 165, (2014):571-580.
Figueiredo, M.V.B. et al., Plant growth-promoting rhizobacteria for improving nodulation and nitrogen fixation in the common bean (Phaseolus vulgaris L.), World J. Microbiol. Biotechnology, vol. 24, (2008)L1187-1193.
Gupta, R.S. et al., Robust demarcation of 17 distinct Bacillus species clades, proposed as novel Bacillaceae genera, by phylogenomics and comparative genomic analyses: description of Robertmurraya kyonggiensis sp. nov. and proposal for an emended genus Bacillus limiting it only to the members of the Subtilis and Cereus clades of species, Int. J. Syst. Evol. Microbiol., vol. 70, (2020):5753-5798.
Halim, M.A. et al., Genome sequence of a Gram-Positive diazotroph, Paenibacillus durus type strain ATCC 35681, American Society for Microbiology, Genome Announcements, vol. 4, 1 (2016):1-2.
Halim, M.A. et al., Transcriptional analysis of nitrogen fixation in Paenibacillus durus during growth in nitrogen-enriched medium, Letters in applied microbiology vol. 72,5 (2021): 610-618.
Hamaoka, K. et al., Diversity of endophytic bacterial microbiota in grapevine shoot xylems varies depending on wine grape-growing region, cultivar, and shoot growth stage, Scientific Reports, vol. 12, (2022):15772.
Hestrin, R. et al., Synergies between mycorrhizal fungi and soil microbial communities increase plant nitrogen acquisition, Communications Biology, vol. 2, (2019):233.
Horn, M.A. et al. Dechloromonas denitrificans sp. nov., Flavobacterium denitrificans sp. nov., Paenibacillus anaericanus sp. nov. and Paenibacillus terrae strain MH72, N2O-producing bacteria isolated from the gut of the earthworm Aporrectodea caliginosa, International Journal of Systematic and Evolutionary Microbiology, vol. 55, (2005):1255-1265.
Huang, W. et al., Comparative genomic analysis reveals metabolic diversity of different Paenibacillus groups, Applied Microbiology and Biotechnology, vol. 104, (2020):10133-10143.
Iniguez, A.L. et al., Nitrogen fixation in wheat provided by Klebsiella penumoniae 342, Molecular Plant-Microbe Interactions, vol. 17, 10 (2004):1078-1085.
Itoh, K. et al., Changes in acetylene reduction activities and nifH genes associated with field- grown sweet potatoes with different nursery farmes and cultivars, Horticulture, vol. 5, 53 (2019).
Kang, A. et al., Nitrogen fertilization modulates beneficial rhizosphere interactions through signaling effect of nitric oxide, Plant Physiology, vol. 00, (2021):1-12.
Kim, K.K. et al., Reclassification of Paenibacillus ginsengisoli as a later heterotypic synonym of Paenibacillus anaericanus, International Journal of Systematic and Evolutionary Microbiology, vol. 61, (2011):2101-2106.
Kim, T. et al., Quantifying nitrogen loss hotspots and mitigation potential for individual fields in the US corn belt with a metamodeling approach, Environm. Res. Lett., vol. 16, (2021):075008.
Kisiel, A. et al., Medicago truncatula Gaertn. as a model for understanding the mechanisms of growth promotion by bacteria from rhizosphere and nodules of alfalfa, Planta, vol. 243, (2016):1169-1189.
Kisiel, A. et al., Oxidative status of Medicago truncatula seedlings after inoculation with rhizobacteria of the genus Pseudomonas Paenibacillus and Sinorhizobium, International Journal of Molecular Sciences, vol. 24, (2023):4781.
Kloepper, J.W. et al., A review of issues related to measuring colonization of plant roots by bacteria, Can. J. Microbiol., vol. 38, (1992).
Korir, H. et al., Co-inoculation effect of rhizobia and plant growth promoting rhizobacteria on common bean growth in a low phosphorus soil, Frontiers in Plant Science, vol. 8, 141 (2017).
Lagunas, B. et al., Rhizobial nitrogen fixation efficiency shapes endosphere bacterial communities and Medicago truncatula host growth, Microbiome, vol. 11, (2023):146.
Lawson, C.E. et al., Common principles and best practices for engineering microbiomes, Nature Reviews, Microbiology, vol. 17, (2019):725-741.
Li, C.Y. et al., Nitrogen-fixing Bacillus sp. associated with Douglas-fir tuberculate ectomycorrhizae, Plant and Soil, vol. 140, (1992):35-40.
Li, Q. et al., Paenibacillus Sinensis sp. nov., a Nitrogen-fixing species isolated from plant rhizospheres, Research Square, (2021).
Li, Y. et al., Diazotroph Paenibacillus triticisoli BJ-18 drives the variation in bacterial, diazotrophic and fungal communities in the rhizosphere and root/shoot endosphere of maize, International Journal of Molecular Sciences, vol. 22, (2021):1460.
Li, Y. et al., Diazotrophic Paenibacillus beijingensis BJ-18 provides nitrogen for plant and promotes plant growth, nitrogen uptake and metabolism, Frontiers in Microbiology, vol. 10, 1119 (2019).
Liu, X. et al., Paenibacillus strains with nitrogen fixation and multiple beneficial properties for promoting plant growth, PeerJ, vol. 7, (2019):e7445.
Logan, N.A. et al., Endospore-forming soil bacteria, Soil Biology, vol. 27, 1-353.
Lopes, L.D. et al., Sugars and jasmonic acid concentration in root exudates affect maize rhizosphere bacterial communities, (2022).
Ma, Y. et al., Paenibacillus sabinae sp. nov., a nitrogen-fixing species isolated from the rhizosphere soils of shrubs, International Journal of Systematic and Evolutionary Microbiology, vol. 57, (2007):6-11.
Mandon, K. et al., Redox regulation in diazotrophic bacteria in interaction with plants, Antioxidants, vol. 10, (2021):880.
Masood, S. et al., Bacillus pumilus promotes the growth and nitrogen uptake of tomato plants under nitrogen fertilization, Scientia Horticulturae, vol. 272, (2020):109581.
No Author, Altura, Plant Nutrition (product information catalogue).
No Author, Ativus PK, Plant Nutrition (product information catalogue).
No Author, Black Label ZN, Plant Nutrition (product information catalogue).
No Author, Enhancing Crop Performance, Activating the Soil (poster—Sound).
No Author, Levitate, Plant Nutrition (product information catalogue).
No Author, Prologue, Lead into P1, Nature Solubilizing Technology (product information catalogue).
No Author, Utrisha N nutrient efficiency optimizer, Application in Corn.
No Author, Utrisha N nutrient efficiency optimizer, Application in Soybean.

(56) References Cited

OTHER PUBLICATIONS

No Author, Utrisha N nutrient efficiency optimizer, specimen label.
Ospina-Betancourth, C. et al., Enrichment of Nitrogen-Fixing Bacteria in a Nitrogen-deficient wasterwater treatment system, Environmental Science and Technology, vol. 54, (2020):3539-3548.
Padda, K.P. et al., Plant growth promotion and nitrogen fixation in canola (Brassica napus) by an endophytic strain of Paenibacillus polymyxa and its GFP-tagged derivative in a long-term study, Botany, vol. 94, 12 (2016):1209-1217.
Pankievicz, V.C.S. et al., Diazotrophic Bacteria and Their Mechanisms to Interact and Benefit Cereals, Molecular Plant-Microbe Interactions, vol. 34, 5 (2021):491-498.
Papik, J. et al., The invisible life inside plants: Deciphering the riddles of endophytic bacterial diversity, Biotechnology advances, vol. 44, (2020).
Park, J. et al., Synergistic effect of co-inoculation with phosphate-solubilizing bacteria, Korean Journal of Agricultural Science, vol. 43, 3 (2016):401-414.
Puri, A. et al., Can a diazotrophic endophyte originally isolated from lodgepole pine colonize an agricultural crop (corn) and promote its growth?, Soil Biology and Biochemistry, vol. 89, (2015):210-216.
Puri, A. et al., Evidence of nitrogen fixation and growth promotion in canola (Brassica napus L.) by an endophytic diazotroph Paenibacillus polymyxa P2b-2R, Biol. Fertl. Soils, (2015).
Puri, A. et al., Seedling growth promotion and nitrogen fixation by a bacterial endophyte Paenibacillus polymyxa P2b-2R and its GFP derivative in corn in a long-term trial, Symbiosis, vol. 69, (2016):123-129.
Puri, A., Plant growth promotion and nitrogen fixation by Paenibacillus polymyxa in corn and canola, B. Tech., Punjab Agricultural University, (2013).
Rodriguez-Gonzalez, C. et al., High resistance of sludge enriched with nitrogen-fixing bacteria to ammonium salts and its potential as a biofertilizer, Bioengineering, vol. 8, 55 (2021).
Rosado, A.S. et al., Genetic diversity of nifH gene sequences in Paenibacillus azotofixans strains and soil samples analyzed by denaturing gradient gel electrophoresis of PCR-amplified gene fragments, Applied and Environmental Microbiology, vol. 64, 8 (1998):2770-2779.
Rozycki, H. et al., Diazotrophic bacteria in root-free soil and in the root zone of pine (Pinus sylvestris L.) and oak (Quercus robur L.), Applied Soil Ecology, vol. 12, (1999):239-250.
Ruiz-Herrera, J. et al., A novel intracellular nitrogen-fixing symbiosis made by Ustilago maydis and Bacillus spp., New Phytologist, vol. 207, (2015):769-777.
Rybakova, D. et al., Endophytes-assisted biocontrol: novel insights in ecology and the mode of action of Paenibacillus, Plant Soil, (2015).
Saifuddin, M. et al., Microbial carbon use efficiency predicted from genome-scale metabolic models, Nature Communications, vol. 10, (2019):3568.
Samain, E. et al., Efficacy and durability of Paenibacillus sp. strain B2 in co-inoculation with Arthrobacter sp. SSM-004 and Microbacterium sp. SSM-001 for growth promotion and resistance induction in wheat against Mycosphaerella graminicola and drought stress, Journal of Plant Pathology and Microbiology, vol. 13, 2 (2022):1000603.
Saxena, A.K. et al., Bacillus species in soil as a natural resource for plant health and nutrition, Journal of Applied Microbiology, vol. 128, (2022):1583-1594.
Seldin, L. et al., Bacillus azotofixans sp. nov., a nitrogen-fixing species from Brazilian soils and grass roots, International Journal of Systematic Bacteriology, vol. 34, 4 (1984):451-456.
Shrestha, A. et al., Enhancement of nitrogen-fixing activity of Enterobacteriaceae strains isolated from sago palm (Metroxylon sagu) by microbial interaction with non-nitrogen fixers, Microbes Environmen., vol. 22, 1 (2007):59-70.
Singh, R.K. et al., Diversity of nitrogen-fixing rhizobacteria associated with sugarcane: a comprehensive study of plant-microbe interactions for growth enhancement in Saccharum spp., BMC Plant Biology, vol. 20, (2020):220.
Singh, R.K. et al., Exploring the corn microbiome: a detailed review on current knowledge, techniques, and future directions, PhytoFrontiers, vol. 2, (2022):158-175.
Smercina, D.N. et al., To fix or not to fix: controls on free-living nitrogen fixation in the rhizosphere, Applied and Environmental Microbiology, vol. 85, 6 (2019):e0256-18.
Solanki, A.C. et al., Co-inoculation of non-symbiotic bacteria bacillus and paraburkholderia can improve the soybean yield, nutrient uptake and soil parameters, Molecular Biotechnology, (2023).
Sprent, J.I. et al., Evolution of nitrogen-fixing symbioses, Proceedings of the Royal Society of Edinburgh, vol. 85B, (1985):215-237.
Stajkovic, O. et al., Isolation and characterization of endophytic non-rhizobial bacteria from root nodules of alfalfa (Medicago sativa L.), Botanica SERBICA, vol. 33, 1 (2009):107-114.
Sun, X. et al., Bacillus velezensis stimulates rhizosphere Pseudomonas stutzeri for plant health through metabolic interactions, ISME Journal, vol. 16, (2022):774-787.
Tang, A. et al., Effects of selected functional bacteria on maize growth and nutrient use efficiency, Microorganisms, vol. 8, (2020):854.
Timmusk, S. et al., Paenibacillus polymyxa invades plant roots and forms biofilms, Applied and Environmental Microbiology, vol. 71, 11 (2005):7292-7300.
Van Deynze, A. et al., Nitrogen fixation in a landrace of maize is supported by a mucilage-associated diazotrophic microbiota, PLOS Biology, vol. 16, (2018):e2006352.
Waller, S. et al., Examining the effects of the nitrogen environment on growth and N2-fizxation of endophytic Herbaspirillum seropedicae in maize seedlings by applying 11C radiotracing, Microorganisms vol. 9, (2021):1582.
Wang, Y. et al., A novel lignin degradation bacterial consortium for efficient pulping, Bioresource Technology, vol. 139, (2013):113-119.
Wang, Z. et al., Complementary resource preferences spontaneously emerge in diauxic microbial communities, Nature Communications, vol. 12, (2021):6661.
Waters, M.T. et al., Strigolactone signaling and evolution, Annu. Rev. Plant Biol., vol. 68, (2017):291-322.
Wen, A. et al., Enabling biological nitrogen fixation for cereal crops in fertilized fields, ACS Synthetic Biology, vol. 10, (2021):3264-3277.
White, J.F. et al., Rhizophagy cycle: an oxidative process in plants for nutrient extraction from symbiotic microbes, Microorganisms, vol. 6, 3 (2018):95.
Wolinska, K.W. et al., Trytophan metabolism and bacterial commensals prevent fungal dysbiosis in Arabidopsis roots, PNAS, vol. 118, 49 (2021):e211115211118.
Worrich, A. et al., Mycelium-mediated transfer of water and nutrients stimulates bacterial activity in dry and oligotrophic environments, Nature Communications, vol. 8, (2017).
Xie, J. et al., Comparative genomic and functional analysis reveal conservation of plant growth promoting traits in Paenibacillus polymyxa and its closely related species, Scientific Reports, vol. 6, (2015):21329.
Xiong, C. et al., Host selection shapes crop microbiome assembly and network complexity, New Phytologist, vol. 229, (2021):1091-1104.
Yang, H. et al., Substrate utilization by endophytic bacteria Paenibacillus polymyxa P2b-2R that may facilitate bacterial entrance and survival inside diverse plant hosts, FACETS, vol. 2, (2017):120-130.
Yoneyama, K. et al., How do nitrogen and phosphorus deficiencies affect strigolactone production and exudation?, Planta, vol. 235, (2012):1197-1207.
Yu, X. et al., Co-inoculation with phosphate-solubilizing and nitrogen-fixing bacteria on solubilization of rock phosphate and their effect on growth promotion and nutrient uptake by walnut, European Journal of Soil Biology, vol. 50, (2012):112-117.
Farges, B. et al. Axenic cultures of Nitrosomonas europaea and Nitrobacter winogradskyi in autotrophic conditions: a new protocol for kinetic studies. Applied biochemistry and biotechnology 167(5):1076-1091 (2012).

(56) References Cited

OTHER PUBLICATIONS

Grommen, R. et al. An improved nitrifying enrichment to remove ammonium and nitrite from freshwater aquaria systems. Aquaculture 211(1-4):115-124 (2002).

Jeong, J W. et al. A Mathematical Model for Examining Growth and Sporulation Processes of Bacillus subtilis. Biotechnology and Bioengineering 35(2):160-184 (1990).

Lindemann, Stephen R. et al. Engineering microbial consortia for controllable outputs. The ISME Journal 10(9):2077-2084 (2016).

Pommerening-Roser, Andreas et al. Phylogenetic Diversity within the Genus Nitrosomonas. Systematic and Applied Microbiology 19(3):344-351 (1996).

Said, Sami Ben, and Dani Or. Synthetic Microbial Ecology: Engineering Habitats for Modular Consortia. Frontiers in Microbiology 18:1125, 1-8 (2017).

Van Kessel, Maartje A.H.J. et al. Complete nitrification by a single microorganism. Nature 528(7583):555-559 (2015).

Aziz, Ramy K. et al. The RAST Server: rapid annotations using subsystems technology. BMC genomics 9(75):1-15 (2008).

Gaby, John Christian and Daniel H Buckley. The Use of Degenerate Primers in qPCR Analysis of Functional Genes Can Cause Dramatic Quantification Bias as Revealed by Investigation of nifH Primer Performance. Microbial ecology 74(3):701-708 (2017).

Hugerth, Luisa W and Anders F Andersson. Analysing Microbial Community Composition through Amplicon Sequencing: From Sampling to Hypothesis Testing. Frontiers in microbiology 8(1561):1-22 (2017).

Kim, Kil Yong. et al. Enterobacter agglomerans, phosphate solubilizing bacteria, and microbial activity in soil: Effect of carbon sources. Soil Biology and Biochemistry 30(8-9):995-1003 (1998).

Mirza, et al. Clinical Significance of Promoter Hypermethylation of ERß and RARß2 in tumor and serum DNA in Indian breast cancer patients. Annals of Surgical Oncology 19(9):3107-3115 (2012).

Needleman, Saul B, and Christian D. Wunsch. A General Method Applicable to the Search for Similarities in the Amino Acid Sequence of Two Proteins. Journal of Molecular Biology 48(3):443-453 (1970).

PCT/US2024/034839 International Search Report and Written Opinion dated Dec. 17, 2024.

PCT/US2024/034839 Invitation to Pay Additional Fees dated Oct. 11, 2024.

Pearson, William R, and David J. Lipman. Improved Tools for Biological Sequence Comparison. Proceedings of the National Academy of Sciences 85(8):2444-2448 (1988).

Poly, Franck. et al. Improvement in the RFLP procedure for studying the diversity of nifH genes in communities of nitrogen fixers in soil. Research in microbiology 152(1):95-103 (2001).

Smith, Temple F., and Michael S. Waterman. Comparison of biosequences. Advances in applied mathematics 2(4):482-489 (1981).

U.S. Appl. No. 18/541,671 Office Action dated Sep. 5, 2024.

U.S. Appl. No. 18/541,671 Notice of Allowance dated Mar. 21, 2025.

* cited by examiner

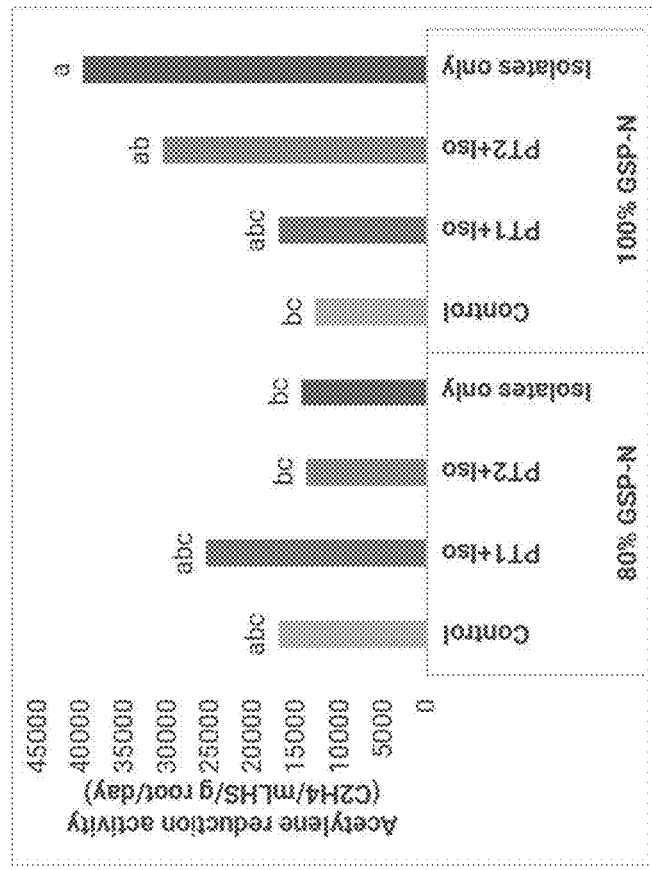
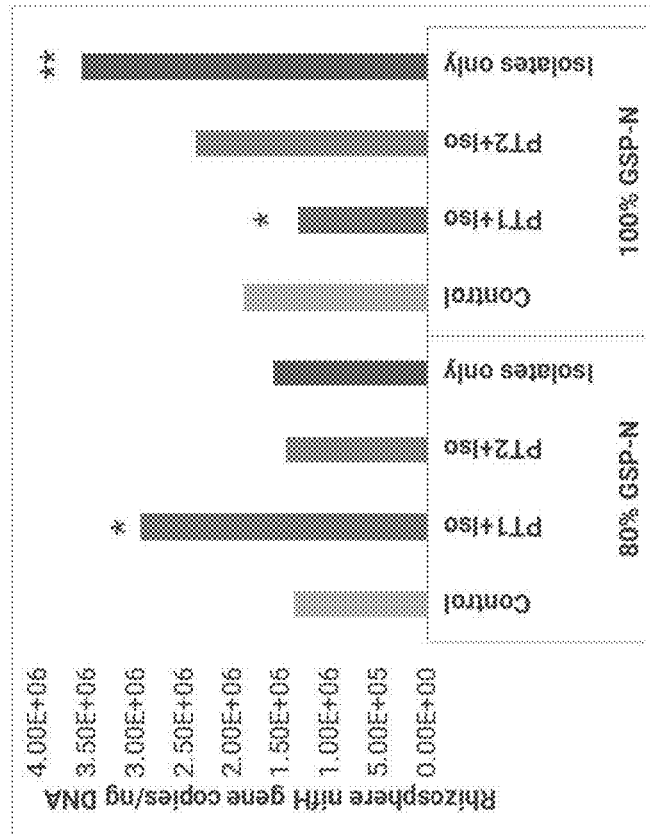
Fig. 3A
Fig. 3B

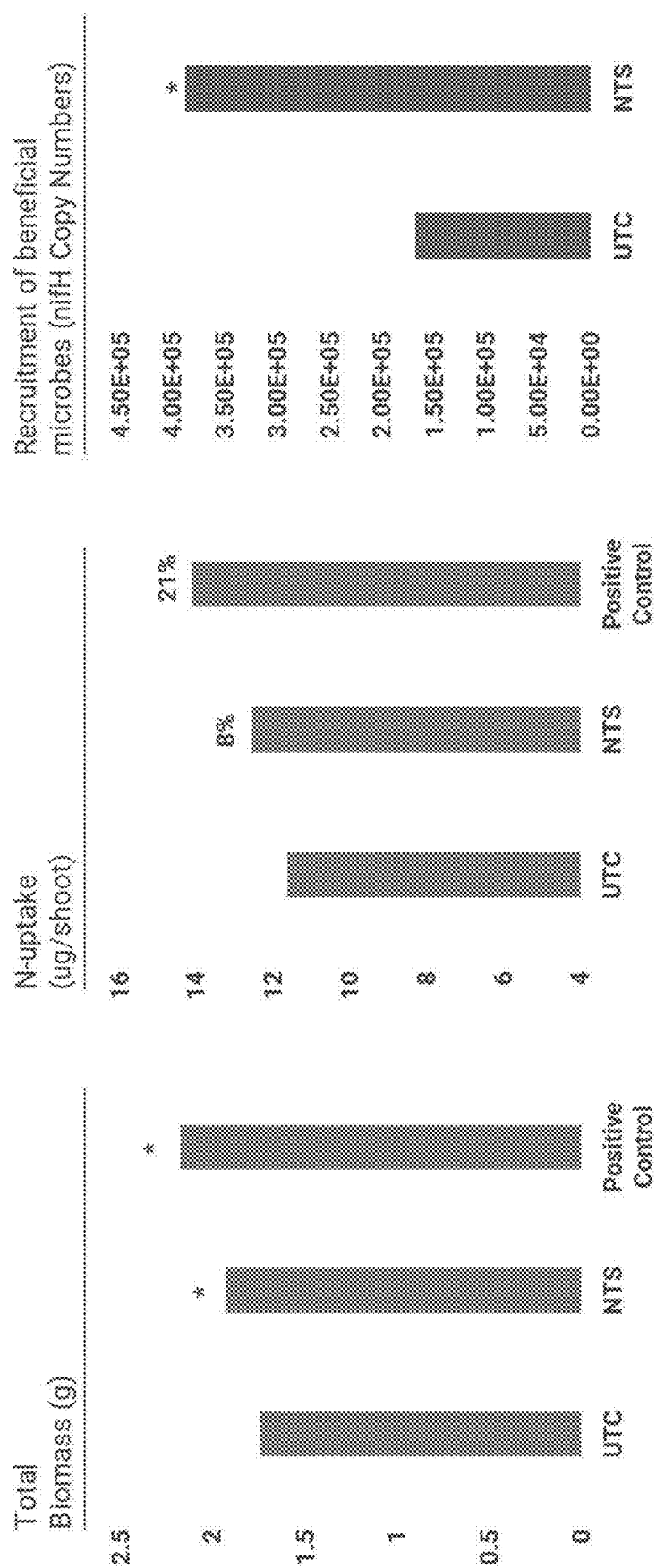

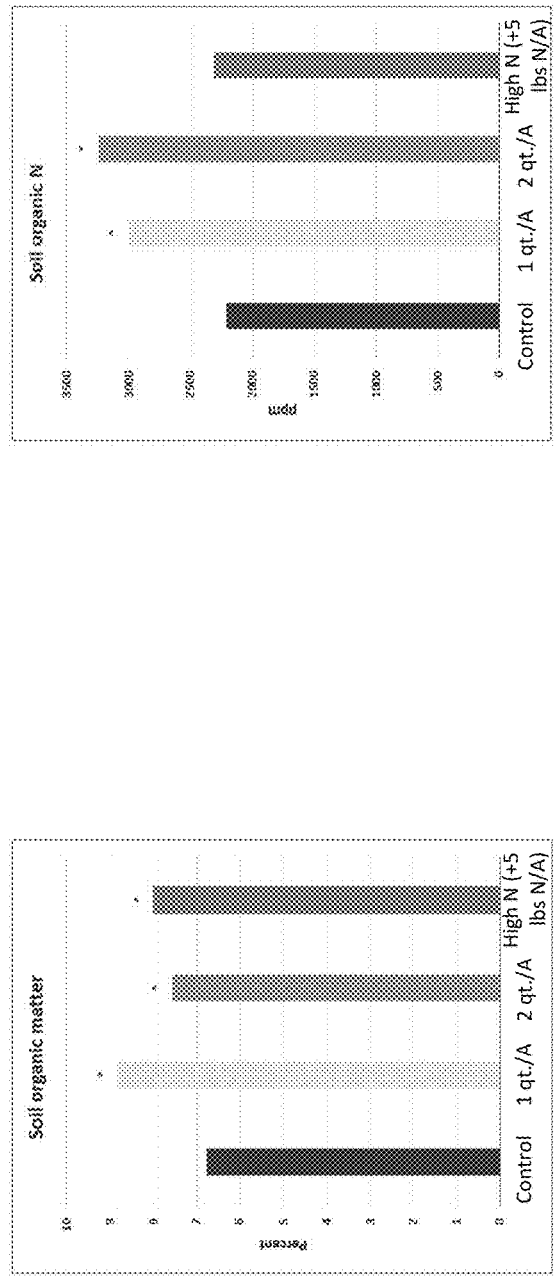
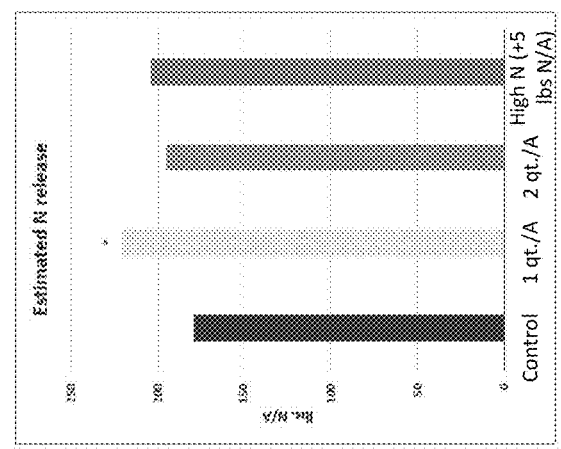
Fig. 9A
Fig. 9B
Fig. 9C

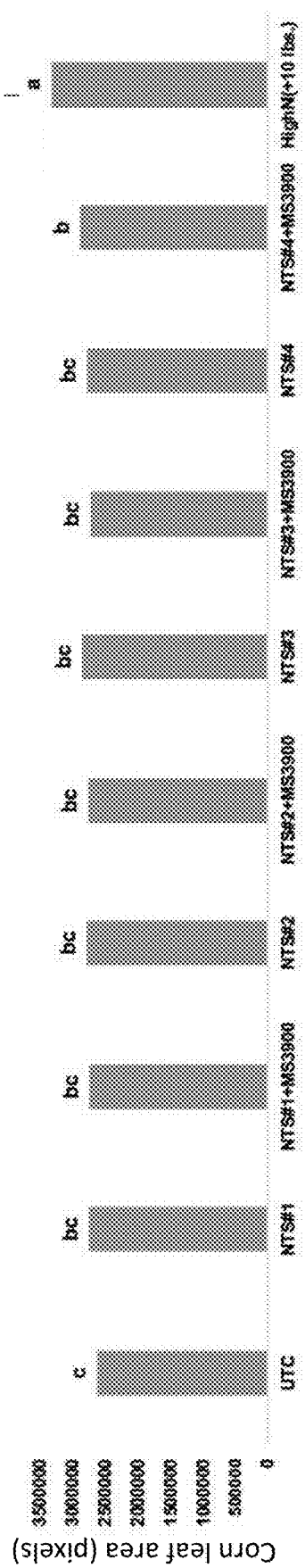
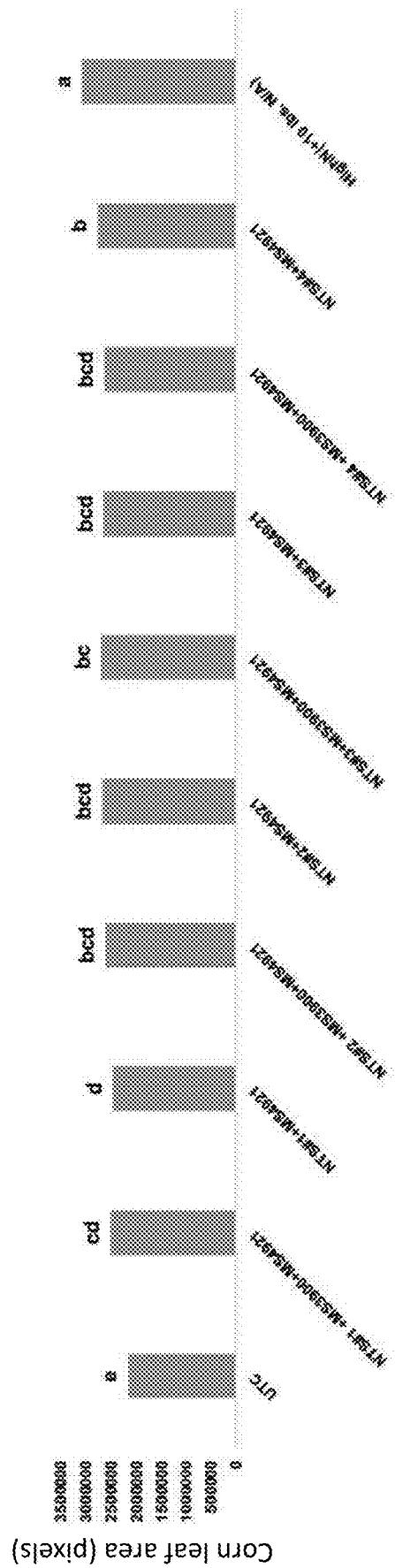
Fig. 28A
Fig. 28B

| Strain designation | Species identification | Root colonization capacity (recovery of isolate from greenhouse grown plants) | | | Root colonization capacity (in sterile system) | |
|---|---|---|---|---|---|---|
| | | Tall fescue | Sorghum bicolor | Corn | Corn | Soybean |
| MS3900 | Bacillus megaterium | YES: Rhizoplane +Endophytic space | YES: Rhizosphere, rhizoplane, and endophytic space | YES: Rhizoplane at 10 days and 30 days | YES: rhizoplane (2 of 4 reps) YES: Endophytic space (1 of 4 reps) | YES: rhizoplane (4 of 4 reps) YES: Endophytic space (2 of 3 reps) |
| MS3907 | Paenibacillus borealis | YES: Rhizoplane +Endophytic space | No | YES: Rhizoplane at 10 days and 30 days | YES: rhizoplane (3 of 4 reps) YES: Endophytic space (3 of 4 reps) | YES: rhizoplane (2 of 4 reps) YES: Endophytic space (3 of 3 reps) |

| | JAN BATCH | FEB BATCH | MAR BATCH | APR BATCH | COMP BATCH | AVG |
|---|---|---|---|---|---|---|
| Total Counts | 3.30E+08 | 3.75E+08 | 7.98E+08 | 2.93E+08 | 6.73E+08 | 4.94E+08 |
| Spore-Formers | 1.61E+06 | 1.62E+06 | 1.20E+06 | 2.18E+06 | 1.77E+06 | 1.68E+06 |
| P-sol (NRBIP) | 1.03E+03 | 5.00E+02 | 4.00E+03 | 5.00E+02 | 1.00E+03 | 1.41E+03 |
| P-sol (HA) | 1.50E+03 | 1.75E+03 | 1.00E+03 | 2.75E+03 | 1.25E+03 | 1.65E+03 |
| P-sol (Phytate) | 7.30E+03 | 9.50E+03 | 1.00E+04 | 2.00E+04 | 1.00E+04 | 1.14E+04 |
| Zinc-Sol | 9.00E+03 | 7.75E+03 | 1.88E+04 | 1.30E+04 | 3.03E+04 | 1.58E+04 |
| Fungal | 8.00E+03 | 1.30E+04 | 1.80E+04 | 1.70E+04 | 3.00E+04 | 1.72E+04 |

Fig. 73

$P_w$ ST WB Top Species (n= 15 samples)

| | Species | Abundance |
|---|---|---|
| 1 | lewinella cohaerens | 9.74 |
| 2 | thauera phenylacetica | 7.35 |
| 3 | thauera mechernichensis | 6.74 |
| 4 | solitalea canadensis | 6.06 |
| 5 | nitrospira moscoviensis | 3.81 |
| Total | | 33.70 |

Fig. 74

| E.C. Number | Enzyme Name | Function | Average % Abundance |
|---|---|---|---|
| EC:1.18.6.1 | Nitrogenase | Nitrogen Fixation | 0.0399% |
| EC:3.5.99.7 | 1-aminocyclopropane-1-carboxylate deaminase (ACC-Deaminase) | Ammonia Production (Nitrogen Fixation) | 0.0195% |
| EC:1.1.5.2 | Quinoprotein glucose dehydrogenase (PQQ, quinone) | Phosphate-Solubilization | 0.0255% |
| | | Zinc-Solubilization | 0.0255% |
| EC:1.1.1.215 | Gluconate 2-dehydrogenase | Phosphate-Solubilization | 0.00653% |
| | | Zinc-Solubilization | 0.00653% |
| EC:3.2.1.4 | Cellulase | Cell wall lysing (Endophytic Capacity and Biocontrol | 0.0634% |
| EC:3.2.1.6 | Endo-1,3(4)-beta-glucanase | | 0.00359% |
| EC:4.2.2.10 | Pectin lyase | | 0.000430% |

Fig. 77

| PwST WB Average | Quinoprotein glucose dehydrogenase (PQQ, quinone) | Nitrogenase | Gluconate 2-dehydrogenase | Cellulase | Pectin Lyase |
|---|---|---|---|---|---|
| | 0.0254977 | 0.0254977 | 0.00652679 | 0.0634395 | 4.3E-06 |

Fig. 78

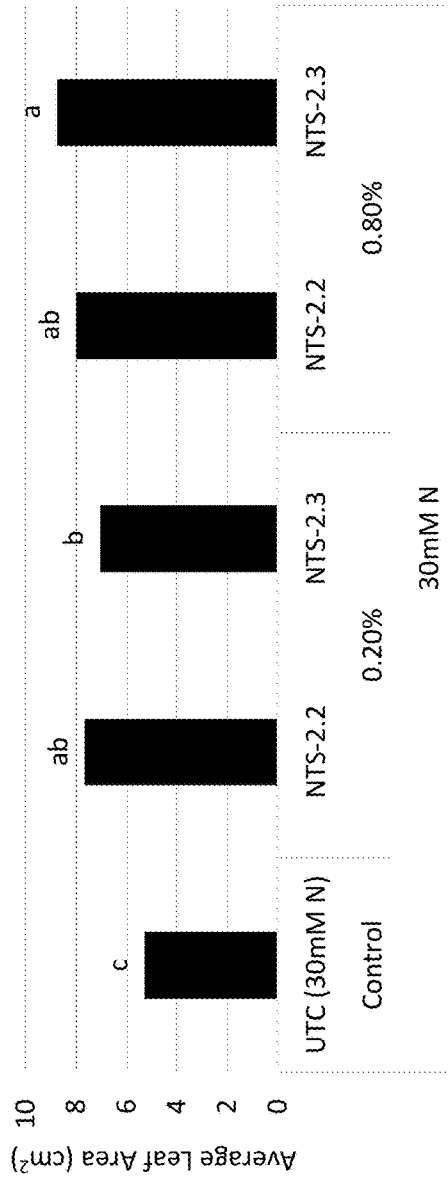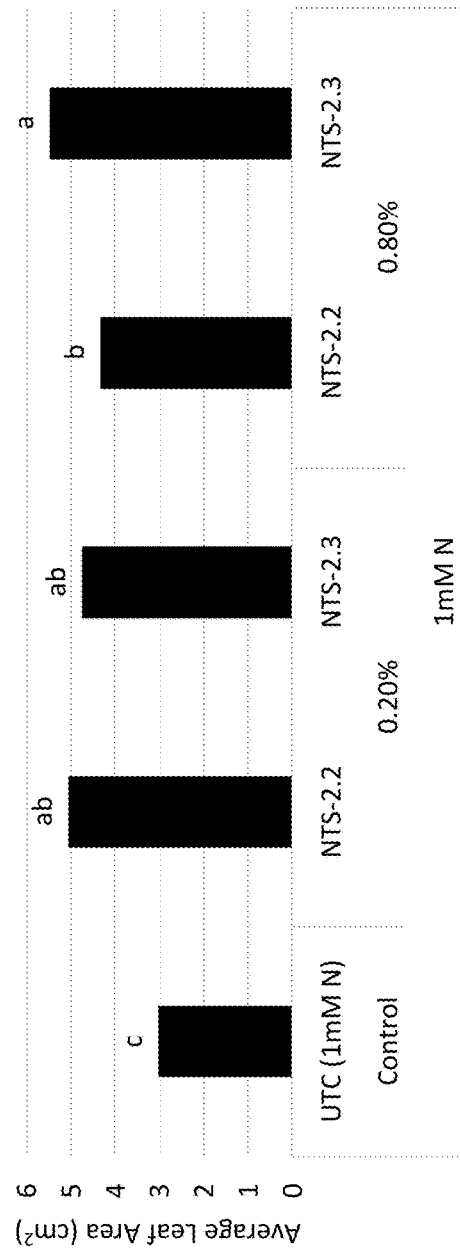
Fig. 90A
Fig. 90B

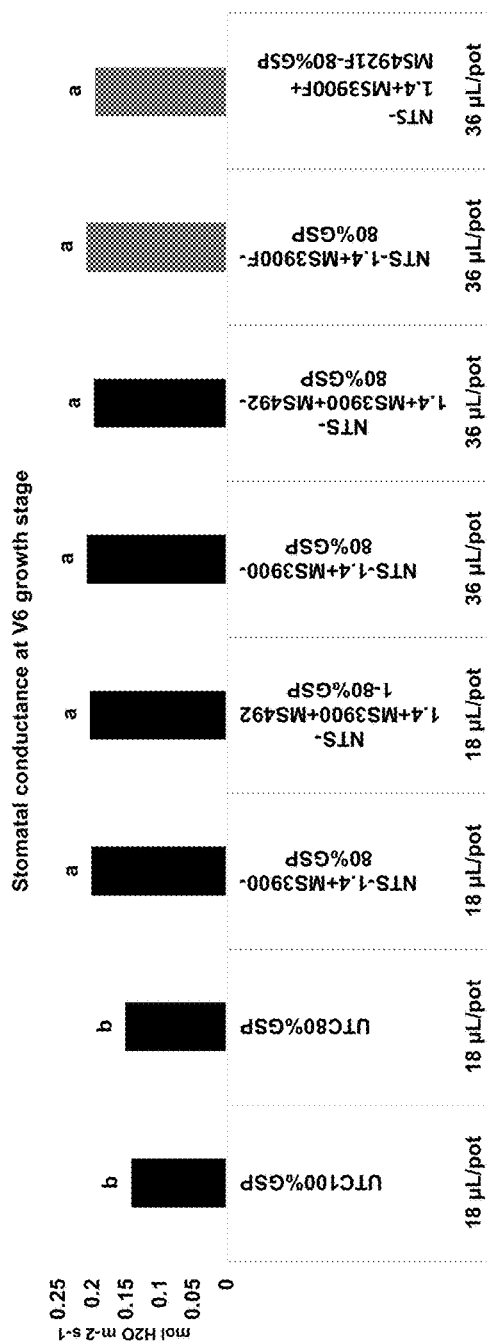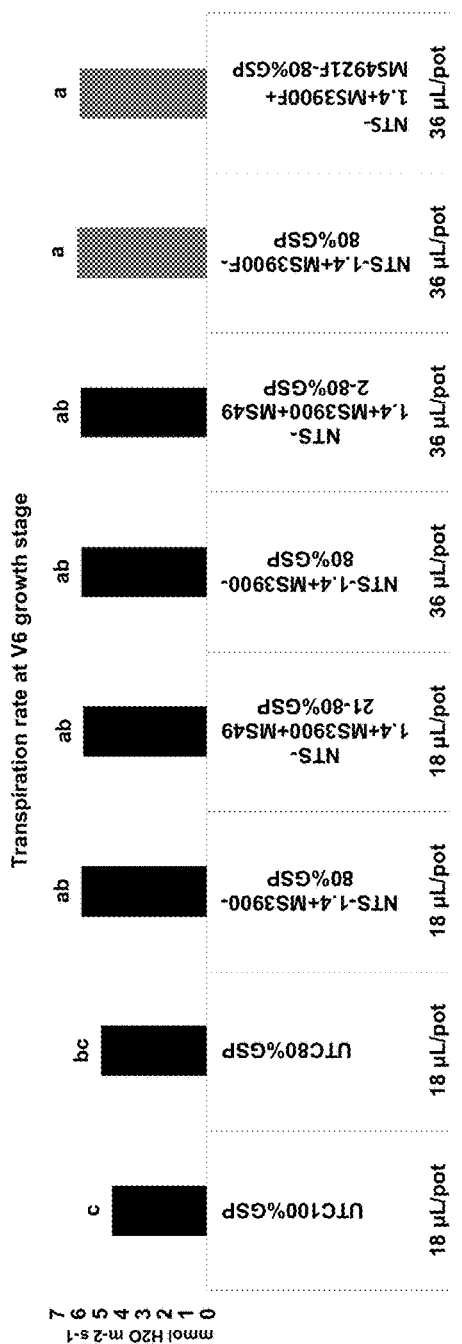

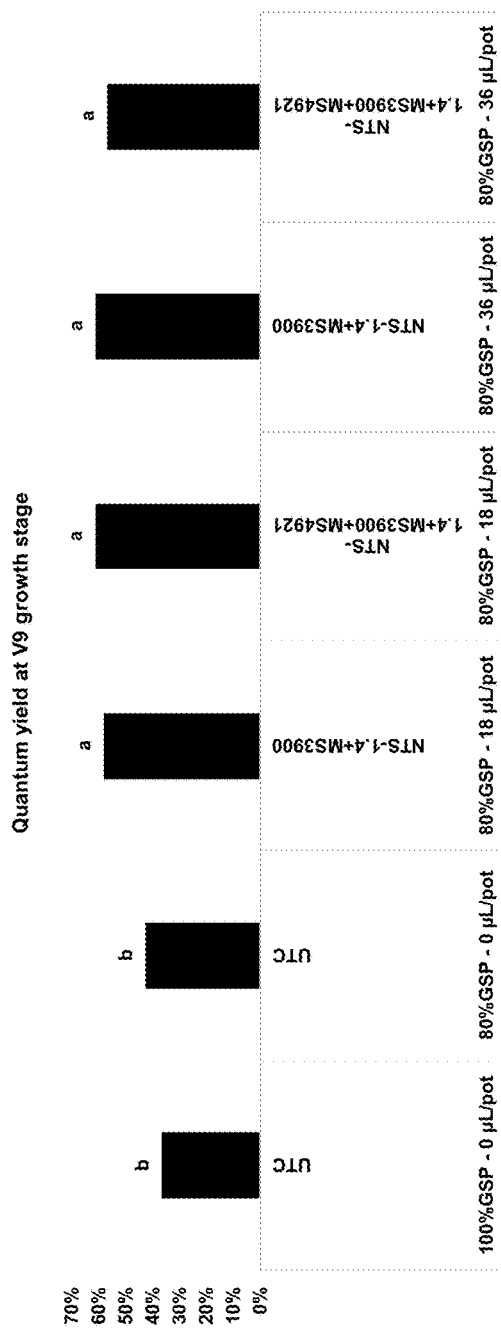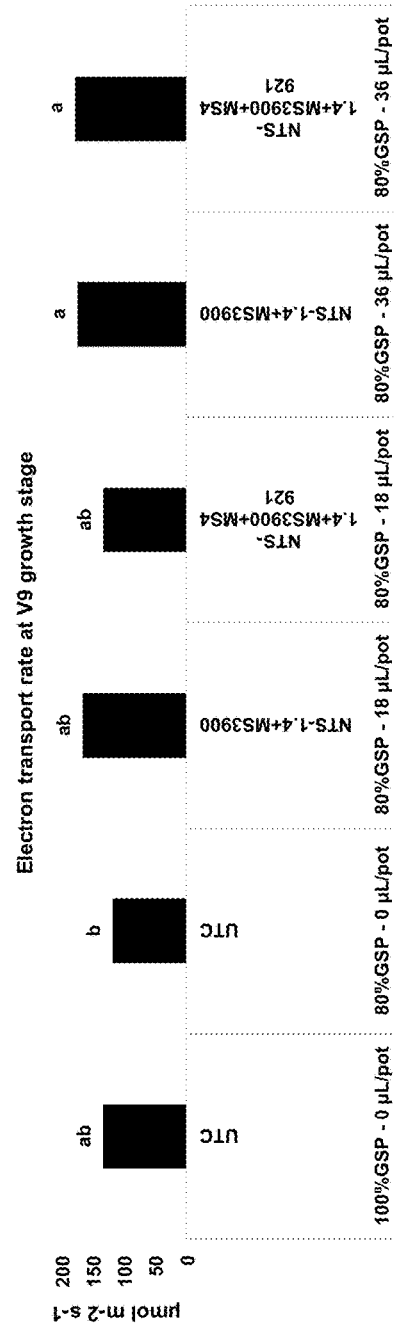

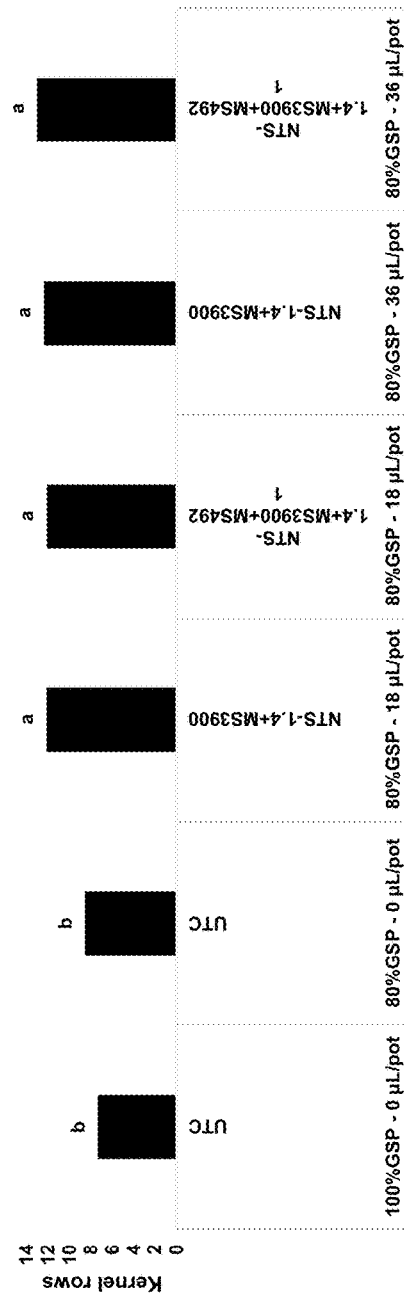
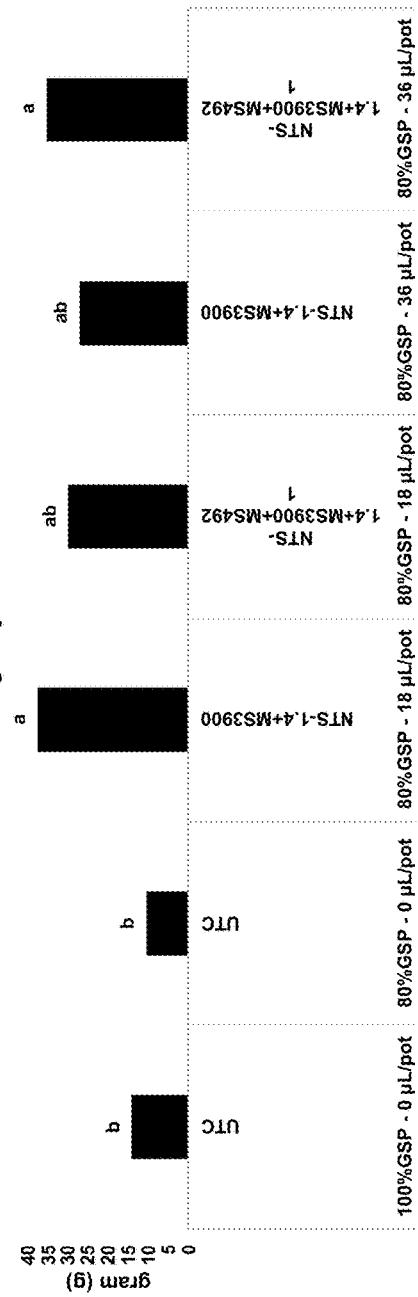
Fig. 120C
Fig. 120D

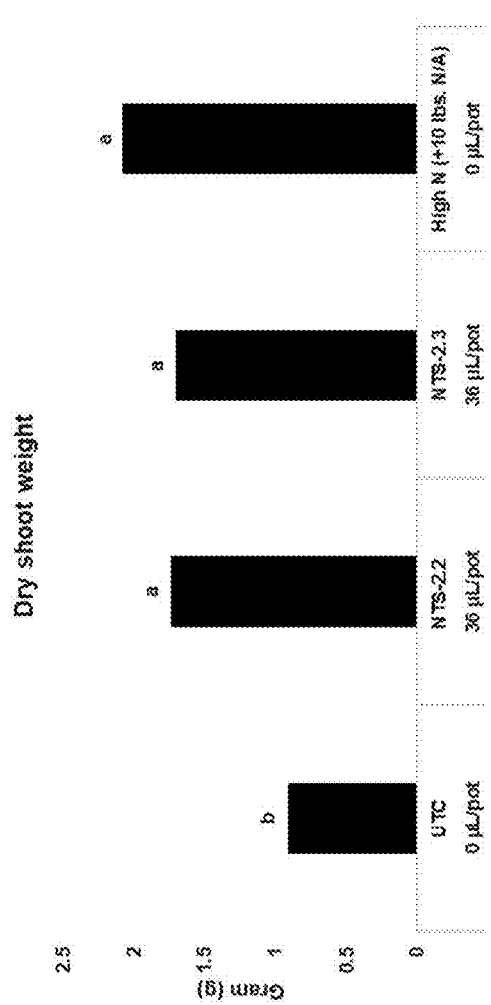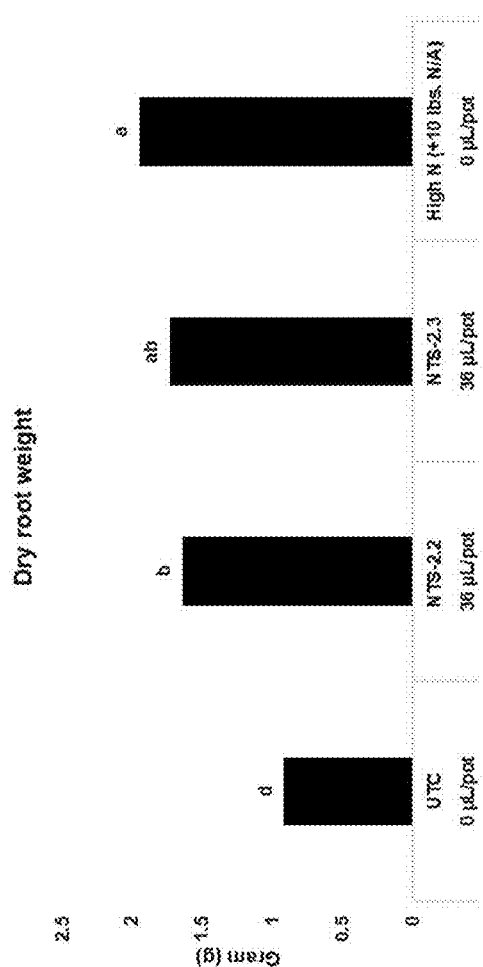
Fig. 132A
Fig. 132B

SEQUENCE LISTING

```
Sequence total quantity: 24
SEQ ID NO: 1               moltype = DNA  length = 1559
FEATURE                    Location/Qualifiers
source                     1..1559
                           mol_type = genomic DNA
                           organism = Bacillus megaterium
SEQUENCE: 1
catttcttcg gagagtttga tcctggctca ggatgaacgc tggcggcgtg cctaatacat   60
gcaagtcgag cgaactgatt agaagcttgc ttctatgacg ttagcggcgg acgggtgagt   120
aacacgtggg caacctgcct gtaagactgg gataacttcg ggaaaccgaa gctaataccg   180
gataggatct tctccttcat gggagatgat tgaaagatgg tttcggctat cacttacaga   240
tgggcccgcg gtgcattagc tagttggtga ggtaacggct caccaaggca acgatgcata   300
gccgacctga gagggtgatc ggccacactg ggactgagac acgcccaga ctcctacggg   360
aggcagcagt agggaatctt ccgcaatgga cgaaagtctg acggagcaac gccgcgtgag   420
tgatgaaggc tttcgggtcg taaaactctg ttgttaggga agaacaagta caagagtaac   480
tgcttgtacc ttgacggtac ctaaccagaa agccacggct aactacgtgc cagcagccgc   540
ggtaatacgt aggtggcaag cgttatccgg aattattggg cgtaaagcgc gcgcaggcgg   600
tttcttaagt ctgatgtgaa agcccacggc tcaaccgtgg agggtcattg gaaactgggg   660
aacttgagtg cagaagagaa aagcggaatt ccacgtgtag cggtgaaatg cgtagagatg   720
tggaggaaca ccagtggcga aggcggcttt ttggtctgta actgacgctg aggcgcgaaa   780
gcgtggggag caaacaggat tagataccct ggtagtccac gccgtaaacg atgagtgcta   840
agtgttagag ggtttccgcc ctttagtgct gcagctaacg cattaagcac tccgcctggg   900
gagtacggtc gcaagactga aactcaaagg aattgacggg ggcccgcaca agcggtggag   960
catgtggttt aattcgaagc aacgcgaaga accttaccag gtcttgacat cctctgacaa   1020
ctctagagat agagcgttcc ccttcggggg acagagtgac aggtggtgca tggttgtcgt   1080
cagctcgtgt cgtgagatgt tgggttaagt cccgcaacga gcgcaaccct tgatcttagt   1140
tgccagcatt tagttgggca ctctaaggtg actgccggtg acaaaccgga ggaaggtggg   1200
gatgacgtca aatcatcatg ccccttatga cctgggctac acacgtgcta caatggatgg   1260
tacaaagggc tgcaagaccg cgaggtcaag ccaatcccat aaaaccattc tcagttcgga   1320
ttgtaggctg caactcgcct acatgaagct ggaatcgcta gtaatcgcgg atcagcatgc   1380
cgcggtgaat acgttcccgg gccttgtaca caccgcccgt cacaccacga gagtttgtaa   1440
cacccgaagt cggtggagta accgtaagga gctagccgcc taaggtggga cagatgattg   1500
gggtgaagtc gtaacaaggt agccgtatcg gaaggtgcgg ctggatcacc tcctttcta   1559

SEQ ID NO: 2               moltype = DNA  length = 1567
FEATURE                    Location/Qualifiers
source                     1..1567
                           mol_type = genomic DNA
                           organism = Paenibacillus borealis
SEQUENCE: 2
ttcaatacaa attggagagt ttgatcctgg ctcaggacga acgctggcgg cgtgcctaat   60
```

```
acatgcaagt cgagcggagt tatgatggag cttgctcctg attaacttag cggcggacgg    120
gtgagtaaca cgtaggcaac ctgccctcaa gactgggata actaccggaa acggtagcta    180
ataccggata atttctttgt tctcctgaag agagaatgaa aggcggagca atctgccact    240
tgaggatggg cctgcggcgc attagctagt tggtgaggta acggctcacc aaggcgacga    300
tgcgtagccg acctgagagg gtgaacggcc acactggact gagacacggc cccagactcc    360
tacgggaggc agcagtaggg aatcttccgc aatgggcgaa agcctgacgg agcaacgccg    420
cgtgagtgat gaaggttttc ggatcgtaaa gctctgttgc cagggaagaa cgtccggtag    480
agtaactgct accggagtga cggtacctga gaagaaagcc ccggctaact acgtgccagc    540
agccgcggta atacgtaggg ggcaagcgtt gtccggaatt attgggcgta aagcgcgcgc    600
aggcggcgat ttaagtctgg tgtttaaacc ttgggctcaa cctggggtcg cactggaaac    660
tggatcgctt gagtacagaa gaggaaagtg gaattccacg tgtagcggtg aaatgcgtag    720
atatgtggag gaacaccagt ggcgaaggcg actttctggg ctgtaactga cgctgaggcg    780
cgaaagcgtg gggagcaaac aggattagat accctggtag tccacgccgt aaacgatgag    840
tgctaggtgt taggggtttc gatacccttg gtgccgaagt taacacagta agcactccgc    900
ctggggagta cggtcgcaag actgaaactc aaaggaattg acgggacccg cacaagcag    960
tggagtatgt ggtttaattc gaagcaacgc gaagaacctt accaggtctt gacatcccga   1020
tgaaagcatt agagatagtg cccctcttcg gagcatcgga gacaggtggt gcatggttgt   1080
cgtcagctcg tgtcgtgaga tgttgggtta gtcccgcaac gagcgcaac ccttgacttt   1140
agttgccagc aggttaagct gggcactcta gagtgactgc cggtgacaaa ccggaggaag   1200
gtggggatga cgtcaaatca tcatgcccct tatgacctgg gctacacacg tactacaatg   1260
gccggtacaa cgggaagcga agccgcgagg tggagccaat cccagcaaag ccggtctcag   1320
ttcggattgc aggctgcaac tcgcctgcat gaagtcggaa ttgctagtaa tcgcggatca   1380
gcatgccgcg gtgaatacgt tcccgggtct tgtacacacc gcccgtcaca ccacgagagt   1440
ttacaacacc cgaagtcggt ggggtaaccc gcaagggagc cagccgccga aggtgggta   1500
gatgattggg gtgaagtcgt aacaaggtag ccgtatcgga aggtgcggct ggatcacctc   1560
ctttcta                                                            1567

SEQ ID NO: 3               moltype = DNA  length = 1557
FEATURE                    Location/Qualifiers
source                     1..1557
                           mol_type = genomic DNA
                           organism = Paenibacillus sonchi
SEQUENCE: 3
taccaattgg agagtttgat cctggctcag gacgaacgct ggcggcgtgc ctaatacatg     60
caagtcgagc ggagtttatc cttcggggta agcttagcgg cggacgggtg agtaacacgt    120
aggcaaccta ccctctagac tgggataact accggaaacg gtagctaata ccggataatt    180
ccttgatcca catgggctaa ggatgaaagg cggagcaatc tgctgctaga ggatgggcct    240
gcggcgcatt agctagttgg tggggtaacg gcctaccaag gcgacgatgc gtagccgacc    300
tgagagggtg aacggccaca ctgggactga gacacggccc agactcctac ggaggcagc    360
agtagggaat cttccgcaat gggcgaaagc ctgacggagc aacgccgcgt gagtgatgaa    420
ggttttcgga tcgtaaagct ctgttgccag ggaagaacgt ccggtagagt aactgctatc    480
ggagtgacgg tacctgagaa gaaagccccg gctaactacg tgccagcagc cgcggtaata    540
cgtaggggc aagcgttgtc cggaattatt gggcgtaaag cgcgcgcagc    600
agtctggtgt ttaaaccttg gctcaacct ggggtcgcac tggaaactgg gcagcttgag    660
tacagaagag gaaagtggaa ttccacgtgt agcggtgaaa tgcgtagaga tgtggaggaa    720
caccagtggc gaaggcgact ttctgggctg taactgacgc tgaggcgcga aagcgtgggg    780
agcaaacagg attagatacc ctggtagtcc acgccgtaaa cgatgagtag tgttaggta    840
gggtttcgat acccttggtg ccgaagttaa cacagtaagc actccgcctg ggagtacggt    900
cgcaagact gaaactcaaa ggaattgacg ggacccgca caagcagtgg agtatgtggt    960
ttaattcgaa gcaacgcgaa gaaccttacc aggtcttgac atccaactaa cgaagcagag   1020
atgcatcagg tgccttcgg ggaaagttga gacaggtgt gcatggttgt cgtcagctcg   1080
tgtcgtgaga tgttgggta gtcccgcaa cgagcgcaac ccttgacttt agttgccagc   1140
aggtgaagct gggcactcta gagtgactgc cggtgacaaa ccggaggaag gtggggatga   1200
cgtcaaatca tcatgcccct tatgacctgg gctacacacg tactacaatg gccggtacaa   1260
cgggaagcga agccgcgagg tggagccaat cccagcaaag ccggtctcag ttcggattgc   1320
aggctgcaac tcgcctgcat gaagtcgaa ttgctagtaa tcgcggatca gcatgccgcg   1380
gtgaatacgt tcccgggtct tgtacacacc gcccgtcaca ccacgagagt ttacaacacc   1440
cgaagtcggt ggggtaaccc gcaagggggc cagccgccga aggtgggta gatgattggg   1500
gtgaagtcgt aacaaggtag ccgtatcgga aggtgcggct ggatcacctc ctttcta      1557

SEQ ID NO: 4               moltype = DNA  length = 1923
FEATURE                    Location/Qualifiers
source                     1..1923
                           mol_type = genomic DNA
                           organism = Bacillus megaterium
SEQUENCE: 4
ttgacgatgg aacaaaaaga agtacaagca tatgaagctg atcagataca agtattagaa     60
ggattagaag ctgttcgtaa acgtccgggg atgtatattg gatcgacgag cgcaaagggt    120
ctacatcatc ttgtatggga aattgtagat aatagtattg gtgaagcgct ggccggctac    180
tgcgatgaaa ttaatgttat tatcgaaaag gataatagta ttacagtcaa agataacggt    240
cgtggaattc cggttggtat tcaagaaaaa atgggcagac ctgccgttga gttatcttca    300
acggttcttc atgccggagg taaatttggc ggcggcggct ataaagtatc tggtggatta    360
cacggtgtag gtgcctcagt tgttaatgca ctttctacct ctttggaagt gcacgtacat    420
cgtgacggta aagttcatta tcaaaaatat gaacgaggtg taccggctgc tgacttaaaa    480
gtagttggag aaaacagataa aacaggtact gttattcaat tccgtccaga cggtgaaatt    540
tttacagaaa cgcttgaata cgattttgat acgttagcta atcgtctgcg tgagttagct    600
tcttaaaatc gtgcattaa aattacgatt gaagacaaac gtgaagaaga taaagacgt    660
gagtatcact atgaaggcgg aattaagtct tacgttgaac acttaaaccg ttcgaaagaa    720
gtgattcacg aagagccaat ctatattgaa ggtaatcgag acaacatttc tgtagaaatt    780
```

```
gctattcaat ataacgatag ctatacaagt aatttatatt cttttgcaaa caatattcac   840
acatatgaag gtggaacgca cgaagcagga tttaaaacag cgttaacgcg tgtaattaac   900
gactatgcac gtaaaaacag cgtatttaaa gacagtgacg ccaatctaac aggtgaagat   960
gttcgtgaag gaattacagc tatcatctct attaagcacc cagatccgca gttcgaagga  1020
caaacaaaaa caaagctggg aaatgtgaa gcaagaacaa ttactgactc tgtgtttgca  1080
gaacacttag aaacttactt gctagagaac cctattgtgg cgaaaaaggt aattgaaaaa  1140
ggtttaatgg ctgcaagagc aagaatggca gctaaaaaag ctcgtgagct tacacgccgt  1200
aaaagcgcgc ttgaaatttc aaacttaccg ggtaaattag cagattgttc atcaaaagat  1260
ccttctatta gcgaactcta tgtagtagag ggtgactctg ccggaggttc agctaagcag  1320
ggaagaagcc gtcatttcca agctatttg cctttacgtg gtaaaattat caacgtagag  1380
aaagcgcgtt tagataaaat tttatctaat aacgaaattc gtacaatcat taccgctcta  1440
ggaacgggta ttggtgacga ttttgatatt tcgaaagccc gctaccataa aattgtgatt  1500
atgcagatg cagacgtaga cggtgcgcat attcgtacgc ttcttctaac gttcttctat  1560
cgctatatga gacagattat tgagcacgga tatgtgtaca ttgctcagcc gcctctttac  1620
aaagtttcac aaggtaaaaa agtggagtac gcgtacaacg atcgtcaatt agaagaggta  1680
ttagcttctt tccctgaagg cgcaaaacca aaccttcagc gttacaaagg tttaggagag  1740
atgaatcctg aacaattatg ggaaacaaca atggatccag agttccgtac ccttcttcag  1800
gtgaacttgc aagatgcaat tgaagctgat gagacatttg aaattttaat gggcgacaaa  1860
gtagaaccac gccgtaattt cattgaagaa aatgctcagt acgtaaaaaa tcttgatatt  1920
taa                                                                1923

SEQ ID NO: 5         moltype = DNA  length = 1911
FEATURE              Location/Qualifiers
source               1..1911
                     mol_type = genomic DNA
                     organism = Paenibacillus borealis
SEQUENCE: 5
atgtcaatga atcaaccgac atatgatgag agccagattc aggtactgga agggctggaa    60
gcggttcgga aacgtcccgg catgtacatt ggctccacta gcgccaaagg tctgcatcat   120
ttggtctggg aggtcgtcga taatagtatc gatgaggcgc tggcaggttt ttgcgaccgg   180
attcaagtga tgattcatga agataacagc gtgactgtta tcgataacgg acggggtatt   240
cctgtcggga agaacgagaa gctgaagaaa tccacgcttg aagttgtaat gactgtcctg   300
catgcaggcg gtaaattcgg cggcggggga tataaggttt ccggcggtct gcacggtgtg   360
gggatctctg ttgtgaatgc attgtccgag aaggtagttg taaaggttaa acgtgacgga   420
cacgtctacc agcaggaata cagacgggt gcgccgcagt atgatatcag ggtaatcgg    480
gataccgatg agactggaac caccaccacc ttccatccgg atcctgagat ttttaccgaa   540
acgactattt tgaatattc aactctgctt accgtatcc gcgagctcgc cttcttgaat    600
aagggtatcg agctgtccct gctggatgaa cggaccggag tctccaatac atttaagtat   660
gatggcggta ttgtggagta tgtgaagtac cttaacgaga aaaagaagc cctgcacgag   720
gacccgatct acgtggaagg ctcacgggat atgatcgcgg ttgaagtggc tctccaatat   780
aacgattcat actcagagaa catctattcc tttgccaaca atatcaacac tcatgaaggc   840
ggtacgcatg aatccggctt caagagcgcc ttgacacgta ttatcaatga ttatgcccgt   900
aaggctggcg ttatcaagga cagcagccag aatctgaccg gagatgatgt acgtgaaggc   960
ttgacggcga ttatttccgt caaaattccc gaaccgcagt tcgaaggcca gaccaagacc  1020
aagcttggga acagcgaagt ccgcgggatt gtggagtccc tgttcggtga aagctgcag   1080
gaattcctgg aagagaaccc tgctgtgtcc cgccgcgtgc tggagaagtc gctgcaggct  1140
tcacgtgcac gtgaagccgc gcgcaaagcc gtgaactga cccgccgcaa gagtgcgctt   1200
gaagtcagtg ccctgccggg taagctggcc gactgctcct ccaaggatgc atcgatcagt  1260
gaactataca ttgtcgaagg tgactctgcg ggtggatcgg ccaagcaagg ccgggaccgt  1320
catttccagg ccatcctgcc gctgcgcggt aagatcctca atgtagagaa ggctcggctt  1380
gaccggatct tgtccaatgc ggaaatacgg gccattatca cagcgctcgg aaccgggatc  1440
agcgatgatt tcgacctctc taaggcacgt taccacaagg ttgtcatcat gaccgatgcg  1500
gatgttgacg gtgcccacat cagaacactg ctgctgactt tcttttaccg ctacatgcgg  1560
aagattgtcg atgccgggta tatcttcatc gcccagccgc cgctgttcaa gattgaacgc  1620
aataaggtta tccgctatgc gcagaccgag aaggaacgcg aggagattat cgcctccttc  1680
ggtgagaacg tgaaggttaa cgttcagcgc tacaaaggtt tgggtgagat gaatgctgcc  1740
cagctctggg atacaacgat ggatcctgag agccgcacta tgctgcaggt aacgattgag  1800
gatgctatgc tcgctgacag tatctttgat acacttatgg gcgataacgt ccagccaaga  1860
tatgaatta tccaggagca cgcccattcc gtcaaaaatc tcgatattta g            1911

SEQ ID NO: 6         moltype = DNA  length = 1911
FEATURE              Location/Qualifiers
source               1..1911
                     mol_type = genomic DNA
                     organism = Paenibacillus sonchi
SEQUENCE: 6
atgtcaatga atcaaccgac atatgatgag agccagattc aggtactgga agggctggag    60
gcagttcgga aacgtcccgg catgtacatc ggttctacca gcgccaaagg tctgcatcat   120
ttggtctggg aggttgtcga taacagtatc gatgaggcgc tggcaggcta ttgcgaccgg   180
attcaagtga agattcatga ggataacagt gttacagtaa tagataatgg acggggtatc   240
cctgtcggtg agaatgtgaa gctgaagaag tcgacgctcg aagtcgtcat gactgtcctg   300
catgcagggg gaaaattcgg cggcggcgga tataaagtat caggcggttt gcacggtgta   360
gggatctccg tcgtaaatgc cttgtccgag aaggttgttg tgaacgtcaa gcgtgacggc   420
cacatctacc agcaggaata tagacgcggt gcgccgcagt atgatatcaa gatcgttggg   480
gataccgatg agacagggac aaccacaacc tttcttccgg atccggagat tttcaccgaa   540
acgacagtgt tgaatatac gacattgctt acacgcattc gcgaattagc cttcttaac    600
aagggtattg agctttcgct gctggatgaa cgcaccggtg tgtcgaatgt ttcaaatac   660
gagggcggta tcgttgagta tgtaaaatat ctgaacgaga aaaagaagc gctgcacgaa   720
gaaccaatct acgtagaagg ctcccgtgat atgattgcgg tggaagtggc tctgcagtat   780
```

```
aacgattcct  atacagagaa  catttactct  tttgccaata  atattaatac  ccatgagggc   840
gggacccatg  aatccggctt  caaaagcgca  ttaacgcgga  tcatcaatga  ctatgcacgt   900
aaaacaggag  ttattaagga  cagcagctcc  aaccttaccg  gtgatgatgt  gcgtgaaggg   960
ctgacggcga  ttatttccgt  taagattcct  gagccgcaat  tgaaggcca   aaccaagacc  1020
aagctgggca  acagtgaagt  ccgcgtgtt   gtagaatctt  tattcggaga  gaagctgcag  1080
gagttcctgg  aagagaatcc  ggcggtgtcc  cggcgtgtgc  tggagaaatc  catgcaggct  1140
tcccgtgccc  gtgaagcggc  ccgcaaggcc  cgtgaactga  cccgccgcaa  aagtgcactt  1200
gaagtaagcg  ccctgccggg  gaagctggct  gactgctcct  ccaaggatgc  ctccatcagc  1260
gagctgtaca  tcgtcgaagg  ggactccgca  ggcggttctg  ccaagcaggg  ccgtgaccgt  1320
catttccagg  caattctgcc  gctgcgcggc  aagatactga  acgttgaaaa  agcgcggctt  1380
gaccgtatat  tgtccaatgc  tgaaatccgg  gcgattatca  ccgctctggg  aaccggtatc  1440
agtgatgatt  tcgatctgtc  caaagcccgt  taccataagg  ttgttatcat  gaccgatgcg  1500
gatgtcgacg  gtgcccatat  cagaaacactg  ctgctgacct  tcttctaccg  ctacatgcgg  1560
aagattatcg  aagcgggcta  tatttacatc  gcccagccgc  cgctgtttaa  gattgagcgc  1620
aataaggtcg  tccgctatgc  tcagaccgag  aaggaacgtg  atgagattat  tgccagcttc  1680
ggcgagaatg  ttaaagtcaa  cgttcaacgg  tataaaggtc  ttggggaaat  gaatgcggca  1740
cagctgtggg  atacgactat  ggaccctgag  agccgtatga  tgctgcaggt  caccatcgag  1800
gatgcgattc  tcgctgacgg  aatctttgat  acgctgtggg  gcgacaatgt  ccagccacga  1860
tatgaattca  ttcaggagaa  tgcgaagtac  gttcggaacc  tggatttcta  a           1911

SEQ ID NO: 7           moltype = DNA   length = 3564
FEATURE                Location/Qualifiers
source                 1..3564
                       mol_type = genomic DNA
                       organism = Bacillus megaterium
SEQUENCE: 7
ttgacaggtc  aactagttca  gtatggacgc  caccgccaac  gcagaagtta  tgctcgtatt   60
agtgaagttt  tagagttacc  gaacttaatc  gagattcaaa  cggcttcata  ccaatggttt  120
ttagatgaag  gtttacgaga  aatgttccaa  gatatttctc  caattgatga  ttttacaggt  180
aacttatcac  tagaatttat  tgattacagc  ttaggtgagc  caaagtattc  agtaggaagg  240
tctaaagaac  gtgatgtaac  ttatgcagca  cctcttcgtg  ttaaggtgcg  gttaattaat  300
aaagaaacag  gtgaagtaaa  agaccaagat  gtgttcatgg  gagatttccc  attgatgacc  360
gaaacaggta  cctttgtaat  taacggtgct  gagcgtgtta  tcgtatcaca  gttggttcgt  420
tcaccaagtg  tttactatag  tggaaagctt  gataaaaacg  gtaaaaaagg  atatacagca  480
actgttatcc  ctaaccgtgg  tgcatggcta  gaatatgaaa  ctgatgcaaa  agatgtagta  540
tacgtgcgta  ttgatcgtac  tcgtaaactg  ccagtaacag  tgctgttacg  cgcgctaggt  600
ttcggttctg  accaagagat  tatcgattta  atcggtgata  atgaatacat  ccgtaatacg  660
cttgaaaaag  ataaacggaa  aacaacggaa  aaagcgctat  tagaaaatcta tgagcgttta  720
cgtccgggtg  aaccaccgac  agttgagaat  gcgaagtctc  tattagtatc  tcgcttcttt  780
gatccaaaac  gatatgactt  agcgaacgta  ggtcgctata  aaattaataa  aaagcttcat  840
atcaaacatc  gctatttaa   tcaaaagcta  gctgaaacat  tagttgatcc  tgaaacaggc  900
gaaattattg  cagaaaaagg  cgcaatgatt  gaccgccgtc  tgctagatcg  cttgattccg  960
atgcttgaag  gtggagtaaa  cttcaaaact  tatagtccgg  ttggtggat   agtagaagac 1020
gatgttacat  tacaatctat  taagatttat  gcgccaaatg  atccagaagg  tgaaaaaatc 1080
atcactgtat  caggtaacgc  atatgtaaca  gaagaagtta  aaaatatcac  acctgctgat 1140
attttagcat  caatcagtta  cttctttaac  ttgcttcatc  aagtaggaga  cacagatgat 1200
atcgaccact  taggtaaccg  tcgtctgcgt  tctgtaggtg  aattgttaca  aaaccaattc 1260
cgtatcggtt  tatctcgtat  ggaacgtgtt  gttcgtgaaa  gaatgtcaat  tcaagacacg 1320
aatacaatca  cacctcaaca  attaattaat  attgcccag   ttattgcggc  gattaaaagag 1380
ttctttggaa  gttctcaatt  atcacagttc  atggatcaaa  cgaatccatt  aggcgaattg 1440
acgcacaaac  gtcgtctttc  agctctagga  cctggtggtt  taacgcgtga  gcgcgctagt 1500
ttcgaagtgc  gtgacgttca  ctactcccac  tatggccgta  tgtgcccgat  tgaaacacca 1560
gagggtccga  atatcgggtt  aatcaactca  ctatcttctt  atgcaaaagt  aaacaaattc 1620
ggtttcatcg  aaacacctta  ccgtcgtatc  gatcctgaaa  caggtaaagt  gacagagcga 1680
attgactact  taacagctga  tgaagaagat  aactatgttg  tagcccaagc  gaacgctcgt 1740
ctaggtgatg  atggttcatt  cttagatgaa  aatgtcgttg  cacgtttccg  tggagaaaac 1800
acggttatcc  gtcgcgatcg  tttagactat  atggatgtat  caccaaaaca  agttgtatct 1860
gccgctacag  catgtatccc  attcttagag  aacgatgact  ctaaccgtgc  attaatgggt 1920
gcgaacatgc  aacgtcaagc  agtaccttta  ttaaatcctg  agcaccaat   cgtaggtaca 1980
ggtatggaat  acgtatctgg  taaagactct  ggtgcagccg  tgatttgtaa  atatcctggc 2040
gttgtagagc  gcgtagaagc  aaaacaaatt  tttgttcgcc  gctatgaaga  agtagacgga 2100
caaaaagtta  aaggtaactt  agatcaatac  aaattattaa  aatttgttcg  ttctaaccaa 2160
ggtacttgtt  acaaccagcg  tccaattgtt  tcagttggcg  acgaagtagt  aaaaggtgag 2220
atcttagccg  acggtccttc  aatggaaaaa  ggtgagcttg  cttaggacg   aaacgtaatg 2280
gttggtttca  tgcatggga   tggttacaac  tatgaggatg  ccatcatcat  gagtgaacgc 2340
cttgtgaaag  acgatgtata  tacgtctgtt  catattgaag  aatatgaatc  tgagtctcgt 2400
gatacgaagc  ttgacctga   agaaattacg  cgtgacattc  caaacgtagg  tgaagatgcg 2460
cttcgcaact  tagatgagcg  tggaatcatc  gcattggtg   cagaagtaaa  agacggagat 2520
cttttagttg  gtaaagtaac  gccaaaaggt  gtaacagaac  taacagctga  agaacgtctt 2580
ctacacgcta  ttttcggtga  aaaagcgcgt  gaagttcgtg  atacttctct  tcgtgtaccg 2640
cacggcggcg  gtgaatcat   tcttgatgtt  aaagtcttca  accgtgaaga  tggggacgaa 2700
ttaccaccag  gtgtaaacca  attagtccgt  gtatatattg  ttcagaagcg  taaaatttct 2760
gaaggtgaca  aaatggccgg  tcgtcacggt  aacaaaggtt  aatttcacg   tatttttacct 2820
gaagaagata  tgccttacct  acatcctggt  acgccaatta  acatcattgt  aaacccatta 2880
ggggtaccat  ctcgtatgaa  catcggtcag  gtgctagagc  ttcatttagg  tatggctgct 2940
cgtaagcttg  gcattcacgt  tgcgtctcca  gtatttgatg  gtgcgcgtga  ggaagatgtt 3000
tgggcaacaa  tcgaagaagc  tggcatgtct  cgtgatgcta  aaacagttct  atatgatggt 3060
cgaacaggtg  aaccattcga  taaccgtgta  tcagtaggaa  tcatgtacat  gatcaaactt 3120
gctcacatgg  tagacgataa  acttcacgct  cgttctactg  gaccatactc  acttgttaca 3180
```

```
caacaaccac ttggtggtaa agcgcagttc ggtggacagc gttttggtga gatggaggta  3240
tgggcacttg aagcatacgg tgctgcttac acattacaag agatcttaac agtgaaatca  3300
gatgacgtag taggtcgtgt gaaaacatac gaagcaattg ttaaaggtga aaacattcca  3360
gaacctggca tacctgaatc gttcaaagta ttaattaaag aactacaaag tttaggtatg  3420
gatgtgaaga tgctttctgc tgacgagcaa gaaattgata tcatggactc agaagaggac  3480
catgagcaac caacagaatc aattattgca gataacgaag aaagcctttc tgaaggacaa  3540
aaagatcctg tcacaaaaga gtaa                                          3564

SEQ ID NO: 8              moltype = DNA  length = 3417
FEATURE                   Location/Qualifiers
source                    1..3417
                          mol_type = genomic DNA
                          organism = Paenibacillus borealis
SEQUENCE: 8
ttgcgggaaa tgttccagga catctcgccg atccaggatt tcacaggtaa tttggtacta   60
gagttcattg attacagcct gggtgaaccg aagtatacgg ttgacgacgc taaagagcgg  120
gacgtaacat atgcggctcc tctgcgtgtg aaggtgcgtc tcatcaataa ggagaccggt  180
gaggtcaaag agcaggaagt gttcatggga gatttccctc tgatgacgga gaccggcact  240
tttattatca atggtgcgga acgggttatt gtcagccagt tggttcgctc tccaagcgtc  300
tatttcagca cgaaagtgga taagaacggc aaaaaaacct acaccgccac agtaattccg  360
aatcgcggag cttggctgga gctggagacc gacgctaagg acatcatgta tgtccgtatc  420
gaccggactc gtaagatccc ggttaccgtg cttctgccta ctctaggcct cggcagtgat  480
gctgaaattc tggaactgct tggtaatgat gaatatattc gcaatacgct ggataaagac  540
aacacggact ctacggagaa ggcgcttatc gaaatttacg agcgtctgcg tccgggcgaa  600
ccaccgcacg ttgacaatgc caagagcctt ttggtcgcac gtttctttga tccgaaacgt  660
tatgatttgg ccaatgtagg ccgttacaaa atcaacaaaa agctgcatat taaaaatgct  720
ctgttcaatc agcgtctggc acaacctttg gtggatgagt ctactggaga atcctggca   780
gaatccggcc aaatggttga ccgccgcctt cttgatgagc tgattcctta ttttgagaag  840
aacgtagctg ccaagaacta ccgtgtaacc ggtgggggtta tggacagcga agatattccg  900
cttcagacga ttgatgtgtt ctcgccaatt gaagaaggcc ggattatcaa actgatcgac  960
aatggcaaca ttgacaagtc ggtcaagcat attactcagg ctgatattat atcctcaatc 1020
agctacttta ttaatctgct gcacggtatc ggcaacactg atgatatcga ccacttgggt 1080
aaccgccgtc tgcgttctgt cggcgaactg ctgcagaatc agttccgtat cggtctgtcc 1140
cgcatggaac gcgttgtccg cgagagaatg tcgattcagg atgccaatgc gatcacaccg 1200
caggcgctga tcaacatccg cccggttatc gcgtcgatta agagttcctt cggtagttca 1260
cagctgtccc agttcatgga tcagacgaac ccgcttgctg aacttacgca caaacgccgt 1320
ctatcggcac tcggacccgg cggtttgacc cgtgaacgcg caggctttga gtccgcgac  1380
gtccatcaca gtcactatgg ccgtatgtgt ccaatcgaaa caccggaagg tccgaatatc 1440
ggtctgatca actccttgtc caccttttgcc cgcatcaata atacggctt tatcgaagca 1500
ccgtatcgtt gggtggatcc aaagacaggc aaagtcactg agcaaattga ttatctgact 1560
gccgatgaag aagataacta tgtagttgca caggcaaatg tactgatcga tgagaatggc 1620
tccttcaagg aagaccaggt tatcgttcgt tataacaaag attcagacaa catcactaca 1680
atgccaagta accgtgttga ctacatggac gtttcgccta acaggttgt atcagtagct 1740
acggcgctca ttccgttcct tgagaacgat gactccaacc gcgcgctgat gggatcgaac 1800
atgcagcgtc aggctgttcc gcttctcatt ccgaaggctc cgcttgtagg aacagggatg 1860
gaacataaat ccgctaagga ctcgggcgta tgtattgtct ccaaatatga cggtattatc 1920
gaacgctcct ctgccaatga aatcggctg cgccgtgttg aggcagttga aggcaaagaa 1980
gttaaaggcg atatcgttaa atataaatta cacaaattta tgcgttcgaa ccagggtacc 2040
tgcattaatc agcgtccgct agccaaacgc ggcgacgttg ttaagaaagg tgatatcctt 2100
gcagacggac catctacgga aatgggcgaa cttgctcttg gccgtaacgt agttgttgcg 2160
ttcatgactt gggaaggcta caactacgag gatgcgatcc tgctgagtga gaagctgggt 2220
aaggaagatg tatacacttc gatccatatc gaggaatacg aatccgaagc ccgtgacacg 2280
aagcttggac ctgaagaaat cacgcgtgat attccaaacg taggggaaga agcgcttcgc 2340
aatctcgatg agcgcggaat tatccggatc ggtgcgaaaa tcaatgccgg cgacattctg 2400
gtaggtaaag ttactccgaa gggcgtaacc gagctgcacg ctgaagaacg tctgctgcac 2460
gctatctttg gtgagaaggc tcgtgaagtc cgcgatacct cttgcgcgt tccacatggt 2520
agtgatggta ttatcgttga cgttaaggtg ttcacgcgtg agaacggcga tgagctgcct 2580
ccaggtgtga atcagctggt tcgtgtctat atcgctcaga aacgtaagat ttctgagggt 2640
gacaagatgg ccggacgtca cggtacacaag ggtgtcgttg cccgtatcct gcctgaagaa 2700
gatatgccgt tccttccgga cggtacaccg gtacaggttg tcctgaaccc gctgggcgta 2760
ccttcccgta tgaacatcgg acaggtgctt gaagtccatc tcggtatggc tgcactgcgt 2820
ctgggtattc acgtggctac tccagtattt gacggagccc gtgagtatga cgtgtttgat 2880
acgatggaag aagccggtat gcagcgtaac ggtaaaactg tgctttatga cggacgtaca 2940
ggcgaacgct ttgagcgtga agttactgtc ggcgtcatgc acatgatcaa gctcgacgac 3000
atggttgacg ataaaattca tgcccgttct acaggtcctt actctctcgt tacacagcag 3060
ccactgggcg gtaaggctca gttcggcgga cagcgttttcg gggaaatgga agtgtgggcg 3120
cttgaagctt acgcgcggc atatacactg caagaaatct tgaccgtgaa gtccgatgac 3180
gtggtcggcc gtgtgaaaac gtacgagtcc attgtcaaag gcgaaaatgt tccagaaccg 3240
ggtgttccgg aatccttcaa ggtattgatc aaggaactgc agtcgctggg tatggatgtt 3300
aagatcctta gcggtgacga gcaggagatt gagatgaagg aactggacgt tgaggacgag 3360
acgtcaggcg ataagctgag cctcaatttg gaaggcgcag aagtcggcat agagtag    3417

SEQ ID NO: 9              moltype = DNA  length = 3417
FEATURE                   Location/Qualifiers
source                    1..3417
                          mol_type = genomic DNA
                          organism = Paenibacillus sonchi
SEQUENCE: 9
ttgcgtgaaa tgtttcagga catctcgcca atccaggatt tcacagggaa tttggtactt   60
```

```
gagttcattg attacagcct aggcgaaccg aagtatacgg ttgacgacgg taaagagcgg   120
gacgtaacat atgcggctcc tctacgtgtg aaggtgcggc tcattaataa ggagaccggt   180
gaggtcaaag agcaggaagt gttcatggga gatttcccgc tgatgacgga gaccggcact   240
tttattatca atggtgcgga acgggttatt gtcagccagt tggttcgctc tccaagcgtc   300
tatttcagca cgaaagtaga taagaacggc aaaaaaacct acaccgccac agtaattcca   360
aaccgcggag cctggcttga actggagacc gacgctaagg atatcatgta tgtccgtatc   420
gaccggaccc gtaaaattcc agttacagtg cttctgcgtg ctctcggttt cggcagtgat   480
gctgaaattc tggaactgct gggtaatgat gaatatattc gcaatacgct ggataaagac   540
aatacggact ccacggagaa ggcgcttatt gaaatttacg agcgtctgcg tccgggtgaa   600
ccgccgacac tggataatgc caagagcctt ttggttgcac gtttcttcga tccaaagcgt   660
tatgacttgg ccaatgtagg ccgttacaaa atcaataaga agctgcacat taagaaccgg   720
ttgtttaacc agcgtctggc acagcctttg gttgatgaat ccactgggga aattctggcg   780
gaatccggac aaatggttga ccgcagactt cttgatgagc tgattcctta ttttgagaag   840
gatgtcgctg ccaagaccta ccgtgttacc gcggagtgc tggacagtga agatatcccg   900
ctgcaaacga tcgatgtatt ctcgccgatc gaggaaggcc gggttatcaa gctgattgcc   960
aacggcaata tcgacaaatc cgttaagcat attacccagg ctgatattat atcctcaatc  1020
agctacttta ttaatctgct gcacggtatc ggcaacacag acgacattga ccacttgggt  1080
aaccgccgtc tgcgttccgt aggtgaattg ctgcagaacc aattccgcat cgggctgtcc  1140
cgtatggaac gcgtagtgcg tgagagaatg tcgattcagg atgcgaatgc aattactccg  1200
caggccctga tcaatattcg tccggtcatc gcgtccatta aagagttctt cggcagctcc  1260
cagctgtcgc agtttatgga ccagacgaac ccgctggcag aacttacgca taagcgtcgt  1320
ctgtctgcac tcggacccgg cggtctgacc cgtgaacgcg ggcttgtcgg agttcgggac  1380
gtgcatcaca gtcactacgg ccggatgtgt ccaatcgaaa caccggaagg tccgaatatc  1440
ggtctgatca actccttgtc cacttttgcc cgcatcaatg aatacggctt tatcgaagct  1500
ccgtaccgtt gggtggatcc gaagaccggc aaggtcacag agcatatcga ttatctgacc  1560
gccgatgaag aagacaacta tgtagttgcg caggcaaacg tgcagattga tgaagatgga  1620
accttaaagg aagatatggt tatcgtccgt tacaacaagg attcagacaa catcacgact  1680
atgcctagta accgtgttga ctacatggac gtttcgccaa aacaggttgt atcggtcgct  1740
acggcgctca ttccgttcct ggagaacgat gactccaacc gcgcactgat gggatctaac  1800
atgcagcgcc aagccgttcc gcttctgatt ccgaaggctc ccttgtcgg tacaggaatg  1860
gagcataagt ccgctaaaga ctccggcgta tgtattgtct ccaaatatga cggtattatt  1920
gaacgctctt ctgccaatga gatctggctg cgccggggtg aaatggttga aggcaaagaa  1980
gtcaaaggtc atatcgttaa atataaatta cacaaattta tgcgttcgaa ccaagggact  2040
tgcataaatc agcgtccgct tgctaaaaga ggcgacattg tgaagaaggg tgacattctt  2100
gcggatggtc cttccaccga aatgggcgag ttggtctctgg gccgcaacgt agttgttgcc  2160
tttatgactt gggaaggtta caactacgag gatgcgatcc tgctgagtga gaagctggtg  2220
aaggaagatg tatacacttc gattcatatc gaggaatacg aatccgaagc tcgtgacacg  2280
aagctgggac ctgaagaaat tacccgtgat attccaaatg tcggtgaaga agcactccgt  2340
aacttggacg aacgcggtat catccgcatt ggtgcgaaa tcaatgccgg tgacatcctt  2400
gtaggtaagg taactcctaa aggtgtaact gaactgactg ctgaagaacg tctgctccat  2460
gcaatcttcg ggaaaaaagc gcgtgaagtt cgcgatacct ccttgcgtgt tccgcatggt  2520
agtgatggta ttatcgttga cgtcaaagta ttcacacgtg agaacggcga tgagctgcct  2580
ccgggtgtaa atcagctggt tcgtgtctac atcgcccaga aacgtaaaat ttctgagggt  2640
gacaaaatgg ccggacgtca cggtaacaag ggtgtcgttg cccgtattct tcctgaggaa  2700
gatatgccat tcctgccgga cggcacaccg gtacaggtag tattgaaccc gctgggcgtt  2760
ccttcccgta tgaacatcgg acaggtgctg gaggtccatc ttggtatggc cgctcttcgt  2820
ctgggcattc atgtagctac tccggtattt gacggtgcc gcgagtatga cgtcttttgat  2880
acgatgaaag aagccggcat tcagcgcaat ggtaagactg tgctgtacga cggacgtaca  2940
ggcgaacgct tcgagcgtga agtaacagtc ggtgtcatgc acatgatcaa gctggcgcac  3000
atggttgatg ataagattca tgcccgttcc acaggtcctt actcactcgt tacccagcag  3060
cctctcggcg gtaaagccca gtttggtgga caacgttttg gggaaatgga agtatggcg   3120
cttgaagctt acggcgctgc ttatacactg caggaaatct tgacggtgaa atccgatgac  3180
gtggttggcc gtgtgaagac gtatgaatcc atcgtcaaag cgagaatct gccggaacct  3240
ggcgtgcctg aagcgttcaa agtattgatc aaggaactgc agtcgcttgg tatggatgtc  3300
aaaatcctca gcgcgtgatga gcaggagatt gagatgaaag aactgacgga tgaggacgag  3360
acgacaggcg acaagctgag ccttaacttg gaaggcgcgg aagtcggaat agagtag     3417

SEQ ID NO: 10           moltype = DNA   length = 1559
FEATURE                 Location/Qualifiers
source                  1..1559
                        mol_type = genomic DNA
                        organism = Bacillus megaterium
SEQUENCE: 10
catttcttcg gagagtttga tcctggctca ggatgaacgc tggcggcgtg cctaatacat    60
gcaagtcgag cgaactgatt agaagcttgc ttctatgacg ttagcggcgg acgggtgagt   120
aacacgtggg caacctgcct gtaagactgg gataacttcg ggaaaccgaa gctaataccg   180
gataggatct tctccttcat gggagatgat tgaaagatgg tttcggctat cacttacaga   240
tgggcccgcg gtgcattagc tagttggtga ggtaacggct caccaaggca acgatgcata   300
gccgacctga gagggtgatc ggccacactg gactgagaca cggcccaga ctcctacggg   360
aggcagcagt agggaatctt ccgcaatgga cgaaagtctg acggagcaac gccgcgtgag   420
tgatgaaggc tttcgggtcg taaaactctg ttgttaggga agaacaagta cgagagtaac   480
tgctcgtacc ttgacggtac ctaaccagaa agccacggct aactacgtgc cagcagccgc   540
ggtaatacgt aggtggcaag cgttatccgg aattattggg cgtaaagcgc gcgcaggcgg   600
tttcttaagt ctgatgtgaa agcccacggc tcaaccgtgg agggtcattg gaaactgggg   660
aacttgagtg cagaagagaa aagcggaatt ccacgtgtag cggtgaaatg cgtagagatg   720
tggaggaaca ccagtggcga aggcggcttt tggtctgta actgacgctg aggcgcgaaa    780
gcgtggggag caaacaggat tagataccct ggtagtccac gccgtaaacg atgagtgcta   840
agtgttagag ggtttccgcc ctttagtgct gcagctaacg cattaagcac tccgcctggg   900
gagtacggtc gcaagactga aactcaaagg aattgacggg ggcccgcaca agcggtggag   960
```

-continued

```
catgtggttt aattcgaagc aacgcgaaga accttaccag gtcttgacat cctctgacaa   1020
ctctagagat agagcgttcc ccttcggggg acagagtgac aggtggtgca tggttgtcgt   1080
cagctcgtgt cgtgagatgt tgggttaagt cccgcaacga gcgcaaccct tgatcttagt   1140
tgccagcatt aagttgggca ctctaaggta actgccggtg acaaaccgga ggaaggtggg   1200
gatgacgtca aatcatcatg cccctatga cctgggctac acacgtgcta caatggatgg   1260
tacaaagggc tgcaagaccg cgaggtcaag ccaatcccat aaaaccattc tcagttcgga   1320
ttgtaggctg caactcgcct acatgaagct ggaatcgcta gtaatcgcgg atcagcatgc   1380
cgcggtgaat acgttcccgg gccttgtaca caccgcccgt cacaccacga gtttgtaa    1440
cacccgaagt cggtggagta accgtaagga gctagccgcc taaggtggga cagatgattg   1500
gggtgaagtc gtaacaaggt agccgtatcg gaaggtgcgc tggatcacc tccttttcta    1559
```

SEQ ID NO: 11          moltype = DNA   length = 1919
FEATURE                Location/Qualifiers
source                 1..1919
                       mol_type = genomic DNA
                       organism = Bacillus megaterium
SEQUENCE: 11

```
ttaaatatca agattttta cgtactgagc attttcttca atgaaattac ggcgtggttc    60
tactttgtcg cccattaaaa tttcaaatgt ctcatcagct tcaattgcat cttgcaagtt   120
cacctgaaga agggtacgga actctggatc cattgttgtt tcccataatt gttcaggatt   180
catctctcct aaacctttgt aacgctgaag gtttggtttt gcgccttcag ggaagaagc    240
taatacctct tctaattgac gatcgttgta cgcgtactcc actttttac cttgtgaaac    300
tttgtaaaga ggcggctgag caatgtacac atatccgtgc tcaataatct gtctcatata   360
gcgatagaag aacgttagaa gaagcgtacg aatatgcgca ccgtctacgt ctgcatctgt   420
cataatcaca attttatggt agcgggcttt cgaaatatca aatcgtcaca atccgtccgt   480
tcctagacg gtatgattgt acgaaatttcg ttattagata aaatttatct aaacgcgctt   540
tctctacgtt gataatttta ccacgtaaag gcaaaatagc ttggaaatga cggcttcttc   600
cctgcttagc tgaacctccg gcagagtcac cctctactac atagagttcg ctaatagaag   660
gatcttttga tgaacaatct gctaatttac ccggtaagtt tgaaatttca agcgcgcttt   720
tacggcgtgt aagctcacga gctttttag ctgccattct tgctcttgca gccattaaac   780
ctttttcaat tacctttttc gccacaatag ggttctctag caagtaagtt tctaagtgtt   840
ctgcaaacac agagtcagta attgttcttg cttcactatt tcccagcttt gttttgttt    900
gtccttcgaa ctgcggatct gggtgcttaa tagagatgat agctgtaatt ccttcacgaa   960
catcttcacc tgttagattg gcgtcactgt cttttaaatac gtcgtttta cgtgcatagt   1020
cgttaattac acgcgttaac gctgtttttaa atcctgcttc gtgcgttcca ccttcatatg   1080
tgtgaatatt gtttgcaaaa gaatataaat tacttgtata gctatcgtta tattgaatag   1140
caatttctac agaaatgttg tctcgattac cttcaatata gattggctct tcgtgaatca   1200
cttctttcga acggttttaag tgttcaacgt aagacttaat tccaccttca tagtgatact   1260
cacgtctttt atcttcttca cgttgtctt caatcgtaat tttaatgccg cgattttaaga   1320
aagctaactc acgcagacga ttagctaacg tatcaaaatc gtattcaagc gttctgtaa    1380
aaatttcacc gtctggacgg aattgaataa cagtaccgtgt ttatctgttt ctccaactac   1440
ttttaagtca gcagccggta cacctcgttc atattttga taatgaactt taccgtcacg   1500
atgtacgtga acttccaaag aggtagaaag tgcattaaca actgaggcac ctacaccgtg   1560
taatccacca gatactttat agccgccgcc accaaattta cctccggcat gaagaaccgt   1620
taagataact tcaacggcag gtctgccatt tttttcttgaa taccaaccgg aattccacga   1680
ccgttatctt tgactgtaat actattatcc ttttcgataa taacatttaat ttcatcgcaa   1740
tagccggcca gcgcttcatc aatactatta tctacaattt cccatacaag atgatgtaga   1800
cccttttgcgc tcgtcgatcc aatatacate cccggacgtt tacgaacagc ttctaatcct   1860
tctaatactt gtatctgatc agcttcatat gcttgtactt cttttgttc catcgtcaa    1919
```

SEQ ID NO: 12          moltype = DNA   length = 3554
FEATURE                Location/Qualifiers
source                 1..3554
                       mol_type = genomic DNA
                       organism = Bacillus megaterium
SEQUENCE: 12

```
ttactctttt gtgacaggat ctttttgtcc ttcagaaaga ctttcttcgt tatctgcaat    60
aattgattct gttggttgct catggtcctc ttctgagtcc atgatatcaa tttcttgctc   120
gtcagcagaa agcatcttca catccatacc taaactttgt agttcttaa ttaatactt     180
gaacgattca ggtatgccag gttctggaat gttttcacct ttaacaattg cttcgtatgt   240
tttcacacga cctactacgt catctgattt cactgttaag atctcttgta atgtgtaagc   300
agcaccgtat gcttcaagtg cccataccctc catctcacca aaacgctgtc caccgaactg   360
cgcttaccca ccaagtggtt gttgtgtaac aagtgagtat ggtccagtag aacgagcgtg   420
aagtttatcg tctaccatgt gagcaagttt gatcatgtac atgattccta ctgatacgca   480
gttatcgaat ggttcacctg ttcgaccatc atatagaact gtttttagcat cacgagacat   540
gccagcttct tcgattgttg cccaaacatc ttcctcacgc gcaccatcaa atactggaga   600
cgcaacgtga atgccaagct tacgagcagc ataccctaaa tgaagctcta gcacctgacc   660
gatgttcata cgagatggta cccctaatgg gtttaacatg atgtcaattg gcgtaccgtc   720
tggtaggtaa ggcatatctt tcaggtaa aatacgtgaa attcacctt tgttaccgtg     780
acgaccggcc atttttgtcac cttcagaaat tttacgcttc tgaacaatat atacacggac   840
taattggttt acacctggtg gtaattcgtc gccatcttca cggttgaaga ctttaacatc    900
aagaatgatt ccaccgccgc cgtgcggtac acgaagagaa gtatcacgaa cttcacgcgc   960
ttttcaccg aaaatagcgt gtagaagacg ttcttcagct gttagttctg ttacaccttt   1020
tggcgttact ttaccaacta aaagatctca tgcttttact tctgcaccaa tgcggatgat   1080
tccacgctca tctaagttgc gaagcgcatc ttcacctacg tttggaatgt cacgcgtaat   1140
ttcttcaggc ccaagcttcg tatcacgaga ctcagattca tattcttcaa tatgaacaga   1200
cgtatataca tcgtctttca caaggcgttc actcatgatg atggcatcct catagttgta   1260
accatcccat gtcatgaaac caaccattac gtttcgtcct aaagcaagct caccttttc    1320
cattgaagga ccgtcggcta agatctcacc tttactact tcgtcgccaa ctgaaacaat   1380
```

-continued

```
tggacgctgg ttgtaacaag taccttggtt agaacgaaca aattttaata atttgtattg 1440
atctaagtta cctttaactt tttgtccgtc tacttcttca tagcggcgaa caaaatttgt 1500
tttgcttcta cgcgctctac aacgccagga tatttacaaa tcacggctgc accagagtct 1560
ttaccagata cgtattccat acctgtacct acgattggtg cttcaggatt taataaaggt 1620
actgcttgac gttgcatgtt cgcacccatt aatgcacggt tagagtcatc gttctctaag 1680
aatgggatac atgctgtagc ggcagataca acttgttttg gtgatacatc catatagtct 1740
aaacgatcgc gacggatgac cgtgtttttct ccacggaaac gtgcaacgac attttcatct 1800
aagaatgaac catcatcacc tagacagacg ttcgcttggg ctacaacata gttatcttct 1860
tcatcagcrg ttaagtagtc aattcgctct gtcactttac ctgtttcagg atcgatacga 1920
cggtaaggtg tttcgatgaa accgaatttg tttacttttg cataagaaga tagtgagttg 1980
attaacccga tattcggacc ctctggtgtt caatcggac atacgcc atagtgggag 2040
tagtgaacgt cacgcacttc gaaaccagcg cgctcacgcg ttaccaccag gtcctagagc 2100
tgaagacgac gtttgtgcgt caatcgctaa tggattcgtt tgatccatga actgtgataa 2160
ttgagaactt ccaaagaact cttaatcgc cgcaatact gggcaatat taattaattg 2220
ttgaggtgtg attgtattcg tgtcttgaat tgacattctt tcacgaacaa cacgttccat 2280
acgggataaa ccgatacgga attggttttg taacaattca ctacgaacg cagacgacgg 2340
ttacctaagt ggtcgatatc atctgtgtct cctacttgat gaagcaagtt aaagaagtaa 2400
ctgattgatg ctaaaatatc agcaggtgag atattttaa cttcttctgt tacatatgcg 2460
ttacctgata cagtgatgat ttttcacctt ctggatcatt tggcgcataa atcttaatag 2520
attgtaatgt aacatcgtct tctactactc caccaaccgg actataagtt tgaagtttac 2580
tccacctcaa gcatcggaat caagcgatct agcagacggc ggtcaatcat tgcgcctttt 2640
tctgcaataa tttcacctgt ttcaggatca actaatgttt tcttgattaaat 2700
aagcgatgtt tgatatgaag ctttttttatt aattttatag cgacctacgt tcgctaagtc 2760
atatcgtttt ggatcaaaga agcgagatac taatagagac ttcgcattct caactgtcgg 2820
tggttcacc ggacgtaaac gctcatagat ttctaatagc gctttttccg ttgtttccgt 2880
attatctttt tcaagcgtat tacggatgta ttcattatca ccgattaaat cgataatctc 2940
ttggtcagaa ccgaaaccta gcgcgcgtaa cagcactgtt actggcagtt acgagtacga 3000
tcaatacgca cgtatactac atcttttgca tcagtttcat attctagcca tgcaccacgg 3060
ttagggataa cagttgctgt atatcctttt ttaccgttttt tatcaagctt tccactatag 3120
taaacacttg gtgaacgaac caactgtgat acgataacgc gctcagcacc gttaattaca 3180
aaggtacctg tttcggtcat caatgggaaa tctcccatga acacatcttg gtctttttact 3240
tcacctgttt ctttattaat taaccgcacc ttaacgaa gaggtgctgc ataagttaca 3300
tcacgttctt tagactctcc tactgaatac tttggctcac ctaagctgta atcaataaat 3360
tctagtgata agttacctgt aaaatcatca attggagaaa tatcttggaa catttctcgt 3420
aaaccttcat ctaaaaacca ttggtatgaa gccgtttgaa tctcgattaa gttcggtaac 3480
tctaaaactt cactaatacg agcataactt ctgcgttggc ggtggcgtcc atactgaact 3540
agttgacctg tcaa                                                  3554

SEQ ID NO: 13          moltype = DNA  length = 867
FEATURE                Location/Qualifiers
source                 1..867
                       mol_type = genomic DNA
                       organism = Paenibacillus borealis
SEQUENCE: 13
atgagacaaa tagctttcta cggtaaaggc ggtatcggca aatcgacaac ttcacaaaac 60
accctggctc agctggcgac aaagttcgga caaagaataa tgatcgtagg ctgtgaccct 120
aaagcagact ccacccgcct tatcctgaat acaaaagcgc agaactctgt gcttgaactg 180
gcggctgagc ttggctcggt agaggatctt gaacttgaag atgtattgca gacaggtttc 240
ggcgacatta tcaacgtaga atgcggcgga cctgaaccgg gtgtaggctg cgcgggacgc 300
gggatcatca ctgccatcaa cttcctggag caggaaggcg cctatcagga tctgatttc 360
gtatcctatg acgttcttgg tgacgttgta tgcggcgatc tgcaatgcc aatccgcgaa 420
ggcaaggcgc aagagatcta tatcgtctgt tccggtgaaa tgatggcaat gtacgcagcg 480
aacaatatcg cccgcgggat cctgaaatat gcgaccagcg gcggcgtgag actgggcggc 540
ctgatctgca cagccgtaa cacagaccgt gaagatgagc tgatcatgga actgccagac 600
cgtctgaaca cgcagatgat ccactttgta ccgcgtgaca atatcgttca gcatgccgag 660
ctgcgcagaa tgactgttgc ccagtataat ccgacccatt cacaagcgaa agaatatgac 720
aagctggctg agaaaatcct caataacaaa atgctgacga tccctactcc gatttctatg 780
gaagagctgc aagagctgct gatggaattc ggcatcatcg aagacgaaga ggctgcaatc 840
aagaagctgc aggcttccgg tcaataa                                     867

SEQ ID NO: 14          moltype = DNA  length = 870
FEATURE                Location/Qualifiers
source                 1..870
                       mol_type = genomic DNA
                       organism = Paenibacillus sonchi
SEQUENCE: 14
atgatgagac aaatagcttt ctacggtaaa ggcggtatcg gtaaatccac aacctcccaa 60
aacacttttgg cccagctcgc aaccaaattc aaacaaagca ttatgatcgt aggctgtgac 120
ccgaaggcag actccacccg cctgattctg aataccaagg cacagaactc ggtcctggca 180
ctggcagccg aactgggctc agtagaggat ttggaactgg aggatgtgct gcagaccggc 240
tttggcgaca ttatcaacgt agagtgcggc ggacctgaac cgggtgtagg ctgtgcaggg 300
cgcggtatca ttactgccat caacttcctg agcaggaag gcgcctatca ggatctggac 360
ttcgtatcct atgacgtatt gggcgacgtt gtatgcggcg gtttcgccat gccgatccgt 420
gaaggcaaag cccaagagat ctatattgta tgttccggtg aaatgatggc gatgtacgcg 480
gccaacaaca ttgcacgcgg tatcctgaaa tatgctacca gcggcggcgt gagactgggc 540
ggactgatct gcaacagccg caacaccgac cgtgaagacg agctgatcat ggagctggcc 600
cgccgtctga acacgcaaat gatccacttc gttccccgtg acaatatcgt tcagcatgcc 660
gagctgcgca gaatgacggt ggcccaatat aaccctgccc atcaacaagc caagaatat 720
gaaattctgg ctgaaaaaat cctcaacaac aaaatgctga ccatccctac cccgattca 780
```

```
atggaagaac tggaagagct gctgatggaa ttcggcatca ttgaagatga agaagctgca   840
ctcaagaagc tgcaggcttc cggccaataa                                    870
```

| SEQ ID NO: 15 | moltype = DNA   length = 20 |
|---|---|
| FEATURE | Location/Qualifiers |
| source | 1..20 |
|  | mol_type = other DNA |
|  | organism = synthetic construct |

SEQUENCE: 15
```
tgcgayccsa argcbgactc                                               20
```

| SEQ ID NO: 16 | moltype = DNA   length = 20 |
|---|---|
| FEATURE | Location/Qualifiers |
| source | 1..20 |
|  | mol_type = other DNA |
|  | organism = synthetic construct |

SEQUENCE: 16
```
aggccrctyt actaccgsta                                               20
```

| SEQ ID NO: 17 | moltype = DNA   length = 20 |
|---|---|
| FEATURE | Location/Qualifiers |
| source | 1..20 |
|  | mol_type = other DNA |
|  | organism = synthetic construct |

SEQUENCE: 17
```
tccggmggty tkcacggtgt                                               20
```

| SEQ ID NO: 18 | moltype = DNA   length = 22 |
|---|---|
| FEATURE | Location/Qualifiers |
| source | 1..22 |
|  | mol_type = other DNA |
|  | organism = synthetic construct |
| misc_difference | 6 |
|  | note = a, c, t, g, unknown or other |
| misc_difference | 18 |
|  | note = a, c, t, g, unknown or other |

SEQUENCE: 18
```
tactgnctac gdctrcanct rc                                            22
```

| SEQ ID NO: 19 | moltype = DNA   length = 20 |
|---|---|
| FEATURE | Location/Qualifiers |
| source | 1..20 |
|  | mol_type = other DNA |
|  | organism = synthetic construct |

SEQUENCE: 19
```
cgkatgtgtc cgattgaaac                                               20
```

| SEQ ID NO: 20 | moltype = DNA   length = 20 |
|---|---|
| FEATURE | Location/Qualifiers |
| source | 1..20 |
|  | mol_type = other DNA |
|  | organism = synthetic construct |

SEQUENCE: 20
```
atgttgatrc tcctacgsta                                               20
```

| SEQ ID NO: 21 | moltype = DNA   length = 20 |
|---|---|
| FEATURE | Location/Qualifiers |
| source | 1..20 |
|  | mol_type = other DNA |
|  | organism = synthetic construct |

SEQUENCE: 21
```
cgctaatggt gtacggtcct                                               20
```

| SEQ ID NO: 22 | moltype = DNA   length = 20 |
|---|---|
| FEATURE | Location/Qualifiers |
| source | 1..20 |
|  | mol_type = other DNA |
|  | organism = synthetic construct |

SEQUENCE: 22
```
ggacttgcct ttcaaaaacg                                               20
```

| SEQ ID NO: 23 | moltype = DNA   length = 20 |
|---|---|
| FEATURE | Location/Qualifiers |
| source | 1..20 |
|  | mol_type = other DNA |
|  | organism = synthetic construct |

SEQUENCE: 23
```
aaagaaaat ggggcaaacc                                                20
```

```
SEQ ID NO: 24        moltype = DNA  length = 20
FEATURE              Location/Qualifiers
source               1..20
                     mol_type = other DNA
                     organism = synthetic construct
SEQUENCE: 24
ctgcatgccc taaatccaac                                              20
```

SYSTEMS FOR PRODUCTION OF PRODUCTS TO PROMOTE NITROGEN USE EFFICIENCY IN PLANTS

CROSS-REFERENCE TO RELATED APPLICATIONS

This application claims priority to U.S. Provisional Patent Application No. 63/509,263, filed on Jun. 20, 2023, U.S. Provisional Patent Application No. 63/510,615, filed on Jun. 27, 2023, and U.S. Provisional Patent Application No. 63/610,535, filed on Dec. 15, 2023, each of which is entirely incorporated herein by reference.

REFERENCE TO A SEQUENCE LISTING

The instant application contains a Sequence Listing which has been submitted electronically in XML format and is hereby incorporated by reference in its entirety. Said XML copy, created on Dec. 12, 2023, is named 63472-716_201_SL.xml and is 52,161 bytes in size.

BACKGROUND

The disclosure is generally related to biostimulant compositions and methods of using such biostimulant compositions to promote plant growth.

Promoting efficient production of food crops and other crops is an important goal for environmental and economic reasons. Plant growth promoting products sourced from organic materials can help to enhance crop growth, improve the efficacy of agricultural products, such as fertilizers, and reduce the environmental impacts of synthetic fertilizers and climate change. There exists a need for plant growth promoting biostimulant compositions that use abundant and available organic feedstocks.

SUMMARY

In an aspect, the present disclosure provides a method of making a biostimulant composition, the method comprising: (a) providing a bioreactor system comprising two or more containers arranged in a series, each of the two or more containers comprising a volume of a working fluid, wherein a first container comprises an established population of a first nitrogen use efficiency-promoting microbial strain; (b) operating the bioreactor system for a duration of time by: (i) transferring into the first container an aqueous feedstock comprising a microbial consortium; (ii) transferring a portion of the working fluid out of each of the two or more containers into either a subsequent container of the bioreactor system or a product outflow stream; (iii) maintaining a concentration of the first nitrogen use efficiency-promoting microbial strain throughout the duration of time in at least the first container at at least 80% of a concentration of the first nitrogen use efficiency-promoting microbial strain at the beginning of the duration of time; and (iv) collecting at least a portion of the product outflow stream as the biostimulant composition; wherein the duration of time is at least 5 days; and wherein the first nitrogen use efficiency-promoting microbial strain is not present in the aqueous feedstock or any other input into the bioreactor system during the duration of time at a concentration that is higher than 1% of the concentration of the first nitrogen use efficiency-promoting microbial strain in the first container.

In some embodiments, the first nitrogen use efficiency-promoting microbial strain is one that performs nitrogen fixation, promotes nitrogen fixation in the tissues of plants, recruits nitrogen fixers to the root zones or other tissues of plants, or increases organic nitrogen content and/or mineralization of organic nitrogen in soil. In some embodiments, the first nitrogen use efficiency-promoting microbial strain is positive for a nifH gene. In some embodiments, the first nitrogen use efficiency-promoting microbial strain is one that promotes plant growth in a nitrogen-poor growth medium. In some embodiments, the nitrogen-poor growth medium comprises nitrate at less than 10 ppm.

In some embodiments, the first nitrogen use efficiency-promoting microbial strain is of the genus *Kosakonia, Klebsiella, Rahnella, Kluyvera, Enterobacter, Achromobacter, Microbacterium, Gluconobacter, Methylobacterium, Pseudomonas, Pantoea, Azospirillum, Azocarus, Herbaspirillum, Burkholderia, Cyanobacteria, Bacillus, Paenibacillus, Kosakonia sacchari, Klebsiella variicola, Rahnella aquatilis, Kluyvera intermedia, Kosakonia pseusosacchari, Enterobacter* spp., *Achromobacter marplatensis, Azopirillum lipoferum, Microbacterium murale, Gluconobacter diazotrophicus,* and *Methylobacterium symbioticum*. In some embodiments, the first nitrogen use efficiency-promoting microbial strain is of the species *Kosakonia sacchari, Klebsiella variicola, Rahnella aquatilis, Kluyvera intermedia, Kosakonia pseusosacchari, Enterobacter* spp., *Achromobacter marplatensis, Azopirillum lipoferum, Microbacterium murale, Gluconobacter diazotrophicus, Methylobacterium symbioticum, Paenibacillus borealis, Bacillus megaterium (Priestia megaterium),* or *Paenibacillus sonchi*.

In some embodiments, the first nitrogen use efficiency-promoting microbial strain is the strain deposited under ATCC Accession No. PTA-127654 (MS3907), the strain deposited under ATCC Accession No. PTA-127653 (MS3900), the strain deposited under ATCC Accession No. PTA-127655 (MS4921), or the strain deposited under ATCC Accession No. PTA-127652 (MS2748).

In some embodiments, the first nitrogen use efficiency-promoting microbial strain is not present in the aqueous feedstock or any other input into the bioreactor system during the duration of time at a concentration of greater than 100 CFU/ml. In some embodiments, the first nitrogen use efficiency-promoting microbial strain is not present in the aqueous feedstock or any other input into the bioreactor system during the duration of time. In some embodiments, the maintaining of step (b)(iii) comprises maintaining the concentration of the first nitrogen use efficiency-promoting microbial strain at at least $1 \times 10^3$ CFU/ml.

In some embodiments, the first container further comprises an established population of a second nitrogen use efficiency-promoting microbial strain and wherein the operating of step (b) further comprises (v) maintaining a concentration of the second nitrogen use efficiency-promoting microbial strain at at least 80% of a concentration of the second nitrogen use efficiency-promoting microbial strain at the beginning of the duration of time; wherein the second nitrogen use efficiency-promoting microbial strain is not present in the aqueous feedstock or any other input into the bioreactor system during the duration of time at a concentration that is higher than 1% of the concentration of the second nitrogen use efficiency-promoting microbial strain in the first container.

In some embodiments, the first container further comprises an established population of a third nitrogen use efficiency-promoting microbial strain and wherein the operating of step (b) further comprises (v) maintaining a concentration of the third nitrogen use efficiency-promoting microbial strain at at least 80% of a concentration of the third nitrogen use efficiency-promoting microbial strain at the beginning of the duration of time; wherein the third nitrogen use efficiency-promoting microbial strain is not present in the aqueous feedstock or any other input into the bioreactor system during the duration of time at a concentration that is higher than 1% of the concentration of the third nitrogen use efficiency-promoting microbial strain in the first container. In some embodiments, before step (b), the first container further comprises an established population of other nitrogen use efficiency-promoting microbes that are not the first nitrogen use efficiency-promoting microbial strain, the second nitrogen use efficiency-promoting microbial strain, or the third nitrogen use efficiency-promoting microbial strain, and wherein step (b)(iii) further comprises maintaining a concentration of the other nitrogen use efficiency-promoting microbes in at least the first container throughout the duration of time at at least $1 \times 10^4$ CFU/ml or at at least 80% of a concentration of the other nitrogen use efficiency-promoting microbes at the beginning of the duration of time, wherein the other nitrogen use efficiency-promoting microbes are not added to the bioreactor system during the duration of time at a concentration that is higher than 1% of the concentration of the other nitrogen use efficiency-promoting microbes in the first container.

In some embodiments, the other nitrogen use efficiency-promoting microbes are not present in the aqueous feedstock or any other input into the bioreactor system at a concentration of greater than $10^5$ CFU/ml. In some embodiments, the population of the other nitrogen use efficiency-promoting microbes in the first container is at least $1 \times 10^4$ CFU/ml at the beginning of the duration of time. In some embodiments, the other nitrogen use efficiency-promoting microbes comprise microbes that perform nitrogen fixation, promote nitrogen fixation in the tissues of plants, recruit nitrogen fixers to the root zones or other tissues of plants, or increases organic nitrogen content and/or mineralization of organic nitrogen in soil. In some embodiments, the other nitrogen use efficiency-promoting microbes are positive for a nifH gene.

In some embodiments, the method further comprises, before step (a), adding an inoculum of the first nitrogen use efficiency-promoting microbial strain to the bioreactor system, wherein the inoculum of the first nitrogen use efficiency-promoting microbial strain produces an initial population of the first nitrogen use efficiency-promoting microbial strain of at least $0.5 \times 10^4$ CFU/ml in at least one container. In some embodiments, before adding the inoculum of the first nitrogen use efficiency-promoting microbial strain, the concentration of the first nitrogen use efficiency-promoting microbial strain is less than $1 \times 10^2$ CFU/ml.

In some embodiments, the aqueous feedstock further comprises an organic material at least partially digestible by microbes present in at least one of the containers.

In some embodiments, before the transferring of step (b)(i), the organic material had been partially digested by microbes endogenous to the organic material. In some embodiments, the method further comprises digesting the organic material in two or more serially connected containers before the transferring of step (b)(i).

In some embodiments, the organic material comprises manure and/or material produced by microbial digestion of manure. In some embodiments, the aqueous feedstock further comprises an inorganic material. In some embodiments, the inorganic material comprises rock phosphate particles. In some embodiments, prior to the transferring of step (b)(i), the rock phosphate particles had been partially digested by microbes present in the aqueous feedstock. In some embodiments, the method further comprises partially digesting the rock phosphate particles in two or more serially connected containers before the transferring of step (b)(i).

In some embodiments, the microbial consortium comprises at least $1 \times 10^5$ CFU/ml. In some embodiments, the microbial consortium comprises microbes derived from manure and from rock phosphate particles. In some embodiments, the operating of step (b) further comprises producing microbial metabolites that directly or indirectly promote nitrogen use efficiency in plants. In some embodiments, the transferring of step (b)(i), the transferring of step (b)(ii), and the collecting of step (b)(iv) are performed continuously throughout the duration of time. In some embodiments, the transferring of step (b)(i), the transferring of step (b)(ii), and the collecting of step (b)(iv) are performed periodically throughout the duration of time.

In some embodiments, the method further comprises adding one or more carbon sources to at least one container of the bioreactor system. In some embodiments, the one or more carbon sources are included in the aqueous feedstock. In some embodiments, the method further comprises maintaining a malate and/or glucose concentration in at least one container of the bioreactor system at a concentration of at least 0.2% w/v in relation to the volume of working fluid in the at least one container. In some embodiments, the method further comprises adding one or more nitrogen sources to at least one container of the bioreactor system.

In some embodiments, the one or more nitrogen sources comprise one or more of ammonium sulfate, ammonium chloride, ammonium nitrate, sodium nitrate, yeast extract, yeast, or any combination thereof. In some embodiments, the method further comprises adding one or more of soy flour, lentil flour, chickpea flour, green pea flour, yellow pea flour, white bean flour, corn flour, cereal flour, corn gluten, soy flour protein, or soy protein hydrolysate, or any combination thereof to at least one container of the bioreactor system. In some embodiments, the soy flour is added, and wherein the soy flour is included in the aqueous feedstock. In some embodiments, the method further comprises maintaining a soy flour concentration in at least one container of the bioreactor system at a concentration of at least 0.2% w/v in relation to the volume of the working fluid in the at least one container.

In some embodiments, the bioreactor system comprises a clarifier container comprising a clarifier working fluid. In some embodiments, the method further comprises separating a supernatant portion of the clarifier working fluid from a floc portion of the clarifier working fluid within the clarifier container. In some embodiments, the separating comprises gravity separation. In some embodiments, the method further comprises folding the floc portion of the clarifier working fluid. In some embodiments, the folding further comprises releasing a population of the first nitrogen use efficiency-promoting microbial strain into the supernatant portion without introducing floc solids into the supernatant portion. In some embodiments, the folding is performed by folding wipers in a bottom portion of the clarifier container.

In some embodiments, the operating further comprises transferring the floc portion from the clarifier container to an earlier container in the bioreactor system. In some embodiments, the product outflow stream comprises the supernatant portion of the clarifier working fluid.

In some embodiments, the method further comprises producing at least $1 \times 10^4$ CFU/ml of the first nitrogen use efficiency-promoting microbial strain in the product outflow stream. In some embodiments, the bioreactor system comprises the first container comprising a volume of a first working fluid, a second container comprising a volume of a second working fluid, and a third container comprising a volume of a third working fluid. In some embodiments, the first container comprises an outlet port fluidly connected to an inlet port of the second container and the second container comprises an outlet port fluidly connected to an input port of the third container. In some embodiments, the third container comprises an outlet port fluidly connected to a clarifier container. In some embodiments, the method further comprises maintaining the volume of each of the first working fluid, the second working fluid, and the third working fluid constant throughout the duration of time.

In some embodiments, step (b) comprises operating the bioreactor system in a hydraulically balanced manner. In some embodiments, the transferring of step (b)(i), the transferring of step (b)(ii), and the collecting of step (b)(iv) are driven by gravity. In some embodiments, the operating comprises maintaining a flow rate that results in a hydraulic retention time of at least 5 days. In some embodiments, the operating comprises maintaining the product outflow stream at a flow rate of at least 100 gallons per day. In some embodiments, the volume of working fluid in each of the two or more containers is at least 100 gallons.

In some embodiments, at least one of the two or more containers is a fluidized bed reactor. In some embodiments, at least one of the two or more containers is a packed bed reactor.

In some embodiments, the method further comprises maintaining at least one of the two or more containers under aerobic conditions. In some embodiments, the method further comprises maintaining at least one of the two or more containers under microaerobic conditions. In some embodiments, the bioreactor system is operated continuously for at least 90 days.

In some embodiments, one or more species of one or more of the following genera are among five most abundant species in the microbial consortium: *Haliscomenobacter, Lewinella, Caldilinea, Terrimonas*, and *Acidobacterium*. In some embodiments, one or more of the following species are among five most abundant species in the microbial consortium: *Lewinella cohaerens, Thauera phenylacetica, Thauera mechernichensis, Solitalea canadensis*, and *Nitrospira moscoviensis*.

In some embodiments, the microbial consortium comprises microbes endogenous to the organic material. In some embodiments, at least a portion of the aqueous feedstock is produced by the method described herein. In some embodiments, at least one of the first working fluid, the second working fluid, or the third working fluid comprises a pH buffering system. In some embodiments, the method further comprises maintaining the pH of at least one of the first working fluid, the second working fluid, or the third working fluid between 6 and 8 throughout the duration of time.

In some embodiments, the aqueous feedstock does not include the first nitrogen use efficiency-promoting microbial strain at a concentration higher than 10 CFU/ml. In some embodiments, the first nitrogen use efficiency-promoting microbial strain is not added to the bioreactor system during the duration of time at a concentration that is higher than 10 CFU/ml.

In some embodiments, the bioreactor system comprises at least one container placed in the series before the first container. In some embodiments, the volume of working fluid of one of the two or more containers comprises the microbial consortium, wherein each microbial consortium is distinct from all of the microbial consortia in other working fluids. In some embodiments, the method further comprises producing a population of sporulated bacteria in the product outflow stream. In some embodiments, the method further comprises producing a population of the first nitrogen use efficiency-promoting microbial strain in the product outflow stream that is sporulated. In some embodiments, the population of the first nitrogen use efficiency-promoting microbial strain that is sporulated comprises at least $1\times10^3$ CFU/ml. In some embodiments, the method further comprises adding an additional population of the first nitrogen use efficiency-promoting microbial strain, the second nitrogen use efficiency-promoting microbial strain, or the third nitrogen use efficiency-promoting microbial strain to the biostimulant product.

A bioreactor system comprising: (a) a stream of an aqueous feedstock in fluid communication with a first container comprising a volume of a first working fluid, wherein the aqueous feedstock comprises a microbial consortium, wherein the first working fluid comprises a population of a first nitrogen use efficiency-promoting strain, wherein a concentration of the first nitrogen use efficiency-promoting microbial strain in the first working fluid is at least 100 times higher than a concentration of the first nitrogen use efficiency-promoting microbial strain in the aqueous feedstock stream or in any other input into the bioreactor system; (b) one or more additional containers arranged in a series that includes the first container, wherein each of the one or more additional containers comprises a volume of a working fluid and is in fluid communication with at least one other container in the series, and wherein at least one of the one or more additional containers comprises a product outflow stream port; and (c) a product outflow stream in fluid communication with the product outflow stream port.

In some embodiments, the first nitrogen use efficiency-promoting microbial strain is one that performs nitrogen fixation, promotes nitrogen fixation in the tissues of plants, recruits nitrogen fixers to the root zones or other tissues of plants, or increases organic nitrogen content and/or mineralization of organic nitrogen in soil. In some embodiments, the first nitrogen use efficiency-promoting microbial strain is positive for a nifH gene. In some embodiments, the first nitrogen use efficiency-promoting microbial strain is one that promotes plant growth in a nitrogen-poor growth medium. In some embodiments, the nitrogen-poor growth medium comprises nitrate at less than 10 ppm.

In some embodiments, the first nitrogen use efficiency-promoting microbial strain is of the genus *Kosakonia, Klebsiella, Rahnella, Kluyvera, Enterobacter, Achromobacter, Microbacterium, Gluconobacter, Methylobacterium, Pseudomonas, Pantoea, Azospirillum, Azocarus, Herbaspirillum, Burkholderia, Cyanobacteria, Bacillus*, or *Paenibacillus*. In some embodiments, the first nitrogen use efficiency-promoting microbial strain is of the species *Kosakonia sacchari, Klebsiella variicola, Rahnella aquatilis, Kluyvera intermedia, Kosakonia pseusosacchari, Enterobacter* spp., *Achromobacter marplatensis, Azopirillum lipoferum, Microbacterium murale, Gluconobacter diazotrophicus, Methylobacterium symbioticum, Paenibacillus borealis, Bacillus megaterium (Priestia megaterium)*, or *Paenibacillus sonchi*.

In some embodiments, the first nitrogen use efficiency-promoting microbial strain is the strain deposited under ATCC Accession No. PTA-127654 (MS3907), the strain deposited under ATCC Accession No. PTA-127653 (MS3900), the strain deposited under ATCC Accession No. PTA-127655 (MS4921), or the strain deposited under ATCC Accession No. PTA-127652 (MS2748).

In some embodiments, the bioreactor system is a continuous flow bioreactor system and the stream of the aqueous feedstock is a continuous stream. In some embodiments, each of the volume of the working fluid is constant. In some embodiments, each of the first container and the one or more additional containers comprises a concentration of the first nitrogen use efficiency-promoting microbial strain that remains at least $1 \times 10^6$ CFU/ml during operation of the bioreactor system. In some embodiments, the aqueous feedstock and any other input into the bioreactor system does not comprise the population of the first nitrogen use efficiency-promoting microbial strain or does not comprise a concentration of the first nitrogen use efficiency-promoting microbial strain at level higher than 100 CFU/ml. In some embodiments, the microbial consortium comprises at least $1 \times 10^5$ CFU/ml of microbes.

In some embodiments, the aqueous feedstock further comprises an organic material digestible by microbes present in the containers. In some embodiments, the organic material comprises manure or material derived from manure. In some embodiments, the aqueous feedstock further comprises rock phosphate particles. In some embodiments, the microbial consortium comprises microbes derived from manure and rock phosphate particles.

In some embodiments, the container comprising the product outflow stream port is a clarifier container configured to separate a portion of a working fluid in the clarifier container into a supernatant portion and a floc portion. In some embodiments, the clarifier container comprises one or more floc folding flights configured to agitate settled floc in the clarifier container without resuspending solids in the floc portion into the supernatant portion. In some embodiments, the system further comprises a floc return stream that flows from the clarifier to an earlier container in the series. In some embodiments, the product outflow stream comprises the supernatant portion. In some embodiments, the product outflow stream comprises at least $1 \times 10^4$ CFU/ml of the first nitrogen use efficiency-promoting microbial strain. In some embodiments, the product outflow stream comprises at least $1 \times 10^2$ CFU/ml of a sporulated form of the first nitrogen use efficiency-promoting microbial strain. In some embodiments, the product outflow stream comprises a total dry weight of 0.2 to 2.5 mg/ml. In some embodiments, the product outflow stream has a chemical oxygen demand between 80 to 500 mg/L. In some embodiments, the product outflow stream has an electrical conductivity between 1.3 and 3.0 mS/cm.

A method comprising: (a) transferring water and rock phosphate into a first container comprising a volume of a first working fluid, wherein products of digestion of manure by microbes derived from the manure are not transferred into the first container; (b) transferring a portion of the first working fluid into a second container comprising a second working fluid; (c) transferring into the second container: (i) a liquid comprising (A) a first microbial consortium comprising microbes derived from a first organic material, and (B) digestion products produced by anaerobic digestion of the first organic material by the microbes; (ii) a second organic material; and (iii) yeast.

In some embodiments, the method further comprises transferring a portion of the second working fluid into a third container comprising a third working fluid, and transferring a portion of the third working fluid into a fourth container comprising a fourth working fluid. In some embodiments, the method further comprises separating a portion of the fourth working fluid into a floc portion and a supernatant portion. In some embodiments, the method further comprises transferring the floc portion to the first container. In some embodiments, the method further comprises maintaining the first container, the second container, the third container, and/or the fourth container under aerobic conditions. In some embodiments, the first container, the second container, the third container, and/or the fourth container are fluidized bed reactors, wherein the rock phosphate is continuously circulated within the first container, the second container, the third container, and/or the fourth container. In some embodiments, a total volume of material added to the first container over a given time period is equal to a total volume of the first working fluid transferred to the second container over a same time period. In some embodiments, a total volume of material transferred into the second container, the third container, and the fourth container over a given time period is equal to a total volume transferred out of the second container, the third container, and the fourth container over a same time period. In some embodiments, the method further comprises maintaining a volume of the first working fluid, a volume of the second working fluid, and a volume of the third working fluid constant.

In some embodiments, the first organic material is manure. In some embodiments, the second organic material is manure. In some embodiments, the yeast is *Saccharomyces cerevisiae*. In some embodiments, the method further comprises producing a product stream from a second microbial consortium, a third microbial consortium, or a fourth microbial consortium, wherein the product stream comprises bacteria from one or more of the following species: *Lewinella cohaerens, Thauera phenylacetica, Thauera mechernichensis, Solitalea canadensis*. In some embodiments, bacteria from one or more of the following species are among the five most abundant microbes in the second microbial consortium: *Lewinella cohaerens, Thauera phenylacetica, Thauera mechernichensis, Solitalea canadensis*, and *Nitrospira moscoviensis*. In some embodiments, the five most abundant microbes in the second microbial consortium do not include bacteria from any of the following genera: *Haliscomenobacter, Caldilinea, Terrimonas*, and *Acidobacterium*. In some embodiments, the second microbial consortium is comprised in a fifth working fluid. In some embodiments, low-rank coal is not transferred into the first container.

A biostimulant composition made by the method described herein or the system described herein.

A method of promoting plant growth comprising contacting a plant, seed, or plant growth medium with the biostimulant composition described herein.

A method of increasing nitrogen use efficiency of a plant, the method comprising contacting a plant, seed, or plant growth medium with the biostimulant composition described herein.

A method of increasing phosphate solubilization in a plant growth medium, the method comprising contacting a plant, seed, or the plant growth medium with the biostimulant composition described herein.

A composition comprising: (a) a *Bacillus megaterium* strain having one or more of the following: (i) a 16S rRNA gene sequence at least 95% identical to SEQ ID NO: 1; (ii) a gyrB gene sequence at least 95% identical to SEQ ID NO: 4; and (iii) an rpoB gene sequence at least 95% identical to SEQ ID NO: 7; and (b) a carrier.

In some embodiments, the *Bacillus megaterium* strain is the MS3900 strain deposited under ATCC Accession No. PTA-127653, or an isolated clone thereof. In some embodiments, the composition further comprises products of digestion of an organic substrate by the *Bacillus megaterium* strain. In some embodiments, the carrier comprises a fertilizer. In some embodiments, the carrier is a solid coated by the *Bacillus megaterium* strain. In some embodiments, the carrier is a liquid. In some embodiments, the composition further comprises an adjuvant selected from a wetting agent, spreading agent, dispersing agent, sticking agent, dust control agent, and adhesive. In some embodiments, the concentration of the *Bacillus megaterium* strain in the composition ranges from $1\times10^3$ to $1\times10^{11}$ CFU/ml.

A composition comprising: (a) a *Paenibacillus borealis* strain having one or more of the following: (i) a 16S rRNA gene sequence at least 95% identical to SEQ ID NO: 2; (ii) a gyrB gene sequence at least 95% identical to SEQ ID NO: 5; (iii) an rpoB gene sequence at least 95% identical to SEQ ID NO: 8; and (iv) a nifH gene sequence at least 95% identical to SEQ ID NO: 13; and (b) a carrier.

In some embodiments, the *Paenibacillus borealis* strain is the MS3907 strain deposited under ATCC Accession No. PTA-127654, or an isolated clone thereof. In some embodiments, the composition further comprises products of digestion of an organic substrate by the *Paenibacillus borealis* strain. In some embodiments, the carrier comprises a fertilizer. In some embodiments, the carrier is a solid coated by the *Paenibacillus borealis* strain. In some embodiments, the carrier is a liquid. In some embodiments, the composition further comprises an adjuvant selected from a wetting agent, spreading agent, dispersing agent, sticking agent, dust control agent, and adhesive. In some embodiments, the concentration of the *Paenibacillus borealis* strain in the composition ranges from $1\times10^3$ to $1\times10^{11}$ CFU/ml.

A composition comprising: (a) a *Paenibacillus sonchi* strain having one or more of the following: (i) a 16S rRNA gene sequence at least 95% identical to SEQ ID NO: 3; (ii) a gyrB gene sequence at least 95% identical to SEQ ID NO: 6; (iii) an rpoB gene sequence at least 95% identical to SEQ ID NO: 9; and (iv) a nifH gene sequence at least 95% identical to SEQ ID NO: 14; and (b) a carrier.

In some embodiments, the *Paenibacillus sonchi* strain is the MS4921 strain deposited under ATCC Accession No. PTA-127655, or an isolated clone thereof. In some embodiments, the composition further comprises products of digestion of an organic substrate by the *Paenibacillus sonchi* strain. In some embodiments, the carrier comprises a fertilizer. In some embodiments, the carrier is a solid coated by the *Paenibacillus sonchi* strain. In some embodiments, the carrier is a liquid. In some embodiments, the composition further comprises an adjuvant selected from a wetting agent, spreading agent, dispersing agent, sticking agent, dust control agent, and adhesive. In some embodiments, the concentration of the *Paenibacillus sonchi* strain in the composition ranges from $1\times10^3$ to $1\times10^{11}$ CFU/ml.

A composition comprising: (a) a *Bacillus megaterium* strain having one or more of the following: (i) a 16S rRNA gene sequence at least 95% identical to SEQ ID NO: 10; (ii) a gyrB gene sequence at least 95% identical to SEQ ID NO: 11; and (iii) an rpoB gene sequence at least 95% identical to SEQ ID NO: 12; and (b) a carrier.

In some embodiments, the *Bacillus megaterium* strain is the MS2748 strain deposited under ATCC Accession No. PTA-127652, or an isolated clone thereof. In some embodiments, the composition further comprises products of digestion of an organic substrate by the *Bacillus megaterium* strain. In some embodiments, the carrier comprises a fertilizer. In some embodiments, the carrier is a solid coated by the *Bacillus megaterium* strain. In some embodiments, the carrier is a liquid. In some embodiments, the composition further comprises an adjuvant selected from a wetting agent, spreading agent, dispersing agent, sticking agent, dust control agent, and adhesive. In some embodiments, the concentration of the *Bacillus megaterium* strain in the composition ranges from $1\times10^3$ to $1\times10^{11}$ CFU/ml. In some embodiments, the composition further comprises at least one or more of the following: (c) a *Bacillus megaterium* strain having one or more of the following: (i) a 16S rRNA gene sequence at least 95% identical to SEQ ID NO: 1; (ii) a gyrB gene sequence at least 95% identical to SEQ ID NO: 4; and (iii) an rpoB gene sequence at least 95% identical to SEQ ID NO: 7; (d) a *Paenibacillus borealis* strain having one or more of the following: (i) a 16S rRNA gene sequence at least 95% identical to SEQ ID NO: 2; (ii) a gyrB gene sequence at least 95% identical to SEQ ID NO: 5; (iii) an rpoB gene sequence at least 95% identical to SEQ ID NO: 8; and (iv) a nifH gene sequence at least 95% identical to SEQ ID NO: 13; and (d) a *Paenibacillus sonchi* strain having one or more of the following: (i) a 16S rRNA gene sequence at least 95% identical to SEQ ID NO: 3; (ii) a gyrB gene sequence at least 95% identical to SEQ ID NO: 6; (iii) an rpoB gene sequence at least 95% identical to SEQ ID NO: 9; and (iv) a nifH gene sequence at least 95% identical to SEQ ID NO: 14.

An isolated strain of the species *Bacillus megaterium* having one or more of the following: (a) a 16S rRNA gene sequence at least 95% identical to SEQ ID NO: 1; (b) a gyrB gene sequence at least 95% identical to SEQ ID NO: 4; and (c) an rpoB gene sequence at least 95% identical to SEQ ID NO: 7.

In some embodiments, the *Bacillus megaterium* strain is the MS3900 strain deposited under ATCC Accession No. PTA-127653, or an isolated clone thereof.

An isolated strain of the species *Paenibacillus borealis* having one or more of the following: (a) a 16S rRNA gene sequence at least 95% identical to SEQ ID NO: 2; (b) a gyrB gene sequence at least 95% identical to SEQ ID NO: 5; (c) an rpoB gene sequence at least 95% identical to SEQ ID NO: 8; and (d) a nifH gene sequence at least 95% identical to SEQ ID NO: 13.

In some embodiments, the *Paenibacillus borealis* strain is the MS3907 strain deposited under ATCC Accession No. PTA-127654, or an isolated clone thereof.

An isolated strain of the species *Paenibacillus sonchi* having one or more of the following: (a) a 16S rRNA gene sequence at least 95% identical to SEQ ID NO: 3; (b) a gyrB gene sequence at least 95% identical to SEQ ID NO: 6; (c) an rpoB gene sequence at least 95% identical to SEQ ID NO: 9; and (d) a nifH gene sequence at least 95% identical to SEQ ID NO: 14.

In some embodiments, the *Paenibacillus sonchi* strain is the MS4921 strain deposited under ATCC Accession No. PTA-127655, or an isolated clone thereof.

An isolated strain of the species *Bacillus megaterium* having one or more of the following: (a) a 16S rRNA gene sequence at least 95% identical to SEQ ID NO: 10; (b) a gyrB gene sequence at least 95% identical to SEQ ID NO: 11; and (c) an rpoB gene sequence at least 95% identical to SEQ ID NO: 12.

In some embodiments, the *Bacillus megaterium* strain is the MS2748 strain deposited under ATCC Accession No. PTA-127652, or an isolated clone thereof.

A method for promoting growth of a plant growing in a medium, the method comprising contacting the plant or the medium with the composition described herein or the isolated strain described herein.

In some embodiments, the contacting increases a plant nitrogen content by at least 5%. In some embodiments, the contacting increases a nitrogen fixation activity in plant tissues by at least 5%. In some embodiments, the contacting increases a population of nitrogen fixing bacteria in the root and root rhizospheres of the plant by at least 5%. In some embodiments, the contacting causes recruitment of nitrogen fixing bacteria present in the medium to the root zone of the plant. In some embodiments, the contacting causes an increase plant growth by at least 10 percent as compared to a control. In some embodiments, the medium comprises soil, a hydroponic medium, turface, or isolite.

A method of enhancing nitrogen fixing activity or plant tissue colonization capability of a bacterium, the method comprising incubating the bacterium in the presence of strain MS3900.

In some embodiments, the bacterium is strain MS3907.

A composition comprising: (a) a microbial consortium comprising one or more bacterial strains selected from MS3900 (ATCC Accession No. PTA-127653), MS3907 (ATCC Accession No. PTA-127654), MS4921 (ATCC Accession No. PTA-127655), and MS2748 (ATCC Accession No. PTA-127652); and (b) metabolites produced by digestion of an organic substrate by microbes within the microbial consortium.

In some embodiments, the microbial consortium further comprises an enriched nitrogen-fixing microbial community. In some embodiments, the organic substrate is derived from cow manure, rock phosphate, or ground plant matter, or any combination thereof. In some embodiments, the microbial consortium comprises microbes derived from cow manure, rock phosphate, or ground plant matter. In some embodiments, the ground plant matter is soy flour, lentil flour, chickpea flour, green pea flour, yellow pea flour, white bean flour, corn flour, cereal flour, corn gluten, soy flour protein, soy protein hydrolysate, or any combination thereof. In some embodiments, the microbial consortium comprises from $5\times10^7$ to $1.5\times10^8$ CFU/ml of bacteria. In some embodiments, the microbial consortium comprises from $5\times10^6$ to $1.5\times10^7$ CFU/ml of nitrogen fixing bacteria. In some embodiments, the microbial consortium comprises from $5\times10^4$ to $5\times10^5$ CFU/ml of spore forming bacteria. In some embodiments, the microbial consortium comprises from $1\times10^3$ to $1\times10^4$ CFU/ml of MS3900 spores. In some embodiments, the microbial consortium comprises from $1\times10^3$ to $1\times10^4$ CFU/ml of MS3907 spores. In some embodiments, the pH of the composition is from 7 to 9. In some embodiments, the COD of the composition is from 120 to 500 mg/L. In some embodiments, the conductivity of the composition is from 0.5 to 2.0 mS/cm. In some embodiments, the composition has a total dry weight of 0.2 to 2.5 mg/ml.

A method of making a biostimulant composition, the method comprising: (a) providing a bioreactor system comprising two or more containers arranged in a series, each of the two or more containers comprising a volume of a working fluid, wherein at least one of the containers comprises a population of a microbial strain derived from an inoculum of the microbial strain that has been added to the bioreactor system and a population of other microbes; (b) operating the bioreactor system for a duration of time by: (i) transferring into a first container an aqueous feedstock comprising a microbial consortium; (ii) transferring a portion of the working fluid out of each of the two or more containers into either a subsequent container of the bioreactor system or a product outflow stream; (iii) collecting at least a portion of the product outflow stream as the biostimulant composition; and (iv) maintaining the population of the microbial strain throughout the duration of time in at least the first container at a level that is at least 80% of the population of the microbial strain at the beginning of the duration of time; wherein the duration of time is at least 5 days; and wherein the microbial strain is not present in the aqueous feedstock or any other input into the bioreactor system during the duration of time at a concentration that is higher than 1% of the concentration of the population of the microbial strain in the first container.

In some embodiments, the microbial strain has a plant growth promoting property. In some embodiments, the method further comprises providing conditions in the bioreactor system that promote establishment of an enriched population of the microbial strain relative to a population of the microbial strain in the aqueous feedstock or any other input into the bioreactor system. In some embodiments, the method further comprises applying a selective pressure in the bioreactor system that favors growth of the microbial strain relative to the other microbes. In some embodiments, the aqueous feedstock further comprises an organic material digestible by the microbial strain and by at least some of the other microbes. In some embodiments, the method further comprises producing metabolites that have the plant growth promoting property by digestion of the organic material.

A method comprising: (a) transferring an aqueous feedstock and an inoculum of an isolated microbe that is capable of promoting nitrogen use efficiency in plants into a first container comprising a volume of a first working fluid, wherein the aqueous feedstock comprises: (i) a first microbial consortium; and (ii) digestion products produced by digestion of an organic substrate by microbes in the first microbial consortium; and (b) incubating the inoculum under conditions that promote growth of the microbe.

In some embodiments, promoting nitrogen use efficiency comprises performing nitrogen fixation, promoting nitrogen fixation in the tissues of plants, recruiting nitrogen fixers to the root zones and other tissues of plants, or increasing organic nitrogen content and/or mineralization of organic nitrogen in soils to enable uptake. In some embodiments, the conditions promote growth of one or more microbes in the first microbial consortium that are capable of promoting nitrogen fixation, nitrogen use efficiency, or recruitment of nitrogen fixing microbes to the roots of plants, or of generating metabolites capable of promoting plant growth, nitrogen fixation, nitrogen use efficiency, or recruitment of nitrogen fixing microbes to the roots of plants. In some embodiments, during the incubating the microbe or one or more microbes in the first microbial consortium generate metabolites capable of promoting nitrogen use efficiency. In some embodiments, the incubating sustains or increases a population of one or more microbes in the microbial consortium capable of promoting plant growth. In some embodiments, the incubating causes the population of the microbe to be at least sustained. In some embodiments, the incubating causes the population of the microbe to increase.

In some embodiments, the incubating causes an enrichment of the population of microbes capable of promoting nitrogen use efficiency. In some embodiments, the conditions sustain the growth of one or more microbes that are capable of promoting nitrogen fixation, nitrogen use efficiency, or recruitment of nitrogen fixing microbes to the roots of plants, or of generating metabolites capable of promoting nitrogen fixation, nitrogen use efficiency, or recruitment of nitrogen fixing microbes to the roots of plants.

In some embodiments, the organic substrate comprises a manure or a lignocellulosic material. In some embodiments, the aqueous feedstock further comprises an inorganic substrate. In some embodiments, the first microbial consortium further comprises microbes derived from the inorganic substrate. In some embodiments, the inorganic substrate comprises rock phosphate.

In some embodiments, the microbe is a bacterium selected from the following: *Kosakonia, Klebsiella, Rahnella, Kluyvera, Enterobacter, Achromobacter, Microbacterium, Gluconobacter, Methylobacterium, Pseudomonas, Pantoea, Azospirillum, Azocarus, Herbaspirillum, Burkholderia, Cyanobacteria, Bacillus,* and *Paenibacillus.* In some embodiments, the microbe is of the species *Kosakonia sacchari, Klebsiella variicola, Rahnella aquatilis, Kluyvera intermedia, Kosakonia pseusosacchari, Enterobacter* spp., *Achromobacter marplatensis, Azopirillum lipoferum, Microbacterium murale, Gluconobacter diazotrophicus, Methylobacterium symbioticum, Paenibacillus borealis, Bacillus megaterium (Priestia megaterium),* and *Paenibacillus sonchi.* In some embodiments, the microbe is the strain deposited under ATCC Accession No. PTA-127654 (MS3907), the strain deposited under ATCC Accession No. PTA-127653 (MS3900), the strain deposited under ATCC Accession No. PTA-127655 (MS4921), or the strain deposited under ATCC Accession No. PTA-127652 (MS2748).

In some embodiments, the aqueous feedstock further comprises one or more carbon sources capable of being metabolized by the microbe or by microbes in the first microbial consortium. In some embodiments, the one or more carbon sources comprise one or more simple sugars. In some embodiments, the one or more simple sugars comprise glucose, malate, lactose, sucrose, or pyruvate, or any combination thereof. In some embodiments, the aqueous feedstock further comprises a nitrogen source. In some embodiments, the nitrogen source comprises one or more of ammonium sulfate, ammonium chloride, ammonium nitrate, sodium nitrate, yeast extract, or yeast, or any combination thereof. In some embodiments, the aqueous feedstock further comprises soy flour, corn flour, cereal flour, corn gluten, soy flour protein, or soy protein hydrolysate, or any combination thereof.

In some embodiments, the aqueous feedstock and the inoculum are transferred separately. In some embodiments, the aqueous feedstock and the inoculum of the isolated microbe are combined together before being transferred into the first container. In some embodiments, the first working fluid comprises (a) a second microbial consortium derived from the aqueous feedstock, and/or (b) digestion products produced by digestion of substances present in the aqueous feedstock by the first microbial consortium and/or the microbe. In some embodiments, the method further comprises transferring a portion of the first working fluid into a second container comprising a second working fluid and incubating the second working fluid in the second container. In some embodiments, the second working fluid comprises (a) a third microbial consortium derived from the first working fluid, and (b) digestion products produced by digestion of substances present in the first working fluid by the third microbial consortium and the microbe.

In some embodiments, the total amount of fluid transferred into the first container over a time period is equal to the amount of the first working fluid transferred into the second container over the same time period. In some embodiments, the volume of the first working fluid in the first container is maintained constant. In some embodiments, transferring the aqueous feedstock into the first container comprises continuously flowing the aqueous feedstock into the first container at a first flow rate, transferring the portion of the first working fluid into the second container comprises continuously flowing the portion of the first working fluid into the second container at a second flow rate. In some embodiments, the first flow rate and the second flow rate are equal.

In some embodiments, the method further comprises transferring a portion of the second working fluid to a third container comprising a third working fluid and incubating the third working fluid in the third container. In some embodiments, the method further comprises transferring a portion of the third working fluid into a fourth container comprising a fourth working fluid and incubating the fourth working fluid in the fourth container. In some embodiments, the first working fluid, the second working fluid, the third working fluid, and the fourth working fluid are maintained at constant volumes. In some embodiments, the microbe is present in the second working fluid, the third working fluid, and/or the fourth working fluid. In some embodiments, the first working fluid and any subsequent working fluids are maintained under microaerobic conditions.

In some embodiments, one or more of the five most abundant microbial species in the first microbial consortium are from the following genera: *Haliscomenobacter, Lewinella, Caldilinea, Terrimonas,* and *Acidobacterium.* In some embodiments, one or more of five most abundant microbial species in the first microbial consortium comprise *Lewinella cohaerens, Thauera phenylacetica, Thauera mechernichensis, Solitalea canadensis,* or *Nitrospira moscoviensis.*

In some embodiments, the method further comprises transferring into the first container one or more additional isolated microbes that are capable of promoting nitrogen use efficiency in plants. In some embodiments, the one or more additional isolated microbes comprise one or more of MS3900, MS3907, MS4921, and MS2748, or any combination thereof. In some embodiments, two or more of MS3900, MS3907, MS4921, and MS2748 are transferred into the first container. In some embodiments, the method further comprises transferring the microbe and/or one or more additional isolated microbes capable of promoting nitrogen use efficiency in plants to the second working fluid, the third working fluid, or the fourth working fluid, or any subsequent working fluid if more than four containers are fluidly connected in the method. In some embodiments, the one or more additional isolated microbes comprise one or more of MS3900, MS3907, MS4921, and MS2748, or any combination thereof.

In some embodiments, the method further comprises filtering the first working fluid, the second working fluid, the third working fluid, the fourth working fluid, or any subsequent working fluid if more than four containers are fluidly connected in the method. In some embodiments, the filtering removes bacteria from the respective working fluid. In some embodiments, the filtering removes at least 99% or at least 99.9% of all bacteria from the respective working fluid. In some embodiments, the filtering produces a sterile fluid. In some embodiments, the pH is monitored and adjusted during the incubation. In some embodiments, the first working fluid is transferred directly to a clarifier in which floc from the first working fluid is separated from the first working fluid. In some embodiments, a portion of the first working fluid is not continuously transferred out of the first container. In some embodiments, the incubation in the first container is operated in a batch mode. In some embodiments, the dissolved oxygen content in the first working fluid during the incubation in the first container is maintained between 0.1 and 0.8 mg/L. In some embodiments, the pH of the first working fluid is between 3.5 and 8 during the incubation in the first container.

In some embodiments, the first working fluid comprises malate at a concentration of at least 0.2% w/v.

In some embodiments, the first working fluid comprises soy flour at a concentration of at least 0.2% w/v.

In some embodiments, the first working fluid comprises aerobic conditions.

In some embodiments, the working fluid in at least one of the one or more additional containers comprises microaerobic conditions.

In some embodiments, the system has a hydraulic retention time of at least 5 days.

In some embodiments, the first working fluid further comprises an established population of a second nitrogen use efficiency-promoting microbial strain, wherein a concentration of the second nitrogen use efficiency-promoting microbial strain in the first working fluid is at least 100 times higher than a concentration of the second nitrogen use efficiency-promoting microbial strain in the aqueous feedstock stream and in any other input into the bioreactor system.

In some embodiments, the first working fluid comprises a total population of microbes positive for a nifH gene of at least $1 \times 10^5$.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings (also "figure" and "FIG." herein), of which:

FIG. 1A depicts the percentage of nitrogen content in V9 growth stage corn plants. FIG. 1B depicts corn yield (in bushels/A).

FIG. 2A depicts results of nitrogen content in V9 growth stage corn plants. FIG. 2B depicts results from corn yield.

FIGS. 3A-3B are a series of graphs showing the recruitment of beneficial nitrogen-fixing microbes in corn plants between control, a first prototype consortia with isolates (MS3900 and MS3907), a second prototype consortia with isolates (MS3900 and MS3907), and isolates only (MS3900 and MS3907). All conditions were tested in 80% GSP and 100% GSP. FIG. 3A depicts the copy number of rhizosphere nifH gene across conditions. FIG. 3B depicts the acetylene reduction activity across conditions.

FIG. 4A shows the base product from NTS-4 (NTS 1.4) had greater nifH enrichment compared to that from the base inoculum. FIG. 4B shows that the base product of NTS-4 (NTS 1.4) had higher nifH content compared to that from the base product of other NTS systems.

FIGS. 5A-5C are a series of graphs showing plant growth promotion (PGP) qualities of the NTS-4 (NTS 1.4) system and controls. FIG. 5A shows NTS-4 (NTS 1.4) has improved corn biomass compared to that from the untreated control condition (UTC). FIG. 5B shows NTS-4 (NTS 1.4) has improved nitrogen content compared to that from UTC. FIG. 5C shows NTS-4 (NTS 1.4) has an increased number of associated nitrogen fixers in corn roots (measured as nifH copy numbers) compared to that from UTC.

FIG. 8A shows root/basal stem nitrogen-fixing capacity. FIG. 8B shows dry shoot weight. FIG. 8C shows shoot nitrogen content.

FIG. 9A-9C are a series of graphs showing measures of nitrogen use efficiency across control, isolates MS3900 and MS3907 applied at 1 qt./A, nitrogen-fixing isolates applied at 2 qt./A, and a High N condition with an additional 5 lbs N/A. Isolates were applied in-furrow to corn. FIG. 9A shows soil organic matter. FIG. 9B shows soil organic nitrogen. FIG. 9C shows estimated nitrogen release.

FIG. 10A shows an airtight jar with root, stem, and soil with 10% acetylene. Gas was analyzed for ethylene content. FIG. 10B shows a concept of acetylene reduction by a nitrogenase enzyme. FIG. 10C shows the result of acetylene reduction of corn roots/basal stem across UTC, NTS-4 (NTS 1.4) with MS3900 and MS4921, NTS-4 (NTS 1.4) with MS4921, and a control condition with added 10 lbs N.

FIG. 11A shows results from V5 growth stage in corn. FIG. 11B shows results from V8 growth stage in corn.

FIG. 21A shows results in corn plants. FIG. 21B shows results in sorghum plants.

FIG. 22A shows that adding MS3900 with MS3907 synergistically improves plant growth under low nitrogen (20 mg N "NC-20"). FIG. 22B shows that adding MS3900 with MS3907 led to similar green leaf area (as measured in pixels) as treatment with MS3907 alone.

FIGS. 28A-28B show the results of corn leaf area measurements between NTS treatment solutions with or without added isolate. NTS-4 systems with MS3900 or MS4921 showed increased corn leaf area compared to that from UTC.

FIG. 35A shows rates of 16 µl/plant and 32 µl/plant resulted in higher percent nitrogen compared to that of other treatments. FIG. 35B shows all rates with isolates MS3900 and MS3907 resulted in higher ppm nitrogen in bulk soil.

FIG. 36A shows that MS4921 alone resulted in highest shoot dry weight. FIG. 36B shows that MS4921 alone and a combination of all three isolates (MS4921, MS3900, and MS3907) led to highest root dry weights.

FIG. 40A shows seed drench of MS4921 at $10^7$ cfu/ml led to the greatest nitrogen fixing capacity. FIG. 40B shows corn treatment results in the greatest N-fixing capacity. Among the MS3907 treatments, seed soak with MS3907 at $10^6$ cfu/ml or MS3907 at $10^5$ cfu/ml led to the greatest N-fixing capacity. The star above a bar indicates the bar denotes the average of the 3 previous bars.

FIG. 41 is a table summarizing plant colonizing properties of MS3900 and MS3907.

FIG. 45A shows that there was evidence of nitrogen recruitment of N-fixing bacteria into the roots with NTS-1.4 base product treatment. FIG. 45B shows that NTS-1.4 treatment resulted in improved rhizosphere nifH content over that of UTC plants.

FIG. 49 shows the level of target isolate MS3907 in base products of the NTS 1.0 systems. Isolate concentration was measured after four months of inoculation in reactor 1.

FIG. 50A shows that the addition of malate had a positive impact on sporulation. FIG. 50B shows that fluidized bed reactors, in NTS-1.2 and NTS-1.4 systems, had a positive impact of MS3907 retention.

FIG. 55A shows recruitment of total bacteria into roots of plants treated with NTS-1.1 and NTS-1.4 solutions. FIG. 55B shows NTS-1.4 had the greatest total bacteria in the rhizosphere compared to that of UTC and other NTS treatments.

FIG. 56A shows that NTS-1 treated plants had the highest dry shoot weights compared to those of UTC plants and other NTS treatments. FIG. 56B shows NTS-1.1, NTS-1.3, and NTS-1.4 treated plants had significantly higher dry roots weights than those of UTC plants.

FIG. 67A shows the prototype 1 (e.g., PT1) system. FIG. 67B shows the prototype 2 (e.g., PT2) system.

FIG. 73 is a table showing the microbial characterization of water-based phosphate solubilizing technology (PwST) whole broth (WB) across four months. Zinc solubilization (Z-sol) and phosphate solubilization (P-sol) were measured in mediums containing different sources of insoluble phosphate (National Botanical Research Institute's phosphate growth medium (NBRIP), hydroxyapatite (HA) medium, and phytate medium).

FIG. 74 is a table depicting the top five bacterial species for PwST WB. WB is a blend of the supernatant and floc at a specific ratio to use for various applications.

FIG. 77 is a table depicting the characteristics of functional enzymes of interest in (PwST) WB samples.

FIG. 78 is a table depicting the average abundance of PQQ, nitrogenase, gluconate 2-dehydrogenase, cellulase, and pectin lyase from PwST WB.

FIG. 84D is a table depicting the measures of each micronutrient, as a percentage of UTC, on Day 6 post-coating.

FIG. 85A shows the average phosphate solubilization in water measured for nutrients after six days. FIG. 85B shows the phosphate solubilization in water between the two conditions for each timepoint.

FIG. 89A shows average leaf area under full N (30 mM N). FIG. 89B shows average leaf area under reduced N (1 mM N).

FIGS. 90A-90B show *Arabidopsis* plant growth using only inorganic N as the nitrogen source in NTS 2.2 and NTS 2.3 systems. FIG. 90A shows average leaf area under full N (30 mM N). FIG. 90B shows average leaf area under reduced N (1 mM N).

FIG. 91A shows shoot surface area with inorganic nitrogen under full N (30 mM N) and reduced N conditions (10 mM, 1 mM N and 0.1 mM N). FIG. 91B shows shoot surface area with inorganic nitrogen under full N (30 mM N) and reduced organic N conditions (1 mM N).

FIG. 93A shows the results from intact solution treatments. FIG. 93B shows the results from metabolite treatments. All NTS system treatments showed greater average leaf area than untreated control, with NTS 1.4 BP intact and metabolite showing the greatest plant growth promotion.

FIGS. 100A-100D show results of plant physiological trait tests following in-furrow or foliar treatment application of NTS 1.4 with MS3900 or MS3900 and MS4921 (gray bars indicate foliar treatment application). FIG. 100A shows results of stomatal conductance. FIG. 100B shows results of transpiration rate. FIG. 100C shows results of photosynthesis quantum yield. FIG. 100D shows results photosynthesis electron transport rate.

FIG. 104A shows results of transpiration rate. FIG. 104B shows results of quantum yield. FIG. 104C shows results of photosynthetic electron transport rate.

FIG. 114A shows rhizosphere soil bacterial diversity (* indicates significantly different from untreated control, $p<0.1$). FIG. 114B shows rhizosphere soil N-fixer abundance (* indicates significantly different from untreated control, $p<0.05$).

Figure 119A:
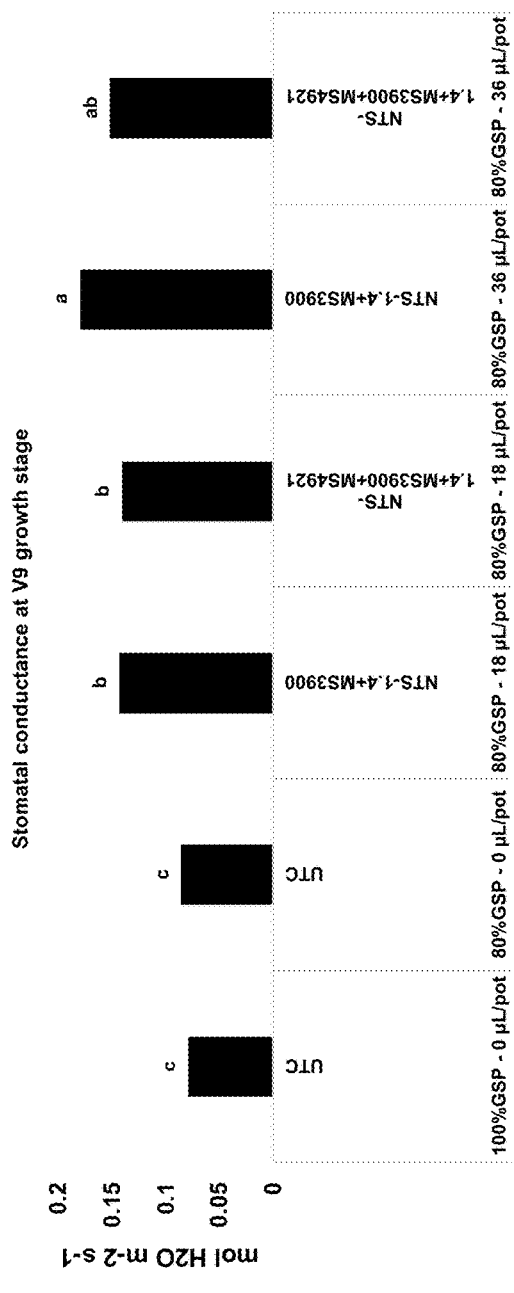
Figure 119B:
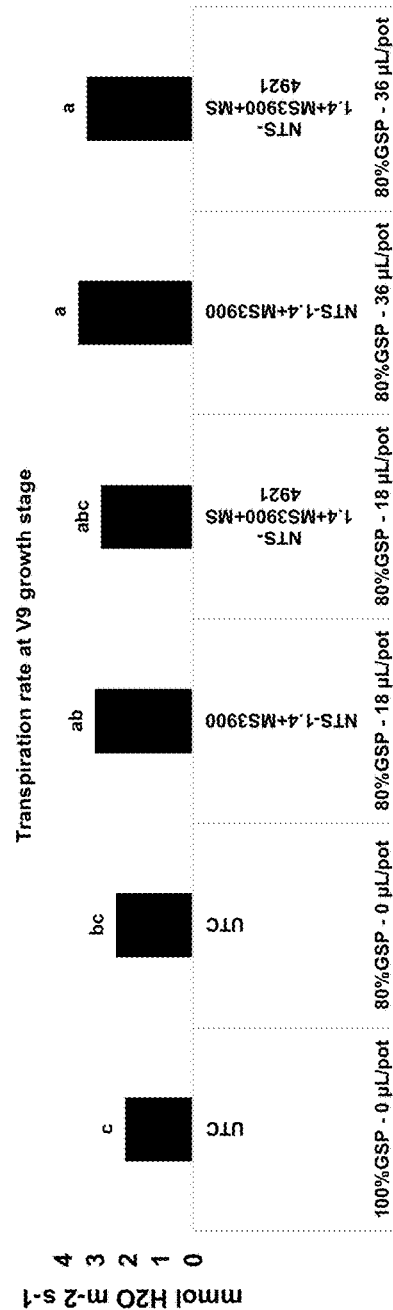

FIGS. 119A-119D show measures of plant physiological parameters in untreated control plants or plants that received in-furrow treatment application of NTS 1.4 solutions with MS3900 or MS3900 and MS4921. FIG. 119A shows results of corn stomatal conductance. FIG. 119B shows results of corn transpiration rate. FIG. 119C shows results of corn quantum yield. FIG. 119D shows results of corn photosynthetic electron transport rate.

Figure 120A:
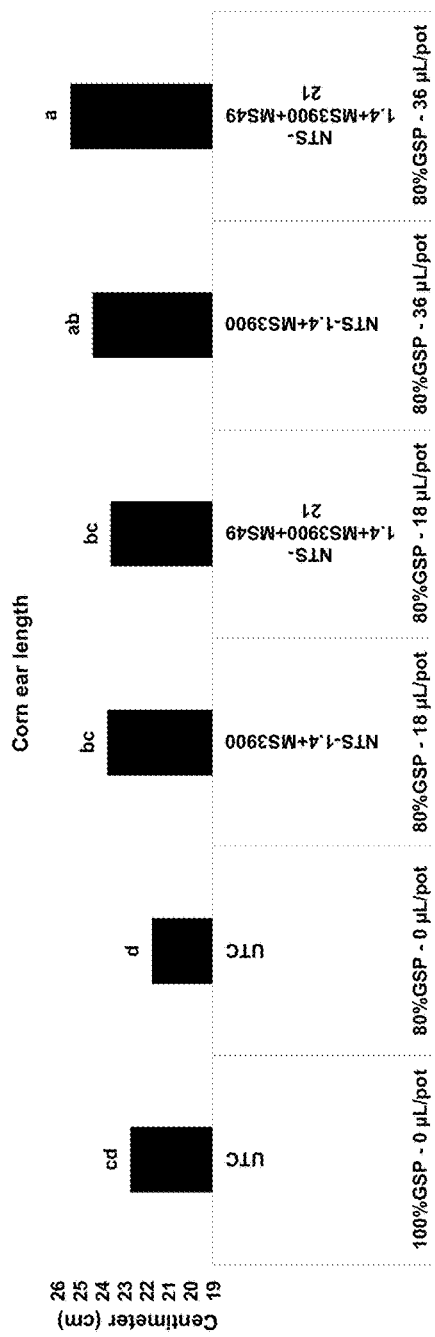
Figure 120B:
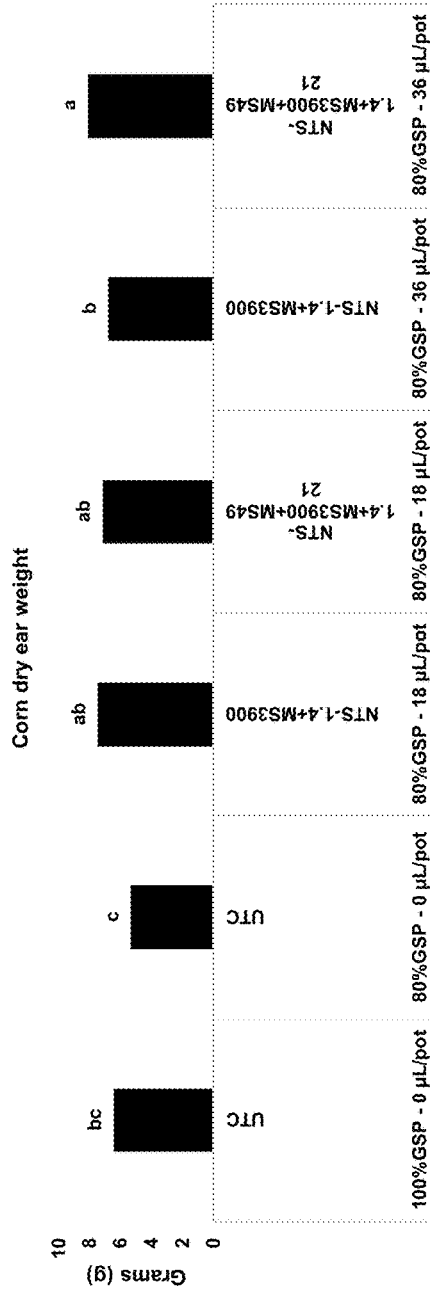

FIGS. 120A-120D show results of grain yields and physical corn ear measures. FIG. 120A shows in-furrow treatment application of NTS 1.4 solutions with MS3900 or MS3900 and MS4921 increased corn ear length. FIG. 120B shows in-furrow treatment application of NTS 1.4 solutions with MS3900 or MS3900 and MS4921. FIG. 120C shows in-furrow treatment application of NTS 1.4 solutions with MS3900 or MS3900 and MS4921. FIG. 120D shows in-furrow treatment application of NTS 1.4 solutions with MS3900 or MS3900 and MS4921.

Figure 121:
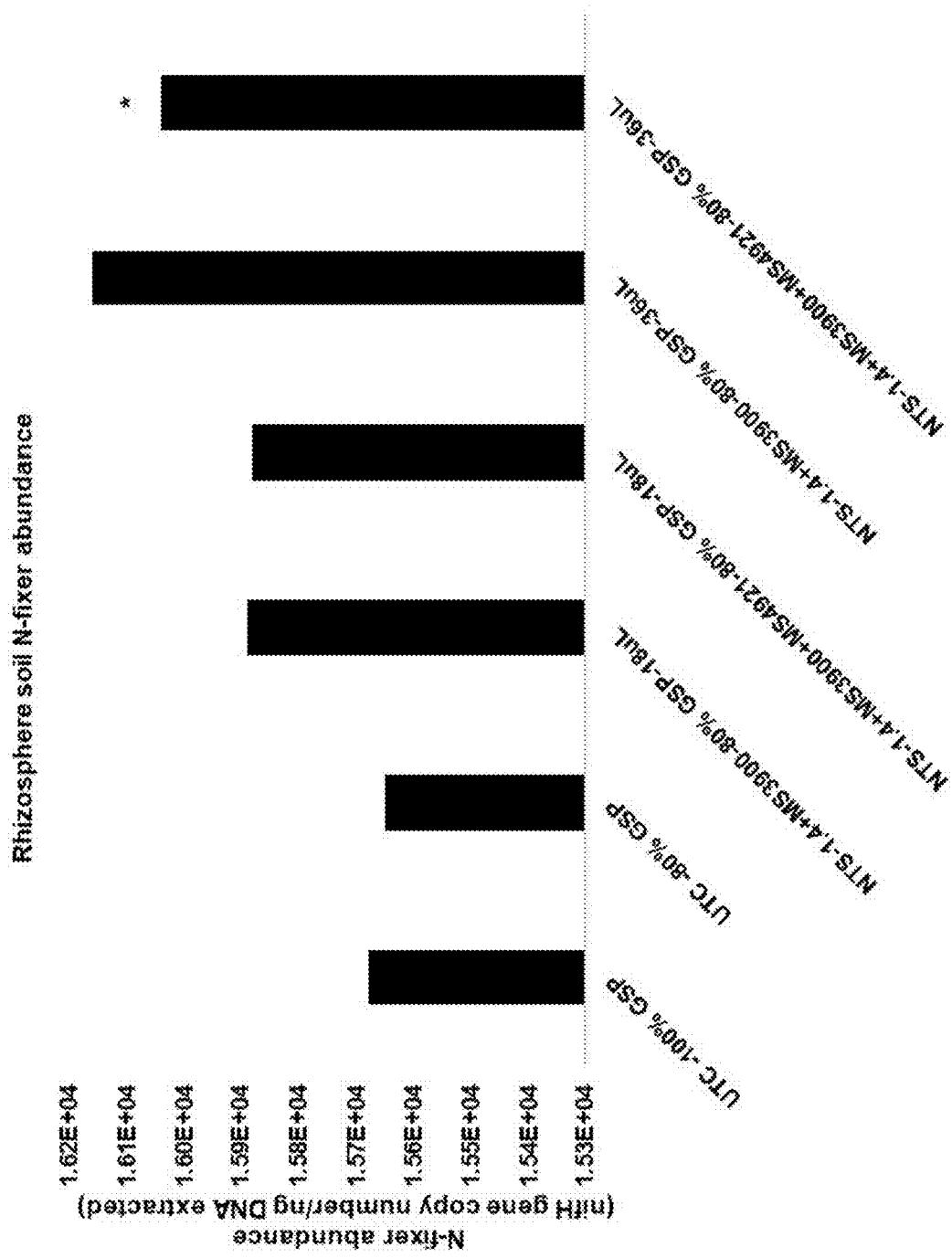

FIG. 121 shows the rhizosphere soil N-fixer abundance significantly increased by NTS1.4 spiked with MS3900 and MS4921 at application rate of 36 µL/pot (* indicates significantly different from untreated control 80% GSP, p<0.1).

Figure 122:
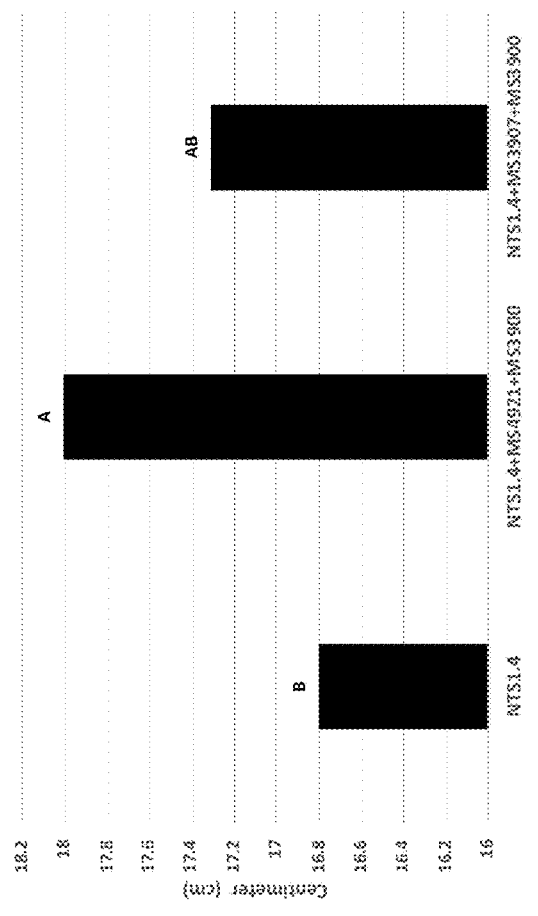

FIG. 122 shows treatment of NTS 1.4 spiked with MS4921 and MS3900.

Figure 123:
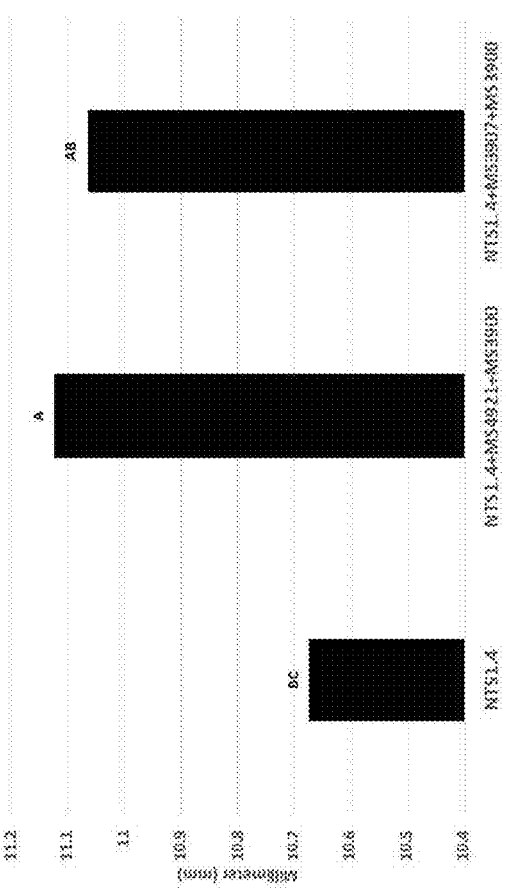

FIG. 123 shows treatment of NTS 1.4 spiked with MS4921 and MS3900 or treatment with NTS 1.4 spiked with MS3907 and MS3900.

Figure 124:
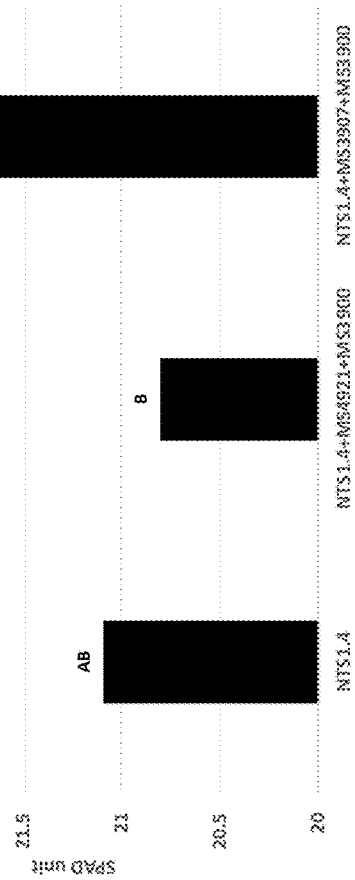

FIG. 124 shows corn leaf chlorophyll levels after treatment with NTS 1.4 spiked with MS3907 and MS3900.

Figure 125:
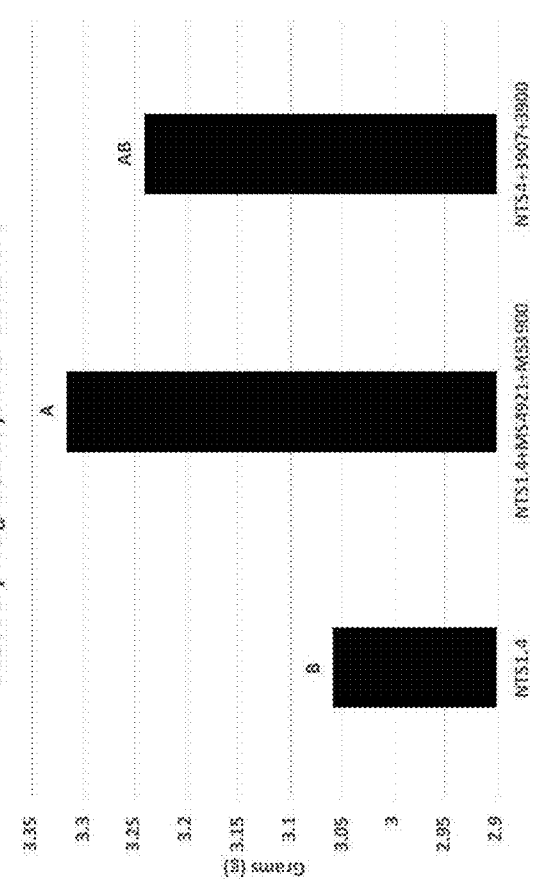

FIG. 125 shows corn shoot dry weight (e.g., shoot biomass) following treatment with NTS-1.4 spiked with MS4921+MS3900.

Figure 126:
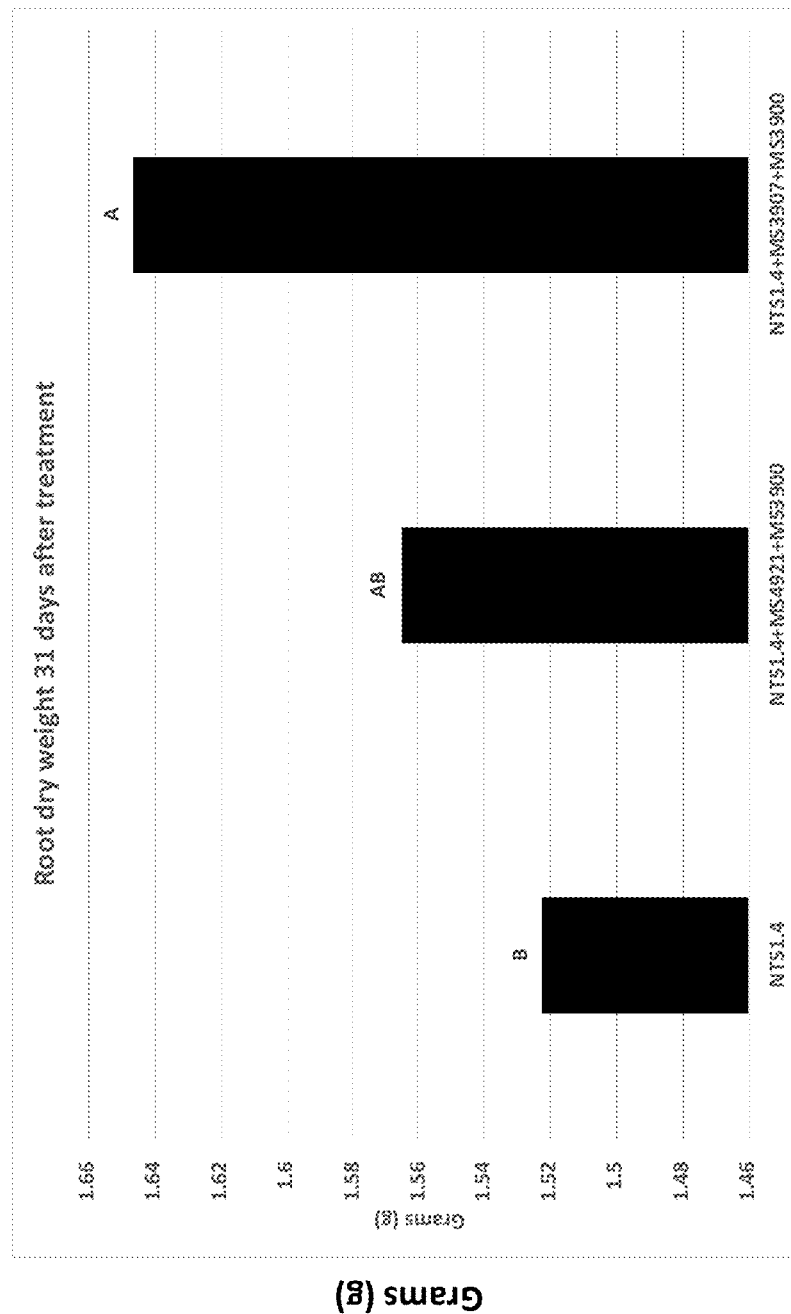

FIG. 126 shows corn root dry weight (e.g., root biomass) following treatment with NTS-1.4 spiked with MS4921+MS3900 or NTS-1.4 spiked with MS3907+MS3900.

Figure 127:
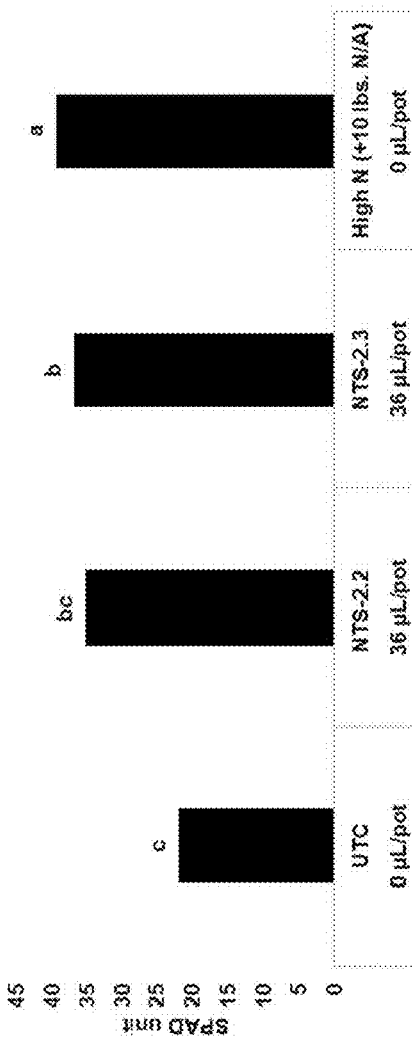

FIG. 127 shows corn leaf chlorophyll contents 17 days after in-furrow treatment application in corn plants receiving NTS-2.2 or NTS-2.3.

Figure 128A:
Figure 128B:
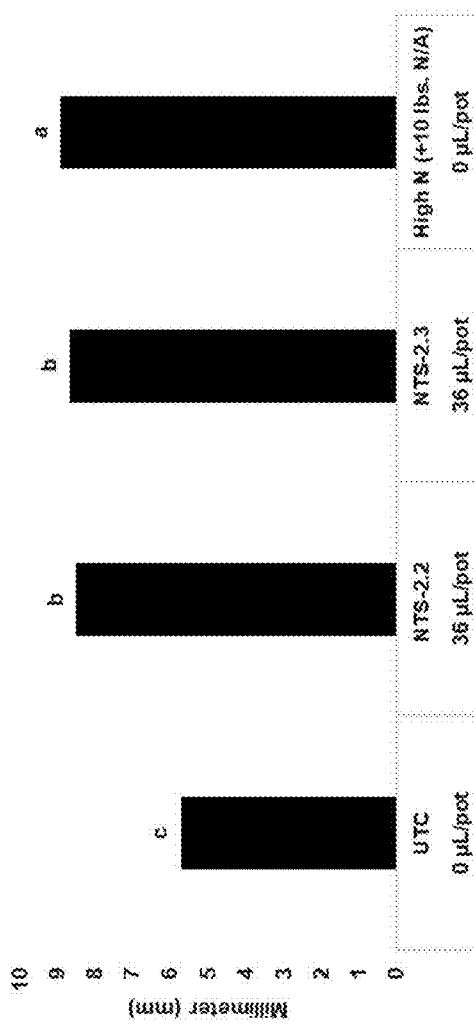

FIGS. 128A-128B show corn plant height and stem diameter measured 17 days after in-furrow treatment application. Both treatment groups receiving products from NTS 2.0 systems showed increased plant height (FIG. 128A) and stem diameter (FIG. 128B) compared to that measured in untreated control plants.

Figure 129:

FIG. 129 shows corn leaf area 18 days after planting and in-furrow treatment application with NTS 2.0 solutions.

Figure 130:
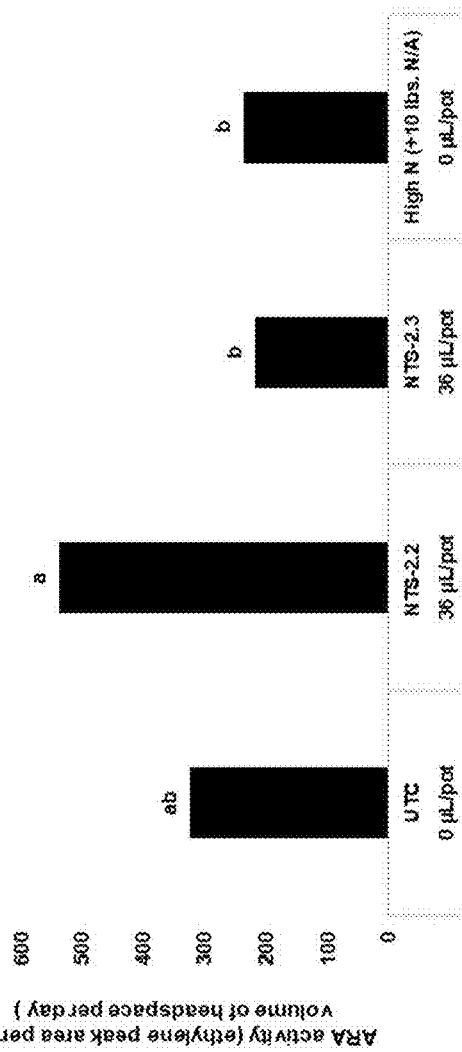

FIG. 130 shows corn root ethylene output from acetylene reduction assay (ARA) in plants treated with NTS-2.2, untreated control and plants treated with NTS-2.3.

Figure 131:
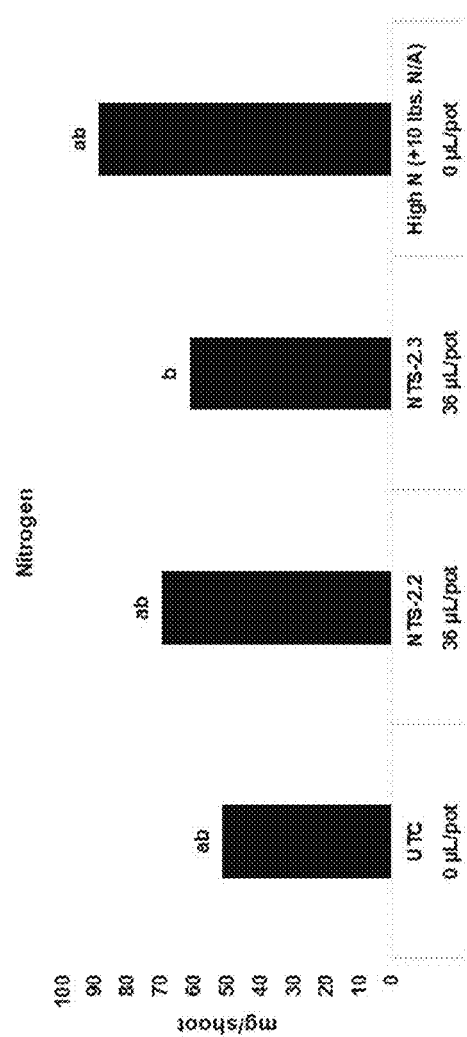

FIG. 131 shows corn shoot nitrogen uptake following in-furrow treatment application with NTS-2.2 and NTS2.3 compared to that from untreated control plants.

FIGS. 132A-132B shows corn biomass between treatment conditions. FIG. 132A shows NTS2.2 and NTS2.3 significantly increased dry shoot biomass by in-furrow treatment application. FIG. 132B shows NTS2.2 and NTS2.3 significantly increased dry root biomass by in-furrow treatment application.

Figure 133:
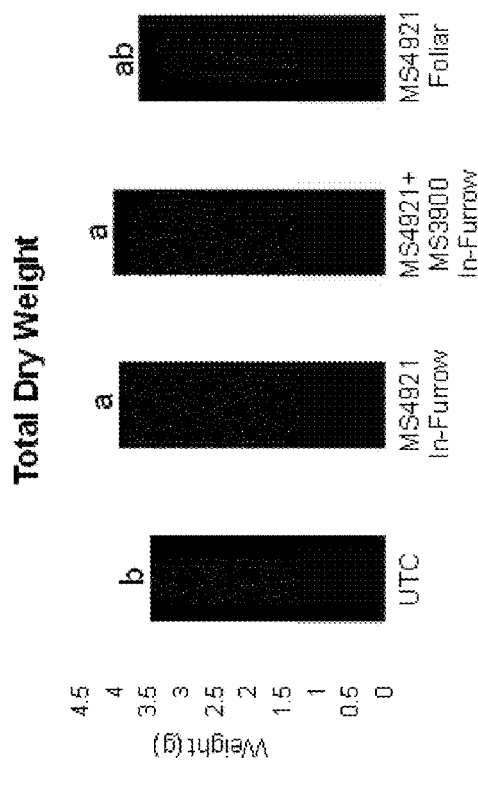

FIG. 133 shows the corn total dry weight from in-furrow and foliar treatments with target isolates. MS4921 was applied alone or in combination with MS3900 as an in-furrow treatment, and MS4921 was also applied alone as a foliar treatment.

Figure 134:
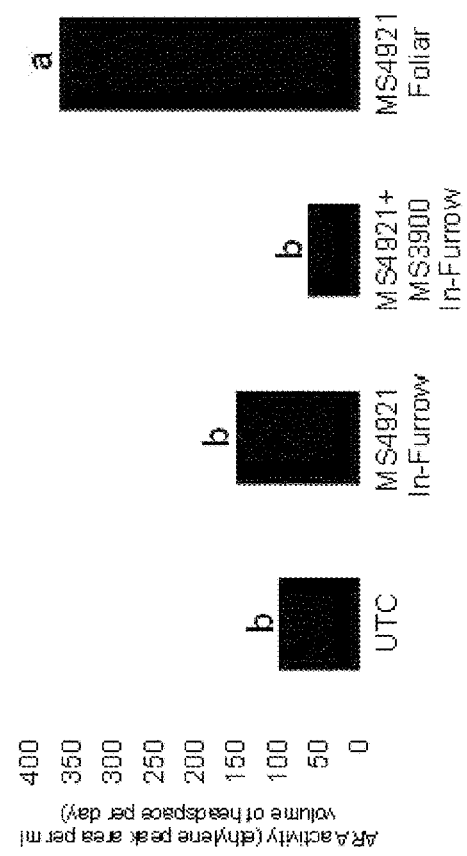

FIG. 134 shows foliar treatment of corn with isolate MS4921 resulted in roots and/or root crowns with greater acetylene reduction activity than that quantified from untreated control (UTC) or the in-furrow treatments with MS4921 or MS4921+MS3900.

Figure 135:
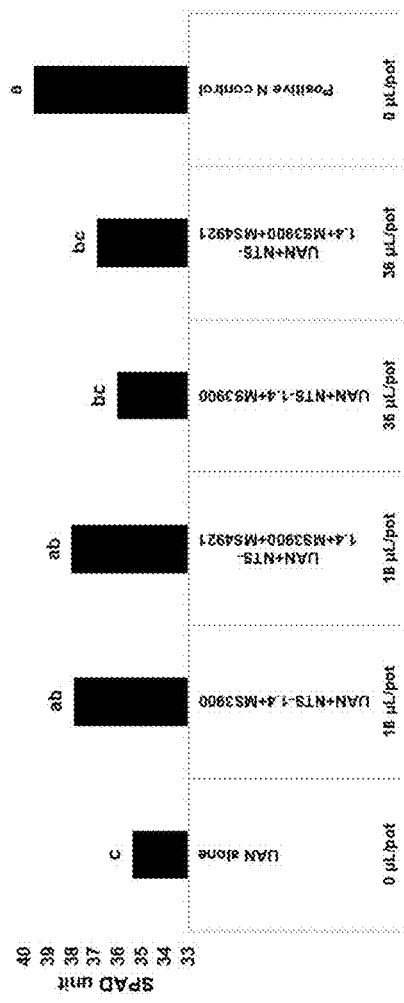

FIG. 135 shows corn leaf chlorophyll content across treatment conditions 7 days after broadcast application with urea ammonium nitrate (UAN) fertilizer. UAN with NTS spiked with MS3900 and MS4921 at 18 µL/pot showed greater chlorophyll content compared to that of UAN alone.

Figure 136:
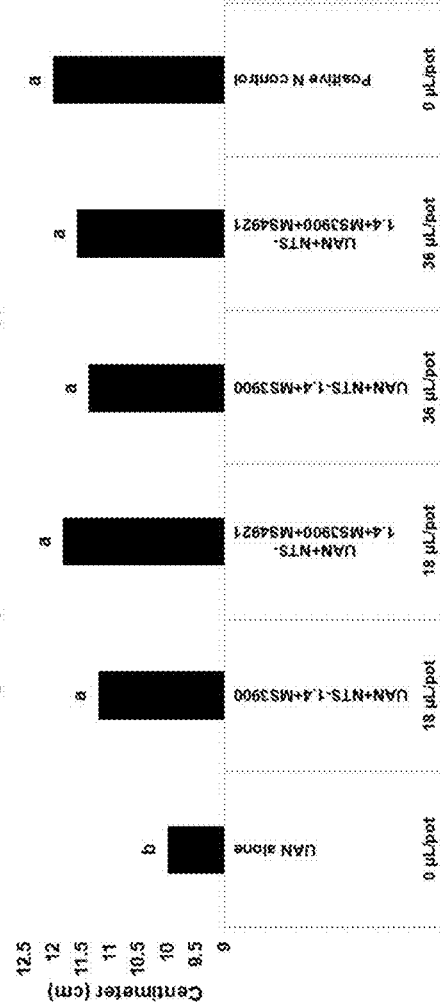

FIG. 136 shows corn plant height 7 days across treatment conditions after broadcast application with urea ammonium nitrate (UAN32) fertilizer. UAN with NTS spiked with MS3900 and MS4921 at 18 µL/pot showed greater plant height compared to that of UAN alone.

Figure 137:
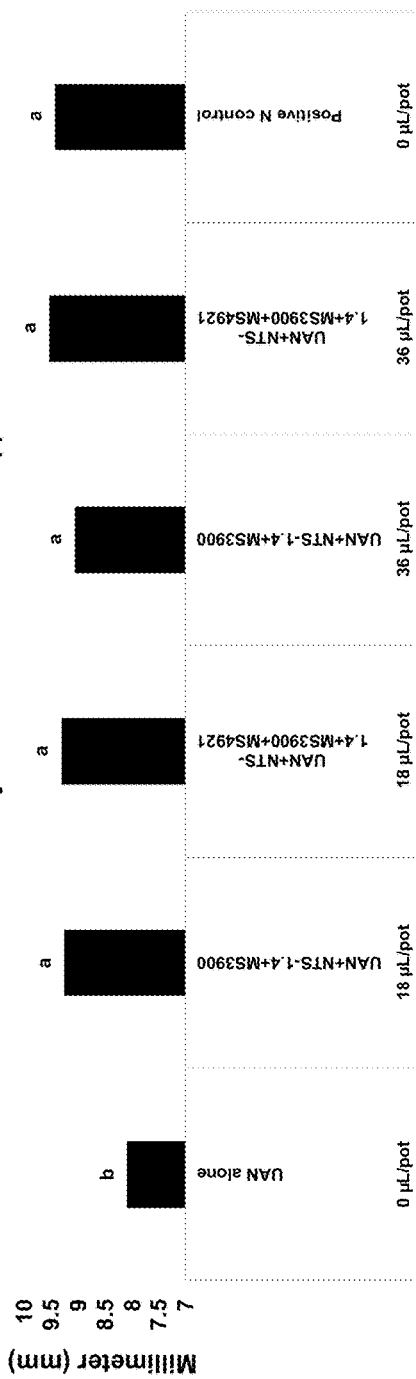

FIG. 137 shows corn stem diameter 7 days across treatment conditions after broadcast application with urea ammonium nitrate (UAN32) fertilizer. UAN with NTS spiked with MS3900 and MS4921 at 36 µL/pot showed greater stem diameter compared to that of UAN alone at 18 µL/pot.

Figure 138:
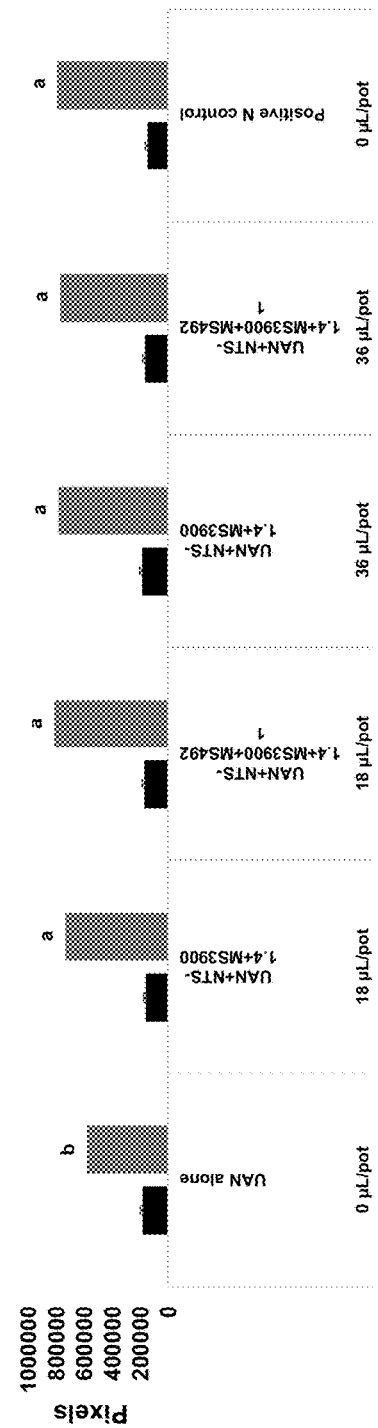

FIG. 138 shows corn leaf area before (12 days after planting, dap) and after broadcast application of treatment (20 days after planting). All UAN with NTS treatment conditions showed greater leaf area at 20 dap compared to that of UAN alone. Black bars indicate 12 dap and gray bars indicate 20 dap.

Figure 139:
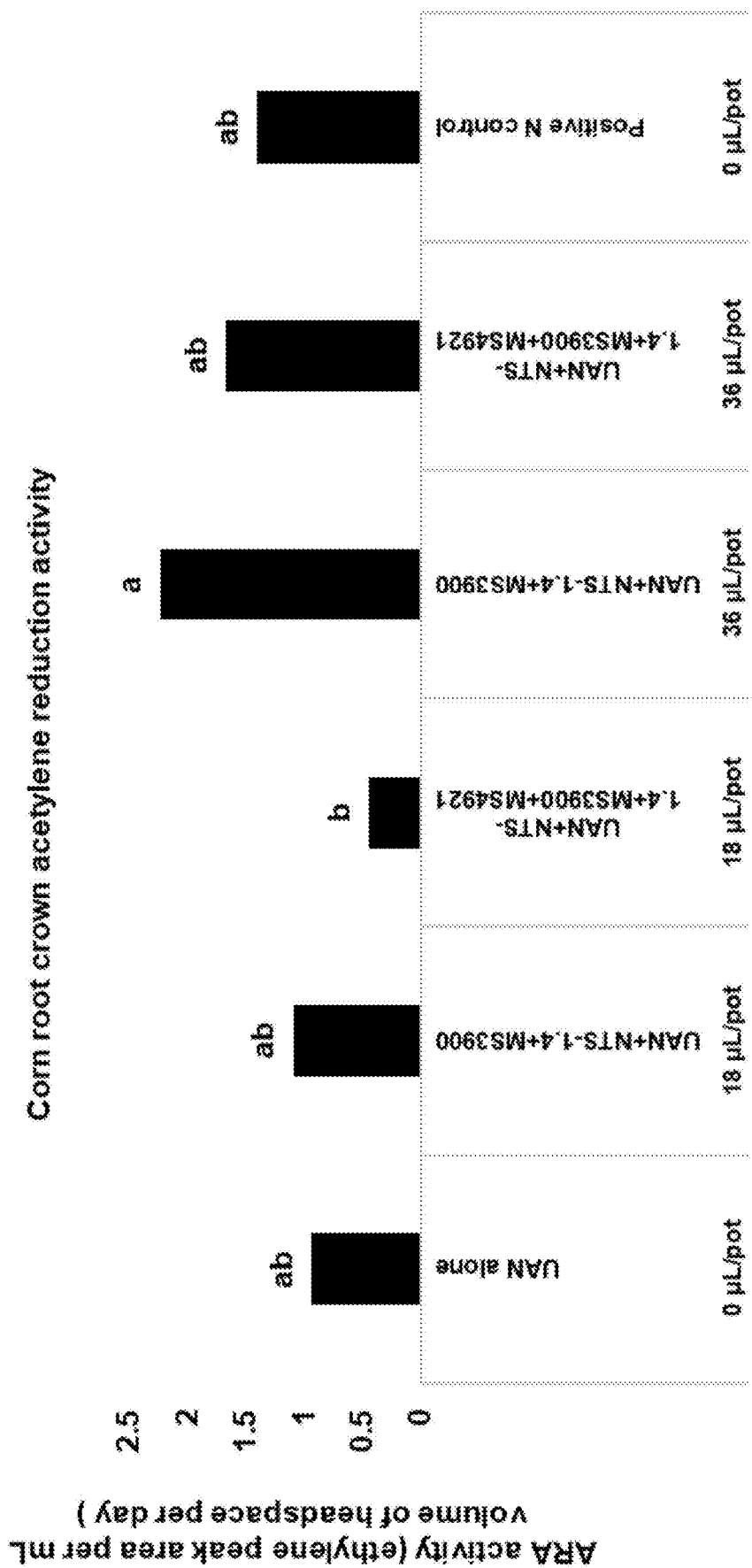

FIG. 139 shows acetylene reduction activity (ARA), as measured by ethylene output, in corn roots/root crown after broadcast application of treatments. UAN with NTS spiked with MS3900 at 36 µL/pot showed the greatest ARA activity across treatment conditions.

DETAILED DESCRIPTION

While various embodiments of the invention have been shown and described herein, it will be obvious to those skilled in the art that such embodiments are provided by way of example only. Numerous variations, changes, and/or substitutions may occur to those skilled in the art without departing from the invention. It should be understood that various alternatives to the embodiments of the invention described herein may be employed.

Described herein are systems and methods that employ microbial digestion of various feedstocks. A system of the present disclosure may comprise a continuous system capable of serialized isolate production (e.g., sIP system). The isolate production of the sIP system can occur within a mixed consortium of microbes. The target isolates of a sIP digestion system may become enriched in the microbial environment and may demonstrate improved efficacy and functionality. The main targeted functionality may be nitrogen use efficiency and/or nitrogen fixation from soil or fertilizer and improved nutrient uptake in plants. A target isolate may possess commercially valuable properties and can be introduced into a continuous (e.g., serialized) reactor system comprised of a complex microbial consortia that has been modified for functionality (e.g., for nitrogen use efficiency). Without wishing to be bound by theory, a target isolate may provide a performance benefit to a microbial community of the digestions systems described herein, providing a chemical and/or functional synergistic relationship as it grows in the system.

The products of digestion methods and systems described herein can include microbes and metabolites produced by microbial digestion of feedstock substrates. In some embodiments, the products of digestion methods and systems described herein can comprise biostimulant compositions that have plant growth promoting properties when applied to plants or to a medium in which plants are growing (e.g., soil). In some embodiments, methods and systems described herein are arranged to selectively promote growth of microbes that have a desired plant growth promoting property themselves or that produce metabolites that have the desired plant growth promoting property, such that the biostimulant product has the desired plant growth promoting property. Applications of the products of the digestion systems described herein may be on dry-fertilizers, applied in conjunction with the application of fertilizers, in formulations with additional components including liquid fertilizers or micronutrient coating formulations, in foliar applications, or any combinations thereof. Applications of the products of the digestion systems described herein may be to a part of a plant, such as a shoot, a stem, a leaf, a lateral bud, a terminal bud, a flower, a leaf axil, a root (e.g., a primary root, a lateral root, a root hair, a root cap), or any combination thereof. These and other features of embodiments disclosed herein are described in more detail below.

I. Certain Definitions

In the following description, certain specific details are set forth in order to provide a thorough understanding of various embodiments. However, one skilled in the art will understand that the embodiments provided may be practiced without these details. Unless the context requires otherwise, throughout the specification and claims which follow, the word "comprise" and variations thereof, such as, "comprises" and "comprising" are to be construed in an open, inclusive sense, that is, as "including, but not limited to." As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. Further, headings provided herein are for convenience only and do not interpret the scope or meaning of the claimed embodiments.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value.

The term "culturing", as used herein, may refer to the propagation of organisms on or in media of various kinds. Non-limiting examples of suitable media include tryptic soy agar (TSA), zinc agar, nutrient medium, lysogeny broth (LB medium), and/or plate count agar.

As used herein, the term "enriched culture" of an isolated microbial strain can refer to a microbial culture wherein the total microbial population of the culture contains a percentage of a target isolated strain. An enriched culture may comprise an increased amount of a target isolated strain and/or a target population of microbes compared to a total microbial population of a culture. An enriched culture may comprise a growing population of a target isolated strain and a population of microbes enriched for a particular functionality (e.g., nitrogen use efficiency) over a time period. An enriched culture may comprise a percentage of a target isolated strain and a population of microbes enriched for a particular functionality (e.g., nitrogen use efficiency). In some embodiments, an enriched culture may comprise a percentage of a target isolated strain, a population of microbes enriched for a particular functionality, and metabolites enriched for a particular functionality (e.g., nitrogen use efficiency). The enriched culture may comprise a percentage of a total bacteria population in a container of digestion system described herein. The enriched culture may comprise a percentage of a total bacteria population in an output product (e.g., biostimulant) described herein. In some embodiments, an enriched culture can refer to a microbial culture wherein the total microbial population of the culture contains at least about 0.001%, at least about 0.01%, at least about 0.05%, at least about 0.1%, at least about 0.5%, at least about 1%, at least about 1.5%, at least about 2%, at least about 2.5%, at least about 5%, at least about 10%, at least about 15%, at least about 20%, at least about 25%, at least about 50%, or at least about 75% of a target isolated strain, a population of microbes enriched for a particular functionality, metabolites enriched for a particular functionality, or any combination thereof. In some embodiments, an enriched culture can refer to a microbial culture wherein the total microbial population of the culture contains at most about 75%, at most about 50%, at most about 25%, at most about 20%, at most about 15%, at most about 10%, at most about 5%, at most about 2.5%, at most about 2%, at most about 1.5%, at most about 1%, or at most about 0.5% of a target isolated strain, a population of microbes enriched for a particular functionality, metabolites enriched for a particular functionality, or any combination thereof. In some embodiments, an enriched culture can refer to a microbial culture wherein the total microbial population of the culture contains from about 0.5% to about 75% of a target isolated strain, a population of microbes enriched for a particular functionality, metabolites enriched for a particular functionality, or any combination thereof. In some embodiments, an enriched culture can refer to a microbial culture wherein the total microbial population of the culture contains from about 0.5% to about 1%, about 0.5% to about 2%, about 0.5% to about 3%, about 0.5% to about 5%, about 0.5% to about 10%, about 0.5% to about 15%, about 0.5% to about 20%, about 0.5% to about 25%, about 0.5% to about 50%, about 0.5% to about 60%, about 0.5% to about 75%, about 1% to about 2%, about 1% to about 3%, about 1% to about 5%, about 1% to about 10%, about 1% to about 15%, about 1% to about 20%, about 1% to about 25%, about 1% to about 50%, about 1% to about 60%, about 1% to about 75%, about 2% to about 3%, about 2% to about 5%, about 2% to about 10%, about 2% to about 15%, about 2% to about 20%, about 2% to about 25%, about 2% to about 50%, about 2% to about 60%, about 2% to about 75%, about 3% to about 5%, about 3% to about 10%, about 3% to about 15%, about 3% to about 20%, about 3% to about 25%, about 3% to about 50%, about 3% to about 60%, about 3% to about 75%, about 5% to about 10%, about 5% to about 15%, about 5% to about 20%, about 5% to about 25%, about 5% to about 50%, about 5% to about 60%, about 5% to about 75%, about 10% to about 15%, about 10% to about 20%, about 10% to about 25%, about 10% to about 50%, about 10% to about 60%, about 10% to about 75%, about 15% to about 20%, about 15% to about 25%, about 15% to about 50%, about 15% to about 60%, about 15% to about 75%, about 20% to about 25%, about 20% to about 50%, about 20% to about 60%, about 20% to about 75%, about 25% to about 50%, about 25% to about 60%, about 25% to about 75%, about 50% to about 60%, about 50% to about 75%, or about 60% to about 75% of a target isolated strain, a population of microbes enriched for a particular functionality, metabolites enriched for a particular functionality, or any combination thereof.

The term "composition" as used herein can refer to a combination of an active agent (e.g., a microbial strain described herein) and at least one other compound, carrier, or composition, which can be inert (for example, a detectable agent or liquid carrier) or active, such as, but not limited to, a fertilizer, nutrient, or pesticide. A microbial composition refers to a composition comprising at least one microbial species. A composition may comprise microbial metabolites generated in a microbial consortium of a digestion system described herein.

An "effective amount", as used herein, can refer to an amount sufficient to effect beneficial and/or desired results. An effective amount can be administered in one or more administrations. An "effective microorganism" may refer to a subject strain exhibiting a degree of promotion of plant health, growth and/or yield, at a statistically significant level, compared to that of an untreated control. In some instances, the expression "an effective amount" can be used herein in reference to that quantity of microbial treatment which can be used to obtain a beneficial or desired result relative to that occurring in an untreated control under suitable conditions of treatment as described herein. For example, the expression "an agriculturally effective amount" can be used herein in reference to that quantity of microbial treatment which can be used to obtain an agriculturally beneficial or desired result relative to that occurring in an untreated control under suitable conditions of treatment as described herein. The effective amount of an agricultural formulation or composition that may be applied for the improvement of plant health, growth and/or yield, can be readily determined.

A "carrier" as used herein can refer to a substance or a composition that support the survival of the microbes. Such carriers may be either organic or non-organic.

"Percentage of sequence identity", as used herein, can be determined by comparing two optimally locally aligned sequences over a comparison window defined by the length of the local alignment between the two sequences. The amino acid sequence in the comparison window may comprise additions or deletions (e.g., gaps or overhangs) as compared to the reference sequence (which does not comprise additions or deletions) for optimal alignment of the two sequences.

Local alignment between two sequences may include segments of each sequence that are deemed to be sufficiently similar according to a criterion that depends on the algorithm used to perform the alignment (e.g. BLAST). The percentage of sequence identity is calculated by determining the number of positions at which the identical nucleic acid base or amino acid residue occurs in both sequences to yield the number of matched positions, dividing the number of matched positions by the total number of positions in the window of comparison and multiplying the result by 100. Optimal alignment of sequences for comparison may be conducted by the local homology algorithm of Smith and Waterman (Add. APL. Math. 2:482, 1981), by the global homology alignment algorithm of Needleman and Wunsch (J Mol. Biol. 48:443, 1970), by the search for similarity method of Pearson and Lipman (Proc. Natl. Acad. Sci. USA 85:2444, 1988), by heuristic implementations of these algorithms (NCBI BLAST, WU-BLAST, BLAT, SIM, BLASTZ), or by inspection. Given that two sequences have been identified for comparison, GAP and BESTFIT may be employed to determine their optimal alignment. Typically, the default values of 5.00 for gap weight and 0.30 for gap weight length are used. The term "substantial sequence identity" between polynucleotide or polypeptide sequences refers to polynucleotide or polypeptide comprising a sequence that has at least about 50% sequence identity, at least about 60% sequence identity, at least about 70% sequence identity, at least about 80% sequence identity, at least about 85% sequence identity, at least about 90% sequence identity, at least about 95% sequence identity, at least about 96% sequence identity, at least about 97% sequence identity, at least about 98% sequence identity, or at least about 99% sequence identity compared to a reference sequence using the programs. In addition, pairwise sequence homology or sequence similarity, as used, refers to the percentage of residues that are similar between two sequences aligned. Families of amino acid residues having similar side chains have been well defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Query nucleic acid and amino acid sequences can be searched against subject nucleic acid or amino acid sequences residing in public or proprietary databases. Such searches can be done using the National Center for Biotechnology Information Basic Local Alignment Search Tool (NCBI BLAST v 2.18) program. The NCBI BLAST program is available on the internet from the National Center for Biotechnology Information (blast.ncbi.nlm.nih.gov/Blast.cgi). Typically the following parameters for NCBI BLAST can be used: Filter options set to "default", the Comparison Matrix set to "BLOSUM62", the Gap Costs set to "Existence: 11, Extension: 1", the Word Size set to 3, the Expect (E threshold) set to 1e−3, and the minimum length of the local alignment set to 50% of the query sequence length. Sequence identity and similarity may also be determined using GenomeQuest™ software (Gene-IT, Worcester Mass. USA).

The term "plant growth promotion" (e.g., "PGP") can refer to processes that can promote plant health, growth, yield, or any combinations thereof. In some embodiments, PGP can encompass a wide range of improved plant properties, including but not limited to, improved nitrogen fixation, improved phosphate uptake, improved zinc uptake, improved root development, increased leaf area, increased plant yield, increased uptake of macronutrients, increased uptake of micronutrients, increased seed germination, enhancing seed germination, enhancing early plant development, improving root growth, improving shoot growth, improving plant height, increasing nutrient uptake, improving tolerance to abiotic stress, mitigating transplant shock, improving plant reproduction, improving soil microbial activity, increased photosynthesis, increased abundance of functional enzymes, increased dry biomass, or an increase in accumulated biomass of the plant. In some embodiments, the microbial strains, isolates, cultures, compositions or synthetic consortia as described herein improve stress tolerance (e.g., tolerance to drought, flood, salinity, heat, pest), improve nutrient uptake, plant health and vigor, improve root development, increase leaf area, increase plant yield, increased uptake of macronutrients, increased uptake of micronutrients, increase seed germination, increased abundance of functional enzymes, increased dry biomass, or an increase in accumulated biomass of the plant. In some embodiments, the microbial strains, isolates, cultures, or compositions as described herein increase the size or mass of a plant or parts thereof, as compared to a control plant, or a plant that has not been treated with a substance, or parts thereof or as compared to a predetermined standard. In some embodiments, the microbial strains, isolates, cultures, compositions or synthetic consortia as described herein improve the health, vigor and yield of a plant, as compared to a control plant or a plant that has not been treated with a substance, but also can survive and multiply in microhabitats associated with the root surface.

As used herein, the term "yield" can refer to the amount of harvestable plant material or plant-derived product, and is normally defined as the measurable produce of economic value of a crop.

For crop plants, "yield" can also mean the amount of harvested material per acre or unit of production. Yield may be defined in terms of quantity or quality. The harvested material may vary from crop to crop, for example, it may be seeds, above ground biomass, roots, fruits, cotton fibers, any other part of the plant, or any plant-derived product which is of economic value.

In some embodiments, the microbial strains, isolates, cultures and compositions according to the embodiments of this application lead to plant growth promotion or plant growth improvement that is an at least 5% increase, at least 10% increase, at least 25% increase, at least 50% increase, at least 75% increase, or at least a 100% increase in the property being measured. In some embodiments, the microbial strains, isolates, cultures and compositions according to the embodiments of this application lead to plant growth promotion or plant growth improvement that is an at least 1%, 2%, 3%, 4%, 5%, 10%, 15%, 20%, 25%, 30%, 35%, 40%, 45%, 50%, 60%, 70%, 80%, 90%, 95%, 96%, 97%, 98%, 99%, or 100% increase in the property being measured. In some embodiments, the microbial strains, isolates, cultures and compositions of this application may produce an above stated percentage increase in nitrogen fixation, an above stated increase in nitrogen content, an above stated increase in nitrogen acquisition, an above stated increase in nitrogen uptake, an above stated increase in total root weight, or in leaf area or in plant product yield (e.g., an above stated percentage increase in plant product weight).

A "control plant", as used herein, can provide a reference point for measuring changes in phenotype of the subject plant, and may be any suitable plant cell, seed, plant component, plant tissue, plant organ or whole plant. A control plant may comprise, but is not limited to, (a) a plant which is genetically identical to the subject plant but which is not exposed to the same treatment (e.g., inoculant treatment) as the subject plant or (b) the subject plant itself, under conditions in which it has not been exposed to a particular treatment such as, for example, an inoculant or combination of inoculants and/or other chemicals. A treated plant may comprise a plant that has had an inoculum of a microbe or a biostimulant composition as described herein applied to any part of the plant (e.g., seed, stem, root, shoot, leaf, or combination thereof). A treated plant may comprise a plant that has had an inoculum of a microbe or a biostimulant composition as described herein applied using an in-furrow application. A treated plant may comprise a plant that has had an inoculum of a microbe or a biostimulant composition as described herein applied using a side-dress application. A treated plant may comprise a plant that has had an inoculum of a microbe or a biostimulant composition as described herein applied to the soil. An untreated plant may comprise a plant that that has not had an inoculum of a microbe or a biostimulant composition as described herein applied directly or indirectly.

"Inoculant" as used herein can refer to any culture or preparation that comprises at least one microorganism. In some embodiments, an inoculant (sometimes as microbial inoculant, or soil inoculant) is an agricultural addition that uses beneficial microbes (including, but not limited to endophytes) to promote plant health, growth, yield, or any combinations thereof. Many of the microbes suitable for use in an inoculant form symbiotic relationships with the target crops where both parties benefit (mutualism). For example, an isolated microbial strain as described herein may benefit from carbon sources from the roots of a plant and the plant may benefit from metabolites generated by metabolism of the microbe. Without wishing to be bound by theory, a plant may be colonized by the isolate and the colonization of the roots may block plant pathogens from accessing the roots. An inoculant (e.g., inoculum of a microbe) can be added at one time point during a digestion system process.

The term "serialized isolate production", (e.g., sIP), can refer to specialized manipulated continuous serialized reactors that may enable the growth and enrichment of the microbes, isolates, target isolates, and/or microorganisms as described herein.

The term "floc" can refer to a mass formed by the aggregation of a number of fine suspended particles. For example, a floc can comprise organic materials recovered from a feedstock, waste, wastewater, and/or sludge material of a fluid used in a digestion system. A floc can comprise biosolids and/or particles from digestion products of organic materials. Floc can comprise an aggregated mass of microorganisms (e.g., bacteria).

The term "whole broth" (e.g., WB) can refer to a blend of supernatant and floc at a ratio for use in the technologies as described herein. A whole broth may comprise microbial populations (e.g., nitrogen use efficiency-promoting microbes), enzymes, fungi, biosolids, or any combination thereof. For example, bacterial genera of a whole broth may comprise *Haliscomenobacter, Lewinella, Caldilinea, Terrimonas, Acidobacterium, Lewinella cohaerens, Thauera phenylacetica, Thauera mechernichensis, Solitalea canadensis, Nitrospira moscoviensis*, or any combination thereof. A whole broth may have plant growth promotion properties. For example, a whole broth may have nitrogen-fixation capacity.

The terms "microbial consortium" or "microbial population" can refer to a group of microorganisms in an environment. Consortiums may be endosymbiotic or ectosymbiotic. Microorganisms in a microbial consortium can include, but are not limited to, bacteria, fungi, yeasts, lichens, algae, protozoa, archaea, molds, or any combinations thereof.

The term "supernatant" (e.g., "base product") can refer to the final product of the digestion system. The supernatant can be measured for amount of a microbial isolate, number of members within a microbial consortium, or types and amount of microbial metabolites with plant growth promotion capacity.

The term "load rate" can refer to a rate at which a source material is introduced into a digestion system. In some embodiments, load rate may refer to "organic load rate" or "hydraulic load rate". Organic load rate comprises a rate at which organic feedstock is introduced into the system. Hydraulic load rate comprises a rate at which a hydraulic source is introduced into the system.

The term "internal recycle rate" can refer to a rate at which a working fluid is recycled within a phase space.

The term "hydraulic feed rate" can refer to a rate at which working fluid is transferred between phase spaces.

The term "hydraulic dwell time" can refer to an amount of time that a working fluid is present in a phase space.

The term "working fluid" can refer to a fluid substance supporting and transporting biology and nutrients through a system of contains. For example, a working fluid may comprise a organic materials, microorganisms (e.g., microbes and/or metabolites), biosolids, macronutrients, micronutrients, organic nutrients, inorganic nutrients, or any combination thereof. A working fluid can comprise a solution that flows throughout a digestion system and may provide an enriched environment for microbes of the digestion system.

Whenever the term "at least," "greater than," or "greater than or equal to" precedes the first numerical value in a series of two or more numerical values, the term "at least," "greater than" or "greater than or equal to" can apply to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" can apply to each of the numerical values in that series of numerical values. For example, less than or equal to 3, 2, or 1 is equivalent to less than or equal to 3, less than or equal to 2, or less than or equal to 1.

II. Multi-Pronged Approach to Nitrogen Use Efficiency

Embodiments of systems and methods described herein produce biostimulant products that may have a multi-modal way of promoting efficient use of nitrogen by plants. Biostimulant products produced by embodiments described herein may be used to promote plant growth by applying the products to plants and/or plant growth media (e.g., soil). One mode of action of products produced in some embodiments is nitrogen-fixing activity of nitrogen fixing bacteria included in the products. Another mode of action may be the recruitment of plant associated nitrogen fixers already present in the soil to the roots of plants, thereby increasing nitrogen fixing activity in the root zone and potentially in other plant tissues if the recruited N-fixing microbes become endophytic and can move systemically throughout the plant. Such recruitment may be accomplished by bacterial metabolites present in the biostimulant product and/or by bacterial isolates. Another mode of action may be increases in soil organic nitrogen and mineralization and uptake of organic nitrogen stimulated by microbes and/or microbial metabolites present in the products produced in embodiments described herein.

Biostimulant products described herein may provide plants with N fixation by microbes directly via microbial endophytes and symbionts present in the products, and indirectly via mineralization or decomposition of organically bound N in soil produced by soil N-fixers. Plants may be provided with N through decomposition of organically bound N in the soil. Embodiments of biostimulant products may also provide plants with the ability to access additional N in soil organic matter. Embodiments of biostimulant products may provide a combination of these strategies to provide better access to biological/organic sources of nitrogen and improve nitrogen use efficiency (NUE).

The following microbe genera can promote nitrogen use efficiency in plants: *Kosakonia, Klebsiella, Rahnella, Kluyvera, Enterobacter, Achromobacter, Microbacterium, Gluconobacter, Methylobacterium, Pseudomonas, Pantoea, Azospirillum, Azocarus, Herbaspirillum, Burkholderia, Cyanobacteria, Bacillus*, and *Paenibacillus*. The following microbe species can promote nitrogen use efficiency in plants: *Kosakonia sacchari, Klebsiella variicola, Rahnella aquatilis, Kluyvera intermedia, Kosakonia pseusosacchari, Enterobacter* spp., *Achromobacter marplatensis, Azopirillum lipoferum, Microbacterium murale, Gluconobacter diazotrophicus, Methylobacterium symbioticum, Paenibacillus borealis, Bacillus megaterium (Priestia megaterium)*, and *Paenibacillus sonchi*. Embodiments of products described herein may include one or more of these microbes. Microbes of these genera may comprise endophytic N fixers (diazotrophs) of monocots.

The inoculum of the microbe, nitrogen use efficiency-promoting microbes of the microbial consortium, nitrogen use efficiency-promoting metabolites, or any combination thereof may be nitrogen use efficiency-promoting microbes in the working fluid of the system and/or in the output product (e.g., base product) of the digestion system. These nitrogen use efficiency-promoting microbes may have a nifH gene. A nifH gene can comprise a gene having at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99.5%, at least about 99.9%, or 100% sequence identity to a nucleotide sequence as set forth in SEQ ID NOs: 13-14. A nifH gene can comprise a gene that encodes a nitrogenase reductase polypeptide. In some embodiments, the nitrogenase reductase polypeptide has an amino acid sequence that has at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, at least about 99.5%, at least about 99.9%, or 100% sequence identity to an amino acid sequence encoded by SEQ ID NO: 13 or 14.

Plant associated N-fixers that may be beneficial in biostimulant products described herein may include those that can associate with plant roots and other tissues and become endophytic, demonstrate nitrogen fixation activity when associated with roots and other plant tissues, and show consistent increases in plant nitrogen use efficiency, or any combination thereof. Biostimulant products may include the following capabilities with respect to nitrogen fixer recruitment: increase the number of associated and/or endophytic N-fixers with plant roots through N-fixer recruitment, nitrogen fixation activity in treated plants, show consistent increases in nitrogen use efficiency, or any combination thereof. Microbial metabolites in biostimulant products may provide for an increased ability of plants to access organically bound nitrogen generated by soil N-fixers and other organic matter, increase soil microbial respiration and biomass, and increase recruitment of beneficial microbes.

In some embodiments, a serialized set of reaction chambers that may be used in a method of producing a biostimulant product are described herein. In some embodiments, conditions within reactor chambers may be established to selectively promote the production of one or more microbes that have a specific desired plant growth promoting effect (e.g., nitrogen use efficiency).

In an aspect, the present disclosure provides a method, comprising (a)transferring an aqueous organic feedstock and an inoculum of a microbe or several microbes that are capable of promoting nitrogen use efficiency in plants into a first container comprising a volume of a first working fluid, wherein the aqueous organic feedstock comprises: (i) a first microbial consortium; and (ii) digestion products produced by digestion of an organic material by microbes in the first microbial consortium; and (b) incubating the inoculum under conditions that promote growth of the nitrogen fixing microbes supplied by the microbial consortia and as well as the specifically introduced microbes, thereby increasing the population of nitrogen fixing microbes and enabling a sustained presence of the specifically introduced microbes.

In some embodiments, the bioreactor system (e.g., the digestion system) comprises an established population of one or more nitrogen use efficiency-promoting microbial strains in one or more containers of the system. An "established population" of a particular microbial strain is a population that remains within an operating bioreactor system without replenishing the microbial strain from outside the bioreactor system. In some embodiments, an established population is one that has not been diminished by more than 1, 3, 5, 10, 15, 20, or 25% during continuous operation of the bioreactor system for at least 5, 10, 15, 20, 25, 30, 60, or 90 days without adding a population of the microbial strain to the bioreactor system at a concentration higher than 1, 10, 50, or 100 CFU/ml. In some embodiments, an established population of a microbial strain has been established by making one or more inoculations of the microbial strain into one or more containers of the bioreactor system. In some embodiments, an established population is a population that is derived from a population that was inoculated into the system at least 10, 30, 60, or 90 days previous.

In some embodiments, a bioreactor system comprises at least one microbial strain. In some embodiments, a bioreactor system comprises at least one nitrogen use efficiency-promoting microbial strain. In some embodiments, a bioreactor system comprises an established population of a first nitrogen use efficiency-promoting microbial strain and an established population of a second nitrogen use efficiency-promoting microbial strain. In some embodiments, the bioreactor system further comprises an established population of a third nitrogen use efficiency-promoting microbial strain. The established populations of the respective microbial strains may be established in individual or combined inoculations into the bioreactor system. An individual inoculation may comprise one inoculum of a microbial strain (e.g., microbe). A combined inoculation may comprise an inoculum comprising at least two microbial strains. The combined inoculation may comprise the same isolated microbial strains. The combined inoculation may comprise an isolated microbial strain and non-isolated microbial strain. The combined inoculation may comprise two or more isolated microbial strains.

In some embodiments, nitrogen use efficiency promotion may comprise increasing nitrogen fixation, promoting nitrogen fixation in the root and other tissues of plants, recruiting nitrogen fixers to the roots of plants, promoting soil organic nitrogen content and mineralization and uptake of organic nitrogen from soil, or any combination thereof. In some embodiments, the microbe is capable of nitrogen fixation, promoting nitrogen fixation in the root and other tissues of plants, recruiting nitrogen fixers to the roots of plants, promoting soil organic nitrogen content and mineralization and uptake of organic nitrogen from soil, or any combination thereof. In some embodiments, the conditions promote growth of one or more microbes in the first microbial consortium that are capable of promoting plant growth, nitrogen fixation, nitrogen use efficiency, or recruitment of nitrogen fixers to the roots of plants, or of generating metabolites capable of promoting plant growth, nitrogen fixation, nitrogen use efficiency, enhancing organic nitrogen in the soil and mineralization and plant uptake of organic nitrogen, or recruitment of nitrogen fixing microbes to the roots of plants. In some embodiments, during the incubating the microbe or one or more microbes in the first microbial consortium, metabolites are produced capable of promoting plant growth and nitrogen use efficiency. In some embodiments, the incubating increases a population of one or more microbes in the microbial consortium capable of promoting plant growth. In some embodiments, the aqueous organic feedstock further comprises an inorganic substrate. In some embodiments, the first microbial consortium further comprises microbes derived from the inorganic substrate. In some embodiments, the inorganic substrate comprises rock phosphate. In some embodiments, the microbe or microbes are of the species *Paenibacillus borealis, Bacillus megaterium*, or *Paenibacillus sonchi*. In some embodiments, the microbe is the *Paenibacillus borealis* strain deposited under ATCC Accession No. PTA-127654 (MS3907), the *Bacillus megaterium* (or *Priestia megaterium*) strain deposited under ATCC Accession No. PTA-127653 (MS3900), the *Paenibacillus sonchi* strain deposited under ATCC Accession No. PTA-127655 (MS4921), or the *Bacillus megaterium* strain deposited under ATCC Accession No. PTA-127652 (MS2748). In some embodiments, the first working fluid comprises (a) a second microbial consortium derived from the aqueous organic feedstock, and/or (b) digestion products produced by digestion of substances present in the organic feedstock by the first microbial consortium and the microbe(s). In some embodiments, the method further comprises transferring a portion of the first working fluid into a second container. The second container can comprise a second working fluid. The method may further comprise incubating the second working fluid in the second container. In some embodiments, the method further comprises transferring a portion of the first working fluid into a second container comprising a second working fluid and incubating the second working fluid in the second container. The second working fluid may comprise a third microbial consortium and the third microbial consortium may be derived from the first working fluid. The second working fluid may comprise digestion products produced by digestion of substances present in the first working fluid by the third microbial consortium, the microbial strain, or any combination thereof. In some embodiments, the second working fluid comprises (a) a third microbial consortium derived from the first working fluid, and (b) digestion products produced by digestion of substances present in the first working fluid by the third microbial consortium and the microbe. In some embodiments, the amount of the aqueous organic feedstock transferred into the first container over a time period is equal to the amount of the first working fluid transferred into the second container over the same time period. In some embodiments, the amount of the aqueous organic feedstock transferred into the first container over a time period is not equal to the amount of the first working fluid transferred into the second container over the same time period. In some embodiments, the volume of the first working fluid in the first container is maintained constant. In some embodiments, the volume of the first working fluid in the first container is not maintained constant. In some embodiments, transferring the aqueous organic feedstock into the first container comprises continuously flowing the aqueous organic feedstock into the first container at a first flow rate, transferring the portion of the first working fluid into the second container comprises continuously flowing the portion of the first working fluid into the second container at a second flow rate, and the first flow rate and the second flow rate are equal. In some embodiments, the method further comprises transferring a portion of the second working fluid to a third container comprising a third working fluid and incubating the third working fluid in the third container. In some embodiments, the method further comprises transferring a portion of the third working fluid into a fourth container comprising a fourth working fluid and incubating the fourth working fluid in the fourth container. In some embodiments, the first working fluid, the second working fluid, the third working fluid, and the fourth working fluid are maintained at constant volumes. In some embodiments, a plant growth promoting product made by the method described herein may promote nitrogen use efficiency in a plant. In some embodiments, a method of promoting nitrogen use efficiency of a plant comprises contacting the plant and/or a medium in which the plant is growing with the product.

III. Microbial Digestion Methods and Systems

A. System Overview

Certain embodiments disclosed herein include methods and systems in which microbes comprised in microbial consortia digest substances provided in a feedstock. The digestion systems may be comprised of a series of separate, fluidly connected containers, also referred to herein as "reactors." In each reactor, a different microbial consortium may be established and maintained throughout continuous operation of the digestion system. The unique microbial consortia present in each reactor may provide for different physiological activities in the different reactors. Thus, different steps in digestion of a feedstock may be performed in different reactors, which may result in (1) a more complete digestion—i.e., more complete breakdown of macromolecules in the feedstock—than other types of digestion systems, and/or (2) production of a variety of microbial digestion products having plant growth promoting properties (e.g., ability to recruit nitrogen fixers to plant tissues or otherwise promote nitrogen use efficiency).

In some embodiments, a reactor or a series of reactors functions to contribute to the growth of one or more microbes having desired plant growth promoting properties and/or to the production of digestion products having plant growth promoting properties. The system can comprise 2, 3, 4, 5, 6, or more reactors. In some embodiments, the operation of a digestion system may lead to growth of one or more microbes having a desired plant growth promoting effect. The one or more microbes may be one or more isolated microbes added separately as an inoculum to the digestion system. The one or more microbes may also be input into the system as part of a feed material that includes a mixture of microbes. The one or more microbes may be endogenous to an organic material such as, for example, a manure, a plant, a lignocellulosic material, or an algae. The one or more microbes may also be endogenous to other types of feed materials, such as rock phosphate or coal. In some embodiments, endogenous microbes are those microbes naturally present in feedstock material (e.g., a manure, a plant, a lignocellulosic material, or an algae). These microbes may naturally reside in a closed system and/or are present in the ecosystem of the feedstock material.

Inputs into digestion systems may include one or more of water, a microbial inoculum, nutrients (e.g., carbon, nitrogen, phosphorous, or any combination thereof), and a digestion substrate. Fluid within reactors of a digestion system may be referred to herein as a "working fluid." In continuous operation, each reactor may have a constant volume of working fluid therein, with the rate of fluid flowing into each reactor matching the rate of fluid flowing out of each reactor. As each reactor may include a different microbial consortium and have different conditions from other reactors, the working fluid within each reactor may be considered to be distinct from working fluids within the other reactors. The total volume of working fluid within a digestion system may be referred to herein as the "total working volume" of the digestion system.

Digestion substrates included in an input stream into a digestion system may include, for example, organic materials that can be digested by microbes in the digestion system. Such organic materials may include, for example, manure, lignocellulosic material, wastewater biosolids, food waste, energy crops, yeast, agricultural waste, algae, or any combination thereof. The manure may be cow manure, chicken manure, horse manure, sheep manure, alpaca manure, rabbit manure, pig manure, guano or any combination thereof. In some embodiments, the manure is a mixture of one, two, three, or more manures. Digestion substrates input into digestion systems may have been subject to a partial digestion before being input into the system. Thus, the input into the system may include products of digestion of an original digestion substrate by microbes endogenous to the original digestion substrate, as well as digestible materials still present in the input. In some embodiments, digestion substrates included in an input stream may include an inorganic substrate. The inorganic substrate may include, for example, sand, vermiculite, perlite, pumice, or any combination thereof. In some embodiments, the inorganic substrates comprises a mineral. In some embodiments, the inorganic substrate comprises rock phosphate.

In some embodiments, a microbial inoculum comprises a single isolated microbe. In some embodiments, the microbial inoculum may comprise between 1 and 5 isolated microbes. In some embodiments, the inoculum may comprise 1, 2, 3, 4 or 5 isolated microbes. In some embodiments, the inoculum may comprise greater than 5 isolated microbes. In some embodiments, in addition to one or more isolated microbes, a microbial inoculum input into a digestion system may include a complex mixture of microbes, which may include at least 5, 10, 20, 25, 50, 100, 200, 225, 250, 275, 300, 350, 400, or more species of microbes.

An inoculum of a microbe as described herein may have at least one plant growth promotion property (e.g., a property of plant growth). A plant growth promotion property may comprise shoot biomass, root biomass, nutrient uptake, crop yield, leaf area, chlorophyll content, increased photosynthesis, heat tolerance, cold tolerance, drought tolerance, or salt tolerance, or total biomass. A digestion system may be configured to enhance production of the inoculum of the microbe. A microbe may be a bacterial species, a fungal species, or an algal species. An inoculum of a microbe may be an individual inoculation of a microbial strain.

In some embodiments, the inoculum of a microbe may comprise at least two isolated microbes. In some embodiments, the inoculum of a microbe may comprise at least one isolated microbe and at least one non-isolated microbe. In some embodiments, the inoculum of a microbe may comprise 1, 2, 3, 4, 5, or more microbes. An inoculum of a microbe may be transferred to a first container (e.g., reactor) of a digestion system one time, two times, three times, four times, five times, or more. An inoculum of a microbe may be transferred to a second container, a third container, a fourth container, a fifth container, a sixth container, or any container of a system described herein.

An inoculum of a microbe may have a concentration of at least about, at most about, or about $1.0 \times 10^2$ cfu/ml, $1.0 \times 10^3$ cfu/ml, $1.0 \times 10^4$ cfu/ml, $1.0 \times 10^5$ cfu/ml, $1.0 \times 10^6$ cfu/ml, $1.0 \times 10^7$ cfu/ml, $1.0 \times 10^8$ cfu/ml, $1.0 \times 10^9$ cfu/ml, $1.0 \times 10^{10}$ cfu/ml, $1.0 \times 10^{11}$ cfu/ml, or $1.0 \times 10^{12}$ cfu/ml, or a range between any of these two values, prior to transferring to a first container of a digestion system. An inoculum of a microbe may have a concentration of at least about, at most about, or about $1.0 \times 10^2$ cfu/ml, $1.0 \times 10^3$ cfu/ml, $1.0 \times 10^4$ cfu/ml, $1.0 \times 10^5$ cfu/ml, $1.0 \times 10^6$ cfu/ml, $1.0 \times 10^7$ cfu/ml, $1.0 \times 10^8$ cfu/ml, $1.0 \times 10^9$ cfu/ml, $1.0 \times 10^{10}$ cfu/ml, $1.0 \times 10^{11}$ cfu/ml, or $1.0 \times 10^{12}$ cfu/ml, or a range between any of these two values, after incubation in a digestion system described herein.

In some embodiments, the inoculum comprises a single microbe. In some embodiments, the inoculum may comprise between 1 and 5 microbes. In some embodiments, the inoculum may comprise at least 1, at least 2, at least 3, at least 4, at least 5, or more microbes. In some embodiments, the inoculum may comprise at most 5, at most 4, at most 3, at most 2, or at most 1 microbe(s).

In some embodiments, the aqueous organic feedstock and microbial inoculum are transferred to the first reactor separately. In some embodiments, the aqueous organic feedstock is transferred to the first reactor before the microbial inoculum. In some embodiments, the microbial inoculum is transferred to the first reactor before the aqueous organic feedstock. In some embodiments, the aqueous organic feedstock and microbial inoculum are transferred to the first reactor together at the same time.

In some embodiments, the aqueous feedstock may not contain the target isolate strain (e.g., an inoculum of the microbe). For example, the aqueous feedstock may not contain the target isolate strain prior to transfer to a first container. The concentration of the target isolate microbial strain may be 0 cfu/ml. In some embodiments, the aqueous feedstock may contain the target isolate strain prior to transfer to a first container. In some embodiments, the aqueous feedstock may contain at most about 5%, at most about 4%, at most about 3%, at most about 2%, at most about 1%, at most about 0.5%, at most about 0.1%, at most about 0.05%, at most about, 0.04%, at most about 0.03%, at most about 0.02%, at most about 0.01%, at most about 0.008%, at most about 0.005%, at most about 0.004%, at most about 0.003%, at most about 0.002%, at most about 0.001%, at most about 0.0001%, or less than about 0.0001% of the target isolate strain. In some embodiments, the aqueous feedstock may not include the microbial strain (e.g., the nitrogen use efficiency-promoting microbial strain) at a concentration higher than about 1 CFU/ml, 2 CFU/ml, 3 CFU/ml, 4 CFU/ml, 5 CFU/ml, 6 CFU/ml, 7 CFU/ml, 8 CFU/ml, 9 CFU/ml, 10 CFU/ml, 11 CFU/ml, 12 CFU/ml, 13 CFU/ml, 14 CFU/ml, 15 CFU/ml, 20 CFU/ml, 25 CFU/ml, 30 CFU/ml, 40 CFU/ml, or 50 CFU/ml.

In some embodiments, the digestion system comprises a clarifier chamber or clarifier tank (CLF). The clarifier may comprise a single in-flow port and a single out-flow port. The clarifier may comprise a single in-flow port and multiple out-flow ports. In some embodiments, the clarifier comprises floc-folding wipers which rotate and release microbes that have been immobilized in the floc without introducing solids in the supernatant. The floc-folding wipers may move a working fluid in the clarifier to re-suspend microbes within the working fluid. In some embodiments, the microbes and/or an amount of target isolate strain may be re-suspended in the solution in the clarifier and transferred to the supernatant (e.g., base product). In some embodiments, the clarifier further comprises a flow line to return floc to the first reactor. The flow line may comprise a conduit from the clarifier to a container or combination of containers of the digestion system (e.g., a first container, a second container, a third container, a fourth container, a fifth container, a sixth container, or any combination thereof). The clarifier may return flow to any container (e.g., a first container, a second container, a third container, a fourth container, a fifth container, a sixth container, or any combination thereof) of a digestion system to provide a recirculation of working fluid. The working fluid recirculated from the clarifier may comprise a different microbial community (e.g., different amounts of microbes) than a working fluid of another container in the digestion system (e.g., a first working fluid, a second working fluid, a third working fluid, a fourth working fluid, a fifth working fluid, and/or a sixth working fluid). Without wishing to be bound by theory, the recirculation of flow from the clarifier to a container of the digestion system may help enrich a microbial community of a microbial consortium of a digestion system by providing working fluid from the clarifier to a different point (e.g., container) of the system. The recirculated working fluid may comprise organic materials, microbes of a microbial consortium, a target isolate, metabolites, or any combination thereof.

In the clarifier, a floc portion of a working fluid (e.g., a clarifier working fluid) may separate from a supernatant portion of a working fluid. The floc-folding wipers of the clarifier may help in separating the working fluid of the clarifier. In some embodiments, the separating may comprise gravity separation. The floc may settle on the bottom of the clarifier and the supernatant may be collected.

Biostimulant compositions produced by a digestion process as described herein may be used as-is or may be further processed before being used. For example, the outflow from the digestion system, referred to herein as "base product," may be concentrated, sterilized, filtered, pasteurized, or dehydrated before being used, or any combination of these. In some embodiments, the base product may be concentrated 2×, 3×, 4×, 5×, 6×, 7×, 8×, 9×, 10×, or more. In some embodiments, the base product may be filter sterilized to remove any bacteria or other microbes in the composition.

In an aspect, provided herein is a method comprising transferring an aqueous organic feedstock into a first container. An inoculum of a microbe may be transferred into a first container. An aqueous organic feedstock may be transferred into a first container. An aqueous organic feedstock and an inoculum of a microbe may be transferred into a first container. The first container may comprise a volume of a first working fluid. The aqueous organic feedstock may comprise a microbial consortium. The aqueous organic feedstock may comprise digestion products produced by digestion of an organic material. The aqueous organic feedstock may comprise a microbial consortium and digestion products produced by digestion of an organic material. The organic material may be digested by one or more microbes in the microbial consortium. The organic material may be digested by a population of microbes of the inoculum of a microbe. The digestion products described herein may comprise sugars (e.g., xylose, mannose, glucose, or any combination thereof), metabolites generated by microbes of the working fluid, fatty acids, dead microorganisms, fragments of dead microorganisms, microorganism fermentation products, enzymes, biological plant growth regulators, organic acids, chelators, or any combination thereof. The method may further comprise incubating the inoculum of a microbe under conditions that selectively promotes growth of the microbes and increases the population of the microbes. The method may further comprise incubating the inoculum of a microbe under conditions that selectively promotes growth of at least a portion of microbes in the microbial consortium. The terms "microbial digestion" and "digestion" can be used interchangeably.

In some embodiments, the digestion is anaerobic digestion. In some embodiments, the digestion is aerobic digestion. In some embodiments, the digestion is microaerobic digestion. In some embodiments, the digestion is aerobic digestion, microaerobic digestion, anaerobic digestion, or some combination thereof. Without wishing to be bound by theory, it is believed that during the digestion process, microbes digest the biomolecules and other nutrients present in the manure, yeast, kelp, and/or produce digestion products that include compounds that promote plant growth and soil health. In some embodiments of a digestion process, the organic feedstock may be mixed with water to make an organic feedstock for an anaerobic digestion system. The anaerobic digestion system may include a mixing tank in which the organic feedstock is mixed to make a fluid feed mixture or working fluid. In some embodiments, the fluid feed mixture may include manure, water, and *Saccharomyces cerevisiae* yeast. In some embodiments, anaerobic digestion comprises a process by which bacteria break down organic biomaterials in the absence of oxygen. The biostimulant may also contain microbes that contribute to the plant-beneficial properties of the biostimulant product. The microbes in the biostimulant product may be derived from the microbial population present in the organic feedstock.

In an exemplary system of the present disclosure, a series of reactors functions to contribute to the growth of an inoculum of a microbe (e.g., isolate) having desired plant growth promoting properties. A series of reactors (e.g., serialized assembly of reactors) may also function to contribute to the production of microbial metabolites having desired plant growth promoting properties. The digestion system described herein can enrich an inoculum of a target microbe, a population of microbes within a microbial consortium with plant-growth promotion properties (e.g., nitrogen use efficiency), a population of metabolites with plant-growth promotion properties (e.g., nitrogen use efficiency), or any combination thereof. This system provides added benefits to other digestion systems in that it can target a functional community of microbes and/or metabolites with specific functionality and enrich and/or maintain the community in the digestion system. The system can comprise two, three, four, five, or more reactors chambers (e.g., containers or chambers). Without wishing to be bound by theory, the serialized reactors enable the growth and enrichment of proprietary specialist target microbes with optimal plant growth promoting properties. The system may direct a flow of working fluid comprising an inoculum, carbon source, and/or nutrient source from an input organic feedstock to produce a base product (BP). A hydraulic source can flow into a reactor via in-flow port to comprise a first working fluid in a reactor tank. A hydraulic source may input into a first reactor or any reactor of the system. In some embodiments, a hydraulic source may input (e.g., flow) into a tank or container prior to a first reactor. In some embodiments, the container may comprise a "complete mixed reactor" (CMR). Other inputs into a system described herein may flow into any reactor of the system, including but not limited to a first reactor, a second reactor, a third reactor, or any other reactor following a first reactor.

An inoculum of a microbe may incubate in a reactor (e.g., container) of a digestion system described herein. In some embodiments, the inoculum of a microbe may be incubated under conditions that selectively enrich and/or retain the inoculum of the microbe in the digestion system. In some cases, the inoculum of the microbe may survive in the digestion system in a vegetative or sporulated state (e.g., a dormant state in the system). Without wishing to be bound by theory, the conditions of reactors of a digestions system (e.g., a hydraulic retention time of the system (e.g., flow rate), floc recirculation, pH level of the system, aerobic conditions, or any combination thereof) may shift the complex microbial consortia of the digestion system to enrich at least a portion of microbes within a microbial consortium with plant growth promotion properties (e.g., nitrogen use efficiency). Incubation of the inoculum of the microbe and/or the portion of microbes within a microbial consortium with plant growth promotion properties may further generate metabolites with plant growth promotion properties (e.g., nitrogen use efficiency).

The inoculum of the microbe may comprise a nitrogen use efficiency-promoting microbial strain that can be maintained as a population of the microbial strain in a bioreactor system described herein. Maintenance (e.g., survival) of an inoculum of a microbe may comprise a population of the microbe configured to maintain its initial amount in the environment caused by conditions in a reactor of the digestion system. Maintenance (e.g., survival) of an inoculum of a microbe may comprise an instance where an amount of the inoculum of the microbe is alive at the end of a retention period of the digestion system (e.g., in a reactor or clarifier chamber). For example, following initial inoculation, a population of a nitrogen use efficiency-promoting microbial strain may survive incubation in conditions (e.g., nutrients, flow rate, pH, aerobic parameters, or any combination thereof) of a digestion system described herein. In some embodiments, at least a portion of microbes of the microbial consortium may enrich (e.g., grow or increase in number). These microbes of the portion of microbes in the microbial consortium may have nitrogen use efficiency capacities. A proportion of the nitrogen use efficiency-promoting microbial strain and nitrogen use efficiency-promoting microbes of the microbial consortium relative to a total population count of bacteria may be maintained in a first container of a digestion system. A proportion of the nitrogen use efficiency-promoting microbial strain and nitrogen use efficiency-promoting microbes of the microbial consortium relative to a total population count of bacteria may be maintained in a second, third, fourth, fifth, sixth, seventh, or eighth container of a digestion system. A maintained population of a nitrogen use efficiency-promoting microbial strain may change its amount in a working fluid of a digestion system less than about 0.001%, less than about 0.01%, less than about 0.1%, less than about 0.5%, less than about 1%, less than about 5%, or less than about 10% over a duration of time. The duration of time may comprise at least about, at most about, or about 1 hour, 2 hours, 3 hours, 4 hours, 5 hours, 6 hours, 12 hours, 18 hours, 24 hours, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 3 months, 4 months, 5 months, 6 months, 9 months, 12 months, 18 months, 24 months, 3 years, 4 years, 5 years, 10 years, or a range between any of these two values.

In some cases, parameters comprising nutrients added to the system, a hydraulic retention time of the system (e.g., flow rate), floc recirculation, pH level of the system, aerobic conditions, or any combination thereof may promote the growth of microbes or at least a portion of microbes in the microbial consortium. These microbes may be nitrogen use efficiency-promoting microbes. An amount of microbes or at least a portion of microbes in the microbial consortium may grow by at least about, at most about, or about 0.00010%, 0.0010%, 0.010%, 0.10%, 1%, 2%, 3%, 4%, 5%, 10%, 15%, 20%, or 30%, or a range between any of these values, as they incubate in conditions of the reactors of the digestion system (e.g., nutrients added to the system, a hydraulic retention time of the system (e.g., flow rate), floc recirculation, pH level of the system, aerobic conditions, or any combination thereof). In some cases, at least a portion of nitrogen use efficiency-promoting microbes in the microbial consortium may enrich and/or grow in the system without addition of the inoculum of the microbe.

Without wishing to be bound by theory, parameters comprising nutrients added to the system, a hydraulic retention time of the system (e.g., flow rate), floc recirculation, pH level of the system, aerobic conditions, or any combination thereof, may inhibit growth of a microbe and/or a population of microbes. Without wishing to be bound by theory, parameters comprising nutrients added to the system, a hydraulic retention time of the system (e.g., flow rate), floc recirculation, pH level of the system, aerobic conditions, or any combination thereof, may inhibit growth of a microbe and/or a population of microbes and enhance growth of a target microbe and/or target population of microbes (e.g., nitrogen use efficiency-promoting microbes). Without wishing to be bound by theory, the parameters of the bioreactor system may cause a selective shift in a microbial population to favor microbes with a targeted functionality (e.g., nitrogen use efficiency). Nutrients (e.g., macronutrients, micronutrients, inorganic nutrients, or any combination thereof) can be present in the digestion system to provide an environment for bacterial growth. The nitrogen-use efficiency promoting microbes can comprise the inoculum of the microbe (e.g., a population of a nitrogen-use efficiency promoting microbial strain), nitrogen-use efficiency promoting microbes of a microbial consortium, nitrogen-use efficiency promoting metabolites produced by the inoculum of the microbe and/or the nitrogen-use efficiency promoting microbes of the microbial consortium, or any combination thereof.

An inoculum of a microbe described herein may contact (e.g., be applied to) a plant. In some embodiments, the contacting of an inoculum of a microbe to a plant may enhance at least one plant growth promotion property of the plant. In some embodiments, one, two, three, four, or more inoculums of a microbe may be transferred to a digestion system. An inoculum of a microbe and another inoculum of a microbe may be the same. An inoculum of a microbe and another inoculum of a microbe may be different. In some embodiments, the inoculum of the microbe and the aqueous organic feedstock are transferred to a container of the digestion system at the same time. In some embodiments, the inoculum of the microbe and the aqueous organic feedstock are not transferred to a container of the digestion system at the same time. In some embodiments, the inoculum of the microbe is transferred to a container of the digestion system prior to the aqueous organic feedstock. In some embodiments, the inoculum of the microbe is transferred to a container of the digestion system after the aqueous organic feedstock.

As a working fluid flows through a digestion system, an absolute number of nitrogen use efficiency-promoting microbes may increase. In some embodiments, an absolute number of nitrogen use efficiency-promoting microbes can be higher in a second container compared an absolute number of nitrogen use efficiency-promoting microbes in a first container. In some embodiments, an absolute number of nitrogen use efficiency-promoting microbes can be higher in a third container compared an absolute number of nitrogen use efficiency-promoting microbes in a first container. In some embodiments, an absolute number of nitrogen use efficiency-promoting microbes can be higher in a fourth container compared an absolute number of nitrogen use efficiency-promoting microbes in a first container. In some embodiments, an absolute number of nitrogen use efficiency-promoting microbes can be higher in a fifth container compared an absolute number of nitrogen use efficiency-promoting microbes in a first container. In some embodiments, an absolute number of nitrogen use efficiency-promoting microbes can be higher in a sixth container compared an absolute number of nitrogen use efficiency-promoting microbes in a first container. In some embodiments, an absolute number of nitrogen use efficiency-promoting microbes can be higher in a seventh container compared an absolute number of nitrogen use efficiency-promoting microbes in a first container. In some embodiments, an absolute number of nitrogen use efficiency-promoting microbes can be higher in an eighth container compared an absolute number of nitrogen use efficiency-promoting microbes in a first container. In some embodiments, an absolute number of nitrogen use efficiency-promoting microbes can be higher in a ninth container compared an absolute number of nitrogen use efficiency-promoting microbes in a first container. In some embodiments, an absolute number of nitrogen use efficiency-promoting microbes can be higher in a tenth container compared an absolute number of nitrogen use efficiency-promoting microbes in a first container.

As working fluid flows through a digestion system, a proportion of nitrogen use efficiency-promoting microbes relative to a total population of bacteria may increase. In some embodiments, a proportion of nitrogen use efficiency-promoting microbes relative to a total population of bacteria can be higher in a second container compared a proportion of nitrogen use efficiency-promoting microbes relative to a total population of bacteria in a first container. In some embodiments, a proportion of nitrogen use efficiency-promoting microbes relative to a total population of bacteria can be higher in a third container compared a proportion of nitrogen use efficiency-promoting microbes relative to a total population of bacteria in a first container. In some embodiments a proportion of nitrogen use efficiency-promoting microbes relative to a total population of bacteria can be higher in a fourth container compared a proportion of nitrogen use efficiency-promoting microbes relative to a total population of bacteria in a first container. In some embodiments, a proportion of nitrogen use efficiency-promoting microbes relative to a total population of bacteria can be higher in a fifth container compared a proportion of nitrogen use efficiency-promoting microbes relative to a total population of bacteria in a first container. In some embodiments, a proportion of nitrogen use efficiency-promoting microbes relative to a total population of bacteria can be higher in a sixth container compared a proportion of nitrogen use efficiency-promoting microbes relative to a total population of bacteria in a first container. In some embodiments, a proportion of nitrogen use efficiency-promoting microbes relative to a total population of bacteria can be higher in a seventh container compared a proportion of nitrogen use efficiency-promoting microbes relative to a total population of bacteria in a first container. In some embodiments, a proportion of nitrogen use efficiency-promoting microbes relative to a total population of bacteria can be higher in an eighth container compared a proportion of nitrogen use efficiency-promoting microbes relative to a total population of bacteria in a first container. In some embodiments, a proportion of nitrogen use efficiency-promoting microbes relative to a total population of bacteria can be higher in a ninth container compared a proportion of nitrogen use efficiency-promoting microbes relative to a total population of bacteria in a first container. In some embodiments, a proportion of nitrogen use efficiency-promoting microbes relative to a total population of bacteria can be higher in a tenth container compared a proportion of nitrogen use efficiency-promoting microbes relative to a total population of bacteria in a first container.

An inoculum of a microbe may generate metabolites in a digestion system as described herein. Microbes of the microbial consortium and/or the inoculum of the microbe may be metabolized by catalytic enzymes to produce metabolites. Metabolites may be generated by microbial metabolism. Metabolites may be generated by enzymes catalyzing biochemical reactions of the organic substrates of the aqueous organic feedstock in a working fluid of a digestion system as described herein. The metabolites generated by the inoculum of the microbe may have a plant growth promotion property. The metabolites generated by the inoculum of the microbe may have two or more plant growth promotion properties. The plant growth promotion properties may comprise shoot biomass, root biomass, nutrient uptake, crop yield, photosynthesis, deaminase activity, acid production, leaf area, chlorophyll content, heat tolerance, cold tolerance, drought tolerance, or salt tolerance, or total biomass. Metabolites may be used in biostimulant compositions and/or may be applied to plants.

In some embodiments, the aqueous organic feedstock comprises metabolites. In some embodiments, the aqueous organic feedstock comprises metabolites produced by microbes endogenous to the organic feedstock. Primary metabolites can include carbohydrates, proteins, fats, vitamins, and nucleic acid components. Metabolites can further comprise alkaloids, amino acids, biogenic amines, carboxylic acids, cresols, terpenoids, phenols (e.g., flavonoids, coumarins, tannins, lignans, stilbenes, or chromones), polyketides, eicosanoids, hormones or derivatives thereof, indoles or derivatives thereof, nucleobases, citric acid, ceramides, diglycerides, triglycerides, amides, alkanes, alcohols, stearates, sterols, organic acids or fatty acids. In some embodiments, metabolites comprise sugars and/or fatty acids. Sugars can comprise fructose, hexose, galactose, glucose, lactose, maltose, sucrose, xylose, or any combination thereof. Fatty acids can comprise stearic acid, lauric acid, myristic acid, palmitic acid, octadecenoic acid, octadecadienoic acid, oleic acid, arachidic acid, behenic acid, erucic acid, adrenic acid, tricosanoic acid, lignoceric acid, nervonic acid, nonadecanoic acid, arachidic acid, myristolic acid, hydroxylated myristic acid, or any combination thereof.

Metabolites generated by the inoculum of the microbe or by at least a portion of microbes of the microbial consortium may be present in a supernatant (e.g., base product) of a digestion system. In some embodiments, the metabolites may be present by weight in a volume of solution (e.g., in mg in 100 ml). In some embodiments, a weight of metabolites per 100 ml of a base product solution can be at least about 10 mg, at least about 20 mg, at least about 30 mg, at least about 40 mg, at least about 50 mg, at least about 60 mg, at least about 70 mg, at least about 80 mg, at least about 90 mg, at least about 100 mg, at least about 120 mg, at least about 140 mg, at least about 160 mg, at least about 180 mg, at least about 200 mg, at least about 220 mg, at least about 240 mg, at least about 260 mg, at least about 280 mg, at least about 300 mg, at least about 400 mg, at least about 500 mg, or greater than about 500 mg. In some embodiments, a weight of metabolites per 100 ml of a base product solution can be at most about 500 mg, at most about 400 mg, at most about 300 mg, at most about 280 mg, at most about 260 mg, at most about 240 mg, at most about 220 mg, at most about 200 mg, at most about 180 mg, at most about 160 mg, at most about 140 mg, at most about 120 mg, at most about 100 mg, at most about 90 mg, at most about 80 mg, at most about 70 mg, at most about 60 mg, at most about 50 mg, at most about 40 mg, at most about 30 mg, at most about 20 mg, at most about 10 mg, or less than about 10 mg. In some embodiments, a weight of metabolites per 100 ml of a base product solution can be from about 10 mg to about 500 mg. In some embodiments, a weight of metabolites per 100 ml of a base product solution can be from about 10 mg to about 20 mg, about 10 mg to about 30 mg, about 10 mg to about 40 mg, about 10 mg to about 50 mg, about 10 mg to about 75 mg, about 10 mg to about 100 mg, about 10 mg to about 125 mg, about 10 mg to about 150 mg, about 10 mg to about 175 mg, about 10 mg to about 250 mg, about 10 mg to about 500 mg, about 20 mg to about 30 mg, about 20 mg to about 40 mg, about 20 mg to about 50 mg, about 20 mg to about 75 mg, about 20 mg to about 100 mg, about 20 mg to about 125 mg, about 20 mg to about 150 mg, about 20 mg to about 175 mg, about 20 mg to about 250 mg, about 20 mg to about 500 mg, about 30 mg to about 40 mg, about 30 mg to about 50 mg, about 30 mg to about 75 mg, about 30 mg to about 100 mg, about 30 mg to about 125 mg, about 30 mg to about 150 mg, about 30 mg to about 175 mg, about 30 mg to about 250 mg, about 30 mg to about 500 mg, about 40 mg to about 50 mg, about 40 mg to about 75 mg, about 40 mg to about 100 mg, about 40 mg to about 125 mg, about 40 mg to about 150 mg, about 40 mg to about 175 mg, about 40 mg to about 250 mg, about 40 mg to about 500 mg, about 50 mg to about 75 mg, about 50 mg to about 100 mg, about 50 mg to about 125 mg, about 50 mg to about 150 mg, about 50 mg to about 175 mg, about 50 mg to about 250 mg, about 50 mg to about 500 mg, about 75 mg to about 100 mg, about 75 mg to about 125 mg, about 75 mg to about 150 mg, about 75 mg to about 175 mg, about 75 mg to about 250 mg, about 75 mg to about 500 mg, about 100 mg to about 125 mg, about 100 mg to about 150 mg, about 100 mg to about 175 mg, about 100 mg to about 250 mg, about 100 mg to about 500 mg, about 125 mg to about 150 mg, about 125 mg to about 175 mg, about 125 mg to about 250 mg, about 125 mg to about 500 mg, about 150 mg to about 175 mg, about 150 mg to about 250 mg, about 150 mg to about 500 mg, about 175 mg to about 250 mg, about 175 mg to about 500 mg, or about 250 mg to about 500 mg.

The term "organic feedstock" described herein can refer to raw biomaterials such as carbon compounds, proteins, and/or carbohydrates. In some embodiments, the organic feedstock may comprise organic substrates comprising cottonseed, algae, neem, orange seed, linseed, jojoba, kusum, rubber seed, alfalfa, sugarcane, Opuntia, coffee, Deccan hemp, or any combination thereof. In some embodiments, the feedstock can comprise an inorganic feedstock. In some embodiments, the organic feedstock may include, but is not limited to, manure, kelp, lignocellulose, wastewater biosolids, food waste, energy crops, glucose solution, ammonium sulfate, oils, fats, grease. In some embodiments, the feedstock is added at the beginning of the system (e.g., into a first reactor and/or a CMR). In some embodiments, the feedstock is added in a middle reactor of the system (e.g., not in the first or last reactor of the system). In some embodiments, the feedstock is added once to the system. In some embodiments, the feedstock is added two, three, four, or more times to the system. In some embodiments, the organic feedstock is a composition of one raw biomaterial. In some embodiments, the organic feedstock is a blend of two, three, four, five, six, seven, eight, nine, ten, or more biomaterials.

Organic feedstock comprising carbon and nitrogen sources can flow into a reactor tank. Organic feedstock comprising carbon and nitrogen sources can flow into a reactor tank via a conduit (e.g., a pipe). In some embodiments, a reactor tank circulates working fluid within itself to recycle working fluid, wherein reactor tanks can comprise out-flow pipes to circulate and recycle working fluid within each tank. Ports and piping between tanks can assist in transferring working fluid to adjacent reactor tanks. A working fluid in a final clarifier of a system may transfer from the reactor tank to a clarifier may produce a supernatant (e.g., base product). Working fluid flows through the serialized reactor system which can aid in selective growth of the added isolate and other microbes present that have the same property as the added isolate. Base product from the clarifier can be accessed and further analyzed for microbial composition. In a digestion system described herein, a working fluid may flow from a mixing chamber through at least one reaction and to a clarifier chamber.

An organic feedstock can comprise digestion products from digestion of organic substrates present in the organic feedstock. Organic substrates may improve stability of the fluid feed mixture. Organic substrates can comprise coconut coir, peat moss, hemp, wood fiber, or any combination thereof. In some embodiments, organic substrates comprise raw biomaterials present in the aqueous organic feedstock. A digestion system may comprise a plurality of microbes and/or microorganisms derived from digestion of organic substrates in an aqueous organic feedstock.

An organic feedstock described herein may comprise various organic and/or biological materials. In some embodiments, the organic feedstock further comprises *Saccharomyces cerevisiae* yeast, *Saccharomyces arboricola* yeast, *Saccharomyces mikatae* yeast, *Saccharomyces jurei* yeast, *Saccharomyces eubayanus* yeast, *Saccharomyces kudriavzevii* yeast, *Saccharomyces uvarum* yeast, or any combination thereof. In some embodiments, the organic feedstock further comprises a lignocellulosic material. In some embodiments, the organic feedstock may be an aqueous mixture of at least one feedstock material and water. In some embodiments, the organic feedstock may be an aqueous mixture of cow manure, *S. cerevisiae* yeast, water, or any combination thereof. An organic feedstock can be an aqueous organic feedstock (e.g., an organic feedstock comprising water).

Parameters of the digestion system, such as flow rate and the solids content of the organic feedstock, may be varied to achieve desired properties in the outflow biostimulant base product. In some embodiments, the hydraulic source is water. In some embodiments, the hydraulic source is a base product of another system. In some embodiments, the hydraulic source is a combination of water and a base product of another system. Water from the hydraulic source can be added to the organic feedstock of the digestion system to make an aqueous organic feedstock.

In some embodiments, the aqueous organic feedstock may further comprise a inorganic substrate. In some embodiments, the aqueous organic feedstock may include more than one inorganic substrate. The inorganic substrate may improve stability of the fluid feed mixture. In some embodiments, the inorganic substrate comprises sand, vermiculite, perlite, diatomaceous earth, pumice, or any combination thereof. In some embodiments, the inorganic substrates comprises a mineral. In some embodiments, the inorganic substrate comprises rock phosphate.

In some embodiments, loading inputs into a reactor can comprise a carbon source, a nitrogen source, a flour, an isolate, or any combination thereof. In some embodiments, the flour is soy flour. In some embodiments, the loading inputs comprise recycled floc from the system. In some embodiments, the loading inputs comprise a whole broth (WB). The inoculum of a microbe as described herein may metabolize the carbon source. Metabolism of carbon by the inoculum of the microbe may comprise transfer of carbon-based moieties of the carbon source to substrates in the working fluid.

The inoculum of a microbe as described herein may metabolize the nitrogen source. Metabolism of nitrogen by the inoculum of the microbe may comprise transfer of nitrogen-based moieties of the nitrogen source to substrates in the working fluid. In some embodiments, the carbon source may be transferred to a first container of the digestion system. In some embodiments, the carbon source may be transferred to a second, third, fourth, fifth, or sixth container of the digestion system. In some embodiments, the nitrogen source may be transferred to a first container of the digestion system. In some embodiments, the nitrogen source may be transferred to a second, third, fourth, fifth, or sixth container of the digestion system.

In some embodiments, the organic feedstock is mixed within a reactor. In some embodiments, the organic feedstock is mixed outside of a reactor. In some embodiments, the organic feedstock is mixed between one, two, three, or more reactors. In some embodiments, the organic feedstock is a homogenous mixture.

In some embodiments, the organic feedstock further comprises a microbial consortium. The terms "microbe", "microbial strain" and "microorganism" may refer to microscopic organisms, including, but not limited to bacteria, fungi, lichens, algae, protozoa, archaea, and/or molds. The terms "microbe" and microorganism" may be used interchangeably herein. The organic feedstock can comprise a microbial consortium with 2, 3, 4, 5, 6, 7, 8, 9, 10, or more microorganisms. The organic feedstock can comprise a microbial consortium with 2, 3, 4, 5, 6, 7, 8, 9, 10, or more groups of microorganisms. The organic feedstock can comprise a microbial consortium with 1 group of microorganisms. The microbial consortium can comprise different microorganisms. The microbial consortium can comprise the same microorganism. The microbes in the consortia may be derived from the microbes originally present within the organic feedstock. The microbes may digest the manure, yeast, other organic raw materials, or any combination thereof to produce digestion products.

In some embodiments, microbes can be added to the start of the system (e.g., into the first reactor). In some embodiments, microbes can be added to the middle of the system (e.g., into a reactor that is not the first reactor or the final reactor of the system) or microbes can be added to the end of the system (e.g., into the final reactor). Microbes can be added concurrently with the organic feedstock. Microbes can be added separately from the organic feedstock. In some embodiments, microbes may be added to the system with the organic feedstock in the same reactor. In some embodiments, microbes may be added to the system with the organic feedstock in different reactors. In some embodiments, microbes may be added to the system prior to the organic feedstock. In some embodiments, microbes may be added to the system after the organic feedstock. In some embodiments, a period of time between addition of microbes to the system and addition of organic feedstock to the system can be at least about 1 minute, at least about 5 minutes, at least about 10 minutes, at least about 15 minutes, at least about 20 minutes, at least about 30 minutes, at least about 40 minutes, at least about 50 minutes, or at least about 1 hours. In some embodiments, a period of time between addition of microbes to the system and addition of organic feedstock to the system can be at most about 2 hours, at most about 1 hours, at most about 45 minutes, at most about 30 minutes, at most about 15 minutes, at most about 10 minutes, at most about 5 minutes, at most about 1 minute, or at most about 30 seconds.

A microbe may have nutrient solubilization properties and/or plant growth promotion properties. For example, a microbe may increase plant growth, increase shoot and/or root biomass, increase crop yield, increase soil enzymatic activity, increase photosynthetic efficiency, lower heavy metal uptake, decrease soil pH, or any combination thereof. A microbe may enhance plant growth on land with high salinity, on land with heavy metal contamination, or on land with drought conditions. A microbe (e.g., isolate) described herein may have nitrogen use efficiency properties.

In some embodiments, the digestion system may comprise a retention time. A retention time may comprise a time an inoculum of a microbe spends in a digestion system or a time an inoculum of a microbe spends following transfer into a first container and until collection from the digestion system. A longer retention time may be advantageous for growth or enrichment of an inoculum of a microbe of the digestion system. A shorter retention time may be advantageous for growth or enrichment of an inoculum of a microbe of the digestion system. A retention time of a digestion system may comprise at least about, at most about, or about 1 day, 2 days, 3 days, 4 days, 5 days, 6 days, 1 week, 2 weeks, 3 weeks, 4 weeks, 1 month, 2 months, 3 months, 6 months, 9 months, 1 year, 2 years, 3 years, 4 years, 5 years, or 10 years, or a range between any of these values. The terms "retention time" and "hydraulic retention time" may be used interchangeably.

In the first reactor, the working fluid may be agitated at a rate that allows heavier or undigested solids to settle to the bottom. An outlet at the top of the first reactors may allow the fluid to flow into the second reactor. An outlet at the bottom of the first reactor may transfer the settled solids back into a reactor tank. Each of the reactors in the series of reactors may have submerged scaffolding that provide a surface for biofilm growth. The scaffolding can be referred to as "fixed media substrates". The flow of fluid from reactor to reactor may comprise a plug flow model, in which particles of an input fluid have the same velocity and direction of motion. In some embodiments, the flow of fluid in the digestion system is driven by gravity. In some embodiments, the flow of fluid in the digestion system is driven by a pump. The outflow from the top of the last reactor, may be used to create a product. Products of the methods and systems as described herein can be biostimulants. Biostimulants can promote plant growth or improve soil quality.

B. Reactors

A digestion process to produce the biostimulant may be performed in a digestion system that includes a series of tanks, containers, or vessels (e.g., reactors) through which the feedstock continuously flows. A reactor can be a fluidly connected container, system, vessel, or tank in which microbial consortia including the microbes, isolates, and/or microorganisms as described herein can be grown. A reactor can be separate or continuous. A reactor may be a physical containment system arranged in a discrete order to favor growth of particular microbes. Types of reactors can include, but are not limited to, fluidized-bed reactors (FBRs) or packed-bed reactors (PBRs).

In some embodiments, reactors may be arranged so that fluid can flow from an outflow port of a reactor into an adjacent reactor or tank. Fluid from near the top of the working fluid in a reactor may flow into the next reactor continuously. Fluid from the middle of a reactor may flow into the next reactor continuously. Fluid from the bottom of a reactor may flow into the next reactor continuously. Fluid may also be reintroduced from any outflow source into the same reactor. In some embodiments, an outflow port is between 0.1 and 35 inches below the top of the working fluid within a reactor. In some embodiments, an outflow port is at least about 1 inch, at least about 2 inches, at least about 5 inches, at least about 10 inches, at least about 20 inches, at least about 50 inches, at least about 100 inches, at least about 250 inches, at least about 500 inches, at least about 750 inches, at least about 1,000 inches, at least about 2,500 inches, at least about 5,000 inches, at least about 7,500 inches, or at least about 10,000 inches below the top of the working fluid within a reactor. In some embodiments, an outflow port is at most about 10,000 inches, at most about 7,500 inches, at most about 5,000 inches, at most about 2,500 inches, at most about 1,000 inches, at most about 750 inches, at most about 500 inches, at most about 250 inches, at most about 100 inches, at most about 50 inches, at most about 20 inches, at most about 10 inches, at most about 5 inches, at most about 2 inches, or at most about 1 inch below the top of the working fluid within a reactor. In some embodiments, the rate of outflowing product from a digestion system may match the rate of inflowing feedstock, providing for a hydraulically balanced flow throughout the system. A reactor within the system may have a unique, stable microbial consortium with distinct physiological characteristics and digestion capabilities as compared to consortia in other tanks in the system. A reactor within the system may have the same microbial consortium with similar physiological characteristics and digestion capabilities as another reactor within the system. Each reactor within the system may have the same volume capacity. Each reactor within the system may have a different volume capacity. The digestion system may comprise at least two reactors. The digestion system may comprise 2, 3, 4, 5, 6, 7, 8, 9, 10, or more reactors. Reactors of a digestion system may be arranged as a serialized assembly of reactors. A serialized assembly of reactors may have conduits (e.g., ports or outputs) connecting each reactor to an adjacent reactor and/or container. A serialized assembly of reactors may have a continuous flow of working fluid through each reactor to the adjacent reactor.

In some embodiments, a reactor may have a single in-flow port and a single out-flow port. In some embodiments, a reactor may have multiple in-flow ports and out-flow ports. In some embodiments, a reactor may have a single in-flow port and multiple out-flow ports. In some embodiments, a reactor may have multiple in-flow ports and a single out-flow port. A reactor may have another in-flow port to provide a carbon source and/or consortium inoculum. An in-flow port may be present at any location of a reactor of the digestion system. An in-flow port may be present at the top of the reactor or at the bottom of the reactor. An out-flow port may be present at the top of the reactor or at the bottom of the reactor. In some embodiments, the out-flow ports or in-flow ports described herein comprise pipes, pumps, ventilations, or other conduits for transferring fluid from one vessel to another.

A reactor may have a single fluid connection. A reactor may have multiple fluid connections. The fluid connections may be present at the top of the working fluid in each reactor or near the top of the working fluid in each reactor. In some embodiments, the reactor may have flow from the bottom of the container back to the top to prevent build-up of sludge in the bottom of the reactor. In some embodiments, a reactor may have stirrers in the bottom of the container. In some embodiments, a reactor may have wipers in the bottom of the container. The wipers may stir the feedstock and prevent clogging within the reactor. The wipers may fold floc and ease floc return.

In some embodiments, the reactors may comprise packed bed reactors. In some embodiments, each of the packed bed reactors has an open cell design to allow free movement of working fluid. A fixed media (e.g., scaffolding) may be secured to the inside of each packed bed reactor. The fixed media comprises materials that increase the contact surface area for the communities of microbes with working fluid. The fixed media also provides a stable platform for anchoring biofilm. The packed bed reactors may be packed with scaffolding to increase surface area within the reactor. The scaffolding within the reactor may increase biofilm. The packed bed reactor may improve contact between the biofilm and substrates within the reactor. The fixed media can be of several types, including durable plastic, polyvinyl chloride (PVC), metal, metal alloy, glass, glass compounds, fiberglass, or any suitably robust inert material. The design and configuration of the fixed media can assume various geometric patterns that allow working fluid to freely move through each packed bed reactor and prevents fouling. Free flow supports controlled hydraulic shearing which in time promotes even distribution of working fluid. In this embodiment, the fixed media is dispersed throughout a cross sectional area of each packed bed reactor.

The scaffolding may comprise tubes, rings, or other packing materials. In some embodiments, the packed bed reactors provided herein may comprise a bundle of tubes or columns. In some embodiments, the scaffolding may comprise hexagonal, grid-like, perforated tubing, or any combination thereof. Without wishing to be bound by theory, hexagonal, grid-like, and/or perforated scaffolding can increase the surface area and the flow through the columns within the container. In some embodiments, the tubes or columns of the scaffolding can comprise a diameter between 0.25 and 50 inches. In some embodiments, the scaffolding can comprise a diameter of at least about 0.5 inches, at least about 0.6 inches, at least about 0.7 inches, at least about 0.8 inches, at least about 0.9 inches, at least about 1 inch, at least about 2 inches, at least about 3 inches, at least about 4 inches, at least about 5 inches, at least about 10 inches, at least about 15 inches, at least about 20 inches, at least about 25 inches, at least about 30 inches, at least about 40 inches, at least about 50 inches, at least about 60 inches, or at least about 75 inches. In some embodiments, the scaffolding can comprise a diameter of at most about 75 inches, at least about 60 inches, at most about 50 inches, at most about 40 inches, at most about 30 inches, at most about 25 inches, at most about 20 inches, at most about 15 inches, at most about 10 inches, at most about 5 inches, at most about 4 inches, at most about 3 inches, at most about 2 inches, at most about 1 inches, at most about 0.9 inches, at most about 0.8 inches, at most about 0.7 inches, at most about 0.6 inches, or at most about 0.5 inches. Without wishing to be bound by theory, a system with packed bed reactors may improve production of bacterial isolates or other microbes. In some embodiments, reactors without scaffolding (i.e., reactors that are not packed bed reactors) improve production of bacterial isolates or other microbes or improves digestion of digestible substrates.

In some embodiments, the reactors may comprise fluidized bed reactors. In fluidized bed reactors, solid particles may be circulated within working fluid of the reactors, which may provide a surface for microbial colonization. Such particles may include, for example, particles of an inorganic substrate such as rock phosphate particles. In some embodiments, the fluidized bed reactors may be the same volume. In some embodiments, the fluidized bed reactors may be different volumes. In some embodiments, the fluidized bed reactors increase uniformity of particle mixing within the digestion system. The solid material of the fluidized bed reactor can have intrinsic fluid-like properties and allow for a more complete mixing. Reduction or elimination of radial and axial concentration gradients can provide for better fluid-solid contact and can achieve better uniformity of particle mixing. In some embodiments, the fluidized bed reactors increase the uniformity of temperature gradients within the digestion system. Without wishing to be bound by theory, the open container of the fluidized bed reactor can provide for a reduction in isolated hot or cold spots in the container, allowing for a uniform temperature distribution of the fluid.

The flow rate of the digestion system may be chosen to allow for sufficient dwell time within each of the reactor for a stable and unique microbial consortium to form within each of the reactors. In some embodiments, working fluid in each reactor is continuously recycled at a rate ratio in a range of approximately 25:1 to 35:1, 25 to 35 gallons per minute of the recycle rate to one gallon per minute of the hydraulic feed rate. In some embodiments, working fluid in each reactor is continuously recycled at a rate ratio of at least about, at most about, or about 10:1, at least about 12:1, at least about 14:1, at least about 16:1, at least about 18:1, at least about 20:1, at least about 22:1, at least about 24:1, at least about 26:1, at least about 28:1, at least about 30:1, at least about 32:1, at least about 34:1, at least about 36:1, at least about 38:1, at least about 40:1, at least about 45:1, or at least about 50:1, or a range between any of these two values. Working fluid may be recycled by a pump to prevent solids settling and to provide sufficient velocity and hydraulic shear to prevent excessive buildup and sloughing of biofilm. A digestion system provided herein may comprise a first flow rate, second flow rate, third flow rate, fourth flow rate, fifth flow rate, sixth flow rate, or seventh flow rate.

Reactors can be maintained at specific temperatures which may aid in digestion and growth of microbial consortia within the system. In some embodiments, a temperature of a reactor is at least about 15° C., at least about 20° C., at least about 21° C., at least about 22° C., at least about 23° C., at least about 24° C., at least about 25° C., at least about 26° C., at least about 27° C., at least about 28° C., at least about 29° C., at least about 30° C., at least about 35° C., at least about 40° C., at least about 45° C., or at least about 50° C. In some embodiments, a temperature of a reactor is at most about 50° C., at most about 45° C., at most about 40° C., at most about 35° C., at most about 30° C., at most about 29° C., at most about 28° C., at most about 27° C., at most about 26° C., at most about 25° C., at most about 24° C., at most about 23° C., at most about 22° C., at most about 21° C., at most about 20° C., or at most about 15° C.

In some embodiments, a temperature of a reactor is about 15° C. to about 45° C. In some embodiments, a temperature of a reactor is about 15° C. to about 20° C., about 15° C. to about 22° C., about 15° C. to about 24° C., about 15° C. to about 26° C., about 15° C. to about 28° C., about 15° C. to about 30° C., about 15° C. to about 32° C., about 15° C. to about 34° C., about 15° C. to about 36° C., about 15° C. to about 40° C., about 15° C. to about 45° C., about 20° C. to about 22° C., about 20° C. to about 24° C., about 20° C. to about 26° C., about 20° C. to about 28° C., about 20° C. to about 30° C., about 20° C. to about 32° C., about 20° C. to about 34° C., about 20° C. to about 36° C., about 20° C. to about 40° C., about 20° C. to about 45° C., about 22° C. to about 24° C., about 22° C. to about 26° C., about 22° C. to about 28° C., about 22° C. to about 30° C., about 22° C. to about 32° C., about 22° C. to about 34° C., about 22° C. to about 36° C., about 22° C. to about 40° C., about 22° C. to about 45° C., about 24° C. to about 26° C., about 24° C. to about 28° C., about 24° C. to about 30° C., about 24° C. to about 32° C., about 24° C. to about 34° C., about 24° C. to about 36° C., about 24° C. to about 40° C., about 24° C. to about 45° C., about 26° C. to about 28° C., about 26° C. to about 30° C., about 26° C. to about 32° C., about 26° C. to about 34° C., about 26° C. to about 36° C., about 26° C. to about 40° C., about 26° C. to about 45° C., about 28° C. to about 30° C., about 28° C. to about 32° C., about 28° C. to about 34° C., about 28° C. to about 36° C., about 28° C. to about 40° C., about 28° C. to about 45° C., about 30° C. to about 32° C., about 30° C. to about 34° C., about 30° C. to about 36° C., about 30° C. to about 40° C., about 30° C. to about 45° C., about 32° C. to about 34° C., about 32° C. to about 36° C., about 32° C. to about 40° C., about 32° C. to about 45° C., about 34° C. to about 36° C., about 34° C. to about 40° C., about 34° C. to about 45° C., about 36° C. to about 40° C., about 36° C. to about 45° C., or about 40° C. to about 45° C.

Reactors may be maintained under aerobic, microaerobic, or anaerobic conditions. The series of reactors in a digestion system may have different aerobic conditions. The series of reactors in a digestion system may have the same aerobic conditions. In some embodiments, a reactor may have the same aerobic condition as an adjacent reactor. In some embodiments, a reactor may have a different aerobic condition than an adjacent reactor. In some embodiments, a digestion system may have aerobic, microaerobic, anaerobic conditions, or any combination thereof.

In some embodiments, aerobic conditions comprise conditions with a dissolved oxygen measurement of greater than 2 mg/L. In some embodiments, aerobic conditions comprise conditions with a dissolved oxygen measurement of at least about 2 mg/L, at least about 3 mg/L, at least about 4 mg/L, at least about 5 mg/L, at least about 6 mg/L, at least about 7 mg/L, at least about 8 mg/L, at least about 9 mg/L, at least about 10 mg/L, at least about 12 mg/L, at least about 14 mg/L, at least about 15 mg/L, or greater than about 15 mg/L. In some embodiments, aerobic conditions comprise conditions with a dissolved oxygen measurement from about 2 mg/L to about 15 mg/L. In some embodiments, aerobic conditions comprise conditions with a dissolved oxygen measurement from about 2 mg/L to about 3 mg/L, about 2 mg/L to about 4 mg/L, about 2 mg/L to about 5 mg/L, about 2 mg/L to about 6 mg/L, about 2 mg/L to about 7 mg/L, about 2 mg/L to about 8 mg/L, about 2 mg/L to about 9 mg/L, about 2 mg/L to about 10 mg/L, about 2 mg/L to about 12 mg/L, about 2 mg/L to about 14 mg/L, about 2 mg/L to about 15 mg/L, about 3 mg/L to about 4 mg/L, about 3 mg/L to about 5 mg/L, about 3 mg/L to about 6 mg/L, about 3 mg/L to about 7 mg/L, about 3 mg/L to about 8 mg/L, about 3 mg/L to about 9 mg/L, about 3 mg/L to about 10 mg/L, about 3 mg/L to about 12 mg/L, about 3 mg/L to about 14 mg/L, about 3 mg/L to about 15 mg/L, about 4 mg/L to about 5 mg/L, about 4 mg/L to about 6 mg/L, about 4 mg/L to about 7 mg/L, about 4 mg/L to about 8 mg/L, about 4 mg/L to about 9 mg/L, about 4 mg/L to about 10 mg/L, about 4 mg/L to about 12 mg/L, about 4 mg/L to about 14 mg/L, about 4 mg/L to about 15 mg/L, about 5 mg/L to about 6 mg/L, about 5 mg/L to about 7 mg/L, about 5 mg/L to about 8 mg/L, about 5 mg/L to about 9 mg/L, about 5 mg/L to about 10 mg/L, about 5 mg/L to about 12 mg/L, about 5 mg/L to about 14 mg/L, about 5 mg/L to about 15 mg/L, about 6 mg/L to about 7 mg/L, about 6 mg/L to about 8 mg/L, about 6 mg/L to about 9 mg/L, about 6 mg/L to about 10 mg/L, about 6 mg/L to about 12 mg/L, about 6 mg/L to about 14 mg/L, about 6 mg/L to about 15 mg/L, about 7 mg/L to about 8 mg/L, about 7 mg/L to about 9 mg/L, about 7 mg/L to about 10 mg/L, about 7 mg/L to about 12 mg/L, about 7 mg/L to about 14 mg/L, about 7 mg/L to about 15 mg/L, about 8 mg/L to about 9 mg/L, about 8 mg/L to about 10 mg/L, about 8 mg/L to about 12 mg/L, about 8 mg/L to about 14 mg/L, about 8 mg/L to about 15 mg/L, about 9 mg/L to about 10 mg/L, about 9 mg/L to about 12 mg/L, about 9 mg/L to about 14 mg/L, about 9 mg/L to about 15 mg/L, about 10 mg/L to about 12 mg/L, about 10 mg/L to about 14 mg/L, about 10 mg/L to about 15 mg/L, about 12 mg/L to about 14 mg/L, about 12 mg/L to about 15 mg/L, or about 14 mg/L to about 15 mg/L. In some embodiments, aerobic conditions comprise conditions with a dissolved oxygen measurement of between 2 mg/L and 10 mg/L. In some embodiments, microaerobic conditions comprise conditions with a dissolved oxygen measurement of less than 2 mg/L. In some embodiments, microaerobic conditions comprise conditions with a dissolved oxygen measurement of at most about 1.99 mg/L, at most about 1.8 mg/L, at most about 1.6 mg/L, at most about 1.5 mg/L, at most about 1.4 mg/L, at most about 1.3 mg/L, at most about 1.2 mg/L, at most about 1.1 mg/L, at most about 1 mg/L, at most about 0.9 mg/L, at most about 0.8 mg/L, at most about 0.7 mg/L, at most about 0.6 mg/L, at most about 0.5 mg/L, at most about 0.4 mg/L, at most about 0.3 mg/L, at most about 0.2 mg/L, at most about 0.1 mg/L, or less than about 0.1 mg/L but not 0 mg/L. In some embodiments, microaerobic conditions comprise conditions with a dissolved oxygen measurement from about 0.1 mg/L to about 1.99 mg/L. In some embodiments, microaerobic conditions comprise conditions with a dissolved oxygen measurement from about 0.1 mg/L to about 0.2 mg/L, about 0.1 mg/L to about 0.3 mg/L, about 0.1 mg/L to about 0.4 mg/L, about 0.1 mg/L to about 0.5 mg/L, about 0.1 mg/L to about 0.8 mg/L, about 0.1 mg/L to about 1 mg/L, about 0.1 mg/L to about 1.2 mg/L, about 0.1 mg/L to about 1.4 mg/L, about 0.1 mg/L to about 1.6 mg/L, about 0.1 mg/L to about 1.8 mg/L, about 0.1 mg/L to about 1.99 mg/L, about 0.2 mg/L to about 0.3 mg/L, about 0.2 mg/L to about 0.4 mg/L, about 0.2 mg/L to about 0.5 mg/L, about 0.2 mg/L to about 0.8 mg/L, about 0.2 mg/L to about 1 mg/L, about 0.2 mg/L to about 1.2 mg/L, about 0.2 mg/L to about 1.4 mg/L, about 0.2 mg/L to about 1.6 mg/L, about 0.2 mg/L to about 1.8 mg/L, about 0.2 mg/L to about 1.99 mg/L, about 0.3 mg/L to about 0.4 mg/L, about 0.3 mg/L to about 0.5 mg/L, about 0.3 mg/L to about 0.8 mg/L, about 0.3 mg/L to about 1 mg/L, about 0.3 mg/L to about 1.2 mg/L, about 0.3 mg/L to about 1.4 mg/L, about 0.3 mg/L to about 1.6 mg/L, about 0.3 mg/L to about 1.8 mg/L, about 0.3 mg/L to about 1.99 mg/L, about 0.4 mg/L to about 0.5 mg/L, about 0.4 mg/L to about 0.8 mg/L, about 0.4 mg/L to about 1 mg/L, about 0.4 mg/L to about 1.2 mg/L, about 0.4 mg/L to about 1.4 mg/L, about 0.4 mg/L to about 1.6 mg/L, about 0.4 mg/L to about 1.8 mg/L, about 0.4 mg/L to about 1.99 mg/L, about 0.5 mg/L to about 0.8 mg/L, about 0.5 mg/L to about 1 mg/L, about 0.5 mg/L to about 1.2 mg/L, about 0.5 mg/L to about 1.4 mg/L, about 0.5 mg/L to about 1.6 mg/L, about 0.5 mg/L to about 1.8 mg/L, about 0.5 mg/L to about 1.99 mg/L, about 0.8 mg/L to about 1 mg/L, about 0.8 mg/L to about 1.2 mg/L, about 0.8 mg/L to about 1.4 mg/L, about 0.8 mg/L to about 1.6 mg/L, about 0.8 mg/L to about 1.8 mg/L, about 0.8 mg/L to about 1.99 mg/L, about 1 mg/L to about 1.2 mg/L, about 1 mg/L to about 1.4 mg/L, about 1 mg/L to about 1.6 mg/L, about 1 mg/L to about 1.8 mg/L, about 1 mg/L to about 1.99 mg/L, about 1.2 mg/L to about 1.4 mg/L, about 1.2 mg/L to about 1.6 mg/L, about 1.2 mg/L to about 1.8 mg/L, about 1.2 mg/L to about 1.99 mg/L, about 1.4 mg/L to about 1.6 mg/L, about 1.4 mg/L to about 1.8 mg/L, about 1.4 mg/L to about 1.99 mg/L, about 1.6 mg/L to about 1.8 mg/L, about 1.6 mg/L to about 1.99 mg/L, or about 1.8 mg/L to about 1.99 mg/L. In some embodiments, anaerobic conditions comprise conditions with a dissolved oxygen measurement of 0 mg/L.

Reactors of a digestion system described herein may comprise a working volume used to hold a volume of working fluid. A working volume of a reactor of a digestion system described herein may be at least about 5 gallons, at least about 10 gallons, at least about 20 gallons, at least about 50 gallons, at least about 75 gallons, at least about 100 gallons, at least about 250 gallons, at least about 500 gallons, at least about 750 gallons, at least about 1,000 gallons, at least about 2,000 gallons, at least about 3,000 gallons, at least about 4,000 gallons, at least about 5,000 gallons, at least about 7,500 gallons, at least about 10,000 gallons, at least about 15,000 gallons, at least about 20,000 gallons, at least about 50,000 gallons, or more than about 50,000 gallons. A working volume of a reactor of a digestion system described herein may be at most about 50,000 gallons, at most about 20,000 gallons, at most about 15,000 gallons, at most about 10,000 gallons, at most about 7,500 gallons, at most about 5,000 gallons, at most about 4,000 gallons, at most about 3,000 gallons, at most about 2,000 gallons, at most about 1,000 gallons, at most about 750 gallons, at most about 500 gallons, at most about 250 gallons, at most about 100 gallons, at most about 75 gallons, at most about 50 gallons, at most about 20 gallons, at most about 10 gallons, at most about 5 gallons, or less than about 5 gallons.

Reactors may be maintained at different pH levels within a digestion system. Reactors may be maintained at the same pH levels within a digestion system. The pH of a reactor in a digestion system may be at least about 4.0, at least about 4.5, at least about 5.0, at least about 5.5, at least about 6.0, at least about 6.5, at least about 7.0, at least about 7.5, at least about 8.0, at least about 8.5, at least about 9.0, at least about 9.5, or at least about 10.0. In some embodiments, the pH of a reactor in a digestion system may be at most about 10.0, at most about 9.5, at most about 9.0, at most about 8.5, at most about 8.0, at most about 7.5, at most about 7.0, at most about 6.5, at most about 6.0, at most about 5.5, at most about 5.0, at most about 4.5, or at most about 4.0.

In some embodiments, the pH of a reactor in a digestion system may be about 3 to about 9. In some embodiments, the pH of a reactor in a digestion system may be about 3 to about 3.5, about 3 to about 4, about 3 to about 4.5, about 3 to about 5, about 3 to about 5.5, about 3 to about 6, about 3 to about 6.5, about 3 to about 7, about 3 to about 7.5, about 3 to about 8, about 3 to about 9, about 3.5 to about 4, about 3.5 to about 4.5, about 3.5 to about 5, about 3.5 to about 5.5, about 3.5 to about 6, about 3.5 to about 6.5, about 3.5 to about 7, about 3.5 to about 7.5, about 3.5 to about 8, about 3.5 to about 9, about 4 to about 4.5, about 4 to about 5, about 4 to about 5.5, about 4 to about 6, about 4 to about 6.5, about 4 to about 7, about 4 to about 7.5, about 4 to about 8, about 4 to about 9, about 4.5 to about 5, about 4.5 to about 5.5, about 4.5 to about 6, about 4.5 to about 6.5, about 4.5 to about 7, about 4.5 to about 7.5, about 4.5 to about 8, about 4.5 to about 9, about 5 to about 5.5, about 5 to about 6, about 5 to about 6.5, about 5 to about 7, about 5 to about 7.5, about 5 to about 8, about 5 to about 9, about 5.5 to about 6, about 5.5 to about 6.5, about 5.5 to about 7, about 5.5 to about 7.5, about 5.5 to about 8, about 5.5 to about 9, about 6 to about 6.5, about 6 to about 7, about 6 to about 7.5, about 6 to about 8, about 6 to about 9, about 6.5 to about 7, about 6.5 to about 7.5, about 6.5 to about 8, about 6.5 to about 9, about 7 to about 7.5, about 7 to about 8, about 7 to about 9, about 7.5 to about 8, about 7.5 to about 9, or about 8 to about 9.

In some embodiments, the reactors may comprise distribution components (e.g., a distribution ring) that is subsurface of the discharge volume. The distribution component can reduce the amount of surface disruption, and/or keep the environment in the reactor anaerobic. The environment of the reactor may be anaerobic, microaerobic, or aerobic. Without wishing to be bound by theory, the microaerobic conditions of the reactors of the digestion system may enrich nitrogen-fixing microbes and/or microbes with nitrogen use efficiency capability in the microbial consortium of the system.

C. Working Fluids and Microbial Consortia

A working fluid may comprise a fluidic substance that moves through a digestion system as described herein. A working fluid can comprise solid components, liquid components, gaseous components, or any combination thereof. A working fluid can comprise microbial consortia, isolated microbes or inoculum of a microbial strain (e.g., target isolates), additional organic and/or materials, or any combination thereof. The mixture of microbial consortia, isolated microbes (e.g., target isolates), additional organic and/or materials within a working fluid may allow for the expansion of microbes or act as a culture for an inoculum of a microbe to grow. A working fluid may comprise a pH, viscosity, temperature, surface tension, adhesion, volume, or any combination thereof that enhances the growth and/or functioning of microbes or microorganisms. In some embodiments, a volume of working fluid within each reactor is continuously being replenished and drawn from. In some embodiments, a volume of working fluid within each reactor is replenished and drawn from in batches (e.g., discontinuously). In some embodiments, a working fluid in a first reactor may comprise a first working fluid. In some embodiments, a working fluid in a second reactor may comprise a second working fluid. In some embodiments, a working fluid in a third reactor may comprise a third working fluid. In some embodiments, a working fluid in a fourth reactor may comprise a fourth working fluid. In some embodiments, a working fluid in a fifth reactor may comprise a fifth working fluid. In some embodiments, at least a portion of the second working fluid may be transferred to the third reactor. In some embodiments, at least a portion of the third working fluid may be transferred to the fourth reactor. In some embodiments, at least a portion of the fourth working fluid may be transferred to the fifth reactor. In some embodiments, a working fluid may be mixed in a reactor (e.g., chamber or container) prior to a first reactor. In some embodiments, the working fluid in each reactor may be distinct from the working fluid in other reactors in the digestion system. Distinct working fluids may comprise different microbial populations. The different microbial populations may include different microbes, (e.g., bacteria, fungi, algae, or any combination thereof). Distinct working fluids may comprise different concentrations of a target isolate. Distinct working fluids may comprise different concentrations of a carbon source and/or a nitrogen source. Distinct working fluids may comprise different microbial populations, different concentrations of a target isolate, different concentrations of a carbon source, different combinations of a nitrogen source, or any combination thereof. The working fluid in a reactor of a digestion system may be similar to a working fluid of a different reactor of the digestion system. The working fluid in each reactor may comprise different microbial populations. The different microbial populations may include different bacteria, fungi, algae, or any combination thereof.

The working fluid within each reactor may comprise different enzymes, which may be produced by microbes within the working fluid. An enzyme within a working fluid may comprise a dehydrogenase, a hydrogenase, an oxidase, a catalase, a peroxidase, a phenol o-hydroxylase, a dextransucrase, an aminotransferase, a rhodanese, a carboxylesterase, a lipase, a phosphatase, a nuclease, a phytase, an arylsulphatase, an amylase, a cellulase, an inulase, a xylanase, a dextranase, a levanase, a poly-galacturonase, a glucosidase, a galactosidase, an invertase, a peptidase, an asparaginase, a glutaminase, an amidase, a urease, an aspartate decarboxylase, a glutamate decarboxylase an aromatic amino acid decarboxylase, or any combination thereof. An enzyme within a working fluid may comprise nitrogenase, 1-aminocyclopropane-1-carboxylate deaminase (e.g., ACC-deaminase), quinoprotein glucose dehydrogenase (e.g., PQQ or quinone), gluconate 2-dehydrogenase, cellulase, endo-1, 3(4)-β-glucanase, pectin lyase, or any combination thereof. The working fluid within each reactor may comprise different concentrations of enzymes. The working fluid within each reactor may comprise a different average abundance of an enzyme. An enzyme may be present at an average abundance of less than 0.001%. An enzyme may be present at an average abundance of greater than 1%. In some embodiments, an enzyme may be present at an average abundance of at least about, at most about, or about 0.0001%, 0.001%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, or a range between any of these two values. The working fluid within each reactor may comprise enzymes with different enzymatic activity. Enzymatic activity may include, but is not limited to, nitrogen fixation, ammonia production, phosphate solubilization, nitrogen use efficiency, cell wall lysing, or any combination thereof.

A working fluid may comprise different digestion products from working fluid within other reactors of the system. In some embodiments, a working fluid may comprise digestion products from an aqueous organic feedstock and microbial consortium at least partially derived from a previous working fluid.

The pH of a working fluid within each reactor may be different from working fluid in other reactors. The pH of a working fluid within each reactor may be the same. The pH of a working fluid may be less than 6. The pH of a working fluid may be greater than 6. The pH of a working fluid may be in a range from 2 to 11. The pH of a working fluid may be at least about, at most about, or about 2, 2.5, 3, 3.5, 4, 4.5, 5, 5.5, 6, 6.5, 7, 7.5, 8, 8.5, 9, 9.5, 10, 10.5, or 11, or a range between any of these two values.

The microbial consortia of the present invention may be stable. In a stable microbial consortium, the identity and relative abundance of bacteria may not appreciably change over time, such as over the space of 1, 2, 3, 4, 5, 6, or 7 days, or 1, 2, 3, 4, or 5 weeks.

In some embodiments, the microbial consortia may be characterized by population analysis. The population analysis may comprise a community analysis, determination of the core community, and computation of a microbial-community distance matrix. In some embodiments, the microbial consortia may be characterized in batches. Characterization of the microbial consortia may be measured in 1, 2, 3, 4, 5, 6, 7, 8 or more batches. From the population analysis, the most abundant species of the microbial consortia may be determined. In some embodiments, the most abundant species of a microbial consortia comprise the top 2, 3, 4, 5, 10, 15, or 20 species. In some embodiments, different reactors may have microbial consortia with different species being the most abundant.

In some embodiments, a first microbial consortium may be established in a mixing chamber, in which various inputs may be mixed into a homogenous aqueous mixture to be input into a digestion reactor. In some embodiments, a digestion system described herein may comprise one or more mixing chambers in which a microbial consortium may be established. The first microbial consortium may be derived from microbes originally present in one or more digestion substrates and/or from other inputs into the mixing chamber. A first microbial consortium may be derived from inputs to a reactor in a digestion system described herein. In some embodiments, a second microbial consortium is established in a first reactor. The second microbial consortium may be derived from microbes within the mixing chamber. In some embodiments, a third microbial consortium is established in a second reactor. The third microbial consortium may be derived from the first working fluid present in the first reactor and transferred to the second reactor. In some embodiments, a fourth microbial consortium is established in a third reactor. The fourth microbial consortium may be derived from the second working fluid present in the second reactor and transferred to the third reactor. In some embodiments, a fifth microbial consortium is established in a fourth reactor. The fifth microbial consortium may be derived from the fourth working fluid present in the fourth reactor and transferred to the fifth reactor. A microbial consortium can be present in any reactor of a digestion system described herein. A microbial consortium can be derived from the working fluid of a reactor of a digestion system described herein. A first microbial consortium may be derived from inputs to a first reactor and may be present in a base product of a digestion system. A first microbial consortium may be present in a first reactor, a second reactor, a third reactor, or a clarifier. Without wishing to be bound by theory, a first microbial consortium in a working fluid may shift its microbial population and form a second microbial consortium. A second microbial consortium may be present in a first reactor, a second reactor, a third reactor, or a clarifier. Without wishing to be bound by theory, a second microbial consortium in a working fluid may shift its microbial population and form a third microbial consortium. A third microbial consortium may be present in a first reactor, a second reactor, a third reactor, or a clarifier. Without wishing to be bound by theory, a third microbial consortium in a working fluid may shift its microbial population and form a fourth microbial consortium. A fourth microbial consortium may be present in a first reactor, a second reactor, a third reactor, or a clarifier. Without wishing to be bound by theory, a fourth microbial consortium in a working fluid may shift its microbial population and form a fifth microbial consortium. A fifth microbial consortium may be present in a first reactor, a second reactor, a third reactor, or a clarifier. Microbial consortia of the digestion system described herein may develop shifts in microbial communities based on conditions (e.g., nutrients, retention time, flow rate, pH, oxygen content, digestion products) of the reactors of the system and the working fluid.

A portion of a first working fluid may be transferred to a second container of a serialized assembly of containers of a digestion system described herein. The working fluid of the second container may comprise a second working fluid. A portion of a second working fluid may be transferred to a third container of a serialized assembly of containers of a digestion system described herein. The working fluid of the third container may comprise a third working fluid. A portion of a third working fluid may be transferred to a fourth container of a serialized assembly of containers of a digestion system described herein. The working fluid of the fourth container may comprise a fourth working fluid. A portion of a fourth working fluid may be transferred to a fifth container of a serialized assembly of containers of a digestion system described herein. The working fluid of the fifth container may comprise a fifth working fluid. A portion of a fifth working fluid may be transferred to a sixth container of a serialized assembly of containers of a digestion system described herein. The working fluid of the sixth container may comprise a sixth working fluid.

The working fluid of a container in the digestion system may incubate in the container. A flow rate of the digestion system may increase or decrease a volume of working fluid. The working fluid of a first, second, third, fourth, fifth, or sixth container may increase in volume over a time period. The working fluid of a first, second, third, fourth, fifth, or sixth container may decrease in volume over a time period. The working fluid of a first, second, third, fourth, fifth, or sixth container may not increase or decrease in volume over a time period. The volume of working fluid in each of the containers of a digestion system may be the same. The volume of working fluid in each of the containers of a digestion system may be different. The volumes of the first working fluid, second working fluid, third working fluid, fourth working fluid, fifth working fluid, and/or sixth working fluid may be constant (e.g., unchanging over a time period). A constant volume may comprise a volume that does not increase or decrease over 1 minute, 5 minutes, 10 minutes, 30 minutes, 1 hours, 5 hours, 12 hours, 1 day, 2 days, 3 days, 4 days, 5 days, or 1 week.

As working fluid flows from each container of digestion system, the working fluid may comprise a flow rate. A first flow rate may comprise a flow rate of an aqueous feedstock inputted into a first container from a source outside the digestion system. A second flow rate may comprise a flow rate of a working fluid from a first container into a second container. A third flow rate may comprise a flow rate of a working fluid from a second container into a third container. A fourth flow rate may comprise a flow rate of a working fluid from a third container into a fourth container. A fifth flow rate may comprise a flow rate of a working fluid from a fourth container into a fifth container. A flow rate (e.g., first flow rate, second flow rate, third flow rate, fourth flow rate, fifth flow rate) may be at least about, at most about, or about 0.5 gallons/min, 1 gallon/min, 5 gallons/min, 10 gallons/min, 15 gallons/min, 20 gallons/min, 25 gallons/min, 30 gallons/min, 40 gallons/min, 50 gallons/min, 100 gallons/min, 200 gallons/min, 300 gallons/min, 400 gallons/min, 500 gallons/min, 1,000 gallons/min, or 10,000 gallons/min, or a range between any of these values.

A microbial consortium can comprise a population of microbes. The population of microbes can be generated from an input to the digestion system. An aqueous organic feedstock inputted into the digestion system may comprise a microbial consortium. Incubation in the digestion system may promote the growth of microbes within a microbial consortium (e.g., a first microbial consortium, a second microbial consortium, a third microbial consortium, a fourth microbial consortium, a fifth microbial consortium, a sixth microbial consortium). The microbes of a microbial consortium or at least a portion of microbes within the microbial consortium may have a desired plant growth promotion property. The plant growth promotion property may comprise shoot biomass, root biomass, nutrient uptake, photosynthetic activity, crop yield, deaminase activity, acid production, leaf area, chlorophyll content, or total biomass.

Reactors of a digestion system may be fluidly connected. A portion of a working fluid in a first container may be transferred to a fluidly connected second container. A portion of a working fluid in a second container may be transferred to a fluidly connected third container. A portion of a working fluid in a third container may be transferred to a fluidly connected fourth container. A portion of a working fluid in a fourth container may be transferred to a fluidly connected fifth container. A portion of a working fluid in a fifth container may be transferred to a fluidly connected sixth container. In some embodiments, a transfer of working fluid between containers of a digestion system described herein may be continuous. A continuous flow of working fluid may comprise a flow of working fluid that does not stop or a flow of working fluid that stops for less than about 5 seconds, less than about 4 seconds, less than about 3 seconds, less than about 2 seconds, less than about 1 second, less than about 0.5 seconds, or less than about 0.1 seconds. A continuous flow of working fluid within a digestion system described herein (e.g., between containers of a digestion system) may have a first flow rate. A continuous flow of working fluid within a digestion system described herein (e.g., between containers of a digestion system) may have a second flow rate. In some embodiments, the first flow rate and the second flow rate are equal. A first flow rate may comprise a flow rate of fluid transferred from a source outside the digestion system into a first container. A second flow rate may comprise a rate of fluid flow from a first container to a second container. In some embodiments, an amount of working fluid and/or aqueous organic feedstock transferred into the first container over a time period is equal to an amount of working fluid and/or aqueous organic feedstock transferred into a second fluidly connected container over the same time period. In some embodiments, the first flow rate and the second flow rate are different.

In some embodiments, a first container of a digestion system comprises a constant volume. In some embodiments, a volume of a first container of a digestion system is different over time. In some embodiments, the flow rate between containers of the digestion system may maintain a constant volume in each container. A first container, a second container, a third container, a fourth container, a fifth container, and/or a sixth container may be maintained at a constant volume. A constant volume may be maintained by a continuous flow of fluid through a digestion system described herein.

In some embodiments, a digestion system may be inoculated with an inoculum of a microbe (e.g., an inoculum of a microbial strain). The inoculum of a microbial strain may be an isolated microbe. An isolated microbe can comprise a microbe grown or enriched outside of a natural environment (e.g., in a culture medium or a streak plate method). In some embodiments, the inoculum of a microbe may comprise a mixture of multiple isolated microbes. The inoculum of a microbe may comprise a mixture of at least about 2, at least about 3, at least about 4, at least about 5, at least about 6, at least about 7, at least about 8, or more isolated microbes.

In some cases, a digestion system may not be reinoculated with an isolate (e.g., microbial strain) or combination of isolates following a first inoculation. Reinoculation of a digestion system may comprise providing a microbial strain following a previous inoculation. Reinoculation of a digestion system may comprise introducing a target isolate (e.g., microbial strain) in a container of the digestion system at a time point during operating of the digestion system. In some cases, a digestion system may be reinoculated with an isolate or combination of isolates at least every 20 days, at least every 50 days, at least every 100 days, at least every 200 days, at least every 300 days, at least every 400 days, at least every 500 days, or more. In some cases, a digestion system may be inoculated with an isolate or combination of isolates on day 1 of a digestion process and reinoculated 1, 2, 3, 4, 5, or more times after day 1 of the digestion process. In some cases, a digestion system may be reinoculated with a microbial strain described herein after operating the digestion system for a time period. For example, a digestion system may be reinoculated with a microbial strain described herein after operating the digestion system for a duration of time of at least about, at most about, or about 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 3 months, 4 months, 5 months, 6 months, 9 months, 12 months, 18 months, 24 months, 3 years, 4 years, 5 years, 10 years, or a range between any of these two values.

In some embodiments, the population of the microbial strain (e.g., concentration of the microbial strain) is maintained (e.g., retained) by at least about 0.00001%, at least about 0.0001%, at least about 0.001%, at least about 0.01%, at least about 0.1%, at least about 0.5%, at least about 1%, at least about 5%, at least 10%, at least about 15%, at least about 20%, at least about 25%, at least about 30%, at least about 35%, at least about 40%, at least about 45%, at least about 50%, at least about 55%, at least about 60%, or at least about 75% from the concentration of the microbial strain added into a container (e.g., a first container) of the digestion system. Biosolids (e.g., floc) may comprise small particles from a working fluid of a digestion system. The biosolids (e.g., floc) may accumulate in a clarifier chamber over time and separate from a supernatant (e.g., base product). In some embodiments, the population of the microbial strain may be retained in the floc (e.g., biosolids) of the digestion system. In some embodiments, a majority (95%, 96%, 97%, 98%, 99%, 99.5%, 99.6%, 99.7%, 99.8%, or 99.9%) of the inoculum of the microbe may be retained in the floc (e.g., biosolids) of the digestion system. Floc may be generated at any point during operating of a bioreactor system as described herein. For example, floc may be generated in a reactor of the bioreactor system (e.g., a first container, a second container, a third container, a fourth container, a fifth container, a sixth container, or any container of the system). For example, floc may be generated in a clarifier chamber of a bioreactor system. In some embodiments, floc may comprise at least a portion of nitrogen use efficiency-promoting microbes generated in a digestion system described herein.

In some embodiments, there may be at least about 1 log CFU/ml, at least about 2 logs CFU/ml, at least about 3 logs CFU/ml, at least about 4 logs CFU/ml, at least about 5 logs CFU/ml, or greater than about 5 logs CFU/ml increase in a concentration of the population of the microbial strain after inoculation in a container (e.g., first container) of the digestion system described herein. In some embodiments, there may be at most about 5 logs CFU/ml, at most about 4 logs CFU/ml, at most about 3 logs CFU/ml, at most about 2 logs CFU/ml, at most about 1 log CFU/ml, or less than about 1 log CFU/ml increase in a concentration of the population of the microbial strain after inoculation in a container (e.g., first container) of the digestion system described herein. In some embodiments, there may be from about 1 log CFU/ml to about 8 logs CFU/ml increase in a concentration of the population of the microbial strain after inoculation in a container (e.g., first container) of the digestion system described herein. In some embodiments, there may be from about 1 log CFU/ml to about 2 logs CFU/ml, about 1 log CFU/ml to about 3 logs CFU/ml, about 1 log CFU/ml to about 4 logs CFU/ml, about 1 log CFU/ml to about 5 logs CFU/ml, about 1 log CFU/ml to about 6 logs CFU/ml, about 1 log CFU/ml to about 7 logs CFU/ml, about 1 log CFU/ml to about 8 logs CFU/ml, about 2 logs CFU/ml to about 3 logs CFU/ml, about 2 logs CFU/ml to about 4 logs CFU/ml, about 2 logs CFU/ml to about 5 logs CFU/ml, about 2 logs CFU/ml to about 6 logs CFU/ml, about 2 logs CFU/ml to about 7 logs CFU/ml, about 2 logs CFU/ml to about 8 logs CFU/ml, about 3 logs CFU/ml to about 4 logs CFU/ml, about 3 logs CFU/ml to about 5 logs CFU/ml, about 3 logs CFU/ml to about 6 logs CFU/ml, about 3 logs CFU/ml to about 7 logs CFU/ml, about 3 logs CFU/ml to about 8 logs CFU/ml, about 4 logs CFU/ml to about 5 logs CFU/ml, about 4 logs CFU/ml to about 6 logs CFU/ml, about 4 logs CFU/ml to about 7 logs CFU/ml, about 4 logs CFU/ml to about 8 logs CFU/ml, about 5 logs CFU/ml to about 6 logs CFU/ml, about 5 logs CFU/ml to about 7 logs CFU/ml, about 5 logs CFU/ml to about 8 logs CFU/ml, about 6 logs CFU/ml to about 7 logs CFU/ml, about 6 logs CFU/ml to about 8 logs CFU/ml, or about 7 logs CFU/ml to about 8 logs CFU/ml increase in a concentration of the population of the microbial strain after inoculation in a container (e.g., first container) of the digestion system described herein.

In some embodiments, there may be at least about 1 log CFU/ml, at least about 2 logs CFU/ml, at least about 3 logs CFU/ml, at least about 4 logs CFU/ml, at least about 5 logs CFU/ml, or greater than about 5 logs CFU/ml decrease in a concentration of the population of the microbial strain after inoculation in a container (e.g., first container) of the digestion system described herein. In some embodiments, there may be at most about 5 logs CFU/ml, at most about 4 logs CFU/ml, at most about 3 logs CFU/ml, at most about 2 logs CFU/ml, at most about 1 log CFU/ml, or less than about 1 log CFU/ml decrease in a concentration of the population of the microbial strain after inoculation in a container (e.g., first container) of the digestion system described herein. In some embodiments, there may be from about 1 log CFU/ml to about 8 logs CFU/ml decrease in a concentration of the population of the microbial strain after inoculation in a container (e.g., first container) of the digestion system described herein. In some embodiments, there may be from about 1 log CFU/ml to about 2 logs CFU/ml, about 1 log CFU/ml to about 3 logs CFU/ml, about 1 log CFU/ml to about 4 logs CFU/ml, about 1 log CFU/ml to about 5 logs CFU/ml, about 1 log CFU/ml to about 6 logs CFU/ml, about 1 log CFU/ml to about 7 logs CFU/ml, about 1 log CFU/ml to about 8 logs CFU/ml, about 2 logs CFU/ml to about 3 logs CFU/ml, about 2 logs CFU/ml to about 4 logs CFU/ml, about 2 logs CFU/ml to about 5 logs CFU/ml, about 2 logs CFU/ml to about 6 logs CFU/ml, about 2 logs CFU/ml to about 7 logs CFU/ml, about 2 logs CFU/ml to about 8 logs CFU/ml, about 3 logs CFU/ml to about 4 logs CFU/ml, about 3 logs CFU/ml to about 5 logs CFU/ml, about 3 logs CFU/ml to about 6 logs CFU/ml, about 3 logs CFU/ml to about 7 logs CFU/ml, about 3 logs CFU/ml to about 8 logs CFU/ml, about 4 logs CFU/ml to about 5 logs CFU/ml, about 4 logs CFU/ml to about 6 logs CFU/ml, about 4 logs CFU/ml to about 7 logs CFU/ml, about 4 logs CFU/ml to about 8 logs CFU/ml, about 5 logs CFU/ml to about 6 logs CFU/ml, about 5 logs CFU/ml to about 7 logs CFU/ml, about 5 logs CFU/ml to about 8 logs CFU/ml, about 6 logs CFU/ml to about 7 logs CFU/ml, about 6 logs CFU/ml to about 8 logs CFU/ml, or about 7 logs CFU/ml to about 8 logs CFU/ml decrease in a concentration of the population of the microbial strain after inoculation in a container (e.g., first container) of the digestion system described herein.

Incubation of a microbial consortium in the digestion system may enrich a microbial community with plant growth promotion properties (e.g., nitrogen use efficiency-promoting microbes). Incubation of the inoculum of the microbe, the nitrogen use efficiency-promoting microbes of the microbial consortium, or any combination thereof may generate metabolites with desired plant growth promotion properties (e.g., nitrogen use efficiency-promoting metabolites. The inoculum of the microbe, nitrogen use efficiency-promoting microbes of the microbial consortium, nitrogen use efficiency-promoting metabolites, or any combination thereof may be nitrogen use efficiency-promoting microbes in the working fluid of the system and/or in the output product (e.g., base product) of the digestion system. A concentration of nitrogen use efficiency-promoting microbes may increase throughout a retention time of a digestion system described herein. The concentration of nitrogen use efficiency-promoting microbes may increase from a first container to a second container of the digestion system. The concentration of nitrogen use efficiency-promoting microbes may increase from a first container to a third container of the digestion system. The concentration of nitrogen use efficiency-promoting microbes may increase from a first container to a fourth container of the digestion system. The concentration of nitrogen use efficiency-promoting microbes may increase from a first container to a fifth container of the digestion system. The concentration of nitrogen use efficiency-promoting microbes may increase from a first container to a sixth container of the digestion system. In some embodiments, an output product (e.g., base product) may have a higher concentration of nitrogen use efficiency-promoting microbes than a concentration of nitrogen use efficiency-promoting microbes in a first container of a digestion system.

In some embodiments, a concentration of nitrogen use efficiency-promoting microbes may increase from a first container to a second container, a third container, a fourth container, a fifth container, and/or a sixth container of a digestion system described herein. In some embodiments, a concentration of nitrogen use efficiency-promoting microbes in a second container, a third container, a fourth container, a fifth container, and/or a sixth container may be at least about 50×, at least about 100×, at least about 200×, at least about 250×, at least about 300×, at least about 400×, at least about 500×, at least about 600×, at least about 700×, at least about an 800×, at least about 900×, at least about 1000×, at least about 1250×, at least about 1500×, at least about 2000×, or greater than about 2000× increased from a concentration of nitrogen use efficiency-promoting microbes in a first container of a digestion system described herein. In some embodiments, a concentration of nitrogen use efficiency-promoting microbes in a second container, a third container, a fourth container, a fifth container, and/or a sixth container may be at most about 2000×, at most about 1500×, at most about 1250×, at most about 1000×, at most about 900×, at most about an 800×, at most about 700×, at most about 600×, at most about 500×, at most about 400×, at most about 300×, at most about 250×, at most about 200×, at most about 100×, at most about 50×, or less than about 50× increased from a concentration of nitrogen use efficiency-promoting microbes in a first container of a digestion system described herein.

In some embodiments, a concentration of nitrogen use efficiency-promoting microbes in a second container, a third container, a fourth container, a fifth container, and/or a sixth container may be from about 25× to about 2,500× increased from a concentration of nitrogen use efficiency-promoting microbes in a first container of a digestion system described herein. In some embodiments, a concentration of nitrogen use efficiency-promoting microbes in a second container, a third container, a fourth container, a fifth container, and/or a sixth container may be from about 25× to about 50×, about 25× to about 100×, about 25× to about 150×, about 25× to about 200×, about 25× to about 250×, about 25× to about 500×, about 25× to about 750×, about 25× to about 1,000×, about 25× to about 1,500×, about 25× to about 2,000×, about 25× to about 2,500×, about 50× to about 100×, about 50× to about 150×, about 50× to about 200×, about 50× to about 250×, about 50× to about 500×, about 50× to about 750×, about 50× to about 1,000×, about 50× to about 1,500×, about 50× to about 2,000×, about 50× to about 2,500×, about 100× to about 150×, about 100× to about 200×, about 100× to about 250×, about 100× to about 500×, about 100× to about 750×, about 100× to about 1,000×, about 100× to about 1,500×, about 100× to about 2,000×, about 100× to about 2,500×, about 150× to about 200×, about 150× to about 250×, about 150× to about 500×, about 150× to about 750×, about 150× to about 1,000×, about 150× to about 1,500×, about 150× to about 2,000×, about 150× to about 2,500×, about 200× to about 250×, about 200× to about 500×, about 200× to about 750×, about 200× to about 1,000×, about 200× to about 1,500×, about 200× to about 2,000×, about 200× to about 2,500×, about 250× to about 500×, about 250× to about 750×, about 250× to about 1,000×, about 250× to about 1,500×, about 250× to about 2,000×, about 250× to about 2,500×, about 500× to about 750×, about 500× to about 1,000×, about 500× to about 1,500×, about 500× to about 2,000×, about 500× to about 2,500×, about 750× to about 1,000×, about 750× to about 1,500×, about 750× to about 2,000×, about 750× to about 2,500×, about 1,000× to about 1,500×, about 1,000× to about 2,000×, about 1,000× to about 2,500×, about 1,500× to about 2,000×, about 1,500× to about 2,500×, or about 2,000× to about 2,500×.

In some embodiments, the absolute population of the microbial inoculum of the digestion system may not decrease by more than about 0.0000010%, 0.000010%, 0.00010%, 0.0010%, 0.010%, 0.1%, 0.5%, 1%, 2%, 3%, 4%, 5%, 6%, 7%, 8%, 9%, 10%, 15%, 20%, or 25% after incubation. In some embodiments, the absolute population of the microbial inoculum of the digestion system may not decrease by more than about 0.0000010%, 0.000010%, 0.00010%, 0.0010%, 0.010%, 0.10%, 0.5%, 1%, 2%, 3%, 4%, 5%, 6%, 7%, 8%, 9%, 10%, 15%, 20%, or 25% after incubation for a retention period of a digestion system (e.g., 1 day, 2 days, 3 days, 4 days, 5 days, 6 days, 1 week, 2 weeks, 3 weeks, 4 weeks, 2 months, 3 months, 4 months, 5 months, 6 months, 1 year, 2 years, 3 years, 4 years, or 5 years). In some embodiments, the absolute population of the microbial inoculum of the digestion system may not decrease by more than about 0.000001%, 0.00001%, 0.0001%, 0.001%, 0.01%, 0.1%, 0.5%, 1%, 2%, 3%, 4%, 5%, 6%, 7%, 8%, 9%, 10%, 15%, 20%, or 25% after incubation without inoculation of additional microbe.

In some embodiments, a proportion of a concentration of nitrogen use efficiency-promoting microbes relative to a total bacterial population count may increase across containers of a fluidly connected digestion system. In some embodiments, a proportion of a concentration nitrogen use efficiency-promoting microbes relative to a total bacterial population count may increase from a first container to a second container of a digestion system described herein. In some embodiments, a proportion of a concentration nitrogen use efficiency-promoting microbes relative to a total bacterial population count may increase from a first container to a third container of a digestion system described herein. In some embodiments, a proportion of a concentration nitrogen use efficiency-promoting microbes relative to a total bacterial population count may increase from a first container to a fourth container of a digestion system described herein. In some embodiments, a proportion of a concentration nitrogen use efficiency-promoting microbes relative to a total bacterial population count may increase from a first container to a fifth container of a digestion system described herein. In some embodiments, a proportion of a concentration nitrogen use efficiency-promoting microbes relative to a total bacterial population count may increase from a first container to a sixth container of a digestion system described herein.

Population of the microbe may be measured using methods including but not limited to spectrophotometers, cell counting, measures of turbidity, hemocytometers, electronic enumeration, determination of nitrogen content, measures of cell mass, quantitative polymerase-chain reaction (qPCR), semi-quantitative PCR, and measures of cell activity.

The addition of the target isolate (e.g., the inoculum of the microbial strain/microbe) can have an added benefit in improving target functionality of working solution in a reactor of the digestion system and/or in the output base product of the digestion system. In some embodiments, addition of the inoculum of the microbial strain can improve the nitrogen use efficiency-promoting solubilization capacity of working fluids and base product of a digestion system compared to working fluids and base product of a digestion system without an inoculum of the microbial.

A digestion system may be inoculated with a microbial strain at the start of a digestion system, which may allow for the microbial strain to flow through the system and working fluids of the reactors. Without wishing to be bound by theory, a digestion system inoculated with a microbial strain may increase a nitrogen use efficiency capacity of a working fluid and/or a base product compared to a working fluid and/or base product of an otherwise identical digestion system with no inoculated microbial strain. Without wishing to be bound by theory, a digestion system inoculated with a microbial strain may increase a nitrogen use efficiency capacity of a working fluid and/or a base product compared to a working fluid and/or base product of an otherwise identical digestion system with the microbial strain added (e.g., spiked) at the end of the system. Without wishing to be bound by theory, a digestion system inoculated with a microbial strain may increase a nitrogen use efficiency capacity of a base product compared to a base product of an otherwise identical digestion system with the microbial strain added (e.g., spiked) at the end of the system. Incubation of the microbial strain in the digestion system may enrich the working fluid with nitrogen use efficiency-promoting microbes and/or generate nitrogen use efficiency-promoting metabolites.

D. Microbial Isolates

Certain microorganisms of the present invention have all of the identifying characteristics of the deposited strains and, in particular, the identifying characteristics of being able to promote nitrogen use efficiency, plant growth, yield, or any combination thereof as described herein. In particular, the preferred microorganisms of the present invention refer to the deposited microorganisms as described herein, and strains derived therefrom.

In some embodiments, the microbial strain is from a *Bacillus* genus. In some embodiments, the bacterial strain is from a *Bacillus megaterium* species. In some embodiments, the bacterial strain is from a bacterial species other than *Bacillus megaterium*. In some embodiments, the *Bacillus megaterium* strain is the strain deposited under ATCC Accession No. PTA-127653, or an isolated clone thereof. In some embodiments, the 16S rRNA gene of the microbial strain comprises the nucleotide sequence of SEQ ID NO: 1. In some embodiments, the microbial strain comprises a 16S rRNA gene comprising a nucleotide sequence that exhibits at least 80%, at least 85%, at least 90%, at least 91%, at least 92%, at least 93%, at least 94%, at least 95%, at least 96%, at least 97%, at least 98%, at least 99%, at least 99.9%, or 100% sequence identity to a nucleotide sequence as set forth in SEQ ID NO: 1. In some embodiments, the gyrB gene of the microbial strain comprises the nucleotide sequence of SEQ ID NO: 4. In some embodiments, the microbial strain comprises a gyrB gene comprising a nucleotide sequence that exhibits at least 80%, at least 85%, at least 90%, at least 91%, at least 92%, at least 93%, at least 94%, at least 95%, at least 96%, at least 97%, at least 98%, at least 99%, at least 99.9%, or 100% sequence identity to a nucleotide sequence as set forth in SEQ ID NO: 4. In some embodiments, the rpoB gene of the microbial strain comprises the nucleotide sequence of SEQ ID NO: 7. In some embodiments, the microbial strain comprises a rpoB gene comprising a nucleotide sequence that exhibits at least 80%, at least 85%, at least 90%, at least 91%, at least 92%, at least 93%, at least 94%, at least 95%, at least 96%, at least 97%, at least 98%, at least 99%, at least 99.9%, or 100% sequence identity to a nucleotide sequence as set forth in SEQ ID NO: 7.

In some embodiments, the bacterial strain is from a *Paenibacillus borealis* species. In some embodiments, the bacterial strain is from a bacterial species other than *Paenibacillus borealis*. In some embodiments, the *Paenibacillus borealis* strain is the strain deposited under ATCC Accession No. PTA-127654, or an isolated clone thereof. In some embodiments, the 16S rRNA gene of the microbial strain comprises the nucleotide sequence of SEQ ID NO: 2. In some embodiments, the microbial strain comprises a 16S rRNA gene comprising a nucleotide sequence that exhibits at least 80%, at least 85%, at least 90%, at least 91%, at least 92%, at least 93%, at least 94%, at least 95%, at least 96%, at least 97%, at least 98%, at least 99%, at least 99.9%, or 100% sequence identity to a nucleotide sequence as set forth in SEQ ID NO: 2. In some embodiments, the gyrB gene of the microbial strain comprises the nucleotide sequence of SEQ ID NO: 5. In some embodiments, the microbial strain comprises a gyrB gene comprising a nucleotide sequence that exhibits at least 80%, at least 85%, at least 90%, at least 91%, at least 92%, at least 93%, at least 94%, at least 95%, at least 96%, at least 97%, at least 98%, at least 99%, at least 99.9%, or 100% sequence identity to a nucleotide sequence as set forth in SEQ ID NO: 5. In some embodiments, the rpoB gene of the microbial strain comprises the nucleotide sequence of SEQ ID NO: 8. In some embodiments, the microbial strain comprises a rpoB gene comprising a nucleotide sequence that exhibits at least 80%, at least 85%, at least 90%, at least 91%, at least 92%, at least 93%, at least 94%, at least 95%, at least 96%, at least 97%, at least 98%, at least 99%, at least 99.9%, or 100% sequence identity to a nucleotide sequence as set forth in SEQ ID NO: 8.

In some embodiments, the bacterial strain is from a *Paenibacillus sonchi* species. In some embodiments, the bacterial strain is from a bacterial species other than *Paenibacillus sonchi*. In some embodiments, the *Paenibacillus sonchi* strain is the strain deposited under ATCC Accession No. PTA-127655, or an isolated clone thereof. In some embodiments, the 16S rRNA gene of the microbial strain comprises the nucleotide sequence of SEQ ID NO: 3. In some embodiments, the microbial strain comprises a 16S rRNA gene comprising a nucleotide sequence that exhibits at least 80%, at least 85%, at least 90%, at least 91%, at least 92%, at least 93%, at least 94%, at least 95%, at least 96%, at least 97%, at least 98%, at least 99%, at least 99.9%, or 100% sequence identity to a nucleotide sequence as set forth in SEQ ID NO: 3. In some embodiments, the gyrB gene of the microbial strain comprises the nucleotide sequence of SEQ ID NO: 6. In some embodiments, the microbial strain comprises a gyrB gene comprising a nucleotide sequence that exhibits at least 80%, at least 85%, at least 90%, at least 91%, at least 92%, at least 93%, at least 94%, at least 95%, at least 96%, at least 97%, at least 98%, at least 99%, at least 99.9%, or 100% sequence identity to a nucleotide sequence as set forth in SEQ ID NO: 6. In some embodiments, the rpoB gene of the microbial strain comprises the nucleotide sequence of SEQ ID NO: 9. In some embodiments, the microbial strain comprises a rpoB gene comprising a nucleotide sequence that exhibits at least 80%, at least 85%, at least 90%, at least 91%, at least 92%, at least 93%, at least 94%, at least 95%, at least 96%, at least 97%, at least 98%, at least 99%, at least 99.9%, or 100% sequence identity to a nucleotide sequence as set forth in SEQ ID NO: 9.

In some embodiments, the bacterial strain is from a *Bacillus megaterium* species. In some embodiments, the bacterial strain is from a bacterial species other than *Bacillus megaterium*. In some embodiments, the *Bacillus megaterium* strain is the strain deposited under ATCC Accession No. PTA-127652, or an isolated clone thereof. In some embodiments, the 16S rRNA gene of the microbial strain comprises the nucleotide sequence of SEQ ID NO: 10. In some embodiments, the microbial strain comprises a 16S rRNA gene comprising a nucleotide sequence that exhibits at least 80%, at least 85%, at least 90%, at least 91%, at least 92%, at least 93%, at least 94%, at least 95%, at least 96%, at least 97%, at least 98%, at least 99%, at least 99.9%, or 100% sequence identity to a nucleotide sequence as set forth in SEQ ID NO: 10. In some embodiments, the gyrB gene of the microbial strain comprises the nucleotide sequence of SEQ ID NO: 11. In some embodiments, the microbial strain comprises a gyrB gene comprising a nucleotide sequence that exhibits at least 80%, at least 85%, at least 90%, at least 91%, at least 92%, at least 93%, at least 94%, at least 95%, at least 96%, at least 97%, at least 98%, at least 99%, at least 99.9%, or 100% sequence identity to a nucleotide sequence as set forth in SEQ ID NO: 11. In some embodiments, the rpoB gene of the microbial strain comprises the nucleotide sequence of SEQ ID NO: 12. In some embodiments, the microbial strain comprises a rpoB gene comprising a nucleotide sequence that exhibits at least 80%, at least 85%, at least 90%, at least 91%, at least 92%, at least 93%, at least 94%, at least 95%, at least 96%, at least 97%, at least 98%, at least 99%, at least 99.9%, or 100% sequence identity to a nucleotide sequence as set forth in SEQ ID NO: 12.

E. Exemplary Digestion System

Figure 66:
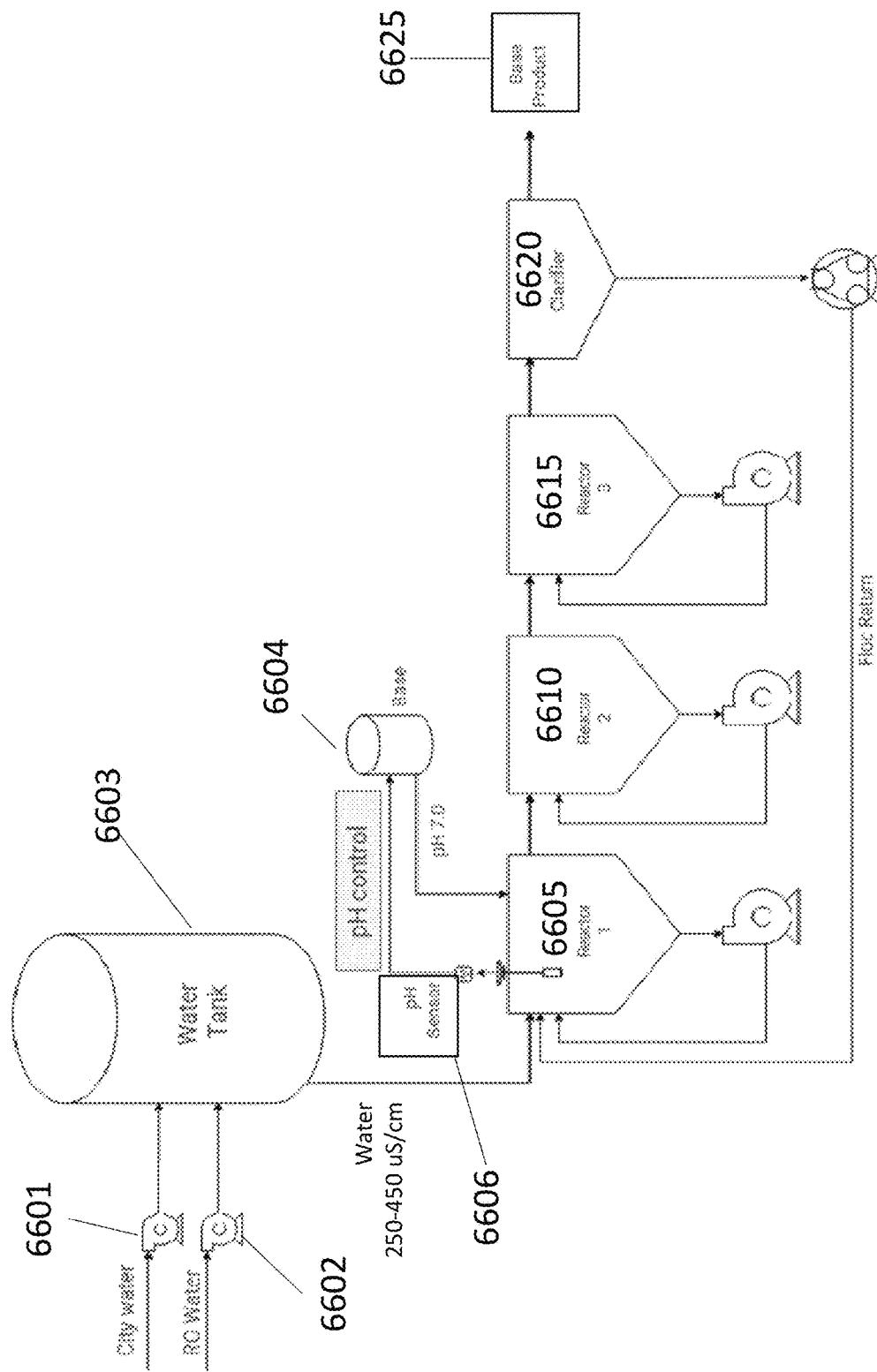
FIG. 66 is an exemplary schematic labelling the parts of a NTS digestion system.
Figures 67A, 67B:
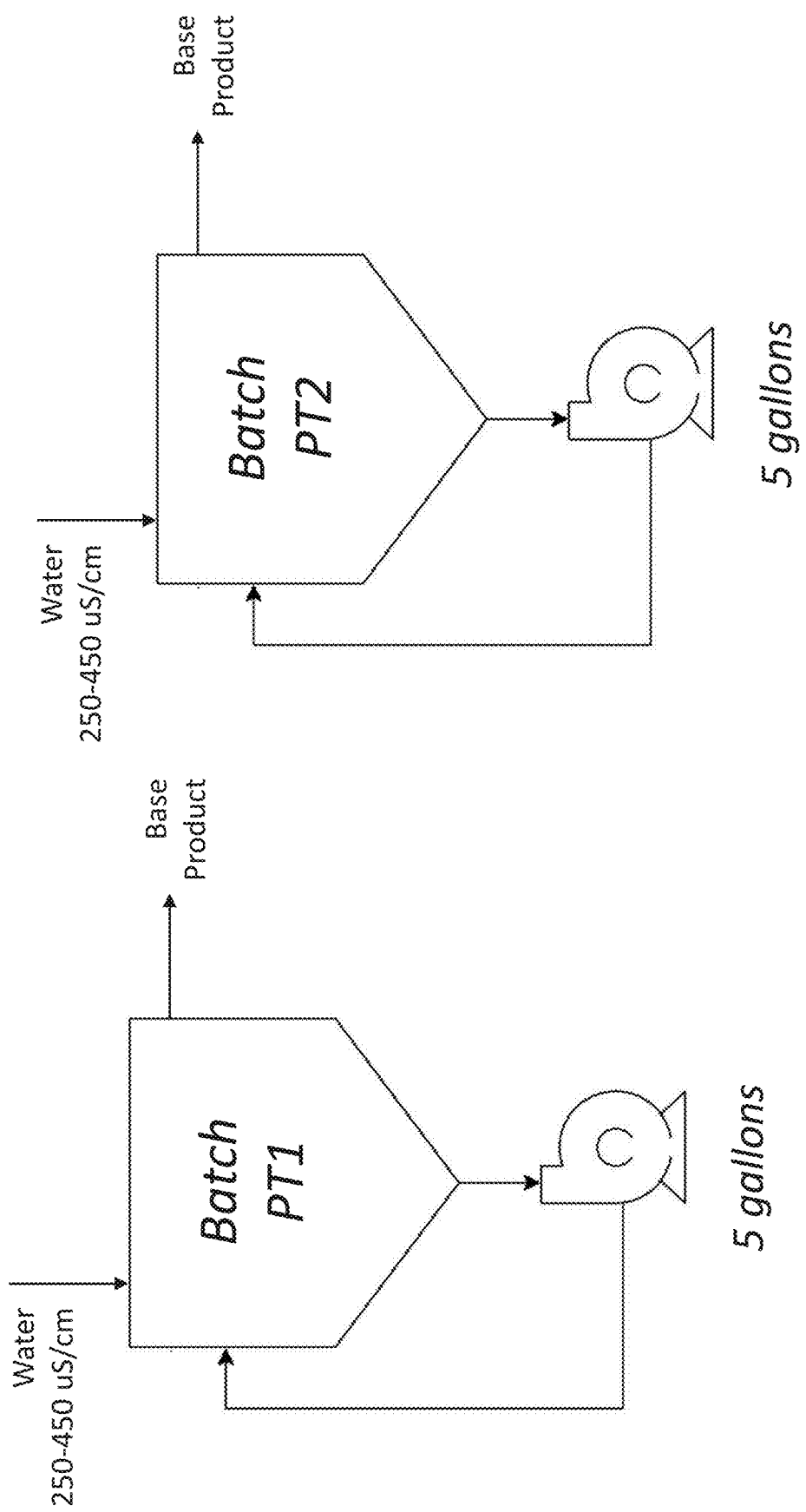
FIGS. 67A-67B are exemplary schematics of the NTS batch systems.
Figure 68:
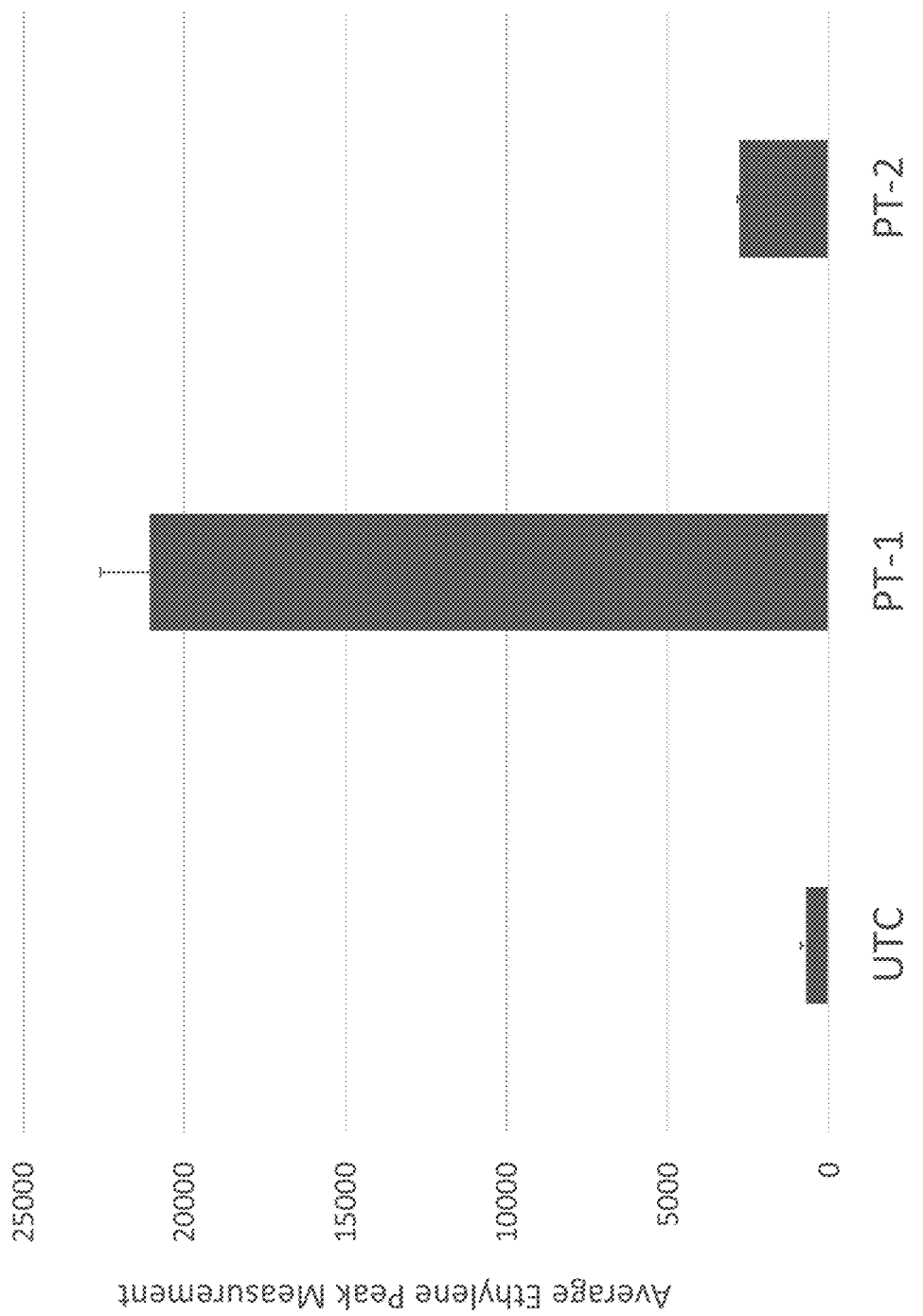
FIG. 68 shows the effects of products from the NTS batch systems (e.g., PT1 and PT2) on ethylene production. PT1 product shows the greatest ethylene peak compared to that from UTC and PT2.

FIG. 66 schematically illustrates an example of a digestion system 6600 with conditions (e.g., microbes) that produce biostimulant products that may have a multi-modal way of promoting efficient use of nitrogen by plants. The system 6600 comprises a water tank 6603 that comprises city water 6601 and RO water 6602. The system 6600 also comprises a first reactor 6605, a second reactor 6610, a third reactor 6615, and/or a clarifier chamber 6620 connected sequentially in which feedstock can continuously flow and microbial consortia as described herein can be grown. The first reactor, second reactor, and/or third reactor may be packed bed reactors with a scaffolding within the reactors or may be fluidized bed reactors without the scaffolding. The water tank 6603 is coupled to the first reactor 6601 and provides continuous flow of water to the first reactor 6601. The system 6600 can also comprise an input channel that flows inputs into the digestion system. In some cases, the inputs into the digestion system are flown into the first reactor through the water tank. In other cases, the input composition can be added to the first reactor. The inputs, as described herein, may comprise one or more of water, a microbial inoculum, nutrients, and/or a digestion substrate (e.g., aqueous organic feedstock).

The system 6600 may comprise a pH sensor 6606, pH controller, and/or a buffer addition system 6604 to detect and/or control the pH in the reactor so that the pH is maintained at a threshold (e.g., pH 7). The buffer addition system 6604 may be automatic. For example, if the pH of the working fluid in the first reactor is below the threshold value, an automatic base (e.g., 3M of NaOH) may be added to the first reactor until the pH reaches the threshold value (e.g., at least about 7).

In some cases, fluid (e.g., working fluid) can flow in a hydraulically balanced manner. The clarifier chamber 6620 produces biostimulant products or digestion products (e.g., base products) 6625.

Fluid (e.g., working fluid) from an outflow port of the first reactor 6605 can flow into the second reactor 6610 continuously. Fluid from an outflow port of the second reactor 6610 can flow into the third reactor 6615 continuously. Fluid from an outflow port of the third reactor 6615 can flow into the clarifier chamber 6620 continuously.

The outflow port may be positioned on the top, middle, and/or bottom of a reactor. Additionally, each reactor or clarifier chamber may comprise another outflow port for reintroducing fluid back into the same reactor or clarifier chamber, and may be pumped back to just below the surface of the same reactor to maintain homogeneous conditions within the working solutions. In some cases, the working fluid from each reactor is recirculated within each reactor from the bottom of the reactor back to just below the surface of the working solution to maintain a homogeneous environment for fermentation. For example, fluid from the first reactor 6605 may be reintroduced back into the first reactor 6605. Biosolids (e.g., floc) may be generated through the process. In some embodiments, floc can be a flocculated mass of microorganisms, extracellular polymeric substance (EPS) and adsorbed organic and inorganic material. A flocculated mass can comprise an aggregated mass of microorganisms, extracellular polymeric substance (EPS) and adsorbed organic and inorganic material.

In some cases, the clarifier chamber 6620 may comprise an outflow port for reintroducing fluid back to the first reactor 6605. In some embodiments, the supernatant (or base product) from the clarifier chamber may be continuously collected, and a portion of the floc at the bottom of the clarifier can be returned to the first reactor at a rate of recirculation of at least about 0.5 L/day, at least about 1.0 L/day, at least about 1.5 L/day, at least about 2.0 L/day, at least about 2.5 L/day, at least about 3.0 L/day, at least about 3.5 L/day, at least about 4.0 L/day, at least about 4.1 L/day, at least about 4.2 L/day, at least about 4.3 L/day, at least about 4.4 L/day, at least about 4.5 L/day, at least about 4.51 L/day, at least about 4.52 L/day, at least about 4.53 L/day, at least about 4.54 L/day, at least about 4.55 L/day, at least about 4.56 L/day, at least about 4.57 L/day, at least about 4.58 L/day, at least about 4.59 L/day, at least about 4.6 L/day, at least about 4.7 L/day, at least about 4.8 L/day, at least about 4.9 L/day, at least about 5.0 L/day, at least about 6.0 L/day, at least about 7.0 L/day, at least about 8.0 L/day, at least about 9.0 L/day, or at least about 10.0 L/day.

In some embodiments, the supernatant (or base product) from the clarifier chamber may be continuously collected, and a portion of the floc at the bottom of the clarifier can be returned to the first reactor at a rate of recirculation of at most about 10.0 L/day, at most about 9.0 L/day, at most about 8.0 L/day, at most about 7.0 L/day, at most about 6.0 L/day, at most about 5.5 L/day, at most about 5.0 L/day, at most about 4.9 L/day, at most about 4.8 L/day, at most about 4.7 L/day, at most about 4.6 L/day, at most about 4.59 L/day, at most about 4.58 L/day, at most about 4.57 L/day, at most about 4.56 L/day, at most about 4.55 L/day, at most about 4.54 L/day, at most about 4.53 L/day, at most about 4.52 L/day, at most about 4.51 L/day, at most about 4.5 L/day, at most about 4.4 L/day, at most about 4.3 L/day, at most about 4.2 L/day, at most about 4.1 L/day, at most about 4.0 L/day, at most about 3.5 L/day, at most about 3.0 L/day, at most about 2.5 L/day, at most about 2.0 L/day, at most about 1.5 L/day, at most about 1.0 L/day, or at most about 0.5 L/day.

In some embodiments, the supernatant (or base product) from the clarifier chamber may be continuously collected, and a portion of the floc at the bottom of the clarifier can be returned to the first reactor at a rate of recirculation of about 0.5 L/day to about 15 L/day. In some embodiments, the supernatant (or base product) from the clarifier chamber may be continuously collected, and a portion of the floc at the bottom of the clarifier can be returned to the first reactor at a rate of recirculation of about 0.5 L/day to about 1 L/day, about 0.5 L/day to about 1.5 L/day, about 0.5 L/day to about 2 L/day, about 0.5 L/day to about 3 L/day, about 0.5 L/day to about 4 L/day, about 0.5 L/day to about 4.5 L/day, about 0.5 L/day to about 5 L/day, about 0.5 L/day to about 7.5 L/day, about 0.5 L/day to about 10 L/day, about 0.5 L/day to about 12 L/day, about 0.5 L/day to about 15 L/day, about 1 L/day to about 1.5 L/day, about 1 L/day to about 2 L/day, about 1 L/day to about 3 L/day, about 1 L/day to about 4 L/day, about 1 L/day to about 4.5 L/day, about 1 L/day to about 5 L/day, about 1 L/day to about 7.5 L/day, about 1 L/day to about 10 L/day, about 1 L/day to about 12 L/day, about 1 L/day to about 15 L/day, about 1.5 L/day to about 2 L/day, about 1.5 L/day to about 3 L/day, about 1.5 L/day to about 4 L/day, about 1.5 L/day to about 4.5 L/day, about 1.5 L/day to about 5 L/day, about 1.5 L/day to about 7.5 L/day, about 1.5 L/day to about 10 L/day, about 1.5 L/day to about 12 L/day, about 1.5 L/day to about 15 L/day, about 2 L/day to about 3 L/day, about 2 L/day to about 4 L/day, about 2 L/day to about 4.5 L/day, about 2 L/day to about 5 L/day, about 2 L/day to about 7.5 L/day, about 2 L/day to about 10 L/day, about 2 L/day to about 12 L/day, about 2 L/day to about 15 L/day, about 3 L/day to about 4 L/day, about 3 L/day to about 4.5 L/day, about 3 L/day to about 5 L/day, about 3 L/day to about 7.5 L/day, about 3 L/day to about 10 L/day, about 3 L/day to about 12 L/day, about 3 L/day to about 15 L/day, about 4 L/day to about 4.5 L/day, about 4 L/day to about 5 L/day, about 4 L/day to about 7.5 L/day, about 4 L/day to about 10 L/day, about 4 L/day to about 12 L/day, about 4 L/day to about 15 L/day, about 4.5 L/day to about 5 L/day, about 4.5 L/day to about 7.5 L/day, about 4.5 L/day to about 10 L/day, about 4.5 L/day to about 12 L/day, about 4.5 L/day to about 15 L/day, about 5 L/day to about 7.5 L/day, about 5 L/day to about 10 L/day, about 5 L/day to about 12 L/day, about 5 L/day to about 15 L/day, about 7.5 L/day to about 10 L/day, about 7.5 L/day to about 12 L/day, about 7.5 L/day to about 15 L/day, about 10 L/day to about 12 L/day, about 10 L/day to about 15 L/day, or about 12 L/day to about 15 L/day.

Figure 63:
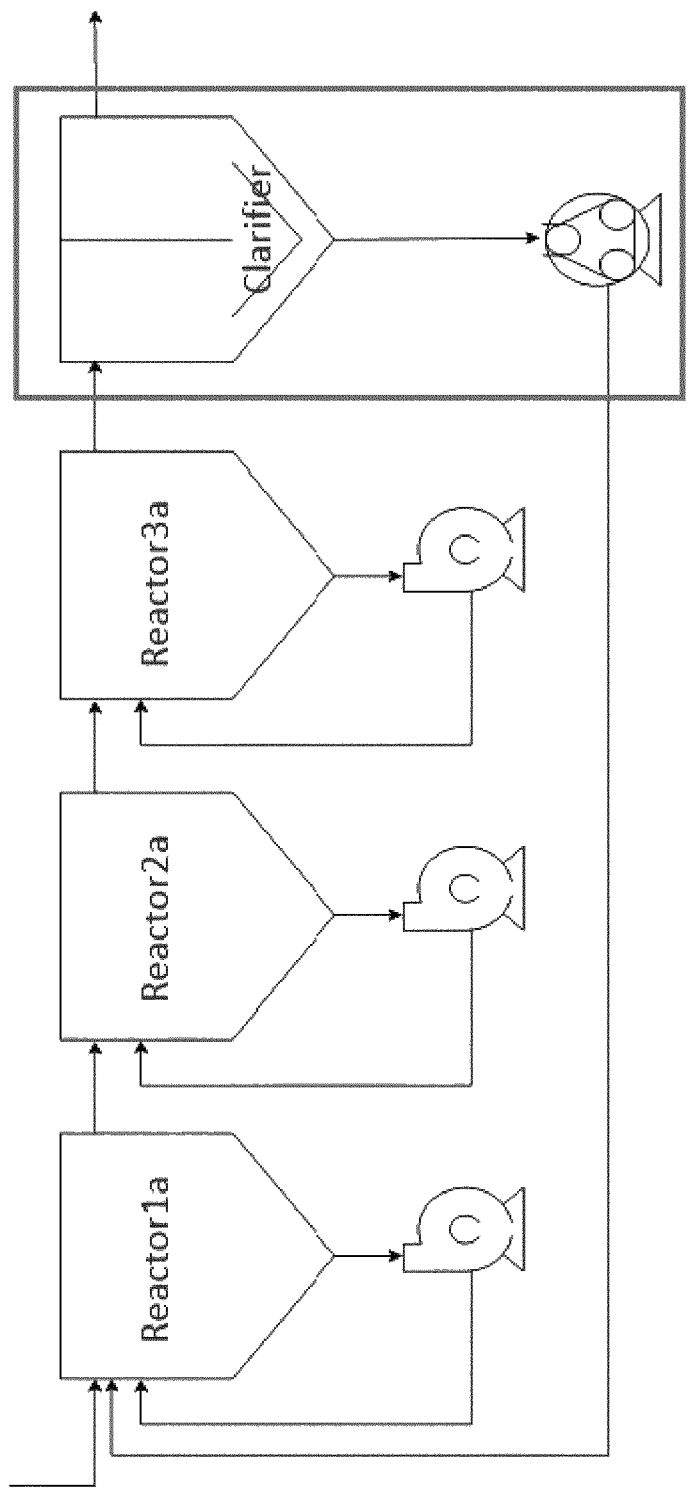
FIG. 63 is an exemplary schematic emphasizing the floc flights present in the clarifier of the NTS 2.0 system.

In some embodiments, the clarifier may comprise a floc flight system (e.g., floc-folding flights) as shown in FIG. 63 that can improve the concentration of the added specific isolate(s) in the base product. With the addition of the floc flights in the clarifier, the concentration of a target isolate in the base product may be maintained at a higher concentration for a longer period. In the clarifier, floc may settle or become immobilized in the bottom of the clarifier. Slow, floc-folding flights may release immobilized amount(s) of the target isolate strain in the floc. The released target isolate can then be returned (e.g., be reinoculated) into the digestion system. The floc-folding flights may re-suspend an amount of target isolate into the supernatant (e.g., base product). In some embodiments, the floc may return back to the system at a concentration of least about a 0.1% v/v rate per day, at least about a 0.5% v/v rate per day, at least about a 1.0% v/v rate per day, at least about a 1.1% v/v rate per day, at least about a 1.2% v/v rate per day, at least about a 1.3% v/v rate per day, at least about a 1.4% v/v rate per day, at least about a 1.5% v/v rate per day, at least about a 1.6% v/v rate per day, at least about a 1.7% v/v rate per day, at least about a 1.8% v/v rate per day, at least about a 1.9% v/v rate per day, at least about a 2.0% v/v rate per day, at least about a 2.1% v/v rate per day, at least about a 2.2% v/v rate per day, at least about a 2.3% v/v rate per day, at least about a 2.4% v/v rate per day, at least about a 2.5% v/v rate per day, at least about a 2.6% v/v rate per day, at least about a 2.7% v/v rate per day, at least about a 2.8% v/v rate per day, at least about a 2.9% v/v rate per day, at least about a 3.0% v/v rate per day, at least about a 4.0% v/v rate per day, at least about a 5.0% v/v rate per day, at least about a 6.0% v/v rate per day, at least about a 7.0% v/v rate per day, at least about a 8.0% v/v rate per day, at least about a 9.0% v/v rate per day, or at least about a 10.0% v/v rate per day.

In some embodiments, the floc may return back to the system at most about a concentration of 10.0% v/v rate per day, 9.0% v/v rate per day, 8.0% v/v rate per day, 7.0% v/v rate per day, 6.0% v/v rate per day, 5.0% v/v rate per day, 4.0% v/v rate per day, 3.0% v/v rate per day, 2.9% v/v rate per day, 2.8% v/v rate per day, 2.7% v/v rate per day, 2.6% v/v rate per day, 2.5% v/v rate per day, 2.4% v/v rate per day, 2.3% v/v rate per day, 2.2% v/v rate per day, 2.1% v/v rate per day, 2.0% v/v rate per day, 1.9% v/v rate per day, 1.8% v/v rate per day, 1.7% v/v rate per day, 1.6% v/v rate per day, 1.5% v/v rate per day, 1.4% v/v rate per day, 1.3% v/v rate per day, 1.2% v/v rate per day, 1.1% v/v rate per day, 1.0% v/v rate per day, 0.5% v/v rate per day, or 0.1% v/v rate per day.

In some embodiments, the floc may return back to the system at a concentration of about 0.1% v/v rate per day to about 15% v/v rate per day. In some embodiments, the floc may return back to the system at a concentration of about 0.1% v/v rate per day to about 0.5% v/v rate per day, about 0.1% v/v rate per day to about 1% v/v rate per day, about 0.1% v/v rate per day to about 1.5% v/v rate per day, about 0.1% v/v rate per day to about 2% v/v rate per day, about 0.1% v/v rate per day to about 3% v/v rate per day, about 0.1% v/v rate per day to about 4% v/v rate per day, about 0.1% v/v rate per day to about 5% v/v rate per day, about 0.1% v/v rate per day to about 7% v/v rate per day, about 0.1% v/v rate per day to about 10% v/v rate per day, about 0.1% v/v rate per day to about 12% v/v rate per day, about 0.1% v/v rate per day to about 15% v/v rate per day, about 0.5% v/v rate per day to about 1% v/v rate per day, about 0.5% v/v rate per day to about 1.5% v/v rate per day, about 0.5% v/v rate per day to about 2% v/v rate per day, about 0.5% v/v rate per day to about 3% v/v rate per day, about 0.5% v/v rate per day to about 4% v/v rate per day, about 0.5% v/v rate per day to about 5% v/v rate per day, about 0.5% v/v rate per day to about 7% v/v rate per day, about 0.5% v/v rate per day to about 10% v/v rate per day, about 0.5% v/v rate per day to about 12% v/v rate per day, about 0.5% v/v rate per day to about 15% v/v rate per day, about 1% v/v rate per day to about 1.5% v/v rate per day, about 1% v/v rate per day to about 2% v/v rate per day, about 1% v/v rate per day to about 3% v/v rate per day, about 1% v/v rate per day to about 4% v/v rate per day, about 1% v/v rate per day to about 5% v/v rate per day, about 1% v/v rate per day to about 7% v/v rate per day, about 1% v/v rate per day to about 10% v/v rate per day, about 1% v/v rate per day to about 12% v/v rate per day, about 1% v/v rate per day to about 15% v/v rate per day, about 1.5% v/v rate per day to about 2% v/v rate per day, about 1.5% v/v rate per day to about 3% v/v rate per day, about 1.5% v/v rate per day to about 4% v/v rate per day, about 1.5% v/v rate per day to about 5% v/v rate per day, about 1.5% v/v rate per day to about 7% v/v rate per day, about 1.5% v/v rate per day to about 10% v/v rate per day, about 1.5% v/v rate per day to about 12% v/v rate per day, about 1.5% v/v rate per day to about 15% v/v rate per day, about 2% v/v rate per day to about 3% v/v rate per day, about 2% v/v rate per day to about 4% v/v rate per day, about 2% v/v rate per day to about 5% v/v rate per day, about 2% v/v rate per day to about 7% v/v rate per day, about 2% v/v rate per day to about 10% v/v rate per day, about 2% v/v rate per day to about 12% v/v rate per day, about 2% v/v rate per day to about 15% v/v rate per day, about 3% v/v rate per day to about 4% v/v rate per day, about 3% v/v rate per day to about 5% v/v rate per day, about 3% v/v rate per day to about 7% v/v rate per day, about 3% v/v rate per day to about 10% v/v rate per day, about 3% v/v rate per day to about 12% v/v rate per day, about 3% v/v rate per day to about 15% v/v rate per day, about 4% v/v rate per day to about 5% v/v rate per day, about 4% v/v rate per day to about 7% v/v rate per day, about 4% v/v rate per day to about 10% v/v rate per day, about 4% v/v rate per day to about 12% v/v rate per day, about 4% v/v rate per day to about 15% v/v rate per day, about 5% v/v rate per day to about 7% v/v rate per day, about 5% v/v rate per day to about 10% v/v rate per day, about 5% v/v rate per day to about 12% v/v rate per day, about 5% v/v rate per day to about 15% v/v rate per day, about 7% v/v rate per day to about 10% v/v rate per day, about 7% v/v rate per day to about 12% v/v rate per day, about 7% v/v rate per day to about 15% v/v rate per day, about 10% v/v rate per day to about 12% v/v rate per day, about 10% v/v rate per day to about 15% v/v rate per day, or about 12% v/v rate per day to about 15% v/v rate per day.

In some embodiments, the floc may return back to the system at a concentration of about 0.1% v/v rate per day to about 3% v/v rate per day. In some embodiments, the floc may return back to the system at a concentration of about 0.1% v/v rate per day to about 0.5% v/v rate per day, about 0.1% v/v rate per day to about 1% v/v rate per day, about 0.1% v/v rate per day to about 1.25% v/v rate per day, about 0.1% v/v rate per day to about 1.5% v/v rate per day, about 0.1% v/v rate per day to about 1.75% v/v rate per day, about 0.1% v/v rate per day to about 2% v/v rate per day, about 0.1% v/v rate per day to about 20.25% v/v rate per day, about 0.1% v/v rate per day to about 2.5% v/v rate per day, about 0.1% v/v rate per day to about 20.75% v/v rate per day, about 0.1% v/v rate per day to about 3% v/v rate per day, about 0.5% v/v rate per day to about 1% v/v rate per day, about 0.5% v/v rate per day to about 1.25% v/v rate per day, about 0.5% v/v rate per day to about 1.5% v/v rate per day, about 0.5% v/v rate per day to about 1.75% v/v rate per day, about 0.5% v/v rate per day to about 2% v/v rate per day, about 0.5% v/v rate per day to about 20.25% v/v rate per day, about 0.5% v/v rate per day to about 2.5% v/v rate per day, about 0.5% v/v rate per day to about 20.75% v/v rate per day, about 0.5% v/v rate per day to about 3% v/v rate per day, about 1% v/v rate per day to about 1.25% v/v rate per day, about 1% v/v rate per day to about 1.5% v/v rate per day, about 1% v/v rate per day to about 1.75% v/v rate per day, about 1% v/v rate per day to about 2% v/v rate per day, about 1% v/v rate per day to about 20.25% v/v rate per day, about 1% v/v rate per day to about 2.5% v/v rate per day, about 1% v/v rate per day to about 20.75% v/v rate per day, about 1% v/v rate per day to about 3% v/v rate per day, about 1.25% v/v rate per day to about 1.5% v/v rate per day, about 1.25% v/v rate per day to about 1.75% v/v rate per day, about 1.25% v/v rate per day to about 2% v/v rate per day, about 1.25% v/v rate per day to about 20.25% v/v rate per day, about 1.25% v/v rate per day to about 2.5% v/v rate per day, about 1.25% v/v rate per day to about 20.75% v/v rate per day, about 1.25% v/v rate per day to about 3% v/v rate per day, about 1.5% v/v rate per day to about 1.75% v/v rate per day, about 1.5% v/v rate per day to about 2% v/v rate per day, about 1.5% v/v rate per day to about 2.25% v/v rate per day, about 1.5% v/v rate per day to about 2.5% v/v rate per day, about 1.5% v/v rate per day to about 2.75% v/v rate per day, about 1.5% v/v rate per day to about 3% v/v rate per day, about 1.75% v/v rate per day to about 2% v/v rate per day, about 1.75% v/v rate per day to about 2.25% v/v rate per day, about 1.75% v/v rate per day to about 2.5% v/v rate per day, about 1.75% v/v rate per day to about 2.75% v/v rate per day, about 1.75% v/v rate per day to about 3% v/v rate per day, about 2% v/v rate per day to about 2.25% v/v rate per day, about 2% v/v rate per day to about 2.5% v/v rate per day, about 2% v/v rate per day to about 2.75% v/v rate per day, about 2% v/v rate per day to about 3% v/v rate per day, about 2.25% v/v rate per day to about 2.5% v/v rate per day, about 2.25% v/v rate per day to about 2.75% v/v rate per day, about 2.25% v/v rate per day to about 3% v/v rate per day, about 2.5% v/v rate per day to about 2.75% v/v rate per day, about 2.5% v/v rate per day to about 3% v/v rate per day, or about 2.75% v/v rate per day to about 3% v/v rate per day.

In some embodiments, as solids accumulate over time in the clarifier chamber, a range of at least about 20-25% solids v/v may be maintained in the digestion system. In some embodiments, additional floc may be harvested from the digestion system and removed. In some embodiments, at least about 5% solids v/v, at least about 10% solids v/v, at least about 15% solids v/v, at least about 16% solids v/v, at least about 17% solids v/v, at least about 18% solids v/v, at least about 19% solids v/v, at least about 20% solids v/v, at least about 21% solids v/v, at least about 22% solids v/v, at least about 23% solids v/v, at least about 24% solids v/v, at least about 25% solids v/v, at least about 26% solids v/v, at least about 27% solids v/v, at least about 28% solids v/v, at least about 29% solids v/v, at least about 30% solids v/v, at least about 35% solids v/v, at least about 40% solids v/v, at least about 45% solids v/v, or at least about 50% solids v/v may be maintained in the digestion system.

In some embodiments, at most about 50% solids v/v, at most about 45% solids v/v, at most about 40% solids v/v, at most about 35% solids v/v, at most about 30% solids v/v, at most about 29% solids v/v, at most about 28% solids v/v, at most about 27% solids v/v, at most about 26% solids v/v, at most about 25% solids v/v, at most about 24% solids v/v, at most about 23% solids v/v, at most about 22% solids v/v, at most about 21% solids v/v, at most about 20% solids v/v, at most about 19% solids v/v, at most about 18% solids v/v, at most about 17% solids v/v, at most about 16% solids v/v, at most about 15% solids v/v, at most about 14% solids v/v, at most about 13% solids v/v, at most about 12% solids v/v, at most about 11% solids v/v, at most about 10% solids v/v, or at most about 5% solids v/v may be maintained in the digestion system.

In some embodiments, about 0.1% solids v/v to about 60% solids v/v may be maintained in the digestion system. In some embodiments, about 0.1% solids v/v to about 1% solids v/v, about 0.1% solids v/v to about 5% solids v/v, about 0.1% solids v/v to about 10% solids v/v, about 0.1% solids v/v to about 15% solids v/v, about 0.1% solids v/v to about 20% solids v/v, about 0.1% solids v/v to about 25% solids v/v, about 0.1% solids v/v to about 30% solids v/v, about 0.1% solids v/v to about 35% solids v/v, about 0.1% solids v/v to about 40% solids v/v, about 0.1% solids v/v to about 50% solids v/v, about 0.1% solids v/v to about 60% solids v/v, about 1% solids v/v to about 5% solids v/v, about 1% solids v/v to about 10% solids v/v, about 1% solids v/v to about 15% solids v/v, about 1% solids v/v to about 20% solids v/v, about 1% solids v/v to about 25% solids v/v, about 1% solids v/v to about 30% solids v/v, about 1% solids v/v to about 35% solids v/v, about 1% solids v/v to about 40% solids v/v, about 1% solids v/v to about 50% solids v/v, about 1% solids v/v to about 60% solids v/v, about 5% solids v/v to about 10% solids v/v, about 5% solids v/v to about 15% solids v/v, about 5% solids v/v to about 20% solids v/v, about 5% solids v/v to about 25% solids v/v, about 5% solids v/v to about 30% solids v/v, about 5% solids v/v to about 35% solids v/v, about 5% solids v/v to about 40% solids v/v, about 5% solids v/v to about 50% solids v/v, about 5% solids v/v to about 60% solids v/v, about 10% solids v/v to about 15% solids v/v, about 10% solids v/v to about 20% solids v/v, about 10% solids v/v to about 25% solids v/v, about 10% solids v/v to about 30% solids v/v, about 10% solids v/v to about 35% solids v/v, about 10% solids v/v to about 40% solids v/v, about 10% solids v/v to about 50% solids v/v, about 10% solids v/v to about 60% solids v/v, about 15% solids v/v to about 20% solids v/v, about 15% solids v/v to about 25% solids v/v, about 15% solids v/v to about 30% solids v/v, about 15% solids v/v to about 35% solids v/v, about 15% solids v/v to about 40% solids v/v, about 15% solids v/v to about 50% solids v/v, about 15% solids v/v to about 60% solids v/v, about 20% solids v/v to about 25% solids v/v, about 20% solids v/v to about 30% solids v/v, about 20% solids v/v to about 35% solids v/v, about 20% solids v/v to about 40% solids v/v, about 20% solids v/v to about 50% solids v/v, about 20% solids v/v to about 60% solids v/v, about 25% solids v/v to about 30% solids v/v, about 25% solids v/v to about 35% solids v/v, about 25% solids v/v to about 40% solids v/v, about 25% solids v/v to about 50% solids v/v, about 25% solids v/v to about 60% solids v/v, about 30% solids v/v to about 35% solids v/v, about 30% solids v/v to about 40% solids v/v, about 30% solids v/v to about 50% solids v/v, about 30% solids v/v to about 60% solids v/v, about 35% solids v/v to about 40% solids v/v, about 35% solids v/v to about 50% solids v/v, about 35% solids v/v to about 60% solids v/v, about 40% solids v/v to about 50% solids v/v, about 40% solids v/v to about 60% solids v/v, or about 50% solids v/v to about 60% solids v/v.

In some embodiments, about 18% solids v/v to about 29% solids v/v. In some embodiments, about 18% solids v/v to about 19% solids v/v, about 18% solids v/v to about 20% solids v/v, about 18% solids v/v to about 21% solids v/v, about 18% solids v/v to about 22% solids v/v, about 18% solids v/v to about 23% solids v/v, about 18% solids v/v to about 24% solids v/v, about 18% solids v/v to about 25% solids v/v, about 18% solids v/v to about 26% solids v/v, about 18% solids v/v to about 27% solids v/v, about 18% solids v/v to about 28% solids v/v, about 18% solids v/v to about 29% solids v/v, about 19% solids v/v to about 20% solids v/v, about 19% solids v/v to about 21% solids v/v, about 19% solids v/v to about 22% solids v/v, about 19% solids v/v to about 23% solids v/v, about 19% solids v/v to about 24% solids v/v, about 19% solids v/v to about 25% solids v/v, about 19% solids v/v to about 26% solids v/v, about 19% solids v/v to about 27% solids v/v, about 19% solids v/v to about 28% solids v/v, about 19% solids v/v to about 29% solids v/v, about 20% solids v/v to about 21% solids v/v, about 20% solids v/v to about 22% solids v/v, about 20% solids v/v to about 23% solids v/v, about 20% solids v/v to about 24% solids v/v, about 20% solids v/v to about 25% solids v/v, about 20% solids v/v to about 26% solids v/v, about 20% solids v/v to about 27% solids v/v, about 20% solids v/v to about 28% solids v/v, about 20% solids v/v to about 29% solids v/v, about 21% solids v/v to about 22% solids v/v, about 21% solids v/v to about 23% solids v/v, about 21% solids v/v to about 24% solids v/v, about 21% solids v/v to about 25% solids v/v, about 21% solids v/v to about 26% solids v/v, about 21% solids v/v to about 27% solids v/v, about 21% solids v/v to about 28% solids v/v, about 21% solids v/v to about 29% solids v/v, about 22% solids v/v to about 23% solids v/v, about 22% solids v/v to about 24% solids v/v, about 22% solids v/v to about 25% solids v/v, about 22% solids v/v to about 26% solids v/v, about 22% solids v/v to about 27% solids v/v, about 22% solids v/v to about 28% solids v/v, about 22% solids v/v to about 29% solids v/v, about 23% solids v/v to about 24% solids v/v, about 23% solids v/v to about 25% solids v/v, about 23% solids v/v to about 26% solids v/v, about 23% solids v/v to about 27% solids v/v, about 23% solids v/v to about 28% solids v/v, about 23% solids v/v to about 29% solids v/v, about 24% solids v/v to about 25% solids v/v, about 24% solids v/v to about 26% solids v/v, about 24% solids v/v to about 27% solids v/v, about 24% solids v/v to about 28% solids v/v, about 24% solids v/v to about 29% solids v/v, about 25% solids v/v to about 26% solids v/v, about 25% solids v/v to about 27% solids v/v, about 25% solids v/v to about 28% solids v/v, about 25% solids v/v to about 29% solids v/v, about 26% solids v/v to about 27% solids v/v, about 26% solids v/v to about 28% solids v/v, about 26% solids v/v to about 29% solids v/v, about 27% solids v/v to about 28% solids v/v, about 27% solids v/v to about 29% solids v/v, or about 28% solids v/v to about 29% solids v/v may be maintained in the digestion system.

In some embodiments, the input composition, as described herein, may comprise a carbon source. The carbon source may be glucose, malate, lactose, sucrose, pyruvate, other simple sugars, or any combination thereof. The carbon source (e.g., glucose, malate) may be added to the first reactor to maintain a concentration of carbon source in the working fluid of 0.2%-20.0% w/v based on the span of the hydraulic retention time of the digestion system. In some embodiments, the carbon source (e.g., glucose, malate) may be added to the first reactor to maintain a concentration of carbon source in the working fluid of a carbon source in working fluid of at least about, at most about, or about 0.1%, 0.25%, 0.5%, 0.75%, 1.0%, 1.25%, 1.5%, 1.75%, 2.0%, 2.5%, 3.0%, 5.0%, 7.5%, or 10.0% w/v, or a range between any two of these values.

In some embodiments, the input composition, as described herein, may comprise a nitrogen source. The nitrogen source may be ammonium sulfate, ammonium chloride, ammonium nitrate, sodium nitrate, yeast extract, yeast, or any combination thereof. The nitrogen source (e.g., ammonium sulfate) may be added to the first reactor to maintain a concentration of nitrogen source in the working fluid of 0.02-0.2% w/v based on the span of the hydraulic retention time of the digestion system. In some embodiments, the nitrogen source (e.g., ammonium sulfate) may be added to the first reactor to maintain a concentration of nitrogen source in the working fluid of a nitrogen source in a working fluid of at least about, at most about, or about 0.005%, 0.01%, 0.015%, 0.02%, 0.025%, 0.03%, 0.035%, 0.04%, 0.045%, 0.05%, 0.055%, 0.06%, 0.065%, 0.07%, 0.075%, 0.1%, 0.125%, 0.15%, 0.175%, 0.2%, 0.25%, 0.3%, 0.4%, 0.5%, 0.75%, 1.0%, 1.5%, 2.0%, 2.5%, or 3.0% w/v, or a range between any two of these values.

In some cases, the quantities added of the carbon and/or nitrogen sources to the system may be relative to the retention time of the system and can be adjusted accordingly if the flow rate changes. For example, a digestion system with a longer retention time may have a larger amount of a carbon source and/or nitrogen source added compared to an amount of a carbon source and/or nitrogen source added to a system with a short retention time.

In some embodiments, the input composition, as described herein, may comprise plant-based materials (e.g., soluble plant-based materials). The plant-based material may be soy flour, corn flour, cereal flour, corn gluten, soy flour protein, soy protein hydrolysate, lentil flour, chickpea flour, green pea flour, yellow pea flour, white bean flour, or any combination thereof. The plant-based material (e.g., soy flour) may be added to the first reactor to at a concentration range of 0.2-3% w/v based on the span of the hydraulic retention time of the digestion system. In some embodiments, the plant-based material (e.g., soy flour) may be added to the first reactor at a concentration range of plant-based material in the working fluid of at least about, at most about, or about 0.05%, 0.075%, 0.1%, 0.125%, 0.15%, 0.175%, 0.2%, 0.25%, 0.3%, 0.5%, 0.75%, 1.0%, 1.5%, 2.0%, 2.5%, 3.0%, 3.5%, 4.0%, 5.0%, 6.0%, 7.0%, 8.0%, 9.0%, or 10.0% w/v, or a range between any two of these values.

In some embodiments, the input composition, as described herein, may comprise calcium carbonate. The calcium carbonate may be added to the first reactor to at a concentration range of 0.02-0.2% w/v based on the span of the hydraulic retention time of the digestion system. In some embodiments, the calcium carbonate may be added to the first reactor to at a concentration range of a calcium carbonate in a working fluid of at least about, at most about, or about 0.005%, 0.075%, 0.01%, 0.015%, 0.02%, 0.025%, 0.03%, 0.05%, 0.075%, 0.1%, 0.125%, 0.15%, 0.175%, 0.2%, 0.225%, 0.25%, 0.275%, 0.3%, 0.4%, 0.5%, 0.6%, 0.75%, 1.0%, 1.5%, 2.0%, 3.0%, 4.0%, or 5.0% w/v, or a range between any two of these values.

In some embodiments, a concentration range of 0.5-4.5% v/v of Whole Broth of a Phosphate Solubilization Technology, PST WB (in a ratio of 1:3 floc:supernatant (SPN)) or the Whole Broth of a Water Based Phosphate Solubilization Technology, PwST WB (in a ratio of 1:3 floc:SPN) may also be added to the first reactor on the span of the hydraulic retention time of the digestion system. The floc:SPN may be a combined mixture of floc (e.g., biosolids) and supernatant from the clarifier. In some embodiments, the concentration range of PST WB or PwST WB in a working fluid of a reactor may be at least about, at most about, or about 0.05%, 0.1%, 0.2%, 0.3%, 0.4%, 0.5%, 0.6%, 0.7%, 0.8%, 0.9%, 1.0%, 1.5%, 2.0%, 2.5%, 3.0%, 3.5%, 4.0%, 4.5%, 5.0%, 5.5%, 6.0%, 6.5%, 7.0%, 7.5%, 10.0%, 120.5%, or 15.0% v/v, or a range between any two of these values.

In some embodiments, the digestion system 6600 may be inoculated with isolates MS3900 and/or MS3907. In some embodiments, the digestion system may be inoculated with isolates MS3900, MS3907, MS4921, and/or any combination thereof.

In some embodiments, the water tank 6603 when coupled to the first reactor 6601 provides continuous flow of water to the first reactor 6601 at an electrical conductivity of at least about 100 microsiemens/centimeter (S/cm), at least about 150 µS/cm, at least about 200 µS/cm, at least about 250 µS/cm, at least about 300 µS/cm, at least about 350 µS/cm, at least about 400 µS/cm, at least about 450 µS/cm, at least about 500 µS/cm, at least about 550 µS/cm, or at least about 600 µS/cm.

In some embodiments, the water tank 6603 when coupled to the first reactor 6601 provides continuous flow of water to the first reactor 6601 at an electrical conductivity of at most about 600 µS/cm, at most about 550 µS/cm, at most about 500 µS/cm, at most about 450 µS/cm, at most about 400 µS/cm, at most about 350 µS/cm, at most about 300 µS/cm, at most about 250 µS/cm, at most about 200 µS/cm, at most about 150 µS/cm, or at most about 100 µS/cm.

In some embodiments, the water tank 6603 when coupled to the first reactor 6601 provides continuous flow of water to the first reactor 6601 at an electrical conductivity of about 50 µS/cm to about 800 µS/cm. In some embodiments, the water tank 6603 when coupled to the first reactor 6601 provides continuous flow of water to the first reactor 6601 at an electrical conductivity of about 50 µS/cm to about 100

μS/cm, about 50 μS/cm to about 200 μS/cm, about 50 μS/cm to about 250 μS/cm, about 50 μS/cm to about 300 μS/cm, about 50 μS/cm to about 350 μS/cm, about 50 μS/cm to about 400 μS/cm, about 50 μS/cm to about 450 μS/cm, about 50 μS/cm to about 500 μS/cm, about 50 μS/cm to about 600 μS/cm, about 50 μS/cm to about 700 μS/cm, about 50 μS/cm to about 800 μS/cm, about 100 μS/cm to about 200 μS/cm, about 100 μS/cm to about 250 μS/cm, about 100 μS/cm to about 300 μS/cm, about 100 μS/cm to about 350 μS/cm, about 100 μS/cm to about 400 μS/cm, about 100 μS/cm to about 450 μS/cm, about 100 μS/cm to about 500 μS/cm, about 100 μS/cm to about 600 μS/cm, about 100 μS/cm to about 700 μS/cm, about 100 μS/cm to about 800 μS/cm, about 200 μS/cm to about 250 μS/cm, about 200 μS/cm to about 300 μS/cm, about 200 μS/cm to about 350 μS/cm, about 200 μS/cm to about 400 μS/cm, about 200 μS/cm to about 450 μS/cm, about 200 μS/cm to about 500 μS/cm, about 200 μS/cm to about 600 μS/cm, about 200 μS/cm to about 700 μS/cm, about 200 μS/cm to about 800 μS/cm, about 250 μS/cm to about 300 μS/cm, about 250 μS/cm to about 350 μS/cm, about 250 μS/cm to about 400 μS/cm, about 250 μS/cm to about 450 μS/cm, about 250 μS/cm to about 500 μS/cm, about 250 μS/cm to about 600 μS/cm, about 250 μS/cm to about 700 μS/cm, about 250 μS/cm to about 800 μS/cm, about 300 μS/cm to about 350 μS/cm, about 300 μS/cm to about 400 μS/cm, about 300 μS/cm to about 450 μS/cm, about 300 μS/cm to about 500 μS/cm, about 300 μS/cm to about 600 μS/cm, about 300 μS/cm to about 700 μS/cm, about 300 μS/cm to about 800 μS/cm, about 350 μS/cm to about 400 μS/cm, about 350 μS/cm to about 450 μS/cm, about 350 μS/cm to about 500 μS/cm, about 350 μS/cm to about 600 μS/cm, about 350 μS/cm to about 700 μS/cm, about 350 μS/cm to about 800 μS/cm, about 400 μS/cm to about 450 μS/cm, about 400 μS/cm to about 500 μS/cm, about 400 μS/cm to about 600 μS/cm, about 400 μS/cm to about 700 μS/cm, about 400 μS/cm to about 800 μS/cm, about 450 μS/cm to about 500 μS/cm, about 450 μS/cm to about 600 μS/cm, about 450 μS/cm to about 700 μS/cm, about 450 μS/cm to about 800 μS/cm, about 500 μS/cm to about 600 μS/cm, about 500 μS/cm to about 700 μS/cm, about 500 μS/cm to about 800 μS/cm, about 600 μS/cm to about 700 μS/cm, about 600 μS/cm to about 800 μS/cm, or about 700 μS/cm to about 800 μS/cm.

In some embodiments, the first reactor 6605, the second reactor 6610, and/or the third reactor 6615 may comprise a volume of working fluid of at least about a 1 gallon, at least about a 2 gallon, at least about a 3 gallon, at least about a 4 gallon, at least about a 5 gallon, at least about a 6 gallon, at least about a 7 gallon, at least about a 8 gallon, at least about a 9 gallon, at least about a 10 gallon, at least about a 11 gallon, at least about a 12 gallon, at least about a 13 gallon, at least about a 14 gallon, at least about a 15 gallon, at least about a 16 gallon, at least about a 17 gallon, at least about a 18 gallon, at least about a 19 gallon, at least about a 20 gallon, at least about a 25 gallon, at least about a 30 gallon, at least about a 40 gallon, or at least about a 50 gallon reactor.

In some embodiments, the first reactor 6605, the second reactor 6610, and/or the third reactor 6615 may comprise a volume of working fluid of at most about a 50 gallon, at most about a 40 gallon, at most about a 30 gallon, at most about a 25 gallon, at most about a 20 gallon, at most about a 19 gallon, at most about a 18 gallon, at most about a 17 gallon, at most about a 16 gallon, at most about a 15 gallon, at most about a 14 gallon, at most about a 13 gallon, at most about a 12 gallon, at most about a 11 gallon, at most about a 10 gallon, at most about a 9 gallon, at most about a 8 gallon, at most about a 7 gallon, at most about a 6 gallon, at most about a 5 gallon, at most about a 4 gallon, at most about a 3 gallon, at most about a 2 gallon, or at most about 1 gallon reactor.

In some embodiments, the first reactor 6605, the second reactor 6610, and/or the third reactor 6615 may comprise a volume of working fluid of about a 1 gallon to 75 gallon reactor. In some embodiments, the first reactor 6605, the second reactor 6610, and/or the third reactor 6615 may comprise a volume of about a 1 gallon to 3 gallon, 1 gallon to 5 gallon, 1 gallon to 7 gallon, 1 gallon to 10 gallon, 1 gallon to 12 gallon, 1 gallon to 15 gallon, 1 gallon to 17 gallon, 1 gallon to 20 gallon, 1 gallon to 25 gallon, 1 gallon to 50 gallon, 1 gallon to 75 gallon, 3 gallon to 5 gallon, 3 gallon to 7 gallon, 3 gallon to 10 gallon, 3 gallon to 12 gallon, 3 gallon to 15 gallon, 3 gallon to 17 gallon, 3 gallon to 20 gallon, 3 gallon to 25 gallon, 3 gallon to 50 gallon, 3 gallon to 75 gallon, 5 gallon to 7 gallon, 5 gallon to 10 gallon, 5 gallon to 12 gallon, 5 gallon to 15 gallon, 5 gallon to 17 gallon, 5 gallon to 20 gallon, 5 gallon to 25 gallon, 5 gallon to 50 gallon, 5 gallon to 75 gallon, 7 gallon to 10 gallon, 7 gallon to 12 gallon, 7 gallon to 15 gallon, 7 gallon to 17 gallon, 7 gallon to 20 gallon, 7 gallon to 25 gallon, 7 gallon to 50 gallon, 7 gallon to 75 gallon, 10 gallon to 12 gallon, 10 gallon to 15 gallon, 10 gallon to 17 gallon, 10 gallon to 20 gallon, 10 gallon to 25 gallon, 10 gallon to 50 gallon, 10 gallon to 75 gallon, 12 gallon to 15 gallon, 12 gallon to 17 gallon, 12 gallon to 20 gallon, 12 gallon to 25 gallon, 12 gallon to 50 gallon, 12 gallon to 75 gallon, 15 gallon to 17 gallon, 15 gallon to 20 gallon, 15 gallon to 25 gallon, 15 gallon to 50 gallon, 15 gallon to 75 gallon, 17 gallon to 20 gallon, 17 gallon to 25 gallon, 17 gallon to 50 gallon, 17 gallon to 75 gallon, 20 gallon to 25 gallon, 20 gallon to 50 gallon, 20 gallon to 75 gallon, 25 gallon to 50 gallon, 25 gallon to 75 gallon, or 50 gallon to 75 gallon reactor.

In some embodiments, the total volume of working fluid within all of the reactors and clarifier may be maintained at 17.5 gallons or 60 gallons. In some embodiments, the total volume of working fluid within all of the reactors and clarifier may be maintained at a volume of least about, at most about, or about 1 gallon, 2 gallons, 5 gallons, 10 gallons, 15 gallons, 17 gallons, 20 gallons, 25 gallons, 30 gallons, 35 gallons, 40 gallons, 45 gallons, 50 gallons, 60 gallons, 65 gallons, 70 gallons, 75 gallons, 80 gallons, 90 gallons, 100 gallons, 125 gallons, or 150 gallons, or a range between any two of these values.

In some embodiments, the hydraulic rate of flow through the digestion system may be 4.6 ml/min to maintain a retention time of 10 days and can be varied accordingly for a retention time from 7 to 21 days depending on production volume requirements. In some embodiments, the hydraulic rate of flow through the digestion system may be a rate of 15 ml/min or 11 ml/min. In some embodiments, the hydraulic rate of flow through the digestion system may be a rate of at least about, at most about, or about 1 ml/min, 2 ml/min, 3 ml/min, 4 ml/min, 4.5 ml/min, 5 ml/min, 5.5 ml/min, 6 ml/min, 6.5 ml/min, 7 ml/min, 7.5 ml/min, 8 ml/min, 9 ml/min, 10 ml/min, 11 ml/min, 12 ml/min, 13 ml/min, 14 ml/min, 14.5 ml/min, 15 ml/min, 15.5 ml/min, 16 ml/min, 16.5 ml/min, 17 ml/min, 17.5 ml/min, 20 ml/min, 22.5 ml/min, or 25 ml/min, or a range between any two of these values.

A retention time may comprise a time a population of an inoculated microbial strain spends in a digestion system or a time a population of the microbial strain spends following transfer into a first container and until collection from the digestion system. A longer retention time may be advantageous for growth or enrichment of a population of the microbial strain of the digestion system. A shorter retention time may be advantageous for growth or enrichment of a population of the microbial strain of the digestion system. In some embodiments, the retention time of the digestion system may be 10 days.

In some embodiments, the retention time of the digestion system may be at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 15 days, at least about 16 days, at least about 17 days, at least about 18 days, at least about 19 days, at least about 20 days, at least about 22 days, or at least about 25 days.

In some embodiments, the retention time of the digestion system may be at most about 25 days, at most about 22 days, at most about 20 days, at most about 19 days, at most about 18 days, at most about 17 days, at most about 16 days, at most about 15 days, at most about 14 days, at most about 13 days, at most about 12 days, at most about 11 days, at most about 10 days, at most about 9 days, at most about 8 days, at most about 7 days, at most about 6 days, at most about 5 days, at most about 4 days, at most about 3 days, at most about 2 days, or at most about 1 day.

In some embodiments, the retention time of the digestion system may be about 1 day to about 30 days. In some embodiments, the retention time of the digestion system may be about 1 day to about 3 days, about 1 day to about 5 days, about 1 day to about 8 days, about 1 day to about 10 days, about 1 day to about 12 days, about 1 day to about 14 days, about 1 day to about 16 days, about 1 day to about 18 days, about 1 day to about 20 days, about 1 day to about 25 days, about 1 day to about 30 days, about 3 days to about 5 days, about 3 days to about 8 days, about 3 days to about 10 days, about 3 days to about 12 days, about 3 days to about 14 days, about 3 days to about 16 days, about 3 days to about 18 days, about 3 days to about 20 days, about 3 days to about 25 days, about 3 days to about 30 days, about 5 days to about 8 days, about 5 days to about 10 days, about 5 days to about 12 days, about 5 days to about 14 days, about 5 days to about 16 days, about 5 days to about 18 days, about 5 days to about 20 days, about 5 days to about 25 days, about 5 days to about 30 days, about 8 days to about 10 days, about 8 days to about 12 days, about 8 days to about 14 days, about 8 days to about 16 days, about 8 days to about 18 days, about 8 days to about 20 days, about 8 days to about 25 days, about 8 days to about 30 days, about 10 days to about 12 days, about 10 days to about 14 days, about 10 days to about 16 days, about 10 days to about 18 days, about 10 days to about 20 days, about 10 days to about 25 days, about 10 days to about 30 days, about 12 days to about 14 days, about 12 days to about 16 days, about 12 days to about 18 days, about 12 days to about 20 days, about 12 days to about 25 days, about 12 days to about 30 days, about 14 days to about 16 days, about 14 days to about 18 days, about 14 days to about 20 days, about 14 days to about 25 days, about 14 days to about 30 days, about 16 days to about 18 days, about 16 days to about 20 days, about 16 days to about 25 days, about 16 days to about 30 days, about 18 days to about 20 days, about 18 days to about 25 days, about 18 days to about 30 days, about 20 days to about 25 days, about 20 days to about 30 days, or about 25 days to about 30 days.

In some embodiment, the digestion system may produce 1.75 gallons of base product flowing from the clarifiers per day. In some embodiment, the digestion system may produce 4.29 gallons of base product flowing from the clarifiers per day. In some embodiment, the digestion system may produce 6 gallons of base product flowing from the clarifiers per day. In some embodiments, the digestion system may produce at least about, at most about, or about 0.5, 0.75, 1.0, 1.25, 1.5, 1.75, 2.0, 2.25, 2.5, 2.75, 3.0, 3.5, 4.0, 4.5, 5.0, 6.0, 7.0, 8.0, 9.0, 10.0, 12.0, or 15.0 gallons of base product flowing from the clarifiers per day, or a range between any two of these values.

In some embodiment, the digestion system may produce 12.25 gallons of base product flowing from the clarifiers per week. In some embodiment, the digestion system may produce 42 gallons of base product flowing from the clarifiers per week. In some embodiment, the digestion system may produce 30 gallons of base product flowing from the clarifiers per week. In some embodiment, the digestion system may produce at least about, at most about, or about 2 gallons, 5 gallons, 7.5 gallons, 10 gallons, 12.5 gallons, 15 gallons, 20 gallons, 25 gallons, 30 gallons, 35 gallons, 40 gallons, 45 gallons, 50 gallons, 55 gallons, 60 gallons, 70 gallons, 80 gallons, 90 gallons, or 100 gallons of base product flowing from the clarifiers per week, or a range between any two of these values.

In some embodiments, the digestion system can have an output of base product of at least about, at most about, or about 100 gallons, 200 gallons, 300 gallons, 400 gallons, 500 gallons, 750 gallons, 1000 gallons, 1500 gallons, 2000 gallons, 2500 gallons, 5000 gallons, 7500 gallons, 10000 gallons, 15000 gallons, 20000 gallons, 25000 gallons, 50000 gallons, 60000 gallons, 70000 gallons, 80000 gallons, 90000 gallons, or 100000 gallons per week, or a range between any two of these values.

In some embodiments, the produced base products from the digestion system can have a pH of 7.39-8.88. In some embodiments, the produced base products from the digestion system can have a pH of at least about, at most about, or about 4, 4.5, 5, 5.5, 6, 6.5, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or 10, or a range between any two of these values.

In some embodiments, the produced base products from the digestion system can have an electrical conductivity (Cond) range of 0.55-4.37 mS/cm. In some embodiments, the produced base products from the digestion system can have an electrical conductivity (Cond) range of at least about, at most about, or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10.0 mS/cm, or a range between any two of these values.

In some embodiments, the produced base products from the digestion system can have a COD of 22-3600 mg/L. In some embodiments, the produced base products from the digestion system can have a COD of at least about, at most about, or about 5, 10, 15, 20, 25, 50, 75, 100, 150, 200, 250, 500, 750, 1000, 1250, 1500, 1750, 2000, 2250, 2500, 2750, 3000, 3250, 3500, 3750, 4000, 4250, 4500, 4750, 5000, 5500, 6000, 6500, 7000, 7500, or 10,000 mg/L, or a range between any two of these values.

In some embodiments, the produced base products from the digestion system can have a total nitrogen (N) content of 0.02-0.07%. In some embodiments, the produced base products from the digestion system can have a total nitrogen (N) content in a working fluid of the digestion system of at least about, at most about, or about 0.005%, 0.01%, 0.0125%, 0.015%, 0.0175%, 0.02%, 0.0225%, 0.025%, 0.0275%, 0.03%, 0.035%, 0.04%, 0.045%, 0.05%, 0.055%, 0.06%, 0.065%, 0.07%, 0.075%, 0.08%, 0.085%, 0.09%, 0.095%, 0.1%, 0.2%, 0.3%, 0.4%, 0.5%, 0.75%, 1.0%, 1.5%, or 2.0%, or a range between any two of these values.

In some embodiments, the produced base products from the digestion system can have a total phosphorous (P) content of 0.00001%. In some embodiments, the produced base products from the digestion system can have a total phosphorous (P) content in a working fluid of the digestion system of at least about, at most about, or about 0.00001%, 0.00005%, 0.0001%, 0.0005%, 0.001%, 0.0025%, 0.005%, 0.0075%, 0.01%, 0.025%, 0.05%, 0.075%, 0.1%, 0.15%, or 0.2%, or a range between any two of these values.

In some embodiments, the produced base products from the digestion system can have a total potassium (K) content of 0.082-0.094%. In some embodiments, the produced base products from the digestion system can have a total potassium (K) content in a working fluid of the digestion system of at least about, at most about, or about 0.00001%, 0.00005%, 0.0001%, 0.00025%, 0.0005%, 0.00075%, 0.001%, 0.0025%, 0.005%, 0.0075%, 0.01%, 0.025%, 0.05%, 0.055%, 0.06%, 0.065%, 0.07%, 0.075%, 0.08%, 0.085%, 0.09%, 0.095%, 0.1%, 0.11%, 0.12%, 0.13%, 0.14%, 0.15%, 0.16%, 0.17%, 0.18%, 0.19%, 0.2%, 0.25%, 0.3%, 0.35%, 0.4%, 0.45%, or 0.5%, or a range between any two of these values.

In some embodiments, the working fluid in each reactor described herein may be circulated within the reactor in such a way as to minimize surface disruption, which maintains the dissolved oxygen within the reactors between 0.14 and 0.5 mg/L. In some embodiments, the dissolved oxygen within the reactors may be at least about, at most about, or about 0.05, 0.075, 0.1, 0.125, 0.15, 0.175, 0.2, 0.25, 0.3, 0.35, 0.4, 0.45, 0.5, 0.55, 0.6, 0.65, 0.7, 0.75, 0.8, 0.9, 1.0, 1.25, 1.5, 1.75, 2.0, 2.5, 5.0, 7.5, or 10.0 mg/L, or a range between any two of these values.

In some embodiments, the working fluid in each reactor described herein may be recirculated (e.g., recycled) within the reactor of the digestion system. In some embodiments, the rate of recirculation within the reactor may be between 4-9 gallons/min. In some embodiments, the rate of recirculation within the reactor may be at least about 0.5 gallon/min, at least about 1 gallon/min, at least about 2 gallons/min, at least about 3 gallons/min, at least about 3.5 gallons/min, at least about 4 gallons/min, at least about 4.5 gallons/min, at least about 5 gallons/min, at least about 5.5 gallons/min, at least about 6 gallons/min, at least about 6.5 gallons/min, at least about 7 gallons/min, at least about 7.5 gallons/min, at least about 8 gallons/min, at least about 8.5 gallons/min, at least about 9 gallons/min, at least about 10 gallons/min, at least about 11 gallons/min, at least about 13 gallons/min, at least about 15 gallons/min, at least about 20 gallons/min, at least about 25 gallons/min, at least about 30 gallons/min, at least about 40 gallons/min, or at least about 50 gallons/min.

In some embodiments, the rate of recirculation within the reactor may be at most about 50 gallons/min, at most about 40 gallons/min, at most about 30 gallons/min, at most about 25 gallons/min, at most about 20 gallons/min, at most about 15 gallons/min, at most about 13 gallons/min, at most about 10 gallons/min, at most about 9 gallons/min, at most about 8 gallons/min, at most about 7.5 gallons/min, at most about 7 gallons/min, at most about 6.5 gallons/min, at most about 6 gallons/min, at most about 5.5 gallons/min, at most about 5 gallons/min, at most about 4.5 gallons/min, at most about 4 gallons/min, at most about 3.5 gallons/min, at most about 3 gallons/min, at most about 2 gallons/min, at most about 1 gallon/min, or at most about 0.5 gallon/min.

In some embodiments, the rate of recirculation within the reactor may be about 0.5 gallons/min to about 30 gallons/min. In some embodiments, the rate of recirculation within the reactor may be about 0.5 gallons/min to about 1 gallon/min, about 0.5 gallons/min to about 2 gallons/min, about 0.5 gallons/min to about 3 gallons/min, about 0.5 gallons/min to about 4 gallons/min, about 0.5 gallons/min to about 6 gallons/min, about 0.5 gallons/min to about 8 gallons/min, about 0.5 gallons/min to about 9 gallons/min, about 0.5 gallons/min to about 10 gallons/min, about 0.5 gallons/min to about 15 gallons/min, about 0.5 gallons/min to about 20 gallons/min, about 0.5 gallons/min to about 30 gallons/min, about 1 gallon/min to about 2 gallons/min, about 1 gallon/min to about 3 gallons/min, about 1 gallon/min to about 4 gallons/min, about 1 gallon/min to about 6 gallons/min, about 1 gallon/min to about 8 gallons/min, about 1 gallon/min to about 9 gallons/min, about 1 gallon/min to about 10 gallons/min, about 1 gallon/min to about 15 gallons/min, about 1 gallon/min to about 20 gallons/min, about 1 gallon/min to about 30 gallons/min, about 2 gallons/min to about 3 gallons/min, about 2 gallons/min to about 4 gallons/min, about 2 gallons/min to about 6 gallons/min, about 2 gallons/min to about 8 gallons/min, about 2 gallons/min to about 9 gallons/min, about 2 gallons/min to about 10 gallons/min, about 2 gallons/min to about 15 gallons/min, about 2 gallons/min to about 20 gallons/min, about 2 gallons/min to about 30 gallons/min, about 3 gallons/min to about 4 gallons/min, about 3 gallons/min to about 6 gallons/min, about 3 gallons/min to about 8 gallons/min, about 3 gallons/min to about 9 gallons/min, about 3 gallons/min to about 10 gallons/min, about 3 gallons/min to about 15 gallons/min, about 3 gallons/min to about 20 gallons/min, about 3 gallons/min to about 30 gallons/min, about 4 gallons/min to about 6 gallons/min, about 4 gallons/min to about 8 gallons/min, about 4 gallons/min to about 9 gallons/min, about 4 gallons/min to about 10 gallons/min, about 4 gallons/min to about 15 gallons/min, about 4 gallons/min to about 20 gallons/min, about 4 gallons/min to about 30 gallons/min, about 6 gallons/min to about 8 gallons/min, about 6 gallons/min to about 9 gallons/min, about 6 gallons/min to about 10 gallons/min, about 6 gallons/min to about 15 gallons/min, about 6 gallons/min to about 20 gallons/min, about 6 gallons/min to about 30 gallons/min, about 8 gallons/min to about 9 gallons/min, about 8 gallons/min to about 10 gallons/min, about 8 gallons/min to about 15 gallons/min, about 8 gallons/min to about 20 gallons/min, about 8 gallons/min to about 30 gallons/min, about 9 gallons/min to about 10 gallons/min, about 9 gallons/min to about 15 gallons/min, about 9 gallons/min to about 20 gallons/min, about 9 gallons/min to about 30 gallons/min, about 10 gallons/min to about 15 gallons/min, about 10 gallons/min to about 20 gallons/min, about 10 gallons/min to about 30 gallons/min, about 15 gallons/min to about 20 gallons/min, about 15 gallons/min to about 30 gallons/min, or about 20 gallons/min to about 30 gallons/min.

IV. Biostimulant Compositions

A biostimulant may enhance water uptake and/or nutrient utilization in a plant and improves soil quality. A biostimulant and/or application of a biostimulant may enhance a yield of a crop. A biostimulant can comprise a microbe and/or microorganism described herein. A biostimulant may be a product of a digestion system as described herein. The inoculum of a microbe described herein may comprise a plant growth promotion property for a biostimulant product. The inoculum of a microbe described herein may be added to a biostimulant comprising humic or fulvic acids, seaweed extracts, liquid manure, or other beneficial bacteria and/or fungi (e.g., *Bacillus* or *rhizobium*). The biostimulant composition may comprise a population of nitrogen use efficiency-promoting microbes enriched in the digestion system. In some embodiments, the biostimulant composition comprises a population of the inoculum of the nitrogen use efficiency-promoting microbe, at least a portion of nitrogen use efficiency-promoting microbes of the microbial consortium, nitrogen use efficiency-promoting metabolites generated in the digestion system, or any combination thereof. The nitrogen use efficiency-promoting microbes enriched in the digestion system described herein may be added to plant extracts, protein hydrolysates, and/or chemical biostimulants. In some embodiments, the present disclosure provides a biostimulant composition comprising chemical species and/or microbes that promote plant growth, including increasing a plant's or crop's nitrogen use efficiency. Biostimulant compositions described herein may include dead microorganisms, sporulated microorganisms, fragments of dead microorganisms, viable microorganisms, microorganism digestion products, microbial metabolites and secondary metabolites, enzymes, biological plant growth regulators, organic acids, chelators, or any combination thereof.

In some embodiments, biostimulant compositions described herein may be characterized by mass spectrometry or NMR spectroscopy. In some embodiments, the biostimulant composition has an associated LC-MS chromatogram. In some embodiments, the biostimulant composition has an associated GC-MS chromatogram. In some embodiments, the biostimulant composition has an associated $^1$H-NMR spectrum. In some embodiments, the biostimulant composition has an associated $^{13}$C-NMR spectrum.

In some embodiments, biostimulant compositions include viable microbes. In some embodiments, the microbes include bacteria that are derived from the bacterial population present in manure, rock phosphate, or other digestion substrates. In some embodiments, the microbes include bacteria that are added to a digestion system as isolated microbial strains. In some embodiments, the bacteria include one or more bacteria of the species *Paenibacillus borealis*, *Bacillus megaterium*, and *Paenibacillus sonchi*. In some embodiments, the bacteria include one or more of bacterial strains MS3907 (ATCC Accession No. PTA-127654), MS3900 (ATCC Accession No. PTA-127653), MS4921 (ATCC Accession No. PTA-127655), or MS2748 (ATCC Accession No. PTA-127652). In some embodiments, any one or any combination of these bacterial species comprises at least about 0.000001%, at least about 0.00001%, at least about 0.00005%, at least about 0.0001%, at least about 0.0005%, at least about 0.001%, at least about 0.0015%, at least about 0.002%, at least about 0.003%, at least about 0.004%, at least about 0.005%, at least about 0.01%, at least about 0.05%, at least about 0.1%, at least about 0.5%, at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20%, or more than about 20% of the total bacterial species present in the biostimulant, as determined by metagenomic sequencing or semi-quantitative PCR sequencing. In some embodiments, any one of these bacterial species comprises at most about 20%, at most about 15%, at most about 14%, at most about 13%, at most about 12%, at most about 11%, at most about 10%, at most about 9%, at most about 8%, at most about 7%, at most about 6%, at most about 5%, at most about 4%, at most about 3%, at most about 2%, at most about 1%, at most about 0.5%, at most about 0.1%, at most about 0.05%, at most about 0.01%, at most about 0.005%, at most about 0.004%, at most about 0.003%, at most about 0.002%, at most about 0.0015%, at most about 0.0005%, at most about 0.0001%, at most about 0.00005%, at most about 0.00001%, at most about 0.000001%, or less than about 0.000001% of the bacterial species present in the biostimulant, as determined by metagenomic sequencing or semi-quantitative PCR sequencing.

In some embodiments, the biostimulant is filter sterilized and does not comprise viable microbes. In some embodiments, the dry weight of the microbial biomass is less than 0.0001% in relation to the total dry weight of the biostimulant composition. In some embodiments, the biostimulant compositions may comprise metabolites from the microbial communities of the digestion system described herein. As working fluid is transferred in a digestion system, metabolites may be generated by metabolism of organic substrates. The metabolites may be produced with or without introduction of an isolate or target isolate. The metabolites may have positive effects on plant health, growth and plant growth promotion properties. In some embodiments, metabolites produced by the digestion systems described herein may enhance nutrient availability and/or nutrient use efficiency.

In some embodiments, the biostimulant comprises to $1 \times 10^8$ CFU/ml of bacteria. In some embodiments, the biostimulant comprises at least about, at most about, or about 100 CFU/ml, 500 CFU/ml, $1 \times 10^3$ CFU/ml, $1 \times 10^4$ CFU/ml, $1 \times 10^5$ CFU/ml, $1 \times 10^6$ CFU/ml, $5 \times 10^6$ CFU/ml, $1 \times 10^7$ CFU/ml, $5 \times 10^7$ CFU/ml, $1 \times 10^8$ CFU/ml, $5 \times 10^8$ CFU/ml, $1 \times 10^9$ CFU/ml, $5 \times 10^9$ CFU/ml, $1 \times 10^{10}$ CFU/ml, $1 \times 10^{11}$ CFU/ml $1 \times 10^{12}$ CFU/ml $1 \times 10^{13}$ CFU/ml $1 \times 10^{14}$ CFU/ml, or $1 \times 10^{15}$ CFU/ml of bacteria, or a range between any two of these values.

In some embodiments, the biostimulant has a pH of from 7 to 8. In some embodiments, the biostimulant has a pH of at least about, at most about, or about 4, 4.5, 5, 5.5, 6, 6.5, 7, 7.5, 8, 8.5, 9, 9.5, 10, 10.5, or 11, or a range between any of these two values. In some embodiments, the density of the biostimulant is about 0.997 to 0.999 g/cm$^3$ or is about 0.998 g/cm$^3$. In some embodiments, the density of the biostimulant is at least about, at most about, or about 0.5, 0.6, 0.7, 0.8, 0.9, 1.0, 1.1, 1.2, 1.3, 1.4, or 1.5, or a range between any of these two values. In some embodiments, the biostimulant has a solids content of 0.01 to 2%. In some embodiments, the biostimulant has a solids content of at least about, at most about, or about 0.001%, 0.01%, 0.05%, 0.1%, 0.5%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 3%, 4%, or 5%, or a range between any of these two values. In some embodiments, the solids content is at least about, at most about, or about 0.01%, 0.05%, 0.1%, 0.15%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, or 2.0% w/w, or a range between any two of these values. In some embodiments, the chemical oxygen demand (COD) of the biostimulant is from 100 to 250 mg/L. In some embodiments, the COD is at least about, at most about, or about 10, 25, 50, 75, 100, 125, 150, 175, 200, 225, 250, 275, 300, 400, or 500 mg/L, or a range between any two of these values. COD values may vary with the concentration rate of the biostimulant, and may increase as concentration increases. In some embodiments, the biostimulant has a total nitrogen content of about 0.0002% w/w or between about 0.0001% and 0.0003% w/w. In some embodiments, the biostimulant has a total nitrogen content of at least about, at most about, or about 0.00001%, 0.00005%, 0.0001%, 0.0002%, 0.0003%, 0.0004%, 0.0005%, 0.001%, or 0.010%, or a range between any of these two values. In some embodiments, the biostimulant has a total phosphorous content of about 0.00001% w/w or between about 0.000005% and 0.000015% w/w. In some embodiments, the biostimulant has a total phosphorus content of at least about, at most about, or about 0.00001%, 0.00002%, 0.00003%, 0.00004%, 0.00005%, 0.00006%, 0.00007%, 0.00008%, 0.00009%, 0.0001%, 0.0002%, 0.0003%, 0.0004%, 0.0005%, 0.001%, or 0.01%, or a range between any of these two values. In some embodiments, the biostimulant has a total potassium content of about 0.0001% w/w or between about 0.00005% and 0.00015% w/w. In some embodiments, the biostimulant has a total potassium content of at least about, at most about, or about 0.00001, 0.00005%, 0.00006%, 0.00007%, 0.00008%, 0.00009%, 0.0001%, 0.0002%, 0.0003%, 0.0004%, 0.0005%, 0.001%, or 0.01%, or a range between any of these two values.

V. Methods of Making a Biostimulant Composition

In some embodiments, a method of making a biostimulant composition is performed using a bioreactor system that comprises two or more containers arranged in a series. A series of containers can include 2, 3, 4, 5, 6, 7 or more containers. The containers may be the same or different. A series of containers may be fluidly connected to the other containers in the series. A series of containers may be arranged such that fluid can flow from a first container to a second container and from a second container to a third container, and so on from each subsequent container to a next container in the series. Referring to a container as a "first container" does not necessarily indicate that the referenced container is the most upstream container in a series of container. In some embodiments, additional containers in a series are upstream of a container referred to as a "first container." In some embodiments, a container that is the most upstream container in a series of fluidly connected containers does not have another container upstream of the container. In some embodiments, a container that is the most upstream container in a series receives an inflow stream such as, for example, a feedstock stream. In some embodiments, a feedstock stream comes from a mixing container, which may be referred to as a mixing tank or complete mix reactor. In some embodiments, components that are placed in a mixing container have a shorter dwell time than working fluids in subsequent containers in the system. In some embodiments, a container that is the most downstream container in a series is a clarifier, which may be configured to separate a supernatant portion of a working fluid from a floc portion of the working fluid. The most downstream container may not be a clarifier and may not be configured to separate different portions of a working fluid. In some embodiments, the most downstream container has an outlet port through which a product outflow stream may exit the most downstream container. Containers arranged in a series may have inflows other than those coming from the neighboring upstream container and may have outflows other than those coming from the neighboring downstream container.

In some embodiments, a method of making a biostimulant composition is described herein as including operating a bioreactor system for a duration of time. It is contemplated that the bioreactor system may be operated both before and after the duration of time in the same way as during the duration of time. Some embodiments of methods described herein may describe steps taking place during a particular duration of time, such as, for example, 5, 10, 15, 30, 60, 90, or 120 days, 5 months, 6 months, 7 months, 8 months, 9 months, 10 months, 11 months, or 1, 2, 3, 4 or 5 years or more. Those described durations of time may be a fraction of a larger duration of time during which the bioreactor system is operating continuously or mostly continuously.

In some embodiments, a bioreactor system that is used in embodiments of methods of making a biostimulant have previously been inoculated with a microbial strain with desired plant growth promoting characteristics (a "target strain") such as, for example, nitrogen use efficiency-promoting properties. The inoculation may have been performed at least 5, 10, 15, 30, 60, 90, or 120 days previous, at least 5, 6, 7, 8, 9, 10, 11 months previous, or at least 1, 2, 3, 4, or 5 years previous to the beginning of a duration of time in which embodiments of the method are performed. In some embodiments, an inoculum establishes an initial population in one or more containers of a bioreactor system of at least $1 \times 10^4$, $1 \times 10^5$, $1 \times 10^6$, or $1 \times 10^7$ CFU/ml, or a range between any two of these values. Without being bound by theory, an inoculation of a target strain may help establish a population of the target strain and/or of other microbes having similar plant growth promoting properties as the target strain that is maintained throughout a duration of time of operating the bioreactor system. In some embodiments, an inoculum of the target strain can be added to the system only once or no more than once every 1, 2, 3, 4, 5, or 10 months. In some embodiments, the inoculum of the strain comprises at least about, at most about, or about $1 \times 10^4$, $1 \times 10^5$, $1 \times 10^6$, $1 \times 10^7$, $1 \times 10^8$, $1 \times 10^9$, $1 \times 10^{10}$, or $1 \times 10^{11}$ total CFU of the target strain, or a range between any two of these values. In some embodiments, the inoculum may not comprise 5, 10, 15, 20, 25, 50, or more different microbial species. In some embodiments, the inoculum comprises only a single target strain and no other microbes. In some embodiments, the inoculum comprises at most 1, 2, 3, 4, or 5 target strains. In some embodiments, the inoculum comprises only a single target strain but is mixed with other microbes. In some embodiments, the target strain is chosen to be added to the bioreactor based on its plant growth promoting properties. In some embodiments, the inoculum is not a part of or mixed with an organic feed material such as, for example, manure, food waste, wastewater, or sewage.

In some embodiments, operating a bioreactor system comprises continuously providing a feedstock inflow into the system, continuously transferring working fluid from each container in the system to a subsequent downstream container in the system, and continuously collecting a product stream from the system. In some embodiments, the flow into and/or out of a container may be performed periodically, for example a volume of feed or working fluid may be transferred once every 1, 5, 10, 30, or 60 seconds. In some embodiments, operating a bioreactor system does not include incubating a fluid in a container without inflow or outflow for more than 1, 5, 10, 15, or 30 minutes, or 1, 5, or 10 hours. In some embodiments, operating the bioreactor system comprises flowing a particular volume of fluid both into and out of the bioreactor system in a particular amount of time. For example, operating the bioreactor system may comprise flowing a volume of fluid that is equal to a fluid capacity of a container of the bioreactor system into and out of the system in 1, 2, 3, 4, 5, 10, 12, 24, or 48 hours, or 3, 4, 5, 6, 7, 8, 9, 10, 11, 12, 13, 14, 15, 16, 17, 18, 19, or 20 days. For example, for a bioreactor system that has a container with a 500 gallon fluid capacity, operating the bioreactor system may comprise flowing 500 gallons into the system and flowing 500 gallons out of the system in 12 hours. Operating a bioreactor system may also comprise flowing fluid through the system at a certain rate given in units of volume over time. For example, operating a bioreactor system may comprise flowing fluid through the system at a rate of at least 5, 10, 15, 20, 50, 100, 200, 300, 400, or 500 gallons per minute. Operating a bioreactor system may also comprise flowing fluid through the system at a certain rate that results in a particular hydraulic retention time. For example, operating a bioreactor system may comprise flowing fluid through the system at a rate that results in a hydraulic retention time of at least 5, 10, or 12 hours, or at least 1, 2, 3, 4, 5, 6, 7, 8, 9, 10, 11, 12, 13, 14, 15, 16, 17, 18, 19, 20, 21, 22, 23, 24, or 25 days, or a range between any two of these values.

In some embodiments, a population of a target strain in a container is maintained at a certain level or within a certain range during operation of the bioreactor system for a given duration of time despite the target strain not being present in any inflow into the bioreactor system during the duration of time. In some embodiments, a population of a target strain in a container may be maintained at a certain level or within a certain range during operation of the bioreactor system for a given duration of time despite the target strain being present only in at most relatively low levels in any inflow into the bioreactor system during the duration of time. For example, the level of the target strain flowing into the system may be at least 1000 times lower than the population of the target strain in one or more containers of the bioreactor system. For example, in some embodiments, the population of the target strain is maintained at a level of at least $1\times10^6$ CFU/ml or at least 80% of that level, while the total inflow into the bioreactor system comprises no more than $1\times10^2$ CFU/ml of the target strain. Thus, in some embodiments, the conditions in the bioreactor are such that the growth rate of the target isolate in one or more containers of the bioreactor system is high enough that the continuous flow of fluid through the system does not substantially deplete the population of the target isolate in the one or more containers. In some embodiments the population of the target isolate is maintained at least about, at most about, or about $1\times10^4$, $1\times10^5$, $1\times10^6$, $1\times10^7$, or $1\times10^8$ CFU/ml, or at least 80% of that level for a period of time of operating the bioreactor system, while the total input into the system does not include the target strain or does not include more than 1, 10, 100, 500, 1000, 1500, 2000, or 5000 CFU/ml of the target strain. In some embodiments, for a duration of time of operating the bioreactor system, the population of the target isolate in one or more containers may be maintained at least about 70, 80, 85, 90, 95, 96, 98, 99, or 100% of the population of the target isolate that was present at the beginning of the duration of time. In some embodiments, the population of the target strain is maintained at a level at least about 100, 500, 1000, 5000, 10000, 15000, or 20000 times higher than the population of the target strain in all inputs into the bioreactor system for a duration of time of operating the bioreactor system. In some embodiments, the duration of time of operating the bioreactor system during which the particular population is maintained at a certain level or within a certain range is at least 1, 5, 10, 15, 30, 45, 60, 75, or 90 days, at least 6, 9, 12, 15, 18, or 24 months, or at least 3, 4, 5, 6, 7, 8, 9, or 10 years.

In some embodiments, one or more containers comprise a population of other microbes having a desirable plant growth promoting property (such as, for example, nitrogen use efficiency promoting properties) in addition to the population of the target isolate. In some embodiments, the population of these other desirable microbes is also maintained at a certain level or within a certain range during a period of time of operating the bioreactor system, despite being present at much lower levels in the inputs into the bioreactor system. For example, the level of the other desirable microbes flowing into the system may be at least 1000 times lower than the population of the other desirable microbes in one or more containers of the bioreactor system. For example, in some embodiments, the population of the other desirable microbes is maintained at a level of at least $1\times10^6$ CFU/ml or at least 80% of that level, while the total inflow into the bioreactor system comprises no more than $1\times10^2$ CFU/ml of the other desirable microbes. Thus, in some embodiments, the conditions in the bioreactor are such that the growth rate of the other desirable microbes in one or more containers of the bioreactor system is high enough that the continuous flow of fluid through the system does not substantially deplete the population of the other desirable microbes in the one or more containers. The other desirable microbes may have nitrogen use efficiency-promoting properties (e.g., enhancing nitrogen-fixing activity, improving recruitment of plant associated nitrogen fixers already present in the soil to the roots of plants, increasing soil organic nitrogen and mineralization and uptake of organic nitrogen stimulated by microbes and/or microbial metabolites, or any combination thereof). The other desirable microbes may be of the bacterial genera: *Kosakonia, Klebsiella, Rahnella, Kluyvera, Enterobacter, Achromobacter, Microbacterium, Gluconobacter, Methylobacterium, Pseudomonas, Pantoea, Azospirillum, Azocarus, Herbaspirillum, Burkholderia, Cyanobacteria, Bacillus, Paenibacillus*, or any combination thereof. The other desirable microbes may be of the bacterial species *Kosakonia sacchari, Klebsiella variicola, Rahnella aquatilis, Kluyvera intermedia, Kosakonia pseusosacchari, Enterobacter* spp., *Achromobacter marplatensis, Azopirillum lipoferum, Microbacterium murale, Gluconobacter diazotrophicus, Methylobacterium symbioticum, Paenibacillus borealis, Bacillus megaterium (Priestia megaterium), Paenibacillus sonchi*, or any combination thereof. In some embodiments the population of the other desirable microbes is maintained at at least $1\times10^4$, $1\times10^5$, $1\times10^6$, $1\times10^7$, or $1\times10^8$ CFU/ml, or at least 80% of that level for a period of time of operating the bioreactor system, while the total input into the system does not include the other desirable microbes or does not include more than 1, 10, 100, 500, 1000, 1500, 2000, or 5000 CFU/ml of the other desirable microbes. In some embodiments, for a duration of time of operating the bioreactor system, the population of the other desirable microbes in one or more containers is maintained at at least 70, 80, 85, 90, 95, 96, 98, 99, or 100% of an initial population of the other desirable microbes present at the beginning of the duration of time. In some embodiments, the population of other desirable microbes is maintained at a level at least 100, 500, 1000, 5000, 10000, 15000, or 20000 times higher than the population of the other desirable microbes in all inputs into the bioreactor system for a duration of time of operating the bioreactor system. In some embodiments, the duration of time of operating the bioreactor system during which the particular population is maintained at a certain level or within a certain range is at least 1, 5, 10, 15, 30, 45, 60, 75, or 90 days, or at least 6, 9, 12, 15, 18, or 24 months.

In some embodiments, operating a bioreactor system disclosed herein provides a synergistic effect in the production of a biostimulant composition. In some embodiments, a bioreactor system that includes an established and/or stable population of a nitrogen use efficiency (NUE)-promoting microbial strain (e.g., one or more of the NUE-promoting strains disclosed herein and/or related strains) produces a biostimulant having a greater nitrogen use efficiency-promoting effect than could be obtained from an otherwise similar bioreactor system that does not have the established population of the NUE-promoting strain. The nitrogen use efficiency-promoting effect of the biostimulant produced according to methods disclosed herein may be greater than a biostimulant produced in an otherwise similar system lacking the established population of the nitrogen use efficiency-promoting strain, even if the latter biostimulant has one or more of the NUE-promoting strains added to it after it is produced. For example, a biostimulant composition produced according to the methods disclosed herein may have greater nitrogen-fixing activity effects compared to a biostimulant composition produced by an otherwise similar system lacking the established population of the nitrogen use efficiency-promoting strain. For example, a biostimulant composition produced according to the methods disclosed herein may have greater recruitment capacity of plant associated nitrogen fixers present in the soil to the roots of plants compared to that of a biostimulant composition produced by an otherwise similar system lacking the established population of the nitrogen use efficiency-promoting strain. For example, a biostimulant composition produced according to the methods disclosed herein may have greater capacity to increase soil organic nitrogen and mineralization and uptake of organic nitrogen compared to that of a biostimulant composition produced by an otherwise similar system lacking the established population of the nitrogen use efficiency-promoting strain. Without being bound by theory, the presence of the target NUE-promoting strain population in the bioreactor system may promote production of NUE-promoting digestion products in the bioreactor system, which are present in the product.

VI. Biostimulant Compositions, Microbial Formulations, and Methods of Use

Biostimulant compositions described herein may be used in methods of increasing nitrogen use efficiency of a plant or crop, which may include contacting a plant, a seed, or a plant growth medium with a biostimulant composition.

In some embodiments, the plant treated with the biostimulant composition may be, for example, crops, vegetables, flowers, foliage plants, turf grasses, trees, shrubs, and the like. Crops may comprise corn, rice, wheat, barley, rye, oat, sorghum, cotton, soybean, peanut, buckwheat, beet, rapeseed, sunflower, sugar cane, marijuana, tobacco, or any combination thereof. Vegetables may comprise solanaceous vegetables (e.g., eggplant, tomato, pimento, pepper, or potato), cucurbitaceous vegetables (e.g., cucumber, pumpkin, zucchini, watermelon, melon, or squash), cruciferous vegetables (e.g., Japanese radish, white turnip, horseradish, kohlrabi, Chinese cabbage, cabbage, leaf mustard, broccoli, or cauliflower), asteraceous vegetables (e.g., burdock, crown daisy, artichoke, or lettuce), liliaceous vegetables (e.g., green onion, onion, garlic, or asparagus), ammiaceous vegetables (e.g., carrot, parsley, celery, or parsnip), chenopodiaceous vegetables (e.g., spinach or Swiss chard), lamiaceous vegetables (e.g., Perilla frutescens, mint, or basil), strawberry, sweet potato, Dioscorea japonica, Colocasia, or any combination thereof. Fruits may comprise pomaceous fruits (e.g., apple, pear, Japanese pear, Chinese quince, or quince), stone fleshy fruits (e.g., peach, plum, nectarine, Prunus mume, cherry fruit, apricot, or prune), citrus fruits (e.g., Citrus unshiu, orange, lemon, rime, or grapefruit), nuts (e.g., chestnuts, walnuts, hazelnuts, almond, pistachio, cashew nuts, or macadamia nuts), berries (e.g., blueberry, cranberry, blackberry, or raspberry), grape, kaki fruit, olive, Japanese plum, banana, coffee, date palm, coconuts, or any combination thereof. Trees may comprise fruit trees, tea, mulberry, flowering plant, roadside trees (e.g., ash, birch, dogwood, Eucalyptus, Ginkgo biloba, lilac, maple, Quercus, poplar, Judas tree, Liquidambar formosana, plane tree, Zelkova, Japanese arborvitae, fir wood, hemlock, juniper, Pinus, Picea, or Taxus cuspidate), or any combination thereof. The term "plant" or "plants" refers to both native and genetically engineered plants. In some embodiments, the biostimulant is applied to a seed of any of the plants described above.

In certain embodiments, biostimulant compositions described herein are applied to soil, applied to fertilizer used to fertilize plants, applied directly to plants, or applied to both soil and plants. In some embodiments, a fertilizer improves plant health, growth and/or yield by providing a nutrient (such as nitrogen, phosphorous, and/or potassium) to the plant. Fertilizers include, but are not limited to, inorganic fertilizers, organic (or natural) fertilizers, granular fertilizers and liquid fertilizers. Granular fertilizers are solid granules, while liquid fertilizers are made from water soluble powders or liquid concentrates that mix with water to form a liquid fertilizer solution. In some embodiments, plants can quickly take up most water-soluble fertilizers, while granular fertilizers may dissolve or decompose over time before plants can access their nutrients. Granular fertilizers may have "slow-release," "timed-release," or "controlled-release" properties, synonymous terms meaning that they release their nutrients slowly over a period of time. Organic fertilizer comes from an organic source such as, but not limited to, compost, manure, blood meal, cottonseed meal, feather meal, crab meal, or others, as opposed to synthetic sources. There are also some natural fertilizers that are not organic, such as Greensand, which contain potassium, iron, calcium, and other nutrients. These are considered suitable for organic gardening because they are not synthesized, but come from natural mineral-rich deposits in the earth. Organic fertilizers may depend on the microbes in the soil to break them down into digestible bits for plants.

In addition to soil, biostimulant compositions may be applied to other plant growth media such as, for example, a hydroponic growth medium. Compositions may be used in in-furrow applications, foliar applications, or both. In some embodiments, the biostimulant composition is applied on its own. When applied on its own, in some embodiments, the composition may be applied before or after application of a fertilizer and/or pesticide. When applied before or after application of a fertilizer and/or pesticide, the composition may be applied sufficiently close in time to the fertilizer and/or pesticide so that the formulation may have its desired effect of enhancing the effect of the fertilizer and/or pesticide. In some embodiments, the composition is applied in conjunction with a fertilizer and/or pesticide. The composition may either be mixed with a fertilizer and/or pesticide or applied simultaneously with a fertilizer and/or pesticide.

In some embodiments, the biostimulant compositions described herein are mixed with a fertilizer or pesticide at a ratio of about 3:1 to about 1:1000 biostimulant to fertilizer or pesticide. In some embodiments, biostimulant compositions are mixed with a fertilizer or pesticide in a ratio of about 1:20 or 1:100 biostimulant to fertilizer or pesticide. Biostimulant compositions described herein may also be coated on particles of fertilizer or pesticide. Particles of fertilizer or pesticide may be coated by, for example, spray drying the biostimulant onto the surface of the fertilizer or by mixing a dehydrated powder form of the biostimulant with the particles, with or without a binder or carrier.

In certain embodiments, the fertilizer is a starter fertilizer. In some embodiments, the fertilizer includes ammonia, urea, ammonium nitrate, ammonium sulfate, ammonium thiosulfate, monoammonium phosphate (MAP), diammonium phosphate (DAP), muriate of potash (MOP), sulfate of Potash (SOP), potassium nitrate (NOP), or any combination thereof. In some embodiments, the starter fertilizer is a 10-34-0 starter fertilizer. In some embodiments, the fertilizer may be an organic fertilizer (e.g., chicken litter, bird quano, manure, fish meal, and/or hydrolysates), a soy protein based fertilizer, a corn protein based fertilizer (e.g., corn gluten), or any combination thereof. In some embodiments, the fertilizer may be pelletized chicken litter.

In certain embodiments, the biostimulant compositions described herein may be applied to soil or an area of plants in an amount of at least about, at most about, or about 0.25, 0.5, 1.0, 1.5, 2.0, 2.5, 3.0, 3.5, 4.0 4.5, 5.0, 6.0, 7.0, 8.0, 9.0, 10.0, 12.0, 15.0, 20.0 quarts per acre of a soil or area of plants (e.g., crops), or a range between any of these two values. In certain embodiments, the biostimulant compositions described herein may be applied to soil or plants in an amount of at least about, at most about, or about 5.0, 6.0, 7.0, 8.0, 9.0, 10.0, 12.0, 15.0, 20.0, 25.0, 30.0, 32.0, 40.0, 50.0, 75.0, 100.0, 120.0, 140.0, 160.0, 180.0, 200.0, 250.0, 300.0 ounces per ton (oz/ton) of a fertilizer or growth medium, or a range between any of these two values. In some embodiments, the formulations may be applied in an amount of about 2 quarts per acre of a soil or area of plants (e.g., crops). In some embodiments, the formulations may be applied in an amount of about 4 quarts per acre of a soil or area of plants (e.g., crops). In some embodiments, the biostimulant composition is applied in an amount of about 0.5, 1, 2, 3, 4, 5, 6, 7, 8, 9, or 10 quarts per acre of a soil or area of plants (e.g., crops). In some embodiments, the biostimulant composition may be applied at 64 oz/ton of plant growth medium (e.g., fertilizer). In some embodiments, the biostimulant composition may be applied at 120 oz/ton of plant growth medium (e.g., fertilizer). In some embodiments, the biostimulant composition may be applied at 160 oz/ton of plant growth medium (e.g., fertilizer). In some embodiments, the amount of biostimulant composition applied is characterized by the dry weight of substances present in the biostimulant composition applied. The dry weight of a given volume of liquid biostimulant composition is the weight of all substances in the volume of biostimulant other than water. In some embodiments, an amount of biostimulant is applied that provides for 0.10 to 10 g by dry weight of digestion products to be applied per acre. In some embodiments, the amount of biostimulant applied provides for at least about, at most about, or about 0.1, 0.5, 1, 2, 3, 4, 5, 6, 7, 8, 9, or 10 g by dry weight of digestion products per acre, or a range within any two of these values. In some embodiments, the amount of biostimulant applied provides for at least about, at most about, or about 0.1, 0.5, 1, 2, 3, 4, 5, 6, 7, 8, 9, or 10 g by dry weight of biostimulant components to be applied, or a range between any two of these values. The amount of biostimulant composition applied may also be characterized in terms of the numbers of colony forming units of bacteria applied. In some embodiments, the amount of biostimulant applied provides for at least about, at most about, or about $1\times10^2$, $5\times10^2$, $1\times10^3$, $5\times10^3$, $1\times10^4$, $5\times10^4$, $1\times10^5$, $5\times10^5$, $1\times10^6$, $5\times10^6$, $1\times10^7$, $5\times10^7$, $1\times10^8$, $5\times10^8$, $1\times10^9$, $5\times10^9$, or $1\times10^{10}$ CFU of bacteria to be applied per acre, or a range between any two of these values.

In some embodiments, biostimulant compositions described herein may be applied in dry form. A biostimulant base product may be dehydrated to make a powdered product that is applied to a growth medium (e.g., soil), to a plant, or to a seed.

In some embodiments, the amount of biostimulant applied is an effective amount to achieve a desired plant growth promoting effect. For instance, an effective amount of a biostimulant base product, such as a product of a digestion system as described herein, to increase corn plant height in comparison to untreated plants can be 0.5 or 1 quarts per acre (qt./A). In some embodiments, an effective amount of a biostimulant base product may be at least about, at most about, or about 0.1, 0.2, 0.3, 0.4, 0.5, 0.6, 0.7, 0.8, 0.9, 1.0, 1.25, 1.5, 1.75, 2.0, 2.5, 3.0, 3.5, 4.0, 4.5, 5.0, 5.5, 6.0, 7.0, 8.0, 9.0, or 10.0 qt/A, or a range between any two of these values. In some embodiments, the biostimulant composition is applied in an effective amount to increase a plant's nitrogen uptake or to increase the population of N-fixing and N-solubilizing microbes in the plant's root zone.

The compositions comprising a biostimulant composition and other components described herein (e.g., a fertilizer) can be formed by mixing the components in a tank (i.e., tank mix). Following mixing, formulations can be bottled or otherwise packaged (e.g., in drums), applied to a field or crop, or mixed with other components. When bottled or otherwise packaged, the end user can mix the formulation with other components prior to application. The biostimulant composition can be mixed with fertilizer by tank mixing, including splash mixing with minimal further mixing, or can be blended into the fertilizer.

In some embodiments, the biostimulant is applied once. In some embodiments, a single application is sufficient to promote plant growth and/or nitrogen use efficiency as described herein. In some embodiments, a biostimulant composition is applied 1, 2, 3, 4, 5 times, or more during a growing season. In some embodiments, applications are 1, 2, 3, 4, 5, or 6 weeks apart. In some embodiments, the biostimulant compositions presented herein may be formulated as a seed treatment. The seeds can be substantially uniformly coated with one or more layers of the microbial compositions disclosed herein using conventional methods of mixing, spraying or any combination thereof through the use of treatment application equipment that is specifically designed and manufactured to accurately, safely, and efficiently apply seed treatment products to seeds. Such equipment uses various types of coating technology such as rotary coaters, drum coaters, fluidized bed techniques, spouted beds, rotary mists or any combination thereof. Liquid seed treatments can be applied via either a spinning "atomizer" disk or a spray nozzle which evenly distributes the seed treatment onto the seed as it moves though the spray pattern. A seed may be mixed or tumbled for an additional period of time to achieve additional treatment distribution and drying. The seeds can be primed or unprimed before coating with the inventive compositions to increase the uniformity of germination and emergence. In an alternative embodiment, a dry powder formulation can be metered onto the moving seed and allowed to mix until completely distributed.

The bacterial isolates described herein can be formulated for plant application to enhance plant growth promotion properties. The biostimulant composition comprising target bacterial isolates of the present invention can be mixed with other components in a tank or similar container. The formulations can be bottled or otherwise packaged, applied to a field or crop, or mixed with other components. When bottled or otherwise packaged, the end user can mix the formulation with other components prior to application. The biostimulant composition can be mixed with fertilizer by tank mixing, including splash mixing with minimal further mixing, or can be blended into the fertilizer. In some embodiments, the biostimulant is applied to the plant or growth medium before planting. In some embodiments, the biostimulant is applied at planting or after planting. In some embodiments, the biostimulant is applied before transplanting the plant. In some embodiments, the biostimulant is applied to the plant or growth medium after transplanting the plant. In some embodiments, the biostimulant is applied to the plant or growth medium while the plant is being transplanted. In some embodiments, the biostimulant is applied as a foliar application (e.g., applied as a liquid fertilizer to the leaves). The biostimulant may be applied as a foliar application at various times after planting. For example, the biostimulant may be applied as a foliar application at least about, at most about, or about 1 hour, 2 hours, 3 hours, 4 hours, 5 hours, 6 hours, 9 hours, 12 hours, 18 hours, 24 hours, 2 days, 3 days, 4 days, 5 days, 6 days, 7 days, 2 weeks, 3 weeks, 4 weeks, 2 months, 3 months, 4 months, 5 months, 6 months, 9 months, 12 months, 15 months, 18 months, 24 months, 3 years, 4 years, or 5 years after planting, or a range between any of these two values. In some embodiments, the biostimulant is applied to a growth medium (e.g., soil) into which the plant is to be transplanted. In some embodiments, the biostimulant is applied to a fertilizer or incorporated into a fertilizer, which is applied before planting, at planting or after planting.

In some embodiments, the microbial formulation described herein have nitrogen use efficiency-promoting properties. The nitrogen use efficiency-promoting microbes may enhance nitrogen fixation in plants. The nitrogen use efficiency-promoting microbes may enhance bioavailability of nitrogen in soil. The nitrogen use efficiency-promoting microbes may enhance plant growth in low nitrogen conditions (e.g., a soil that does not contain nitrogen or nitrogen levels below 10 ppm). Low nitrogen conditions in a soil may comprise conditions of less than about 80%, 70%, 60%, 50%, 40%, or 30% the recommended nitrogen level suitable for crop growth as specified by a soil test. For example, a nitrogen-poor growth medium may comprise nitrate at a concentration of less than about 1 ppm, 5, 10, 12, 15, 18, 20, 25, 30, 35, 40, 50, 75, 100 or less than 100 ppm. A nitrogen-poor growth medium may comprise nitrate at a concentration of at most about 100, 75, 50, 40, 35, 30, 25, 20, 18, 15, 12, 10, 5, 1, or less than 1 ppm. A nitrogen-poor growth medium may comprise nitrate at a concentration from about 1 ppm to about 50 ppm. A nitrogen-poor growth medium may comprise nitrate at a concentration from about 1 ppm to about 2 ppm, about 1 ppm to about 3 ppm, about 1 ppm to about 4 ppm, about 1 ppm to about 5 ppm, about 1 ppm to about 10 ppm, about 1 ppm to about 15 ppm, about 1 ppm to about 20 ppm, about 1 ppm to about 25 ppm, about 1 ppm to about 30 ppm, about 1 ppm to about 40 ppm, about 1 ppm to about 50 ppm, about 2 ppm to about 3 ppm, about 2 ppm to about 4 ppm, about 2 ppm to about 5 ppm, about 2 ppm to about 10 ppm, about 2 ppm to about 15 ppm, about 2 ppm to about 20 ppm, about 2 ppm to about 25 ppm, about 2 ppm to about 30 ppm, about 2 ppm to about 40 ppm, about 2 ppm to about 50 ppm, about 3 ppm to about 4 ppm, about 3 ppm to about 5 ppm, about 3 ppm to about 10 ppm, about 3 ppm to about 15 ppm, about 3 ppm to about 20 ppm, about 3 ppm to about 25 ppm, about 3 ppm to about 30 ppm, about 3 ppm to about 40 ppm, about 3 ppm to about 50 ppm, about 4 ppm to about 5 ppm, about 4 ppm to about 10 ppm, about 4 ppm to about 15 ppm, about 4 ppm to about 20 ppm, about 4 ppm to about 25 ppm, about 4 ppm to about 30 ppm, about 4 ppm to about 40 ppm, about 4 ppm to about 50 ppm, about 5 ppm to about 10 ppm, about 5 ppm to about 15 ppm, about 5 ppm to about 20 ppm, about 5 ppm to about 25 ppm, about 5 ppm to about 30 ppm, about 5 ppm to about 40 ppm, about 5 ppm to about 50 ppm, about 10 ppm to about 15 ppm, about 10 ppm to about 20 ppm, about 10 ppm to about 25 ppm, about 10 ppm to about 30 ppm, about 10 ppm to about 40 ppm, about 10 ppm to about 50 ppm, about 15 ppm to about 20 ppm, about 15 ppm to about 25 ppm, about 15 ppm to about 30 ppm, about 15 ppm to about 40 ppm, about 15 ppm to about 50 ppm, about 20 ppm to about 25 ppm, about 20 ppm to about 30 ppm, about 20 ppm to about 40 ppm, about 20 ppm to about 50 ppm, about 25 ppm to about 30 ppm, about 25 ppm to about 40 ppm, about 25 ppm to about 50 ppm, about 30 ppm to about 40 ppm, about 30 ppm to about 50 ppm, or about 40 ppm to about 50 ppm.

In certain embodiments, biostimulant compositions described herein may be applied to soil, applied to fertilizer used to fertilize plants, applied directly to plants, or applied to both soil and plants. A "fertilizer" as used herein means a compound or composition that is added to plants or soil to improve plant health, growth and/or yield. In some embodiments, a fertilizer improves plant health, growth and/or yield by providing a nutrient (such as the ones described herein) to the plant. Fertilizers include, but are not limited to, inorganic fertilizers, organic (or natural) fertilizers, granular fertilizers and liquid fertilizers. Granular fertilizers may be solid granules, while liquid fertilizers may be made from water soluble powders or liquid concentrates that mix with water to form a liquid fertilizer solution. In some embodiments, plants can quickly take up most water-soluble fertilizers, while granular fertilizers, in some examples, may need a while to dissolve or decompose before plants can access their nutrients. High-tech granular fertilizers have "slow-release," "timed-release," or "controlled-release" properties, synonymous terms meaning that they release their nutrients slowly over a period of time. Organic fertilizer comes from an organic source such as, but not limited to, compost, manure, blood meal, cottonseed meal, feather meal, crab meal, or others, as opposed to synthetic sources. There may be also some natural fertilizers that are not organic, such as Greensand, which contain potassium, iron, calcium, and other nutrients. These may be considered suitable for organic gardening because they are not synthesized, but come from natural mineral-rich deposits in the earth. Organic fertilizers depend on the microbes in the soil to break them down into digestible bits for plants. In some embodiments, organic fertilizers encourage soil microbes, earthworms, and other flora more than synthetic fertilizers do, because most organic fertilizers don't add excess salts and acid to the soil. Inorganic fertilizers may be also known as synthetic or artificial fertilizers. Inorganic fertilizers may be manufactured.

Compositions may also be applied directly to a plant seed. In addition to soil, biostimulant compositions may be applied to other plant growth media such as, for example, a hydroponic growth medium. Compositions may be used in in-furrow applications, foliar applications, or both. In some embodiments, the biostimulant composition is applied on its own. When applied on its own, in some embodiments, the composition is applied before or after application of a fertilizer. When applied before or after application of a fertilizer, the composition is applied sufficiently close in time to the fertilizer so that the formulation may have its desired effect of enhancing the effect of the fertilizer. In some embodiments, the composition is applied in conjunction with a fertilizer. The composition may either be mixed with a fertilizer or applied simultaneously with a fertilizer.

In some embodiments, the biostimulant compositions described herein may be mixed with a fertilizer at a ratio of at least about, at most about, or about 3:1 to about 1:100 biostimulant to fertilizer, or a range between any of these ratios. A biostimulant composition described herein may be mixed with a fertilizer at a ratio of at least about 2:1, 3:1, 4:1, 5:1, 6:1, 7:1, 8:1, 9, or 10:1 biostimulant composition to fertilizer. A biostimulant may be mixed with a fertilizer at a range of at least about, at most about, or about 0.01%, 0.1%, 0.5%, 1%, 1.5%, 2%, 2.5%, 5%, 6%, 7%, 8%, 9%, 10%, 11%, 12%, 13%, 14%, or 15%, or a range between any of these two values. In some embodiments, biostimulant compositions may be mixed with a fertilizer in a ratio of about 1:20 biostimulant to fertilizer. Biostimulant compositions described herein may also be coated on particles of fertilizer. Particles of fertilizer may be coated by, for example, spray drying the biostimulant onto the surface of the fertilizer or by mixing a dehydrated powder form of the biostimulant with the particles, with or without a binder or carrier.

In an aspect, the present disclosure may provide a microbial formulation comprising: (a) a *Bacillus megaterium* strain having one or more of the following: (i) a 16S rRNA gene sequence at least 95% identical to SEQ ID NO: 1; (ii) a gyrB gene sequence at least 95% identical to SEQ ID NO: 4; and (iii) a rpoB gene sequence at least 95% identical to SEQ ID NO: 7; and a carrier. In some embodiments, the formulation may comprise additional products of digestion of an organic material by a *Bacillus megaterium* strain. A carrier may be a fertilizer as described herein and the fertilizer may include, ammonia, urea, ammonium nitrate, ammonium sulfate, ammonium thiosulfate, monoammonium phosphate (MAP), diammonium phosphate (DAP), muriate of potash (MOP), sulfate of Potash (SOP), potassium nitrate (NOP). A carrier may also be coated by a micronutrient. The carrier of the formulation described herein may be a liquid or a solid. The concentration of the *Bacillus megaterium* strain may be at least about, at most about, or about $1\times10^2$ CFU, $5\times10^2$ CFU, $1\times10^3$ CFU, $5\times10^3$ CFU, $1\times10^4$ CFU, $5\times10^4$ CFU, $1\times10^5$ CFU, $5\times10^5$ CFU, $1\times10^6$ CFU, $5\times10^6$ CFU, $1\times10^7$ CFU, $5\times10^7$ CFU, $1\times10^8$ CFU, $5\times10^8$ CFU, $1\times10^9$ CFU, $5\times10^9$ CFU, $1\times10^{10}$ CFU, or $1\times10^{11}$ CFU or a range between any of these values.

In another aspect, the present disclosure may provide an isolated strain of the species *Bacillus megaterium* having one or more of the following: (a) a 16S rRNA gene sequence at least 95% identical to SEQ ID NO: 1; (b) a gyrB gene sequence at least 95% identical to SEQ ID NO: 4; and (c) a rpoB gene sequence at least 95% identical to SEQ ID NO: 7. In some embodiments, a method may be utilized which comprises contacting a plant or a medium with a microbial formulation described herein. Without wishing to be bound by theory, a plant contacted by the microbial formulation described herein may lead to an increase in nitrogen fixation or a nitrogen use efficiency of the plant. The increase in solubilized zinc may be at least about, at most about, or about 1%, 2%, 3%, 4%, 5%, 6%, 7%, 8%, 9%, 12%, 15%, 18%, 20%, 25%, 30%, 35%, 40%, 45%, 50%, 60%, 75%, or 100%, or a range between any of these two values.

In some embodiments, the microbial formulation described herein may increase the nitrogen fixation activity in plant tissues by at least about, at most about, or about 1%, 2%, 3%, 4%, 5%, 10%, 20%, 30%, 40%, 50%, 55%, 60%, 65%, 70%, 75%, 80%, 85%, 90%, 95%, 99%, 99.5%, or 100%, or a range between any of these two values.

In some embodiments, the microbial formulation described herein may increase the plant nitrogen content by at least about, at most about, or about 1%, 2%, 3%, 4%, 5%, 10%, 20%, 30%, 40%, 50%, 55%, 60%, 65%, 70%, 75%, 80%, 85%, 90%, 95%, 99%, 99.5%, or 100%, or a range between any of these two values.

In some embodiments, the microbial formulation described herein may increase the population of nitrogen fixing bacteria in the root and root rhizospheres by at least about, at most about, or about 1%, 2%, 3%, 4%, 5%, 10%, 20%, 30%, 40%, 50%, 55%, 60%, 65%, 70%, 75%, 80%, 85%, 90%, 95%, 99%, 99.5%, or 100%, or a range between any of these two values.

In an aspect, the present disclosure may provide a microbial formulation comprising: (a) a *Paenibacillus borealis* strain having one or more of the following: (i) a 16S rRNA gene sequence at least 95% identical to SEQ ID NO: 2; (ii) a gyrB gene sequence at least 95% identical to SEQ ID NO: 5; and (iii) a rpoB gene sequence at least 95% identical to SEQ ID NO: 8; and a carrier. In some embodiments, the formulation may comprise additional products of digestion of an organic material by a *Paenibacillus borealis* strain. A carrier may be a fertilizer as described herein and the fertilizer may include, ammonia, urea, ammonium nitrate, ammonium sulfate, ammonium thiosulfate, monoammonium phosphate (MAP), diammonium phosphate (DAP), muriate of potash (MOP), sulfate of Potash (SOP), potassium nitrate (NOP). A carrier may also be coated by a micronutrient. The carrier of the formulation described herein may be a liquid or a solid. The concentration of the *Paenibacillus borealis* strain may be at least about, at most about, or about $1\times10^2$ CFU, $5\times10^2$ CFU, $1\times10^3$ CFU, $5\times10^3$ CFU, $1\times10^4$ CFU, $5\times10^4$ CFU, $1\times10^5$ CFU, $5\times10^5$ CFU, $1\times10^6$ CFU, $5\times10^6$ CFU, $1\times10^7$ CFU, $5\times10^7$ CFU, $1\times10^8$ CFU, $5\times10^8$ CFU, $1\times10^9$ CFU, $5\times10^9$ CFU, $1\times10^{10}$ CFU, or $1\times10^{11}$ CFU, or a range between any of these values.

In another aspect, the present disclosure may provide an isolated strain of the species *Paenibacillus borealis* having one or more of the following: (a) a 16S rRNA gene sequence at least 95% identical to SEQ ID NO: 2; (b) a gyrB gene sequence at least 95% identical to SEQ ID NO: 5; and (c) a rpoB gene sequence at least 95% identical to SEQ ID NO: 8. In some embodiments, a method may be utilized which comprises contacting a plant or a medium with a microbial formulation described herein. Without wishing to be bound by theory, a plant contacted by the microbial formulation described herein may lead to an increase in nitrogen fixation or a nitrogen use efficiency of the plant. The increase in solubilized zinc may be at least about, at most about, or about 1%, 2%, 3%, 4%, 5%, 6%, 7%, 8%, 9%, 10%, 12%, 15%, 18%, 20%, 25%, 30%, 35%, 40%, 45%, 50%, 60%, 75%, or 100%, or a range between any of these two values.

In some embodiments, the microbial formulation described herein may increase the nitrogen fixation activity in plant tissues by at least about, at most about, or about 1%, 2%, 3%, 4%, 5%, 10%, 20%, 30%, 40%, 50%, 55%, 60%, 65%, 70%, 75%, 80%, 85%, 90%, 95%, 99%, 99.5%, or 100%, or a range between any of these two values.

In some embodiments, the microbial formulation described herein may increase the plant nitrogen content by at least about, at most about, or about 1%, 2%, 3%, 4%, 5%, 10%, 20%, 30%, 40%, 50%, 55%, 60%, 65%, 70%, 75%, 80%, 85%, 90%, 95%, 99%, 99.5%, or 100%, or a range between any of these two values.

In some embodiments, the microbial formulation described herein may increase the population of nitrogen fixing bacteria in the root and root rhizospheres by at least about, at most about, or about 1%, 2%, 3%, 4%, 5%, 10%, 20%, 30%, 40%, 50%, 55%, 60%, 65%, 70%, 75%, 80%, 85%, 90%, 95%, 99%, 99.5%, or 100%, or a range between any of these two values.

In an aspect, the present disclosure may provide a microbial formulation comprising: (a) a *Paenibacillus sonchi* strain having one or more of the following: (i) a 16S rRNA gene sequence at least 95% identical to SEQ ID NO: 3; (ii) a gyrB gene sequence at least 95% identical to SEQ ID NO: 6; and (iii) a rpoB gene sequence at least 95% identical to SEQ ID NO: 9; and a carrier. In some embodiments, the formulation may comprise additional products of digestion of an organic material by a *Paenibacillus sonchi* strain. A carrier may be a fertilizer as described herein and the fertilizer may include, ammonia, urea, ammonium nitrate, ammonium sulfate, ammonium thiosulfate, monoammonium phosphate (MAP), diammonium phosphate (DAP), muriate of potash (MOP), sulfate of Potash (SOP), potassium nitrate (NOP). A carrier may also be coated by a micronutrient. The carrier of the formulation described herein may be a liquid or a solid. The concentration of the *Paenibacillus sonchi* strain may be at least about, at most about, or about $1\times10^2$ CFU, $5\times10^2$ CFU, $1\times10^3$ CFU, $5\times10^3$ CFU, $1\times10^4$ CFU, $5\times10^4$ CFU, $1\times10^5$ CFU, $5\times10^5$ CFU, $1\times10^6$ CFU, $5\times10^6$ CFU, $1\times10^7$ CFU, $5\times10^7$ CFU, $1\times10^8$ CFU, $5\times10^8$ CFU, $1\times10^9$ CFU, $5\times10^9$ CFU, $1\times10^{10}$ CFU, or $1\times10^{11}$ CFU, or a range between any of these values.

In another aspect, the present disclosure may provide an isolated strain of the species *Paenibacillus sonchi* having one or more of the following: (a) a 16S rRNA gene sequence at least 95% identical to SEQ ID NO: 3; (b) a gyrB gene sequence at least 95% identical to SEQ ID NO: 6; and (c) a rpoB gene sequence at least 95% identical to SEQ ID NO: 9. In some embodiments, a method may be utilized which comprises contacting a plant or a medium with a microbial formulation described herein. Without wishing to be bound by theory, a plant contacted by the microbial formulation described herein may lead to an increase in nitrogen fixation or a nitrogen use efficiency of the plant. The increase in solubilized zinc may be at least about, at most about, or about 1%, 2%, 3%, 4%, 5%, 6%, 7%, 8%, 9%, 10%, 12%, 15%, 18%, 20%, 25%, 30%, 35%, 40%, 45%, 50%, 60%, 75%, or 100%, or a range between any of these two values.

In some embodiments, the microbial formulation described herein may increase the nitrogen fixation activity in plant tissues by at least about, at most about, or about 1%, 2%, 3%, 4%, 5%, 10%, 20%, 30%, 40%, 50%, 55%, 60%, 65%, 70%, 75%, 80%, 85%, 90%, 95%, 99%, 99.5%, or 100%, or a range between any of these two values.

In some embodiments, the microbial formulation described herein may increase the plant nitrogen content by at least about, at most about, or about 1%, 2%, 3%, 4%, 5%, 10%, 20%, 30%, 40%, 50%, 55%, 60%, 65%, 70%, 75%, 80%, 85%, 90%, 95%, 99%, 99.5%, or 100%, or a range between any of these two values.

In some embodiments, the microbial formulation described herein may increase the population of nitrogen fixing bacteria in the root and root rhizospheres by at least about, at most about, or about 1%, 2%, 3%, 4%, 5%, 10%, 20%, 30%, 40%, 50%, 55%, 60%, 65%, 70%, 75%, 80%, 85%, 90%, 95%, 99%, 99.5%, or 100%, or a range between any of these two values.

In an aspect, the present disclosure may provide a microbial formulation comprising: (a) a *Bacillus megaterium* strain having one or more of the following: (i) a 16S rRNA gene sequence at least 95% identical to SEQ ID NO: 10; (ii) a gyrB gene sequence at least 95% identical to SEQ ID NO: 11; and (iii) a rpoB gene sequence at least 95% identical to SEQ ID NO: 12; and a carrier. In some embodiments, the formulation may comprise additional products of digestion of an organic material by a *Bacillus megaterium* strain. A carrier may be a fertilizer as described herein and the fertilizer may include, ammonia, urea, ammonium nitrate, ammonium sulfate, ammonium thiosulfate, monoammonium phosphate (MAP), diammonium phosphate (DAP), muriate of potash (MOP), sulfate of Potash (SOP), potassium nitrate (NOP). A carrier may also be coated by a micronutrient. The carrier of the formulation described herein may be a liquid or a solid. The concentration of the *Bacillus megaterium* strain may be at least about, at most about, or about $1\times10^2$ CFU, $5\times10^2$ CFU, $1\times10^3$ CFU, $5\times10^3$ CFU, $1\times10^4$ CFU, $5\times10^4$ CFU, $1\times10^5$ CFU, $5\times10^5$ CFU, $1\times10^6$ CFU, $5\times10^6$ CFU, $1\times10^7$ CFU, $5\times10^7$ CFU, $1\times10^8$ CFU, $5\times10^8$ CFU, $1\times10^9$ CFU, $5\times10^9$ CFU, $1\times10^{10}$ CFU, or $1\times10^{11}$ CFU, or a range between any of these values.

In another aspect, the present disclosure may provide an isolated strain of the species *Bacillus megaterium* having one or more of the following: (a) a 16S rRNA gene sequence at least 95% identical to SEQ ID NO: 10; (b) a gyrB gene sequence at least 95% identical to SEQ ID NO: 11; and (c) a rpoB gene sequence at least 95% identical to SEQ ID NO: 12. In some embodiments, a method may be utilized which comprises contacting a plant or a medium with a microbial formulation described herein. Without wishing to be bound by theory, a plant contacted by the microbial formulation described herein may lead to an increase in nitrogen fixation or a nitrogen use efficiency of the plant. The increase in solubilized zinc may be at least about, at most about, or about 1%, 2%, 3%, 4%, 5%, 6%, 7%, 8%, 9%, 10%, 12%, 15%, 18%, 20%, 25%, 30%, 35%, 40%, 45%, 50%, 60%, 75%, or 100%, or a range between any of these two values.

In some embodiments, the microbial formulation described herein may increase the nitrogen fixation activity in plant tissues by at least about, at most about, or about 1%, 2%, 3%, 4%, 5%, 10%, 20%, 30%, 40%, 50%, 55%, 60%, 65%, 70%, 75%, 80%, 85%, 90%, 95%, 99%, 99.5%, or 100%, or a range between any of these two values.

In some embodiments, the microbial formulation described herein may increase the plant nitrogen content by at least about, at most about, or about 1%, 2%, 3%, 4%, 5%, 10%, 20%, 30%, 40%, 50%, 55%, 60%, 65%, 70%, 75%, 80%, 85%, 90%, 95%, 99%, 99.5%, or 100%, or a range between any of these two values.

In some embodiments, the microbial formulation described herein may increase the population of nitrogen fixing bacteria in the root and root rhizospheres by at least about, at most about, or about 1%, 2%, 3%, 4%, 5%, 10%, 20%, 30%, 40%, 50%, 55%, 60%, 65%, 70%, 75%, 80%, 85%, 90%, 95%, 99%, 99.5%, or 100%, or a range between any of these two values.

In some embodiments, biostimulant compositions described herein may be applied in dry form. A biostimulant base product may be dehydrated to make a powdered product that is applied to a growth medium (e.g., soil), to a plant, or to a seed. In some embodiments, the biostimulant product can be a lyophilized powder or spray dried powder.

In some embodiments, the biostimulant compositions presented herein may be formulated as a seed treatment. It is contemplated that the seeds can be substantially uniformly coated with one or more layers of the microbial compositions disclosed herein using conventional methods of mixing, spraying or any combination thereof through the use of treatment application equipment that is specifically designed and manufactured to accurately, safely, and efficiently apply seed treatment products to seeds. Such equipment uses various types of coating technology such as rotary coaters, drum coaters, fluidized bed techniques, spouted beds, rotary mists or any combination thereof. Liquid seed treatments can be applied via either a spinning "atomizer" disk or a spray nozzle which evenly distributes the seed treatment onto the seed as it moves though the spray pattern. A seed may be mixed or tumbled for an additional period of time to achieve additional treatment distribution and drying. The seeds can be primed or unprimed before coating with the inventive compositions to increase the uniformity of germination and emergence. In an alternative embodiment, a dry powder formulation can be metered onto the moving seed and allowed to mix until completely distributed.

In some other embodiments, the solid or liquid microbial compositions described herein may contain functional agents capable of protecting seeds from the harmful effects of selective herbicides such as activated carbon, nutrients (fertilizers), and other agents capable of improving the germination and quality of the products or any combination thereof. Seed coating methods and compositions can be particularly useful when they are modified by the addition of a microbial composition of the present disclosure. Such coating methods and apparatus for application are disclosed in, for example, one of the embodiments of the present invention. Such coating methods and apparatus for their application are disclosed in, for example, U.S. Pat. Nos. 5,918,413; 5,554,445; 5,389,399; 4,759,945; and 4,465,017. Seed coating compositions are disclosed, for example, in U.S. Patent. Application. No. US20100154299, U.S. Pat. Nos. 5,939,356; 5,876,739; 5,849,320; 5,791,084; 5,661,103; 5,580,544, 5,328,942; 4,735,015; 4,634,587; 4,372,080, 4,339,456; and 4,245,432.

A variety of additives can be added to the seed treatment formulations comprising the inventive compositions. Binders can be added and may include those composed of an adhesive polymer that can be natural or synthetic without phytotoxic effect on the seed to be coated. The binder may be selected from the group consisting of polyvinyl acetates, polyvinyl acetate copolymers, ethylene vinyl acetate (EVA) copolymers, polyvinyl alcohols, polyvinyl alcohol copolymers, celluloses, including ethylcelluloses, methylcelluloses, hydroxymethylcelluloses, hydroxypropylcelluloses and carboxymethylcellulose, polyvinylpyrolidones, polysaccharides, including starch, modified starch, dextrins, maltodextrins, alginate and chitosans, fats, oils, proteins, including gelatin and zeins, gum arabics, shellacs, vinylidene chloride and vinylidene chloride copolymers, calcium lignosulfonates, acrylic copolymers, polyvinylacrylates, polyethylene oxide, acrylamide polymers and copolymers, polyhydroxyethyl acrylate, methylacrylamide monomers, and poly chloroprene.

In some specific embodiments, in addition to the microbial cells or spores, the coating can further comprise a layer of adherent. The adherent may be non-toxic, biodegradable, and adhesive. Examples of such materials include, but are not limited to, polyvinyl acetates, polyvinyl acetate copolymers, polyvinyl alcohols, polyvinyl alcohol copolymers, celluloses, such as methyl celluloses, hydroxymethyl celluloses, and hydroxymethyl propyl celluloses, dextrins, alginates, sugars, molasses, polyvinyl pyrrolidones, polysaccharides, proteins, fats, oils, gum arabics, gelatins, syrups, and starches.

Various additives, such as adherents, dispersants, surfactants, and nutrient and buffer ingredients, can also be included in the seed treatment formulation. Other conventional seed treatment additives include, but are not limited to, coating agents, wetting agents, buffering agents, and polysaccharides. At least one agriculturally acceptable carrier can be added to the seed treatment formulation such as water, solids or dry powders. The dry powders can be derived from a variety of materials such as calcium carbonate, gypsum, vermiculite, talc, humus, activated charcoal, and various phosphorous compounds.

In some embodiments, a seed coating composition can comprise at least one filler which is an organic or inorganic, natural or synthetic component with which the active components may be combined to facilitate its application onto the seed. A filler may comprise an inert solid such as clays, natural or synthetic silicates, silica, resins, waxes, solid fertilizers (for example ammonium salts), natural soil minerals, such as kaolins, clays, talc, lime, quartz, attapulgite, montmorillonite, bentonite or diatomaceous earths, or synthetic minerals, such as silica, alumina or silicates, in particular aluminum or magnesium silicates.

A seed treatment formulation may include one or more of the following ingredients: other pesticides, including compounds that act below the ground; fungicides, such as captan, thiram, metalaxyl, fludioxonil, oxadixyl, and isomers of each of those materials, and the like; herbicides, including compounds selected from glyphosate, carbamates, thiocarbamates, acetamides, triazines, dinitroanilines, glycerol ethers, pyridazinones, uracils, phenoxys, ureas, and benzoic acids; herbicidal safeners such as benzoxazine, benzhydryl derivatives, N,N-diallyl dichloroacetamide, various dihaloacyl, oxazolidinyl and thiazolidinyl compounds, ethanone, naphthalic anhydride compounds, and oxime derivatives; chemical fertilizers; and/or biological fertilizers. The seed treatment formulation may also comprise macronutrients and micronutrients. These ingredients may be added as a separate layer on the seed or alternatively may be added as part of the a seed coating using a microbial composition of the present disclosure.

The amount of the microbial composition or other ingredients used in the seed treatment may not inhibit germination of the seed, or cause phytotoxic damage to the seed.

The formulation that is used to treat the seed can be in the form of a suspension; emulsion; slurry of particles in an aqueous medium (e.g., water); wettable powder; wettable granules (dry flowable); and dry granules. If formulated as a suspension or slurry, the concentration of the active ingredient in the formulation may be about 0.5% to about 99% by weight (w/w), or may be about 5-40%. If formulated as a suspension or slurry, the concentration of the active ingredient in the formulation may be at least about, at most about, or about 0.1%, 0.5%, 1%, 2%, 3%, 4%, 5%, 10%, 15%, 20%, 25%, 30%, 35%, 40%, 45%, 50%, 60%, 70%, 80%, 90%, 95%, 96%, 97%, 98%, 99%, 99.5%, or 99.9%, or a range between any of these two values.

Other conventional inactive or inert ingredients can be incorporated into the formulation. Such inert ingredients include but are not limited to: conventional sticking agents; dispersing agents such as methylcellulose, for example, serve as combined dispersant/sticking agents for use in seed treatments; polyvinyl alcohol; lecithin, polymeric dispersants (e.g., polyvinylpyrrolidone/vinyl acetate); thickeners (e.g., clay thickeners to improve viscosity and reduce settling of particle suspensions); emulsion stabilizers; surfactants; antifreeze compounds (e.g., urea), dyes, colorants, and the like.

Coating formulations can be applied to seeds by a variety of methods, including, but not limited to, mixing in a container (e.g., a bottle or bag), mechanical application, tumbling, spraying, and immersion. A variety of active or inert material can be used for contacting seeds with microbial compositions according to the present disclosure, such as conventional film-coating materials including but not limited to water-based film coating materials such as SEPIRET™ (Seppic, Inc., N.J.) and OPACOAT™ (Berwind Pharm. Services, P.A.)

The amount of a microbial composition described herein that may be used for the treatment of the seed will vary depending upon the type of seed and the type of active ingredients, but the treatment will comprise contacting the seeds with an agriculturally effective amount of the inventive composition. An effective amount may refer to an amount of a composition that may be sufficient to affect beneficial or desired results. An effective amount can be administered in one or more administrations.

In addition to the coating layer, the seed may be treated with one or more of the following ingredients: other pesticides including fungicides and herbicides; herbicidal safeners; and/or fertilizers. These ingredients may be added as a separate layer or alternatively may be added in the coating layer. The microorganism-treated seeds may also be enveloped with a film overcoating to protect the coating.

A plant seed capable of germinating to form a plant can be treated with microbial compositions or formulations as described herein. Suitable seeds may comprise seeds of cereals, coffee, cole crops, fiber crops, flowers, fruits, legume, oil crops, trees, tuber crops, vegetables, as well as other plants of the monocotyledonous, and dicotyledonous species. Crop seeds may be coated include, but are not limited to, bean, carrot, corn, cotton, grasses, lettuce, peanut, pepper, potato, rapeseed, rice, rye, sorghum, soybean, sugar beet, sunflower, tobacco, or tomato seeds. For example, corn seeds, soybean seeds, sorghum seeds, or any combination thereof may be coated with the present microbial compositions.

VII. Methods of Promoting Plant Growth

Embodiments of biostimulant compositions may be used in methods of promoting plant growth for a variety of different plants and conditions. In some embodiments, contacting a plant, seed, or growth medium with the biostimulant promotes plant growth by, for example, increasing growth rate, yield at harvest, production, stem thickness, fruit abundance and/or size, grain production, leaf surface area, root surface area, root length, root depth, shoot thickness, or total biomass, as compared to a plant that has not received the treatment. A control plant may comprise, but is not limited to, (a) a plant which is genetically identical to the subject plant but which is not exposed to the same treatment (e.g., inoculant treatment) as the subject plant or (b) the subject plant itself, under conditions in which it has not been exposed to a particular treatment such as, for example, an inoculant or combination of inoculants and/or other chemicals. In some embodiments, a population of the microbial strain (e.g., a target isolate) or a biostimulant composition described herein may improve a property of plant growth. A property of plant growth (e.g., plant growth promotion property) may comprise shoot biomass, root biomass, nutrient uptake, crop yield, deaminase activity, acid production, leaf area, total biomass, nitrogen fixation, phosphate solubilization, nitrogen use efficiency, photosynthetic activity, chlorophyll content, or plant height.

In some embodiments, contacting a plant (e.g., root, stem, or leaf), seed, or growth medium with the biostimulant promotes plant growth by, for example, increasing a plant's nitrogen use efficiency. In some embodiments, treatment with a biostimulant described herein reduces the amount of nitrogen required for a crop to produce the same yield. In some embodiments, treatment with a biostimulant described herein increases the yield of a crop while keeping the amount of nitrogen provided to the crop stable. For instance, application of a biostimulant described herein and 80% of the amount of nitrogen typically provided to a crop may provide the same or higher yield as providing 100% of the typical nitrogen amount without the biostimulant. In addition, application of a biostimulant described herein and 100% of the typical nitrogen amount may provide a higher crop yield than application of 100% of the typical nitrogen amount without the biostimulant.

In some embodiments, a population of a microbial strain as described herein (e.g., a target isolate) or a biostimulant composition described herein may improve a property of plant growth. A property of plant growth (e.g., plant growth promotion property) may comprise shoot biomass, root biomass, nutrient uptake, crop yield, photosynthetic activity, deaminase activity, acid production, leaf area, total biomass, nitrogen fixation, nitrogen use efficiency, chlorophyll content, or plant height. In some embodiments, a population of a microbial strain as described herein (e.g., a target isolate) or a biostimulant composition described herein may be capable of promoting nitrogen use efficiency in a plant. In some cases, the inoculum of the microbe can be configured to improve nitrogen uptake in a plant. In some embodiments, a biostimulant composition comprising the inoculum of a microbe described herein may be capable of promoting nitrogen use efficiency.

Shoot biomass may be an important characteristic of plant growth, wherein a healthy plant may have a heavier shoot. In some embodiments, a heavier shoot (e.g., greater shoot biomass) may indicate better plant growth. In some embodiments, a lighter shoot (e.g., lower shoot biomass) may indicate better plant growth. In some embodiments, a population of a microbial strain as described herein (e.g., a target isolate) or a biostimulant composition described herein may increase a shoot biomass of a plant treated by the microbe (e.g., a target isolate) or the biostimulant composition by at least about 5%, at least about 10%, at least about 12%, at least about 15%, at least about 18%, at least about 20%, at least about 25%, at least about 30%, at least about 35%, at least about 40%, or at least about 50% compared to that of an untreated control plant. In some embodiments, a population of a microbial strain as described herein (e.g., a target isolate) or a biostimulant composition described herein may increase a shoot biomass of a plant treated by the microbe (e.g., a target isolate) or the biostimulant composition by at most about 50%, at most about 40%, at most about 35%, at most about 30%, at most about 25%, at most about 20%, at most about 18%, at most about 15%, at most about 12%, at most about 10%, or at most about 5% compared to that of an untreated control plant. In some embodiments, a population of a microbial strain as described herein (e.g., a target isolate) or a biostimulant composition described herein may increase a shoot biomass of a plant treated by the microbe (e.g., a target isolate) or the biostimulant composition from about 1% to about 50% compared to that of an untreated control plant. In some embodiments, a population of a microbial strain as described herein (e.g., a target isolate) or a biostimulant composition described herein may increase a shoot biomass of a plant treated by the microbe (e.g., a target isolate) or the biostimulant composition from about 1% to about 2%, about 1% to about 5%, about 1% to about 8%, about 1% to about 10%, about 1% to about 12%, about 1% to about 15%, about 1% to about 18%, about 1% to about 20%, about 1% to about 30%, about 1% to about 40%, about 1% to about 50%, about 2% to about 5%, about 2% to about 8%, about 2% to about 10%, about 2% to about 12%, about 2% to about 15%, about 2% to about 18%, about 2% to about 20%, about 2% to about 30%, about 2% to about 40%, about 2% to about 50%, about 5% to about 8%, about 5% to about 10%, about 5% to about 12%, about 5% to about 15%, about 5% to about 18%, about 5% to about 20%, about 5% to about 30%, about 5% to about 40%, about 5% to about 50%, about 8% to about 10%, about 8% to about 12%, about 8% to about 15%, about 8% to about 18%, about 8% to about 20%, about 8% to about 30%, about 8% to about 40%, about 8% to about 50%, about 10% to about 12%, about 10% to about 15%, about 10% to about 18%, about 10% to about 20%, about 10% to about 30%, about 10% to about 40%, about 10% to about 50%, about 12% to about 15%, about 12% to about 18%, about 12% to about 20%, about 12% to about 30%, about 12% to about 40%, about 12% to about 50%, about 15% to about 18%, about 15% to about 20%, about 15% to about 30%, about 15% to about 40%, about 15% to about 50%, about 18% to about 20%, about 18% to about 30%, about 18% to about 40%, about 18% to about 50%, about 20% to about 30%, about 20% to about 40%, about 20% to about 50%, about 30% to about 40%, about 30% to about 50%, or about 40% to about 50%. In some embodiments, a population of a microbial strain as described herein (e.g., a target isolate) or a biostimulant composition described herein may increase a shoot biomass of a plant treated by the microbe (e.g., a target isolate) or the biostimulant composition from about 1%, about 2%, about 5%, about 8%, about 10%, about 12%, about 15%, about 18%, about 20%, about 30%, about 40%, or about 50% compared to that of an untreated control plant.

Root biomass may be an important characteristic of plant growth, wherein a healthy plant may have a larger root (e.g., heavier root and greater root biomass). In some embodiments, a heavier root (e.g., greater root biomass) may indicate better plant growth. In some embodiments, a lighter root (e.g., lower root biomass) may indicate better plant growth. In some embodiments, a population of a microbial strain as described herein (e.g., a target isolate) or a biostimulant composition described herein may increase a root biomass of a plant treated by the microbe (e.g., a target isolate) or the biostimulant composition by at least about 5%, at least about 10%, at least about 12%, at least about 15%, at least about 18%, at least about 20%, at least about 25%, at least about 30%, at least about 35%, at least about 40%, or at least about 50% compared to that of an untreated control plant. In some embodiments, a population of a microbial strain as described herein (e.g., a target isolate) or a biostimulant composition described herein may increase a root biomass of a plant treated by the microbe (e.g., a target isolate) or the biostimulant composition by at most about 50%, at most about 40%, at most about 35%, at most about 30%, at most about 25%, at most about 20%, at most about 18%, at most about 15%, at most about 12%, at most about 10%, or at most about 5% compared to that of an untreated control plant. In some embodiments, a population of a microbial strain as described herein (e.g., a target isolate) or a biostimulant composition described herein may increase a root biomass of a plant treated by the microbe (e.g., a target isolate) or the biostimulant composition from about 1% to about 2%, about 1% to about 5%, about 1% to about 8%, about 1% to about 10%, about 1% to about 12%, about 1% to about 15%, about 1% to about 18%, about 1% to about 20%, about 1% to about 30%, about 1% to about 40%, about 1% to about 50%, about 2% to about 5%, about 2% to about 8%, about 2% to about 10%, about 2% to about 12%, about 2% to about 15%, about 2% to about 18%, about 2% to about 20%, about 2% to about 30%, about 2% to about 40%, about 2% to about 50%, about 5% to about 8%, about 5% to about 10%, about 5% to about 12%, about 5% to about 15%, about 5% to about 18%, about 5% to about 20%, about 5% to about 30%, about 5% to about 40%, about 5% to about 50%, about 8% to about 10%, about 8% to about 12%, about 8% to about 15%, about 8% to about 18%, about 8% to about 20%, about 8% to about 30%, about 8% to about 40%, about 8% to about 50%, about 10% to about 12%, about 10% to about 15%, about 10% to about 18%, about 10% to about 20%, about 10% to about 30%, about 10% to about 40%, about 10% to about 50%, about 12% to about 15%, about 12% to about 18%, about 12% to about 20%, about 12% to about 30%, about 12% to about 40%, about 12% to about 50%, about 15% to about 18%, about 15% to about 20%, about 15% to about 30%, about 15% to about 40%, about 15% to about 50%, about 18% to about 20%, about 18% to about 30%, about 18% to about 40%, about 18% to about 50%, about 20% to about 30%, about 20% to about 40%, about 20% to about 50%, about 30% to about 40%, about 30% to about 50%, or about 40% to about 50%. In some embodiments, a population of a microbial strain as described herein (e.g., a target isolate) or a biostimulant composition described herein may increase a shoot of a plant treated by the microbe (e.g., a target isolate) or the biostimulant composition biomass from about 1%, about 2%, about 5%, about 8%, about 10%, about 12%, about 15%, about 18%, about 20%, about 30%, about 40%, or about 50% compared to that of an untreated control plant.

Total plant biomass may be an important characteristic of plant growth, wherein a healthy plant may have a larger plant (e.g., a heavier plant with a greater plant biomass). In some embodiments, a heavier total biomass (e.g., greater total biomass) may indicate better plant growth. In some embodiments, a lighter total biomass (e.g., lower total biomass) may indicate better plant growth. In some embodiments, a population of a microbial strain as described herein (e.g., a target isolate) or a biostimulant composition described herein may increase a total biomass of a plant treated by the microbe (e.g., a target isolate) or the biostimulant composition by at least about 5%, at least about 10%, at least about 12%, at least about 15%, at least about 18%, at least about 20%, at least about 25%, at least about 30%, at least about 35%, at least about 40%, at least about 50%, at least about 60%, or at least about 75% compared to that of an untreated control plant. In some embodiments, a population of a microbial strain as described herein (e.g., a target isolate) or a biostimulant composition described herein may increase a total biomass of a plant treated by the microbe (e.g., a target isolate) or the biostimulant composition by at most about 75%, at most about 60%, at most about 50%, at most about 40%, at most about 35%, at most about 30%, at most about 25%, at most about 20%, at most about 18%, at most about 15%, at most about 12%, at most about 10%, or at most about 5% compared to that of an untreated control plant. In some embodiments, a population of a microbial strain as described herein (e.g., a target isolate) or a biostimulant composition described herein may increase a total biomass of a plant treated by the microbe (e.g., a target isolate) or the biostimulant composition from about 3% to about 75% compared to that of an untreated control plant. In some embodiments, a population of a microbial strain as described herein (e.g., a target isolate) or a biostimulant composition described herein may increase a total biomass of a plant treated by the microbe (e.g., a target isolate) or the biostimulant composition from about 3% to about 5%, about 3% to about 8%, about 3% to about 10%, about 3% to about 12%, about 3% to about 15%, about 3% to about 20%, about 3% to about 25%, about 3% to about 30%, about 3% to about 40%, about 3% to about 50%, about 3% to about 75%, about 5% to about 8%, about 5% to about 10%, about 5% to about 12%, about 5% to about 15%, about 5% to about 20%, about 5% to about 25%, about 5% to about 30%, about 5% to about 40%, about 5% to about 50%, about 5% to about 75%, about 8% to about 10%, about 8% to about 12%, about 8% to about 15%, about 8% to about 20%, about 8% to about 25%, about 8% to about 30%, about 8% to about 40%, about 8% to about 50%, about 8% to about 75%, about 10% to about 12%, about 10% to about 15%, about 10% to about 20%, about 10% to about 25%, about 10% to about 30%, about 10% to about 40%, about 10% to about 50%, about 10% to about 75%, about 12% to about 15%, about 12% to about 20%, about 12% to about 25%, about 12% to about 30%, about 12% to about 40%, about 12% to about 50%, about 12% to about 75%, about 15% to about 20%, about 15% to about 25%, about 15% to about 30%, about 15% to about 40%, about 15% to about 50%, about 15% to about 75%, about 20% to about 25%, about 20% to about 30%, about 20% to about 40%, about 20% to about 50%, about 20% to about 75%, about 25% to about 30%, about 25% to about 40%, about 25% to about 50%, about 25% to about 75%, about 30% to about 40%, about 30% to about 50%, about 30% to about 75%, about 40% to about 50%, about 40% to about 75%, or about 50% to about 75% compared to that of an untreated control plant.

Nutrient uptake may be an important characteristic of plant growth, wherein a healthy plant may have a greater nutrient uptake. In some embodiments, a greater nutrient uptake may indicate better plant growth. In some embodiments, a lower nutrient uptake may indicate better plant growth. In some embodiments, a population of a microbial strain as described herein (e.g., a target isolate) or a biostimulant composition described herein may increase a level of nutrient uptake. In some embodiments, a plant may be treated by a population of a microbial strain (e.g., a target isolate) or a biostimulant composition described herein. The nutrients may comprise sulfur, nitrogen, potassium, phosphorus, magnesium, calcium, zinc, boron, copper, iron, or manganese. In some embodiments, a population of a microbial strain as described herein (e.g., a target isolate) or a biostimulant composition described herein may increase a level of nutrient uptake of a plant treated by the microbe (e.g., a target isolate) or the biostimulant composition by at least about 0.5%, at least about 1%, at least about 1.5%, at least about 2%, at least about 3%, at least about 5%, at least about 10%, at least about 12%, at least about 15%, at least about 18%, at least about 20%, at least about 25%, at least about 30%, at least about 35%, at least about 40%, at least about 50%, at least about 60%, or at least about 75% compared to that of an untreated control plant. In some embodiments, a population of a microbial strain as described herein (e.g., a target isolate) or a biostimulant composition described herein may increase a level of nutrient uptake of a plant treated by the microbe (e.g., a target isolate) or the biostimulant composition by at most about 75%, at most about 60%, at most about 50%, at most about 40%, at most about 35%, at most about 30%, at most about 25%, at most about 20%, at most about 18%, at most about 15%, at most about 12%, at most about 10%, at most about 5%, at most about 3%, at most about 2%, at most about 1.5%, at most about 1%, or at most about 0.5% compared to that of an untreated control plant. In some embodiments, a population of a microbial strain as described herein (e.g., a target isolate) or a biostimulant composition described herein may increase a level of nutrient uptake of a plant treated by the microbe (e.g., a target isolate) or the biostimulant composition from about 0.1% to about 50% compared to that of an untreated control plant. In some embodiments, a population of a microbial strain as described herein (e.g., a target isolate) or a biostimulant composition described herein may increase a level of nutrient uptake of a plant treated by the microbe (e.g., a target isolate) or the biostimulant composition from about 0.10% to about 0.2%, about 0.10% to about 0.5%, about 0.10% to about 1%, about 0.1% to about 2%, about 0.1% to about 3%, about 0.1% to about 5%, about 0.10% to about 10%, about 0.10% to about 15%, about 0.10% to about 20%, about 0.10% to about 25%, about 0.1% to about 50%, about 0.2% to about 0.5%, about 0.2% to about 1%, about 0.2% to about 2%, about 0.2% to about 3%, about 0.2% to about 5%, about 0.2% to about 10%, about 0.2% to about 15%, about 0.2% to about 20%, about 0.2% to about 25%, about 0.2% to about 50%, about 0.5% to about 1%, about 0.5% to about 2%, about 0.5% to about 3%, about 0.5% to about 5%, about 0.5% to about 10%, about 0.5% to about 15%, about 0.5% to about 20%, about 0.5% to about 25%, about 0.5% to about 50%, about 1% to about 2%, about 1% to about 3%, about 1% to about 5%, about 1% to about 10%, about 1% to about 15%, about 1% to about 20%, about 1% to about 25%, about 1% to about 50%, about 2% to about 3%, about 2% to about 5%, about 2% to about 10%, about 2% to about 15%, about 2% to about 20%, about 2% to about 25%, about 2% to about 50%, about 3% to about 5%, about 3% to about 10%, about 3% to about 15%, about 3% to about 20%, about 3% to about 25%, about 3% to about 50%, about 5% to about 10%, about 5% to about 15%, about 5% to about 20%, about 5% to about 25%, about 5% to about 50%, about 10% to about 15%, about 10% to about 20%, about 10% to about 25%, about 10% to about 50%, about 15% to about 20%, about 15% to about 25%, about 15% to about 50%, about 20% to about 25%, about 20% to about 50%, or about 25% to about 50% compared to that of an untreated control plant.

Crop yield may be an important characteristic of plant growth, wherein healthy plants may produce more crops. In some embodiments, a greater crop yield may indicate better plant growth. In some embodiments, a population of a microbial strain as described herein (e.g., a target isolate) or a biostimulant composition described herein may increase a crop yield. Crops may comprise corn, grains, cotton, fruits, tree nuts, rice, soybeans, oil crops, sugar, vegetables, pulses, or wheat. In some embodiments, a population of a microbial strain as described herein (e.g., a target isolate) or a biostimulant composition described herein may increase a crop yield of a plant treated by the microbe (e.g., a target isolate) or the biostimulant composition by at least about 0.5%, at least about 1%, at least about 1.5%, at least about 2%, at least about 3%, at least about 5%, at least about 10%, at least about 12%, at least about 15%, at least about 18%, at least about 20%, at least about 25%, at least about 30%, at least about 35%, at least about 40%, at least about 50%, at least about 60%, or at least about 75% compared to that of an untreated control plant. In some embodiments, a population of a microbial strain as described herein (e.g., a target isolate) or a biostimulant composition described herein may increase a crop yield of a plant treated by the microbe (e.g., a target isolate) or the biostimulant composition by at most about 75%, at most about 60%, at most about 50%, at most about 40%, at most about 35%, at most about 30%, at most about 25%, at most about 20%, at most about 18%, at most about 15%, at most about 12%, at most about 10%, at most about 5%, at most about 3%, at most about 2%, at most about 1.5%, at most about 1%, or at most about 0.5% compared to that of an untreated control plant. In some embodiments, a population of a microbial strain as described herein (e.g., a target isolate) or a biostimulant composition described herein may increase a crop yield of a plant treated by the microbe (e.g., a target isolate) or the biostimulant composition from about 0.1% to about 50% compared to that of an untreated control plant. In some embodiments, a population of a microbial strain as described herein (e.g., a target isolate) or a biostimulant composition described herein may increase a crop yield of a plant treated by the microbe (e.g., a target isolate) or the biostimulant composition from about 0.1% to about 0.2%, about 0.1% to about 0.5%, about 0.1% to about 1%, about 0.1% to about 2%, about 0.1% to about 3%, about 0.1% to about 5%, about 0.1% to about 10%, about 0.1% to about 15%, about 0.1% to about 20%, about 0.1% to about 25%, about 0.1% to about 50%, about 0.2% to about 0.5%, about 0.2% to about 1%, about 0.2% to about 2%, about 0.2% to about 3%, about 0.2% to about 5%, about 0.2% to about 10%, about 0.2% to about 15%, about 0.2% to about 20%, about 0.2% to about 25%, about 0.2% to about 50%, about 0.5% to about 1%, about 0.5% to about 2%, about 0.5% to about 3%, about 0.5% to about 5%, about 0.5% to about 10%, about 0.5% to about 15%, about 0.5% to about 20%, about 0.5% to about 25%, about 0.5% to about 50%, about 1% to about 2%, about 1% to about 3%, about 1% to about 5%, about 1% to about 10%, about 1% to about 15%, about 1% to about 20%, about 1% to about 25%, about 1% to about 50%, about 2% to about 3%, about 2% to about 5%, about 2% to about 10%, about 2% to about 15%, about 2% to about 20%, about 2% to about 25%, about 2% to about 50%, about 3% to about 5%, about 3% to about 10%, about 3% to about 15%, about 3% to about 20%, about 3% to about 25%, about 3% to about 50%, about 5% to about 10%, about 5% to about 15%, about 5% to about 20%, about 5% to about 25%, about 5% to about 50%, about 10% to about 15%, about 10% to about 20%, about 10% to about 25%, about 10% to about 50%, about 15% to about 20%, about 15% to about 25%, about 15% to about 50%, about 20% to about 25%, about 20% to about 50%, or about 25% to about 50% compared to that of an untreated control plant.

Average leaf area may be an important characteristic of plant growth, wherein a healthy plant may have a larger leave or larger leaves. In some embodiments, a larger leaf (e.g., greater average leaf area) may indicate better plant growth. In some embodiments, a smaller leaf (e.g., lower average leaf area) may indicate better plant growth. In some embodiments, a population of a microbial strain as described herein (e.g., a target isolate) or a biostimulant composition described herein may increase an average leaf area. A population of a microbial strain as described herein (e.g., a target isolate) or a biostimulant composition described herein may increase an average leaf area of a plant treated by the microbe (e.g., a target isolate) or the biostimulant composition by at least about 5%, at least about 10%, at least about 12%, at least about 15%, at least about 18%, at least about 20%, at least about 25%, at least about 30%, at least about 35%, at least about 40%, at least about 50%, at least about 60%, or at least about 75% compared to that of an untreated control plant. A population of a microbial strain as described herein (e.g., a target isolate) or a biostimulant composition described herein may increase an average leaf area of a plant treated by the microbe (e.g., a target isolate) or the biostimulant composition by at most about 75%, at most about 60%, at most about 50%, at most about 40%, at most about 35%, at most about 30%, at most about 25%, at most about 20%, at most about 18%, at most about 15%, at most about 12%, at most about 10%, or at most about 5% compared to that of an untreated control plant. A population of a microbial strain as described herein (e.g., a target isolate) or a biostimulant composition described herein may increase an average leaf area of a plant treated by the microbe (e.g., a target isolate) or the biostimulant composition from about 3% to about 75% compared to that of an untreated control plant. A population of a microbial strain as described herein (e.g., a target isolate) or a biostimulant composition described herein may increase an average leaf area of a plant treated by the microbe (e.g., a target isolate) or the biostimulant composition from about 3% to about 5%, about 3% to about 8%, about 3% to about 10%, about 3% to about 12%, about 3% to about 15%, about 3% to about 20%, about 3% to about 25%, about 3% to about 30%, about 3% to about 40%, about 3% to about 50%, about 3% to about 75%, about 5% to about 8%, about 5% to about 10%, about 5% to about 12%, about 5% to about 15%, about 5% to about 20%, about 5% to about 25%, about 5% to about 30%, about 5% to about 40%, about 5% to about 50%, about 5% to about 75%, about 8% to about 10%, about 8% to about 12%, about 8% to about 15%, about 8% to about 20%, about 8% to about 25%, about 8% to about 30%, about 8% to about 40%, about 8% to about 50%, about 8% to about 75%, about 10% to about 12%, about 10% to about 15%, about 10% to about 20%, about 10% to about 25%, about 10% to about 30%, about 10% to about 40%, about 10% to about 50%, about 10% to about 75%, about 12% to about 15%, about 12% to about 20%, about 12% to about 25%, about 12% to about 30%, about 12% to about 40%, about 12% to about 50%, about 12% to about 75%, about 15% to about 20%, about 15% to about 25%, about 15% to about 30%, about 15% to about 40%, about 15% to about 50%, about 15% to about 75%, about 20% to about 25%, about 20% to about 30%, about 20% to about 40%, about 20% to about 50%, about 20% to about 75%, about 25% to about 30%, about 25% to about 40%, about 25% to about 50%, about 25% to about 75%, about 30% to about 40%, about 30% to about 50%, about 30% to about 75%, about 40% to about 50%, about 40% to about 75%, or about 50% to about 75% compared to that of an untreated control plant.

A population of a microbial strain as described herein (e.g., a target isolate) or a biostimulant composition described herein may increase an average leaf area of a plant treated by the microbe (e.g., a target isolate) or the biostimulant composition from about 60% to about 250% compared to that of an untreated control plant. A population of a microbial strain as described herein (e.g., a target isolate) or a biostimulant composition described herein may increase an average leaf area of a plant treated by the microbe (e.g., a target isolate) or the biostimulant composition from about 60% to about 70%, about 60% to about 80%, about 60% to about 90%, about 60% to about 100%, about 60% to about 110%, about 60% to about 125%, about 60% to about 150%, about 60% to about 175%, about 60% to about 200%, about 60% to about 250%, about 70% to about 80%, about 70% to about 90%, about 70% to about 100%, about 70% to about 110%, about 70% to about 125%, about 70% to about 150%, about 70% to about 175%, about 70% to about 200%, about 70% to about 250%, about 80% to about 90%, about 80% to about 100%, about 80% to about 110%, about 80% to about 125%, about 80% to about 150%, about 80% to about 175%, about 80% to about 200%, about 80% to about 250%, about 90% to about 100%, about 90% to about 110%, about 90% to about 125%, about 90% to about 150%, about 90% to about 175%, about 90% to about 200%, about 90% to about 250%, about 100% to about 110%, about 100% to about 125%, about 100% to about 150%, about 100% to about 175%, about 100% to about 200%, about 100% to about 250%, about 110% to about 125%, about 110% to about 150%, about 110% to about 175%, about 110% to about 200%, about 110% to about 250%, about 125% to about 150%, about 125% to about 175%, about 125% to about 200%, about 125% to about 250%, about 150% to about 175%, about 150% to about 200%, about 150% to about 250%, about 175% to about 200%, about 175% to about 250%, or about 200% to about 250% compared to that of an untreated control plant.

Chlorophyll is an important photosynthetic pigment in plants. Management of chlorophyll content may help optimize light absorption, photosynthesis, and growth for a plant. In some embodiments, a population of a microbial strain as described herein (e.g., a target isolate) or a biostimulant composition described herein may increase chlorophyll content in a plant. In some embodiments, a population of a microbial strain as described herein (e.g., a target isolate) or a biostimulant composition described herein may increase chlorophyll content of a plant treated by the microbe (e.g., a target isolate) or the biostimulant composition by at least 1%, at least about 2%, at least about 3%, at least about 4%, at least about 5%, at least about 10%, at least about 12%, at least about 15%, at least about 18%, at least about 20%, at least about 25%, at least about 30%, at least about 35%, at least about 40%, or at least about 50% compared to that of an untreated control plant. In some embodiments, a population of a microbial strain as described herein (e.g., a target isolate) or a biostimulant composition described herein may increase chlorophyll content of a plant treated by the microbe (e.g., a target isolate) or the biostimulant composition by at most about 50%, at most about 40%, at most about 35%, at most about 30%, at most about 25%, at most about 20%, at most about 18%, at most about 15%, at most about 12%, at most about 10%, at most about 5%, at most about 4%, at most about 3%, at most about 2%, or at most about 1% compared to that of an untreated control plant. In some embodiments, a population of a microbial strain as described herein (e.g., a target isolate) or a biostimulant composition described herein may increase chlorophyll content of a plant treated by the microbe (e.g., a target isolate) or the biostimulant composition from about 0.5% to about 50% compared to that of an untreated control plant. In some embodiments, a population of a microbial strain as described herein (e.g., a target isolate) or a biostimulant composition described herein may increase chlorophyll content of a plant treated by the microbe (e.g., a target isolate) or the biostimulant composition from about 0.5% to about 1%, about 0.5% to about 2%, about 0.5% to about 3%, about 0.5% to about 4%, about 0.5% to about 5%, about 0.5% to about 8%, about 0.5% to about 10%, about 0.5% to about 15%, about 0.5% to about 20%, about 0.5% to about 25%, about 0.5% to about 50%, about 1% to about 2%, about 1% to about 3%, about 1% to about 4%, about 1% to about 5%, about 1% to about 8%, about 1% to about 10%, about 1% to about 15%, about 1% to about 20%, about 1% to about 25%, about 1% to about 50%, about 2% to about 3%, about 2% to about 4%, about 2% to about 5%, about 2% to about 8%, about 2% to about 10%, about 2% to about 15%, about 2% to about 20%, about 2% to about 25%, about 2% to about 50%, about 3% to about 4%, about 3% to about 5%, about 3% to about 8%, about 3% to about 10%, about 3% to about 15%, about 3% to about 20%, about 3% to about 25%, about 3% to about 50%, about 4% to about 5%, about 4% to about 8%, about 4% to about 10%, about 4% to about 15%, about 4% to about 20%, about 4% to about 25%, about 4% to about 50%, about 5% to about 8%, about 5% to about 10%, about 5% to about 15%, about 5% to about 20%, about 5% to about 25%, about 5% to about 50%, about 8% to about 10%, about 8% to about 15%, about 8% to about 20%, about 8% to about 25%, about 8% to about 50%, about 10% to about 15%, about 10% to about 20%, about 10% to about 25%, about 10% to about 50%, about 15% to about 20%, about 15% to about 25%, about 15% to about 50%, about 20% to about 25%, about 20% to about 50%, or about 25% to about 50% compared to that of an untreated control plant.

Chlorophyll content may be measured by a SPAD unit (e.g., an index value having a correlation to chlorophyll density). Thus, improved chlorophyll content may be quantified as an increase in SPAD units of a plant and can be an indication of improved plant health and/or growth. In some embodiments, a plant treated with a population of a microbial strain as described herein (e.g., a target isolate) or a biostimulant composition described herein may have a leaf chlorophyll content of at least about 22 SPAD units SPAD units, at least about 22.5 SPAD units, at least about 23 SPAD units, at least about 23.25 SPAD units, at least about 24 SPAD units, at least about 24.5 SPAD units, at least about 25 SPAD units, at least about 25.5 SPAD units, at least about 26 SPAD units, at least about 27 SPAD units, at least about 28 SPAD units, at least about 29 SPAD units, at least about 30, or greater than about 30 SPAD units. In some embodiments, a plant treated with a population of a microbial strain as described herein (e.g., a target isolate) or a biostimulant composition described herein may have a leaf chlorophyll content of at most about 30 SPAD units, at most about 29 SPAD units, at most about 28 SPAD units, at most about 27 SPAD units, at most about 26 SPAD units, at most about 25.5 SPAD units, at most about 25 SPAD units, at most about 24.5 SPAD units, at most about 24 SPAD units, at most about 23.5 SPAD units, at most about 23 SPAD units, at most about 22.5 SPAD units, at most about 22, or less than about 22 SPAD units. In some embodiments, a plant treated with a population of a microbial strain as described herein (e.g., a target isolate) or a biostimulant composition described herein may have a leaf chlorophyll content from about 21 SPAD units to about 35 SPAD units. In some embodiments, a plant treated with a population of a microbial strain as described herein (e.g., a target isolate) or a biostimulant composition described herein may have a leaf chlorophyll content from about 21 SPAD units to about 22 SPAD units, about 21 SPAD units to about 23 SPAD units, about 21 SPAD units to about 24 SPAD units, about 21 SPAD units to about 25 SPAD units, about 21 SPAD units to about 26 SPAD units, about 21 SPAD units to about 27 SPAD units, about 21 SPAD units to about 28 SPAD units, about 21 SPAD units to about 29 SPAD units, about 21 SPAD units to about 30 SPAD units, about 21 SPAD units to about 32 SPAD units, about 21 SPAD units to about 35 SPAD units, about 22 SPAD units to about 23 SPAD units, about 22 SPAD units to about 24 SPAD units, about 22 SPAD units to about 25 SPAD units, about 22 SPAD units to about 26 SPAD units, about 22 SPAD units to about 27 SPAD units, about 22 SPAD units to about 28 SPAD units, about 22 SPAD units to about 29 SPAD units, about 22 SPAD units to about 30 SPAD units, about 22 SPAD units to about 32 SPAD units, about 22 SPAD units to about 35 SPAD units, about 23 SPAD units to about 24 SPAD units, about 23 SPAD units to about 25 SPAD units, about 23 SPAD units to about 26 SPAD units, about 23 SPAD units to about 27 SPAD units, about 23 SPAD units to about 28 SPAD units, about 23 SPAD units to about 29 SPAD units, about 23 SPAD units to about 30 SPAD units, about 23 SPAD units to about 32 SPAD units, about 23 SPAD units to about 35 SPAD units, about 24 SPAD units to about 25 SPAD units, about 24 SPAD units to about 26 SPAD units, about 24 SPAD units to about 27 SPAD units, about 24 SPAD units to about 28 SPAD units, about 24 SPAD units to about 29 SPAD units, about 24 SPAD units to about 30 SPAD units, about 24 SPAD units to about 32 SPAD units, about 24 SPAD units to about 35 SPAD units, about 25 SPAD units to about 26 SPAD units, about 25 SPAD units to about 27 SPAD units, about 25 SPAD units to about 28 SPAD units, about 25 SPAD units to about 29 SPAD units, about 25 SPAD units to about 30 SPAD units, about 25 SPAD units to about 32 SPAD units, about 25 SPAD units to about 35 SPAD units, about 26 SPAD units to about 27 SPAD units, about 26 SPAD units to about 28 SPAD units, about 26 SPAD units to about 29 SPAD units, about 26 SPAD units to about 30 SPAD units, about 26 SPAD units to about 32 SPAD units, about 26 SPAD units to about 35 SPAD units, about 27 SPAD units to about 28 SPAD units, about 27 SPAD units to about 29 SPAD units, about 27 SPAD units to about 30 SPAD units, about 27 SPAD units to about 32 SPAD units, about 27 SPAD units to about 35 SPAD units, about 28 SPAD units to about 29 SPAD units, about 28 SPAD units to about 30 SPAD units, about 28 SPAD units to about 32 SPAD units, about 28 SPAD units to about 35 SPAD units, about 29 SPAD units to about 30 SPAD units, about 29 SPAD units to about 32 SPAD units, about 29 SPAD units to about 35 SPAD units, about 30 SPAD units to about 32 SPAD units, about 30 SPAD units to about 35 SPAD units, or about 32 SPAD units to about 35 SPAD units.

Application of the biostimulant composition may improve photosynthetic activity of a plant. Enhanced photosynthesis may result in more energy for the plant which may be metabolized and used to fuel the plant. Photosynthetic activity may be measured by a quantum yield and/or an electron transport rate of a plant. A quantum yield of photosynthesis can be a percentage of energetic efficiency of photoautotrophy. In some embodiments, a greater quantum yield may indicate more efficient photosynthetic activity and a healthier plant. In some embodiments, a plant treated with a population of a microbial strain as described herein (e.g., a target isolate) or a biostimulant composition described herein may have a quantum yield of at least about 45%, at least about 50%, at least about 55%, at least about 60%, at least about 61%, at least about 62%, at least about 63%, at least about 64%, at least about 65%, at least about 66%, at least about 67%, at least about 68%, at least about 69%, at least about 70%, at least about 75%, at least about 80%, or greater than about 80%. In some embodiments, a plant treated with a population of a microbial strain as described herein (e.g., a target isolate) or a biostimulant composition described herein may have a quantum yield of at most about 80%, at most about 75%, at most about 70%, at most about 69%, at most about 68%, at most about 67%, at most about 66%, at most about 65%, at most about 64%, at most about 63%, at most about 62%, at most about 61%, at most about 60%, at most about 55%, at most about 50%, at most about 45%, or less than about 45%. In some embodiments, a plant treated with a population of a microbial strain as described herein (e.g., a target isolate) or a biostimulant composition described herein may have a quantum yield from about 40% to about 80%. In some embodiments, a plant treated with a population of a microbial strain as described herein (e.g., a target isolate) or a biostimulant composition described herein may have a quantum yield from at most about 80%. In some embodiments, a plant treated with a population of a microbial strain as described herein (e.g., a target isolate) or a biostimulant composition described herein may have a quantum yield from about 40% to about 45%, about 40% to about 50%, about 40% to about 55%, about 40% to about 60%, about 40% to about 62%, about 40% to about 64%, about 40% to about 66%, about 40% to about 68%, about 40% to about 70%, about 40% to about 75%, about 40% to about 80%, about 45% to about 50%, about 45% to about 55%, about 45% to about 60%, about 45% to about 62%, about 45% to about 64%, about 45% to about 66%, about 45% to about 68%, about 45% to about 70%, about 45% to about 75%, about 45% to about 80%, about 50% to about 55%, about 50% to about 60%, about 50% to about 62%, about 50% to about 64%, about 50% to about 66%, about 50% to about 68%, about 50% to about 70%, about 50% to about 75%, about 50% to about 80%, about 55% to about 60%, about 55% to about 62%, about 55% to about 64%, about 55% to about 66%, about 55% to about 68%, about 55% to about 70%, about 55% to about 75%, about 55% to about 80%, about 60% to about 62%, about 60% to about 64%, about 60% to about 66%, about 60% to about 68%, about 60% to about 70%, about 60% to about 75%, about 60% to about 80%, about 62% to about 64%, about 62% to about 66%, about 62% to about 68%, about 62% to about 70%, about 62% to about 75%, about 62% to about 80%, about 64% to about 66%, about 64% to about 68%, about 64% to about 70%, about 64% to about 75%, about 64% to about 80%, about 66% to about 68%, about 66% to about 70%, about 66% to about 75%, about 66% to about 80%, about 68% to about 70%, about 68% to about 75%, about 68% to about 80%, about 70% to about 75%, about 70% to about 80%, or about 75% to about 80%.

The respiratory electronic transport chain of plants couples electron transfer from organic substrates to oxygen molecules. Measures of an electron transport rate can quantify photosynthetic activity of a plant. In some embodiments, a greater electron transport rate may indicate more efficient photosynthetic activity and a healthier plant. In some embodiments, a plant treated with a population of a microbial strain as described herein (e.g., a target isolate) or a biostimulant composition described herein may have an electron transport rate of at least about 100 $\mu$mol m$^{-2}$ s$^{-1}$, at least about 110 $\mu$mol m$^{-2}$ s$^{-1}$, at least about 120 $\mu$mol m$^{-2}$ s$^{-1}$, at least about 130 $\mu$mol m$^{-2}$ s$^{-1}$, at least about 140 $\mu$mol m$^{-2}$ s$^{-1}$, at least about 150 $\mu$mol m$^{-2}$ s$^{-1}$, at least about 155 $\mu$mol m$^{-2}$ s$^{-1}$, at least about 160 $\mu$mol m$^{-2}$ s$^{-1}$, at least about 165 $\mu$mol m$^{-2}$ s$^{-1}$, at least about 170 $\mu$mol m$^{-2}$ s$^{-1}$, at least about 175 $\mu$mol m$^{-2}$ s$^{-1}$, at least about 180 $\mu$mol m$^{-2}$ s$^{-1}$, at least about 185 $\mu$mol m$^{-2}$ s$^{-1}$, at least about 190 $\mu$mol m$^{-2}$ s$^{-1}$, at least about 200 $\mu$mol m$^{-2}$ s$^{-1}$, or greater than about 200 $\mu$mol m$^{-2}$ s$^{-1}$. In some embodiments, a plant treated with a population of a microbial strain as described herein (e.g., a target isolate) or a biostimulant composition described herein may have an electron transport rate of at most about 200 $\mu$mol m$^{-2}$ s$^{-1}$, at most about 190 $\mu$mol m$^{-2}$ s$^{-1}$, at most about 185 $\mu$mol m$^{-2}$ s$^{-1}$, at most about 180 $\mu$mol m$^{-2}$ s$^{-1}$, at most about 175 $\mu$mol m$^{-2}$ s$^{-1}$, at most about 170 $\mu$mol m$^{-2}$ s$^{-1}$, at most about 165 $\mu$mol m$^{-2}$ s$^{-1}$, at most about 160 $\mu$mol m$^{-2}$ s$^{-1}$ at most about 155 $\mu$mol m$^{-2}$ s$^{-1}$ at most about 150 $\mu$mol m$^{-2}$ s$^{-1}$, at most about 140 $\mu$mol m$^{-2}$ s$^{-1}$, at most about 130 µmol m$^{-2}$ s$^{-1}$, at most about 120 µmol m$^{-2}$ s$^{-1}$, at most about 110 µmol m$^{-2}$ s$^{-1}$, at most about 100 µmol m$^{-2}$ s$^{-1}$, or less than about 100 µmol m$^{-2}$ s$^{-1}$. In some embodiments, a plant treated with a population of a microbial strain as described herein (e.g., a target isolate) or a biostimulant composition described herein may have an electron transport rate from about 100 µmol m–2 s–1 to about 200 µmol m–2 s–1. In some embodiments, a plant treated with a population of a microbial strain as described herein (e.g., a target isolate) or a biostimulant composition described herein may have an electron transport rate from about 100 µmol m–2 s–1 to about 110 µmol m–2 s–1, about 100 µmol m–2 s–1 to about 120 µmol m–2 s–1, about 100 µmol m–2 s–1 to about 130 µmol m–2 s–1, about 100 µmol m–2 s–1 to about 140 µmol m–2 s–1, about 100 µmol m–2 s–1 to about 150 µmol m–2 s–1, about 100 µmol m–2 s–1 to about 160 µmol m–2 s–1, about 100 µmol m–2 s–1 to about 170 µmol m–2 s–1, about 100 µmol m$^{-2}$ s$^{-1}$ to about 180 µmol m–2 s–1, about 100 µmol m–2 s–1 to about 190 µmol m–2 s–1, about 100 µmol m–2 s–1 to about 200 µmol m–2 s–1, about 110 µmol m–2 s–1 to about 120 µmol m–2 s–1, about 110 µmol m–2 s–1 to about 130 µmol m–2 s–1, about 110 µmol m–2 s–1 to about 140 µmol m–2 s–1, about 110 µmol m–2 s–1 to about 150 µmol m–2 s–1, about 110 µmol m–2 s–1 to about 160 µmol m$^{-2}$ s$^{-1}$, about 110 µmol m–2 s–1 to about 170 µmol m–2 s–1, about 110 µmol m–2 s–1 to about 180 µmol m–2 s–1, about 110 µmol m–2 s–1 to about 190 µmol m–2 s–1, about 110 µmol m–2 s–1 to about 200 µmol m–2 s–1, about 120 µmol m–2 s–1 to about 130 µmol m–2 s–1, about 120 µmol m–2 s–1 to about 140 µmol m–2 s–1, about 120 µmol m–2 s–1 to about 150 µmol m–2 s–1, about 120 µmol m$^{-2}$ s$^{-1}$ to about 160 µmol m–2 s–1, about 120 µmol m–2 s–1 to about 170 µmol m–2 s–1, about 120 µmol m–2 s–1 to about 180 µmol m–2 s–1, about 120 µmol m–2 s–1 to about 190 µmol m–2 s–1, about 120 µmol m–2 s–1 to about 200 µmol m–2 s–1, about 130 µmol m–2 s–1 to about 140 µmol m–2 s–1, about 130 µmol m–2 s–1 to about 150 µmol m–2 s–1, about 130 µmol m–2 s–1 to about 160 µmol m$^{-2}$ s$^{-1}$, about 130 µmol m–2 s–1 to about 170 µmol m–2 s–1, about 130 µmol m–2 s–1 to about 180 µmol m–2 s–1, about 130 µmol m–2 s–1 to about 190 µmol m–2 s–1, about 130 µmol m–2 s–1 to about 200 µmol m–2 s–1, about 140 µmol m–2 s–1 to about 150 µmol m–2 s–1, about 140 µmol m–2 s–1 to about 160 µmol m–2 s–1, about 140 µmol m–2 s–1 to about 170 µmol m–2 s–1, about 140 µmol m$^{-2}$ s$^{-1}$ to about 180 µmol m–2 s–1, about 140 µmol m–2 s–1 to about 190 µmol m–2 s–1, about 140 µmol m–2 s–1 to about 200 µmol m–2 s–1, about 150 µmol m–2 s–1 to about 160 µmol m–2 s–1, about 150 µmol m–2 s–1 to about 170 µmol m–2 s–1, about 150 µmol m–2 s–1 to about 180 µmol m–2 s–1, about 150 µmol m–2 s–1 to about 190 µmol m–2 s–1, about 150 µmol m–2 s–1 to about 200 µmol m$^{-2}$ s$^{-1}$, about 160 µmol m–2 s–1 to about 170 µmol m–2 s–1, about 160 µmol m–2 s–1 to about 180 µmol m–2 s–1, about 160 µmol m–2 s–1 to about 190 µmol m–2 s–1, about 160 µmol m–2 s–1 to about 200 µmol m–2 s–1, about 170 µmol m–2 s–1 to about 180 µmol m–2 s–1, about 170 µmol m–2 s–1 to about 190 µmol m–2 s–1, about 170 µmol m–2 s–1 to about 200 µmol m–2 s–1, about 180 µmol m$^{-2}$ s$^{-1}$ to about 190 µmol m–2 s–1, about 180 µmol m–2 s–1 to about 200 µmol m–2 s–1, or about 190 µmol m–2 s–1 to about 200 µmol m–2 s–1.

Plant height may be an important characteristic of plant growth, wherein a taller plant may indicate a healthier plant. In some embodiments, a taller plant may indicate better plant growth. In some embodiments, a shorter plant may indicate better plant growth. In some embodiments, a population of a microbial strain as described herein (e.g., a target isolate) or a biostimulant composition described herein may increase a plant height of a plant. In some embodiments, a population of a microbial strain as described herein (e.g., a target isolate) or a biostimulant composition described herein may increase a plant height of a plant treated by the microbe (e.g., a target isolate) or the biostimulant composition by at least 1%, at least about 2%, at least about 3%, at least about 4%, at least about 5%, at least about 10%, at least about 12%, at least about 15%, at least about 18%, at least about 20%, at least about 25%, at least about 30%, at least about 35%, at least about 40%, or at least about 50% compared to that of an untreated control plant. In some embodiments, a population of a microbial strain as described herein (e.g., a target isolate) or a biostimulant composition described herein may increase a plant height of a plant treated by the microbe (e.g., a target isolate) or the biostimulant composition by at most about 50%, at most about 40%, at most about 35%, at most about 30%, at most about 25%, at most about 20%, at most about 18%, at most about 15%, at most about 12%, at most about 10%, at most about 5%, at most about 4%, at most about 3%, at most about 2%, or at most about 1% compared to that of an untreated control plant. In some embodiments, a population of a microbial strain as described herein (e.g., a target isolate) or a biostimulant composition described herein may increase a plant height of a plant treated by the microbe (e.g., a target isolate) or the biostimulant composition from about 0.5% to about 50% compared to that of an untreated control plant. In some embodiments, a population of a microbial strain as described herein (e.g., a target isolate) or a biostimulant composition described herein may increase a plant height of a plant treated by the microbe (e.g., a target isolate) or the biostimulant composition from about 0.5% to about 1%, about 0.5% to about 2%, about 0.5% to about 3%, about 0.5% to about 4%, about 0.5% to about 5%, about 0.5% to about 8%, about 0.5% to about 10%, about 0.5% to about 15%, about 0.5% to about 20%, about 0.5% to about 25%, about 0.5% to about 50%, about 1% to about 2%, about 1% to about 3%, about 1% to about 4%, about 1% to about 5%, about 1% to about 8%, about 1% to about 10%, about 1% to about 15%, about 1% to about 20%, about 1% to about 25%, about 1% to about 50%, about 2% to about 3%, about 2% to about 4%, about 2% to about 5%, about 2% to about 8%, about 2% to about 10%, about 2% to about 15%, about 2% to about 20%, about 2% to about 25%, about 2% to about 50%, about 3% to about 4%, about 3% to about 5%, about 3% to about 8%, about 3% to about 10%, about 3% to about 15%, about 3% to about 20%, about 3% to about 25%, about 3% to about 50%, about 4% to about 5%, about 4% to about 8%, about 4% to about 10%, about 4% to about 15%, about 4% to about 20%, about 4% to about 25%, about 4% to about 50%, about 5% to about 8%, about 5% to about 10%, about 5% to about 15%, about 5% to about 20%, about 5% to about 25%, about 5% to about 50%, about 8% to about 10%, about 8% to about 15%, about 8% to about 20%, about 8% to about 25%, about 8% to about 50%, about 10% to about 15%, about 10% to about 20%, about 10% to about 25%, about 10% to about 50%, about 15% to about 20%, about 15% to about 25%, about 15% to about 50%, about 20% to about 25%, about 20% to about 50%, or about 25% to about 50% compared to that of an untreated control plant.

EXAMPLES

The following examples are provided to further illustrate some embodiments of the present disclosure, but are not intended to limit the scope of the disclosure; it will be understood by their exemplary nature that other procedures, methodologies, or techniques known to those skilled in the art may alternatively be used.

Example 1: Identification and Screening of Target MS2748, MS3900, MS3907, and MS4921 Strains Plant growth promotion screening for bacterial strains was completed at Painted Flower Farm in Denton Texas. Strains were grown in spore media (per 1 L: Peptone 3.3 g, Beef extract 1.0 g, NaCl 5.0 g, K2HHPO4 2.0 g, KCl 1.0 g, MgSO4·7H2O 0.25 g, MnSO4 0.01 g, Lactose 5 g) for 48-96 hours. Spores were diluted in sterile water to $10^4$, $10^5$, $10^6$ and $10^7$ and applied to a corn seed in a container as 1 mL over the seed in the pot. The potting mix was 1:1:1 (Denton soil:sand:peat mix). Plants were fertilized with full nutrition. After 3-4 weeks growth, plants were harvest and growth determined as fresh weight normalized to the water-only treated plant for that test.

Each strain was tested for the capacity for nitrogen fixation through testing for growth on modified NFb solid and semi-solid nitrogen free media. Phosphate solubilization screening was completed using media modified from. Hydroxylapatite (calcium tri-phosphate, $Ca_5(PO_4)_3OH$) as the inorganic P source. The CAS test for siderophore production in based on a color change surrounding producer microorganisms, from blue to purple (e.g., a traditional CAS assay for siderophores of the catechol type) or from blue to orange (e.g., for microorganisms that produce hydroxamates). This method was modified by making the CAS solution liquid to be mixed 1:1 with supernatant of the T-Media minimal media broths. IAA (indole-3-acetic acid) is an auxin like substance found to increase the number of roots in plants colonized by these rhizobacteria. Isolates were screened for IA production, cellulase activity, and ammonia production from organic N (peptone).

Selected isolates were sub-cultured to ensure purity before colony-PCR was performed. The nifH gene was amplified by inoculating a barely-visible quantity of single-morphology bacterial culture from an agar plate into a 30 uL PCR reaction using a sterile toothpick. Each 30 uL PCR reaction consisted of 15 uL of AmpliTaq Gold 360 Master Mix (Thermo Fisher Scientific), 1.5 uL of forward primer, 1.5 uL of reverse primer, 1.5 uL of 10 mg/mL Bovine Serum Albumin (BSA), and 10.5 uL of molecular-grade sterile water. The PCR primers used to amplify the nifH gene were PolF (5'TGCGAYCCSAARGCBGACTC 3') and PolR (3'ATSGCCATCATYTCRCCGGA 5'), both at a working concentration of 0.5 uM. Conditions for the PCR run were 95° C. for 5 minutes, followed by 30 cycles of 94° C. for 1 minute, 55° C. for 1 minute, and 72° C. for 2 minutes. Finally, reactions were held at 72° C. for 5 minutes, followed by a hold at 4° C.

After the PCR run, 1 uL of each PCR reaction was run on a gel using the Lonza FlashGel system to confirm amplification of the nifH gene. PCR reactions positive for amplification were cleaned using the QIAquick PCR Purification Kit according to manufacturer's instructions and then at least 20 uL of purified PCR reaction was shipped to Eurofins Genomics for sequencing.

TABLE 1

Results for screening of MS3900, MS3907, and MS2748 for plant growth promotion and plants growth promoting traits.

| Strain designation | Species identification | Isolation source | # of corn tests better than the UTC / total # of tests | Average Corn growth over UTC (in %) | Qualitative PGP trait screening results (0, 1, or 2 based on positive and negative controls) | | | | | | Confirmed N-fixer by DNA detection of nifH gene |
|---|---|---|---|---|---|---|---|---|---|---|---|
| | | | | | Growth on N-free medium | P-solubi-lization | Iron acqui-sition | Auxin production | Cellulase activity | Organic N to ammonia | |
| MS3900 | Bacillus megaterium | Wheat Endophyte, PST WB treated | 4/4 | 13.32 | 2 | 2 | 0 | 0 | 2 | 2 | No |
| MS3907 | Paenibacillus borealis | Wheat Endophyte, Accomplish LM treated | 3/4 | 8.94 | 2 | 0 | 0 | 1 | 1 | 0 | Yes |
| MS2748 | Bacillus megaterium | Corn root slurry | 7/10 | 0.61 | 1 | 1 | 1 | 1 | 1 | 1 | No |

Genome sequencing for strains MS3900, MS3907, MS2748, and MS4921 was by Molecular Research using standard methods for DNA extraction and DNA sequencing (2×250 bp and 4 million reads) using the Illumina NovaSeq 6000 system. MRDNA assembled the reads into contigs as part of the service. Contigs were annotated using RAST (Aziz et al. 2008, BMC Genomics 9:75). Whole genome sequences from related strains and species were taken from the publicly available National Center for Biotechnology Information (NCBI) database, Genbank.

Exemplary sequences for strains MS3900, MS3907, MS2748, and MS4921 can be found in Tables 2-4 and 43.

TABLE 2

Exemplary 16S rRNA Sequences of Bacterial Isolates

| SEQ ID NO. | Bacterial Gene | Sequence |
|---|---|---|
| 1 | MS3900 | CATTTCTTCGGAGAGTTTGATCCTGGCTCAGGATGAACGCTGG CGGCGTGCCTAATACATGCAAGTCGAGCGAACTGATTAGAAGC |

TABLE 2-continued

Exemplary 16S rRNA Sequences of Bacterial Isolates

| SEQ ID NO. | Bacterial Gene | Sequence |
|---|---|---|
| | | TTGCTTCTATGACGTTAGCGGCGGACGGGTGAGTAACACGTGG
GCAACCTGCCTGTAAGACTGGGATAACTTCGGGAAACCGAAGC
TAATACCGGATAGGATCTTCTCCTTCATGGGAGATGATTGAAA
GATGGTTTCGGCTATCACTTACAGATGGGCCCGCGGTGCATTA
GCTAGTTGGTGAGGTAACGGCTCACCAAGGCAACGATGCATAG
CCGACCTGAGAGGGTGATCGGCCACACTGGGACTGAGACACGG
CCCAGACTCCTACGGGAGGCAGCAGTAGGGAATCTTCCGCAAT
GGACGAAAGTCTGACGGAGCAACGCCGCGTGAGTGATGAAGGC
TTTCGGGTCGTAAAACTCTGTTGTTAGGGAAGAACAAGTACAA
GAGTAACTGCTTGTACCTTGACGGTACCTAACCAGAAAGCCAC
GGCTAACTACGTGCCAGCAGCCGCGGTAATACGTAGGTGGCAA
GCGTTATCCGGAATTATTGGGCGTAAAGCGCGCGCAGGCGGTT
TCTTAAGTCTGATGTGAAAGCCCACGGCTCAACCGTGGAGGGT
CATTGGAAACTGGGGAACTTGAGTGCAGAAGAGAAAAGCGGAA
TTCCACGTGTAGCGGTGAAATGCGTAGAGATGTGGAGGAACAC
CAGTGGCGAAGGCGGCTTTTTGGTCTGTAACTGACGCTGAGGC
GCGAAAGCGTGGGGAGCAAACAGGATTAGATACCCTGGTAGTC
CACGCCGTAAACGATGAGTGCTAAGTGTTAGAGGGTTTCCGCC
CTTTAGTGCTGCAGCTAACGCATTAAGCACTCCGCCTGGGGAG
TACGGTCGCAAGACTGAAACTCAAAGGAATTGACGGGGGCCCG
CACAAGCGGTGGAGCATGTGGTTTAATTCGAAGCAACGCGAAG
AACCTTACCAGGTCTTGACATCCTCTGACAACTCTAGAGATAG
AGCGTTCCCCTTCGGGGGACAGAGTGACAGGTGGTGCATGGTT
GTCGTCAGCTCGTGTCGTGAGATGTTGGGTTAAGTCCCGCAAC
GAGCGCAACCCTTGATCTTAGTTGCCAGCATTTAGTTGGGCAC
TCTAAGGTGACTGCCGGTGACAAACCGGAGGAAGGTGGGGATG
ACGTCAAATCATCATGCCCCTTATGACCTGGGCTACACACGTG
CTACAATGGATGGTACAAAGGGCTGCAAGACCGCGAGGTCAA
CCAATCCCATAAAACCATTCTCAGTTCGGATTGTAGGCTGCAA
CTCGCCTACATGAAGCTGGAATCGCTAGTAATCGCGGATCAGC
ATGCCGCGGTGAATACGTTCCCGGGCCTTGTACACACCGCCCG
TCACACCACGAGAGTTTGTAACACCCGAAGTCGGTGGAGTAAC
CGTAAGGAGCTAGCCGCCTAAGGTGGGACAGATGATTGGGGTG
AAGTCGTAACAAGGTAGCCGTATCGGAAGGTGCGGCTGGATCA
CCTCCTTTCTA |
| 2 | MS3907 | TTCAATACAAATTGGAGAGTTTGATCCTGGCTCAGGACGAACG
CTGGCGGCGTGCCTAATACATGCAAGTCGAGCGGAGTTATGAT
GGAGCTTGCTCCTGATTAACTTAGCGGCGGACGGGTGAGTAAC
ACGTAGGCAACCTGCCCTCAAGACTGGGATAACTACCGGAAAC
GGTAGCTAATACCGGATAATTTCTTTGTTCTCCTGAAGAGAGA
ATGAAAGGCGGAGCAATCTGCCACTTGAGGATGGGCCTGCGGC
GCATTAGCTAGTTGGTGAGGTAACGGCTCACCAAGGCGACGAT
GCGTAGCCGACCTGAGAGGGTGAACGGCCACACTGGGACTGAG
ACACGGCCCAGACTCCTACGGGAGGCAGCAGTAGGGAATCTTC
CGCAATGGGCGAAAGCCTGACGGAGCAACGCCGCGTGAGTGAT
GAAGGTTTTCGGATCGTAAAGCTCTGTTGCCAGGGAAGAACGT
CCGGTAGAGTAACTGCTACCGGAGTGACGGTACCTGAGAAGAA
AGCCCCGGCTAACTACGTGCCAGCAGCCGCGGTAATACGTAGG
GGGCAAGCGTTGTCCGGAATTATTGGGCGTAAAGCGCGCGCAG
GCGGCGATTTAAGTCTGGTGTTTAAACCTTGGGCTCAACCTGG
GGTCGCACTGGAAACTGGATCGCTTGAGTACAGAAGAGGAAAG
TGGAATTCCACGTGTAGCGGTGAAATGCGTAGATATGTGGAGG
AACACCAGTGGCGAAGGCGACTTTCTGGGCTGTAACTGACGCT
GAGGCGCGAAAGCGTGGGGAGCAAACAGGATTAGATACCCTGG
TAGTCCACGCCGTAAACGATGAGTGCTAGGTGTTAGGGGTTTC
GATACCCTTGGTGCCGAAGTTAACACAGTAAGCACTCCGCCTG
GGGAGTACGGTCGCAAGACTGAAACTCAAAGGAATTGACGGGG
ACCCGCACAAGCAGTGGAGTATGTGGTTTAATTCGAAGCAACG
CGAAGAACCTTACCAGGTCTTGACATCCCGATGAAAGCATTAG
AGATAGTGCCCCTCTTCGGAGCATCGGAGACAGGTGGTGCATG
GTTGTCGTCAGCTCGTGTCGTGAGATGTTGGGTTAAGTCCCGC
AACGAGCGCAACCCTTGACTTTAGTTGCCAGCAGGTTAAGCTG
GGCACTCTAGAGTGACTGCCGGTGACAAACCGGAGGAAGGTGG
GGATGACGTCAAATCATCATGCCCCTTATGACCTGGGCTACAC
ACGTACTACAATGGCCGGTACAACGGGAAGCGAAGCCGCGAGG
TGGAGCCAATCCCAGCAAAGCCGGTCTCAGTTCGGATTGCAGG
CTGCAACTCGCCTGCATGAAGTCGGAATTGCTAGTAATCGCGG
ATCAGCATGCCGCGGTGAATACGTTCCCGGGTCTTGTACACAC
CGCCCGTCACACCACGAGAGTTTACAACACCCGAAGTCGGTGG
GGTAACCCGCAAGGGAGCCAGCCGCCGAAGGTGGGGTAGATGA
TTGGGGTGAAGTCGTAACAAGGTAGCCGTATCGGAAGGTGCGG
CTGGATCACCTCCTTTCTA |

TABLE 2-continued

Exemplary 16S rRNA Sequences of Bacterial Isolates

| SEQ ID NO. | Bacterial Gene | Sequence |
|---|---|---|
| 3 | MS4921 | TACCAATTGGAGAGTTTGATCCTGGCTCAGGACGAACGCTGGC<br>GGCGTGCCTAATACATGCAAGTCGAGCGGAGTTTATCCTTCGG<br>GGTAAGCTTAGCGGCGGACGGGTGAGTAACACGTAGGCAACCT<br>ACCCTCTAGACTGGGATAACTACCGGAAACGGTAGCTAATACC<br>GGATAATTCCTTGATCCACATGGGCTAAGGATGAAAGGCGGAG<br>CAATCTGCTGCTAGAGGATGGGCCTGCGGCGCATTAGCTAGTT<br>GGTGGGGTAACGGCCTACCAAGGCGACGATGCGTAGCCGACCT<br>GAGAGGGTGAACGGCCACACTGGGACTGAGACACGGCCCAGAC<br>TCCTACGGGAGGCAGCAGTAGGGAATCTTCCGCAATGGGCGAA<br>AGCCTGACGGAGCAACGCCGCGTGAGTGATGAAGGTTTTCGGA<br>TCGTAAAGCTCTGTTGCCAGGGAAGAACGTCCGGTAGAGTAAC<br>TGCTATCGGAGTGACGGTACCTGAGAAGAAAGCCCCGGCTAAC<br>TACGTGCCAGCAGCCGCGGTAATACGTAGGGGCAAGCGTTGT<br>CCGGAATTATTGGGCGTAAAGCGCGCGCAGGCGGCTGCTTAAG<br>TCTGGTGTTTAAACCTTGGGCTCAACCTGGGGTCGCACTGGAA<br>ACTGGGCAGCTTGAGTACAGAAGAGGAAAGTGGAATTCCACGT<br>GTAGCGGTGAAATGCGTAGAGATGTGGAGGAACACCAGTGGCG<br>AAGGCGACTTTCTGGGCTGTAACTGACGCTGAGGCGCGAAAGC<br>GTGGGGAGCAAACAGGATTAGATACCCTGGTAGTCCACGCCGT<br>AAACGATGAGTGCTAGGTGTTAGGGGTTTCGATACCCTTGGTG<br>CCGAAGTTAACACAGTAAGCACTCCGCCTGGGGAGTACGGTCG<br>CAAGACTGAAACTCAAAGGAATTGACGGGGACCCGCACAAGCA<br>GTGGAGTATGTGGTTTAATTCGAAGCAACGCGAAGAACCTTAC<br>CAGGTCTTGACATCCAACTAACGAAGCAGAGATGCATCAGGTG<br>CCCTTCGGGGAAAGTTGAGACAGGTGGTGCATGGTTGTCGTCA<br>GCTCGTGTCGTGAGATGTTGGGTTAAGTCCCGCAACGAGCGCA<br>ACCCTTGACTTTAGTTGCCAGCAGGTGAAGCTGGGCACTCTAG<br>AGTGACTGCCGGTGACAAACCGGAGGAAGGTGGGGATGACGTC<br>AAATCATCATGCCCCTTATGACCTGGGCTACACACGTACTACA<br>ATGGCCGGTACAACGGGAAGCGAAGCCGCGAGGTGGAGCCAAT<br>CCCAGCAAAGCCGGTCTCAGTTCGGATTGCAGGCTGCAACTCG<br>CCTGCATGAAGTCGGAATTGCTAGTAATCGCGGATCAGCATGC<br>CGCGGTGAATACGTTCCCGGGTCTTGTACACACCGCCCGTCAC<br>ACCACGAGAGTTTACAACACCCGAAGTCGGTGGGGTAACCCGC<br>AAGGGGGCCAGCCGCCGAAGGTGGGGTAGATGATTGGGGTGAA<br>GTCGTAACAAGGTAGCCGTATCGGAAGGTGCGGCTGGATCACC<br>TCCTTTCTA |
| 10 | MS2748 | CATTTCTTCGGAGAGTTTGATCCTGGCTCAGGATGAACGCTGG<br>CGGCGTGCCTAATACATGCAAGTCGAGCGAACTGATTAGAAGC<br>TTGCTTCTATGACGTTAGCGGCGGACGGGTGAGTAACACGTGG<br>GCAACCTGCCTGTAAGACTGGGATAACTTCGGGAAACCGAAGC<br>TAATACCGGATAGGATCTTCTCCTTCATGGGAGATGATTGAAA<br>GATGGTTTCGGCTATCACTTACAGATGGGCCCGCGGTGCATTA<br>GCTAGTTGGTGAGGTAACGGCTCACCAAGGCAACGATGCATAG<br>CCGACCTGAGAGGGTGATCGGCCACACTGGGACTGAGACACGG<br>CCCAGACTCCTACGGGAGGCAGCAGTAGGGAATCTTCCGCAAT<br>GGACGAAAGTCTGACGGAGCAACGCCGCGTGAGTGATGAAGGC<br>TTTCGGGTCGTAAAACTCTGTTGTTAGGGAAGAACAAGTACGA<br>GAGTAACTGCTCGTACCTTGACGGTACCTAACCAGAAAGCCAC<br>GGCTAACTACGTGCCAGCAGCCGCGGTAATACGTAGGTGGCAA<br>GCGTTATCCGGAATTATTGGGCGTAAAGCGCGCGCAGGCGGTT<br>TCTTAAGTCTGATGTGAAAGCCCACGGCTCAACCGTGGAGGGT<br>CATTGGAAACTGGGGAACTTGAGTGCAGAAGAGAAAAGCGGAA<br>TTCCACGTGTAGCGGTGAAATGCGTAGAGATGTGGAGGAACAC<br>CAGTGGCGAAGGCGGCTTTTTGGTCTGTAACTGACGCTGAGGC<br>GCGAAAGCGTGGGGAGCAAACAGGATTAGATACCCTGGTAGTC<br>CACGCCGTAAACGATGAGTGCTAAGTGTTAGAGGGTTTCCGCC<br>CTTTAGTGCTGCAGCTAACGCATTAAGCACTCCGCCTGGGGAG<br>TACGGTCGCAAGACTGAAACTCAAAGGAATTGACGGGGGCCCG<br>CACAAGCGGTGGAGCATGTGGTTTAATTCGAAGCAACGCGAAG<br>AACCTTACCAGGTCTTGACATCCTCTGACAACTCTAGAGATAG<br>AGCGTTCCCCTTCGGGGACAGAGTGACAGGTGGTGCATGGTT<br>GTCGTCAGCTCGTGTCGTGAGATGTTGGGTTAAGTCCCGCAAC<br>GAGCGCAACCCTTGATCTTAGTTGCCAGCATTAAGTTGGGCAC<br>TCTAAGGTGACTGCCGGTGACAAACCGGAGGAAGGTGGGGATG<br>ACGTCAAATCATCATGCCCCTTATGACCTGGGCTACACACGTG<br>CTACAATGGATGGTACAAAGGGCTGCAAGACCGCGAGGTCAAG<br>CCAATCCCATAAAACCATTCTCAGTTCGGATTGTAGGCTGCAA |

TABLE 2-continued

Exemplary 16S rRNA Sequences of Bacterial Isolates

| SEQ ID NO. | Bacterial Gene | Sequence |
|---|---|---|
| | | CTCGCCTACATGAAGCTGGAATCGCTAGTAATCGCGGATCAGC<br>ATGCCGCGGTGAATACGTTCCCGGGCCTTGTACACACCGCCCG<br>TCACACCACGAGAGTTTGTAACACCCGAAGTCGGTGGAGTAAC<br>CGTAAGGAGCTAGCCGCCTAAGGTGGGACAGATGATTGGGGTG<br>AAGTCGTAACAAGGTAGCCGTATCGGAAGGTGCGGCTGGATCA<br>CCTCCTTTCTA |

TABLE 3

Exemplary gyrB Gene Sequences of Bacterial Isolates

| SEQ ID NO. | Bacterial Gene | Sequence |
|---|---|---|
| 4 | MS3900 | TTGACGATGGAACAAAAAGAAGTACAAGCATATGAAGCTGATC<br>AGATACAAGTATTAGAAGGATTAGAAGCTGTTCGTAAACGTCC<br>GGGGATGTATATTGGATCGACGAGCGCAAAGGGTCTACATCAT<br>CTTGTATGGGAAATTGTAGATAATAGTATTGATGAAGCGCTGG<br>CCGGCTATTGCGATGAAATTAATGTTATTATCGAAAAGGATAA<br>TAGTATTACAGTCAAAGATAACGGTCGTGGAATTCCGGTTGGT<br>ATTCAAGAAAAAATGGGCAGACCTGCCGTTGAAGTTATCTTAA<br>CGGTTCTTCATGCCGGAGGTAAATTTGGCGGCGGCGGCTATAA<br>AGTATCTGGTGGATTACACGGTGTAGGTGCCTCAGTTGTTAAT<br>GCACTTTCTACCTCTTTGGAAGTGCACGTACATCGTGACGGTA<br>AAGTTCATTATCAAAAATATGAACGAGGTGTACCGGCTGCTGA<br>CTTAAAAGTAGTTGGAGAAACAGATAAAACAGGTACTGTTATT<br>CAATTCCGTCCAGACGGTGAAATTTTTACAGAAACGCTTGAAT<br>ACGATTTTGATACGTTAGCTAATCGTCTGCGTGAGTTAGCTTT<br>CTTAAATCGTGGCATTAAAATTACGATTGAAGACAAACGTGAA<br>GAAGATAAAAGACGTGAGTATCACTATGAAGGCGGAATTAAGT<br>CTTACGTTGAACACTTAAACCGTTCGAAAGAAGTGATTCACGA<br>AGAGCCAATCTATATTGAAGGTAATCGAGACAACATTTCTGTA<br>GAAATTGCTATTCAATATAACGATAGCTATACAAGTAATTTAT<br>ATTCTTTTGCAAACAATATTCACACATATGAAGGTGGAACGCA<br>CGAAGCAGGATTTAAAACAGCGTTAACGCGTGTAATTAACGAC<br>TATGCACGTAAAAACAGCGTATTTAAAGACAGTGACGCCAATC<br>TAACAGGTGAAGATGTTCGTGAAGGAATTACAGCTATCATCTC<br>TATTAAGCACCCAGATCCGCAGTTCGAAGGACAAACAAAAACA<br>AAGCTGGGAAATAGTGAAGCAAGAACAATTACTGACTCTGTGT<br>TTGCAGAACACTTAGAAACTTACTTGCTAGAGAACCCTATTGT<br>GGCGAAAAAGGTAATTGAAAAAGGTTTAATGGCTGCAAGAGCA<br>AGAATGGCAGCTAAAAAAGCTCGTGAGCTTACACGCCGTAAAA<br>GCGCGCTTGAAATTTCAAACTTACCGGGTAAATTAGCAGATTG<br>TTCATCAAAAGATCCTTCTATTAGCGAACTCTATGTAGTAGAG<br>GGTGACTCTGCCGGAGGTTCAGCTAAGCAGGGAAGAAGCCGTC<br>ATTTCCAAGCTATTTTGCCTTTACGTGGTAAAATTATCAACGT<br>AGAGAAAGCGCGTTTAGATAAAATTTTATCTAATAACGAAATT<br>CGTACAATCATTACCGCTCTAGGAACGGGTATTGGTGACGATT<br>TTGATATTTCGAAAGCCCGCTACCATAAAATTGTGATTATGAC<br>AGATGCAGACGTAGACGGTGCGCATATTCGTACGCTTCTTCTA<br>ACGTTCTTCTATCGCTATATGAGACAGATTATTGAGCACGAT<br>ATGTGTACATTGCTCAGCCGCCTCTTTACAAAGTTTCACAAGG<br>TAAAAAAGTGGAGTACGCGTACAACGATCGTCAATTAGAAGAG<br>GTATTAGCTTCTTTCCCTGAAGGCGCAAAACCAAACCTTCAGC<br>GTTACAAAGGTTTAGGAGAGATGAATCCTGAACAATTATGGGA<br>AACAACAATGGATCCAGAGTTCCGTACCCTTCTTCAGGTGAAC<br>TTGCAAGATGCAATTGAAGCTGATGAGACATTTGAAATTTTAA<br>TGGGCGACAAAGTAGAACCACGCCGTAATTTCATTGAAGAAAA<br>TGCTCAGTACGTAAAAAATCTTGATATTTAA |
| 5 | MS3907 | ATGTCAATGAATCAACCGACATATGATGAGAGCCAGATTCAGG<br>TACTGGAAGGGCTGGAAGCGGTTCGGAAACGTCCCGGCATGTA<br>CATTGGCTCCACTAGCGCCAAAGGTCTGCATCATTTGGTCTGG<br>GAGGTCGTCGATAATAGTATCGATGAGGCGCTGGCAGGTTTTT<br>GCGACCGGATTCAAGTGATGATTCATGAAGATAACAGCGTGAC<br>TGTTATCGATAACGGACGGGGTATTCCTGTCGGAGAGAACGAG<br>AAGCTGAAGAAATCCACGCTTGAAGTTGTAATGACTGTCCTGC<br>ATGCAGGCGGTAAATTCGGCGGCGGGGGATATAAGGTTTCCGG<br>CGGTCTGCACGGTGTGGGGATCTCTGTTGTGAATGCATTGTCC<br>GAGAAGGTAGTTGTAAAGGTTAAACGTGACGGACACGTCTACC<br>AGCAGGAATACAGACGGGGTGCGCCGCAGTATGATATCAGGGT<br>AATCGGGGATACCGATGAGACTGGAACCACCACCACCTTCCAT |

TABLE 3-continued

Exemplary gyrB Gene Sequences of Bacterial Isolates

| SEQ ID NO. | Bacterial Gene | Sequence |
|---|---|---|
| | | CCGGATCCTGAGATTTTTACCGAAACGACTATTTTTGAATATT<br>CAACTCTGCTTACCCGTATCCGCGAGCTCGCCTTCTTGAATAA<br>GGGTATCGAGCTGTCCCTGCTGGATGAACGGACCGGAGTCTCC<br>AATACATTTAAGTATGATGGCGGTATTGTGGAGTATGTGAAGT<br>ACCTTAACGAGAAAAAGAAGCCCTGCACGAGGACCCGATCTA<br>CGTGGAAGGCTCACGGGATATGATCGCGGTTGAAGTGGCTCTC<br>CAATATAACGATTCATACTCAGAGAACATCTATTCCTTTGCCA<br>ACAATATCAACACTCATGAAGGCGGTACGCATGAATCCGGCTT<br>CAAGAGCGCCTTGACACGTATTATCAATGATTATGCCCGTAAG<br>GCTGGCGTTATCAAGGACAGCAGCCAGAATCTGACCGGAGATG<br>ATGTACGTGAAGGCTTGACGGCGATTATTTCCGTCAAAATTCC<br>CGAACCGCAGTTCGAAGGCCAGACCAAGACCAAGCTTGGGAAC<br>AGCGAAGTCCGCGGGATTGTGGAGTCCCTGTTCGGTGAGAAGC<br>TGCAGGAATTCCTGGAAGAGAACCCTGCTGTGTCCCGCCGCGT<br>GCTGGAGAAGTCGCTGCAGGCTTCACGTGCACGTGAAGCCGCG<br>CGCAAAGCCCGTGAACTGACCCGCCGCAAGAGTGCGCTTGAAG<br>TCAGTGCCCTGCCGGGTAAGCTGGCCGACTGCTCCTCCAAGGA<br>TGCATCGATCAGTGAACTATACATTGTCGAAGGTGACTCTGCG<br>GGTGGATCGGCCAAGCAAGGCCGGGACCGTCATTTCCAGGCCA<br>TCCTGCCGCTGCGCGGTAAGATCCTCAATGTAGAGAAGGCTCG<br>GCTTGACCGGATCTTGTCCAATGCGGAAATACGGGCCATTATC<br>ACAGCGCTCGGAACCGGGATCAGCGATGATTTCGACCTCTCTA<br>AGGCACGTTACCACAAGGTTGTCATCATGACCGATGCGGATGT<br>TGACGGTGCCCACATCAGAACACTGCTGCTGACTTTCTTTTAC<br>CGCTACATGCGGAAGATTGTCGATGCCGGGTATATCTTCATCG<br>CCCAGCCGCCGCTGTTCAAGATTGAACGCAATAAGGTTATCCG<br>CTATGCGCAGACCGAGAAGGAACGCGATGAGATTATCGCCTCC<br>TTCGGTGAGAACGTGAAGGTTAACGTTCAGCGCTACAAAGGTT<br>TGGGTGAGATGAATGCTGCCCAGCTCTGGGATACAACGATGGA<br>TCCTGAGAGCCGCACTATGCTGCAGGTAACGATTGAGGATGCT<br>ATGCTCGCTGACAGTATCTTTGATACACTTATGGGCGATAACG<br>TCCAGCCAAGATATGAATTTATCCAGGAGCACGCCCATTCCGT<br>CAAAAATCTCGATATTTAG |
| 6 | MS4921 | ATGTCAATGAATCAACCGACATATGATGAGAGCCAGATTCAGG<br>TACTGGAAGGGCTGGAGGCAGTTCGGAAACGTCCCGGCATGTA<br>CATCGGTTCTACCAGCGCCAAAGGTCTGCATCATTTGGTCTGG<br>GAGGTTGTCGATAACAGTATCGATGAGGCGCTGGCAGGCTATT<br>GCGACCGGATTCAAGTGAAGATTCATGAGGATAACAGTGTTAC<br>AGTAATAGATAATGGACGGGGTATCCCTGTCGGTGAGAATGTG<br>AAGCTGAAGAAGTCGACGCTCGAAGTCGTCATGACGGTCCTGC<br>ATGCAGGGGGAAAATTCGGCGGCGGCGGATATAAAGTATCAGG<br>CGGTTTGCACGGTGTAGGGATCTCCGTCGTAAATGCCTTGTCC<br>GAGAAGGTTGTTGTGAACGTCAAGCGTGACGGCCACATCTACC<br>AGCAGGAATATAGACGCGGTGCGCCGCAGTATGATATCAAGAT<br>CGTTGGGGATACCGATGAGACAGGGACAACCACAACCTTTCTT<br>CCGGATCCGGAGATTTTCACCGAAACGACAGTGTTTGAATATA<br>CGACATTGCTTACACGCATTCGCGAATTAGCCTTTCTTAACAA<br>GGGTATTGAGCTTTCGCTGCTGGATGAACGCACCGGTGTGTCG<br>AATGTTTTCAAATACGAGGGCGGTATCGTTGAGTATGTAAAAT<br>ATCTGAACGAGAAAAAGAAGGCTGCACGAAGAACCAATCTA<br>CGTAGAAGGCTCCCGTGATATGATTGCGGTGGAAGTGGCTCTG<br>CAGTATAACGATTCCTATACAGAGAACATTTACTCTTTTGCCA<br>ATAATATTAATACCCATGAGGGCGGGACCCATGAATCCGGCTT<br>CAAAAGCGCATTAACGCGGATCATCAATGACTATGCACGTAAA<br>ACAGGAGTTATTAAGGACAGCAGCTCCAACCTTACCGGTGATG<br>ATGTGCGTGAAGGGCTGACGGCGATTATTTCCGTTAAGATTCC<br>TGAGCCGCAATTTGAAGGCCAAACCAAGACCAAGCTGGGCAAC<br>AGTGAAGTCCGCGGTGTTGTAGAATCTTTATTCGGAGAGAAGC<br>TGCAGGAGTTCCTGGAAGAGAATCCGGCGGTGTCCCGGCGTGT<br>GCTGGAGAAATCCATGCAGGCTTCCCGTGCCCGTGAAGCGGCC<br>CGCAAGGCCCGTGAACTGACCCGCCGCAAAAGTGCACTTGAAG<br>TAAGCGCCCTGCCGGGGAAGCTGGCTGACTGCTCCTCCAAGGA<br>TGCCTCCATCAGCGAGCTGTACATCGTCGAAGGGGACTCCGCA<br>GGCGGTTCTGCCAAGCAGGGCCGTGACCGTCATTTCCAGGCAA<br>TTCTGCCGCTGCGCGGCAAGATACTGAACGTTGAAAAAGCGCG<br>GCTTGACCGTATATTGTCCAATGCTGAAATCCGGGCGATTATC<br>ACCGCTCTGGGAACCGGTATCAGTGATGATTTCGATCTGTCCA<br>AAGCCCGTTACCATAAGGTTGTTATCATGACCGATGCGGATGT<br>CGACGGTGCCCATATCAGAACACTGCTGCTGACCTTCTTCTAC<br>CGCTACATGCGGAAGATTATCGAAGCGGGCTATATTTACATCG<br>CCCAGCCGCCGCTGTTTAAGATTGAGCGCAATAAGGTCGTCCG<br>CTATGCTCAGACCGAGAAGGAACGTGATGAGATTATTGCCAGC<br>TTCGGCGAGAATGTTAAAGTCAACGTTCAACGGTATAAAGGTC<br>TTGGGGAAATGAATGCGGCACAGCTGTGGGATACGACTATGGA |

TABLE 3-continued

Exemplary gyrB Gene Sequences of Bacterial Isolates

| SEQ ID NO. | Bacterial Gene | Sequence |
|---|---|---|
| | | CCCTGAGAGCCGTATGATGCTGCAGGTCACCATCGAGGATGCG<br>ATTCTCGCTGACGGAATCTTTGATACGCTGATGGGCGACAATG<br>TCCAGCCACGATATGAATTCATTCAGGAGAATGCGAAGTACGT<br>TCGGAACCTGGATTTCTAA |
| 11 | MS2748 | TTAAATATCAAGATTTTTTACGTACTGAGCATTTTCTTCAATG<br>AAATTACGGCGTGGTTCTACTTTGTCGCCCATTAAAATTTCAA<br>ATGTCTCATCAGCTTCAATTGCATCTTGCAAGTTCACCTGAAG<br>AAGGGTACGGAACTCTGGATCCATTGTTGTTTCCCATAATTGT<br>TCAGGATTCATCTCTCCTAAACCTTTGTAACGCTGAAGGTTTG<br>GTTTTGCGCCTTCAGGGAAAGAAGCTAATACCTCTTCTAATTG<br>ACGATCGTTGTACGCGTACTCCACTTTTTTACCTTGTGAAACT<br>TTGTAAAGAGGCGGCTGAGCAATGTACACATATCCGTGCTCAA<br>TAATCTGTCTCATATAGCGATAGAAGAACGTTAGAAGAAGCGT<br>ACGAATATGCGCACCGTCTACGTCTGCATCTGTCATAATCACA<br>ATTTTATGGTAGCGGGCTTTCGAAATATCAAATCGTCACAATC<br>CGTCCGTTCCTAGAGCGGTATGATTGTACGAATTTCGTTATTA<br>GATAAAATTTATCTAAACGCGCTTTCTCTACGTTGATAATTTT<br>ACCACGTAAAGGCAAAATAGCTTGGAAATGACGGCTTCTTCCC<br>TGCTTAGCTGAACCTCCGGCAGAGTCACCCTCTACTACATAGA<br>GTTCGCTAATAGAAGGATCTTTTGATGAACAATCTGCTAATTT<br>ACCCGGTAAGTTTGAAATTTCAAGCGCGCTTTTACGGCGTGTA<br>AGCTCACGAGCTTTTTTAGCTGCCATTCTTGCTCTTGCAGCCA<br>TTAAACCTTTTTCAATTACCTTTTTCGCCACAATAGGGTTCTC<br>TAGCAAGTAAGTTTCTAAGTGTTCTGCAAACACAGAGTCAGTA<br>ATTGTTCTTGCTTCACTATTTCCCAGCTTTGTTTTTGTTTGTC<br>CTTCGAACTGCGGATCTGGGTGCTTAATAGAGATGATAGCTGT<br>AATTCCTTCACGAACATCTTCACCTGTTAGATTGGCGTCACTG<br>TCTTTAAATACGCTGTTTTTACGTGCATAGTCGTTAATTACAC<br>GCGTTAACGCTGTTTTAAATCCTGCTTCGTGCGTTCCACCTTC<br>ATATGTGTGAATATTGTTTGCAAAAGAATATAAATTACTTGTA<br>TAGCTATCGTTATATTGAATAGCAATTTCTACAGAAATGTTGT<br>CTCGATTACCTTCAATATAGATTGGCTCTTCGTGAATCACTTC<br>TTTCGAACGGTTTAAGTGTTCAACGTAAGACTTAATTCCACCT<br>TCATAGTGATACTCACGTCTTTTATCTTCTTCACGTTTGTCTT<br>CAATCGTAATTTTAATGCCGCGATTTAAGAAAGCTAACTCACG<br>CAGACGATTAGCTAACGTATCAAAATCGTATTCAAGCGTTTCT<br>GTAAAAATTTCACCGTCTGGACGGAATTGAATAACAGTACCTG<br>TTTATCTGTTTCTCCAACTACTTTTAAGTCAGCAGCCGGTACA<br>CCTCGTTCATATTTTTGATAATGAACTTTACCGTCACGATGTA<br>CGTGCACTTCCAAAGAGGTAGAAAGTGCATTAACAACTGAGGC<br>ACCTACACCGTGTAATCCACCAGATACTTTTATAGCCGCCGCCA<br>CCAAATTTACCTCCGGCATGAAGAACCGTTAAGATAACTTCAA<br>CGGCAGGTCTGCCATTTTTTCTTGAATACCAACCGGAATTCCA<br>CGACCGTTATCTTTGACTGTAATACTATTATCCTTTTCGATAA<br>TAACATTAATTTCATCGCAATAGCCGGCCAGCGCTTCATCAAT<br>ACTATTATCTACAATTTCCCATACAAGATGATGTAGACCCTTT<br>GCGCTCGTCGATCCAATATACATCCCCGGACGTTTACGAACAG<br>CTTCTAATCCTTCTAATACTTGTATCTGATCAGCTTCATATGC<br>TTGTACTTCTTTTTGTTCCATCGTCAA |

TABLE 4

Exemplary rpoB Gene Sequences of Bacterial Isolates

| SEQ ID NO. | Bacterial Gene | Sequence |
|---|---|---|
| 7 | MS3900 | TTGACAGGTCAACTAGTTCAGTATGGACGCCACCGCCAACGCA<br>GAAGTTATGCTCGTATTAGTGAAGTTTTAGAGTTACCGAACTT<br>AATCGAGATTCAAACGGCTTCATACCAATGGTTTTTAGATGAA<br>GGTTTACGAGAAATGTTCCAAGATATTTCTCCAATTGATGATT<br>TTACAGGTAACTTATCACTAGAATTTATTGATTACAGCTTAGG<br>TGAGCCAAAGTATTCAGTAGGAGAGTCTAAAGAACGTGATGTA<br>ACTTATGCAGCACCTCTTCGTGTTAAGGTGCGGTTAATTAATA<br>AAGAAACAGGTGAAGTAAAAGACCAAGATGTGTTCATGGGAGA<br>TTTCCCATTGATGACCGAAACAGGTACCTTTGTAATTAACGGT<br>GCTGAGCGTGTTATCGTATCACAGTTGGTTCGTTCACCAAGTG<br>TTTACTATAGTGGAAAGCTTGATAAAACGGTAAAAAGGATA<br>TACAGCAACTGTTATCCCTAACCGTGGTGCATGGCTAGAATAT<br>GAAACTGATCAAAAGATGTAGTATACGTGCGTATTGATCGTA<br>CTCGTAAACTGCCAGTAACAGTGCTGTTACGCGCGCTAGGTTT |

TABLE 4-continued

Exemplary rpoB Gene Sequences of Bacterial Isolates

| SEQ ID NO. | Bacterial Gene | Sequence |
|---|---|---|
| | | CGGTTCTGACCAAGAGATTATCGATTTAATCGGTGATAATGAA<br>TACATCCGTAATACGCTTGAAAAAGATAATACGGAAACAACGG<br>AAAAAGCGCTATTAGAAATCTATGAGCGTTTACGTCCGGGTGA<br>ACCACCGACAGTTGAGAATGCGAAGTCTCTATTAGTATCTCGC<br>TTCTTTGATCCAAAACGATATGACTTAGCGAACGTAGGTCGCT<br>ATAAAATTAATAAAAAGCTTCATATCAAACATCGCTTATTTAA<br>TCAAAAGCTAGCTGAAACATTAGTTGATCCTGAAACAGGCGAA<br>ATTATTGCAGAAAAAGGCGCAATGATTGACCGCCGTCTGCTAG<br>ATCGCTTGATTCCGATGCTTGAAGGTGGAGTAAACTTCAAAAC<br>TTATAGTCCGGTTGGTGGAGTAGTAGAAGACGATGTTACATTA<br>CAATCTATTAAGATTTATGCGCCAAATGATCCAGAAGGTGAAA<br>AAATCATCACTGTATCAGGTAACGCATATGTAACAGAAGAAGT<br>TAAAAATATCACACCTGCTGATATTTTAGCATCAATCAGTTAC<br>TTCTTTAACTTGCTTCATCAAGTAGGAGACACAGATGATATCG<br>ACCACTTAGGTAACCGTCGTCTGCGTTCTGTAGGTGAATTGTT<br>ACAAAACCAATTCCGTATCGGTTTATCTCGTATGGAACGTGTT<br>GTTCGTGAAAGAATGTCAATTCAAGACACGAATACAATCACAC<br>CTCAACAATTAATTAATATTCGCCCAGTTATTGCGGCGATTAA<br>AGAGTTCTTTGGAAGTTCTCAATTATCACAGTTCATGGATCAA<br>ACGAATCCATTAGGCGAATTGACGCACAAACGTCGTCTTTCAG<br>CTCTAGGACCTGGTGGTTTAACGCGTGAGCGCGCTGGTTTCGA<br>AGTGCGTGACGTTCACTACTCCCACTATGGCCGTATGTGCCCG<br>ATTGAAACACCAGAGGGTCCGAATATCGGGTTAATCAACTCAC<br>TATCTTCTTATGCAAAAGTAAACAAATTCGGTTTCATCGAAAC<br>ACCTTACCGTCGTATCGATCCTGAAACAGGTAAAGTGACAGAG<br>CGAATTGACTACTTAACAGCTGATGAAGAAGATAACTATGTTG<br>TAGCCCAAGCGAACGCTCGTCTAGGTGATGATGGTTCATTCTT<br>AGATGAAAATGTCGTTGCACGTTTCCGTGGAGAAAACACGGTT<br>ATCCGTCGCGATCGTTTAGACTATATGGATGTATCACCAAAAC<br>AAGTTGTATCTGCCGCTACAGCATGTATCCCATTCTTAGAGAA<br>CGATGACTCTAACCGTGCATTAATGGGTGCGAACATGCAACGT<br>CAAGCAGTACCTTTATTAAATCCTGAAGCACCAATCGTAGGTA<br>CAGGTATGGAATACGTATCTGGTAAAGACTCTGGTGCAGCCGT<br>GATTTGTAAATATCCTGGCGTTGTAGAGCGCGTAGAAGCAAAA<br>CAAATTTTTGTTCGCCGCTATGAAGAAGTAGACGGACAAAAAG<br>TTAAAGGTAACTTAGATCAATACAAATTATTAAAATTTGTTCG<br>TTCTAACCAAGGTACTTGTTACAACCAGCGTCCAATTGTTTCA<br>GTTGGCGACGAAGTAGTAAAAGGTGAGATCTTAGCCGACGGTC<br>CTTCAATGGAAAAAGGTGAGCTTGCTTTAGGACGAAACGTAAT<br>GGTTGGTTTCATGACATGGGATGGTTACAACTATGAGGATGCC<br>ATCATCATGAGTGAACGCCTTGTGAAAGACGATGTATATACGT<br>CTGTTCATATTGAAGAATATGAATCTGAGTCTCGTGATACGAA<br>GCTTGGACCTGAAGAAATTACGCGTGACATTCCAAACGTAGGT<br>GAAGATGCGCTTCGCAACTTAGATGAGCGTGGAATCATCCGCA<br>TTGGTGCAGAAGTAAAAGACGGAGATCTTTTAGTTGGTAAAGT<br>AACGCCAAAAGGTGTAACAGAACTAACAGCTGAAGAACGTCTT<br>CTACACGCTATTTTCGGTGAAAAAGCGCGTGAAGTTCGTGATA<br>CTTCTCTTCGTGTACCGCACGGCGGCGGTGAATCATTCTTGA<br>TGTTAAAGTCTTCAACCGTGAAGATGGGGACGAATTACCACCA<br>GGTGTAAACCAATTAGTCCGTGTATATATTGTTCAGAAGCGTA<br>AAATTTCTGAAGGTGACAAAATGGCCGGTCGTCACGGTAACAA<br>AGGTGTAATTTCACGTATTTTACCTGAAGAAGATATGCCTTAC<br>CTACCAGACGGTACGCCAATTGACATCATGTTAAACCCATTAG<br>GGGTACCATCTCGTATGAACATCGGTCAGGTGCTAGAGCTTCA<br>TTTAGGTATGGCTGCTCGTAAGCTTGGCATTCACGTTGCGTCT<br>CCAGTATTTGATGGTGCGCGTGAGGAAGATGTTTGGGCAACAA<br>TCGAAGAAGCTGGCATGTCTCGTGATGCTAAAACAGTTCTATA<br>TGATGGTCGAACAGGTGAACCATTCGATAACCGTGTATCAGTA<br>GGAATCATGTACATGATCAAACTTGCTCACATGGTAGACGATA<br>AACTTCACGCTCGTTCTACTGGACCATACTCACTTGTTACACA<br>ACAACCACTTGGTGGTAAAGCGCAGTTCGGTGGACAGCGTTTT<br>GGTGAGATGGAGGTATGGGCACTTGAAGCATACGGTGCTGCTT<br>ACACATTACAAGAGATCTTAACAGTGAAATCAGATGACGTAGT<br>AGGTCGTGTGAAAACATACGAAGCAATTGTTAAAGGTGAAAAC<br>ATTCCAGAACCTGGCATACCTGAATCGTTCAAAGTATTAATTA<br>AAGAACTACAAAGTTTAGGTATGGATGTGAAGATGCTTTCTGC<br>TGACGAGCAAGAAATTGATATCATGGACTCAGAAGAGGACCAT<br>GAGCAACCAACAGAATCAATTATTGCAGATAACGAAGAAAGCC<br>TTTCTGAAGGACAAAAAGATCCTGTCACAAAAGAGTAA |
| 8 | MS3907 | TTGCGGGAAATGTTCCAGGACATCTCGCCGATCCAGGATTTCA<br>CAGGTAATTTGGTACTAGAGTTCATTGATTACAGCCTGGGTGA<br>ACCGAAGTATACGGTTGACGACGCTAAAGAGCGGGACGTAACA<br>TATGCGGCTCCTCTGCGTGTGAAGGTGCGTCTCATCAATAAGG<br>AGACCGGTGAGGTCAAAGAGCAGGAAGTGTTCATGGGAGATTT |

TABLE 4-continued

Exemplary rpoB Gene Sequences of Bacterial Isolates

| SEQ ID NO. | Bacterial Gene | Sequence |
|---|---|---|
| | | CCCTCTGATGACGGAGACCGGCACTTTTATTATCAATGGTGCG
GAACGGGTTATTGTCAGCCAGTTGGTTCGCTCTCCAAGCGTCT
ATTTCAGCACGAAAGTGGATAAGAACGGCAAAAAAACCTACAC
CGCCACAGTAATTCCGAATCGCGGAGCTTGGCTGGAGCTGGAG
ACCGACGCTAAGGACATCATGTATGTCCGTATCGACCGGACTC
GTAAGATCCCGGTTACCGTGCTTCTGCGTGCTCTAGGCTTCGG
CAGTGATGCTGAAATTCTGGAACTGCTTGGTAATGATGAATAT
ATTCGCAATACGCTGGATAAAGACAACACGGACTCTACGGAGA
AGGCGCTTATCGAAATTTACGAGCGTCTGCGTCCGGGCGAACC
ACCGACACTTGACAATGCCAAGAGCCTTTTGGTCGCACGTTTC
TTTGATCCGAAACGTTATGATTTGGCCAATGTAGGCCGTTACA
AAATCAACAAAAAGCTGCATATTAAAAATCGTCTGTTCAATCA
GCGTCTGGCACAACCTTTGGTGGATGAGTCTACTGGAGAAATC
CTGGCAGAATCCGGCCAAATGGTTGACCGCCGCCTGCTTGATG
AGCTGATTCCTTATTTTGAGAAGAACGTAGCTGCCAAGAACTA
CCGTGTAACCGGTGGGGTTATGGACAGCGAAGATATTCCGCTT
CAGACGATTGATGTGTTCTCGCCAATTGAAGAAGGCCGGATTA
TCAAACTGATCGCCAATGGCAACATTGACAAGTCGGTCAAGCA
TATTACTCAGGCTGATATTATATCCTCAATCAGCTACTTTATT
AATCTGCTGCACGGTATCGGCAACACTGATGATATCGACCACT
TGGGTAACCGCCGTCTGCGTTCTGTCGGCGAACTGCTGCAGAA
TCAGTTCCGTATCGGTCTGTCCCGCATGGAACGCGTTGTCCGC
GAGAGAATGTCGATTCAGGATGCCAATGCGATCACACCGCAGG
CGCTGATCAACATCCGCCCGGTTATCGCGTCGATTAAAGAGTT
CTTCGGTAGTTCACAGCTGTCCCAGTTCATGGATCAGACGAAC
CCGCTTGCTGAACTTACGCACAAACGCCGTCTATCGGCACTCG
GACCCGGCGGTTTGACCCGTGAACGCGCAGGCTTTGAAGTCCG
CGACGTCCATCACAGTCACTATGGCCGTATGTGTCCAATCGAA
ACACCGGAAGGTCCGAATATCGGTCTGATCAACTCCTTGTCCA
CCTTTGCCCGCATCAATGAATACGGCTTTATCGAAGCACCGTA
TCGTTGGGTGGATCCAAAGACAGGCAAAGTCACTGAGCAAATT
GATTATCTGACTGCCGATGAAGAAGATAACTATGTAGTTGCAC
AGGCAAATGTACTGATCGATGAGAATGGCTCCTTCAAGGAAGA
CCAGGTTATCGTTCGTTATAACAAAGATTCAGACAACATCACT
ACAATGCCAAGTAACCGTGTTGACTACATGGACGTTTCGCCTA
AACAGGTTGTATCAGTAGCTACGGCGCTCATTCCGTTCCTTGA
GAACGATGACTCCAACCGCGCGCTGATGGGATCGAACATGCAG
CGTCAGGCTGTTCCGCTTCTCATTCCGAAGGCTCCGCTTGTAG
GAACAGGGATGGAACATAAATCCGCTAAGGACTCGGGCGTATG
TATTGTCTCCAAATATGACGGTATTATCGAACGCTCCTCTGCC
AATGAAATCTGGCTGCGCCGTGTTGAGGCAGTTGAAGGCAAAG
AAGTTAAAGGCGATATCGTTAAATATAAATTACACAAATTTAT
GCGTTCGAACCAGGGTACCTGCATTAATCAGCGTCCGCTAGCC
AAACGCGGCGACGTTGTTAAGAAAGGTGATATCCTTGCAGACG
GACCATCTACGGAAATGGGCGAACTTGCTCTTGGCCGTAACGT
AGTTGTTGCGTTCATGACTTGGGAAGGCTACAACTACGAGGAT
GCGATCCTGCTGAGTGAGAAGCTGGTTAAGGAAGATGTATACA
CTTCGATCCATATCGAGGAATACGAATCCGAAGCCCGTGACAC
GAAGCTTGGACCTGAAGAAATCACGCGTGATATTCCAAACGTA
GGGGAAGAAGCGCTTCGCAATCTCGATGAGCGCGGAATTATCC
GGATCGGTGCGGAAATCAATGCCGGCGACATTCTGGTAGGTAA
AGTTACTCCGAAGGGCGTAACCGAGCTGACCGCTGAAGAACGT
CTGCTGCACGCTATCTTTGGTGAGAAGGCTCGTGAAGTCCGCG
ATACCTCTTTGCGCGTTCCACATGGTAGTGATGGTATTATCGT
TGACGTTAAGGTGTTCACGCGTGAGAACGGCGATGAGCTGCCT
CCAGGTGTGAATCAGCTGGTTCGTGTCTATATCGCTCAGAAAC
GTAAGATTTCTGAGGGTGACAAGATGGCCGGACGTCACGGTAA
CAAGGGTGTCGTTGCCCGTATCCTGCCTGAAGAAGATATGCCG
TTCCTTCCGGACGGTACACCGGTACAGGTTGTCCTGAACCCGC
TGGGCGTACCTTCCCGTATGAACATCGGACAGGTGCTTGAAGT
CCATCTCGGTATGGCTGCACTGCGTCTGGGTATTCACGTGGCT
ACTCCAGTATTTGACGGAGCCCGTGAGTATGACGTGTTTGATA
CGATGGAAGAAGCCGGTATGCAGCGTAACGGTAAAACTGTGCT
TTATGACGGACGTACAGGCGAACGCTTTGAGCGTGAAGTTACT
GTCGGCGTCATGCACATGATCAAGCTCGCGCACATGGTTGACG
ATAAAATTCATGCCCGTTCTACAGGTCCTTACTCTCTCGTTAC
ACAGCAGCCACTGGGCGGTAAGGCTCAGTTCGGCGGACAGCGT
TTCGGGGAAATGGAAGTGTGGGCGCTTGAAGCTTACGGCGCGG
CATATACACTGCAAGAAATCTTGACCGTGAAGTCCGATGACGT
GGTCGGCCGTGTGAAAACGTACGAGTCCATTGTCAAAGGCGAA
AATGTTCCAGAACCGGGTGTTCCGGAATCCTTCAAGGTATTGA
TCAAGGAACTGCAGTCGCTGGGTATGGATGTTAAGATCCTTAG
CGGTGACGAGCAGGAGATTGAGATGAAGGAACTGGACGATGAG
GACGAGACGTCAGGCGATAAGCTGAGCCTCAATTTGGAAGGCG
CAGAAGTCGGCATAGAGTAG |

TABLE 4-continued

Exemplary rpoB Gene Sequences of Bacterial Isolates

| SEQ ID NO. | Bacterial Gene | Sequence |
| --- | --- | --- |
| 9 | MS4921 | TTGCGTGAAATGTTTCAGGACATCTCGCCAATCCAGGATTTCA
CAGGGAATTTGGTACTTGAGTTCATTGATTACAGCCTAGGCGA
ACCGAAGTATACGGTTGACGACGCTAAAGAGCGGGACGTAACA
TATGCGGCTCCTCTACGTGTGAAGGTGCGGCTCATTAATAAGG
AGACCGGTGAGGTCAAAGAGCAGGAAGTGTTCATGGGAGATTT
CCCGCTGATGACGGAGACCGGCACTTTTATTATCAATGGTGCG
GAACGGGTTATTGTCAGCCAGTTGGTTCGCTCTCCAAGCGTCT
ATTTCAGCACGAAAGTAGATAAGAACGGCAAAAAAACCTACAC
CGCCACAGTAATTCCAAACCGCGGAGCCTGGCTTGAACTGGAG
ACCGACGCTAAGGATATCATGTATGTCCGTATCGACCGGACCC
GTAAAATTCCAGTTACAGTGCTTCTGCGTGCTCTCGGTTTCGG
CAGTGATGCTGAAATTCTGGAACTGCTGGGTAATGATGAATAT
ATTCGCAATACGCTGGATAAAGACAATACGGACTCCACGGAGA
AGGCGCTTATTGAAATTTACGAGCGTCTGCGTCCGGGTGAACC
GCCGACACTGGATAATGCCAAGAGCCTTTTGGTTGCACGTTTC
TTCGATCCAAAGCGTTATGACTTGGCCAATGTAGGCCGTTACA
AAATCAATAAGAAGCTGCACATTAAGAACCGGTTGTTTAACCA
GCGTCTGGCACAGCCTTTGGTTGATGAATCCACTGGGGAAATT
CTGGCGGAATCCGGACAAATGGTTGACCGCAGACTTCTTGATG
AGCTGATTCCTTATTTTGAGAAGGATGTCGCTGCCAAGACCTA
CCGTGTTACCGGCGGAGTGCTGGACAGTGAAGATATCCCGCTG
CAAACGATCGATGTATTCTCGCCGATCGAGGAAGGCCGGGTTA
TCAAGCTGATTGCCAACGGCAATATCGACAAATCCGTTAAGCA
TATTACCCAGGCTGATATTATATCCTCAATCAGCTACTTTATT
AATCTGCTGCACGGTATCGGCAACACAGACGACATTGACCACT
TGGGTAACCGCCGTCTGCGTTCCGTAGGTGAATTGCTGCAGAA
CCAATTCCGCATCGGGCTGTCCCGTATGGAACGCGTAGTCGT
GAGAGAATGTCGATTCAGGATGCGAATGCAATTACTCCGCAGG
CCCTGATCAATATTCGTCCGGTCATCGCGTCCATTAAAGAGTT
CTTCGGCAGCTCCCAGCTGTCGCAGTTTATGGACCAGACGAAC
CCGCTGGCAGAACTTACGCATAAGCGTCGTCTGTCTGCACTCG
GACCCGGCGGTCTGACCCGTGAACGCGCGGGCTTTGAAGTTCG
GGACGTGCATCACAGTCACTACGGCCGGATGTGTCCAATCGAA
ACACCGGAAGGTCCGAATATCGGTCTGATCAACTCCTTGTCCA
CTTTTGCCCGCATCAATGAATACGGCTTTATCGAAGCTCCGTA
CCGTTGGGTGGATCCGAAGACCGGCAAGGTCACAGAGCATATC
GATTATCTGACCGCCGATGAAGAAGACAACTATGTAGTTGCGC
AGGCAAACGTGCAGATTGATGAAGATGGAACCTTTAAGGAAGA
TATGGTTATCGTCCGTTACAACAAGGATTCAGACAACATCACG
ACTATGCCTAGTAACCGTGTTGACTACATGGACGTTTCGCCAA
AACAGGTTGTATCGGTCGCTACGGCGCTCATTCCGTTCCTGGA
GAACGATGACTCCAACCGCGCACTGATGGGATCTAACATGCAG
CGCCAAGCCGTTCCGCTTCTGATTCCGAAGGCTCCGCTTGTCG
GTACAGGAATGGAGCATAAGTCCGCTAAAGACTCCGGCGTATG
TATTGTCTCCAAATATGACGGTATTATTGAACGCTCTTCTGCC
AATGAGATCTGGCTGCGCCGGGTTGAAATGGTTGAAGGCAAAG
AAGTCAAAGGTGATATCGTTAAATATAAATTACACAAATTTAT
GCGTTCGAACCAAGGGACTTGCATAAATCAGCGTCCGCTTGCT
AAAAGAGGCGACATTGTGAAGAAGGGTGACATTCTTGCGGATG
GTCCTTCCACCGAAATGGGCGAGTTGGCTCTGGGCCGCAACGT
AGTTGTTGCCTTTATGACTTGGGAAGGTTACAACTACGAGGAT
GCGATCCTGCTGAGTGAGAAGCTGGTGAAGGAAGATGTATACA
CTTCGATTCATATCGAGGAATACGAATCCGAAGCTCGTGACAC
GAAGCTGGGACCTGAAGAAATTACCCGTGATATTCCAAATGTC
GGTGAAGAAGCACTCCGTAACTTGGACGAACGCGGTATCATCC
GCATTGGTGCGGAAATCAATGCCGGTGACATCCTTGTAGGTAA
GGTAACTCCTAAAGGTGTAACTGAACTGACTGCTGAAGAACGT
CTGCTCCATGCAATCTTCGGGGAAAAAGCGCGTGAAGTTCGCG
ATACCTCCTTGCGTGTTCCGCATGGTAGTGATGGTATTATCGT
TGACGTCAAAGTATTCACACGTGAGAACGGCGATGAGCTGCCT
CCGGGTGTAAATCAGCTGGTTCGTGTCTACATCGCCCAGAAAC
GTAAAATTTCTGAGGGTGACAAAATGGCCGGACGTCACGGTAA
CAAGGGTGTCGTTGCCCGTATTCTTCCTGAGGAAGATATGCCA
TTCCTGCCGGACGGCACACCGGTACAGGTAGTATTGAACCCGC
TGGGCGTTCCTTCCCGTATGAACATCGGACAGGTGCTGGAGGT
CCATCTTGGTATGGCCGCTCTTCGTCTGGGCATTCATGTAGCT
ACTCCGGTATTTGACGGTGCCCGCGAGTATGACGTCTTTGATA
CGATGGAAGAAGCCGGCATGCAGCGCAATGGTAAGACTGTGCT
GTACGACGACGTACAGGCGAACGCTTCGAGCGTGAAGTAACA
GTCGGTGTCATGCACATGATCAAGCTGGCGCACATGGTTGATG
ATAAGATTCATGCCCGTTCCACAGGTCCTTACTCACTCGTTAC
CCAGCAGCCTCTCGGCGGTAAAGCCCAGTTTGGTGGACAACGT
TTCGGGGAAATGGAAGTATGGGCGCTTGAAGCTTACGGCGCTG
CTTATACACTGCAGGAAATCTTGACGGTGAAATCCGATGACGT |

TABLE 4-continued

Exemplary rpoB Gene Sequences of Bacterial Isolates

| SEQ ID NO. | Bacterial Gene | Sequence |
|---|---|---|
| | | GGTTGGCCGTGTGAAGACGTATGAATCCATCGTCAAAGGCGAG<br>AATCTGCCGGAACCTGGCGTGCCTGAAGCGTTCAAAGTATTGA<br>TCAAGGAACTGCAGTCGCTTGGTATGGATGTCAAAATCCTCAG<br>CGGTGATGAGCAGGAGATTGAGATGAAAGAACTGGACGATGAG<br>GACGAGACGACAGGCGACAAGCTGAGCCTTAACTTGGAAGGCG<br>CGGAAGTCGGAATAGAGTAG |
| 12 | MS2748 | TTACTCTTTTGTGACAGGATCTTTTTGTCCTTCAGAAAGACTT<br>TCTTCGTTATCTGCAATAATTGATTCTGTTGGTTGCTCATGGT<br>CCTCTTCTGAGTCCATGATATCAATTTCTTGCTCGTCAGCAGA<br>AAGCATCTTCACATCCATACCTAAACTTTGTAGTTCTTTAATT<br>AATACTTTGAACGATTCAGGTATGCCAGGTTCTGGAATGTTTT<br>CACCTTTAACAATTGCTTCGTATGTTTTCACACGACCTACTAC<br>GTCATCTGATTTCACTGTTAAGATCTCTTGTAATGTGTAAGCA<br>GCACCGTATGCTTCAAGTGCCCATACCTCCATCTCACCAAAAC<br>GCTGTCCACCGAACTGCGCTTTACCACCAAGTGGTTGTTGTGT<br>AACAAGTGAGTATGGTCCAGTAGAACGAGCGTGAAGTTTATCG<br>TCTACCATGTGAGCAAGTTTGATCATGTACATGATTCCTACTG<br>ATACACGGTTATCGAATGGTTCACCTGTTCGACCATCATATAG<br>AACTGTTTTAGCATCACGAGACATGCCAGCTTCTTCGATTGTT<br>GCCCAAACATCTTCCTCACGCGCACCATCAAATACTGGAGACG<br>CAACGTGAATGCCAAGCTTACGAGCAGCCATACCTAAATGAAG<br>CTCTAGCACCTGACCGATGTTCATACGAGATGGTACCCCTAAT<br>GGGTTTAACATGATGTCAATTGGCGTACCGTCTGGTAGGTAAG<br>GCATATCTTCTTCAGGTAAAATACGTGAAATTACACCTTTGTT<br>ACCGTGACGACCGGCCATTTTGTCACCTTCAGAAATTTTACGC<br>TTCTGAACAATATATACACGGACTAATTGGTTTACACCTGGTG<br>GTAATTCGTCGCCATCTTCACGGTTGAAGACTTTAACATCAAG<br>AATGATTCCACCGCCGCCGTGCGGTACACGAAGAGAAGTATCA<br>CGAACTTCACGCGCTTTTTCACCGAAAATAGCGTGTAGAAGAC<br>GTTCTTCAGCTGTTAGTTCTGTTACACCTTTTGGCGTTACTTT<br>ACCAACTAAAAGATCTCCGTCTTTTACTTCTGCACCAATGCGG<br>ATGATTCCACGCTCATCTAAGTTGCGAAGCGCATCTTCACCTA<br>CGTTTGGAATGTCACGCGTAATTTCTTCAGGCCCAAGCTTCGT<br>ATCACGAGACTCAGATTCATATTCTTCAATATGAACAGACGTA<br>TATACATCGTCTTTCACAAGGCGTTCACTCATGATGATGGCAT<br>CCTCATAGTTGTAACCATCCCATGTCATGAAACCAACCATTAC<br>GTTCGTCCTAAAGCAAGCTCACCTTTTTCCATTGAAGGACCG<br>TCGGCTAAGATCTCACCTTTTACTACTTCGTCGCCAACTGAAA<br>CAATTGGACGCTGGTTGTAACAAGTACCTTGGTTAGAACGAAC<br>AAATTTTAATAATTTGTATTGATCTAAGTTACCTTTAACTTTT<br>TGTCCGTCTACTTCTTCATAGCGGCGAACAAAATTTGTTTTGC<br>TTCTACGCGCTCTACAACGCCAGGATATTTACAAATCACGGCT<br>GCACCAGAGTCTTTACCAGATACGTATTCCATACCTGTACCTA<br>CGATTGGTGCTTCAGGATTTAATAAAGGTACTGCTTGACGTTG<br>CATGTTCGCACCCATTAATGCACGGTTAGAGTCATCGTTCTCT<br>AAGAATGGGATACATGCTGTAGCGGCAGATACAACTTGTTTTG<br>GTGATACATCCATATAGTCTAAACGATCGCGACGGATGACCGT<br>GTTTTCTCCACGGAAACGTGCAACGACATTTTCATCTAAGAAT<br>GAACCATCATCACCTAGACGAGCGTTCGCTTGGGCTACAACAT<br>AGTTATCTTCTTCATCAGCTGTTAAGTAGTCAATTCGCTCTGT<br>CACTTTACCTGTTTCAGGATCGATACGACGGTAAGGTGTTTCG<br>ATGAAACCGAATTTGTTTACTTTTGCATAAGAAGATAGTGAGT<br>TGATTAACCCGATATTCGGACCCTCTGGTGTTTCAATCGGACA<br>CATACGGCCATAGTGGGAGTAGTGAACGTCACGCACTTCGAAA<br>CCAGCGCGCTCACGCGTTACCACCAGGTCCTAGAGCTGAAGAC<br>GACGTTTGTGCGTCAATCGCTAATGGATTCGTTTGATCCATGA<br>ACTGTGATAATTGAGAACTTCCAAAGAACTCTTTAATCGCCGC<br>AATAACTGGGCGAATATTAATTAATTGTTGAGGTGTGATTGTA<br>TTCGTGTCTTGAATTGACATTCTTTCACGAACAACACGTTCCA<br>TACGGGATAAACCGATACGGAATTGGTTTTGTAACAATTCACT<br>ACAGAACGCAGACGACGGTTACCTAAGTGGTCGATATCATCTG<br>TGTCTCCTACTTGATGAAGCAAGTTAAAGAAGTAACTGATTGA<br>TGCTAAAATATCAGCAGGTGAGATATTTTTAACTTCTTCTGTT<br>ACATATGCGTTACCTGATACAGTGATGATTTTTCACCTTCTGG<br>ATCATTTGGCGCATAAATCTTAATAGATTGTAATGTAACATCG<br>TCTTCTACTACTCCACCAACCGGACTATAAGTTTGAAGTTTAC<br>TCCACCTCAAGCATCGGAATCAAGCGATCTAGCAGACGGCGGT<br>CAATCATTGCGCCTTTTTCTGCAATAATTTCACCTGTTTCAGG<br>ATCAACTAATGTTTCAGCTAGCTTTTGATTAAATAAGCGATGT<br>TTGATATGAAGCTTTTTTATTAATTTTATAGCGACCTACGTTC<br>GCTAAGTCATATCGTTTTGGATCAAAGAAGCGAGATACTAATA<br>GAGACTTCGCATTCTCAACTGTCGGTGGTTCACCCGGACGTAA<br>ACGTCATAGATTTCTAAATAGCGCTTTTTCCGTTGTTTCCGTA<br>TTATCTTTTTCAAGCGTATTACGGATGTATTCATTATCACCGA |

TABLE 4-continued

Exemplary rpoB Gene Sequences of Bacterial Isolates

| SEQ ID NO. | Bacterial Gene | Sequence |
|---|---|---|
| | | TTAAATCGATAATCTCTTGGTCAGAACCGAAACCTAGCGCGCG<br>TAACAGCACTGTTACTGGCAGTTACGAGTACGATCAATACGCA<br>CGTATACTACATCTTTTGCATCAGTTTCATATTCTAGCCATGC<br>ACCACGGTTAGGGATAACAGTTGCTGTATATCCTTTTTTACCG<br>TTTTTATCAAGCTTTCCACTATAGTAAACACTTGGTGAACGAA<br>CCAACTGTGATACGATAACACGCTCAGCACCGTTAATTACAAA<br>GGTACCTGTTTCGGTCATCAATGGGAAATCTCCCATGAACACA<br>TCTTGGTCTTTTACTTCACCTGTTTCTTTATTAATTAACCGCA<br>CCTTAACACGAAGAGGTGCTGCATAAGTTACATCACGTTCTTT<br>AGACTCTCCTACTGAATACTTTGGCTCACCTAAGCTGTAATCA<br>ATAAATTCTAGTGATAAGTTACCTGTAAAATCATCAATTGGAG<br>AAATATCTTGGAACATTTCTCGTAAACCTTCATCTAAAAACCA<br>TTGGTATGAAGCCGTTTGAATCTCGATTAAGTTCGGTAACTCT<br>AAAACTTCACTAATACGAGCATAACTTCTGCGTTGGCGGTGGC<br>GTCCATACTGAACTAGTTGACCTGTCAA |

20

TABLE 43

Exemplary nifH Gene Sequences of Bacterial Isolates

| SEQ ID NO. | Bacterial Gene | Sequence |
|---|---|---|
| 13 | MS3907 | ATGAGACAAATAGCTTTCTACGGTAAAGGCGGTATCGGCAAAT<br>CGACAACTTCACAAAACACCCTGGCTCAGCTGGCGACAAAGTT<br>CGGACAAAGAATAATGATCGTAGGCTGTGACCCTAAAGCAGAC<br>TCCACCCGCCTTATCCTGAATACAAAAGCCCAGAACTCTGTGC<br>TTGAACTGGCGGCTGAGCTTGGCTCGGTAGAGGATCTTGAACT<br>TGAAGATGTATTGCAGACAGGTTTCGGCGACATTATCAACGTA<br>GAATGCGGCGGACCTGAACCGGGTGTAGGCTGCGCGGGACGCG<br>GGATCATCACTGCCATCAACTTCCTGGAGCAGGAAGGCGCCTA<br>TCAGGATCTGGATTTCGTATCCTATGACGTTCTTGGTGACGTT<br>GTATGCGGCGGTTTCGCAATGCCAATCCGCGAAGGCAAGGCGC<br>AAGAGATCTATATCGTCTGTTCCGGTGAAATGATGGCAATGTA<br>CGCAGCGAACAATATCGCCCGCGGGATCCTGAAATATGCGACC<br>AGCGGCGGCGTGAGACTGGGCGGCCTGATCTGCAACAGCCGTA<br>ACACAGACCGTGAAGATGAGCTGATCATGGAACTCGCCAGACG<br>TCTGAACACGCAGATGATCCACTTTGTACCGCGTGACAATATC<br>GTTCAGCATGCCGAGCTGCGCAGAATGACTGTTGCCCAGTATA<br>ATCCGACCCATTCACAAGCGAAAGAATATGAAAAGCTGGCTGA<br>GAAAATCCTCAATAACAAAATGCTGACGATCCCTACTCCGATT<br>TCTATGGAAGAGCTGGAAGAGCTGCTGATGGAATTCGGCATCA<br>TCGAAGACGAAGAGGCTGCAATCAAGAAGCTGCAGGCTTCCGG<br>TCAATAA |
| 14 | MS4921 | ATGATGAGACAAATAGCTTTCTACGGTAAAGGCGGTATCGGTA<br>AATCCACAACCTCCCAAAACACTTTGGCCCAGCTCGCAACCAA<br>ATTCAAACAAAGAATTATGATCGTAGGCTGTGACCCGAAGGCA<br>GACTCCACCCGCCTGATTCTGAATACCAAGGCACAGAACTCGG<br>TCCTGGAGCTGGCAGCCGAACTGGGCTCAGTAGAGGATTTGGA<br>ACTGGAGGATGTGCTGCAGACCGGCTTTGGCGACATTATCAAC<br>GTAGAGTGCGGCGGACCTGAACCGGGTGTAGGCTGTGCAGGGC<br>GCGGTATCATTACTGCCATCAACTTCCTGGAGCAGGAAGGCGC<br>CTATCAGGATCTGGACTTCGTATCCTATGACGTATTGGGCGAC<br>GTTGTATGCGGCGGTTTCGCCATGCCGATCCGTGAAGGCAAAG<br>CCCAAGAGATCTATATTGTATGTTCCGGTGAAATGATGGCGAT<br>GTACGCGGCCAACAACATTGCACGCGGTATCCTGAAATATGCT<br>ACCAGCGGCGGCGTGAGACTGGGCGGACTGATCTGCAACAGCC<br>GCAACACCGACCGTGAAGACGAGCTGATCATGGAGCTGGCCCG<br>CCGTCTGAACACGCAAATGATCCACTTCGTTCCCCGTGACAAT<br>ATCGTTCAGCATGCCGAGCTGCGCAGAATGACGGTGGCCCAAT<br>ATAACCCTGCCCATCAACAAGCCAAAGAATATGAAATTCTGGC<br>TGAAAAAATCCTCAACAACAAAATGCTGACCATCCCTACCCCG<br>ATTTCAATGGAAGAACTGGAAGAGCTGCTGATGGAATTCGGCA<br>TCATTGAAGATGAAGAAGCTGCACTCAAGAAGCTGCAGGCTTC<br>CGGCCAATAA |

Example 2: Plant Growth Promoting Bacterial Isolates

Bacterial strain MS3907 was isolated. Genomic sequence analysis indicates that MS3907 is a strain of the species *Paenibacillus borealis*. MS3907 is an endophyte of wheat and genomic analysis suggests that it is specially evolved to live in the rhizosphere of plants. MS3907 is a nitrogen fixing bacterial strain. MS3907 was found to be a spore former, capable of colonizing corn roots and other tissues, capable of promoting plant growth in low nitrogen conditions, an endophyte, and without genes associated with human pathogenesis or associated with antibiotics used currently in medicine.

Figure 70:
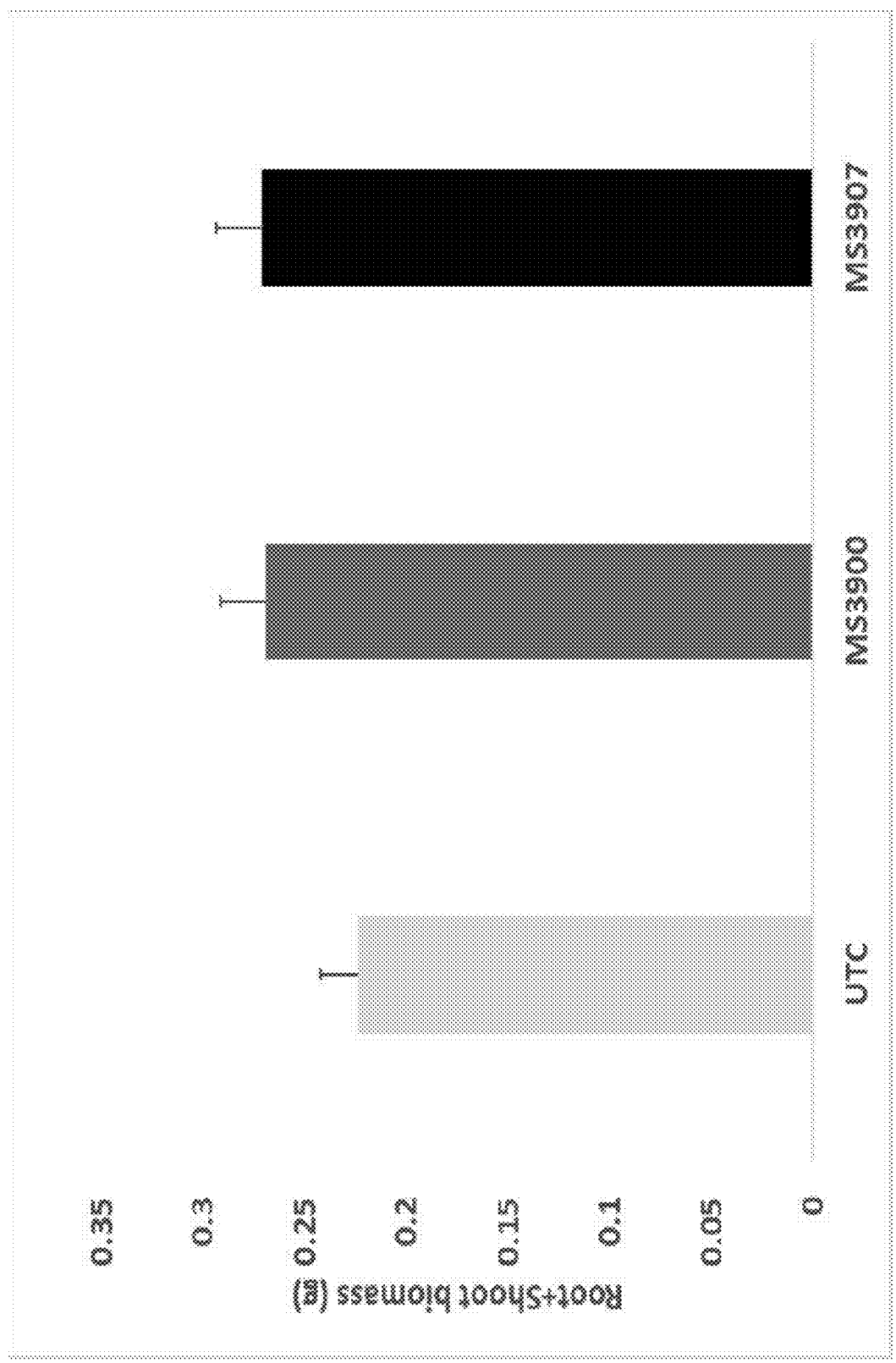
FIG. 70 shows application of MS3900 and MS3907 resulted in greater root and shoot biomass compared to that from UTC.

Bacterial strain MS3900 was isolated. Genomic sequence analysis indicates that MS3900 is a strain of the species *Bacillus megaterium*. MS3900 is an endophyte of wheat. MS3900 is a phosphate solubilizing bacterial strain. MS3900 was found to be a spore former, capable of colonizing corn roots, capable of promoting plant growth in low nitrogen conditions, an endophyte, and without genes associated with human pathogenesis or associated with antibiotics used currently in medicine. MS3900 improves the root colonization and NUE performance of N-fixing isolates. It also improves plant nitrogen use efficiency. Tall Fescue seed, planted at a density of 25 seed per 3.5" diameter pots containing a potting mix of 9:1 Isolite:Sunshine mix, was treated with a 10 ml drench application of MS3900 or MS3907 (both at approximately $10^6$ cfu/ml) or with a 10 ml drench of water (untreated control). There were 10 pot replicates per treatment. Each pot, after the plants were thinned to ensure all pots had the same seedling count (approximately 20 plants/pot), were fertilized with a 100 mls Hoagland solutions prepared without any nitrogen (without-N) but also supplemented with 2 g KH2PO4/L. further fertilization was done weekly with Hoagland's without N at 100 ml/pot. Plants were harvested at 5 weeks, and total dry weight was obtained. MS3900 and MS3907 had significantly higher biomass than the untreated control (FIG. 70).

Bacterial strain MS4921 was isolated. Genomic sequence analysis indicates that MS4921 is a strain of the species *Paenibacillus sonchi*. MS4921 is a nitrogen fixing strain. MS4921 was found to be a spore former, capable of colonizing corn roots and other tissues, capable of promoting plant growth in low nitrogen conditions, an endophyte, and without genes associated with human pathogenesis or associated with antibiotics used currently in medicine.

Figure 71:
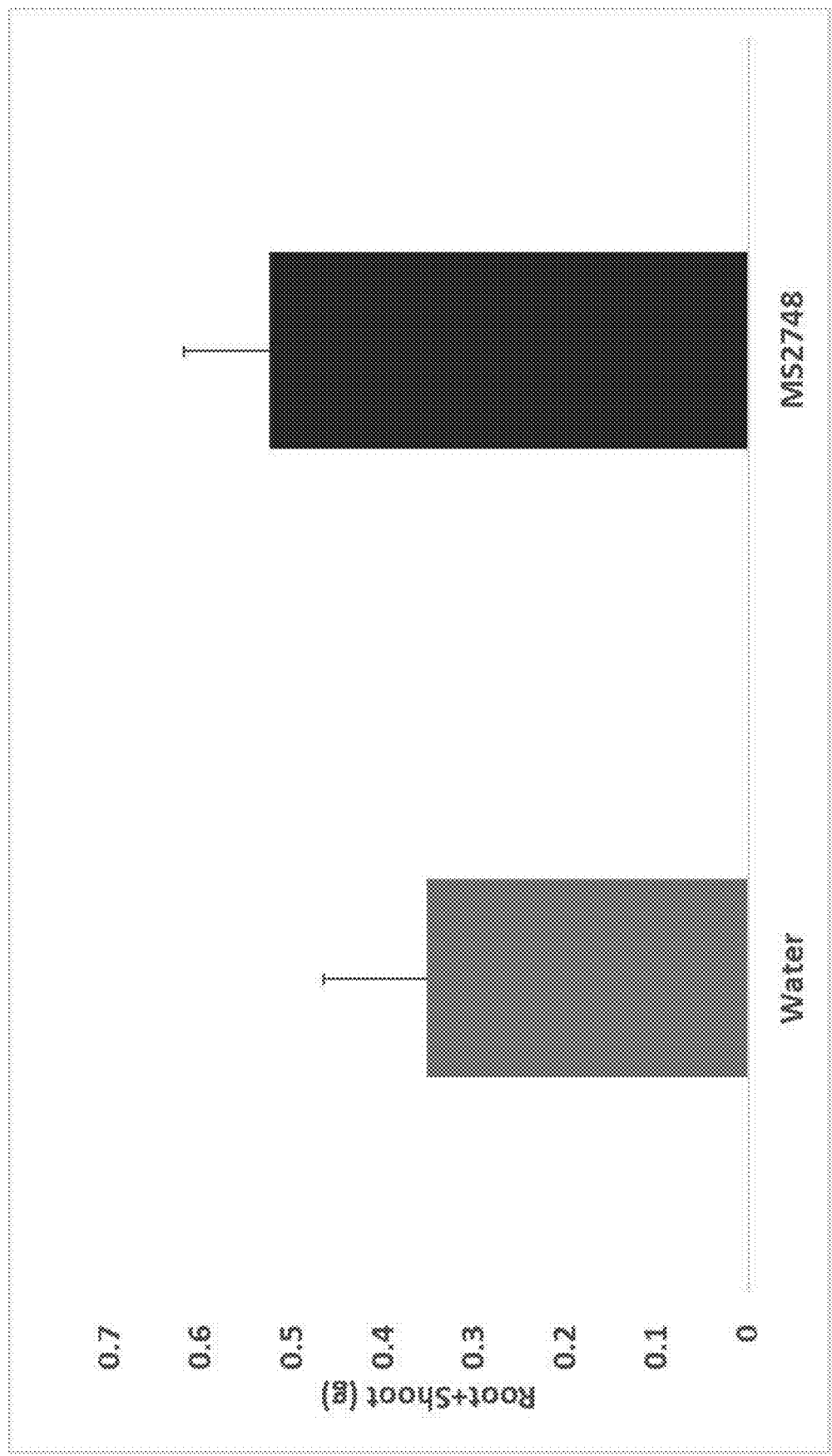
FIG. 71 shows application of MS2748 resulted in greater root and shoot biomass compared to that from UTC.

Bacterial strain MS2748 was isolated from corn roots using N-free nutrient media. DNA sequencing of the 16S rRNA gene indicates that MS2748 is a strain of the species *Bacillus megaterium*. MS2748 is a spore former with siderophore production, IAA production, and P solubilization capabilities. MS2748 was tested on ryegrass grown in Isolite-Sunshine potting mix (9:1 v/v) at a density of 25 plants per pot (10 replicates). 10 ml isolate suspension was applied on each pot at a CFU concentration of $10^7$/ml. The pots were fertilized with Hoagland's solution without Nitrogen (100 ml/week) that was supplemented with KH2PO4 at 2 g/L. Tests of the effect of MS2748 on growth of ryegrass in media with no nitrogen added showed an improvement in plant survival and biomass production. This indicates that MS2748 improved nitrogen use efficiency. This indicates that MS2748 can improve nitrogen use efficiency (FIG. 71).

The nitrogen fixing strains MS3907 and MS4921 were found to fix nitrogen in inoculated plants and to demonstrate improved nitrogen use efficiency in greenhouse and outdoor pot studies.

Figures 1A, 1B:
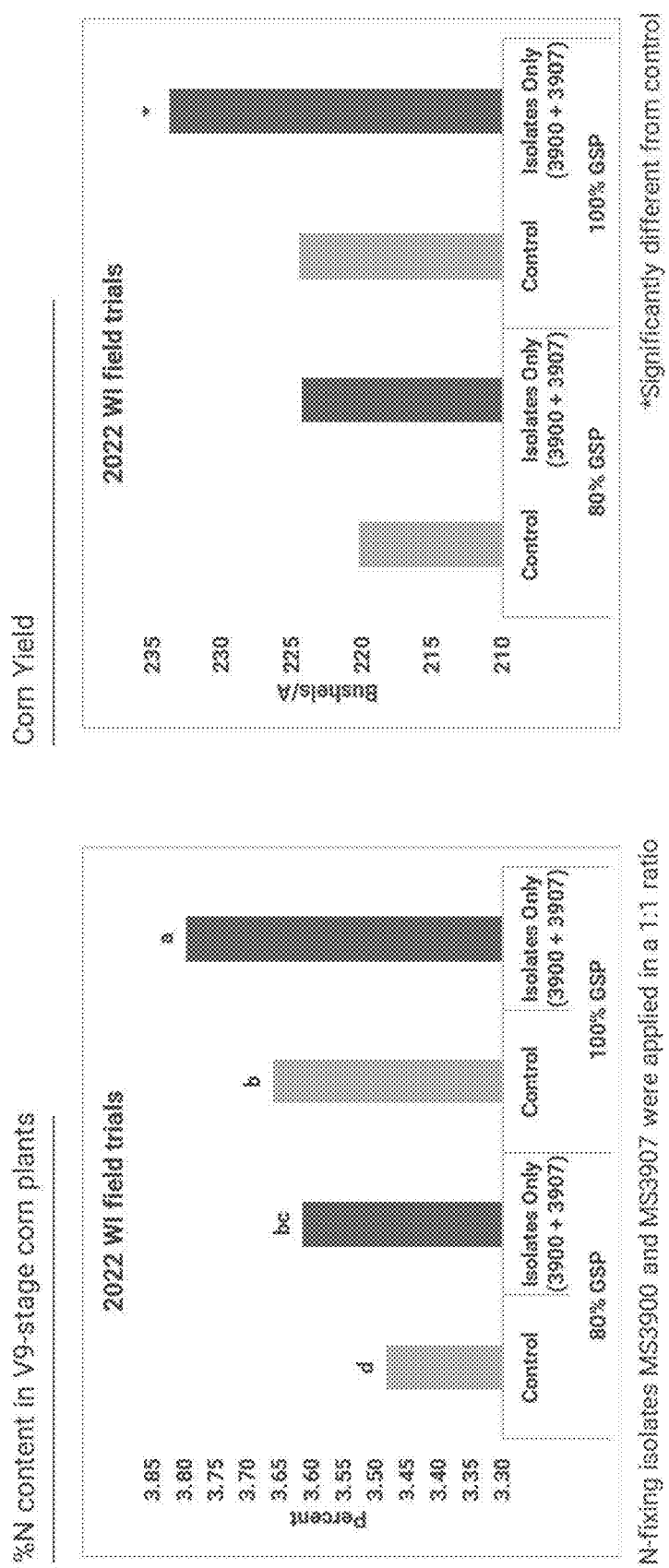
FIGS. 1A-1B are a series of graphs showing corn nitrogen content and yield between control and a combination of MS3900 and MS3907 isolates.

A field study testing the effect of isolates MS3900 and MS3907 on corn growth in a field study are shown in FIGS. 1A and 1B.

Example 3: Digestion System Using Plant Growth Promoting Isolates

A. NTS-1.1, NTS-1.2, NTS-1.3, NTS-1.4, NTS-2.2, and NTS-2.3 Systems

Figure 6:
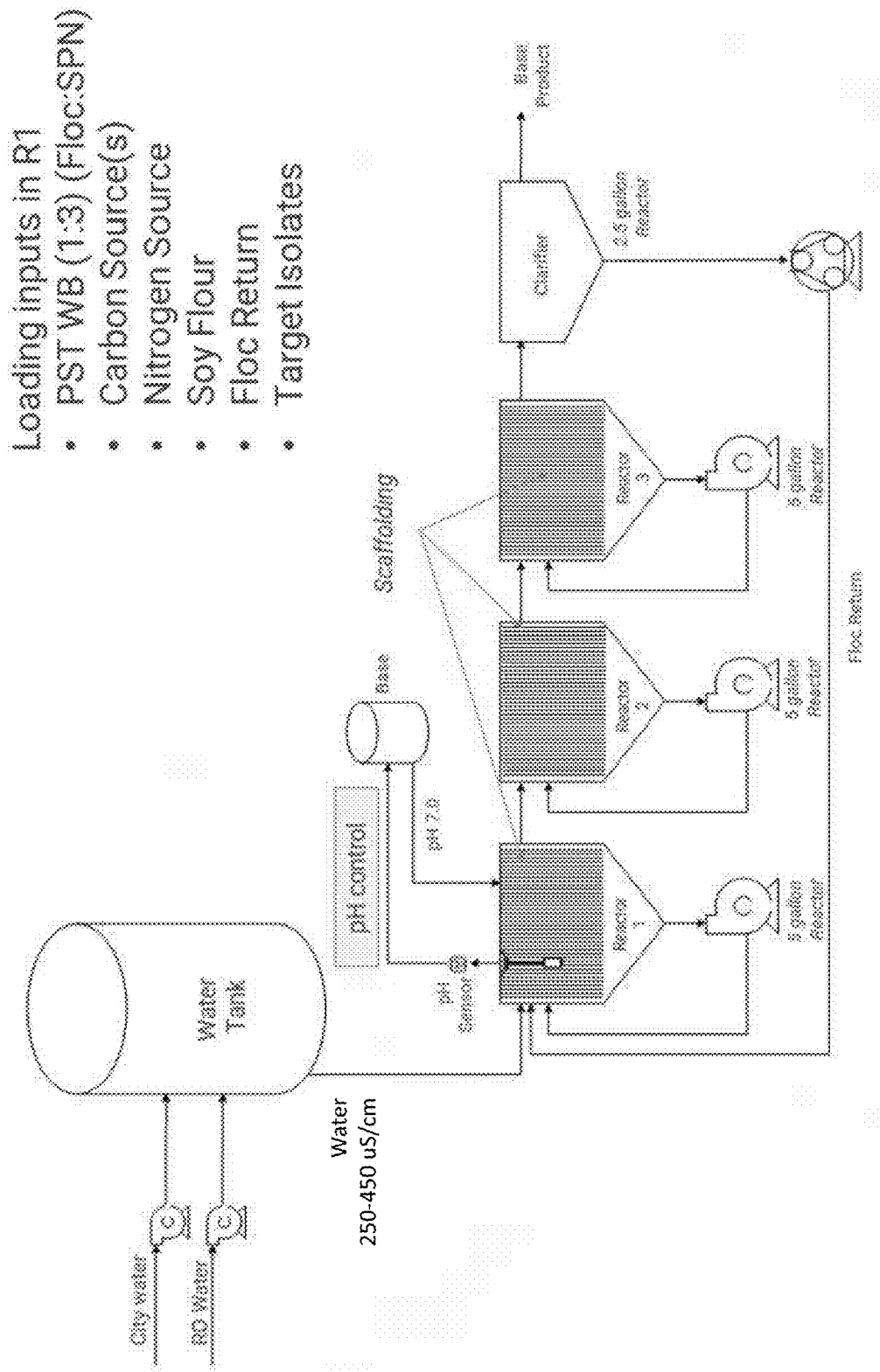
FIG. 6 shows an exemplary schematic of a NTS system with packed bed reactors.

Four separate systems NTS-1.1, NTS-1.2, NTS-1.3, and/or NTS-1.4 (NTS 1.0 systems) for production of nitrogen use efficiency promoting products by digestion of organic feedstock were built and operated. These four systems were down-flow systems. Each of the systems included a series of three 5-gallon reactor chambers (Reactor 1, Reactor 2, and/or Reactor 3) with continuous flow of working fluid from one reactor to the next and ultimately to the clarifier chamber, which is a 2.5 gallon reactor. Initially, a water tank is connected to Reactor 1 and provides continuous flow of water to Reactor 1 at an electrical conductivity ranging from 250-450 microsiemens/centimeter (µS/cm). The water tank comprised water from a city water source and a reverse osmosis (RO) water source. Reactor 1 is also coupled to a pH sensor, pH controller, and/or automatic buffer addition system to maintain the pH at 7.0±0.1. When the pH of the working solution in Reactor 1 gets below the set threshold, there is an automatic base (3M NaOH) addition until a pH of 7.0 or higher is reached. In some cases, the working fluid in each reactor is recirculated from the bottom of the reactor and pumped back to just below the surface of the same reactor to maintain homogeneous conditions within the working solutions. Biosolids (floc) is generated through the process. The solids are collected in the clarifier chamber where a portion is recycled back upstream of the process. The three reactors of the NTS-1.1 and/or NTS-1.3 systems were packed bed reactors with scaffolding within the reactors. The three reactors of the NTS-1.2 and/or NTS-1.4 systems were fluidized bed reactors, which lacked the scaffolding. In some cases, the reactors comprised a distribution ring that is subsurface of the discharge volume, reduced the amount of surface disruption, and kept the environment in the reactor anaerobic. A diagram of the NTS-1.1 and NTS-1.3 systems is shown in FIG. 6. A diagram of the NTS-1.2 and NTS-1.4 systems is shown in FIG. 7.

Figure 7:
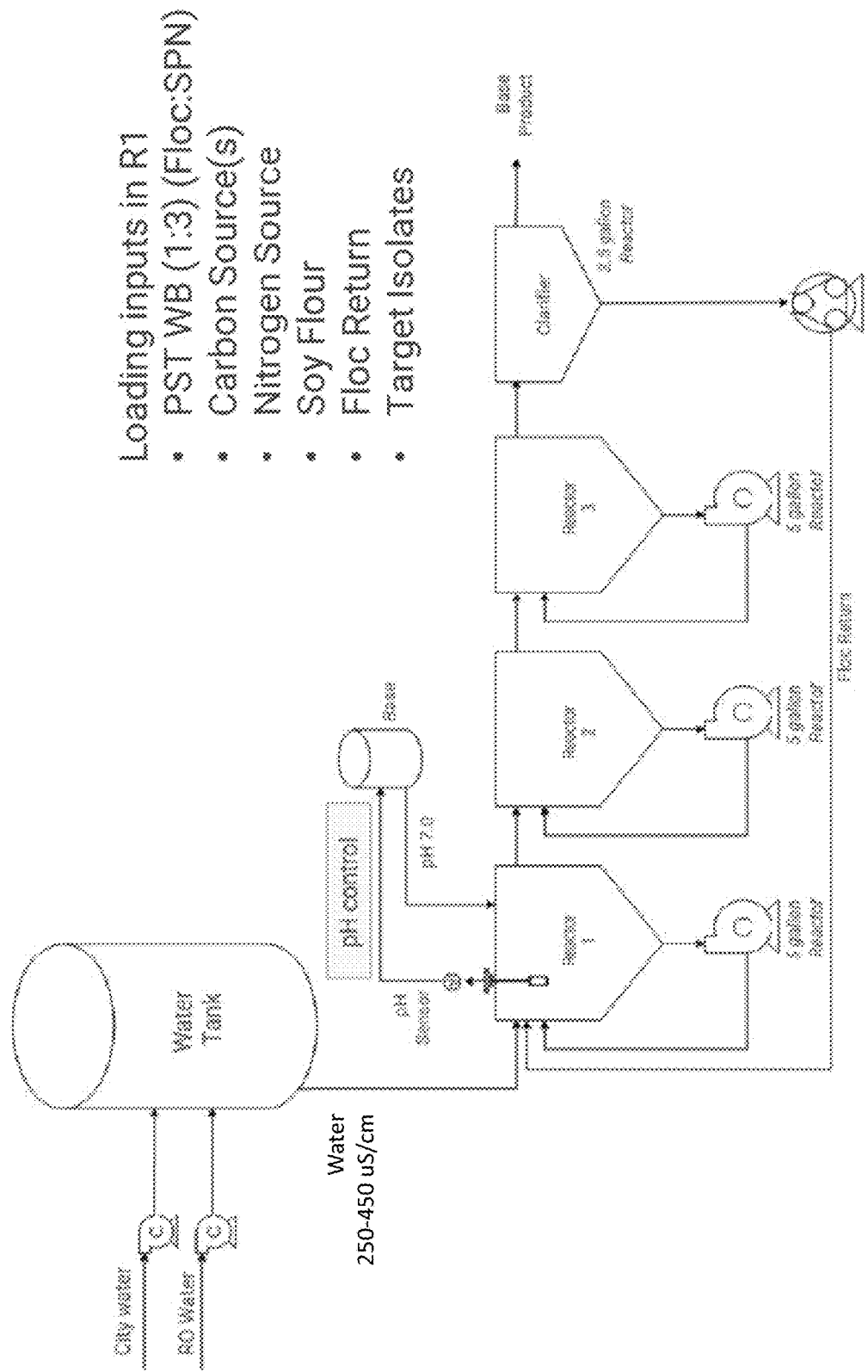
FIG. 7 shows an exemplary schematic of a NTS system with fluidized bed reactors.

As shown in FIG. 6 and FIG. 7, fluid from the top of Reactor 1 continuously flowed into Reactor 2 in a hydraulically balanced fashion. In each of NTS-1.1, NTS-1.2, NTS-1.3, and NTS-1.4, glucose and ammonium sulfate were added to Reactor 1 to maintain a concentration range of 0.2-2.0% w/v and 0.02-0.2% w/v, respectively, based on the span of the hydraulic retention time of the system. Malate was also added to Reactor 1 of the NTS-1.3, and/or NTS-1.4 systems at a concentration range of 0.2-2.0% w/v based on the span of the hydraulic retention time of the system. A concentration range of 0.5-4.5% v/v of Whole Broth of a Phosphate Solubilization Technology, PST WB (in a ratio of 1:3 floc:supernatant (SPN)) or the Whole Broth of a Water Based Phosphate Solubilization Technology, PwST WB (in a ratio of 1:3 floc:SPN) was also added to Reactor 1 on the span of the hydraulic retention time of the system. Soy flour, calcium carbonate were added to Reactor 1 at a concentration range of 0.2-3.0% w/v and, respectively, based on the span of the hydraulic retention time of the system. Fluid from the top of the Reactor 2 was continuously flowed into Reactor 3 in a hydraulically balanced fashion. In some cases, fluid from the top of a third reactor was flowed into a separation chamber (clarifier), where solids were allowed to settle. The hydraulic rate was 4.6 mL/min. The supernatant (or base product) from the clarifier was continuously collected, and a portion of the floc at the bottom of the clarifier was returned to Reactor 1 at a rate of 1.32 L/day.

Two additional scaled up separate systems NTS-2.2 and/or NTS-2.3 (NTS 2.0 systems) were built based on the NTS-1.4 design and process for optimization at a larger scale. These two systems were down-flow systems. The two systems also each ran cooler than the NTS-1.1, NTS-1.2, NTS-1.3, and/or NTS-1.4 systems due to scale. For example, the NTS-2.2 and NTS-2.3 system temperature for the first reactor was around 20% lower than the temperatures from the NTS-1.1, NTS-1.2, NTS-1.3, and/or NTS-1.4 systems.

Figure 62:
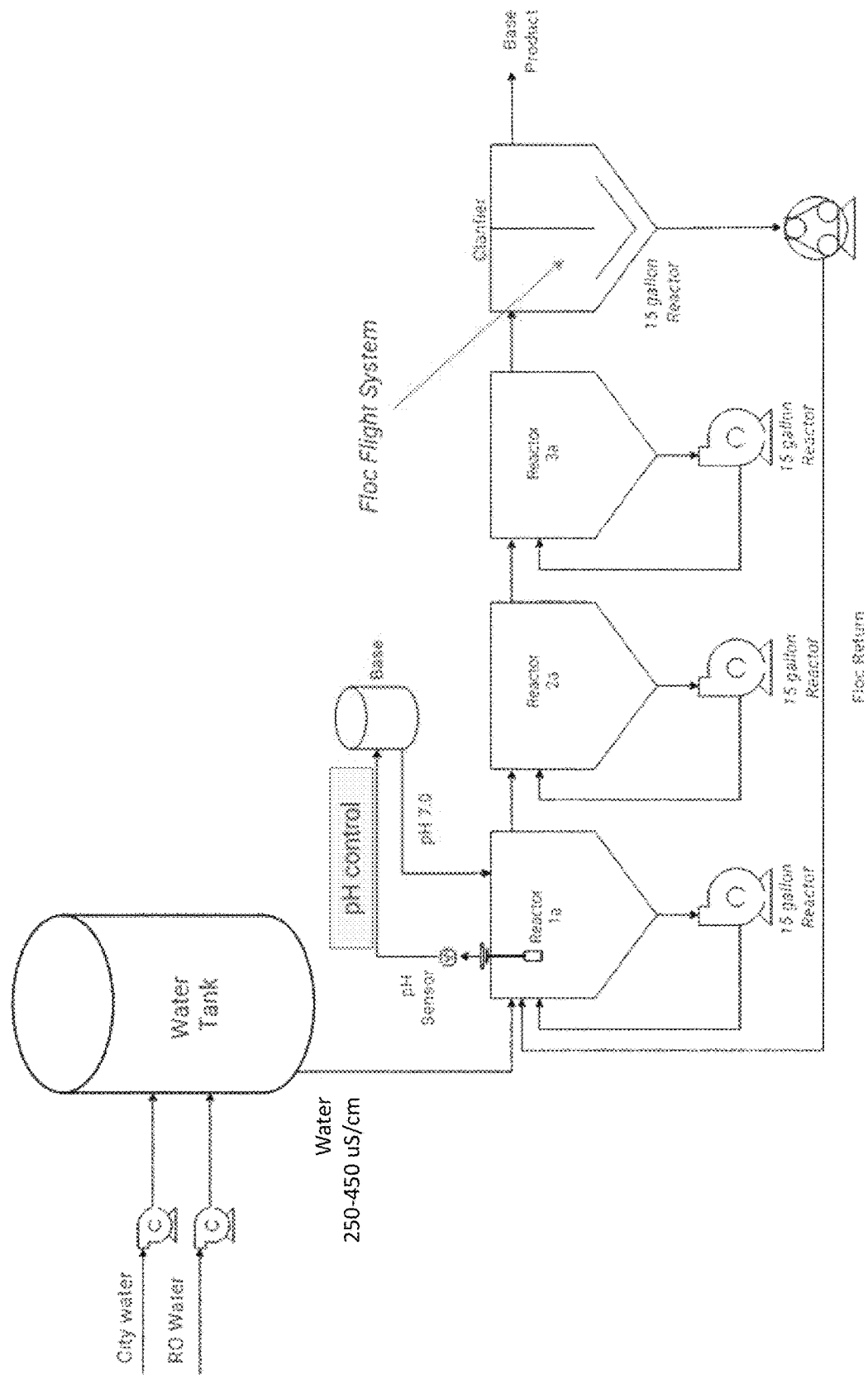
FIG. 62 is an exemplary schematic of a NTS 2.0 system with floc flights present in the clarifier.

NTS-2.2 is inoculated with isolates MS3900 and/or MS3907; and NTS-2.3 is inoculated with isolates MS3900, MS3907, and/or MS4921. Each of the scaled up systems included a series of three 15 gallon reactor chambers (Reactor Ta, Reactor 2a, and/or Reactor 3a) with continuous flow of working fluid from one reactor to the next and ultimately to the clarifier chamber, which is a 15 gallon reactor. Initially, a water tank is connected to Reactor 1a and provides continuous flow of water to Reactor Ta at an electrical conductivity ranging from 250-450 microsiemens/centimeter (µS/cm). The water tank comprised water from a city water source and a reverse osmosis (RO) water source. Reactor Ta is also coupled to a pH sensor connected to a pH controller to provide an automatic buffer addition to maintain the pH at 7.0±0.1. When the pH drops below the set point, the pump connected to the controller will add base (3N NaOH) until the pH is again within the desired threshold. In some cases, the working fluid from each reactor is recirculated within each reactor from the bottom of the reactor back to just below the surface of the working solution to maintain a homogeneous environment for the fermentation. For example, a portion of the working fluid from reactor Ta is recycled back into Reactor Ta. The three reactors of the NTS-2.2 and/or NTS-2.3 systems were fluidized bed reactors, which lacked scaffolding. In some cases, the reactors comprised a distribution ring that is subsurface of the discharge volume, which reduced the amount of surface disruption, and kept the environment in the reactor anaerobic. A diagram of the NTS-2.2 and/or NTS-2.3 systems is shown in FIG. 62. As shown in FIG. 62, fluid from the top of Reactor Ta continuously flowed into Reactor 2a in a hydraulically balanced fashion. In each of NTS-2.2 and NTS-2.3, glucose and ammonium sulfate were added to Reactor Ta to maintain a concentration range of 0.2-2.0% w/v and 0.02-0.2% w/v, respectively, based on the span of the hydraulic retention time of the system. Malate was also added to Reactor 1a of both systems at a concentration range of 0.2-2.0% w/v based on the span of the hydraulic retention time of the system. A concentration range of 0.5-4.5% v/v of Whole Broth of a Phosphate Solubilization Technology, PST WB (in a ratio of 1:3 floc:supernatant (SPN)) or the Whole Broth of a Water Based Phosphate Solubilization Technology, PwST WB (in a ratio of 1:3 floc:SPN) was also added to Reactor Ta based on the span of the hydraulic retention time of the system. Soy flour and calcium carbonate were added to Reactor Ta at a concentration range of 0.2-3.0% w/v and 0.02-0.2% w/v, respectively, based on the span of the hydraulic retention time of the system. Fluid from the top of the Reactor 2a was continuously flowed into Reactor 3a in a hydraulically balanced fashion. In some cases, fluid from the top of a third reactor was flowed into a separation chamber (clarifier), where solids were allowed to settle. The hydraulic rate for NTS-2.2 and/or NTS-2.3 were 15.77 mL/min and 11.27 mL/min respectively. The supernatant (or base product) from the clarifier was continuously collected, and a portion of the floc at the bottom of the clarifier was returned to Reactor Ta at a concentration of 4.54 L/day. The clarifier comprised a floc flight system (e.g., floc-folding flights) as shown in FIG. 63 that can improve the concentration of the added specific isolate(s) in the base product. The floc returned back to the system as a 2% v/v rate per day. Additionally, solids management was maintained at 20-25% range in the system. For example, as solids accumulate over time in the clarifier chamber, a range of 20-25% solids v/v is maintained. Additional floc is harvested from the system and removed.

The PST WB indicated as an input into R1 (in FIGS. 6 and 7) or R1a (FIG. 62) refer to a product of a separate serialized digestion system (the PwST or PST system), which has as an input an aqueous feed comprising (1) a microbial consortium derived from digestion of cow manure by microbes endogenous to the manure and (2) rock phosphate. The PwST system and PST system are described in more detail in Examples 16 and 23 below, respectively. The whole broth (WB) product of the PwST system includes supernatant and floc solids with their associated microbial consortia. The PwST WB input into the NTS systems contains floc and supernatant (SPN) in a ratio of floc to supernatant of 1:3. The carbon source input into the NTS systems includes either glucose (NTS-1.1 & NTS-1.2) or glucose and malate (NTS-1.3, NTS-1.4, NTS-2.2, and/or NTS-2.3). Aside from the carbon source input, inputs also came from a nitrogen source and isolates. In some cases, the quantities added of the carbon and nitrogen sources to the systems are relative to the retention time of the systems and can be adjusted accordingly if the flow rate changes, since the NTS systems are continuous. The specific isolates (or targeted isolates) input into the NTS-1.1, NTS-1.2, NTS-1.3, NTS-1.4, and/or NTS-2.2 systems were MS3907 & MS3900 spores. The "target isolates" input into the NTS-2.3 system was MS3907, MS3900, and/or MS4921 spores. The "floc return" input comes from an outlet at the bottom of the clarifier (CLF) chamber.

The NTS systems were operated with a continuous flow of input and from reactor to reactor. The total volume of working fluid within all of the reactors and clarifiers of NTS-1.1, NTS-1.2, NTS-1.3, and/or NTS-1.4 systems was maintained at 17.5 gallons. The hydraulic rate of flow through these four systems was 4.6 ml/min to maintain a retention time of 10 days and can be varied accordingly for a retention time from 7 to 21 days depending on production volume requirements. The total volume of working fluid within all of the reactors and clarifiers was of NTS-2.2 and/or NTS-2.3 systems was maintained at 60 gallons. The hydraulic rate of flow through these two systems was 15.77 ml/min and 11.27 ml/min for NTS-2.2 and NTS-2.3, respectively. The retention time of the NTS-1.1, NTS-1.2, NTS-1.3, NTS-1.4, and/or NTS-2.2 systems was 10 days. The retention time of the NTS-2.3 system was 14 days. The NTS-1.1, NTS-1.2, NTS-1.3, and/or NTS-1.4 systems produced 1.75 gallons of base product flowing from the clarifiers per day. The NTS-2.2 and/or NTS-2.3 systems produced 6 gallons of base product flowing from the clarifiers per day and 4.29 gallons of base product flowing from the clarifiers per day respectively. The NTS-1.1, NTS-1.2, NTS-1.3, and/or NTS-1.4 systems produced 12.25 gallons of base product flowing from the clarifiers per week. The NTS-2.2 and/or NTS-2.3 systems produced 42 gallons of base product flowing from the clarifiers per week and 30 gallons of base product flowing from the clarifiers per week respectively. The NTS-2.2 and/or NTS-2.3 systems resulted in a 3.43 total system volume scale up. The scale up of NTS-1.4 system to NTS-2.0 systems used retention time as the constant variable to determine scale factors.

The produced NTS-1.0 base products had an average pH of 7.9-8.13, an average COD of 180-200 ppm, a total nitrogen (N) content of 0.02%, a total phosphorous (P) content of 0.00001%, and a total potassium (K) content of 0.094%. The NTS products included MS3907 and/or MS3900. MS3907 and/or MS3900 can appear in the biofilm within the reactors. In some cases, the NTS product may appear in other areas of the system aside from the biofilm. In some cases, isolates can contribute their metabolites to the system whether or not they are in the base product. Analysis of the bacterial content of the NTS products showed the presence of a microbial consortium enriched for nitrogen fixing bacteria. In some cases, MS4921 is expected to be present in the reactors, base product, final product, floc, and/or biofilm. The produced NTS-1.1 base products has a pH range of 7.39-8.71, and electrical conductivity (Cond) range of 0.55-2.06 mS/cm, a chemical oxygen demand (COD) range of 22-240 mg/L. The produced NTS-1.2 base products has a pH range of 7.43-8.36, and electrical conductivity (Cond) range of 0.55-1.72 mS/cm, a chemical oxygen demand (COD) range of 81.95-670 mg/L. The produced NTS-1.3 base products has a pH range of 8.05-8.66, and electrical conductivity (Cond) range of 1.63-2.64 mS/cm, a chemical oxygen demand (COD) range of 15-176 mg/L. The produced NTS-1.4 base products has a pH range of 8.11-8.88, and electrical conductivity (Cond) range of 1.63-2.64 mS/cm, a chemical oxygen demand (COD) range of 89.65-815 mg/L. The produced NTS-2.2 base products has a pH range of 7.62-8.65, and electrical conductivity (Cond) range of 2.6-4.37 mS/cm, a chemical oxygen demand (COD) range of 190-400 mg/L. The produced NTS-2.2 base products has a pH range of 7.74-8.65, and electrical conductivity (Cond) range of 2.59-4.37 mS/cm, a chemical oxygen demand (COD) range of 230-400 mg/L.

The working fluid in each reactor described herein is circulated within the reactor in such a way as to minimize surface disruption, which maintains the dissolved oxygen within the reactors between 0.14 and 0.45 mg/L. The NTS-1.1, NTS-1.2, NTS-1.3, NTS-1.4, NTS-2.2 and/or NTS-2.3 systems encompasses a microaerobic process. In the NTS-1.1 system, the dissolved oxygen in Reactor 1 was 0.22 mg/L, in Reactor 2 was 0.18 mg/L, in Reactor 3 was 0.2 mg/L, and/or in the Clarifier was 0.15 mg/L. In the NTS-1.2 system, the dissolved oxygen in Reactor 1 was 0.17 mg/L, in Reactor 2 was 0.15 mg/L, in Reactor 3 was 0.15 mg/L, and/or in the Clarifier was 0.13 mg/L. In the NTS-1.3 system, the dissolved oxygen in Reactor 1 was 0.16 mg/L, in Reactor 2 was 0.14 mg/L, in Reactor 3 was 0.45 mg/L, and/or in the Clarifier was 0.13 mg/L. In the NTS-1.4 system, the dissolved oxygen in Reactor 1 was 0.15 mg/L, in Reactor 2 was 0.13 mg/L, in Reactor 3 was 0.14 mg/L, and/or in the Clarifier was 0.14 mg/L. In the NTS-2.2 system, the dissolved oxygen in Reactor 1a was 0.21 mg/L, in Reactor 2a was 0.21 mg/L, and/or in Reactor 3a was 0.2 mg/L. In the NTS-2.3 system, the dissolved oxygen in Reactor 1a was 0.2 mg/L, in Reactor 2a was 0.22 mg/L, and/or in Reactor 3a was 0.19 mg/L.

B. NTS-1.5 System

In an example, NTS-1.5 is a continuous serialized system that was built to look at the base technology without the inoculation of the target isolates. The system was designed to compare the base technology performance, efficacy, and chemical profile, when no target isolates were added to the process. The process most closely resembled the NTS-1.4, in design, process ranges, and all inputs (except the target isolates) added at similar concentration ranges, based on the hydraulic retention time of the system. The system was also a fluidized bed-based system that utilized PwST WB at a 1:3 floc:supernatant ratio as the microbial inoculum. This specific system comprised three reactors that used a down-flow orientation of the hydraulic re-circulation within each reactor and that were followed by a clarifier chamber from which the byproducts were recovered, (1) the floc that was separated by gravity and (2) the supernatant that was collected as the main product output of the system. Floc that was recovered from the clarifier was returned upstream of the system to Reactor 1. Reactor 1, Reactor 2, and Reactor 3 each had a working volume of 5 gallons. The clarifier chamber of NTS-1.5 system had a working volume of 2.5 gallons. The total working volume for the NTS-1.5 system was 17.5 gallons.

In NTS-1.5, glucose and ammonium sulfate were added to Reactor ito maintain a concentration range of 0.2-2.0% w/v and 0.02-0.2% w/v, respectively, based on the span of the hydraulic retention time of the system. Malate was also added to Reactor 1 at a concentration range of 0.2-2.0% w/v based on the span of the hydraulic retention time of the system. A concentration range of 0.5-4.5% v/v of Whole Broth of a Phosphate Solubilization Technology, PST WB (in a ratio of 1:3 floc:supernatant (SPN)) was also added to Reactor 1 on the span of the hydraulic retention time of the system. Soy flour and calcium carbonate were added to Reactor 1 at a concentration range of 0.2-3.0% w/v and 0.02-0.2%, respectively, based on the span of the hydraulic retention time of the system. The hydraulic rate of flow through the NTS-1.5 line was about 4.6 ml/min to maintain a retention time of 10 days and could be varied accordingly for a retention time from 7 to 21 days depending on production volume requirements with a hydraulic rate range between 2.19-6.57 mL/min. The total volume of working fluid within all the reactors and clarifier of the NTS-1.5 line was maintained at 17.5 gallons.

The NTS-1.5 systems produced 12.25 gallons of base product (BP) flowing from the clarifiers per week. The produced NTS-1.5 base product had a pH range of 7.30-8.40, electrical conductivity (Cond) range of 0.50-2.46 mS/cm, and a chemical oxygen demand (COD) range of 22-300 mg/L. The working fluid in each reactor R1-R3 was circulated within the reactor in such a way as to minimize surface disruption, which maintained the dissolved oxygen within the reactors between 0.14 and 0.22 mg/L. Similar to the NTS-1.1, NTS-1.2, NTS-1.3, NTS-1.4 systems, the NTS-1.5 system encompassed a microaerobic process. In the NTS-1.5 system, the dissolved oxygen in Reactor 1 was 0.19 mg/L, in Reactor 2 was 0.18 mg/L, in Reactor 3 was 0.22 mg/L, and/or in the Clarifier was 0.14 mg/L.

The hydraulic rate of flow through the digestion system may be 4.60 mL/min to maintain a retention time of 10 days and can be varied accordingly for a retention time from 7 to 21 days depending on production volume requirements. Because of this, the amount of product produced per day ranged from 0.83 to 2.50 gallons. The amount of product produced per week ranged from 8.75 to 17.50 gallons.

C. NTS-2.2 and NTS-2.3 Systems

In an example, NTS-2.2 and/or NTS-2.3 were built based on the NTS-1.4 design and process for optimization at a larger scale. Similarly as described in the above section, each of the scaled up systems included a series of three 15 gallon reactor chambers (Reactor 1a, Reactor 2a, and/or Reactor 3a) with continuous flow of working fluid from one reactor to the next and ultimately to the clarifier chamber, which is a 15 gallon reactor. Initially, a water tank is connected to Reactor 1a and provides continuous flow of water to Reactor 1a at an electrical conductivity ranging from 250-450 microsiemens/centimeter (S/cm). The water tank comprised water from a city water source and a reverse osmosis (RO) water source. Reactor 1a is also coupled to a pH sensor connected to a pH controller to provide an automatic buffer addition to maintain the pH at 7.0±0.1. When the pH drops below the set point, the pump connected to the controller will add base (3M NaOH) until the pH is again within the desired threshold. In some cases, the working fluid from each reactor is recirculated within each reactor from the bottom of the reactor back to just below the surface of the working solution to maintain an homogeneous environment for the fermentation. For example, a portion of the working fluid from reactor 1a is recycled back into Reactor 1a. The three reactors of the NTS-2.2 and/or NTS-2.3 systems were fluidized bed reactors, which lacked the scaffolding. In some cases, the reactors comprised a distribution ring that is subsurface of the discharge volume, reduced the amount of surface disruption, and kept the environment in the reactor anaerobic. A diagram of the NTS-2.2 and/or NTS-2.3 systems is shown in FIG. 62.

The retention time of NTS 2.2 and NTS 2.3 can be set at 10 days and the hydraulic rate can be varied accordingly for a retention time from 7 to 21 days depending on production volume requirements. As shown in FIG. 62, fluid from the top of Reactor 1a continuously flowed into Reactor 2a in a hydraulically balanced fashion. The "target isolates" input into the NTS-2.2 system were MS3907 & MS3900; and the "target isolates" input into the NTS-2.3 system was MS3907, MS3900, and/or MS4921. These target isolates were inoculated into Reactor 1a. In each of NTS-2.2 and NTS-2.3, glucose and ammonium sulfate were added to Reactor 1a to maintain a concentration range of 0.2-2.0% w/v and 0.02-0.2% w/v, respectively, based on the span of the hydraulic retention time of the system. Malate was also added to Reactor 1a of both systems at a concentration range of 0.2-2.0% w/v based on the span of the hydraulic retention time of the system. A concentration range of 0.5-4.5% v/v of Whole Broth of a Phosphate Solubilization Technology, PST WB (in a ratio of 1:3 floc:supernatant (SPN)) or Whole Broth of a Water Based Phosphate Solubilization Technology, PwST WB (in a ratio of 1:3 floc:SPN) was also added to Reactor 1a based on the span of the hydraulic retention time of the system. Soy flour and calcium carbonate were added to Reactor 1a at a concentration range of 0.2-3.0% w/v and 0.02-0.2% w/v, respectively, based on the span of the hydraulic retention time of the system. Fluid from the top of the Reactor 2a was continuously flowed into Reactor 3a in a hydraulically balanced fashion. In some cases, fluid from the top of a third reactor was flowed into a separation chamber (clarifier), where solids were allowed to settle. The hydraulic rate for NTS-2.2 and/or NTS-2.3 were 15.77 mL/min and 11.27 mL/min respectively. The supernatant (or base product) from the clarifier was continuously collected, and a portion of the floc at the bottom of the clarifier was returned to Reactor 1a at a concentration of 2% v/v per day. The clarifier comprised a floc flight system (e.g., floc-folding flights) as shown in FIG. 63 that can improve the concentration of target isolated in the base product. The floc returned back to the system as a 2% v/v rate per day. Additionally, solids management was maintained at 20-25% range in the system.

In an example, as scaled-up versions of NTS 1.4, NTS 2.2 and NTS 2.3 provide conditions for enrichment of a nitrogen-fixing microbial community (Table 24) and their Base Product solutions are expected to have nitrogen fixation capacity as measured with the ARA assay (described herein in Example 12). Similarly to the NTS 1.0 systems, NTS 2.2 and NTS 2.3 output solutions either intact or filter sterilized (e.g., metabolites only) are expected to provide plant growth promotion in high throughput assays with *Arabidopsis* as well as in greenhouse experiments in multiple crops such as corn, sorghum, fescue, wheat, canola, soybean, tomato. As a result, it is expected that there may be a positive effect on growth, yield and N content in crops grown in outdoor pot studies and field trials with crops like corn, sorghum, wheat and soybean. The produced base products of the NTS 2.2 and NTS 2.3 lines are expected to have a pH range of 7.8-8.88, electrical conductivity (Cond) range of 1.50-2.8 mS/cm, and a chemical oxygen demand (COD) range of 80-500 mg/L.

TABLE 24

Nitrogen-fixing Microbial Communities from NTS-2.2 and NTS-2.3 Solutions. Reactor 1a input inoculum refers to the expected output of PwST WB (1:3 floc:SPN) inoculum at 1% into Reactor 1a without any other feed components added for enrichment.

| System | Reactor 1a Input Inoculum (cn/mL) | Base Product (cn/mL) |
|---|---|---|
| NTS-2.2 | $1.8 \times 10^5$ | $6.8 \times 10^5$-$1.6 \times 10^7$ |
| NTS-2.3 | $1.8 \times 10^5$ | $1.3 \times 10^6$-$1.6 \times 10^7$ |

These output solutions with the additional enrichment/retention of one or more of the target isolates, are expected to improve N content in plants measured by 1. *Arabidopsis* nitrogen stress relief, using only 10 mM ammonium salts, 2. measuring N nutrient levels in plant leaves after treatment with NTS solutions in greenhouse and outdoor pot assays, 3. ARA to evaluate nitrogen fixation capacity of plant roots and stems after treatment with NTS solutions, 4. evaluating recruitment of other beneficial microbes from the rhizosphere, and 5. performing a 15N labelled study to quantify the contribution of N2 fixation after treatment when compared to a control.

D. NTS-3.0 System

This is a production-scale version based on the NTS-2.3 system. The line is a continued serialized system. The system is a fluidized bed-based system that utilizes PST WB or $P_w$ST WB at a 1:3 floc:supernatant ratio as the microbial inoculum. This specific system comprises five reactors that use a down-flow orientation of the hydraulic re-circulation within each reactor and that are followed by a clarifier chamber from which the by products are recovered, (1) the floc that is separated by gravity and (2) the supernatant that is collected as the main product output of the system. Floc that is recovered from the clarifier is returned upstream of the system to Reactor 1. The addition of the PST WB or $P_w$ST WB is added to the hydraulic tank (rather than to R1) of the system at the same rate as the NTS-2.3 line, based on the hydraulic retention time of the system.

In NTS-3.0, glucose and ammonium sulfate are added to Reactor 1 to maintain a concentration range of 0.2-2.0% w/v and 0.02-0.2% w/v, respectively, based on the span of the hydraulic retention time of the system. Malate is also added to Reactor 1 at a concentration range of 0.2-2.0% w/v based on the span of the hydraulic retention time of the system. A concentration range of 0.5-4.5% v/v of Whole Broth of a Water Based Phosphate Solubilization Technology, PwST WB (in a ratio of 1:3 floc:SPN) is added to the hydraulic source tank based on the span of the hydraulic retention time of the system. Soy flour is added to Reactor 1 at a concentration range of 0.2-3.0% w/v, based on the span of the hydraulic retention time of the system. Fluid from the top of the Reactor 1 is continuously flowed into Reactor 2 in a hydraulically balanced fashion. Fluid from the top of the Reactor 2 is continuously flowed into Reactor 3, and from Reactor 3 to 4, and from 4 to 5, in a hydraulically balanced fashion. In some cases, fluid from the top of a fifth reactor is flowed into a separation chamber (clarifier), where solids are allowed to settle. The supernatant (or base product) from the clarifier is continuously collected, and a portion of the floc at the bottom of the clarifier is returned to Reactor 1 at a rate of 2% v/v of the system total volume.

The hydraulic rate of flow through the NTS-3.0 line is about 1.14 L/min to maintain a retention time of 14 days and can be varied accordingly for a retention time from 7 to 21 days depending on production volume requirements with a hydraulic rate range between 0.75-2.25 L/min. The total volume of working fluid within all the reactors and clarifier of the NTS-3.0 system is maintained at 6,000 gallons. In the NTS-3.0 line, the hydraulic rate of flow through the digestion system may be 1.13 L/min to maintain a retention time of 14 days and can be varied accordingly for a retention time from 7 to 21 days depending on production volume requirements. Because of this, the amount of product that is produced per day can range from 285.71 to 857.14 gallons. The amount of product that is produced per week can range from 2,000 to 6,000 gallons.

The NTS-3.0 system is built based on the NTS-2.3 design and process for optimization at a larger scale. The scaled-up systems includes a series of six 1,000 gallon reactor chambers (Reactor 1b, Reactor 2b, Reactor 3b, Reactor 4b, and/or Reactor 5b) with continuous flow of working fluid from one reactor to the next and ultimately to the clarifier chamber, which is a 1,000 gallon reactor. Initially, a water tank is connected to Reactor 1b and provides continuous flow of water to Reactor 1b at an electrical conductivity ranging from 250-450 microsiemens/centimeter (µS/cm). The water tank comprises water from a city water source. Reactor 1b is also coupled to a pH sensor connected to a pH controller to provide an automatic buffer addition to maintain the pH at 7.0±0.1. When the pH drops below the set point, the pump connected to the controller adds base (3M NaOH) until the pH is again within the desired threshold. The working fluid from each reactor is recirculated within each reactor from the bottom of the reactor back to just below the surface of the working solution to maintain a homogeneous environment for the fermentation. For example, a portion of the working fluid from Reactor 1b is recycled back into Reactor 1b. The six reactors of the NTS-3.0 systems are fluidized bed reactors, which lack the scaffolding. The reactors can comprise a distribution ring that is subsurface of the discharge volume, reducing the amount of surface disruption, and keeping the environment in the reactor anaerobic. The hydraulic rate of flow through these systems is 1.13 L/min to maintain a retention time of 14 days and is varied accordingly for a retention time from 7 to 21 days depending on production volume requirements. Fluid from the top of Reactor 1b continuously flows into Reactor 2b in a hydraulically balanced fashion. The "target isolates" input into the NTS-3.0 system are MS3907, MS3900, and/or MS4921. These target isolates are inoculated into Reactor 1b. In NTS-3.0, glucose and ammonium sulfate are added to Reactor 1 to maintain a concentration range of 0.2-2.0% w/v and 0.02-0.2% w/v, respectively, based on the span of the hydraulic retention time of the system. Malate is also added to Reactor 1b at a concentration range of 0.2-2.0% w/v based on the span of the hydraulic retention time of the system. A concentration range of 0.5-4.5% v/v of Whole Broth of a Phosphate Solubilization Technology, PST WB (in a ratio of 1:3 floc:supernatant (SPN)) is added to the hydraulic source tank based on the span of the hydraulic retention time of the system. Soy flour is added to Reactor 1b at a concentration range of 0.2-3.0% w/v, based on the span of the hydraulic retention time of the system. Fluid from the top of the Reactor 1 is continuously flowed into Reactor 2b in a hydraulically balanced fashion. Fluid from the top of the Reactor 2 is continuously flowed into Reactor 3b, and from Reactor 3b to 4b, and from 4b to 5b, in a hydraulically balanced fashion. In some cases, fluid from the top of a fifth reactor is flowed into a separation chamber (clarifier), where solids are allowed to settle. The supernatant (or base product) from the clarifier is continuously collected, and a portion of the floc at the bottom of the clarifier is returned to Reactor 1 at a rate of 2% v/v of the system total volume. The clarifier comprises a floc flight system (e.g., floc-folding flights) that can improve the concentration of target isolated in the base product. The floc returns back to the system as a 2% v/v rate per day. Additionally, solids management is maintained at 20-25% range in the system.

E. NTS-4.0 System NTS-4.0 is built based on the NTS-3.0 design and process for optimization at a larger scale. The scaled-up system potentially includes a series of six 10,000 gallon reactor chambers (similarly including Reactor 1b, Reactor 2b, Reactor 3b, Reactor 4b, and/or Reactor 5b) with continuous flow of working fluid from one reactor to the next and ultimately to the clarifier chamber, which is a 10,000 gallon reactor. Initially, a water tank is connected to Reactor 1b and provides continuous flow of water to Reactor 1b at an electrical conductivity ranging from 250-450 microsiemens/centimeter (µS/cm). The water tank comprises water from a city water source. Reactor 1b is also coupled to a pH sensor connected to a pH controller to provide an automatic buffer addition to maintain the pH at 7.0±0.1. When the pH drops below the set point, the pump connected to the controller adds base (3M NaOH) until the pH is again within the desired threshold. In some cases, the working fluid from each reactor is recirculated within each reactor from the bottom of the reactor back to just below the surface of the working solution to maintain a homogeneous environment for the fermentation. For example, a portion of the working fluid from reactor 1b is recycled back into Reactor 1b. The six reactors of the NTS-4.0 systems are fluidized bed reactors, which lack the scaffolding. In some cases, the reactors comprise a distribution ring that is subsurface of the discharge volume, reducing the amount of surface disruption, and keeping the environment in the reactor anaerobic. The hydraulic rate of flow through these systems is 11.27 L/min to maintain a retention time of 14 days and can be varied accordingly for a retention time from 7 to 21 days depending on production volume requirements hydraulic rate range between 7.5-22.5 L/min. The "target isolates" input into the NTS-4.0 system are MS3907, MS3900, and/or MS4921. These target isolates are inoculated into Reactor 1b. In NTS-4.0, glucose and ammonium sulfate are added to Reactor 1 to maintain a concentration range of 0.2-2.0% w/v and 0.02-0.2% w/v, respectively, based on the span of the hydraulic retention time of the system. Malate is also added to Reactor 1b at a concentration range of 0.2-2.0% w/v based on the span of the hydraulic retention time of the system. A concentration range of 0.5-4.5% v/v of Whole Broth of a Water Based Phosphate Solubilization Technology, PwST WB or PST WB (in a ratio of 1:3 floc:SPN) is added to the hydraulic source tank based on the span of the hydraulic retention time of the system. Soy flour is added to Reactor 1b at a concentration range of 0.2-3.0% w/v, based on the span of the hydraulic retention time of the system. Fluid from the top of the Reactor 1 is continuously flowed into Reactor 2 in a hydraulically balanced fashion. Fluid from the top of the Reactor 2 is continuously flowed into Reactor 3, and from Reactor 3 to 4, and from 4 to 5, in a hydraulically balanced fashion. In some cases, fluid from the top of a fifth reactor is flowed into a separation chamber (e.g., clarifier), where solids are allowed to settle. The supernatant (or base product) from the clarifier is continuously collected, and a portion of the floc at the bottom of the clarifier is returned to Reactor 1 at a rate of 2% v/v of the system total volume. The clarifier comprises a floc flight system (e.g., floc-folding flights) that improves the concentration of target isolated in the base product. The floc returns back to the system as a 2% v/v rate per day. Additionally, solids management is maintained at 20-25% range in the system. The production rate of product for the NTS-4.0 system is 4,285.71 gallons per day and 30,000 gallons per week based on the hydraulic retention time of the system. The system output has a range of 2,857.14-8,571.43 gallons per day based on the hydraulic retention time range of 7-21 days. The system output can have a range of 20,000-60,000 gallons per week based on the hydraulic retention time range of 7-21 days.

Example 4. Plant Growth Promotion Properties of NTS Products and Isolates

Figure 2B:
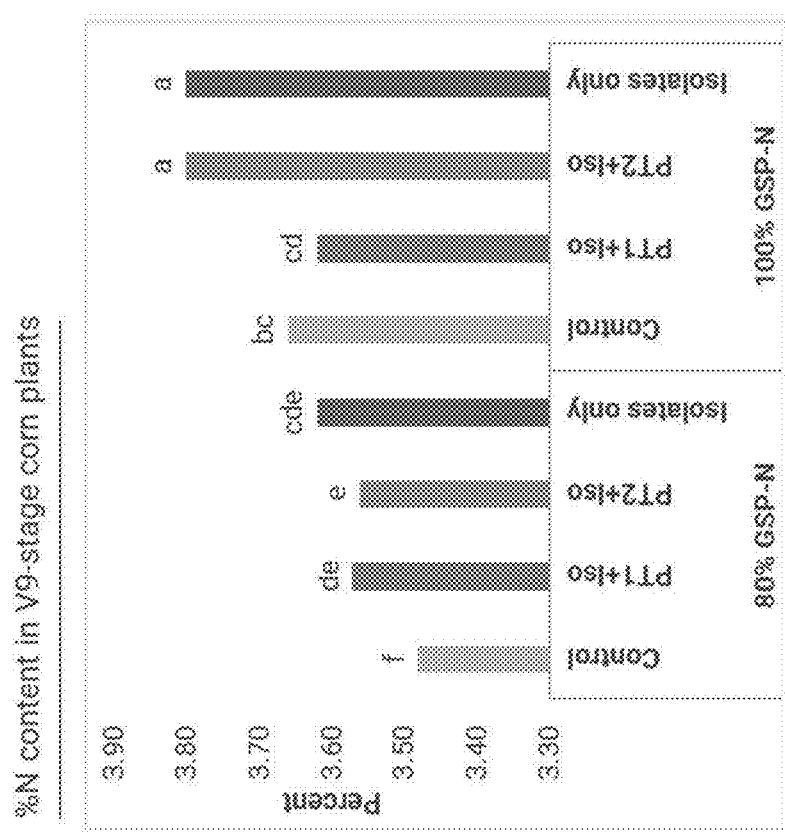
FIGS. 2A-2B are a series of graphs showing nitrogen content and yield in corn plants between control, a first prototype consortia with isolates (MS3900 and MS3907), a second prototype consortia with isolates (MS3900 and MS3907), and isolates only (MS3900 and MS3907). All conditions were tested in 80% GSP and 100% GSP.
Figure 2A:
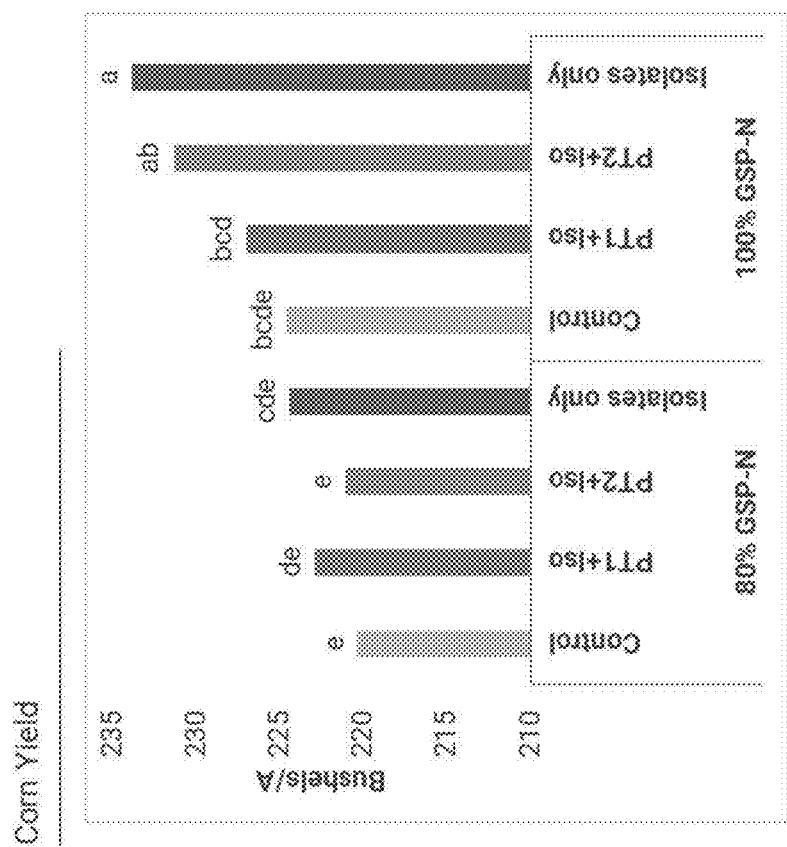

Results of a field study showing the effects of products of NTS digestion systems ("PT1" and "PT2") in combination with isolates MS3907 and MS3900 ("Iso") as well as the isolates alone, on nitrogen content and corn yield are shown in FIGS. 2A and 2B. FIGS. 3A and 3B show the effects of the digestion system products PT1 and PT2 and isolates on recruitment of beneficial microbes and nitrogen fixing activity in corn roots.

Figures 4A, 4B:
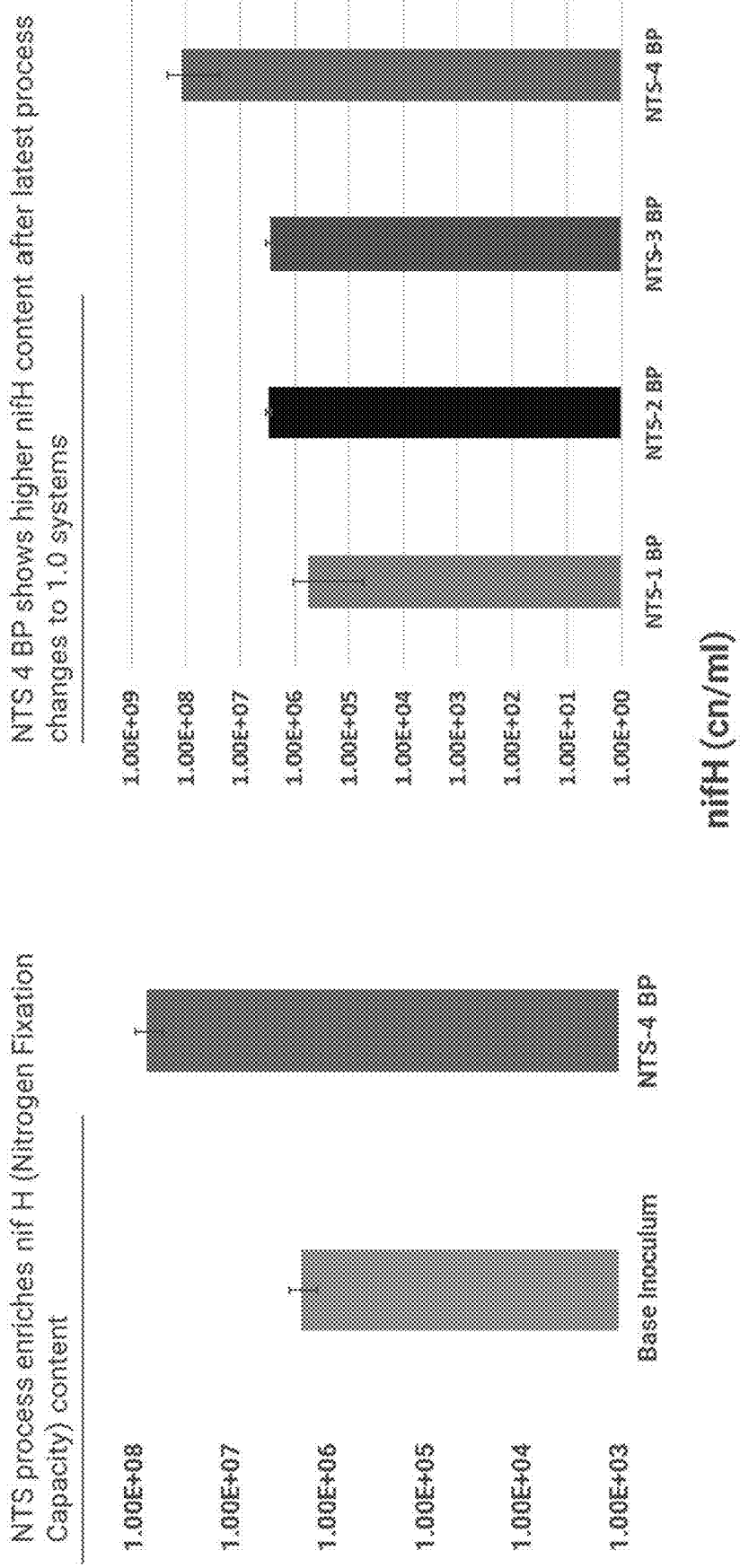
FIGS. 4A-4B are a series of graphs showing the levels of nifH gene abundance of NTS systems.

FIGS. 4A and 4B show results of an analysis of products of the four different NTS digestion system variants (NTS-1 (product of NTS-1.1), NTS-2 (product of NTS-1.2), NTS-3 (product of NTS-1.3), and NTS-4 (product of NTS-1.4)) for nitrogen fixation capacity content (nifH). "BP" indicates that the product is the unfiltered base product produced by the systems.

FIGS. 5A-5C show results of testing the effects of NTS-4 (referred to as "NTS" in FIGS. 5A-5C) on growth and nitrogen fixing activity of corn plants.

Figures 8A, 8B, 8C:
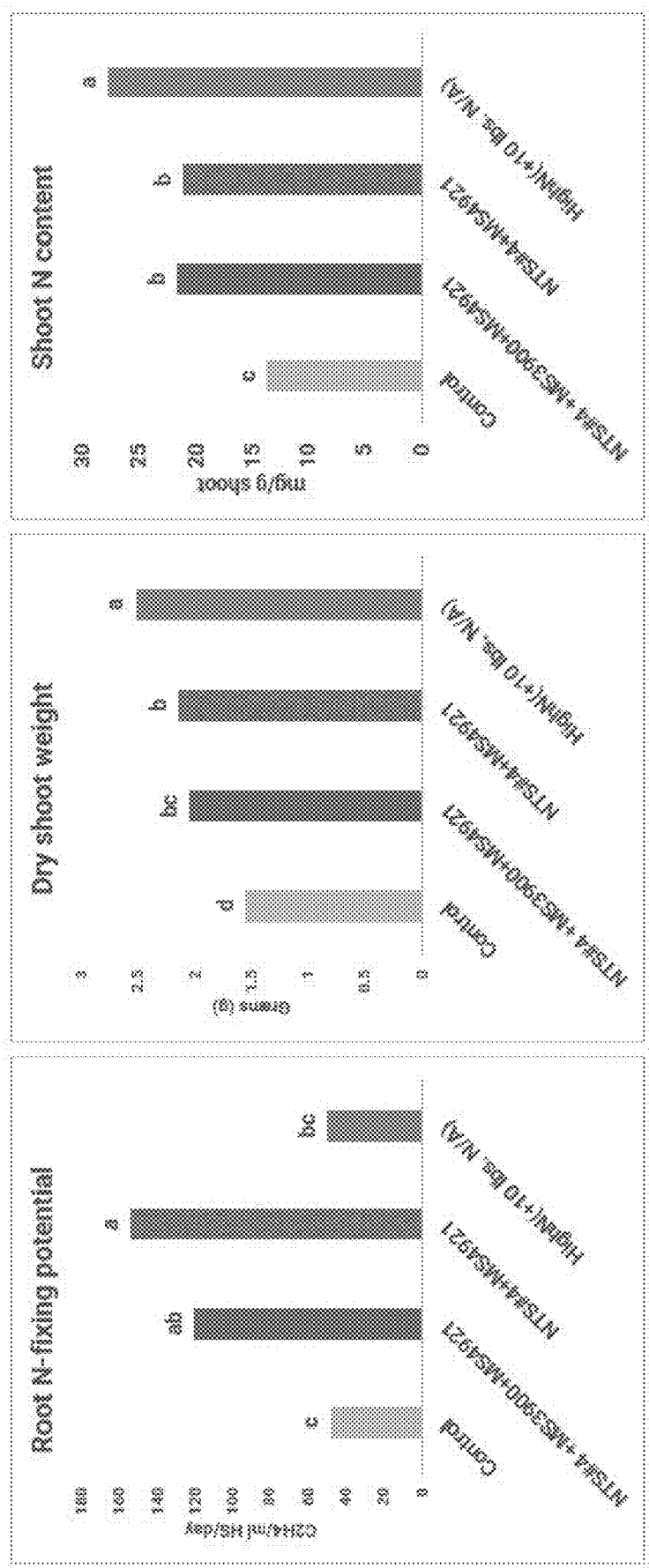
FIGS. 8A-8C are a series of graphs showing measures of nitrogen use efficiency across a control condition, NTS-4 with MS3900 and MS4921 isolates, NTS-4 with MS4921, and a HighN condition with an additional 10 lbs N/A.

FIGS. 8A-8C depict the effects of the NTS system (NTS #4, e.g., NTS 1.4) in combination with isolates (1) MS3900 and MS4921, or (2) MS4921 on measures of nitrogen use efficiency (NUE). The products may aid in corn nitrogen fixation, shoot growth, and/or shoot nitrogen content/uptake. The concentration of each isolate was $10^4$ cfu/ml added to the NTS solution. Two greenhouse experiments were conducted using a 1:1:1 Turface-peat-Denton sandy loam soil mix for plant growth and nitrogen use efficiency in corn. The 15 cm round pots were used with six treatments and 12 replicates. Welter Seed WS095 hybrid corn seed was used for the greenhouse tests and plants were thinned based on their uniform growth after the germination. The corn plants were harvested at 35 days after planting. NTS treatments and a negative control were fertilized with 10 lbs. N/A and the HighN control was fertilized with 20 lbs. N/A using urea ammonium nitrate solution (UAN32). NTS treatments were applied in-furrow at 2 qt./A. The corn shoots were oven dried at 70° C. for 48 hours and then weighed in grams. The dried shoot samples were sent for nitrogen content analysis.

The soil organic matter, organic nitrogen, and estimated nitrogen release were measured in percent (%), parts per million (PPM), and pounds per acre (lbs./A). The bulk soil samples (100 ong/replicate) were sent to Waypoint Analytical Laboratories Inc. (Memphis, USA) for nitrogen content analysis. FIGS. 9A-9C show the effects of application of isolates MS3900 and MS3907 alone applied in-furrow to corn. The isolates applied at 1 qt./A or 2 qt./A showed significantly increased soil organic matter (FIG. 9A), soil organic nitrogen (FIG. 9B), and estimated nitrogen release (FIG. 9C).

Figure 10B:
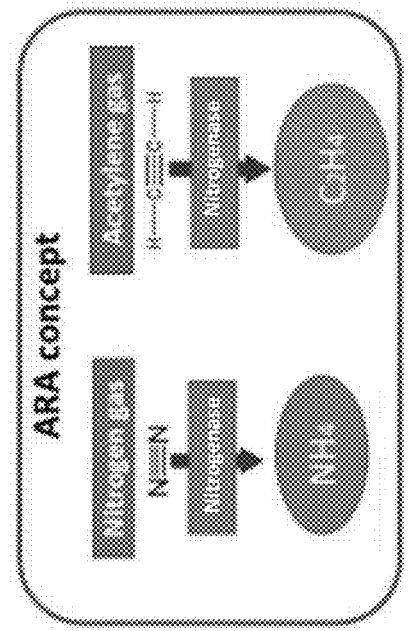
FIGS. 10A-10C show improved nitrogen fixing capacity of microbes to plants grown in a greenhouse test across testing conditions.
Figure 10C:
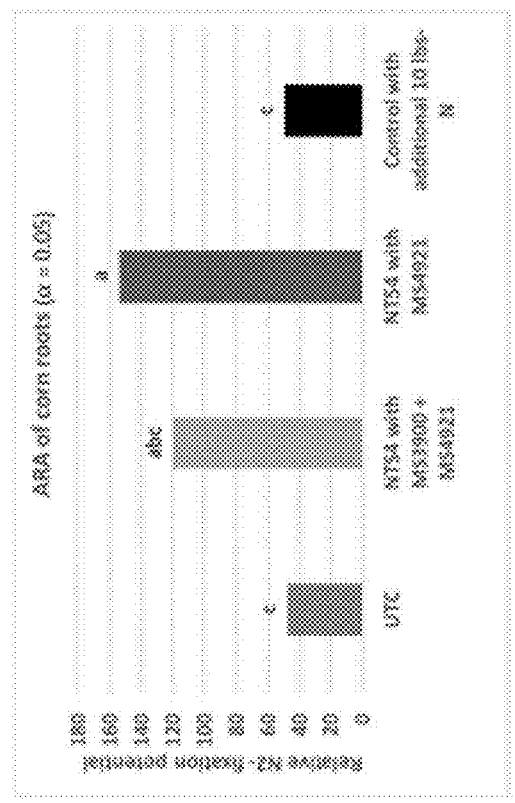
Figure 10A:
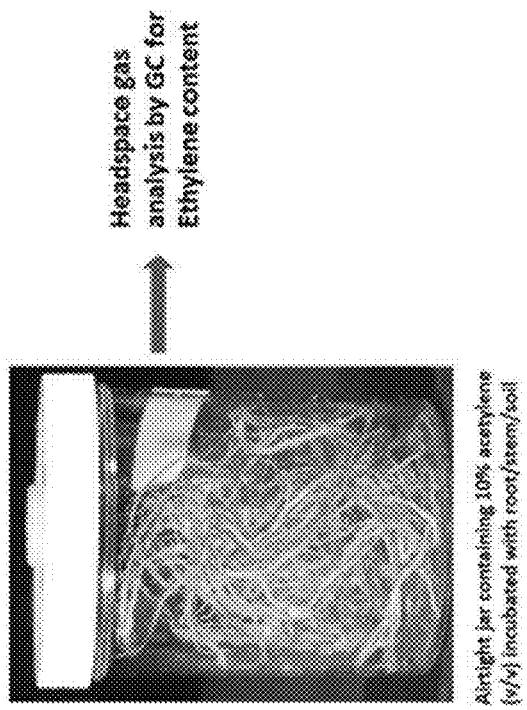

FIG. 10A depicts ajar containing 10% acetylene (v/v) with roots. Headspace gas analysis was conducted by gas chromatography to measure ethylene content. FIG. 10B shows a conceptual schematic for the acetylene reduction assay. Nitrogen gas is broken down via nitrogenase to ammonium ($NH_4$) and acetylene gas is broken down via nitrogenase to ethylene ($C_2H_4$). FIG. 10C shows the increase in N-fixing capacity for corn treatments with the NTS system (NTS4, e.g., NTS 1.4) in combination with isolates (MS3900 and MS4921, or MS4921 alone). Relative nitrogen fixation capacity from NTS treatment conditions was compared with UTC and control with an additional 10 lbs of nitrogen. NTS4 with MS4921 showed the greatest nitrogen fixation capacity.

Example 5: Rainout Shelter Experiment

The objective of this study was to evaluate one NTS reactor product candidate, to which were added MS3900 alone or with MS3900 and MS4921 at $10^4$ CFU/mL each, applied in-furrow at 18 and 36 µL/plant on corn for PGP and NUE efficacy. The was Dyna-grow AC250 hybrid corn and the growing medium was 1:1:1 Profile MVP® Turface-peat-Denton sandy loam soil mix.

Fertilizer for 80% grower standard practice was: MESZ (12-40-0-10S-1Zn) at 32.8 lbs., nitrogen at planting (2.79 g/pot) and at 65.6 lbs., nitrogen side-dress at V6 stage (4.66 g/pot) and Potash at 73 lbs./A (1.04 g/pot), UAN 32 at 40 lbs./A, and/or N side-dress (1.368 mL/pot). Fertilizer for 100% grower standard practice was: MESZ (12-40-0-10S-1Zn) at 41 lbs., nitrogen at planting (3.48 g/pot) and at 82 lbs., nitrogen side-dress at V6 stage (5.82 g/pot) and Potash at 91.25 lbs./A (1.3 g/pot). An additional application of UAN 32 at 50 lbs./A, and nitrogen side-dress (1.7 mL/pot) was applied at the Vt growth stage.

Irrigation was maintained at least 90% field capacity throughout the season. For pest control, granular imidacloprid (Marathon) was applied at planting and then use broad-spectrum foliar pest control products at labelled intervals through the season. Weed control was maintained within the rainout shelter.

TABLE 5

Treatment Conditions for Rainout Shelter Study

| Treatment | A.I. µl/40 cm pot | ml volume/seed hole | Stock solution for 20 replicates µl A.I./10 ml |
|---|---|---|---|
| UTC - 100% GSP | 0 | 0.5 | 0 |
| UTC - 80% GSP | 0 | 0.5 | 0 |
| NTS#4 + MS3900 - 80% GSP - 1 qt./A. | 18 | 0.5 | 360 |

TABLE 5-continued

Treatment Conditions for Rainout Shelter Study

| Treatment | A.I. µl/40 cm pot | ml volume/seed hole | Stock solution for 20 replicates µl A.I./10 ml |
|---|---|---|---|
| NTS#4 + MS3900 + MS4921 - 80% GSP - 1 qt./A | 18 | 0.5 | 360 |
| NTS#4 + MS3900 - 80% GSP - 2 qt./A | 36 | 0.5 | 720 |
| NTS#4 + MS3900 + MS4921 - 80% GSP - 2 qt./A | 36 | 0.5 | 720 |

Corn was planted on Day 1 and fertilizer was applied on Day 4. Side-dress UAN32 fertilizer was next applied on Day 45 at the V6 growth stage. Corn growth stages are characterized by a V followed by a number, identifying the number leaf to emerge. UAN fertilizer was applied for the final time on Day 81 at the Vt growth stage. The Vt growth stage is approximately 2 to 3 days prior to silk appearing and when the last branch of the tassel is visible. A randomized complete block design was used with trade 10 gallon pots, at 40 cm diameter tops. There was one plant per pot and 20 replicates in the study.

120 pots with 40 cm diameter were filled with the growing medium. Three corn seeds were planted in each pot 2 in. deep. 0.5 ml of treatment solution was pipetted over the seed and the seed was covered with growing medium. Starter fertilizer (MESZ 12-40-10S-1Zn) was applied 2 inches away from the seed and 2 inches deep. The fertilizer was then watered in thoroughly. Next, MESZ fertilizer was side-dressed at the V6 growth stage. Soil plant analysis development (SPAD) measurements were taken from the youngest, fully-expanded leaf weekly throughout the season. Licor®-600PF porometer and fluorometer readings were taken 3 times during the season. Ear leaves were collected at the beginning of the silking stage. Bulk four ear leaf samples from four plants of each treatment were taken to make five replicates for nutrient analysis. Plant height was evaluated at vegetative and reproductive stage (distance from the ground to the highest leaf collar/arch or the top of the tassel). Stem diameter was measured at harvest. At harvest, the following measurements were taken: grain yield (at 15.5% grain moisture), grain nutrient analysis, harvest index (grain/above-ground biomass), ear length, and ear weight. The data of leaf chlorophyll contents, plant physiological traits, corn tillers, plant heights, stem diameter, and dry shoot biomass were analyzed with JMP 16 software (SAS Institute, Cary, NC, USA) using the Fit model procedure at the $p<0.1$ level of significance.

Figure 11A:
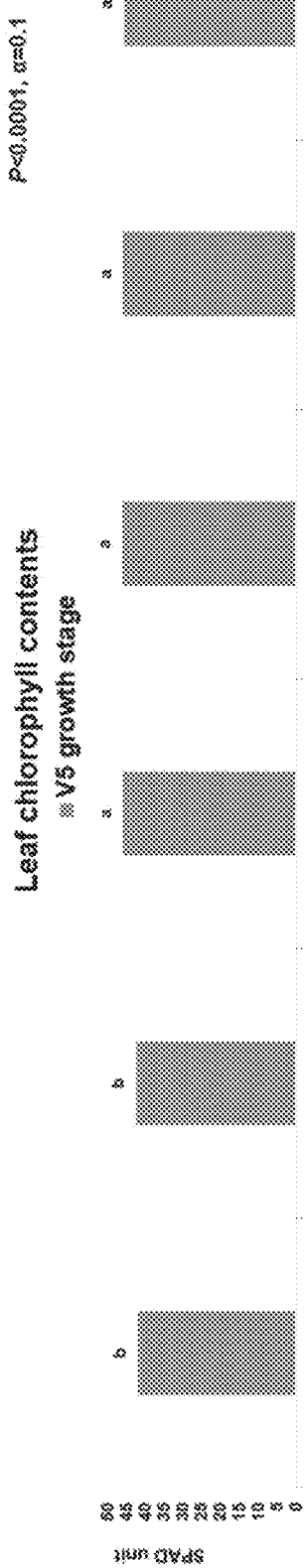
FIGS. 11A-11B are a series of graph showing leaf chlorophyll contents across treatment conditions.
Figure 11B:
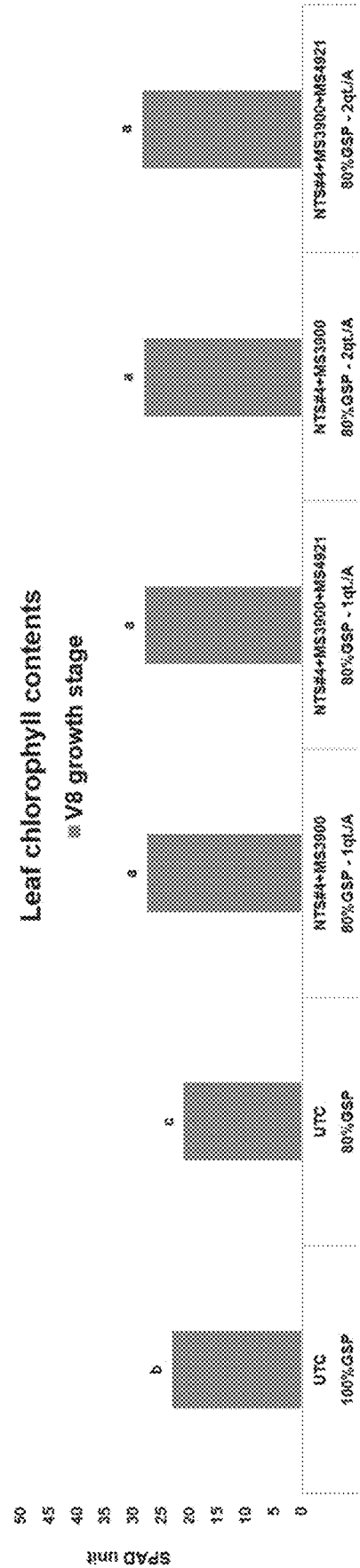

The leaf chlorophyll contents were measured from a fully expanded leaf at V5 and V8 growth stages using a Chlorophyll Meter, SPAD (Soil Plant Analysis Development-502, Konica Minolta, Tokyo, Japan). Three different positions on the leaf were measured and their average was recorded for the leaf chlorophyll contents. FIGS. 11A-11B show corn leaf chlorophyll contents at two growth stages. FIG. 11A shows leaf chlorophyll contents at V5 growth stage of corn (five leaves with collars) and FIG. 11B shows leaf chlorophyll contents at V8 growth stage of corn (eight leaves with collars). All NTS treated plants showed significantly increased leaf chlorophyll contents using both application rates (1 qt./A and/or 2 qt./A) and were significantly higher than the 100% GSP control.

Figure 12:
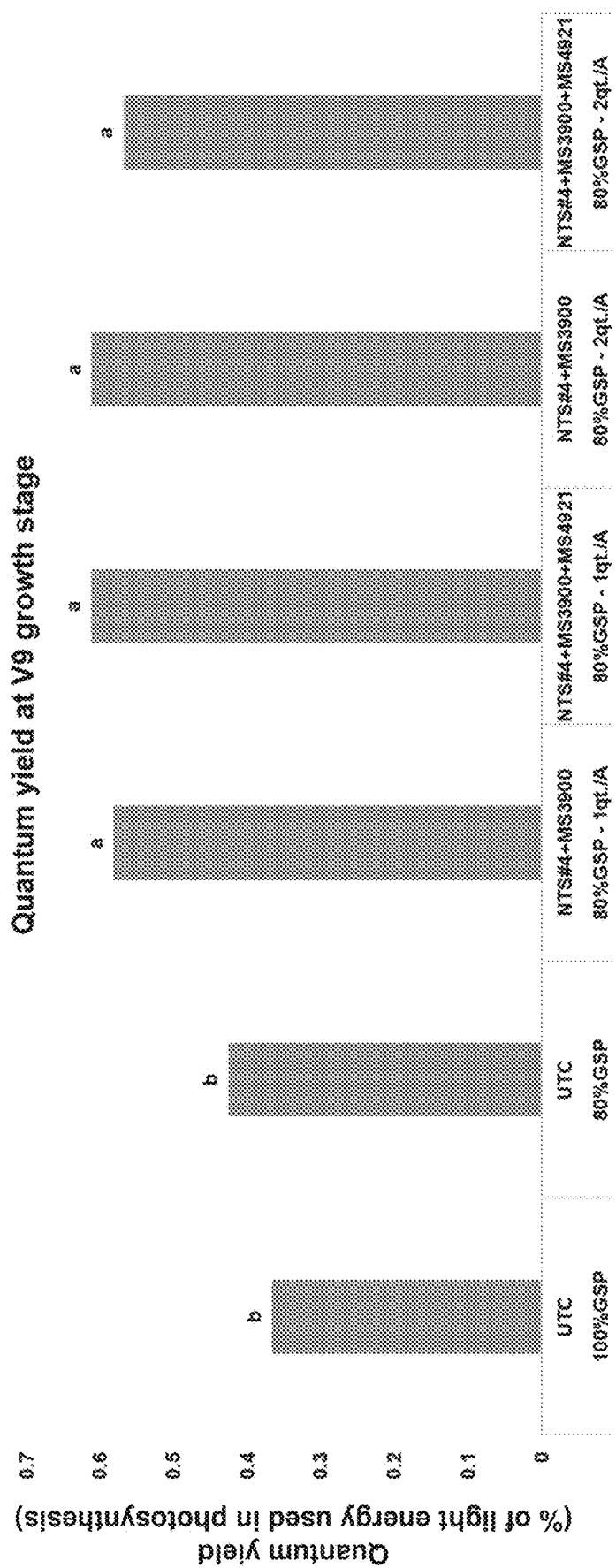
FIG. 12 is a graph depicting the photosynthetic quantum yield across treatment conditions tested in corn at V9 growth stage. NTS treatments at both applications rates and isolates showed increased photosystem light capture efficiency.
Figure 13:
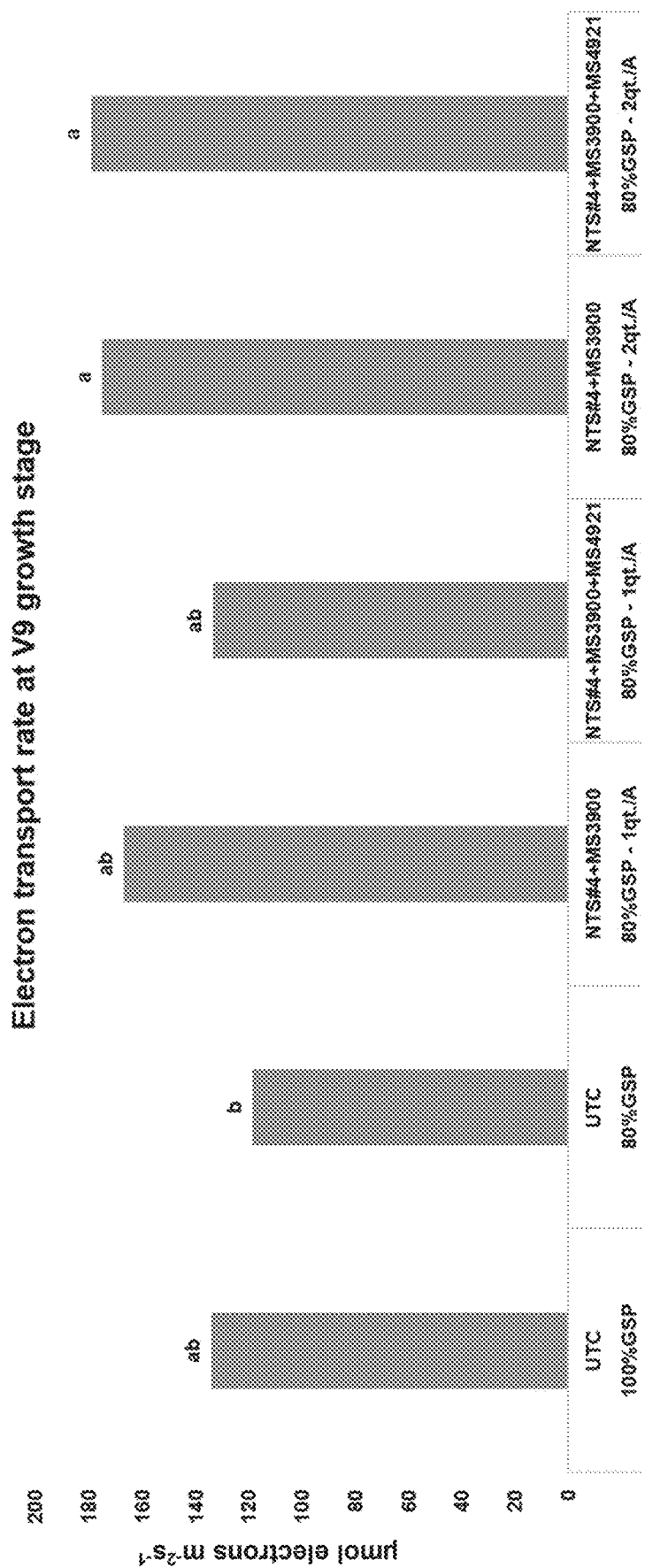
FIG. 13 is a graph depicting photosynthetic electron transport rate across treatment conditions in corn at V9 growth stage.

Plant physiological traits such as the stomatal conductance, transpiration rate, chlorophyll a fluorescence/quantum yield (QY), and electron transport rate (ETR) were measured using a LICOR 600 Porometer/Fluorometer Portable Photosynthesis System (Li-Cor, Inc. Lincoln, NE, USA) and irrigated the pots up to 90% soil moisture capacity. FIG. 12 shows the quantum yield (as percentage of light energy used in photosynthesis) at different growth stages. NTS treatments using either or both application rates (e.g., 1 qt./A and/or 2 qt./A) and with either one or two added isolates showed increased photosystem light capture efficiency. FIG. 13 shows the electron transport rate (i.e., photosynthesis capacity to assimilate carbon, µmoles $e^-/m_2/s$) at different growth stages. NTS treatment conditions with either or both application rates (e.g., 1 qt./A and/or 2 qt./A) and one or two added isolates showed various photosystem energy transfer to ATP production results. The NTS treatments at 2 qt./A showed the greatest electron transport rate.

Figure 14:
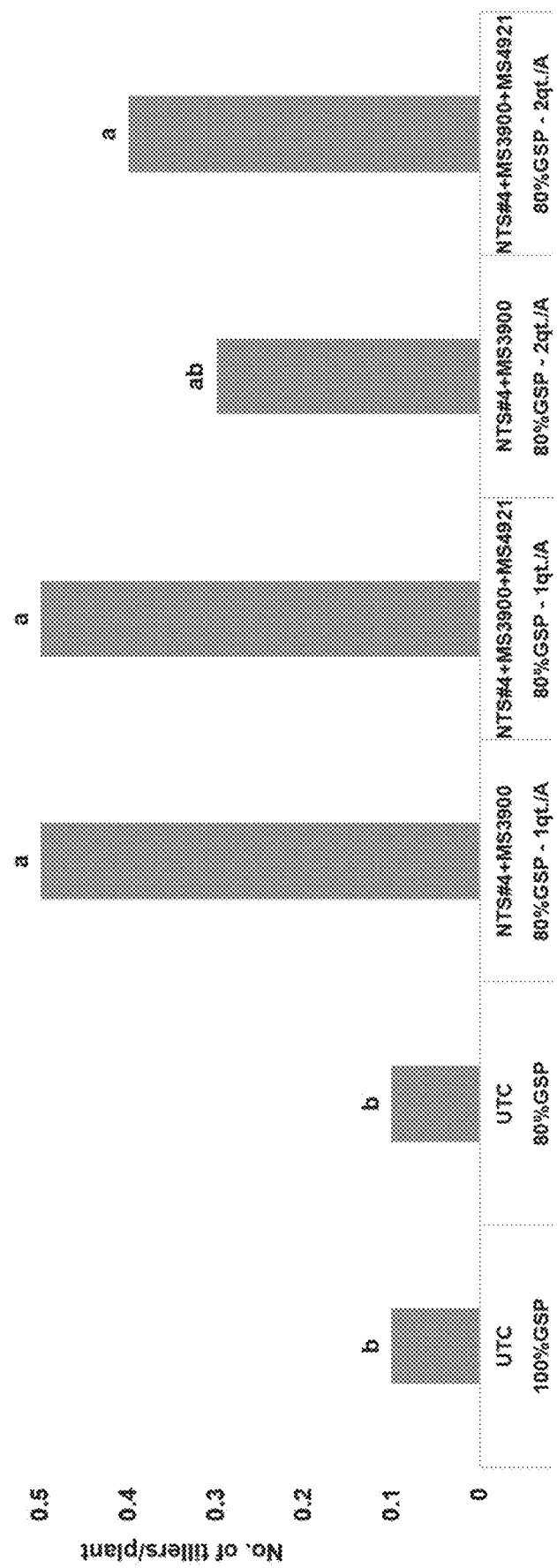
FIG. 14 is a graph depicting the number of corn tillers per corn plant across treatment conditions, measured at V5 growth stage.
Figure 15:
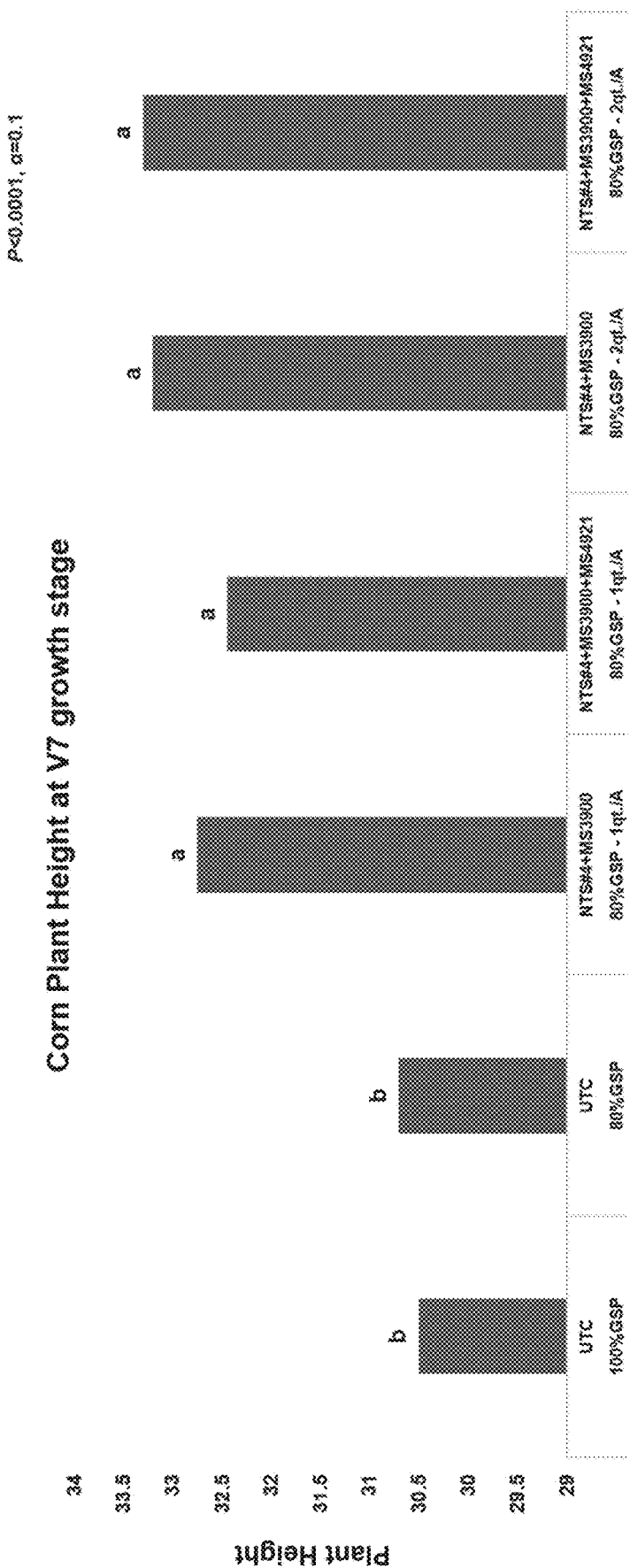
FIG. 15 is a graph depicting corn plant height across treatment conditions, measured at V7 growth stage.
Figure 16:
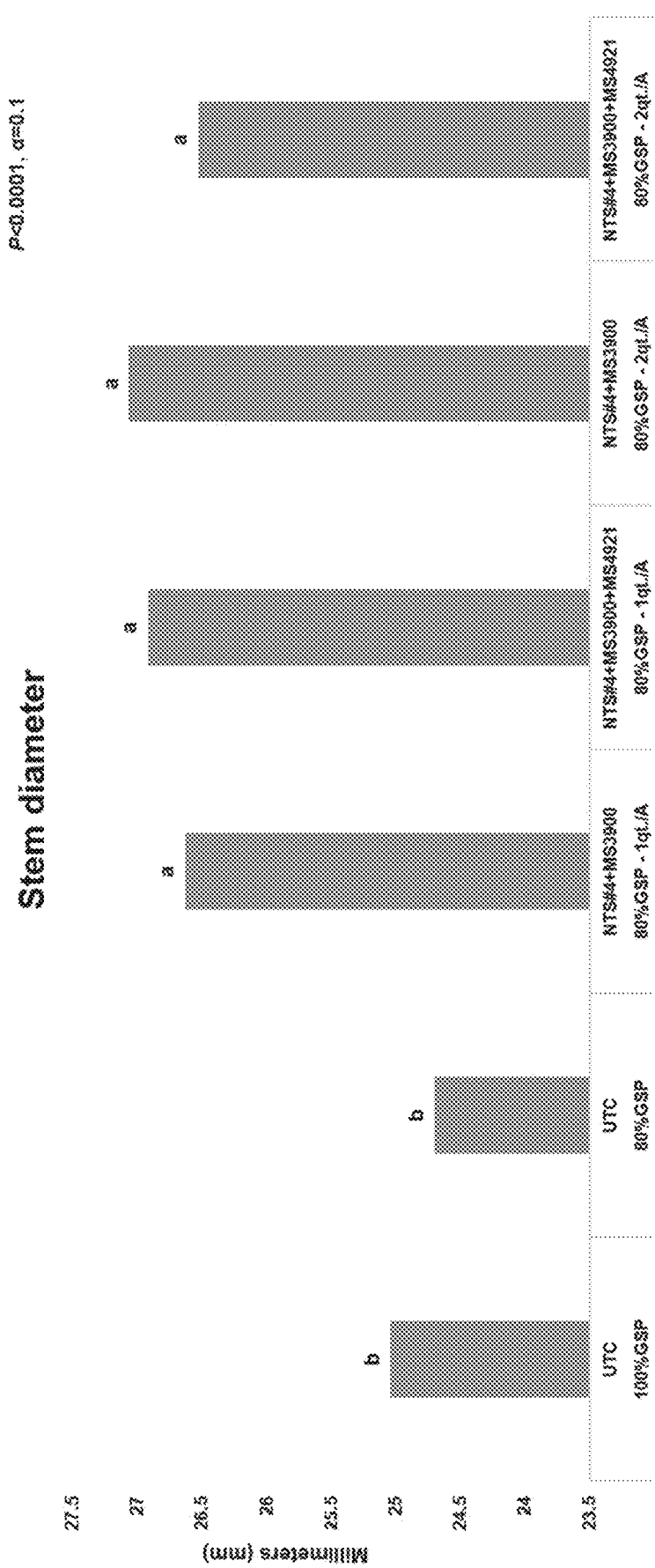
FIG. 16 is a graph depicting the stem diameter across treatment conditions.

The corn tillers were counted at vegetative 5 (V5) growth stage for each treatment. The plant heights were measured in from the soil to the leaf collar number three at V7 growth stage. The stem diameters were measured at V8 growth stage. The plant heights and stem diameters were measured in centimeters and millimeters. FIG. 14 shows number of corn tillers per plant at the V5 growth stage. The NTS treatment conditions at the 1 qt./A in-furrow application rate promoted greater tiller production (e.g., NTS #4 with MS3900, NTS #4 with MS3900 and MS4921). This may be an indication of better overall plant health and biomass production potential. FIG. 15 shows corn plant height across treatment conditions. The NTS-treated plants showed significantly increased corn plant height using either or both application rates and one or two added isolates compared to corn height from untreated control (UTC) conditions. FIG. 16 shows the stem diameter across treatment conditions. All NTS-treated plants showed increased stem diameter using either or both application rates (e.g., 1 qt./A and/or 2 qt./A) and one or two spiked isolates compared to stem diameter from UTC conditions. There were no differences among NTS treatment conditions.

Figure 17:
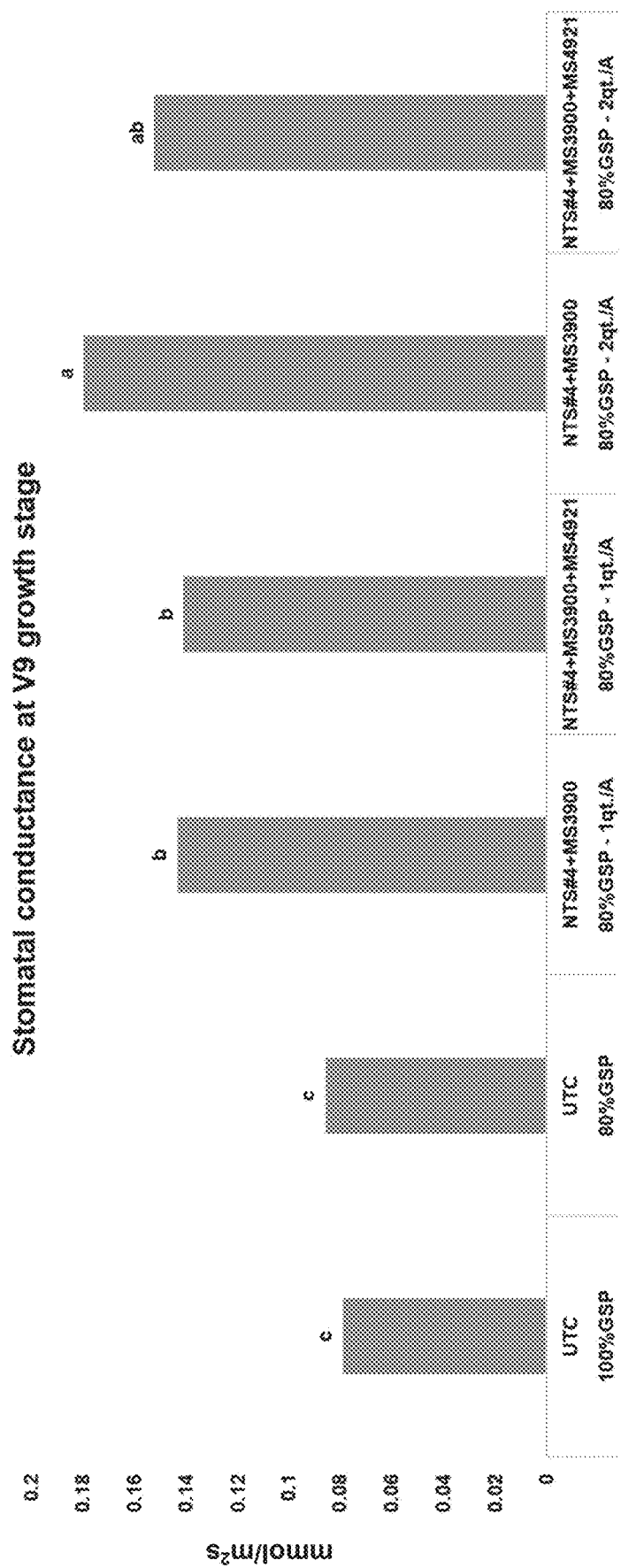
FIG. 17 is a graph depicting the stomatal conductance (the rate of $CO_2$ and $H_2O$ gas exchange) across treatment conditions in corn, at V9 growth stage.

FIG. 17 shows the level of stomatal conductance (i.e., the rate of $CO_2$ and $H_2O$ gas exchange, mmol H2O/m2/s) across treatment conditions. Across NTS-treated plants, those treated at the 2 qt./A application rate showed improved gas exchange compared to that from the 1 qt./A NTS-treated plants. All NTS-treated plant conditions showed greater stomatal conductance compared to that from UTC conditions.

Figure 18:
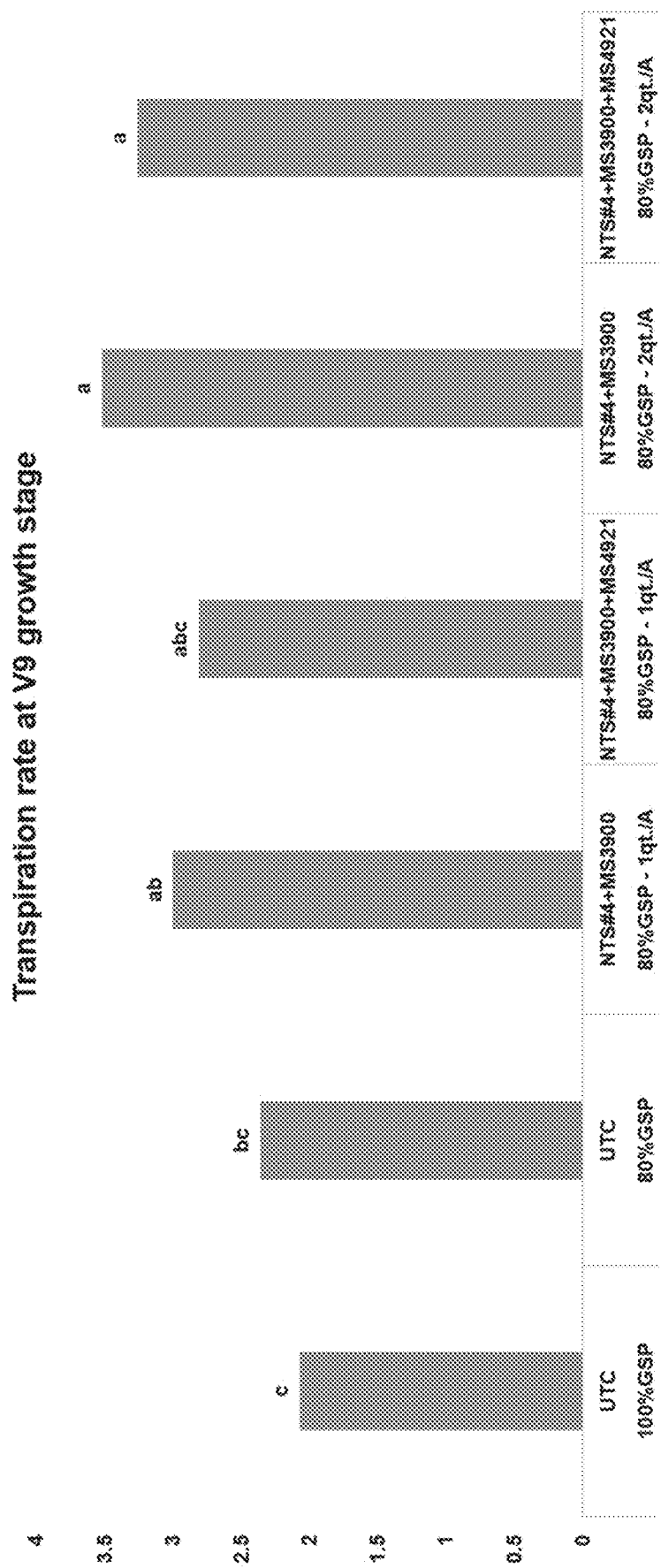
FIG. 18 is a graph depicting the transpiration rate (efficiency of water movement into and through the plant) across treatment conditions, measured at V9 growth stage in corn.

FIG. 18 shows the transpiration rate (i.e., efficiency of water movement into and through a plant, mmol H2O/m2/s) across treatment conditions. Across NTS-treated plants, those treated at the 2 qt./A application rate showed superior transpiration rates compared to those from the 1 qt./A NTS-treated plants. This trend is similar to the gas exchange results of FIG. 17. All NTS-treated plant conditions showed greater transpiration rates compared to those from UTC conditions.

Figure 19:
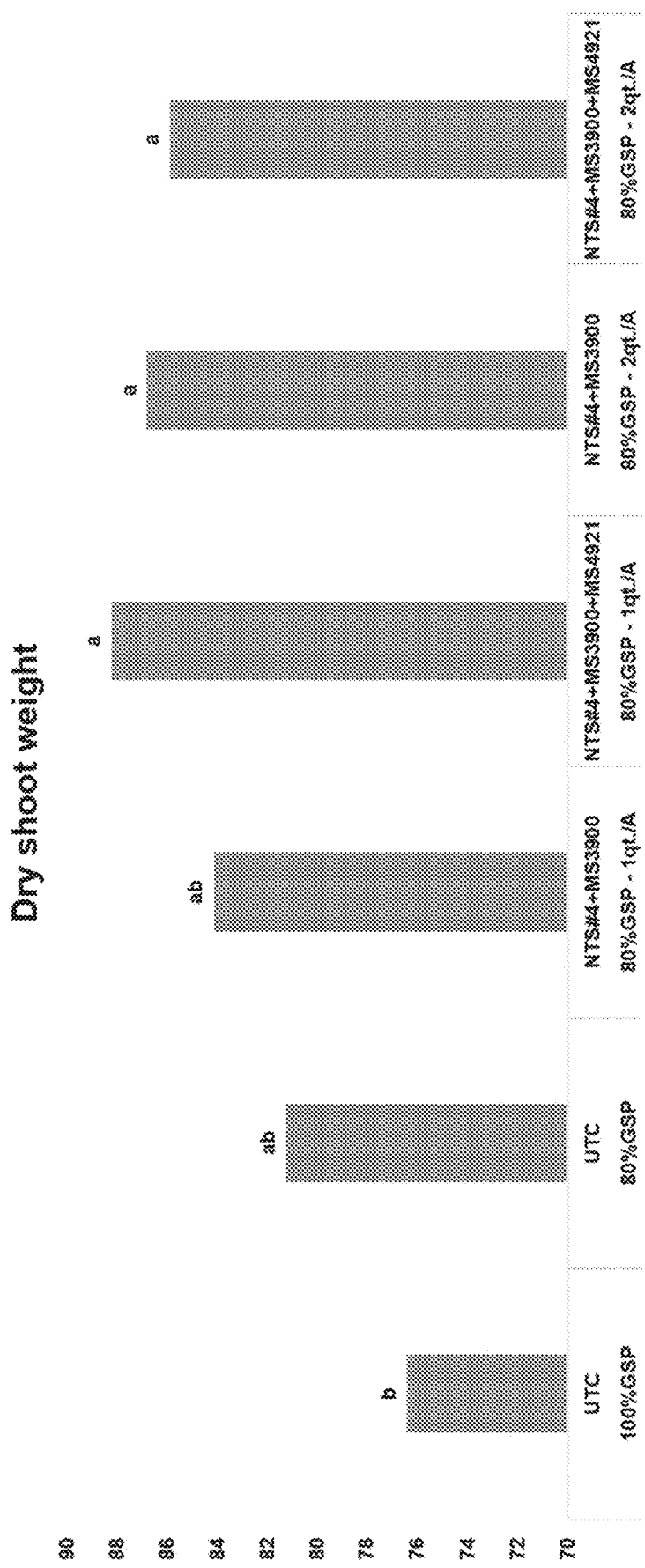
FIG. 19 is a graph depicting the corn dry biomass, measured as dry shoot weight, across treatment conditions.

FIG. 19 depicts the dry shoot weight of corn plants (e.g., corn dry biomass) across treatment conditions. The NTS-treated plants showed increased shoot dry biomass compared to that from UTC conditions.

Figure 20:
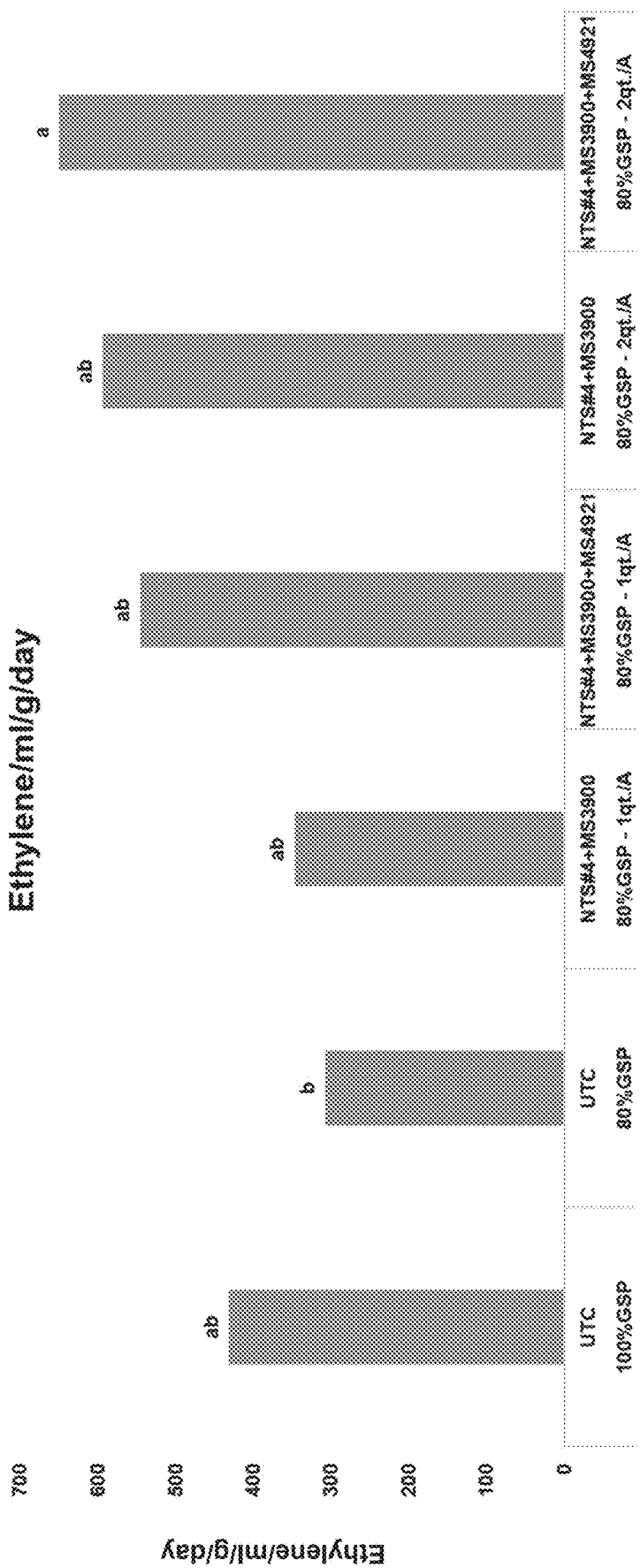
FIG. 20 is a graph depicting results of acetylene reduction in corn root/basal stem, measured across treatment conditions.

FIG. 20 shows nitrogenase activity (acetylene reduction measures) across treatment conditions (e.g., corn root acetylene reduction assay (ARA)). Acetylene reduction potentials of roots were measured as a proxy to nitrogenase activity. The NTS treatment condition with 2 qt./A application rate with both isolates (e.g., NTS #4 with MS3900 and MS4921) showed significantly increased nitrogen-fixing potential.

Example 6: Nitrogen Fixation and Plant Growth Promotion Properties of Target MS2748, MS3900, MS3907, and MS4921 Strains Table 6 shows the results of Digital DNA-DNA hybridization (DDH estimate) relatedness between MS3907 and six closely related species or strains. DNA-DNA relatedness using DDH values of greater than 70% indicate strains belong to the same species and greater than 79% may indicate strains that belong to the same sub-species. The probabilities that MS3907 is in the same species or subspecies as the comparator strains was also calculated.

TABLE 6

Results of the DNA-DNA Hybridization Test for MS3907 strain

| Comparator strains | DDH estimate [confidence interval] | Probability that DDH >70% (i.e., same species) | Probability that DDH >79% (i.e., same subspecies) |
| --- | --- | --- | --- |
| *Paenibacillus borealis* DSM 13188 | 29.90% [27.5-32.4%] | 0.1% | 0.04% |
| *Paenibacillus* sp. FSL P4-0081 | 29.70% [27.4-32.2%] | 0.09% | 0.04% |
| *Paenibacillus* sp. FSL R5-0912 | 29.90% [27.5-32.4%] | 0.1% | 0.04% |
| *Paenibacillus silagei* DSM 101953 | 25.50% [23.1-28%] | 0.01% | 0.01% |
| *Paenibacillus tritici* LMG 29502 | 26.80% [24.4-29.3%] | 0.02% | 0.01% |
| *Paenibacillus rhizoplanae* DSM 103963 | 25.60% [23.2-28%] | 0.01% | 0.01% |

Genes for N-fixation and siderophore production were found in MS3907. The ipdC gene was absent, but IAA activity was measured. This may result due to that the IAA production in MS3907 is via the indole-3-acetamide (IAM) pathway and not the IPyA pathway.

TABLE 7

Exemplary Genes of MS3907

| Function | Representative gene | Number of gene copies | Specific function |
| --- | --- | --- | --- |
| Nitrogen fixation | nifH | 1 | Nitrogenase pathway |
| Auxin/IAA production (IPyA pathway) | ipdC | Absent | indolepyruvate decarboxylase, IAA synthesis, Blasted against the MS3907 genome to double check. * |
| Production and capture of siderophores for iron acquisition | fhuB | 2 | Ferrichrome transport and production system pathway |
| | asbA | Absent | siderophore biosynthesis protein, petrobactin, catechol-type siderophore |
| Plant Abiotic stress mitigation | accd | Absent | 1-aminocyclopropane-1-carboxylate (ACC) deaminase |

MS3907 that was grown as a single-isolate bacterial culture in nitrogen-free nutrient media showed nitrogenase activity more than a negative control in the acetylene reduction assay (Table 8). The N-free medium was prepared by adding 10 mL of the base inoculum (e.g., PST WB or PwST WB), 0.2 g of D-glucose, 0.2 g of di-sodium DL-malate, 0.2 g of soluble starch, 0.2 g of D-mannitol, and 0.4 g of Noble agar to 90 mL of Type I water. The media was then adjusted to pH 7.0 and sterilized by autoclaving before being aseptically dispensed into 21 mL screw-cap vials (MilliporeSigma, Burlington, MA). An overnight culture of MS3907 (200 uL) in Tryptic Soy Broth (MilliporeSigma, Burlington, MA) was diluted into 9 mL of sterile 0.1% HMP buffer and vortexed to mix. This diluted culture preparation was used to inoculate the vials containing 5 mL of N-free medium by dropping the diluted culture onto the media below. A sterile 10 uL loop was then used to stab the agar in the vial. Vials were re-capped with sterile foil and incubated at room temperature (~22° C.) at 150 rpm for 3 days. Un-inoculated vials were also incubated to serve as negative controls (UTC). After 3 days, vials were removed from incubation and sealed with 18 mm magnetic screw-top caps with septa (MilliporeSigma, Burlington, MA). Then, 2.2 mL of headspace gas was withdrawn from each vial and 1.5 mL of pre-warmed acetylene and 0.7 mL of air were injected. Vials were re-incubated at room temperature (~22° C.) at 150 rpm for 72 hours before loading directly into the GC for analysis. The instrument used for analysis was an Agilent 8890 GC/MS equipped with a flame ionization detector (FID) and an $Al_2O_3$ column ($Na_2SO_4$ deactivated) with Helium as carrier gas (2 ml/min). The injector was set at 200 C and 0.5 mL of sample was injected for analysis. The FID detector was set at 250° C. and the oven at 40° C. for 2 minutes, followed by 40-140° C. at 40° C./minute.

TABLE 8

N-fixing activity for MS3907

| N-fixing activity proxy | Negative control (blank) | MS3907 Rep 1 | MS3907 Rep 2 |
|---|---|---|---|
| Ethylene Production (Relative Concentration) | 1,775 | 3,644 | 11,010 |

Figure 21A:
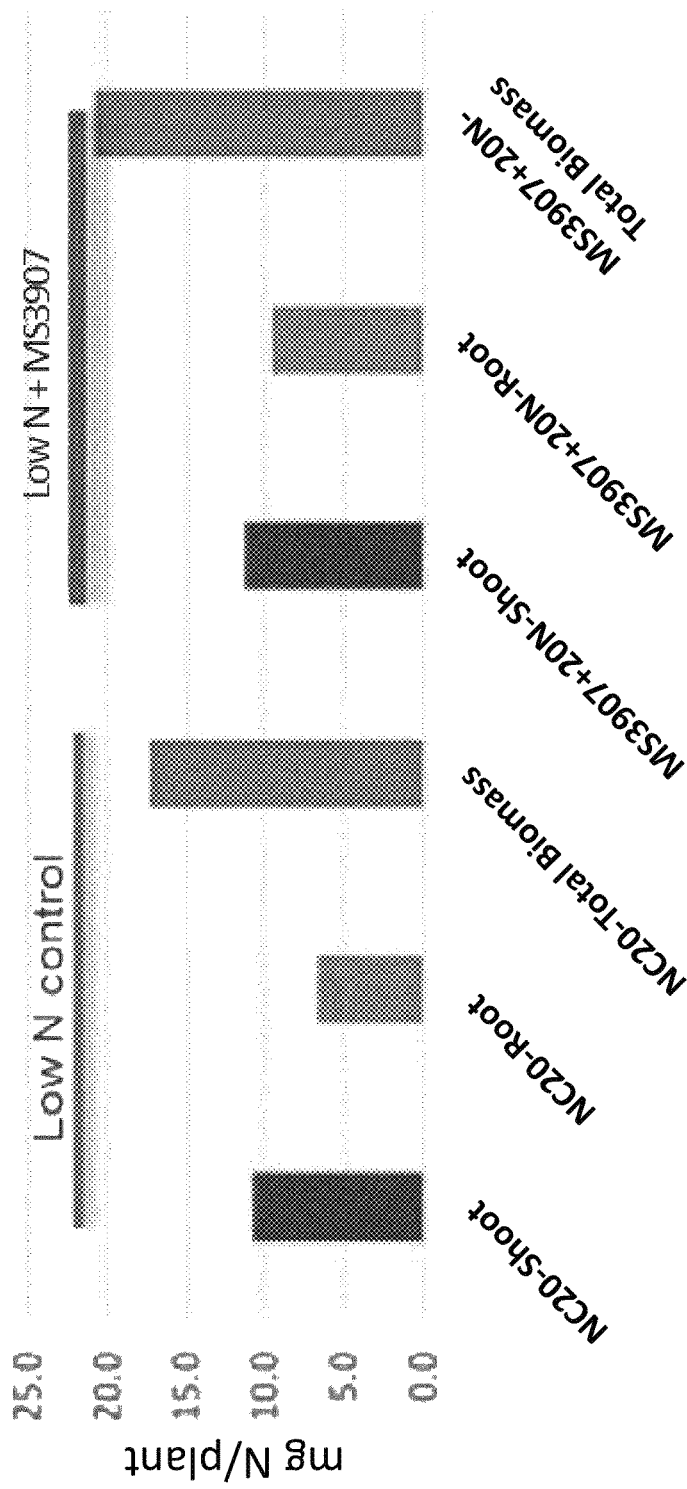
FIGS. 21A-21B show increased plant nitrogen content in plants treated with MS3907.
Figure 21B:
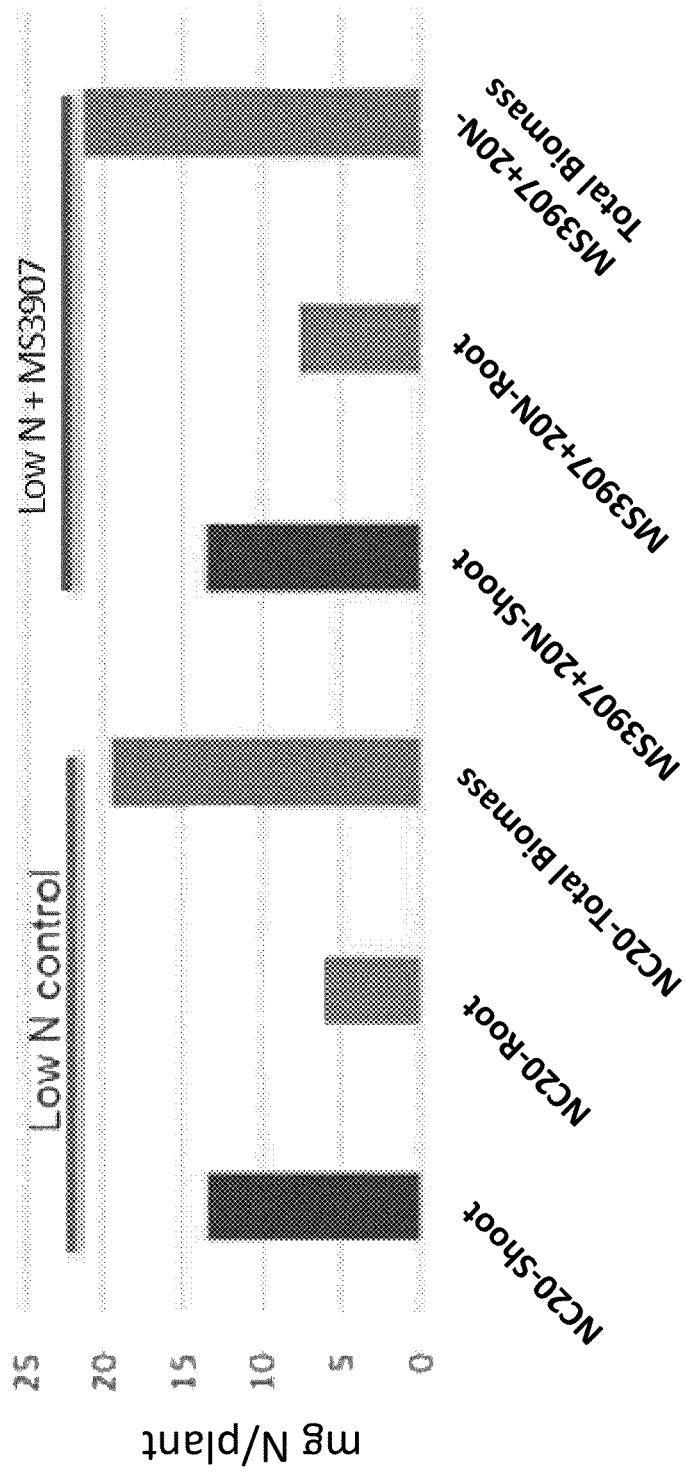

The total nitrogen content in corn and sorghum was positively affected by MS3907 treatments (FIGS. 21A-21B). Corn and sorghum grain seed were sown (3 seeds and 15 seed respectively) in pots of a sandy loam soil in the greenhouse, treated with 10 mL of the MS3907 spores in sterile water at $10^4$ CFU/mL or just sterile water (NC20, negative control 20 mg N), and seeds were covered with a thin layer of soil. Plants were thinned after 1 week. Fertilization was 100 ml Hoagland's+200 mg KH2PO4 with 470 µl UAN-32/L (for 20 mg N per pot) applied after thinning and 100 ml Hoagland's without N/pot per week (1.34 g/L solution from second week). Plants were harvested after 5 weeks. N-uptake/content was measured by tissue nitrogen analysis of the root and shoot.

Table 9 shows the results of Digital DNA-DNA hybridization (DDH estimate) relatedness between MS3900 and *Bacillus megaterium* strain ATCC 14581.

TABLE 9

Results of the DNA-DNA Hybridization Test for MS3900 strain

| Comparator strain | DDH estimate [confidence interval] | Probability that DDH >70% (i.e., same species) | Probability that DDH >79% (i.e., same subspecies) |
|---|---|---|---|
| *Priestia megaterium* type strain ATCC 14581 | 73.80% [70.7-76.6%] | 84.18% | 35.8% |

MS3900 was found to have strong phosphate solubilizing capacity and was capable of growing on N-free nutrient medium. MS3900, MS4921, MS2748, and MS3907 strains were streaked onto Hydroxylapatite Ca5(PO4)3OH media (per L: Glucose 10 g, Hydroxylapatite 4.0 g, NaCl 1 g, MgSO4·7H2O 2 g, NH4Cl 5 g, agar 15 g, bromophenol blue 0.25% 5 mL pH indicator). Microbes with a strong capacity for inorganic, insoluble phosphate solubilization could grow in the nutrient media. MS3900 and MS2748 showed growth due to strong phosphate solubilization.

TABLE 43

Results of the DNA-DNA Hybridization Test for MS2748 strain

| Comparator strain | DDH estimate [confidence interval] | Probability that DDH >70% (i.e., same species) | Probability that DDH >79% (i.e., same subspecies) |
|---|---|---|---|
| *Bacillus megaterium* strain ATCC 14581 | 70.80% [67.8-73.6%] | 79.68% | 30.18% |

Figures 22A, 22B:
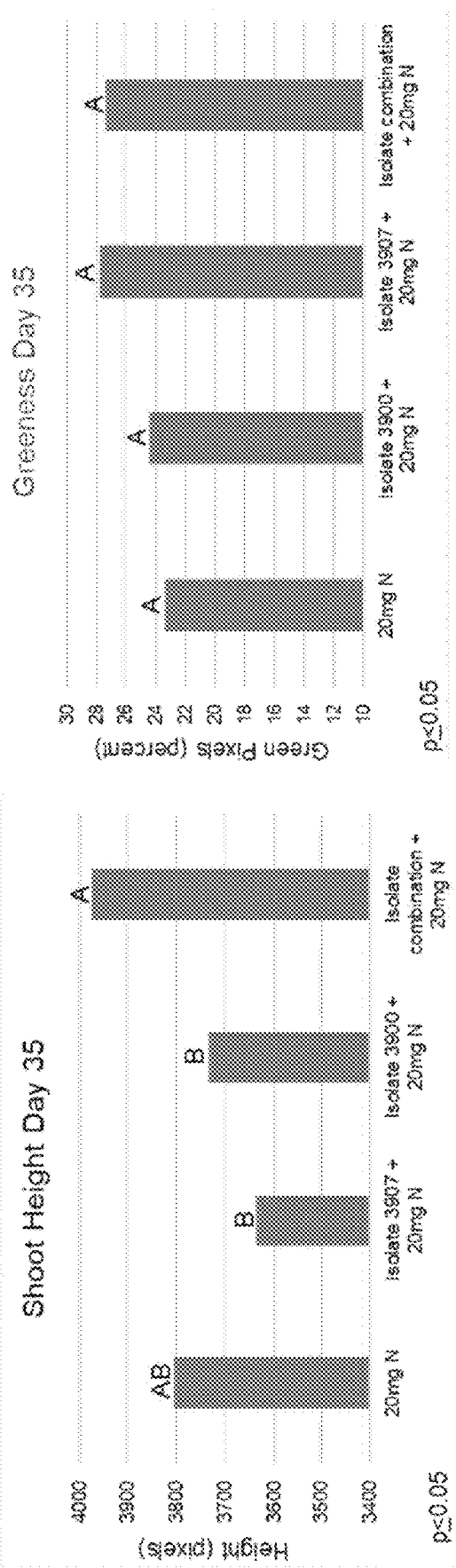
FIGS. 22A-22B show the plant growth promotion traits following treatment with MS3900, MS3907, or both isolates.

As assay was developed to determine if MS3907 and MS3900 were endophytes of corn. Isolates were inoculated onto corn seeds. Seedlings were then grown in a sterile system. Roots were then removed and externally sterilized. Root segments were placed on a nutrient media. Roots were placed either directly (with all root-associated microbes) or surface sterilized before placing on medium (putative endophytes). MS3907 and MS3900 were both found to be root colonizers and endophytes. In a greenhouse test in sorghum grain (as described herein), seeds were treated with 10 mL per pot of sterile water, Isolate MS3907, Isolate MS3900 or Isolates MS3907 and MS3900 in combination together at $10^5$ CFU each. Shoot height and greenness were measured using a Confluence plant Gazer imaging system (Des Moines, IA) using the sideview pixels along the central axis and percent green pixels, respectively. The combination of isolates (MS3907+MS3900) led to improved plant growth under low nitrogen (FIGS. 22A-22B).

Bacterial strain MS4921 was isolated. Genomic sequence analysis indicates that MS4921 is a strain of the species *Paenibacillus sonchi*. MS4921 is a nitrogen fixing strain. MS4921 was found to be a spore former, capable of colonizing corn roots, capable of promoting plant growth in low nitrogen conditions, an endophyte, and is free of any toxin genes or genes that encode for antibiotics currently used in human health.

Table 10 shows the results of Digital DNA-DNA hybridization (DDH estimate) relatedness between MS4921 and six closely related species or strains.

TABLE 10

Results of the DNA-DNA Hybridization Test for MS4921 strain.

| Comparator strains | DDH estimate [confidence interval] | Probability that DDH > 70% (i.e., same species) | Probability that DDH > 79% (i.e., same subspecies) |
|---|---|---|---|
| *Paenibacillus sonchi* genomovar *Oryzarum* (strain CAS34 T) | 78.50% [75.6-81.2%] | 89.39% | 45% |
| *Paenibacillus sonchi* genomovar *Riograndensis* (strain SBR5 T) | 77.00% [74-79.7%] | 87.94% | 42.04% |
| *Paenibacillus sonchi* genomovar *Sonchi* (strain X19-5 T) | 72.50% [69.5-75.3%] | 82.4% | 33.38% |
| *Paenibacillus sonchi* (strain IIRRBNF1) | 72.00% [69-74.8%] | 81.62% | 32.4% |

TABLE 10-continued

Results of the DNA-DNA Hybridization Test for MS4921 strain.

| Comparator strains | DDH estimate [confidence interval] | Probability that DDH > 70% (i.e., same species) | Probability that DDH > 79% (i.e., same subspecies) |
|---|---|---|---|
| *Paenibacillus jilunlii* (strain 23019$^T$) | 51.20% [48.5-53.8%] | 22.46% | 4.68% |
| *Paenibacillus graminis* (strain DSM 15220$^T$) | 47.50% [44.9-50.1%] | 12.93% | 2.73% |

Genes for N-fixation and siderophore production were also found in MS4921 (Table 11).

TABLE 11

Exemplary Genes of MS4921

| Function | Representative gene | Number of gene copies MS4921 | Number of gene copies MS3907 | Specific function |
|---|---|---|---|---|
| Nitrogen fixation | nifH | 1 | 1 | Nitrogenase pathway |
| Auxin/IAA production (IPyA pathway) | ipdC | Absent | Absent | indolepyruvate decarboxylase, IAA synthesis, |
| Production and capture of siderophores for iron acquisition | fhuB | 1 | 2 | Ferrichrome transport and production system pathway |
|  | asbA | 2 | Absent | siderophore biosynthesis protein, petrobactin, catechol-type siderophore |
| Plant Abiotic stress mitigation | accd | Absent | Absent | 1-aminocyclopropane-1-carboxylate (ACC) deaminase |

Example 7: Optimization of NTS Process Design

Determination of Aeration and WB Ratio

A shake flask study was designed to understand process environment optimization for target isolate MS3907. The study looked at both aerobic (high aeration) and anaerobic (low aeration) fermentations. The shake flasks were set for seven days shaking at 200 rpm for aerobic shake flasks and both 100 and 50 rpm for anaerobic at 30° C. Two-hundred-and fifty-mL flasks were used and the total working volume for aerobic conditions were 100 mL and 200 mL for anaerobic. The main hydraulic source for these experiments was water with an electrical conductivity range of 250-450 uS/cm. A microbial inoculum used for enrichment of nitrogen use efficiency bacteria and metabolites, PST WB at different ratios of floc:supernatant were used and applied at a v/v rate. Spore preps of target isolate MS3907 were used at a 2% v/v inoculum rate. Additional inputs such as soy flour, glucose, and ammonium sulfate were incorporated at 1.5%, 1.0%, and 0.1% v/v rate, respectively. The experiment looked at the survivability of the target isolate MS3907 as the sole target isolate in the shake flask or in combination with MS3900 in the shake flask when combined with the PST WB mixed consortium. Table 12 shows a list of treatments.

TABLE 12

List of treatments for shake flask study

| Internal Code | Aeration | RPM | PST WB ratio (Floc:SPN) |
|---|---|---|---|
| A | Anaerobic | 50 | 1:1 |
| B | Anaerobic | 50 | 2:1 |
| C | Anaerobic | 50 | 1:9 |
| D | Anaerobic | 50 | 0:1 |
| E | Anaerobic | 100 | 1:1 |
| F | Anaerobic | 100 | 2:1 |
| G | Anaerobic | 100 | 1:9 |
| H | Anaerobic | 100 | 0:1 |
| I | Aerobic | 200 | 1:1 |
| J | Aerobic | 200 | 2:1 |
| K | Aerobic | 200 | 1:9 |
| L | Aerobic | 200 | 0:1 |

After seven days, shake flask solutions were streaked out on quarter-strength Tryptic Soy Agar (Difco, TSA). Plates were incubated for 7 days at 30° C. Isolate MS3907 showed an improved recovery under anaerobic conditions (50 and 100 rpm) with a PST WB ratio of 0:1 Floc:SPN.

Figure 23:
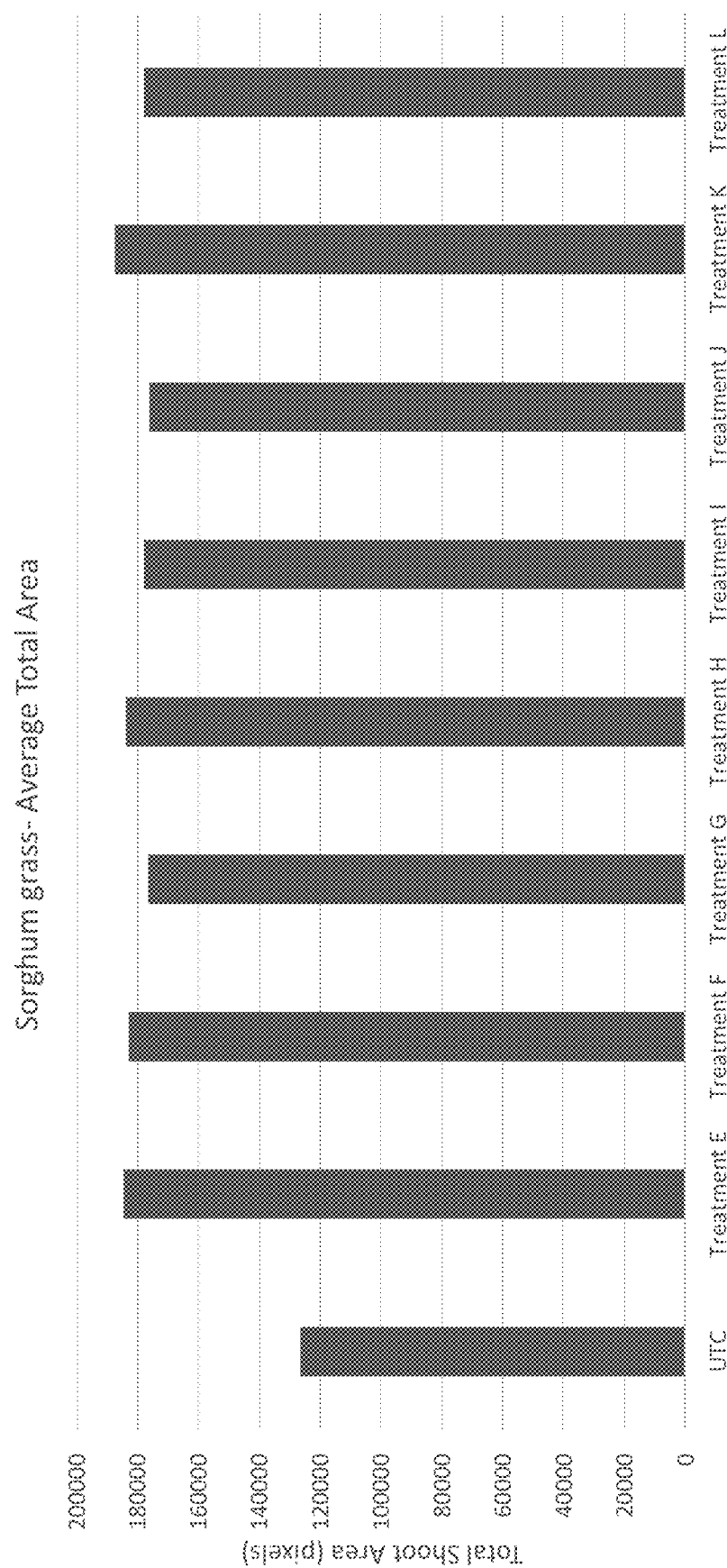
FIG. 23 shows results from the sorghum grass study testing shake flasks using isolates with different aeration. All treatments showed significantly more leaf area than that of untreated control (UTC). ANOVA student's t-test ($p<0.05$) Levels not connected by same letter are significantly different.

The shake flask solutions described above were tested in sorghum grass. A greenhouse rapid test was set up to evaluate the plant growth promotion of the shake flask solutions under no N-fertilization. The growing medium for this experiment was isolite: Berger BM6 potting mix at a 9:1 ratio v/v into a 4×4×3.75" size pots. A total of sixteen seeds were sown per pot with thinning to the lowest germination number after one week. Seeds were placed over the surface of the potting mix and a total of 10 mL per treatment were applied to the top of the seeds. The seeds and application were then covered with 100 mL of potting mix. Experiment took place in the greenhouse and were watered from bottom up from a saucer. Within the first week (5-7 days) pots were thinned to a minimum 9 per pot. Plants were then fertilized with 100 mL containing 0.0402 grams of Hoagland's without N and 0.2 grams of KH2PO4. The plants were then imaged after 14 days. A total of 10 replicates per treatment were used. Imaging data was used as the main metric to evaluate plant growth promotion. After 14 days, all treatments showed significantly more leaf area compared to that from the untreated control (FIG. 23).

Figure 24:
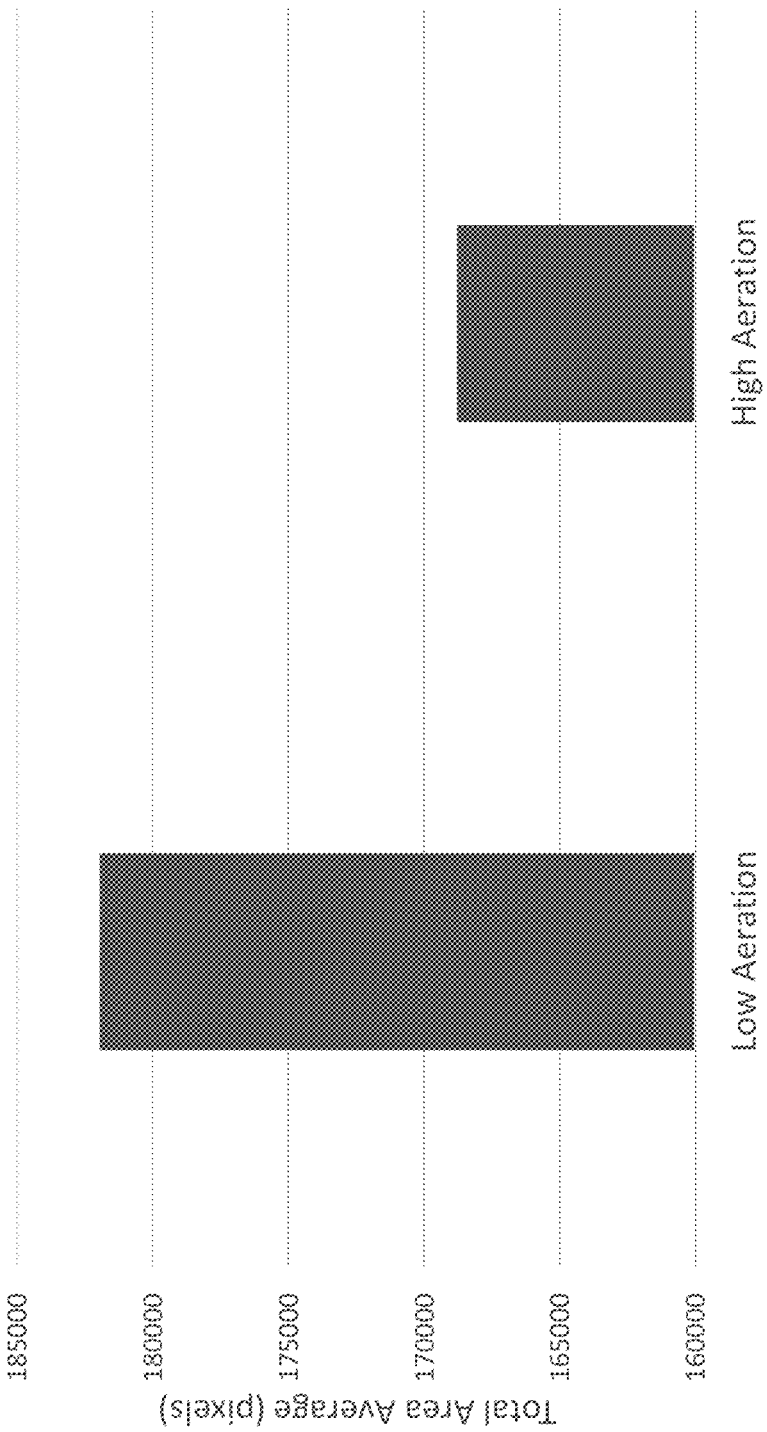
FIG. 24 shows average pixel shoot area when shake flasks performance is grouped by aeration conditions.

Treatments were then analyzed for trends. Total shoot area performance for the shake flasks were grouped by the type of aeration. Shake flasks E-H solutions were generated under anaerobic conditions (e.g., low aeration) while shake flasks I-L were generated under aerobic conditions (e.g., high aeration). The low aeration grouped shake flasks showed greater average pixel shoot area compared to that from high aeration grouped shake flasks (FIG. 24).

Figure 25:
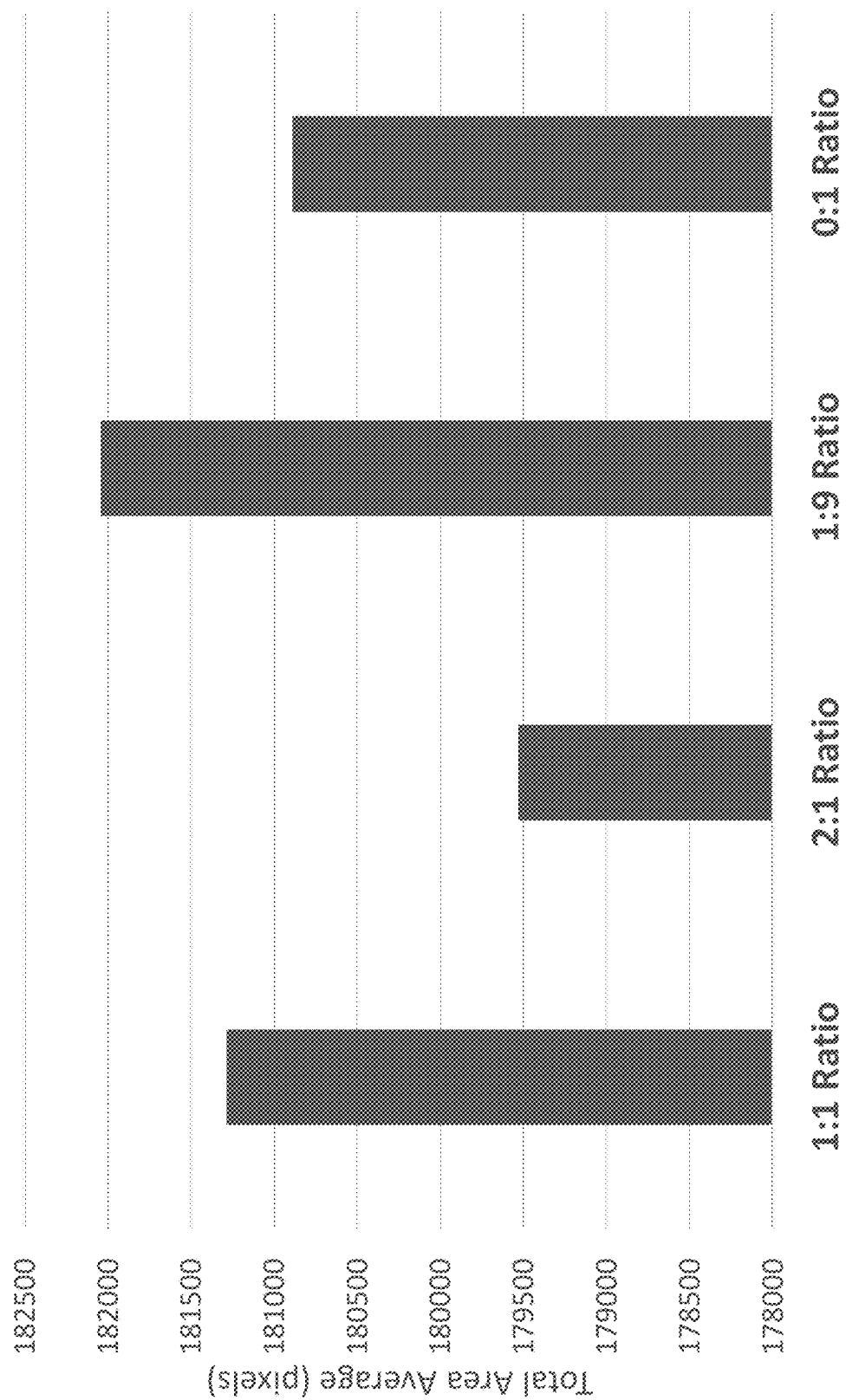
FIG. 25 shows average performance of shake flasks when different ratios of PST WB are used. Shake flask treatments were grouped based on the ratio of PST WB used under both aerobic and anaerobic conditions.

Shake flask treatments were also grouped based on the ratio of PST WB used under both aerobic and anaerobic conditions. The ratios of PST WB were 1:1 PST WB, 2:1 PST WB, 1:9 PST WB, and 0:1 PST WB. The treatment with 1:9 PST WB ratio showed numerically higher plant growth promotion over other treatments (FIG. 25).

Target isolate MS3907 was able to be recovered from anaerobic shake flasks at both 50 and 100 rpm with a PST WB of 0:1 floc:SPN. When the shake flasks solutions were looked at for plant growth promotion in sorghum grass, all shake flasks at either fermentation aeration or PST WB inoculum ratio performed significantly better than the untreated control. When treatments were grouped by fermentation aeration, low aeration solutions trended higher in more shoot biomass pixels than high aeration treatments. When shake flask treatments were grouped by PST WB ratio, all treatments performed similar with treatments with 1:9 PST WB ratio had numerically higher plant growth promotion over other treatments. Based on the information, a system with low aeration (anaerobic) and a higher proportion of SPN in the WB, will provide favorable conditions when applied to a serialized system to retain and probably enrich target isolate MS3907 as well as to generate an output solution with NUE and PGP properties.

Determination of PST Component Utilization

A parallel shake flask experiment was set up looking at different components of the PST as microbial inoculums for NUE enrichment. PST WB (1:1) floc:SPN was used as well as PST SPN alone and incorporated in a similar manner to the previous shake flask experiment at 1.0% v/v. The study looked at both aerobic and anaerobic fermentations. The shake flasks were set for seven days shaking at 200 rpm for aerobic shake flasks and both 100 and 50 rpm for anaerobic at 30° C. Two-hundred- and fifty-mL flasks were used and the total working volume for aerobic conditions were 100 mL and 200 mL for anaerobic. The main hydraulic source for these experiments was water with a conductivity range of 250-450 uS/cm. A microbial inoculum used for enrichment of nitrogen use efficiency bacteria and metabolites, PST WB at different ratios of floc:supernatant were used and applied at a v/v rate. Spore preps of target isolate MS3907 were used at a 1% v/v inoculum rate. Additional inputs such as soy flour, glucose, and ammonium sulfate were incorporated at 1.5%, 1.0%, and 0.1% v/v rate, respectively.

Anaerobic conditions favored an enrichment of the nifH component with both the WB (1:1) component as well as the SPN only. When PST SPN only was used as the main microbial inoculum, there was an increase in nifH gene detected per ng DNA when the target isolates MS3907 and MS3900 were not present.

The purpose of the experiment was to understand the optimization of the conditions and environments that could select for enrichment of nitrogen use efficiency (NUE). Under anaerobic conditions, there is a clear enrichment of nifH per ng DNA when compared to the aerobic counterparts. When the solutions were tested for acetylene reduction, there was higher activity under anaerobic shake flask with PST SPN as the microbial inoculum. A reduction of the ratio of the WB (1:1) may be ideal for enrichment of NUE by increasing the SPN content in the microbial inoculum.

Characterization of NTS Batch System and Effects of Batch System Product on Plant Growth Promotion Two separate systems NTS-PT1 and NTS-PT2 (e.g., NTS batch systems) were developed for production of nitrogen use efficiency promoting products by digestion of organic feedstock. These two systems were down-flow systems and ran between 7-10 days. Each system included one 5-gallon reactor chamber. A water tank was connected to the system to provide continuous flow of water to the reactor at an electrical conductivity ranging from 250-450 microsiemens/centimeter (μS/cm). The water tank comprised water from a city water source and a reverse osmosis (RO) water source. The reactor of the NTS-PT1 and NTS-PT2 systems were fluidized bed reactors, which lacked scaffolding. In some cases, the working fluid in each reactor is recirculated from the bottom of the reactor and pumped back to just below the surface of the same reactor to maintain homogeneous conditions within the working solutions. Diagrams of the NTS-PT1 and NTS-PT2 systems are shown in FIGS. 67A and 67B.

In each of NTS-PT1 and NTS-PT2, glucose and ammonium sulfate were added to the batch system to maintain a concentration range of 0.2-2.0% w/v and 0.02-0.2% w/v, respectively. A concentration range of 0.5-4.5% v/v of PST WB (in a ratio of 1:1 floc:supernatant (SPN)) was also added NTS-PT2 and concentration range of 0.5-4.5% v/v of the PST SPN was added to the NTS-PT1. Soy flour was added to the batch system at a concentration range of 0.2-3.0% w/v.

The produced NTS-PT1 base products had a pH range of 4.0-8.0 during the batch process. The produced NTS-PT2 base products had a pH range of 3.8-8.0 during the batch process. No buffer and/or pH adjustment was implemented during the fermentation process. In the NTS-PT1 batch system, the dissolved oxygen range was 0.19-0.9 mg/L during the batch process. In the NTS-PT1 batch system, the dissolved oxygen range was 0.12-0.7 mg/L during the batch process.

Acetylene reduction assays were conducted from the output solutions of the NTS-PT1 and NTS-PT2 systems. Methods were similar as to those in Example 11. The products of both systems showed N-fixing capacity (FIG. 68).

A rapid greenhouse assay experiment was set up to evaluate the efficacy of the NTS-Batch systems PT-1 and PT-2 in a nitrogen-free fertilizer system. Corn was planted in 4×4 inch pots with a soil medium consisting of 1:1:1 mixture of Turface: sifted Whitesboro (local town) soil; and ProMix. Three seeds were planted initially and later thinned to one seed following treatment. The treatments were diluted to 16 ml/L or 32 ml/L. The diluted treatments were added at the rate of 0.5 ml per pot directly over the seeds prior to covering them with soil and this resulted in rates of 2 qt/acre and 4 qt/acre. For fertilization, 4.02 g/L N-free Hoagland's+2 g/L $KH_2PO_4$ was delivered at a rate of 100 ml per pot at planting time. Done only once during the experiment. Pots were watered from the top of the pot when needed. The experiment ran for 14 days and leaf area using a plant imaging system was used as the main metric for promotion of plant growth over the UTC. Images were taken at 10 and 14 days of the experiment and the NTS-PT1 and NTS-PT2 were evaluated at rates of 2 qt/acre and 4 qt/acre.

Figure 69A:
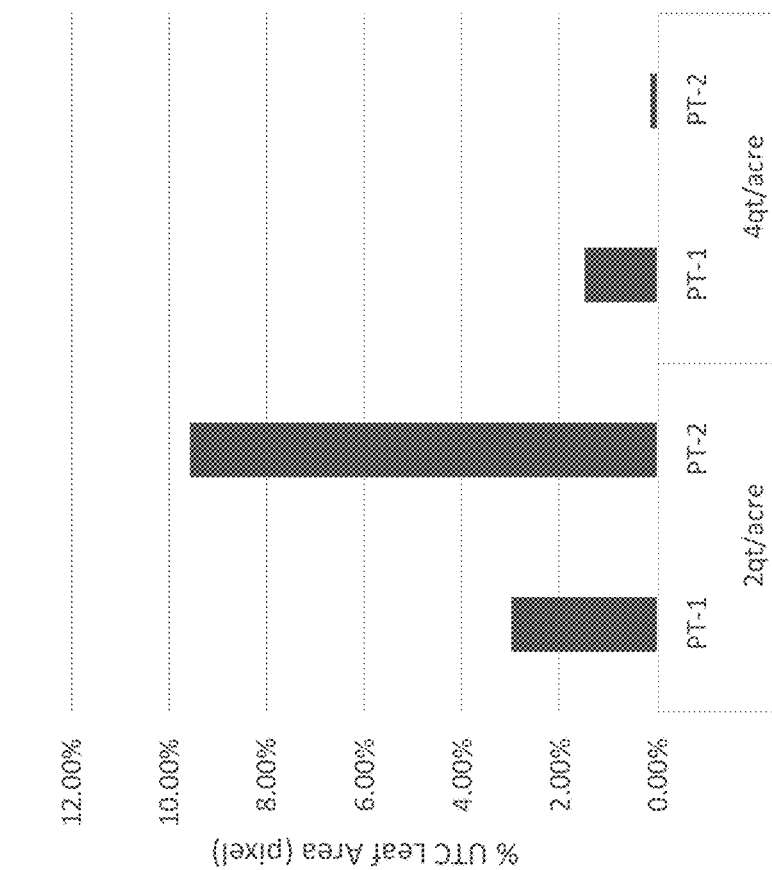
FIGS. 69A-69B show two graphs with results from a plant growth promotion test of the PT1 and PT2. Products of the NTs batch system were applied at 2 qt/acre or 4 qt/acre. On both Day 10 (FIG. 69A) and Day 14 (FIG. 69B), PT2 showed the greatest leaf area compared to that from PT1.
Figure 69B:
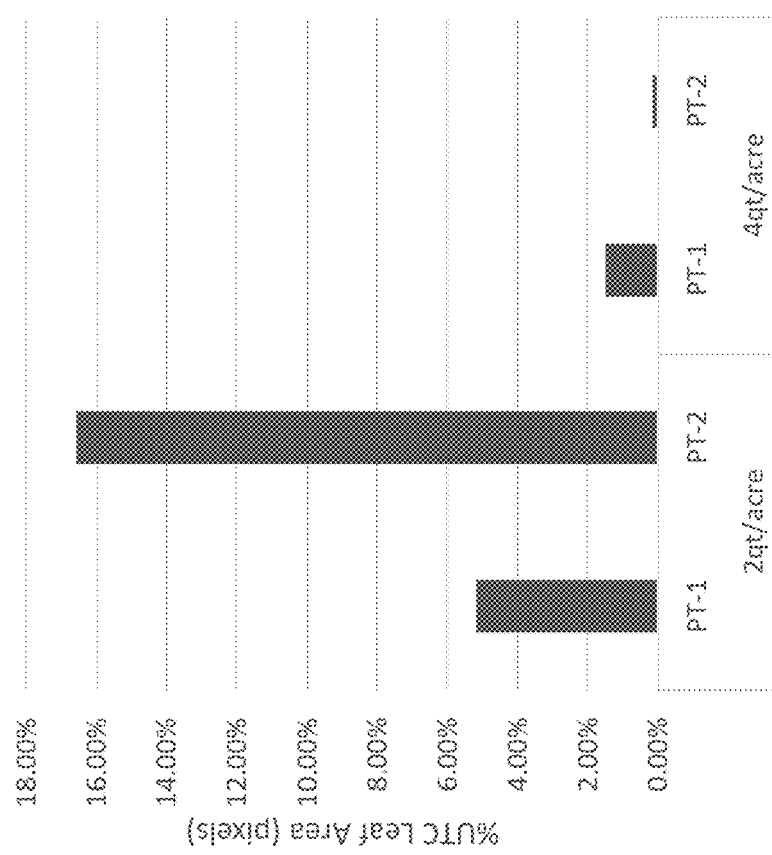

Results showed both batch systems having greater leaf area in both imaging times over the untreated control. Both systems performed better at the 2 qt/acre rate at the Day 10 and Day 14 timepoints (FIGS. 69A-69B). NTS-PT2 at 2 qt/A showed the greatest leaf area compared to that of NTS-PT1 at 2 qt/A.

Characterization of Hydraulic Retention Time and Number of Reactors in System

The initial design of the NTS-1.0 lines consisted of three reactors: R1, R2, and the Clarifier. The initial hydraulic retention time of the systems was 7 days. The systems were tested in *Arabidopsis* for plant growth promotion. NTS-1.0 base product solutions were tested in *Arabidopsis* for plant growth promoting ability, using average leaf area (in cm2) as the primary metric. All systems were tested under two rates, 0.05% and 0.2% v/v. *Arabidopsis thaliana* (genotype Col-O) seedlings were germinated and grown for 7 days on ½ strength MS media (Murashige & Skoog Basal Medium with Vitamins, M519) plates in the growth chamber before transplanting into rockwool cubes for plant growth assays. Rockwool cubes were used as an inert substrate for growing *Arabidopsis* in a hydroponic-like system. The rockwool cubes are fitted into a 6-well tray and each treatment consisted of three replicate well trays. Nine, 1 L ½ strength MS media (Murashige & Skoog Basal Medium with Vitamins, M519) solutions were made. The test substance was then added at the rate given below in Table 13, and the pH of the solution was raised to 5.7. Forty mL of each 1 L treatment solution was dispensed to each rockwool cube. Then, each wetted cube received one *Arabidopsis* seedling. *Arabidopsis* plants grew on an LED light cart for 12 days. Leaf area was determined using the ImageJ software package. All the data collected were put through JMP for ANOVA analysis.

TABLE 13

Components of each test solution

| | | |
|---|---|---|
| 1. | ½MS Media+ | UTC |
| 2. | ½MS Media+ | 0.05% NTS-1.1 Base Product Solution (v/v) (0.5 mL/L) |

TABLE 13-continued

Components of each test solution

| | | |
|---|---|---|
| 3. | ½MS Media+ | 0.05% NTS-1.2 Base Product Solution (v/v) (0.5 mL/L) |
| 4. | ½MS Media+ | 0.05% NTS-1.3 Base Product Solution (v/v) (0.5 mL/L) |
| 5. | ½MS Media+ | 0.05% NTS-1.4 Base Product Solution (v/v) (0.5 mL/L) |
| 6. | ½MS Media+ | 0.2% NTS-1.1 Base Product Solution (v/v) (2.0 mL/L) |
| 7. | ½MS Media+ | 0.2% NTS-1.2 Base Product Solution (v/v) (2.0 mL/L) |
| 8. | ½MS Media+ | 0.2% NTS-1.3 Base Product Solution (v/v) (2.0 mL/L) |
| 9. | ½MS Media+ | 0.2% NTS-1.4 Base Product Solution (v/v) (2.0 mL/L) |

Figure 26:
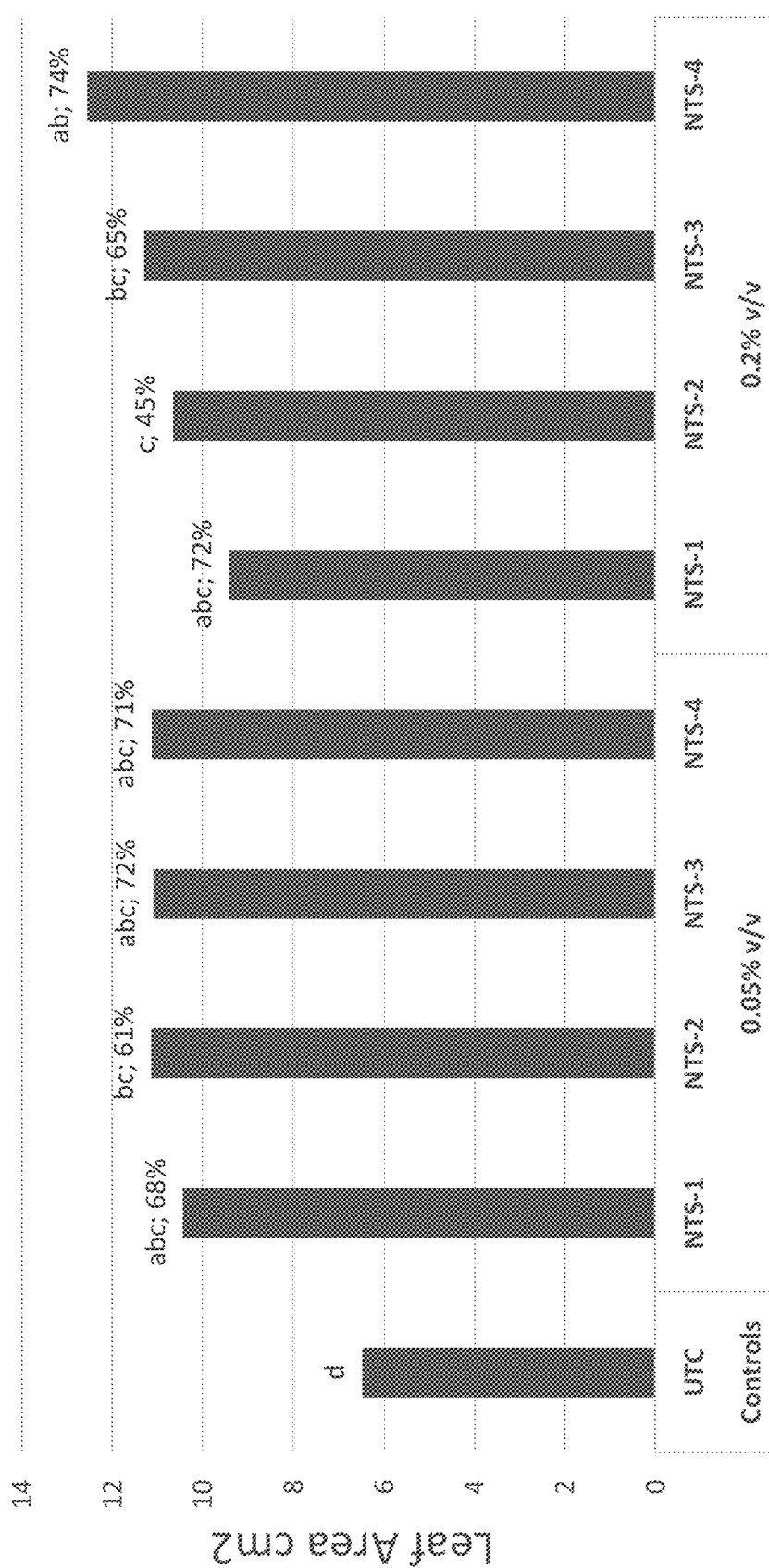
FIG. 26 shows results from an *Arabidopsis* plant growth promotion rockwool test for NTS 1.1, 1.2, 1.3 and 1.4 lines with three reactors. All treatments showed numerically greater average leaf area measurement from the UTC with all having significant plant growth promotion ($p=0.0008$).

All base product solutions across all systems showed consistent PGP activity over the UTC control (FIG. 26). All treatments showed numerically greater average leaf area measurement from the UTC with all having significant plant growth promotion (p=0.0008).

Figure 27:
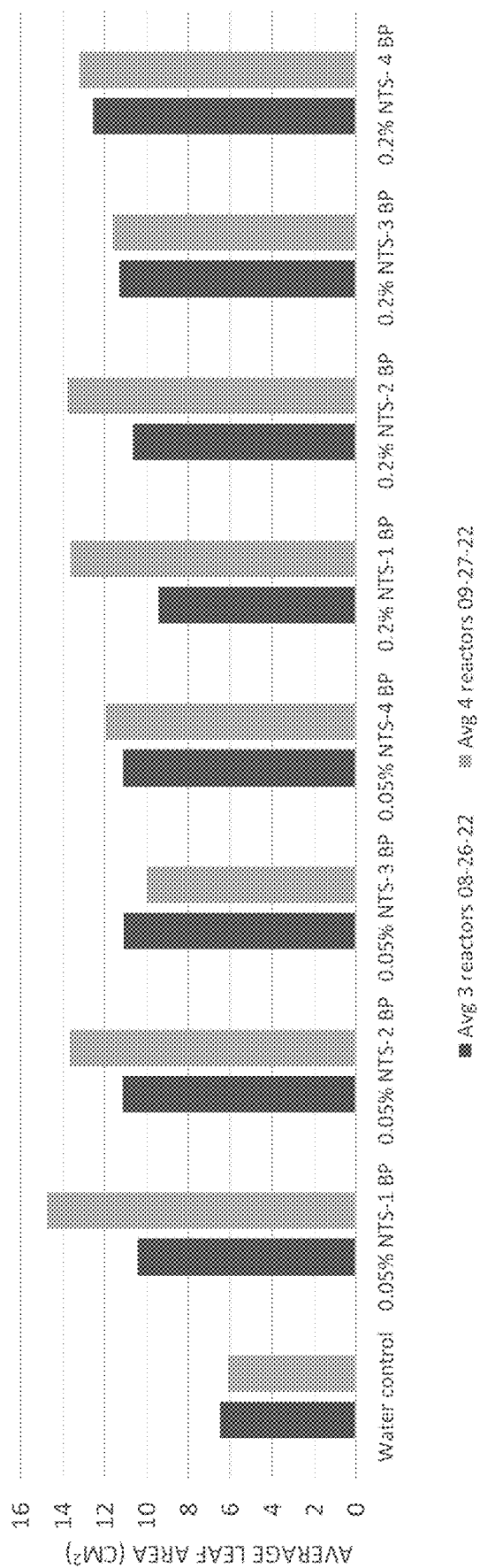
FIG. 27 shows results across NTS 1.0 systems with either three or four reactors in the system. There was a general increase of performance in the output solutions when the retention time of the system was extended by about 42.86%.

Each of the four lines received an additional reactor (R3) in the same volume as R1 and R2. This extended the hydraulic retention time of the system by about 42.86% (10 days). The solution was then tested again in *Arabidopsis* for plant growth promotion in same manner as the previous test. The additional reactor and extended hydraulic retention time showed improvements in plant growth promotion in most lines (FIG. 27). There was a general increase of performance in the output solutions when the retention time of the system was extended by about 42.86%.

Example 8: Evaluation of NTS Products with Isolates on Plant Growth Promotion and Nitrogen Use Efficiency (NUE)

The four NTS reactor products (NTS-1, NTS-2, NTS-3, and NTS-4) were spiked with MS4921 alone or MS3900+ MS4921 to $10^4$ CFU/mL each, and applied in-furrow at 36 μL/plant on corn. The tested plant was Welter Seed WS095 hybrid corn and growing medium was 1:1:1 Profile MVP® turface-peat-Denton sandy loam soil mix. The fertilizer was UAN32 (32-0-0) at 15 lbs. N/A, TSP (0-46-0) at 20 lbs. P/A, Potash (0-0-60) at 200 lbs./A and 15 lbs./A, Jackpot micronutrient fertilizer at 1 fl. oz./gal in 50 ml (0.78%) with $Na_2MoO_4 \cdot 2H2O$, 4.1 mg/pot for 12" pot mixed together. There were 10 treatments, with 15 replicates to make 150 pots total, with each pot being 15 cm round. The experiment followed a randomized complete block design and there was one plant per pot. Table 14 lists the treatments for the study.

TABLE 14

Treatment conditions

| Treatment code | Treatment | A.I. μl/15 cm pot | ml volume/seed hole | Stock solution for 20 replicates μl A.I./10 ml |
|---|---|---|---|---|
| A | RO water only | 0 | 0.5 (RO H2O only) | 0 |
| B | NTS#1 with MS3900 and MS4921 | 36 | 0.5 | 720 |
| C | NTS#1 with MS4921 | 36 | 0.5 | 720 |
| D | NTS#2 with MS3900 and MS4921 | 36 | 0.5 | 720 |
| E | NTS#2 with MS4921 | 36 | 0.5 | 720 |

TABLE 14-continued

Treatment conditions

| Treatment code | Treatment | A.I. µl/15 cm pot | ml volume/seed hole | Stock solution for 20 replicates µl A.I./10 ml |
|---|---|---|---|---|
| F | NTS#3 with MS3900 and MS4921 | 36 | 0.5 | 720 |
| G | NTS#3 with MS4921 | 36 | 0.5 | 720 |
| H | NTS#4 with MS3900 and MS4921 | 36 | 0.5 | 720 |
| I | NTS#4 with MS4921 | 36 | 0.5 | 720 |
| J | High N fertilization (+10 lbs. N/A) | 0 | 0.5 (RO H2O only) | 0 |

The 150 15 cm diameter pots were filled with the growing medium. Three corn seeds were plant 2 inches deep in each pot. 0.5 ml of treatment solution was pipetted over the seed, simulating in-furrow application and the seeds were covered with growing medium. After full emergence, plants were thinned to one plant per pot, selecting for uniform plant size. An 8 liter stock solution of fertilizer was used for treatments A-I and the amount of components is given in Table 15. All components were thoroughly mixed.

TABLE 15

Components of 8 L Stock Fertilizer Solution

| | |
|---|---|
| 50 lbs. N/A = 67 µL UAN/pot * 150 pots = 10,050 µl | 10.7 ml UAN32/8 L |
| 20 lbs. P/A = 0.084 g TSP/pot * 150 pots = 12.6 g | 13.44 g TSP/8 L |
| 200 lbs. K/A = 0.638 g potash/pot * 150 pots = 95.7 g | 102.1 g potash/8 L |
| Sodium molybdate = 4.1 mg/pot * 150 pots = 615 mg | 656 mg/8 L |
| 15 lbs. Sulfur/A = 669 mg K2SO4/pot * 150 = 100.35 g (Part of potassium is supplemented with K2SO4 | 160.6 g/8 L |
| 1 oz/gal. Jackpot micronutrients | 62.5 ml/8 L |

A 1 liter stock solution of fertilizer was used for treatment J and the amount of components is given in Table 16. All components were thoroughly mixed.

TABLE 16

Components of 1 L Stock Fertilizer Solution

| | |
|---|---|
| 15 lbs. N/A = 113 µL UAN/pot * 20 pots = 2,260 µl | 2.3 mL UAN/L |
| 20 lbs. P/A = 0.084 g TSP/pot * 20 pots = 2.52 g | 2.5 g TSP/L |
| 200 lbs. K/A= 0.638 g potash/pot * 20 pots = 12.76 g | 12.8 g potash/L |
| Sodium molybdate = 4.1 mg/pot * 20 pots = 82 mg | 82 mg/L |
| 15 lbs. Sulfur/A = 669 mg K2SO4/pot * 20 pots = 13.4 g (Part of potassium is supplemented with K2SO4) | 13.4 g/L |
| 1 oz/gal of Jackpot micronutrients | 7.8 ml/L |

The fertilizer was applied 50 ml per pot after thinning. Plants were randomized and arranged into RCBD design with 15 blocks. The plants were watered with RO water as necessary. The experiment duration was 4 weeks.

Leaf area was measured every 5 days and within a day of harvest. Plant height was measured at harvest (cm from soil to 1st leaf node or collar). Largest stem diameter was taken at harvest. Soil plant analysis development (SPAD) was measured just before harvest. Median photos were taken of each treatment. Dry root and shoot weights were measured after harvest. The dried shoots were divided from the 15 pots of each treatment into five sub-samples by rep number (sub-sample 1=reps 1-3, sub-sample 2=reps 4-6, sub-sample 3=reps 7-9, sub-sample 4=reps 10-12, sub-sample 5=reps 13-15). The sub-samples were then measured for basic shoot tissue nutrient analysis.

For each metric, an ANOVA was performed and if $P<0.1$, LSD was performed at $\alpha=0.1$. For leaf area growth rate, a camera angle was selected and rotation or shoot area [sv1+sv2+((tv1+tv2)/2)] that best correlates with shoot mass plus side view of plant height was taken at 5-day intervals, starting on the day of initial treatment, until harvest. The growth rate in leaf area or shoot area and plant height was then determined over time. The Bayesian effect sizes were determined for each treatment relative to the water control. Final leaf area measurement from the same camera angle and rotation as above or shoot area was determined. In the ANOVA model, the initial leaf area measurement was included as an independent variable, which, when run, performed a covariance analysis that controlled the variability occurring at the first leaf area measurement. Plant height and stem diameter were taken. Dry biomass total, root mass, and shoot mass were also measured. Macronutrients and micronutrients of the shoot were analyzed. The common language effect sizes for each treatment vs. UTC and for each metric were calculated.

As shown previously in FIG. 9A, the NTS-4 with MS4921 treatment condition alone showed greatest root nitrogen-fixing potential compared to that of control. Both NTS-4 treatment conditions, spiked with both MS3900 and MS4921 or MS4921 alone, showed greater dry shoot weight and shoot nitrogen content compared to that from control (FIGS. 9B-9C). As shown in FIGS. 28A and 28B, the NTS-4 with MS3900 and NTS-4 with MS4921 treatments showed significantly increased corn leaf area compared to that from untreated control (UTC).

Example 9: Nitrogen Use Efficiency Corn Field Trials

A field trial was conducted to determine if the NTS materials can enhance nutrient use efficiency in both full and reduced nitrogen fertility programs.

The NTS treatment conditions were: NTS prototype shake flask I with nitrogen-fixing isolates (MS3900 and MS3907), NTS prototype shake flask II with nitrogen-fixing isolates (MS3900 and MS3907), and nitrogen-fixing isolates alone (MS3900 and MS3907). Each NTS treatment was paired with either Grower's Standard Practice (GSP) 100% recommended N fertility or Grower's Standard Practice (GSP) 80% recommended N fertility. All treatments were applied at planting in furrow at 2 quarts per acre as a standalone without starter fertilizer. Soil samplings were taken at six timepoints: baseline soil sample from trial area; at V4-V6 growth stage, the root ball with soil attached plus 3 inches of stalk, with three individual rep composites; at V4-V6 growth stage, above ground biomass, with composite of the same three reps of root ball samples; at R5-R6 growth stage, the root ball with soil attached plus 6 inches of stalk, with three individual rep composites; at R5-R6 growth stage, above ground biomass, with composite of the same three reps of root ball samples; and post-harvest grain samples with composite of three individual reps.

Both vigor and stand count measurements were taken at the V2-V3 growth stage. Measurements were also taken of the preharvest stand counts, grain moisture, and grain yield.

Figure 29:
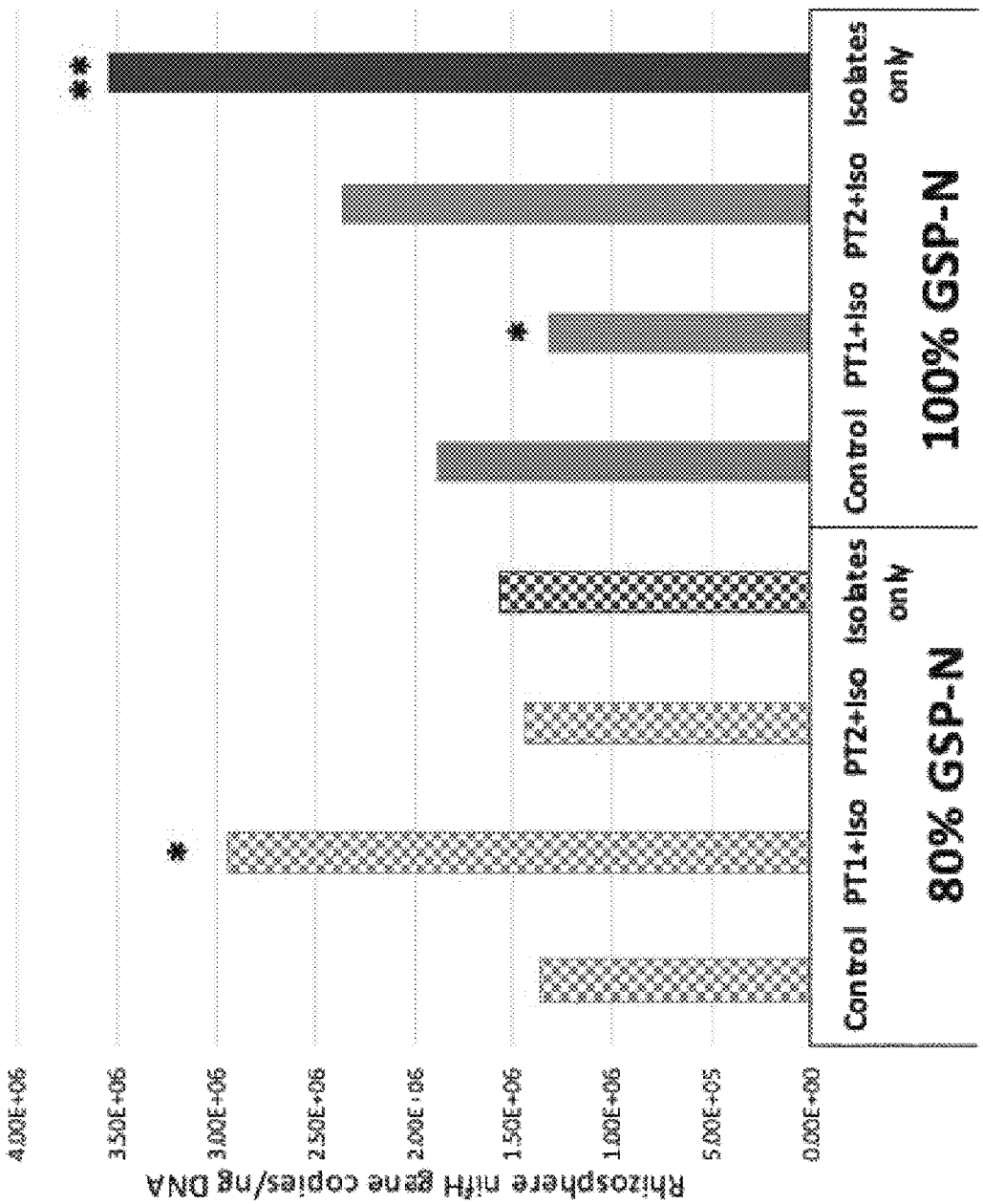
FIG. 29 shows isolates only (MS3900 and MS3907) demonstrated higher nitrogen fixer recruitment compared to that from control plants.
Figure 30:
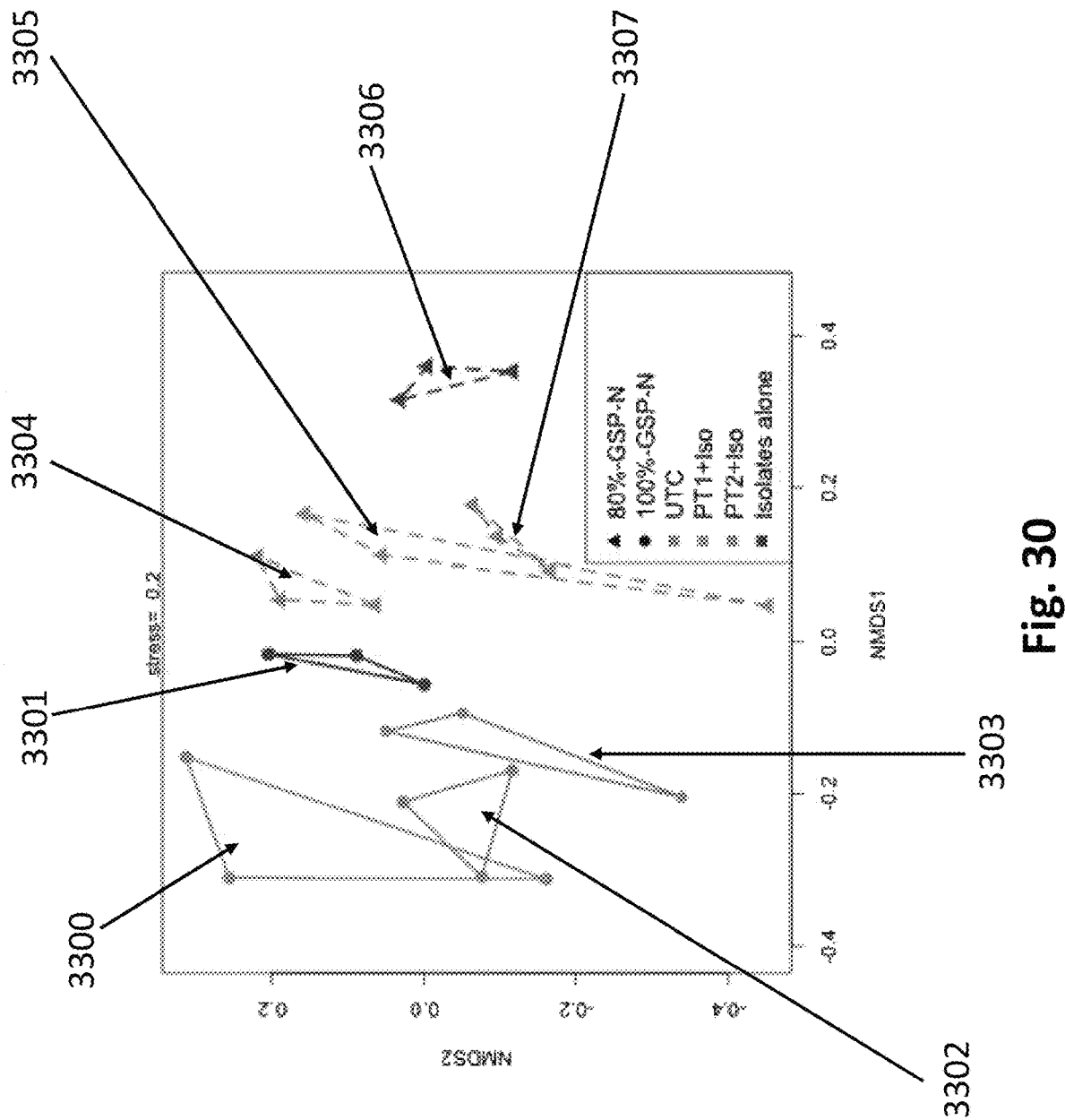
FIG. 30 shows there were significantly different N-fixing community compositions in the root zone between treatment conditions. 3300-3303 show N-fixing communities with 80%-GSP-N and 3304-3307 show N-fixing communities with 100%-GSP-N. 3000 is the N-fixing community of UTC at 80%-GSP, 3301 is the N-fixing community of PT1+Iso at 80% GSP-N, 3302 is the N-fixing community of PT2+Iso at 80% GSP-N, 3303 is the N-fixing community of Isolate alone at 80% GSP-N, 3304 is the N-fixing community of UTC at 100%-GSP-N, 3305 is the N-fixing community of PT1+Iso at 100%-GSP-N, 3306 is the N-fixing community of PT2+Iso at 100%-GSP-N, and 3307 is the N-fixing community of Isolate alone at 100%-GSP-N.
Figure 31:
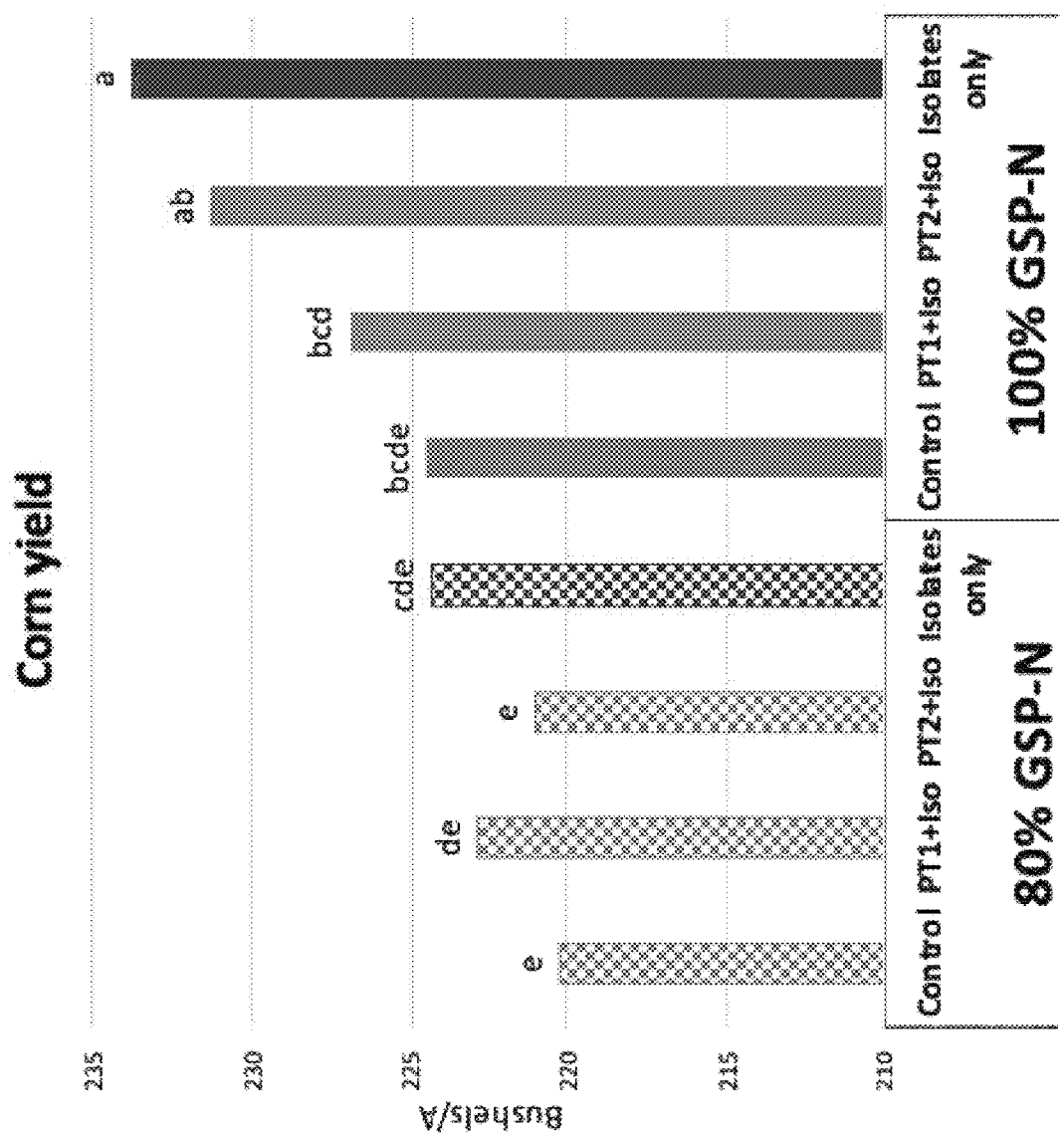
FIG. 31 shows isolates only (MS3900 and MS3907) demonstrated highest corn yield compared to other treatment conditions.
Figure 32:
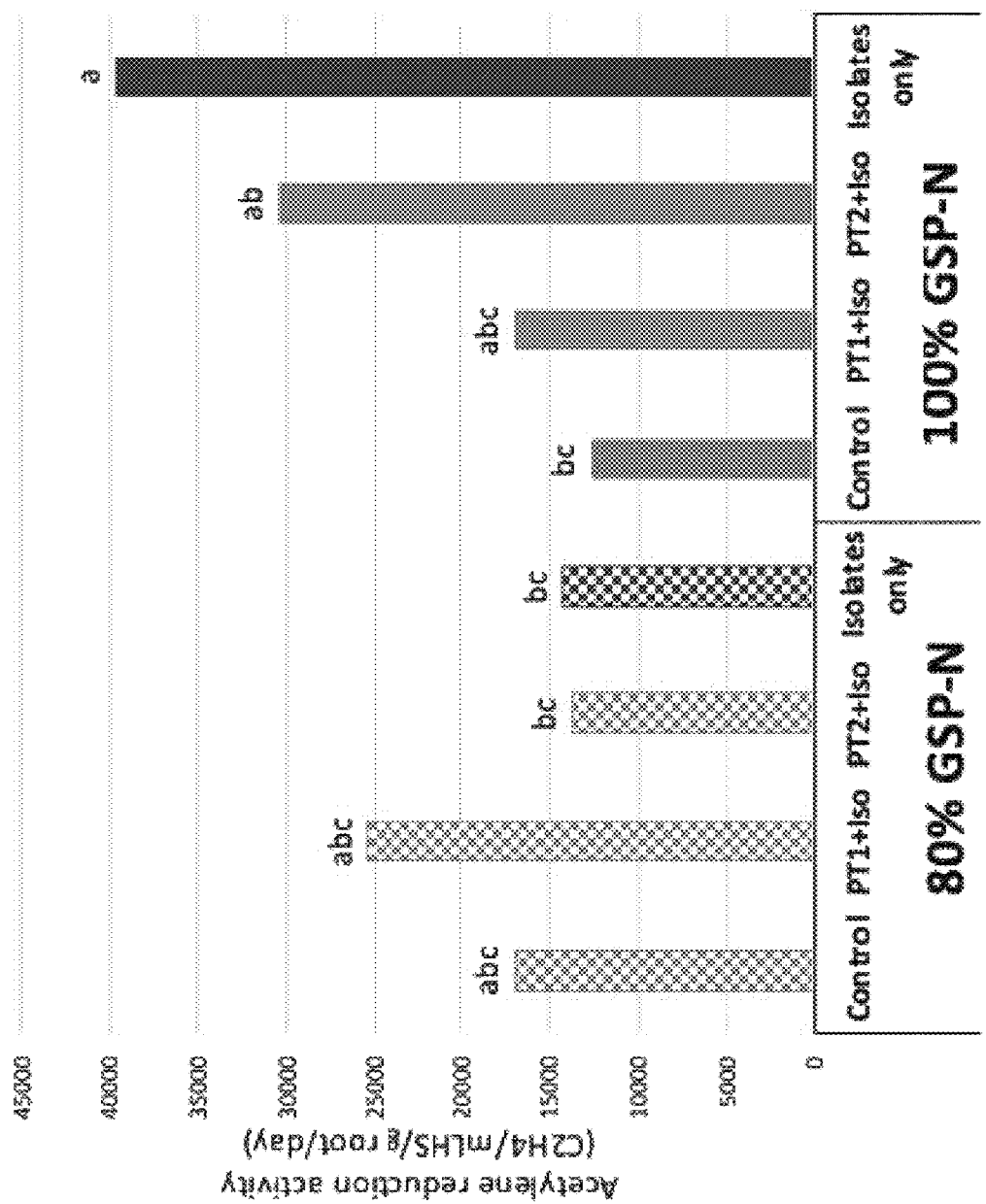
FIG. 32 shows that plants treated with isolates only (MS3900 and MS3907) demonstrated more N-fixing activity in corn roots/basal stem.
Figure 33:
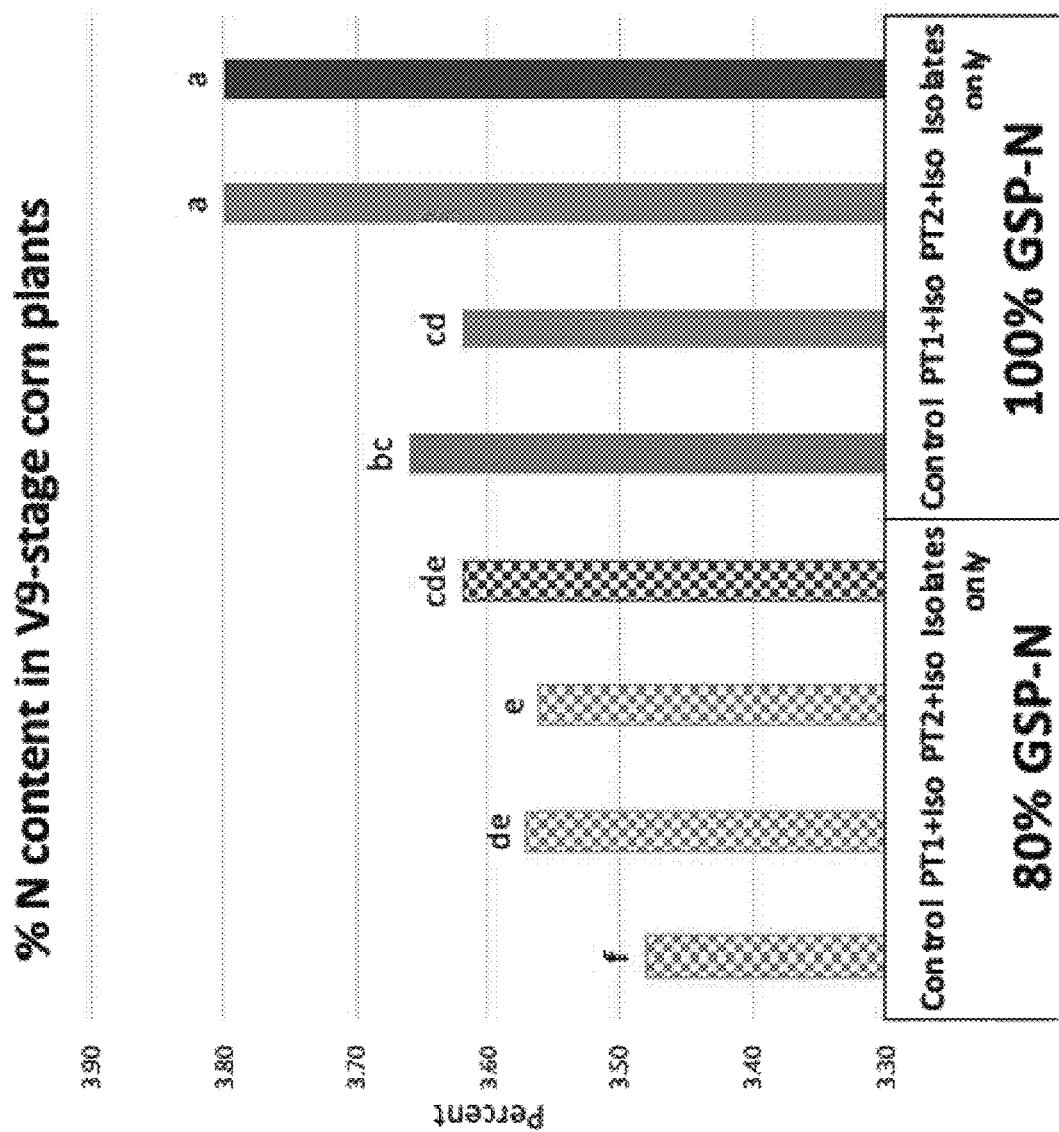
FIG. 33 shows isolates only (MS3900 and MS3907) and prototype consortia solution NTS-PT2 (e.g., NTS batch product) with added isolates demonstrated high plant nitrogen content.

All three reps from all treatments were sampled. Once the samples were sorted, the rhizospheres were removed from the bulk soil and weighed out for DNA extractions. The rhizosphere was then mixed with the remaining bulk soil for analyses. Rhizosphere soil was captured for DNA-based analysis of recruitment of nitrogen fixers and qPCR detection of MS3907 and MS3900. The isolates-only treatment condition with MS3900 and MS3907 showed the most N-fixers in the root zone compared to that from other conditions (FIG. 29). DNA from rhizosphere soil from field plants was extracted using the MP Biomedical, FastDNA SPIN kit for soil (Solon, Ohio), as directed. DNA concentration was quantified using Qbit ds DNA BR Assay kit, as directed. All DNA were normalized to the same concentration then sent out for next generation DNA sequencing by Molecular Research Labs (MR DNA, Shallowater, TX) using their standard protocols including the Illumina platform, 20K reads and amplification and sequencing of the nitrogen fixing population (nifH gene, Poly PCR primers (Poly et al., Res. Microbiol. 152 (2001) 95-10$^3$)). Visualization of the nitrogen fixing community composition was completed using the metaMDS function in the Vegan package in R. The rhizosphere N-fixing bacterial communities of corn treated with the Isolates-only treatment are clearly different from the untreated control communities (FIG. 30). There was also significantly different N-fixing community composition in the root zone between treatment conditions. Biomass for carbon and nitrogen was measured to establish an increase in organic nitrogen balance in the soil. The isolates only as well as the isolates in combination with the NTS prototype shake flasks at 100% GSP showed greater corn yield compared to that of other treatment conditions (FIG. 31). Acetylene reduction assays were conducted on soil and root crown (which included the basal portion of the stem). The isolates-only treatment condition with MS3900 and MS3907 showed greater N-fixing activity in corn roots/root crown as measured by the acetylene reduction assay (FIG. 32). The isolates-only as well as the isolates in combination with the prototype consortia showed increased percentage of nitrogen content in V9-growth stage corn plants (FIG. 33). Since the communities were different by treatment the activity for N-fixation (FIG. 32) and overall abundance of N-fixers (FIG. 29) was also different. Differences in rhizosphere community composition, N-fixing activity and abundance of N-fixers is strong evidence in support of recruitment. Treatments improved recruitment of N-fixing bacteria from the surrounding bulk soil into the rhizosphere that aided in plant N-content (FIG. 33) and yield improvements (FIG. 31).

Example 10: Evaluation of Plant Growth Promotion Properties of Isolates with Different In-Furrow Application Rates on Corn Isolates were also tested at different rate titrations to assess their effect on plant growth. Treatment conditions can be found in Table 17. Six different in-furrow cfu rates were tested, using a 1:1 blend of MS3900 and MS3907 isolates normalized to 104 cfu/ml, for PGP efficacy on corn, to determine the cfu application rate per plant for future NUE greenhouse experiments. Isolates were tested on a conventional non-GMO corn cultivar Welter Seed WS095 hybrid corn with a growing medium comprising 1:1:1 Profile MVP® Turface-peat-Denton sandy loam soil. The fertilizer was UAN at 10 lbs. N/A, TSP at 20 lbs. P/A, Potash at 200 lbs./A, Jackpot micronutrient fertilizer at 1 fl. oz./gal in 50 ml (0.78%); Na2MoO4·2H2O, 4.1 mg/pot for 12" pot mixed together.

TABLE 17

Treatment conditions for isolate titration

| Treatment code | μL treatment (a.i.)/ plant | Equivalent a.i. qt./A assuming 30,000 plant density/A | CFUs/ plant | ml carrier | mls a.i. for 10 ml stock solution |
|---|---|---|---|---|---|
| A | 0 (neg. control) | 0 | 0 | 0.5 | 0 |
| B | 8 | 0.25 | 80 | 0.5 | 1.6 |
| C | 16 | 0.51 | 160 | 0.5 | 3.2 |
| D | 32 | 1.01 | 320 | 0.5 | 6.4 |
| E | 64 | 2.03 | 640 | 0.5 | 12.8 |
| F | 0 (+5 lbs N control) | 0 | 0 | 0.5 | 0 |

There were 6 treatments with 12 replicates for a total of 72 pots, each pot measuring 15 cm round. The experimental design followed a two 6×6 Latin square design with 1 plant per pot. Pots were first filled with the growing medium. Three corn seeds were planted at 2 inches deep and 0.5 ml of treatment solution was pipetted over the seed. The seeds were then covered with growing medium. After full emergence, the plants were thinned to one plant per pot, selecting for uniform plant size. Fifty ml of fertilizer solutions was applied per pot after thinning. The plants were then randomized and arranged into two 6×6 Latin squares and watered with reverse osmosis (RO) water as necessary. The experiment duration was 3 weeks.

Leaf area was measured every 5 days and within a day of harvest. Plant height was measured at harvest (cm from soil to 1$^{st}$ leaf node or collar) and the largest stem diameter was taken at harvest. SPAD was measured just before harvest and representative photos of each treatment (treatment median for leaf area) were taken. Dry root and shoot weights were calculated after harvest. The dried shoots were divided from the 12 pots of each treatment into four sub-samples by rep number (sub-sample 1=reps 1-3, sub-sample 2=reps 4-6, sub-sample 3=reps 7-9, sub-sample 4=reps 10-12). Samples were then sent out for basic shoot tissue nutrient analysis.

For each metric, an ANOVA was performed and if P<0.1, LSD was performed at α=0.1. For leaf area growth rate, a camera angle was selected and rotation or shoot area [sv1+sv2+((tv1+tv2)/2)] that best correlates with shoot mass plus side view of plant height was taken at 5-day intervals, starting on the day of initial treatment, until harvest. The growth rate in leaf area or shoot area and plant height was then determined over time. The Bayesian effect sizes were determined for each treatment relative to the water control. Final leaf area measurement from the same camera angle and rotation as above or shoot area was determined. In the ANOVA model, the initial leaf area measurement was included as an independent variable, which, when run, performed a covariance analysis that controlled the variability occurring at the first leaf area measurement. Plant height and stem diameter were taken. Dry biomass total, root mass, and shoot mass were also measured. Macronutrients and micronutrients of the shoot were analyzed. The common language effect sizes for each treatment vs. UTC and for each metric were calculated.

Figure 34A:
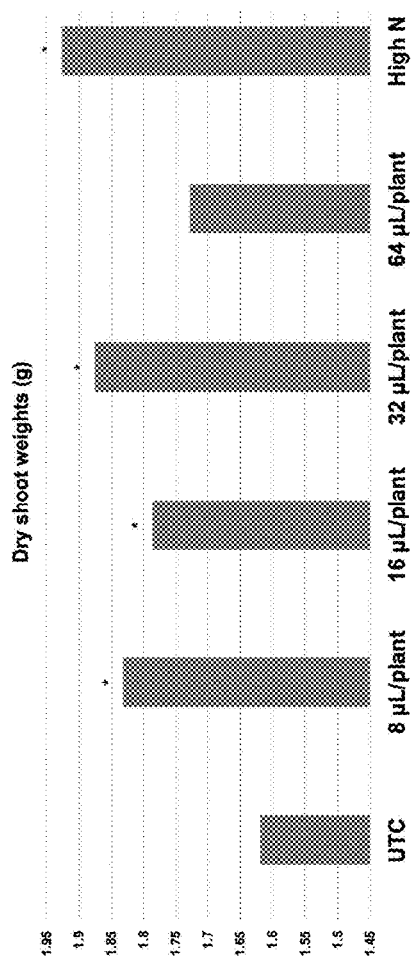
FIGS. 34A-34B shows the results of a titration assay with isolates MS3900 and MS3907. Plants treated with the isolates at low rates (8 µl/plant and 16 µl/plant) showed high dry shoot weights (FIG. 34A) and dry root weights (FIG. 34B).
Figure 34B:
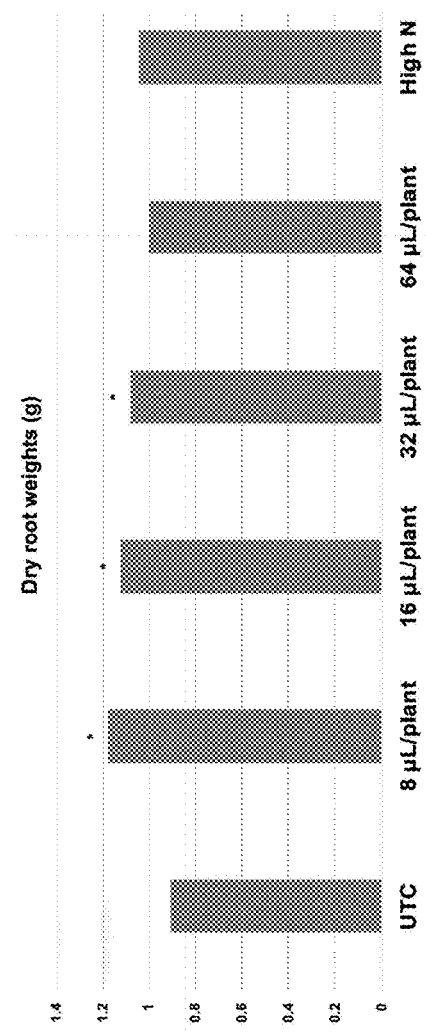

The soil organic matter, organic nitrogen, and estimated nitrogen release were measured in percent (%), parts per million (PPM), and pounds per acre (lbs./A). The bulk soil samples (100 g/replicate) were sent for nitrogen content analysis. Application of MS3900 and MS3907 each at $10^4$ CFU/mL at 8 μl/plant and 32 μl/plant showed the greatest dry shoot weight compared to that of other conditions (FIG. 34A). All isolate conditions except for isolates at 64 μl/plant showed significantly greater dry shoot weight compared to that from UTC. Application of MS3900 and MS3907 at 8 μl/plant showed the greatest dry root weight compared to other treatment conditions (FIG. 34B).

Figure 35A:
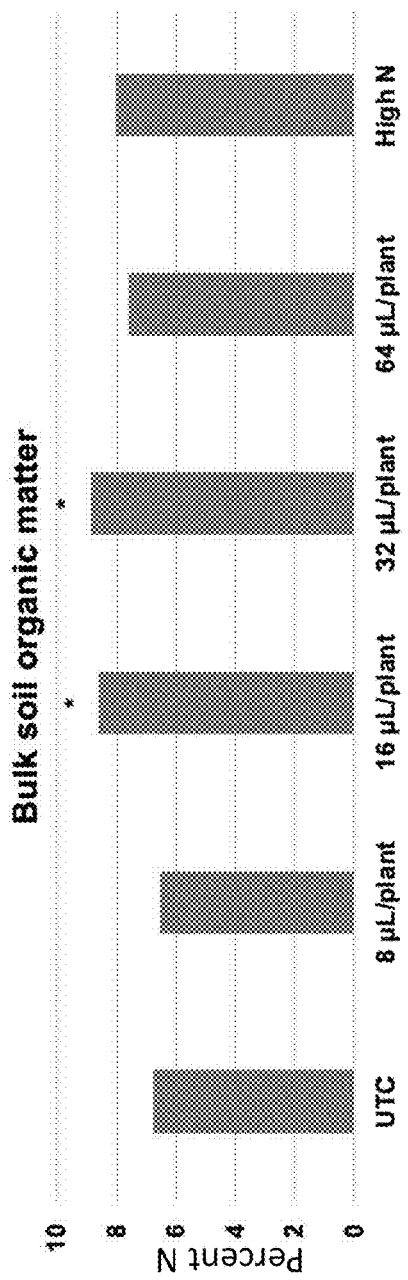
FIGS. 35A-35B show the results of isolate treatment on nitrogen in bulk soil.
Figure 35B:
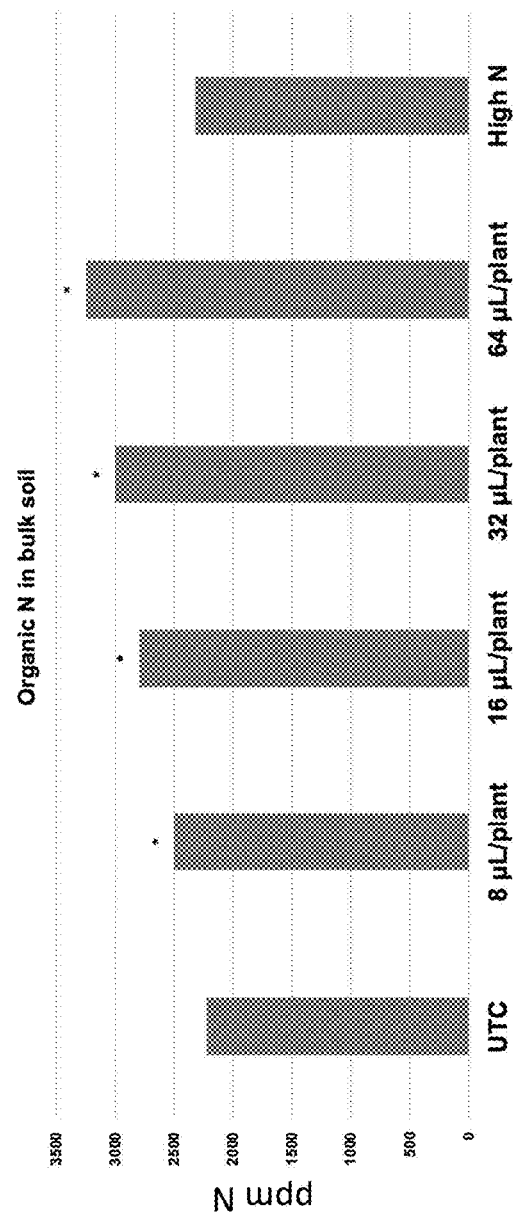

Bulk soil matter and organic nitrogen in bulk soil were measured in the same rate titration study with MS3900 and MS3907. Application of isolates at 16 μl/plant and 32 μl/plant showed the greatest increase in bulk soil, compared to that from UTC, High N fertilizer condition, and other isolate application rates (FIG. 35A). All application rates of the two isolates resulted in greater organic nitrogen in bulk soil, compared to that from UTC and High N fertilizer conditions (FIG. 35B).

Figure 36A:
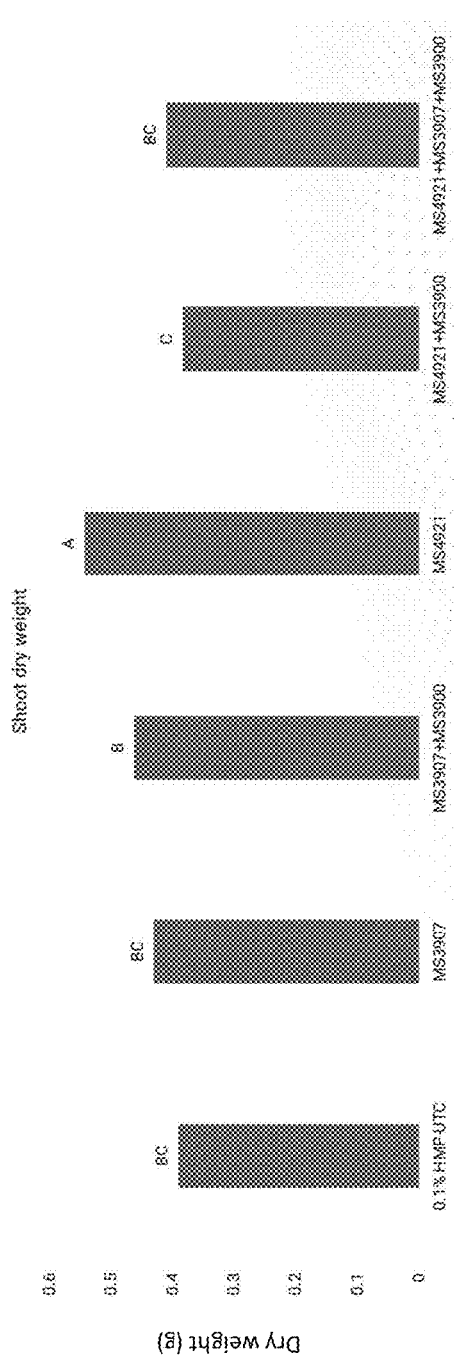
FIGS. 36A-36B show the results of isolate treatments on dry weights.
Figure 36B:
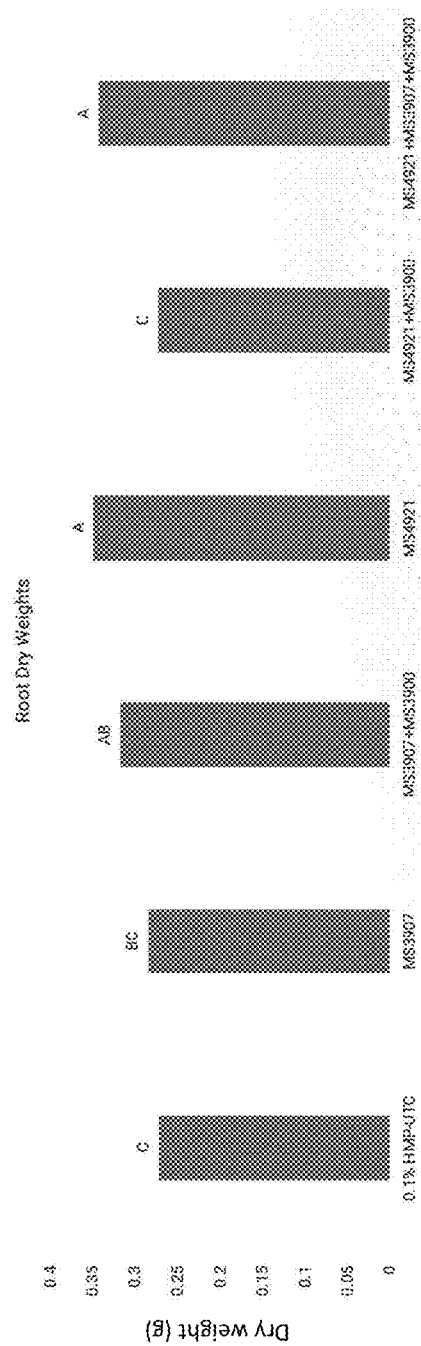

To assess how isolates contributed to plant dry weights, isolates MS4921 or MS3907 were tested either alone or in combination with MS3900 or all three isolates together in corn plants grown in Greenhouse. Each treatment consisted of 32 μl of each isolate diluted to 0.5 ml volume with 0.10% HMP. The pots were fertilized with 15 lbs N/acre as UAN-32 together with other nutrients as recommended in soil analysis. The plant shoot and root biomass were measured 4 weeks after seed sowing. MS4921 alone showed the greatest shoot dry weight compared to that from UTC and other isolates (FIG. 36A). MS4921 alone and the combination of MS3900, MS3907, and MS4921 showed the greatest root dry weight compared to other treatment conditions (FIG. 36B).

Example 11: ARA, Root Colonization, and Endophyte Assay Methods

Acetylene reduction into ethylene, which measures the activity of nitrogenase, the bacterial enzyme involved in nitrogen fixation. Acetylene gas was reduced to ethylene gas through the nitrogenase enzyme present only in nitrogen-fixing bacteria and archaea. The ethylene formed from acetylene was measured over time and the rate of the nitrogen-fixing activity was determined.

ARA of Single Isolate

The 1:10 N-free medium was prepared by adding 10 mL of base inoculum (e.g., PST WB 1:1), 0.2 g of D-glucose, 0.2 g of di-sodium DL-malate, 0.2 g of soluble starch, 0.2 g of D-mannitol, and 0.4 g of Noble agar to 90 mL of ultrapure water. The media was then adjusted to pH 7.0 and sterilized by autoclaving before being aseptically dispensed into screw-cap vials. An overnight culture of MS4921 (200 uL) in Tryptic Soy Broth was diluted into 9 mL of sterile 0.1% HMP buffer and vortexed to mix. This diluted culture preparation was used to inoculate the vials containing 5 mL of N-free medium by dropping the diluted culture onto the media below. A sterile 10 uL loop was then used to stab the agar in the vial. Vials were re-capped and incubated at room temperature at 150 rpm for 3 days. Un-inoculated vials were also incubated to serve as negative controls (e.g., UTC). After 3 days, vials were removed from incubation and sealed with magnetic screw-top caps with septa. Half of the vials in each group (e.g., UTC and MS4921) were flushed with N2 gas for 4 minutes to create a microaerophilic headspace. Then, 2.2 mL of headspace gas was withdrawn from each vial and 1.5 mL of pre-warmed acetylene and 0.7 mL of air were injected. Vials were re-incubated at room temperature at 150 rpm for 72 hours before loading directly into the GC for analysis.

The samples were analyzed on an Agilent 8890 GC/MS equipped with a flame ionization detector (FID) and with an $Al_2O_3$ column ($Na_2SO_4$ deactivated) with Helium as carrier gas (2 ml/min). The injector was set at 200 C and 0.5 mL of sample was injected for analysis. The Flame Ionization Detector was set at 250° C. and the oven at 40° C. for 2 minutes, followed by 40-140° C. at 40° C. per minute.

Figure 37:
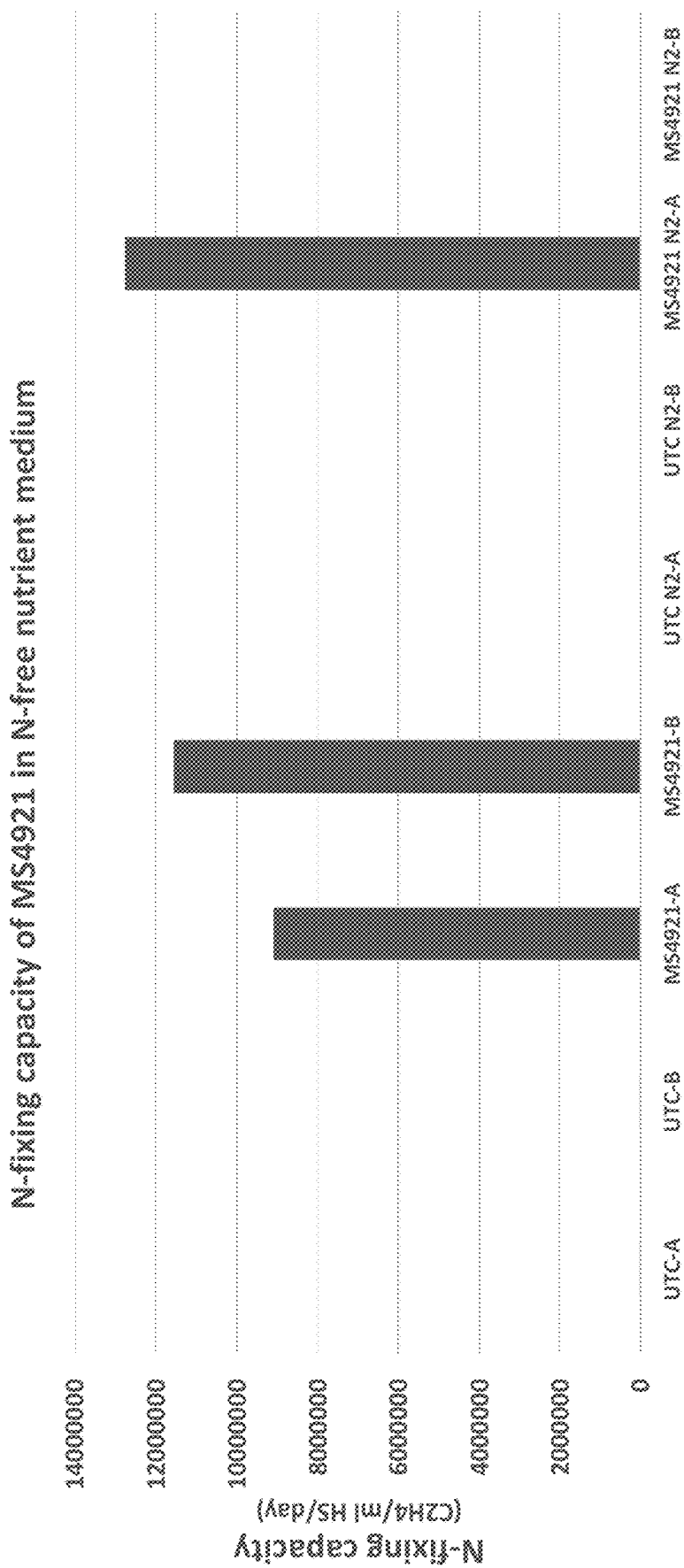
FIG. 37 shows strong acetylene reduction assay in single isolate culture in nitrogen-free nutrient media, with or without nitrogen headspace flushing (N2). UTC designates untreated control, i.e. the N-free media was not inoculated; A or B=replicate A or replicate B; N2 designates the headspace was flushed with nitrogen gas before injecting acetylene to remove all oxygen.

The results from the GC analysis showed that samples containing the single isolate of MS4921 had increased acetylene reduction activity in nitrogen-free nutrient media compared to samples that did not contain MS4921 (FIG. 37). Ethylene peak area/ml volume headspace per day was measured. Milliliters of headspace was used as the bases because the total volume of the root varied from plant to plant. Measurements were normalized per day because there was varied incubation time (48 hours to 120 hours).

The increased acetylene reduction activity was present with or without flushing of nitrogen from the headspace of the sample vial.

ARA of Sterile System Seedlings

The corn seedling was removed from the water agar in the 50 mL conical tube using sterile forceps. Using sterile scissors, the root system was cut at the point where the leaf begins (e.g., where the stem turns green) and allowed to drop onto a clean weight boat below. The forceps were then used to insert the entire root system (including seed) into the screw-top ARA vial. This process was then repeated with the next seedling from the same treatment, so that there were 2 seedling root systems in each vial. Sterile water or Hoagland's+Carbon solution (500 uL) was added to the vial. The Hoagland's+Carbon solution was prepared by dissolving 0.268 g of Hoagland No. 2 Basal Salt Mixture Without Nitrogen into 150 mL of ultrapure water and adding 0.4 g each of D-Glucose, di-Sodium DL-Malate, soluble starch, and D-Mannitol, mixing until dissolved. The solution was then adjusted to a final volume of 200 mL with ultrapure water and autoclaved. These vials were then sealed with magnetic screw-top caps with septa, 2 mL of headspace gas was removed following sealing, and then injected with 2 mL of acetylene. Roots were incubated with acetylene at 30° C. for 3 days and then loaded directly into the GC for analysis as described herein.

Figure 38:
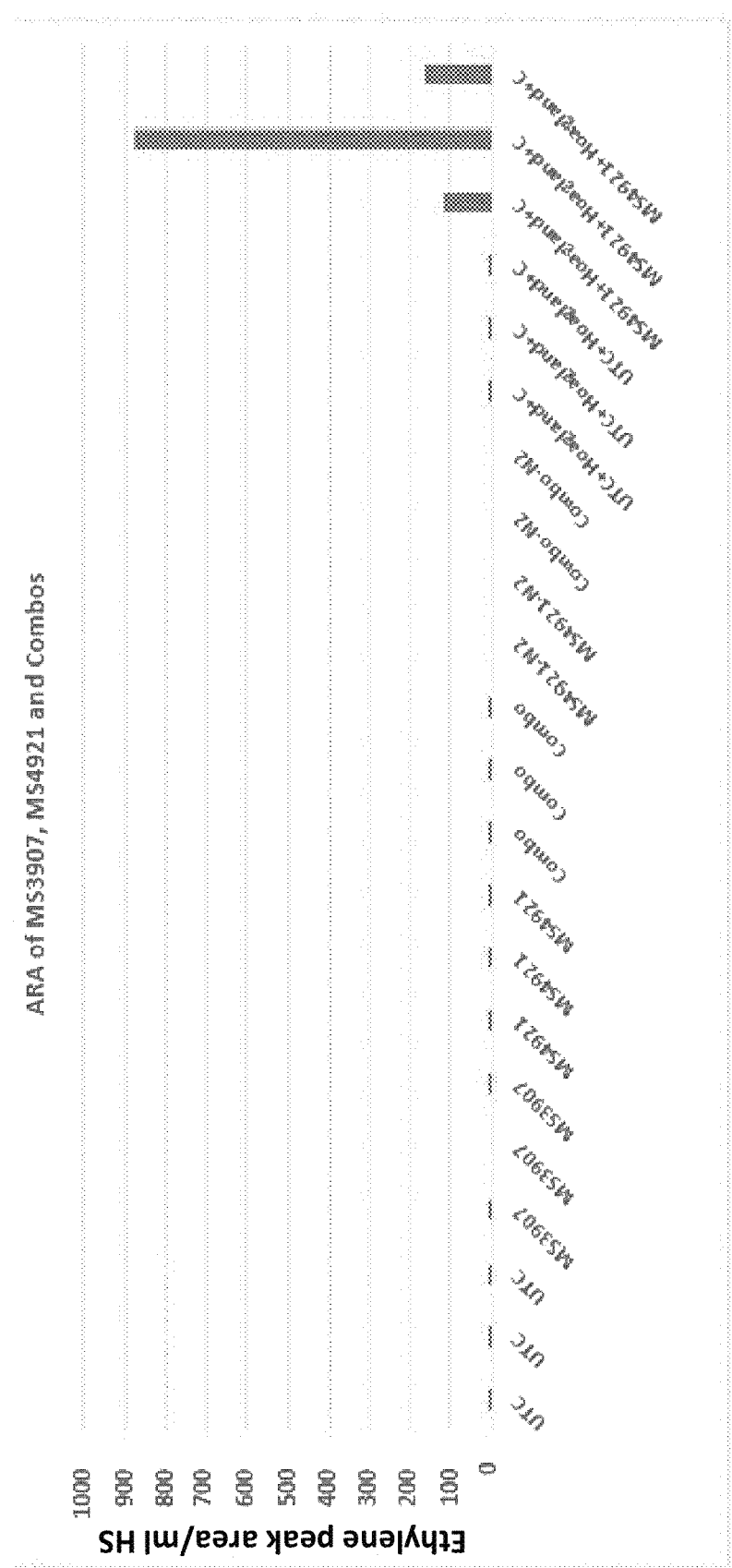
FIG. 38 shows addition of carbon and nutrients (Hoagland+C) boosts acetylene reduction of MS4921 in sterile system corn roots.

Different combinations of single isolates, combinations of isolates, combinations of single isolates and Hoagland's+Carbon solution and selected samples with nitrogen gas flushing to remove all oxygen (—N2) were tested with the corn seedlings (FIG. 38). The majority of the single isolate cultures and combination of isolates cultures had similar acetylene reduction activity as the un-inoculated, water-only treated corn plants (e.g. UTC versus MS3907). However, cultures containing the MS4921 isolate with Hoagland's+Carbon solution had increased levels of acetylene reduction activity (ARA) (FIG. 38).

The ARA was next tested in corn that had been treated with end product solutions from NTS versions NTS-1, NTS-2, NTS-3, and NTS-4, or with just water (e.g., negative control) in a non-sterile greenhouse test. Each of the end product solutions were either supplemented with MS4921 alone or with a combination of MS4921+MS3900 at $10^4$ CFU/mL each. The end product solution with added isolates was applied to the corn seeds in pots at planting using a simulated in-furrow application at 2 qt/acre. The growing medium was a 1:1:1 Turface-peat-Denton sandy loam soil mix. Fertilization was UAN32 (32-0-0) @ 15 lbs. N/A+TSP (0-46-0) @ 20 lbs. P/A+Potash (0-0-60) @ 200 lbs./A+15 lbs./A S+Jackpot micronutrient fertilizer @1 fl. oz./gal in 50 ml (0.78%); $Na_2MoO4 \cdot 2H2O$, 4.1 mg/pot for 12" pot mixed together. At harvest, roots were analyzed for ARA as described.

Figure 39:
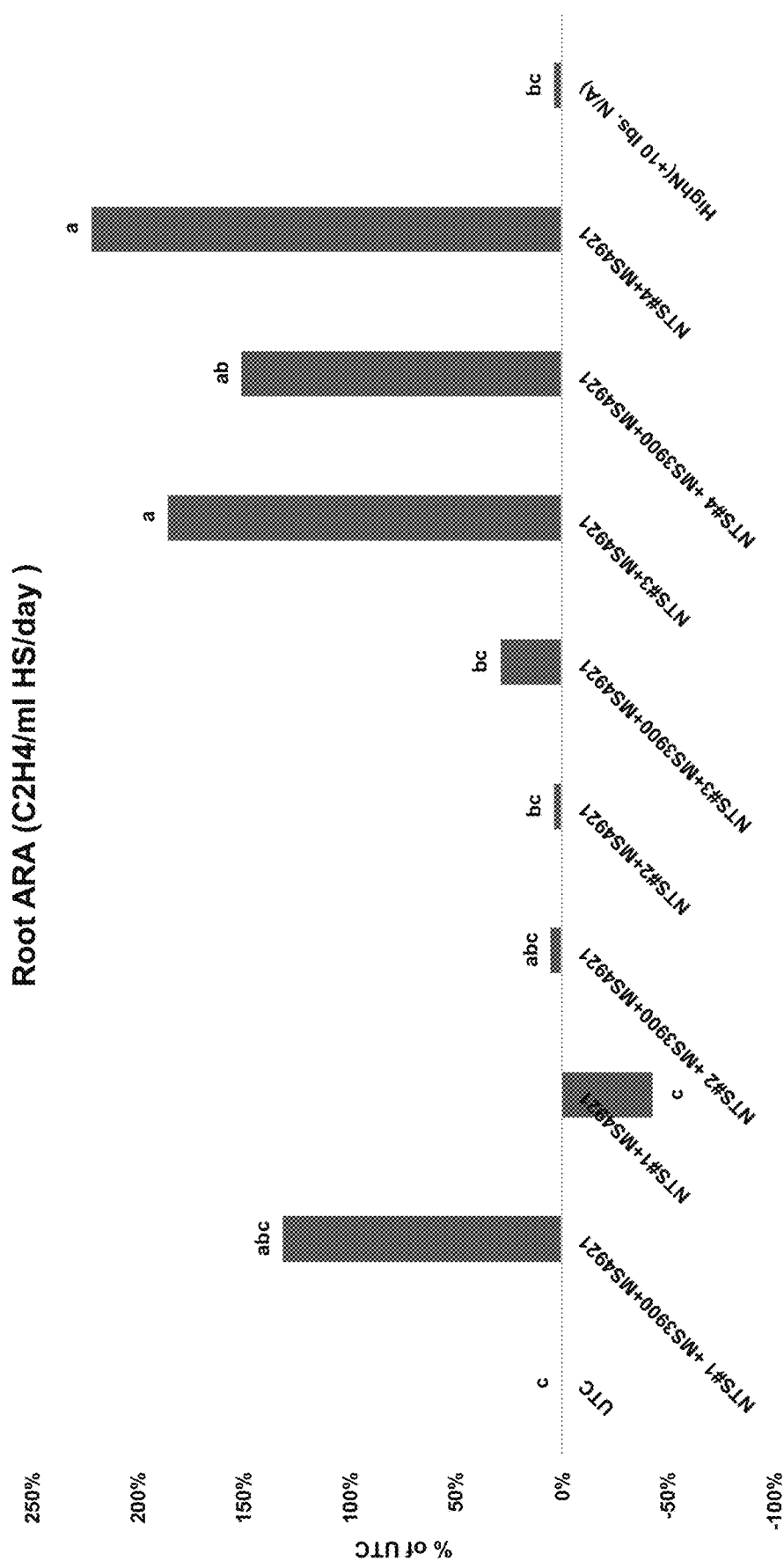
FIG. 39 shows treatment with NTS-1.4 solution with MS4921 led to highest root acetylene reduction, as measured as % UTC.

The ARA analysis results showed that corn roots of plants treated with the end products of NTS-1, NTS-2, NTS-3, or NTS-4 supplemented with either MS4921 alone or with MS3390+MS4921 had increased ARA compared to corn roots of plants only treated with water (FIG. 39).

The ARA of corn seedlings from two application types were tested: seed dench and seed soak.

Figure 40A:
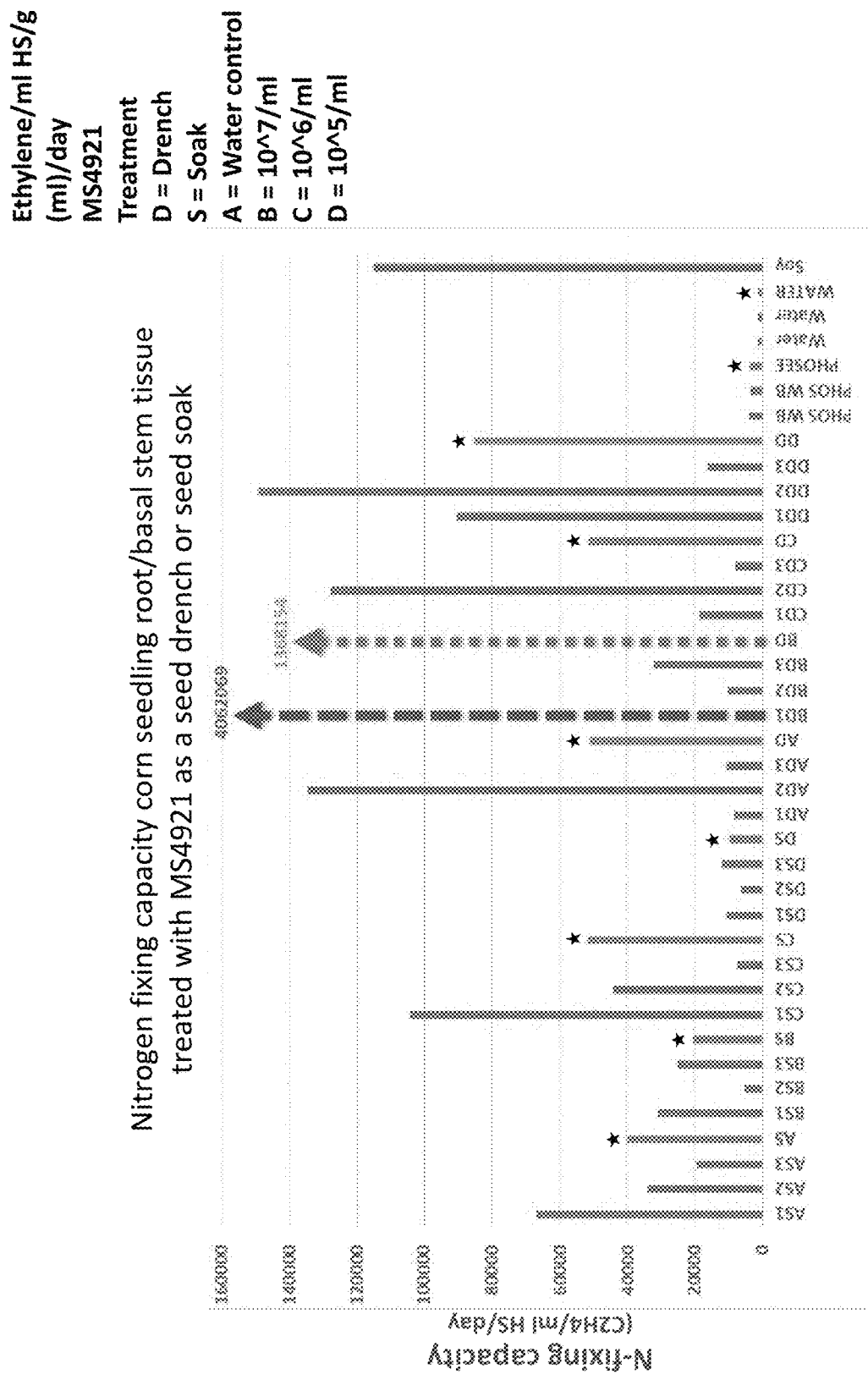
FIGS. 40A-40B show results of nitrogen fixing capacity of MS4921 or MS3907 as seed drench or seed soak on corn seedlings.
Figure 40B:
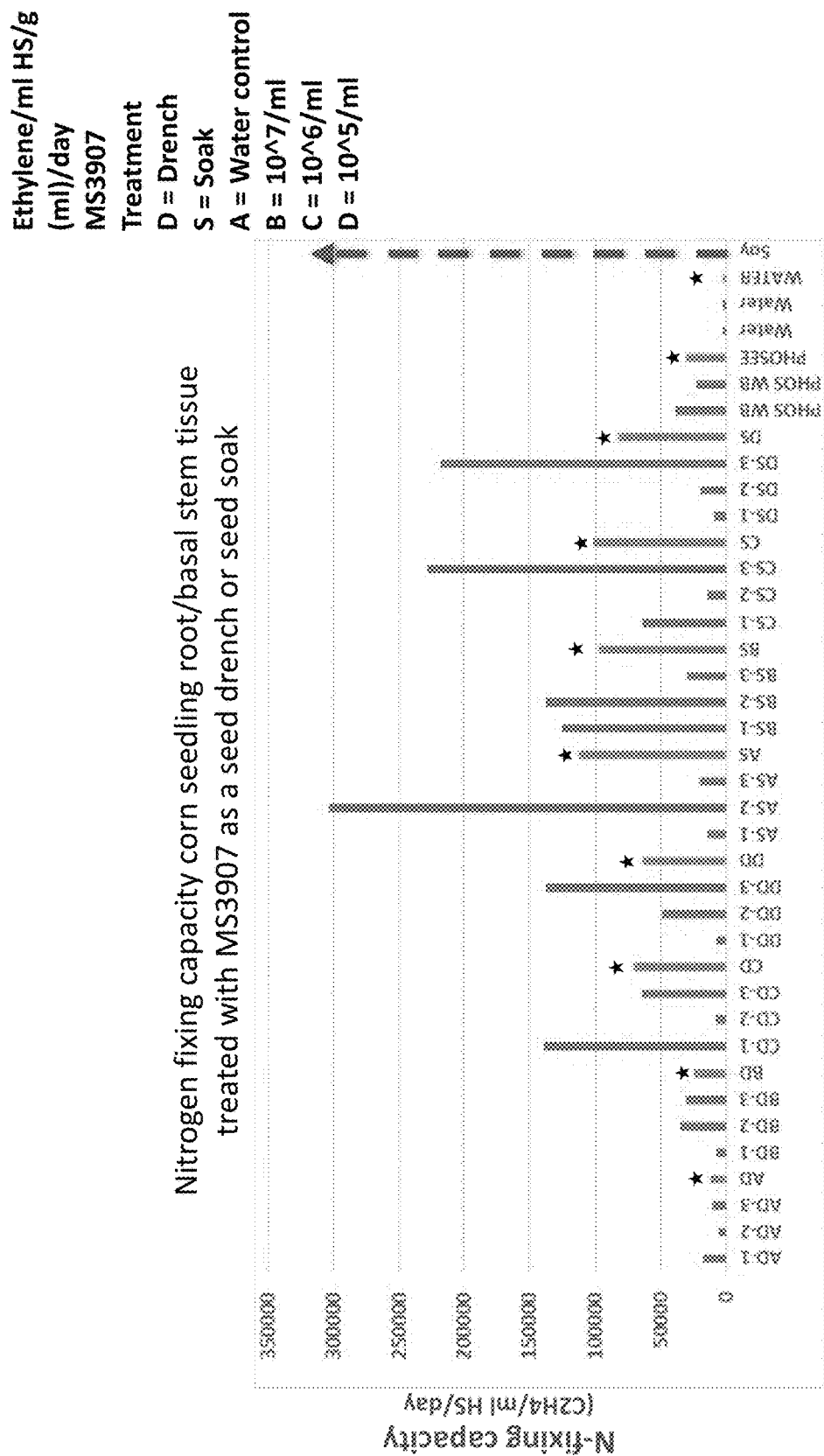

Spores of each isolate (MS3907 or MS4921) were diluted in sterile 0.1% HMP (Hexa meta phosphate buffer) to $10^5$ CFU, $10^6$ CFU or $10^7$ CFU. Corn seeds were soaked in the dilute spore solutions for 4 hours then planted or the spores were directly applied as a 1 mL drench to each seed in a container. The container (4 cm diameter and 21 cm high) was filled 150 g of a 1:1:1 mix (sandy loam soil:peat:sand). Each treatment had three replicate plants. Container racks of corn incubated in a growth chamber set at 24 C with 16 hour light and 8 hour dark for 8 days. At harvest, roots were washed and 2 cm of the stem and whole roots were placed in 21 mL GC vials for acetylene injection and incubation. The seedlings from each application type were prepared for analysis as described herein and analyzed with GC for ARA using root/basal stem material. Controls for the ARA test included the base inoculum (2 mL) as a positive control with 2 replicates and water-only (2 mL) as negative controls. Also, we included one other positive control, nodules from a soybean plant. The corn seedling treatment codes are: A=untreated control, water only, B=Isolate at $10^7$ CFU/mL, C=Isolate at $10^6$ CFU/mL, D=Isolate at $10^5$ CFU/mL, D=drench application and S=soak application. Orange bars are the average for three replicates (FIGS. 40A and 40B). Dotted lines indicate the values were too high and off the scale of the graph. The GC analysis showed that seed drenched plants grown with MS4921 supplemented had increased root/basal stem nitrogen-fixing activity compared to plants only treated/grown with water (FIG. 40A). The ARA results from the three replicates were additionally averaged together (AS, BS, and CS in FIG. 40A). Additionally, the GC analysis showed that seed-soaked plants grown with MS3907 supplemented had increased root/basal stem nitrogen-fixing activity compared to plants only grown/treated with water (FIG. 40B). Seed soaking did not result in increased root/basal stem nitrogen-fixing activity for MS4921 treated corn seeds but did for MS3907 suggesting that application methods in this test impacted root/basal stem nitrogen fixing activity.

Another greenhouse test was set up specifically to measure ARA activity in stems of corn treated with MS3900 and MS4921 isolates together in non-sterile conditions. Corn seed was planted in a 1:1:1 Turface-peat-sandy loam soil mix. Treatments were applied at planting over the seed in the pot and included 128 uL MS3900 and MS4921 each at $10^4$ CFU/mL (equivalent of 4 qt/A) or water-only, negative control and n=6 replicate pots each. Fertilization included: UAN @ 10 lbs. N/A+TSP @ 20 lbs. P/A+Potash @ 200 lbs./A+Jackpot micronutrient fertilizer @1 fl. oz./gal in 50 ml (0.78%); $Na_2MoO4 \cdot 2H2O$, 4.1 mg/pot for 12" pot mixed together. Plants grew in the greenhouse for 14 days. At harvest, root and leaf material were removed, stems were placed directly in 21 mL GC vials for injection of acetylene, incubation, and quantification of the ethylene produced, as described. The stem tissue of corn seeds treated with MS3900 and MS4921 has much greater nitrogen fixing capacity than the stem tissue of water-only treated corn seeds.

Root Colonization Test
Sterile System

Corn seeds were surface sterilized by mixing in 70% ethanol for 1 minute, followed by 5% (v/v) household bleach for 5 minutes, and then rinsing three times with sterile water for 1 minute each time. The seeds were dried in the hood for at least 1 hour. Dried, sterilized seeds were placed into 10 mL of bacterial inoculum (either a 1:10 or 1:100 dilution of 24-48 hour bacterial culture of MS3907 or MS3900 in sterile, ultrapure water) and incubated with shaking (200 rpm) for 2 hours at room temperature. Seeds were then removed from the bacterial solution and dried in a hood in sterile petri plates until completely dry. Dry seeds were placed into a sterile, 50 mL conical tube containing 15 mL of 0.4% water agar using sterile forceps. Four or five tubes were inoculated for each treatment and each experiment included a set of untreated controls (UTC) treated with water only. Seeded conical tubes were placed into a Percival Growth Chamber set to a 16-hour day at 24° C./8-hr night at 22° C. cycle. Corn seedlings were allowed to grow in the growth chamber for 9-11 days before harvesting.

Each corn seedling was removed from the sterile conical tubes with sterilized forceps. The seedling's root system was pressed against a labelled ¼-strength Tryptic Soy Agar plate for 3-5 seconds, creating a 'root stamp' to capture the extent of colonization of the seedling roots. The 'root stamp' plate was allowed to fully dry before being incubated at 30° C. for 3-5 days. Plates were checked after incubation for presence of target isolates, and the identity of the target isolation was confirmed, if necessary, by PCR amplification and sequencing of the 16S rRNA gene.

The results of this experiment showed the seeds incubated with MS3900 or MS3907 formed colonies from the root stamp of the corn plants on Tryptic Soy Agar plates, which depicted that MS3900 and MS3907 were able to colonize the root. In addition, when the same Tryptic Soy Agar plate were stamped with roots from seeds incubated with MS3907 and with roots from seeds incubated with MS3900, there was an increase in the number of colonies from both isolates.

Greenhouse System

To test for the isolates capacity to colonize roots in a non-sterile system, multiple greenhouse tests were run without the addition of nitrogen fertilizer. Specifically, tall fescue, sorghum, and corn were tested. Each test was run under similar conditions in the greenhouse. Tall fescue and corn were planted in isolite potting mix. Sorghum was planted in sandy loam soil. Fertilization included Hoagland's (without-N) supplemented with 2 g KH2PO4/L at 100 ml/pot. Isolates were prepared by growing in TSB (tryptic soy broth) for 3 days at 30 C and 200 rpm. Then, isolates were diluted in sterile 0.10% HMP (hexa-meta phosphate) to the same optical density (OD 600 nm) of ~0.5 and 10 mL was applied to each pot at planting. The negative control plants received only 10 mL of sterile 0.1% HMP. After 4 weeks plants were harvested. At harvest, for the sorghum test, rhizosphere soil samples were collected and was analyzed for the presence of the target isolates by dilution plating onto ¼ strength TSA plates and incubated for 7 days at 30 C. MS3900 or MS3907 was detected by visual confirmation of the colony type and verified by DNA sequencing of the 16S rRNA gene. At harvest, fine roots (less than 1 cm diameter) were collected from at least 3 replicate plants of each treatment. Roots were rinsed of soil or isolite with sterile water. Then, roots were moved to a sterile mortar and pestle tube (BioPLAs Inc. Cat #4030 PB) with 1 mL sterile water. Roots were vortexed for 5 sec, sonicated for 5 min and vortexed for 15 sec. We consider this a rhizoplane sample. A portion of this rhizoplane wash solution was analyzed by dilution plating to recover the isolates as above for the rhizosphere soil. The remaining fine roots were surface sterilized, cut and placed onto ¼ TSA plates as indicated below for the sterile system endophyte test. For the tall fescue plants, the rhizoplane and endophytic space habitats were combined. For tall fescue, the root in the rhizoplane wash solution were ground by hand with the sterile mortar for one minute to release endophytes from inside the root. This is considered to be a rhizoplane+endophytic space sample or a "root extract" sample. The root extract sample was analyzed by dilution plate to try and recover the isolates. FIG. 41 summarizes the results of root colonization experiments performed on MS3900 and MS3907 in various greenhouse plants.

Endophyte Assay

Corn seeds were surface sterilized by mixing in 70% ethanol for 1 minute, followed by 5% (v/v) household bleach for 5 minutes, and then rinsing three times with sterile water for 1 minute each time. The seeds were dried in the hood for at least 1 hour. Dried, sterilized seeds were placed into 10 mL of bacterial inoculum (either a 1:10 or 1:100 dilution of 24-48 hour MS3900, MS3907, or MS4921 bacterial culture in sterile, ultrapure water) and incubated with shaking (200 rpm) for 2 hours at room temperature. Seeds were then removed from the bacterial solution and dried in a hood in sterile petri plates until completely dry. Dry seeds were placed into a sterile, 50 mL conical tube containing 15 mL of 0.4% water agar using sterile forceps. Five tubes were inoculated for each treatment and each experiment included a set of untreated controls (UTC) treated with water only and a set of positive control tubes treated with *Stenotrophomonas maltophilia*, a gram-negative plant endophyte. Seeded conical tubes were placed into a Percival Growth Chamber set to a 16-hour day at 24° C./8-hr night at 22° C. cycle. Corn seedlings were allowed to grow in the growth chamber for 9-11 days before harvesting.

At harvest, the 4 corn seedlings with the best growth were selected from each set of 5 tubes for processing. Each corn seedling was removed from the sterile conical tubes with sterilized forceps. The seedling's root system was pressed against a labelled ¼ TSA plate for 3-5 seconds, creating a 'root stamp' to capture the extent of colonization of the seedling roots. Then, the entire root system of the seedling was cut off using sterile scissors and dropped into a 50 mL conical tube containing 25 mL of 70% ethanol and washed with agitation for 1 minute. Next, seedlings were washed in 25 mL of 2% sodium hypochlorite (e.g., bleach) solution for 3 minutes. Seedlings were washed once again in 25 mL of 70% ethanol for 30 seconds. Between each sterilization step, the bleach or ethanol was poured or pipetted off and seedlings received a quick rinse in sterile, ultrapure water. Finally, seedlings were washed twice in sterile, ultrapure water for 1 minute each time. The sterilized root system ensured that only putative endophytes remained in the root system.

The sterilized root system was removed from the conical tube with sterile forceps and transferred to a sterile, empty petri plate. The entire root system of the seedling was cut into ¼-inch pieces and arranged on 1-2 labelled ¼ TSA plates. These root pieces were allowed to fully dry before being incubated at 30° C. for 3-5 days on the TSA plates. A wash water sample (100 uL) from each sterilized seedling was plated onto a ¼-strength Tryptic Soy Agar plate as a sterility check. Plates were checked after incubation period for presence of target isolates and identity of the target isolates was confirmed, if necessary, by PCR amplification and sequencing of the 16S rRNA gene. As a positive control, root system for some plants were not sterilized prior to plating on the TSA plate.

The results of this experiment showed the seeds incubated with MS3900 or MS3907 formed colonies from non-sterilized root systems of the corn plants on Tryptic Soy Agar plates. In addition, plates with the sterilized root systems also had colonies formed specifically at the end of the roots, which showed that the MS3900 and MS3907 not only were able to colonize the roots of the corn plant, not were also endophytes in the root system (FIG. 41).

Additionally, when the same Tryptic Soy Agar plate contained roots from seeds incubated with MS3907 and with root from seeds incubated with MS3900, there was an increase in the number of colonies from both isolates observed on the plate compared to when roots from seeds incubated with only one type of isolate was present per plate. This result showed that incubating MS3907 with MS3900 improved the ability of MS3907 to colonize the root of the corn plants.

For corn seeds incubated with MS4921 in different tests in a sterile system, the root systems of those plants showed root colonization from all 12 seedlings inoculated and MS4921 was recovered from inside the root systems of all four seedlings tested. MS4921 was shown to be a strong root colonizer and an endophyte of corn.

Corn Stem Test

Figure 65:
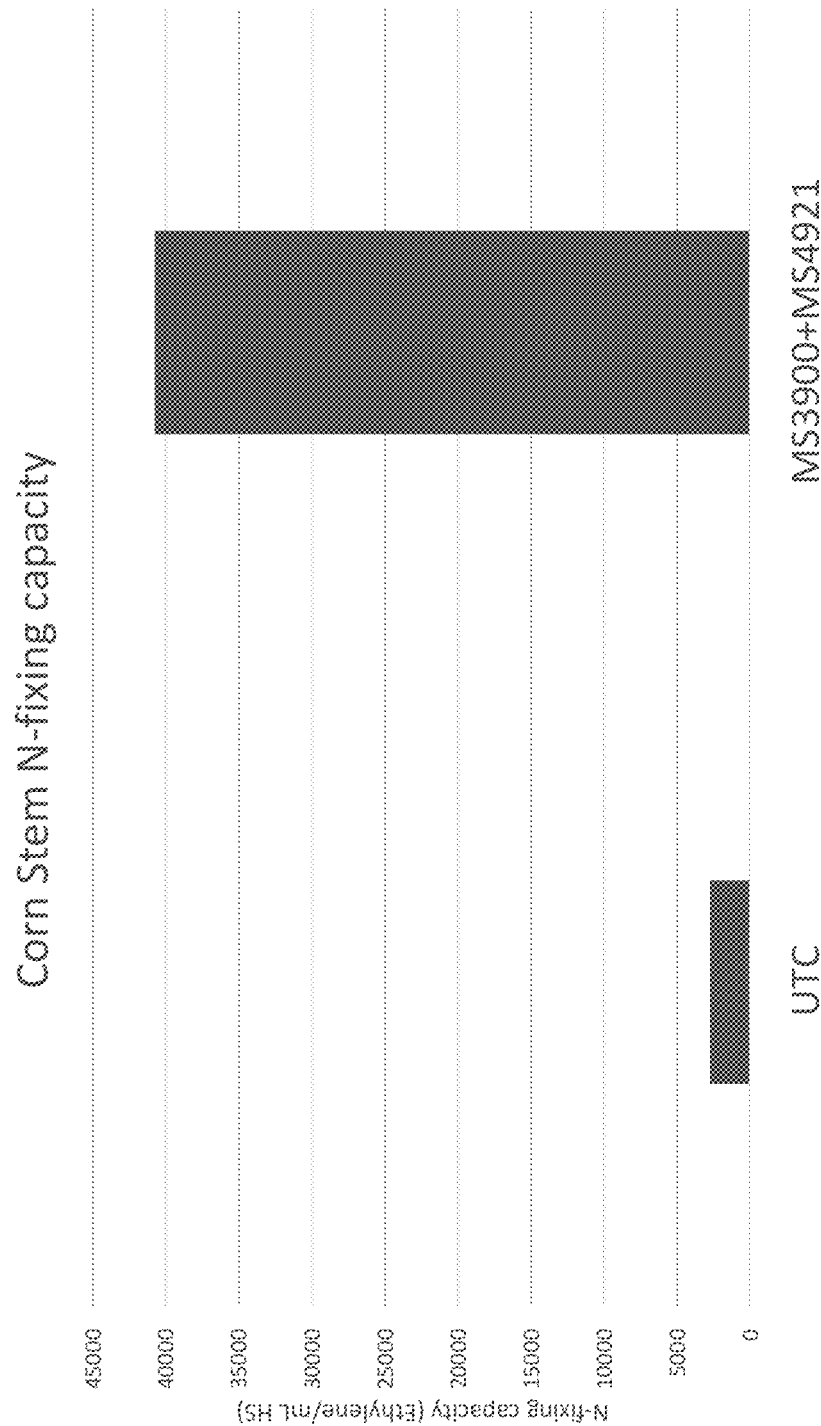
FIG. 65 shows ARA activity of corn stems tissue. Application of MS3900 and MS4921 together resulted in greater N-fixing capacity compared to that of UTC.

Acetylene reduction was also tested in corn stem tissue in a greenhouse test for a 14 day harvest. Isolates MS3900 and MS3907 were shown to provide ARA benefits in tissue (FIG. 65). Treatment with MS3900 and MS3907 together showed greater N-fixation capacity compared to untreated controls.

Example 12: Analysis of Nitrogen Fixation and nifH Content from NTS Base Product The capacity of the microbes in the microbe consortium to fix nitrogen was measured by quantifying nifH, a nitrogen-fixing gene. 75 milliliters (mL) of the microbe consortium solution was centrifuged and the resulting cellular pellet was resuspended in Qiagen's Solution MBL. Garnet beads were supplemented by volume of 0.5 mL to Lysing Matrix E homogenization beads. The sample was then transferred to a bead beater and the sample was homogenized at a setting of 4 meters/second (m/s) for 40 seconds. The tube was centrifuged and supernatant transferred to a new tube. Hard to lyse microbes were re-extracted from the pelleted debris by treating with 250 microliters (µL) of 17 milligrams/mL (mg/mL) lysozyme and incubated at 40° C. for 10 minutes. Following lysozyme treatment, the DNA was purified using the QIAamp BiOstic Bactermia Kit and concentration was determined with a Qubit™ Fluorimeter.

The isolated DNA was analyzed via qPCR using SYBR Green. Degenerate PCR primers, PolF/PolR, were picked to capture a wide number of expected nitrogen-fixing microbes (Gabby and Buckley, 2017). The qPCR output values were normalized to the DNA concentrations and to the starting PCR volume to determine nifH copy numbers per milliliter (cn/mL) of the starting microbe consortia solution. In some instances nifH is expressed as copy numbers per nanogram (cn/ng) of the starting microbe consortia DNA.

Following process optimization, the base product of NTS-4 was tested for nitrogen enrichment capacity. Compared to 1:30 PST WB, the NTS-4 product showed superior nitrogen fixation capacity, measured as greater nifH content (FIG. 4A). Nitrogen fixation capacity was measured across NTS system—NTS-1.1, NTS-1.2, NTS-1.3, and NTS-1.4—and the results showed that NTS-4 displayed higher nifH content compared to that from other NTS 1.0 systems (FIG. 4B). NTS-4 was applied to corn to examine recruitment of N-fixers compared to untreated control plants. NTS-4 showed greater nifH copy number compared to UTC, demonstrating recruitment of beneficial microbes (FIG. 5C).

Figure 42:
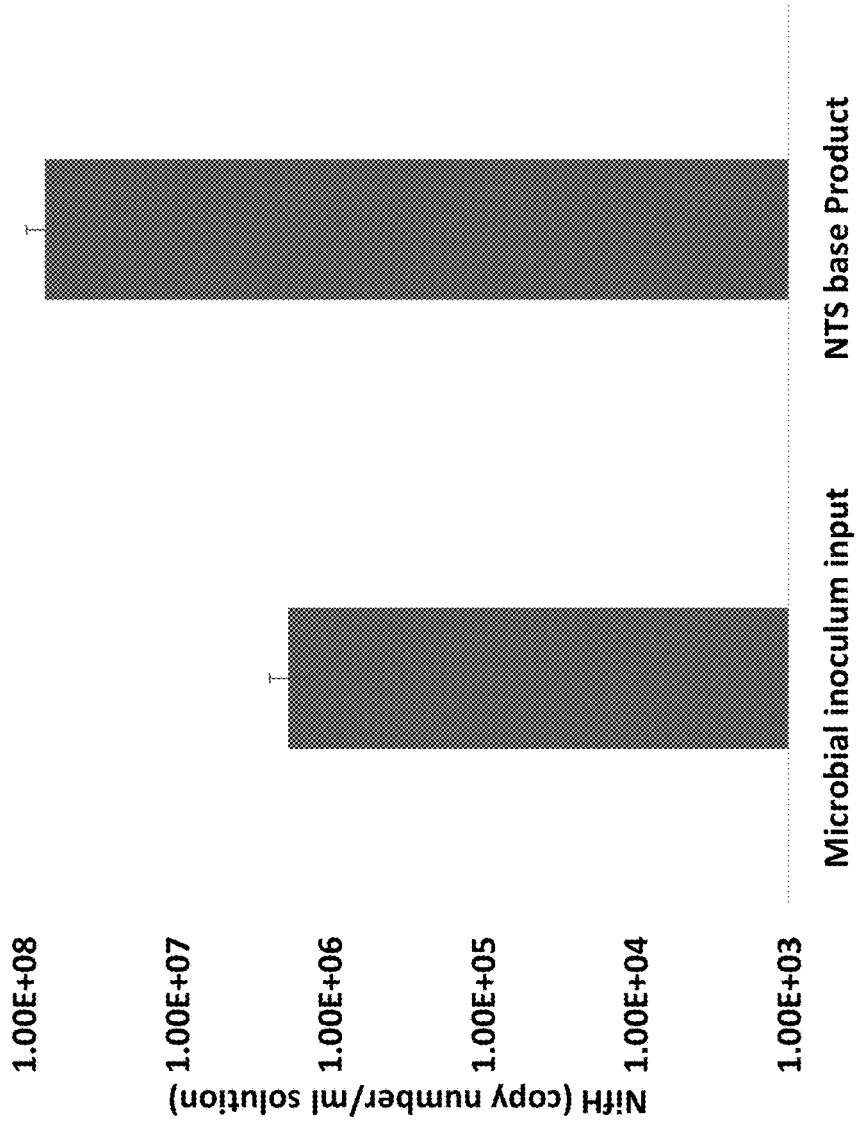
FIG. 42 shows that NTS base product enriches nifH content from starting inoculum.

The starting inoculum (e.g., PST WB) and the final product of the NTS system was tested. The PST microbial inoculum solution comprised a 1:3 ratio of floc:SPN. The starting inoculum and WB for the PST microbial inoculum solution was tested to determine the quantity of nifH for each respective solution. The starting inoculum had about $1.0 \times 10^6$ copy numbers per milliliter (cn/mL) of nifH, while the NTS product solution (NTS base product) had over $1.0 \times 10^7$ cn/mL (FIG. 42), which showed that the NTS system enriched the quantity of nifH in the PHOSEE microbial inoculum solution. Additionally, a 1:1 PST microbial inoculum solution WB at a dilution of $10^{-4}$ was shown to fix nitrogen when the WB was grown in nitrogen-free media at 30° C. for 3 days.

Figure 43:
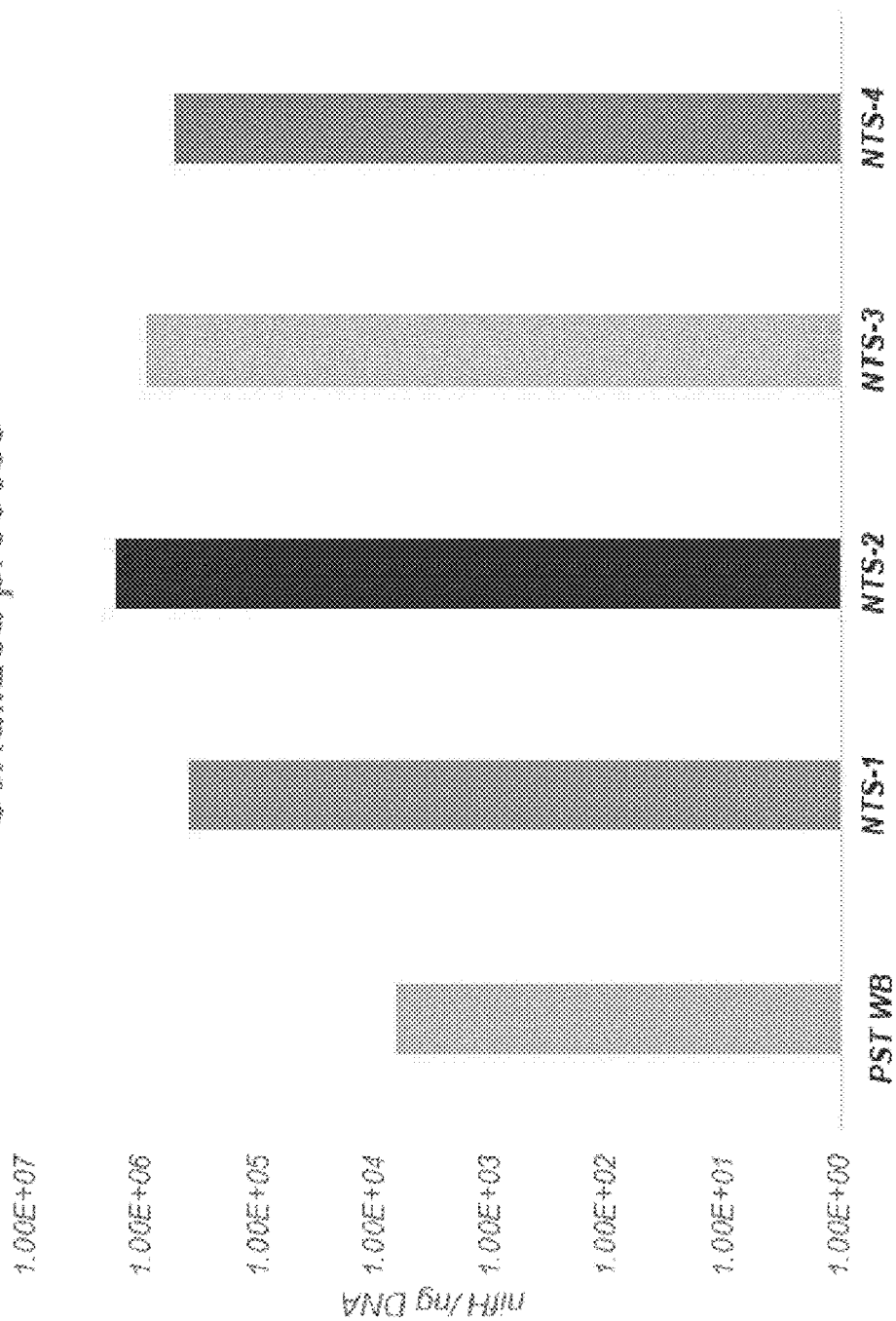
FIG. 43 shows results of NTS 1.0 systems tested for nifH enrichment. NTS-2 (e.g., NTS 1.2) showed the greatest nifH enrichment from starting inoculum.
Figure 44:
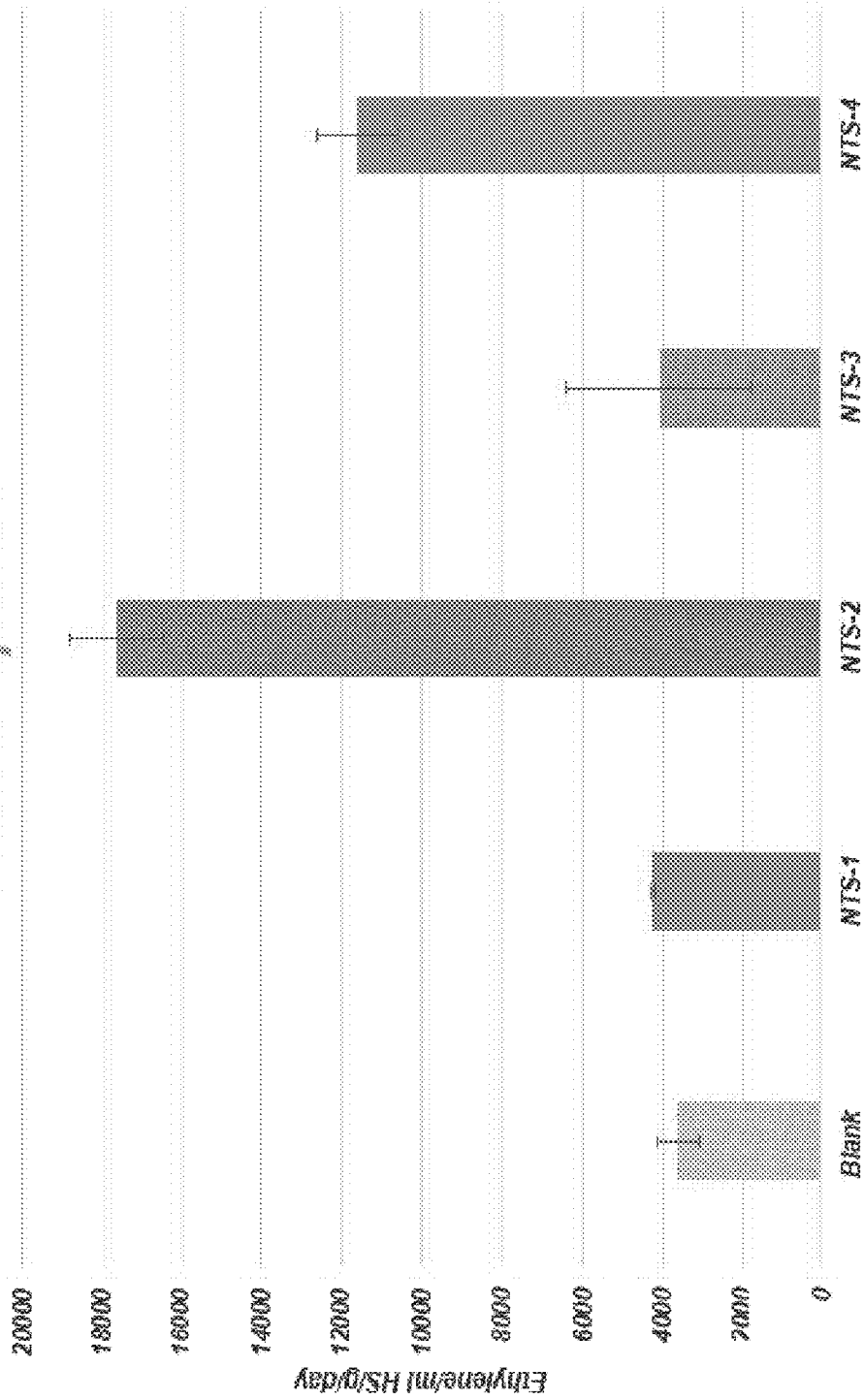
FIG. 44 shows results of NTS 1.0 systems tested for nitrogen fixation capacity in an acetylene reduction assay. NTS-2 (e.g., NTS 1.2) showed the highest level of ethylene released.

The quantity of the nifH gene was measured in the starting microbial inoculum (e.g., PST WB) and in the end product of different versions of the serialized NTS system (e.g., NTS-1.1, NTS-2.2, NTS-2.3, and NTS-2.4). The amount of nifH per nanogram of DNA (nifH/ng DNA) increased from less than $1.0 \times 10^4$ nifH/ng DNA in the starting microbial inoculum to over $1.0 \times 10^5$ nifH/ng DNA in each of the NTS system stages (FIG. 43). The capacity of nitrogen fixation of the end product of each version of the NTS system was also tested using an Acetylene Reduction Assay, as described below. The end products at the second NTS version (e.g., NTS-1.2) and the fourth NTS version (e.g., NTS-1.4) of the NTS 1.0 systems had greater levels of acetylene reduction activity compared to the sterile media blank control (FIG. 44).

The end products of each stage of NTS system was then tested for the ability to recruit nitrogen-fixing microbes to the roots of corn plants. Corn plants were planted in a 1:1:1 Profile MVP® Turface-peat-Denton sandy loam soil mix in a 15-centimeter pot. Each pot, except for the positive control, was fertilized with 50 ml liquid fertilizer solution containing UAN32 (urea ammonium nitrate 32-0-0) at 10 pounds nitrogen (N)/A rate (1.8%)+TSP (triple super phosphate 0-45-0-15Ca) at 20 pounds phosphorus (P)/)A rate (3.36%)+potash (potassium chloride 0-0-60) at 200 pounds potassium (K)/A rate (25.52%)+Jackpot® micronutrient fertilizer solution (0.78%)+4.1 mg (0.01%) of $Na_2MoO_4$ $2H_2O$ (sodium molybdate dihydro)). The positive control was fertilized with UAN32 at 20 lbs. N/A (3.57%)+ the same levels of the other nutrients as above. The first NTS version end product (NTS-1.1), the second NTS version end product (NTS-1.2), the third NTS version end product (NTS-1.3), the fourth NTS version end product (NTS-1.4), or a negative control (e.g., water or UTC) was applied to the soil of the corn plants at a rate of 36 microliters (μL) per 15 cm pot at planting in a Latin square design. The experimentation design, as described herein, additionally included a positive group which included corn plants with higher nitrogen fertilization at planting (20 pounds of N/A fertilizer). Each group of end products, positive control, or negative control had 12 replicate pots. The Greenhouse codes for where the corn was grown and the corresponding treatment solution is shown below in Table 18. The corn plants were grown for at least 4 weeks prior to harvest.

TABLE 18

Greenhouse Codes and Corresponding Corn Treatment Solution

| Greenhouse Code | Treatment description |
| --- | --- |
| A | Water (UTC) |
| B | NTS-1.1 |
| C | NTS-1.2 |
| D | NTS-1.3 |
| E | NTS-1.4 |
| F | Higher N fertilization (+10 lbs. N/A) (positive control) |

At harvest, the rhizosphere soil and the fine roots from randomly selected corn plants from each group was collected. Fine roots were washed of soil and processed as described herein to create a root extract solution (rhizoplane+endophytic space solution). The DNA from the rhizosphere soil and the root extracts were extracted per the protocol described above. Following DNA extraction, the DNA was either used for qPCR to determine levels of 16S and nifH in the samples or analyzed via next generation sequencing. The qPCR protocol used for this analysis is described above.

For the qPCR, the measurement of 16S in the DNA determined the total amount of bacteria present in that sample and the measurement of nifH determined the amount of nitrogen-fixing microbes are present in that sample. The qPCR data was also compared against the DNA extracted from the untreated (e.g., negative control) corn plants.

Figure 45A:
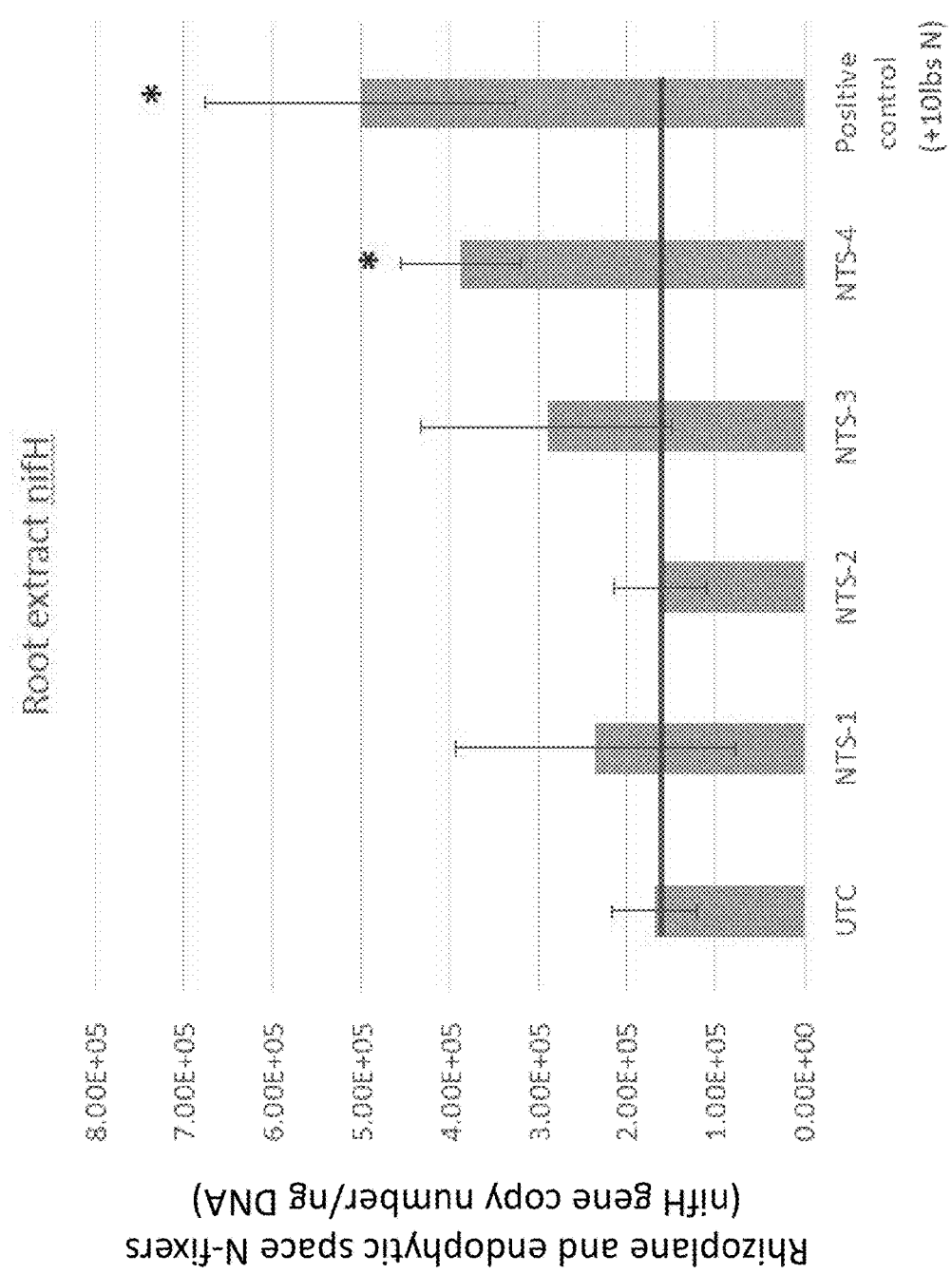
FIGS. 45A-45B show the N-fixing bacteria of NTS 1.0 systems in root extracts.
Figure 45B:
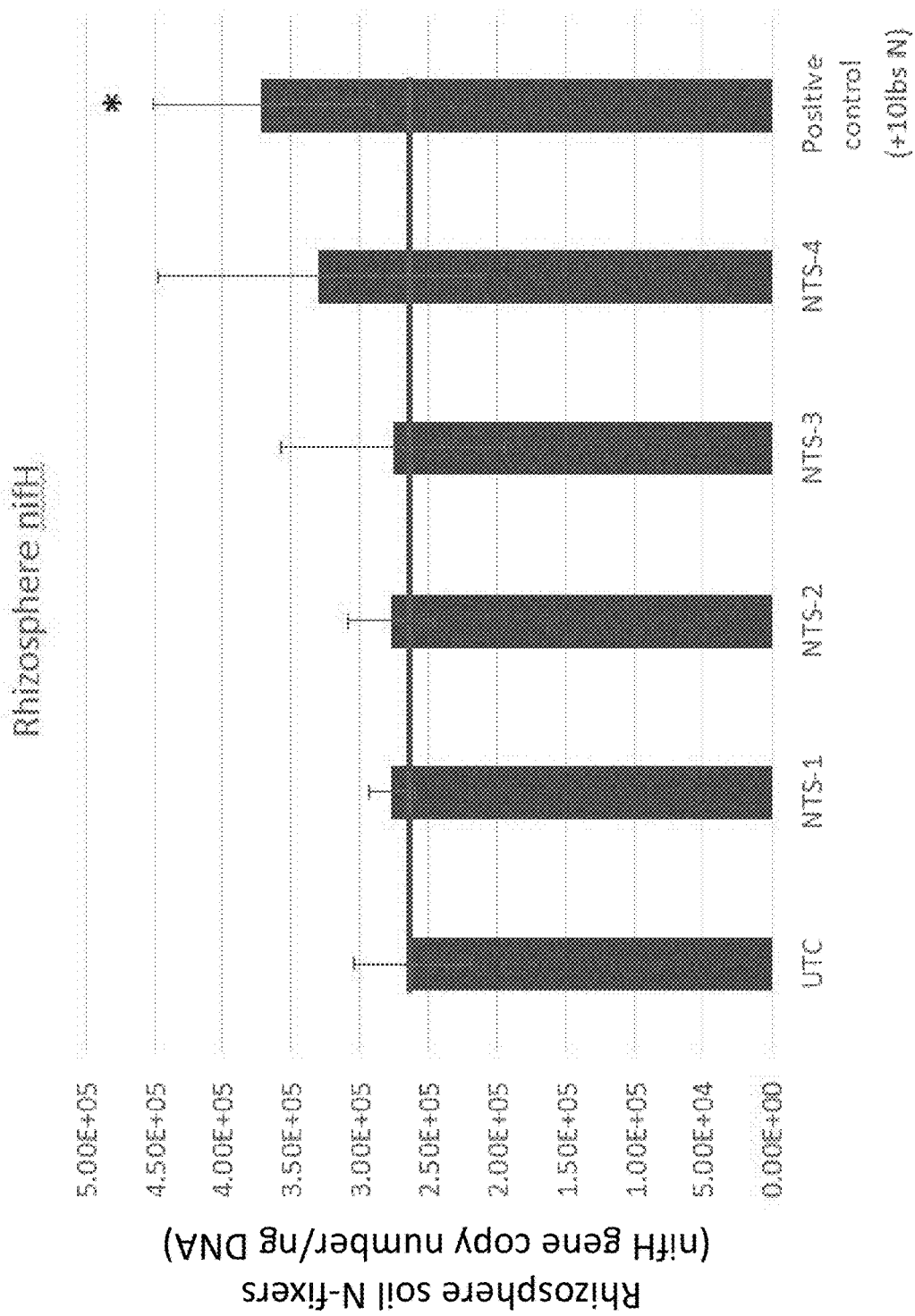

When the DNA from the root extracts was analyzed, the amount of nifH present in the root extracts was significantly higher in corn plants treated with the NTS-1.4 end product compared to corn plants treated with the negative control, which suggested the recruitment of nitrogen-fixing microbes into the roots of corn plants treated with the NTS-4 end product (FIG. 45A). Additionally, DNA from the rhizosphere soil also showed an increased level of nifH in soil of corn plants treated with the NTS-1.4 end product compared to corn plants treated with the negative control (FIG. 45B).

Figure 46A:
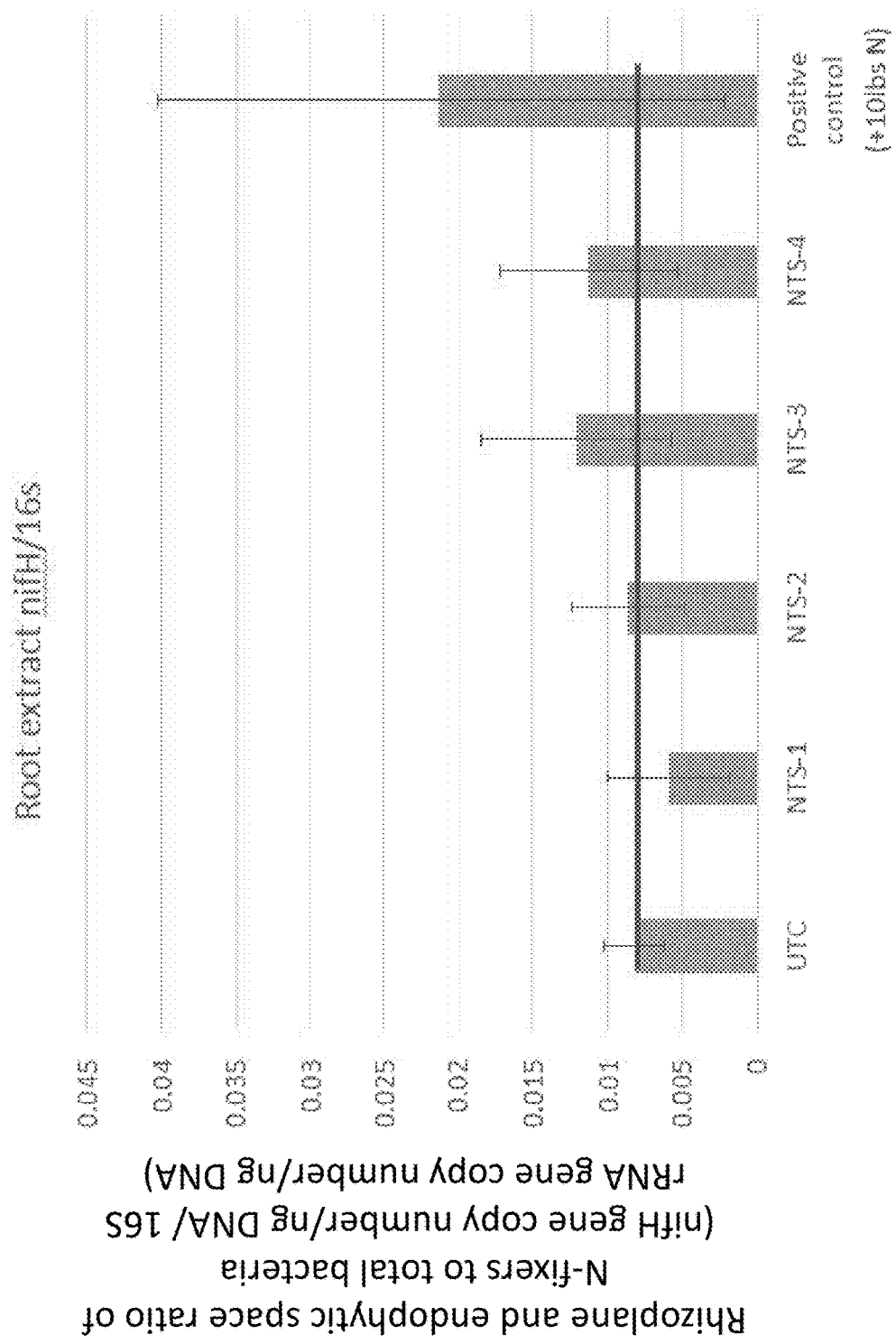
FIGS. 46A-46B show the effects of NTS 1.0 system base products on the ratio of nifH gene to 16S rRNA gene content in root extracts (FIG. 46A) and rhizosphere (FIG. 46B).
Figure 46B:
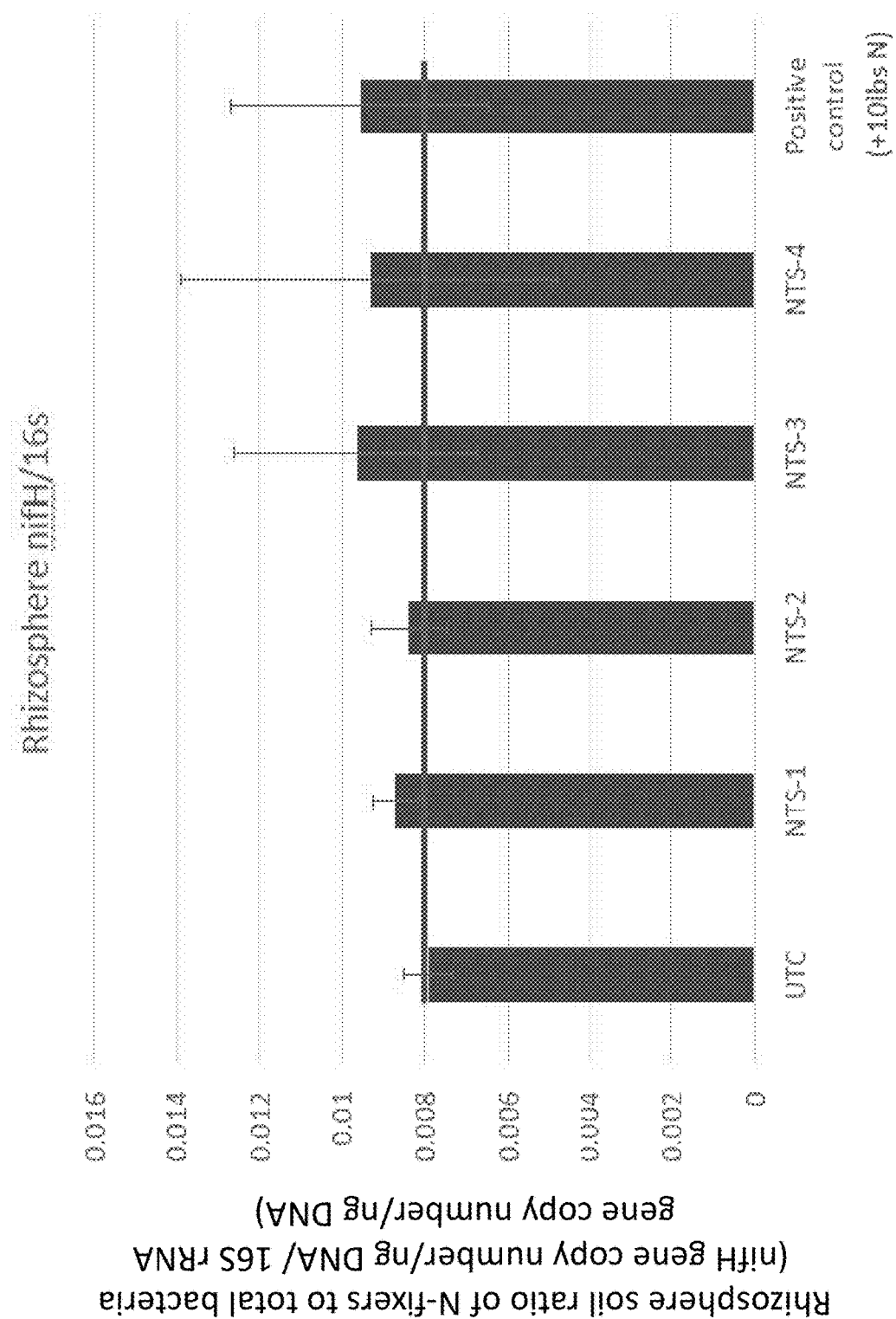

The resulting qPCR data from the measurement of 16S and nifH in the same sample was used to determine the percentage of the total bacterial community from that corn plant that was nitrogen-fixing microbes (e.g., level of nifH divided by the level of 16S in the sample). This analysis determined that corn plants treated with the end product from NTS-3 or NTS-4 had increased percentages of nitrogen-fixing microbes out of the total bacterial community in both the root extract (FIG. 46A) and the rhizosphere soil (FIG. 46B) compared to corn plants treated with the negative control.

Example 13: Process Design and Optimization of NTS Systems—Nitrogenase Activity and Acetylene Reduction Assays Acetylene Reduction Assay for NTS Base Product Solutions Nitrogenases are the enzymes responsible for the reduction of nitrogen ($N_2$) to ammonia ($NH_3$) in the process of Nitrogen fixation. To measure the N2 fixation capacity of the output of the NTS systems, three 4-mL replicate samples were incubated on a rotary shaker at 30° C. and 60 rpm in 21 mL vials sealed with 18 mm magnetic screw-top caps with septa (MilliporeSigma, Burlington, MA) after replacing 12% (v/v) of air in the headspace with acetylene. Water was used as negative control (UTC) following the same procedure used for the samples. After 72 hours of incubation, 0.5 mL of the headspace of all UTC and sample replicates was sampled and injected directly into a GC equipped with a flame ionization detector (FID) for analysis (Agilent 8890 with an $Al_2O_3$ column, $Na_2SO_4$ deactivated, with Helium as carrier gas (2 ml/min)). The injector was set at 200° C. with a split injection of 5:1, the FID detector was maintained at 250° C., and the oven at 40° C. for 2 minutes, followed by a ramp of 40° C./minute from 40 to 140° C.

Figure 47:
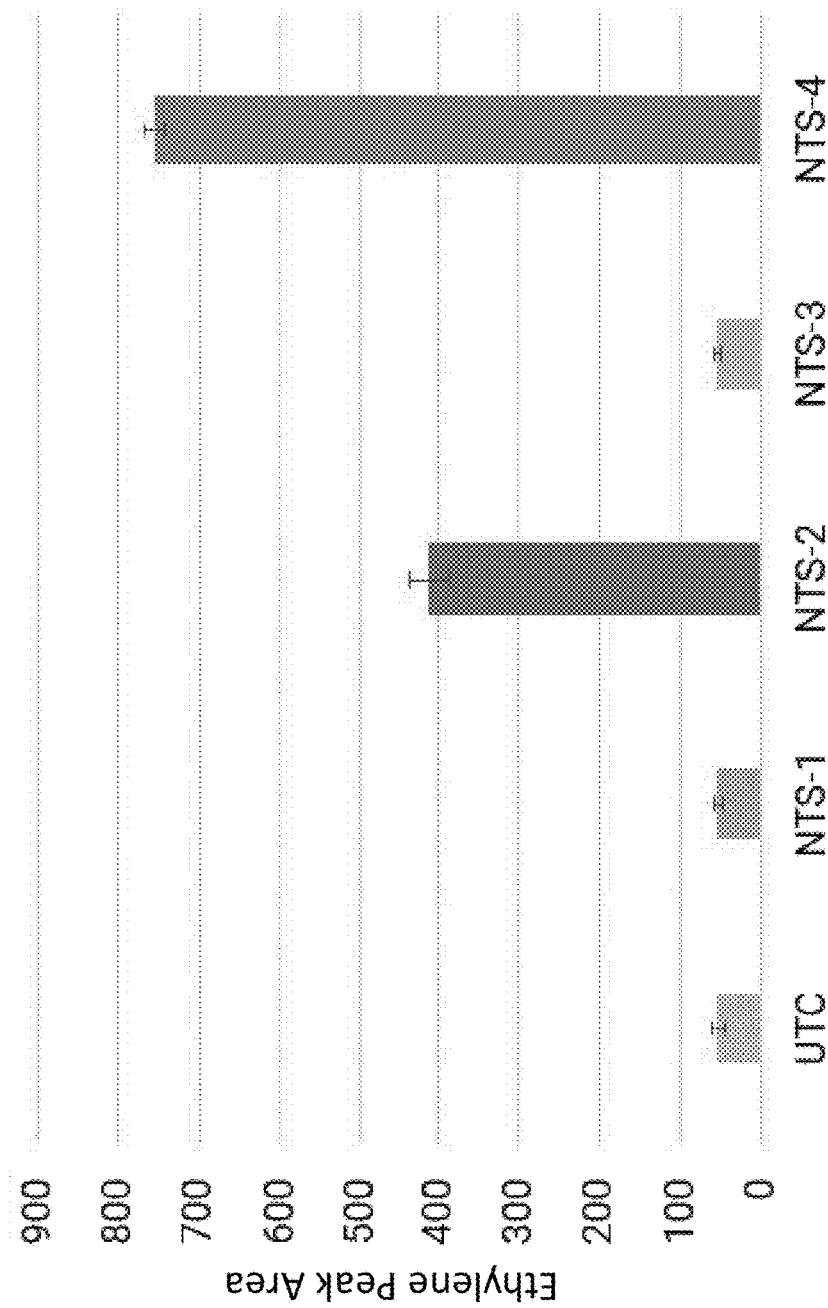
FIG. 47 shows the capacity of NTS 1.0 systems in an acetylene reduction assay, used as a proxy to nitrogenase activity. NTS-1.4 showed the highest levels of ethylene production.
Figure 48:
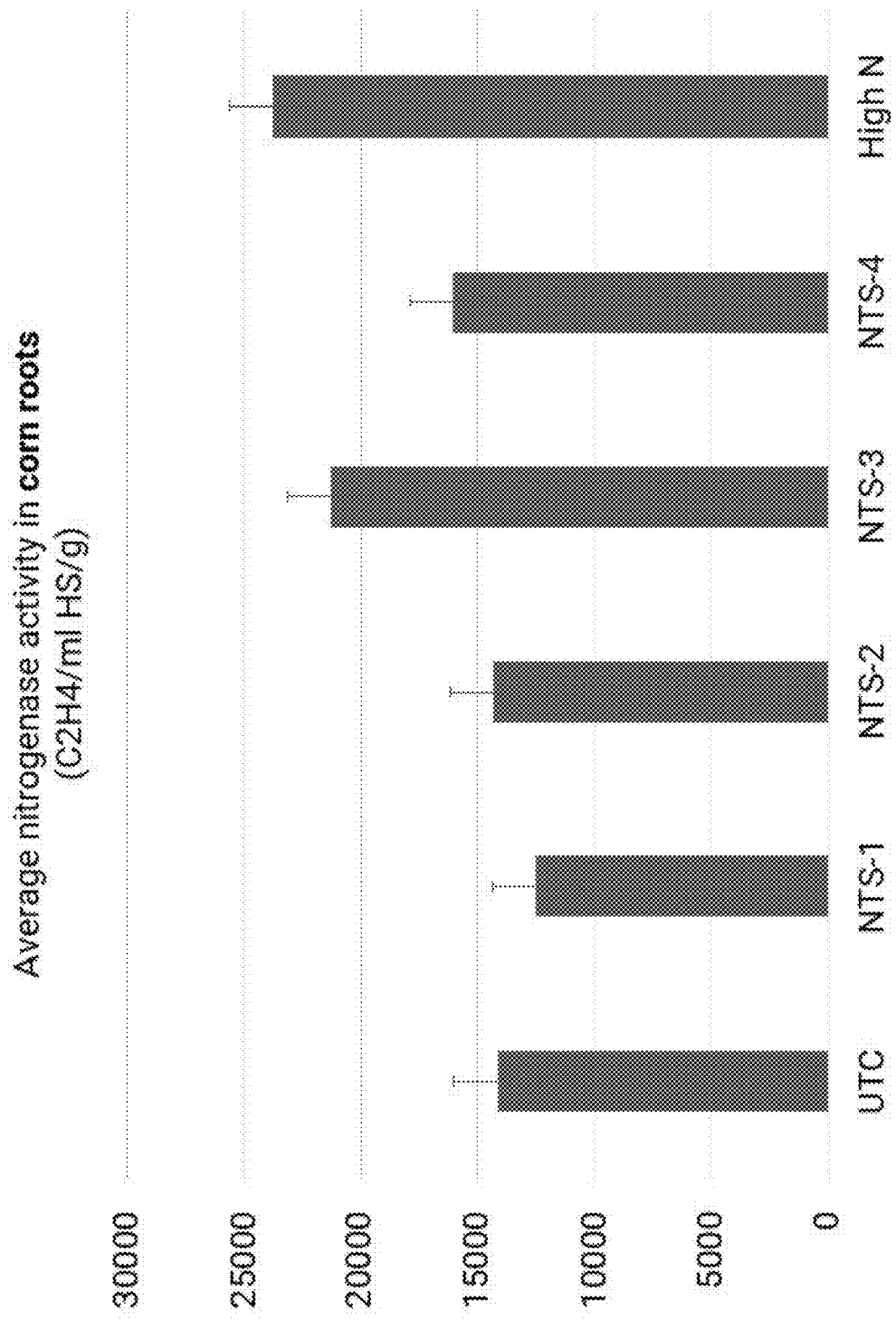
FIG. 48 shows the capacity of NTS 1.0 systems in an acetylene reduction assay of corn roots, with an additional control of High N (e.g., high nitrogen).

Ethylene was identified using an ethylene standard and ethylene production followed determining the peak area under the curve. The average ethylene produced per hour was compared across the NTS 1.0 systems (FIG. 47). The NTS-4 system showed the greatest capacity to fix nitrogen compared to the capacity of the other NTS systems and UTC. The average nitrogenase activity was measured in corn roots across NTS 1.0 systems and compared with UTC and a High N control condition (FIG. 48). The NTS-3 system showed the greatest nitrogenase activity compared to the other NTS 1.0 system, and the High N control showed the highest nitrogenase activity overall.

Quantification of *Paenibacillus Borealis* MS3907 and *Bacillus megaterium* MS3900 from N-Trifecta Base Product Solutions NTS product solutions were serially diluted in 0.1% hexametaphosphate buffer and plated spanning three 10-fold dilutions in duplicate on quarter-strength Tryptic Soy Agar (Becton-Dickinson) with supplemented solidifying agar to 12 g/L (Difco Agar Technical). Plates were incubated at 30° C. for seven days. Colonies of *Paenibacillus borealis* MS3907 and *Bacillus megaterium* MS3900 morphologies were counted and averaged. Colonies were then streaked out to fresh ¼ strength TSA plates for isolation. Colony-direct PCR was used to verify a subset of these isolates.

Spore-forming bacteria, including isolates MS3907 and MS3900, were enumerated by heating NTS product solutions at 60° C. for 15 min, then cooled to room temperature. Pasteurized solutions were serial diluted in 0.1% hexametaphosphate buffer and plated spanning three 10-fold dilutions in duplicate on quarter-strength Tryptic Soy Agar (Becton-Dickinson) with supplemented solidifying agar to 12 g/L (Difco Agar Technical). Plates were incubated at 30° C. for 5 days. Total spore-forming colonies, *Paenibacillus borealis* MS3907 morphologies, and *Bacillus megaterium* MS3900 morphologies were counted and averaged. Colonies were then streaked out to fresh quarter-strength TSA plates for isolation. Colony-direct PCR was used to verify a subset of the *Paenibacillus borealis* MS3907 and *Bacillus megaterium* MS3900 isolates.

PCR for *Paenibacillus borealis* MS3907: Genes for isolate MS3907 were screened from full genome compared to *Paenibacillus borealis* type strain. The gene encoding a cyanate hydratase, MS3907_peg.3387, was chosen for specificity to our MS3907 isolate compared to closely related species (Primer pair: MS3907_cynS_F_275 (5'-CGCTAATGGTGTACGGTCCT, MS3907_cynS_R_428 (3'-GCAAAAACTTTCCGTTCAGG). PCR reactions were set up with 0.5 µM of each primer, 1× AmpliTaq Gold 360 MasterMix (2×), and nuclease-free water. A sterile toothpick was touched to the surface of the colony and mixed into the PCR reaction. PCR was performed by denaturing at 95° C. for 10 min followed by 30 cycles of denaturation at 95° C. for 30 sec, annealing at 51° C. for 30 sec, and extension at 72° C. for 30 sec along with a final extension at 72° C. for 5 minutes.

PCR for *Bacillus megaterium* MS3900: Genes for isolate MS3900 were screened from full genome compared to *Bacillus megaterium* type strain. The gene encoding an inner membrane protein translocase component, YidC, MS3900_peg.6272, was chosen for specificity to our MS3900 isolate compared to closely related species (Primer pair: MS3900_yidC_F_(5'-AAAAGAAAATGGGGCAAACC, MS3900_yidC_R (5'-CTGCATGCCCTAAATCCAAC).

PCR reactions were set up with 0.2 µM of each primer, 1× AmpliTaq Gold 360 MasterMix (2×), and nuclease-free water. A sterile toothpick was touched to the surface of the colony and mixed into the PCR reaction. PCR was performed by denaturing at 95° C. for 10 min followed by 30 cycles of denaturation at 95° C. for 15 sec, annealing at 55° C. for 15 sec, and extension at 72° C. for 15 sec along with a final extension at 72° C. for 7 minutes.

Figure 49:
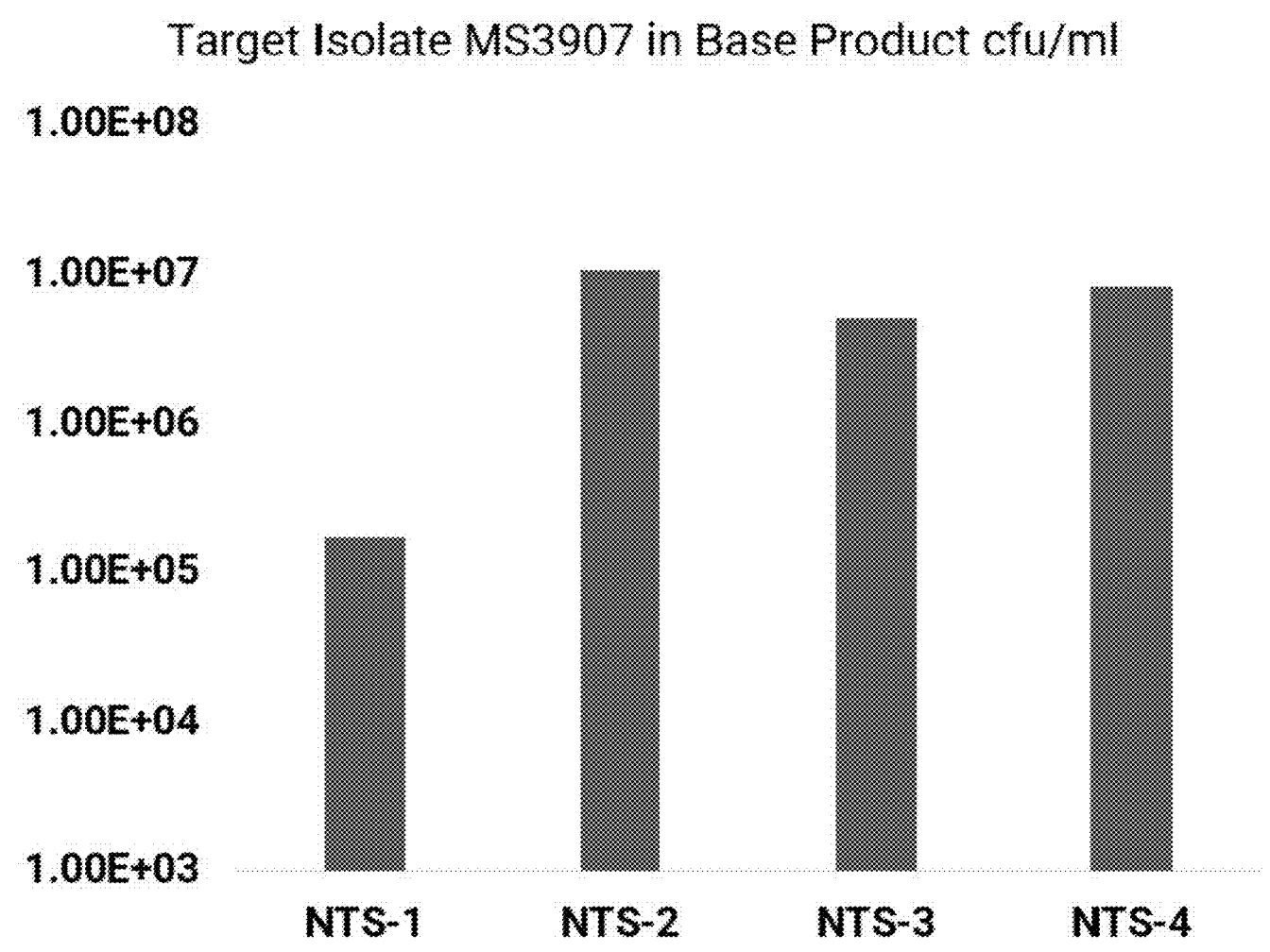

Different process designs and inputs create different enrichment environments for proprietary target isolate MS3907 in NTS 1.0 reactors. Isolate concentration was measured after 4 months of inoculation in reactor 1 of NTS 1.0 reactors. Base product of NTS-2, NTS-3, and NTS-1.4 showed similar levels of isolate MS3907 (FIG. 49). All showed higher levels of MS3907 than that of NTS-1.

Figure 50A:
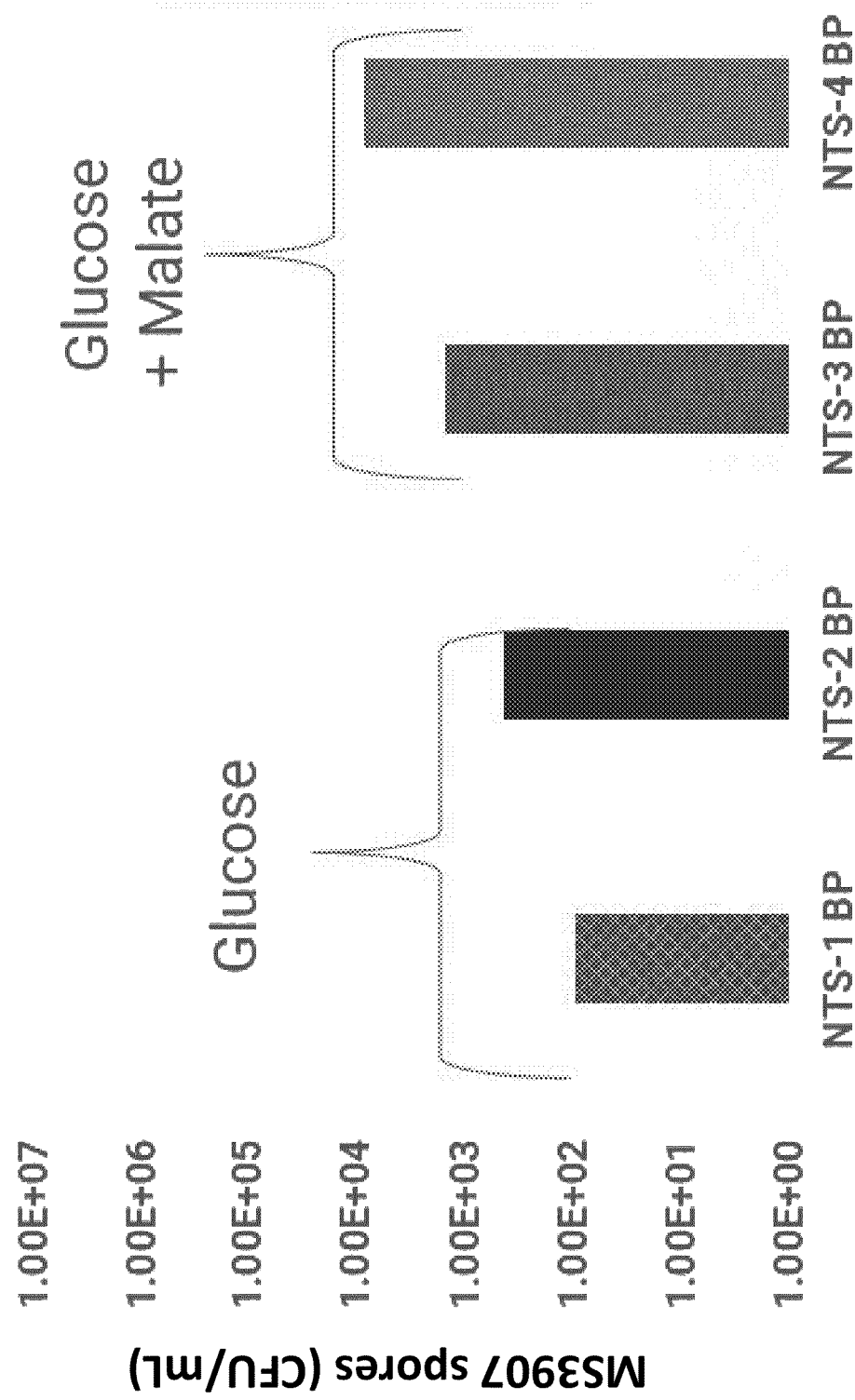
FIGS. 50A-50B show the results of MS3907 sporulation and retention in the base products of NTS 1.0 systems.
Figure 50B:
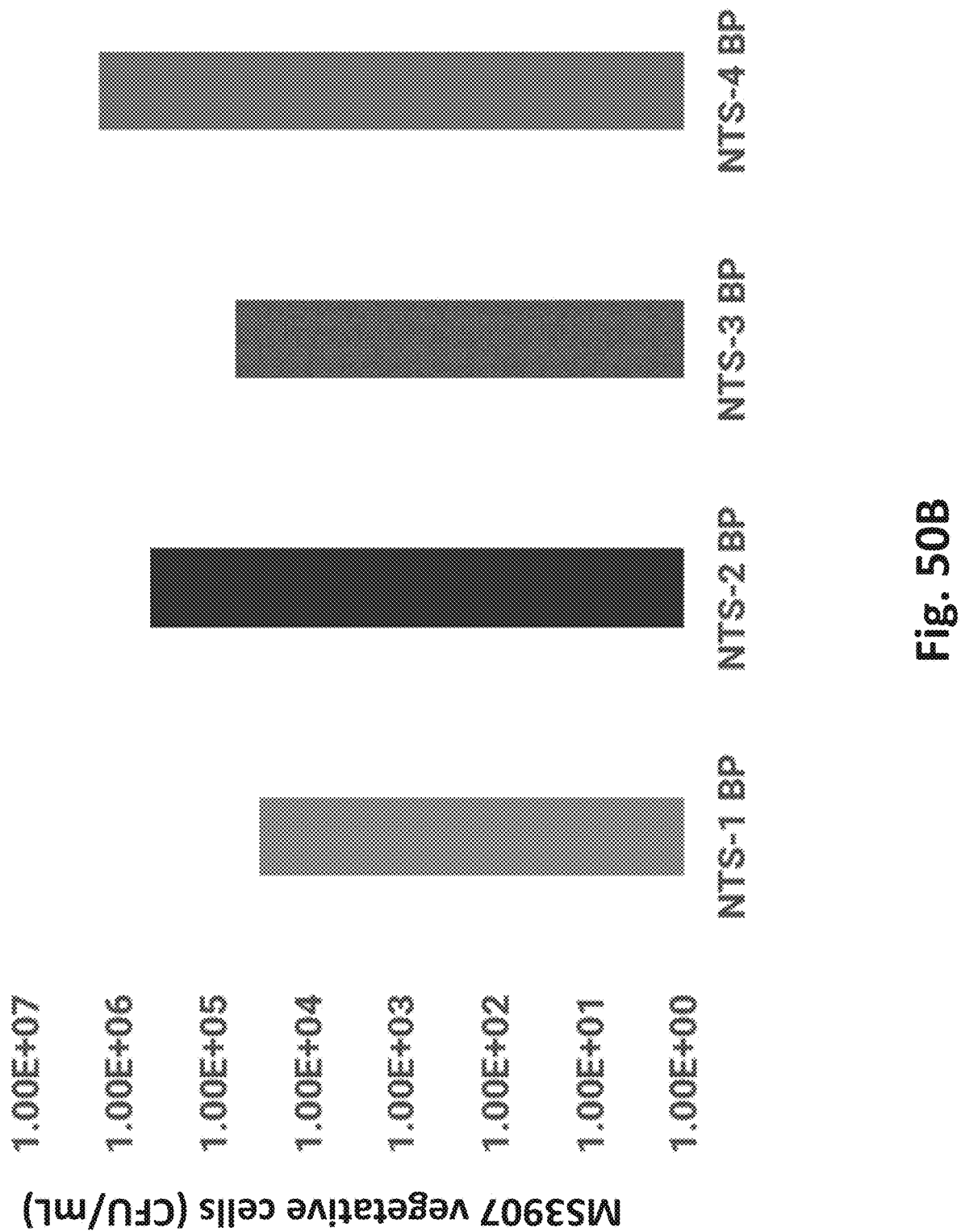

The NTS 1.0 systems were set up with different inputs and reactors to test for potential effects on MS3907 sporulation and retention. NTS 1.1 and NTS 1.2 had glucose as a carbon input source and NTS 1.3 and NTS 1.4 had both glucose and malate as carbon input sources. NTS 1.1 and NTS 1.3 had packed bed reactor systems, whereas NTS 1.2 and NTS 1.4 had fluidized bed reactor systems. Visual counts of MS3907 from heated base product showed that the addition of malate had a positive impact on MS3907 sporulation, with a greater number of spores in the NTS-3 and NTS-4 systems (FIG. 50A). Visual count from unheated base product showed that fluidized bed reactors contributed to greater MS3907 retention compared to that from systems with packed bed reactors (FIG. 50B).

Semi-Quantification from of *Paenibacillus Borealis* Isolate MS3907 and *Bacillus megaterium* Isolate MS3900 from DNA Extractions of NTS Base Product Solutions Genes for isolate MS3907 were screened from full genome compared to *Paenibacillus borealis* type strain. The gene encoding a cyanate hydratase, peg.3387, was chosen for specificity to our MS3907 isolate compared to closely related species (Primer pair: MS3907_cynS_F_275 (5'-CGCTAATGGTGTACGGTCCT), MS3907_cynS_R_428 (3'-GCAAAAACTTTCCGTTCAGG). PCR reactions were set up using 2 µL of DNA extracted from NTS Base Product solutions, 0.5 µM of each primer, 1× AmpliTaq Gold 360 MasterMix (2×), and nuclease-free water. Three biological replicates were run separately. PCR was performed by denaturing at 95° C. for 5 min followed by 30 cycles of denaturation at 95° C. for 30 sec, annealing at 51° C. for 30 sec, and extension at 72° C. for 30 sec along with a final extension at 72° C. for 5 minutes.

PCR for *Bacillus megaterium* MS3900: Genes for isolate MS3900 were screened from full genome compared to *Bacillus megaterium* type strain. The gene encoding an inner membrane protein translocase component, YidC, MS3900_peg.6272, was chosen for specificity to our MS3900 isolate compared to closely related species (Primer pair: MS3900_yidC_F_(5'-

AAAAGAAAATGGGGCAAACC, MS3900_yidC_R (5'-CTGCATGCCCTAAATCCAAC).

PCR reactions were set up using 0.5 uL of DNA extracted from NTS Base Product solutions, with 0.2 μM of each primer, 1× AmpliTaq Gold 360 MasterMix (2×), and nuclease-free water. A sterile toothpick was touched to the surface of the colony and mixed into the PCR reaction. PCR was performed by denaturing at 95° C. for 5 min followed by 30 cycles of denaturation at 95° C. for 15 sec, annealing at 55° C. for 15 sec, and extension at 72° C. for 15 sec along with a final extension at 72° C. for 7 minutes.

PCR reactions were ran using Lonza's FlashGel™ System for 5 min at 175 V. Samples are run alongside of standards consisting of 10-fold dilutions of known cynS copy number PCR products from MS3907 genomic DNA or from known yidC copy number PCR products from MS3900 genomic DNA. Intensity of bands for each replicate are compared and binned into a range of cynS or yidC copy number compared to the standards. The ranges were normalized to the original DNA concentration, amount of PCR reaction, and original volume of solution used for DNA extraction to yield cynS or yidC copy number per mL of NTS Base Product. Final copy numbers/mL came from averaging all three reps of the upper and lower ranges.

*Arabidopsis* PGP Protocols

Figure 51:
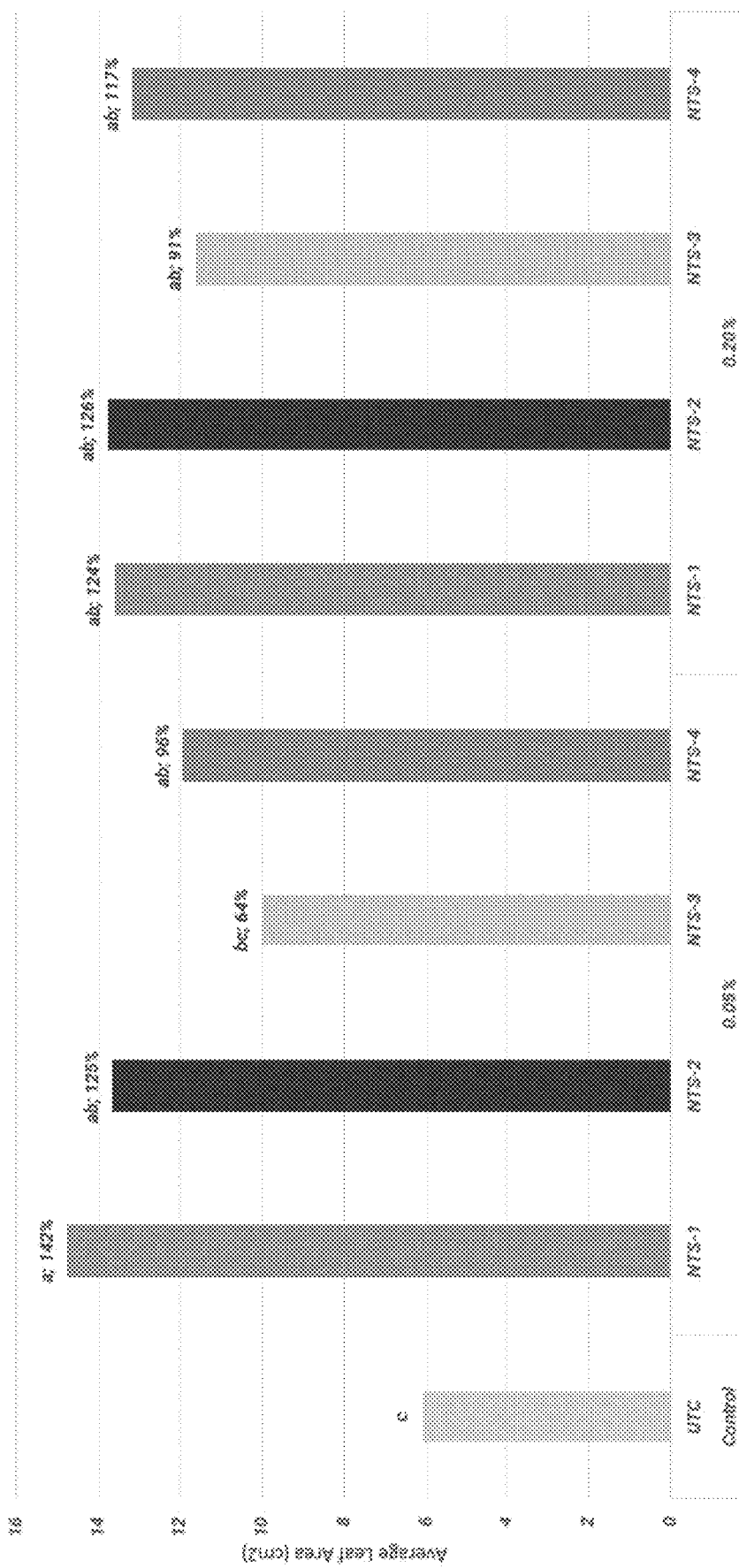
FIG. 51 shows the average leaf area in *Arabidopsis* across NTS 1.0 systems at 0.05% or 0.2% application rate. NTS-1 at a 0.05% application rate showed the greatest plant growth promotion capacity compared to that of UTC and other NTS treatment conditions.

NTS-1.0 base product solutions were tested in *Arabidopsis* for plant growth promoting ability, using average leaf area (in cm$^2$) as the primary metric. All systems were tested under two rate, 0.05% and 0.2% v/v. *Arabidopsis thaliana* (genotype Col-0) seedlings were germinated and grown for 7 days on 1 strength MS media (Murashige & Skoog Basal Medium with Vitamins, M519) plates in the growth chamber before transplanting into rockwool cubes for plant growth assays. Rockwool cubes were used as an inert substrate for growing *Arabidopsis* in a hydroponic-like system. The rockwool cubes were fitted into a 6-well tray and each treatment consisted of three replicate well trays. Eleven, 1 L ½ strength MS media (Murashige & Skoog Basal Medium with Vitamins, M519) solutions were made. The test substance was then added at the rate given below in Table 19, and the pH of the solution was raised to 5.7. Forty mL of each 1 L treatment solution was dispensed to each rockwool cube. Then, each wetted cube received one *Arabidopsis* seedling. *Arabidopsis* plants grew on an LED light cart for 12 days. Leaf area was determined using the ImageJ software package. All the data collected were put through JMP for ANOVA analysis. All treatments showed numerically greater average leaf area measurement from the UTC with NTS-1 having the most significant plant growth promotion (p=0.17871) (FIG. 51). All base product solutions across all systems showed consistent PGP activity over the UTC control.

TABLE 19

Treatments for testing plates.

| 1. | ½MS Media+ | UTC |
| 2. | ½MS Media+ | 0.05% NTS-1.1 Base Product Solution (v/v) (0.5 mL/L) |
| 3. | ½MS Media+ | 0.05% NTS-1.2 Base Product Solution (v/v) (0.5 mL/L) |
| 4. | ½MS Media+ | 0.05% NTS-1.3 Base Product Solution (v/v) (0.5 mL/L) |
| 5. | ½MS Media+ | 0.05% NTS-1.4 Base Product Solution (v/v) (0.5 mL/L) |
| 6. | ½MS Media+ | 0.2% NTS-1.1 Base Product Solution (v/v) (2.0 mL/L) |
| 7. | ½MS Media+ | 0.2% NTS-1.2 Base Product Solution (v/v) (2.0 mL/L) |
| 8. | ½MS Media+ | 0.2% NTS-1.3 Base Product Solution (v/v) (2.0 mL/L) |
| 9. | ½MS Media+ | 0.2% NTS-1.4 Base Product Solution (v/v) (2.0 mL/L) |

Example 14: Process Design and Optimization of NTS Systems—Plant Growth Promotion Properties Nutrient status was evaluated across NTS 1.0 systems in corn plants and compared with nutrient status from untreated controls. The nutrient levels across NTS 1.0 systems are shown in Tables 20-21 as a percentage of UTC.

TABLE 20

Nutrient status for NTS systems

| % UTC | N | S | P | K | Mg | Ca |
| --- | --- | --- | --- | --- | --- | --- |
| NTS-1 | 1% | 1% | -2% | 13% | 5% | 7% |
| NTS-2 | 7% | 5% | 12% | 20% | 8% | 3% |
| NTS-3 | 0% | 0% | 18% | 13% | 7% | 0% |
| NTS-4 | 3% | -7% | 30% | 17% | -1% | -1% |
| High N | 48% | 23% | 23% | 43% | 35% | 24% |

TABLE 21

Nutrient status for NTS systems

| % UTC | B | Zn | Mn | Fe | Cu |
| --- | --- | --- | --- | --- | --- |
| NTS-1 | -19% | -8% | -4% | 17% | -17% |
| NTS-2 | -8% | 4% | 0% | 8% | -29% |
| NTS-3 | -16% | -4% | -7% | 49% | -33% |
| NTS-4 | -29% | -8% | -4% | 133% | -5% |
| High N | 9% | 30% | -1% | 92% | -18% |

Figure 52:
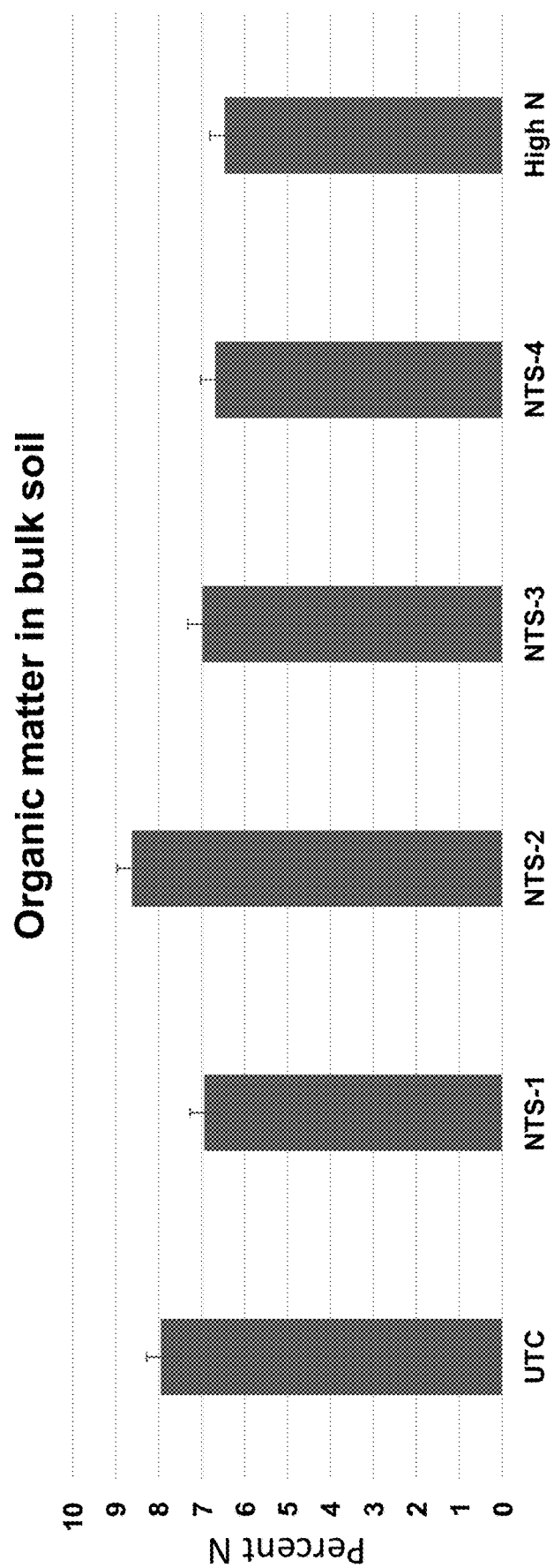
FIG. 52 shows the effects of NTS solutions on nitrogen levels in soil. NTS-1.2 product showed the highest percentage nitrogen in bulk soil compared to that of other NTS solutions.
Figure 53:
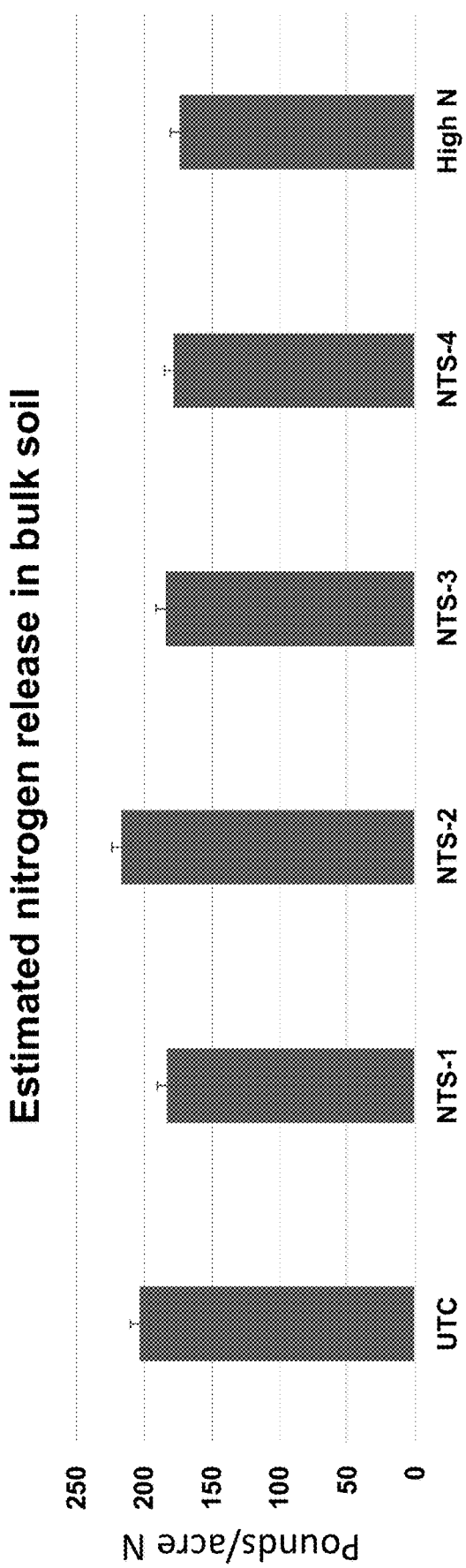
FIG. 53 shows that NTS-1.2 solution had the greatest estimated nitrogen release (ENR) in bulk soil compared to that of UTC and other NTS solutions. ENR is an estimate of the amount of nitrogen (lbs/acre) that will be released over the season.
Figure 54:
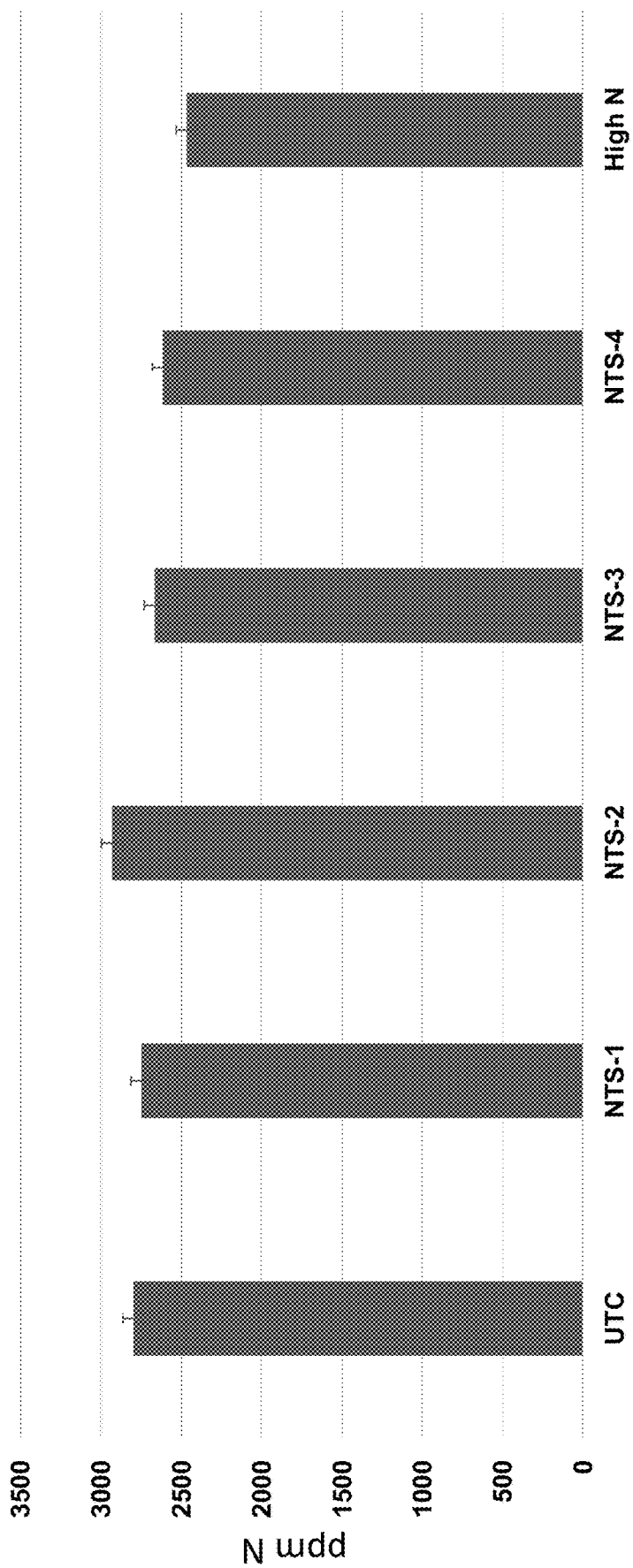
FIG. 54 shows that plants treated with NTS-1.2 solution exhibited increased organic nitrogen in bulk soil compared to that of UTC and other NTS treatments.

The organic matter in bulk soil was also tested across NTS systems. Percent organic matter is a measurement of the amount of plant and animal residue in the soil. The organic matter serves as a reserve for many essential nutrients, especially nitrogen. During the growing season, a part of this reserve nitrogen is made available to the plant through bacterial activity. NTS-1.2 was shown to have the greatest percent organic matter in bulk soil compared to that of the other NTS systems and UTC (FIG. 52). Estimated nitrogen release in bulk soil was also compared across systems to test the level of nitrogen in the soil. The ENR is an estimate of the amount of nitrogen (lbs./acre) that will be released over a season. NTS-2 was shown to have the greatest estimated nitrogen release compared to that of the other NTS systems and UTC (FIG. 53). Across NTS-treated plant growing soils, NTS-2 treatment led to increased organic nitrogen, compared to levels seen in UTC and other NTS 1.0-treated plants (FIG. 54).

Figure 55A:
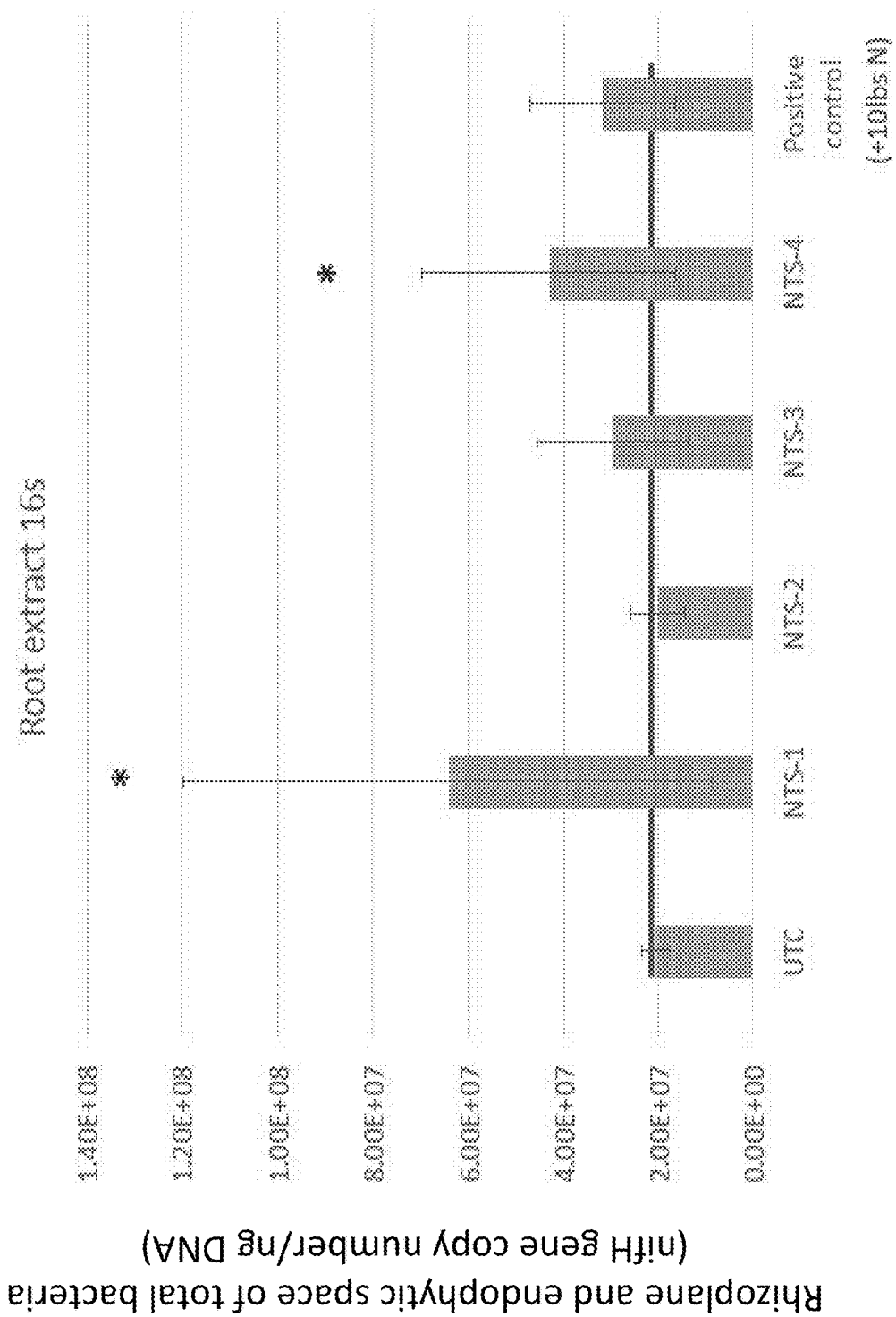
FIGS. 55A-55B show the abundance of total bacteria in root extracts of plants treated with NTS 1.0 system solutions.
Figure 55B:
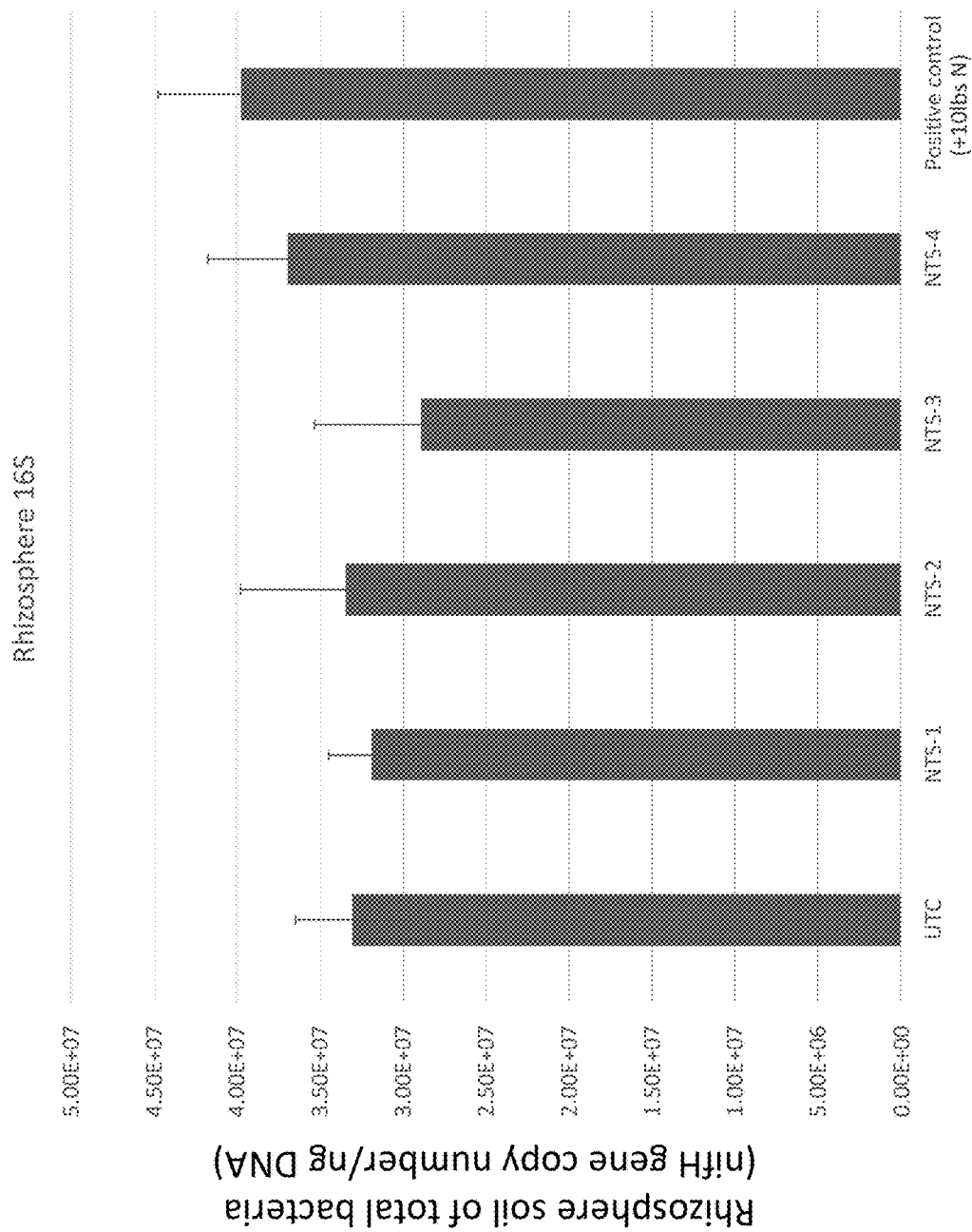

NTS 1.0 systems were tested in corn plants for bacterial recruitment in 1:1:1 mix (1:1:1 Profile MVP®-peat-Denton sandy loam soil mix) potting matrix. The abundance of total bacteria in root extracts showed recruitment in NTS-1.1 and NTS-1.4 treated plants (FIG. 55A). There was evidence of recruitment of total bacteria into the roots with NTS-1.1 and NTS-1.4 line base product treatment. The variation in the NTS-1.1 treatment condition was noticeably high. NTS-4 treated plants also showed the greatest total bacteria in the rhizosphere compared to that from UTC and other NTS treated plants (FIG. 55B).

Figures 56A, 56B:
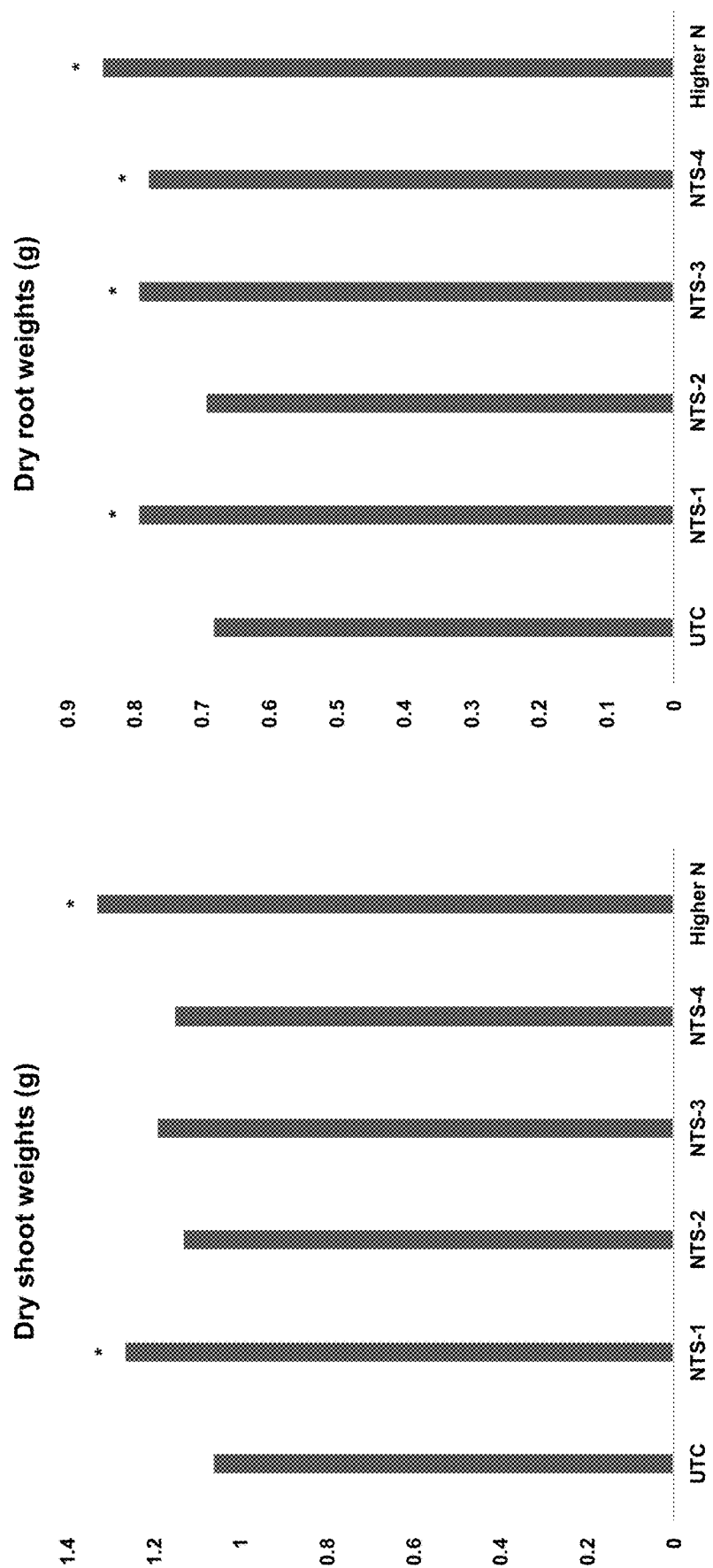
FIGS. 56A-56B show plant growth promotion of plants treated with NTS 1.0 solutions.

The effects of the four NTS 1.0 reactor products on NUE and early corn plant growth promotion was evaluated. NTS products were applied at 36 μL/plant and the growing medium was 1:1:1 Profile MVP®-peat-Denton sandy loam soil mix. Plants treated with NTS-1 showed significantly greater dry shoot weights than that from UTC plants (FIG. 56A). There was a 74% probability that using NTS-1 produced greater dry shoot weights than the UTC. NTS-1, NTS-3, and NTS-4 treated plants all showed significantly greater dry root weights compared to that from UTC plants (FIG. 56B). There was a 73% probability that using NTS-1, NTS-3, and NTS-4 produced greater dry root weights than the UTC.

Figure 57:
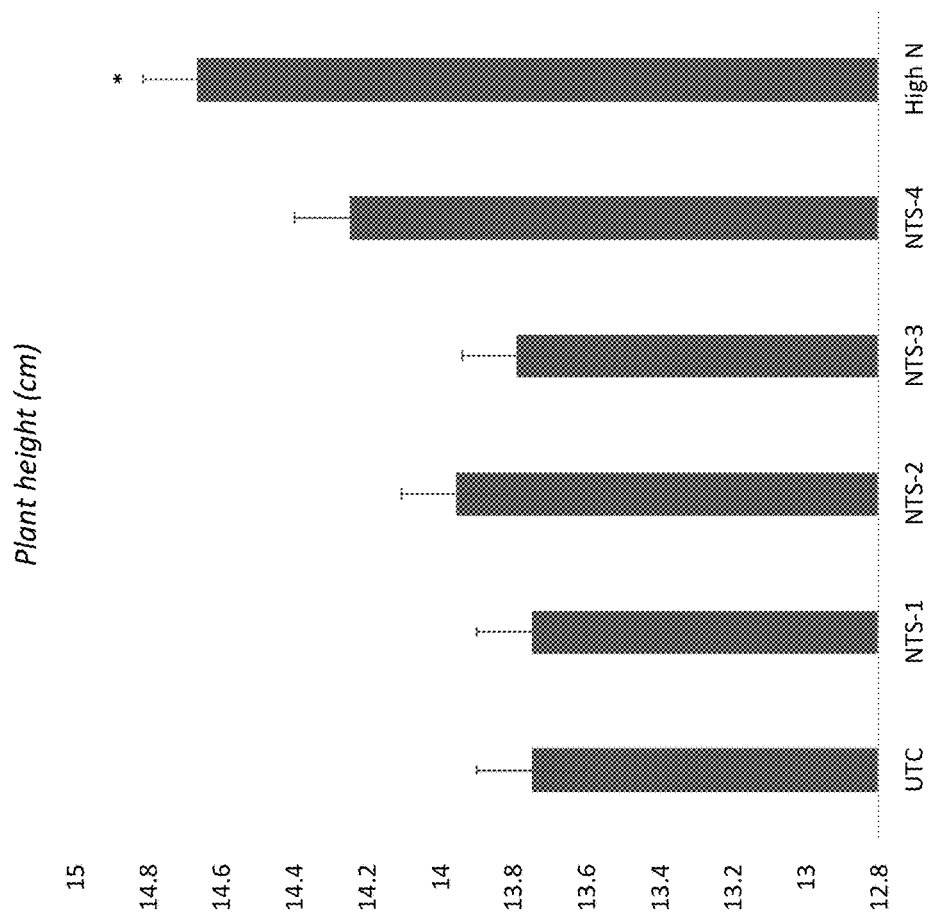
FIG. 57 shows the NTS-1.2 and 1.4 treated plants increased plant height greater than the UTC.
Figure 58:
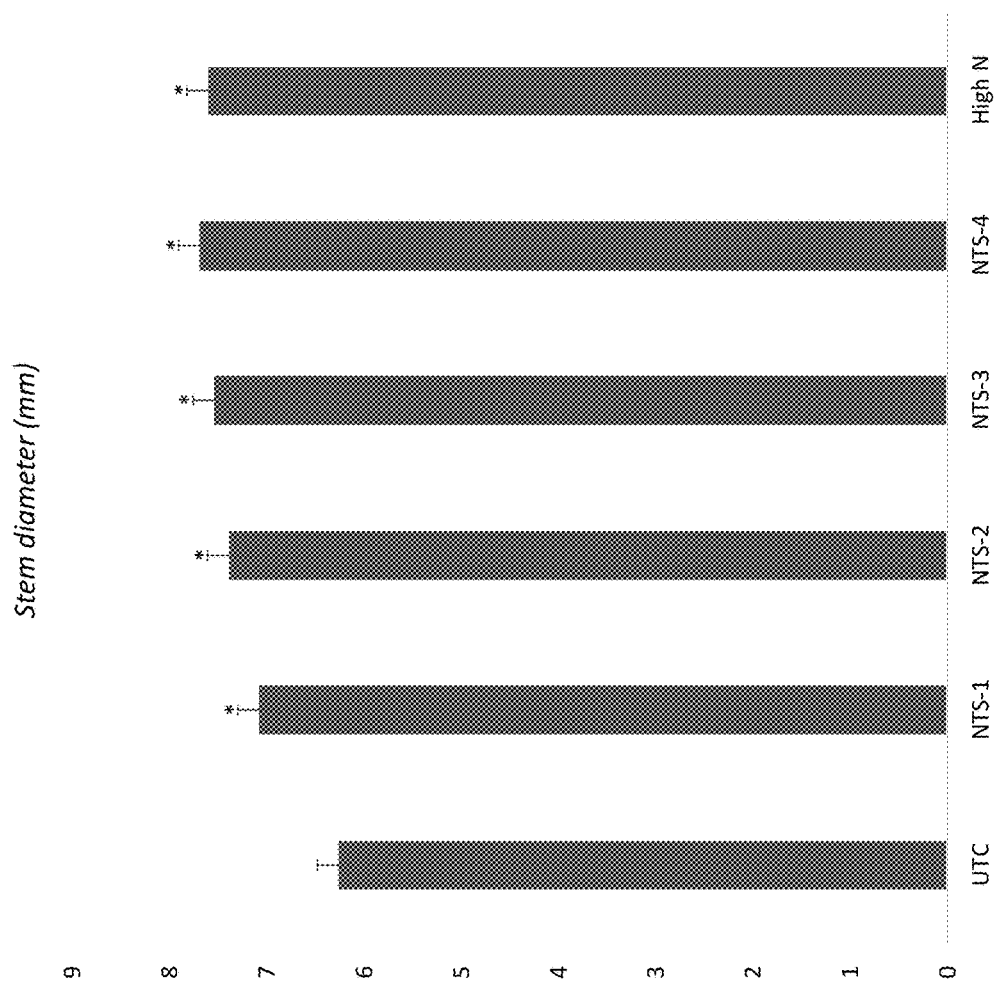
FIG. 58 shows all NTS treated plants had significantly greater stem diameter than that of UTC plants.
Figure 59:
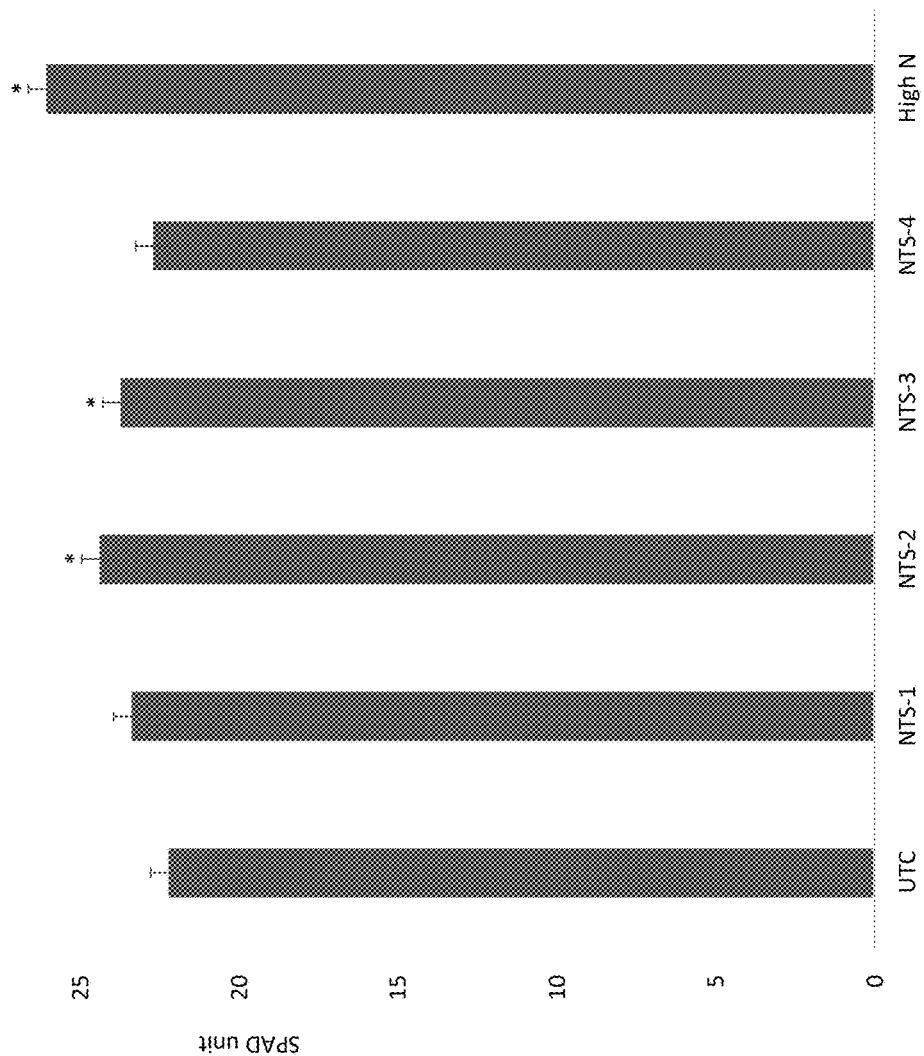
FIG. 59 shows NTS-1.2 and NTS-1.3 treated plants had significantly greater leaf chlorophyll content than that of UTC plants.
Figure 60:
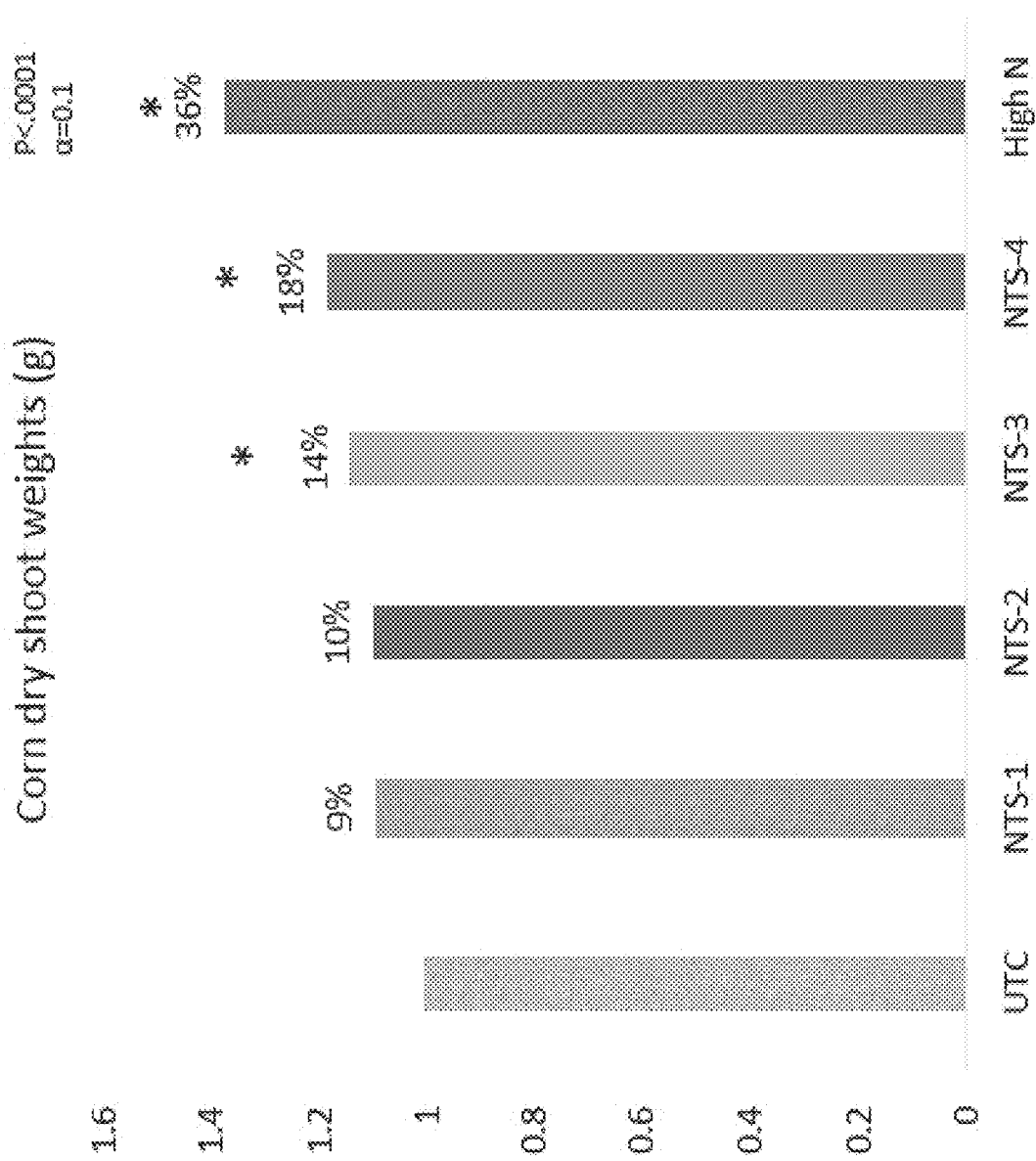
FIG. 60 shows the effects of NTS solutions on corn shoot dry weights. NTS-1.3 and NTS-1.4 treated plants had significantly higher dry shoot weights than that of UTC.
Figure 61:
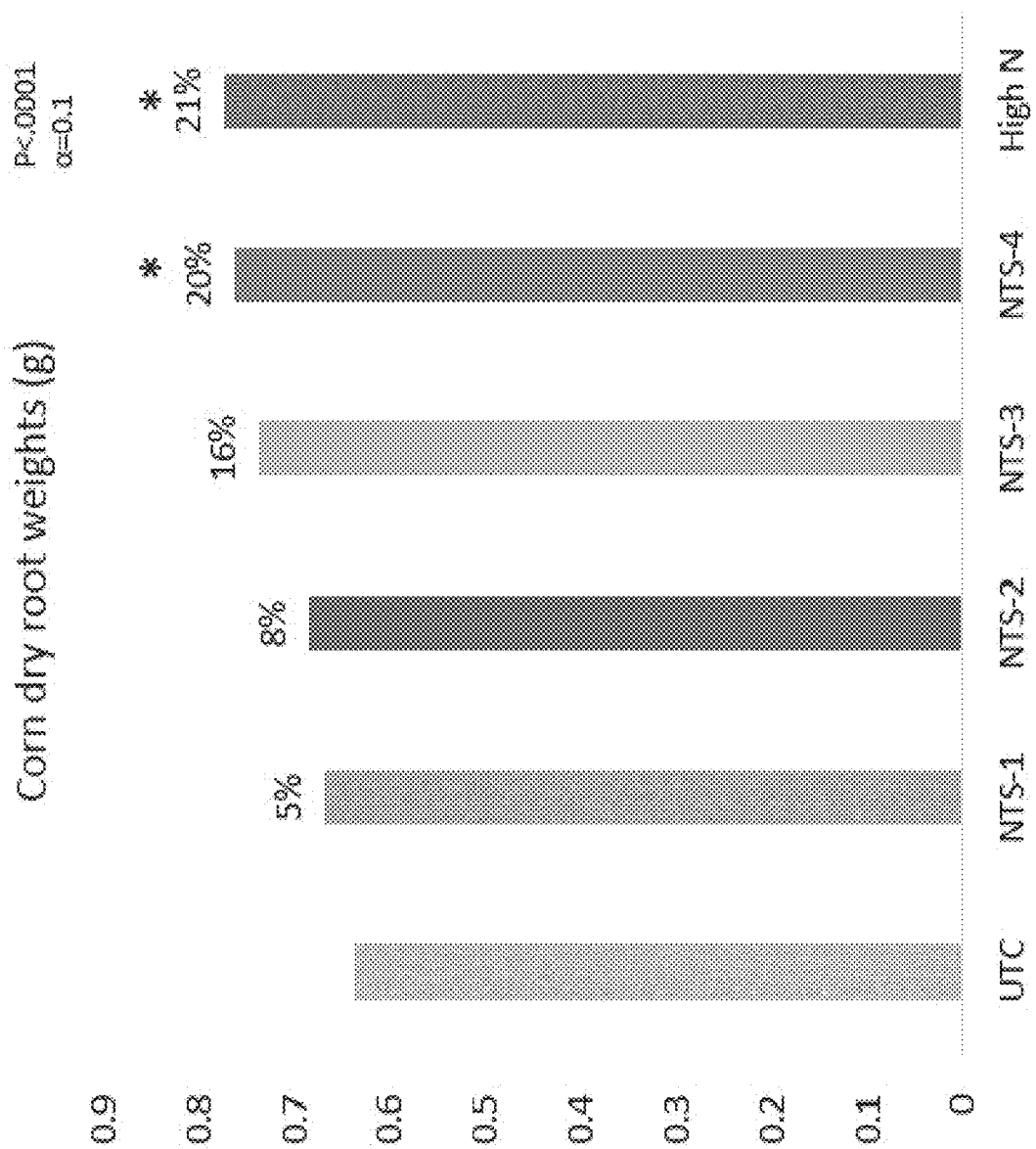
FIG. 61 shows the effects of NTS solutions on corn shoot dry weights in a separate study. NTS-4 treated plants had significantly higher dry shoot weights than that of UTC.

NTS systems were also tested on plant growth promoting metrics including plant height, stem diameter, and leaf chlorophyll content. NTS-4 showed increased plant height, which is the cm length from the soil to the highest corn node with a leaf collar, compared to that from other NTS-treated corn plants and UTC (FIG. 57). All NTS-treated systems showed significantly increased stem diameter, the greatest width in the stem, compared to that of UTC (FIG. 58). There was a 74, 81, 84, and 86% probability (common language effect sizes that using the NTS-1-4), respectively, produced greater stem diameter than the UTC. NTS-2 and NTS-3 systems showed significantly increased leaf chlorophyll content, as measured using a SPAD meter (Spectrum Technologies) and recording the average reading from three points along the length of the youngest, fully expanded, corn leaf of each plant, compared to that of UTC (FIG. 59). There was a 77 and 70% probability that using the NTS-2 and NTS-3 produced greater SPAD readings than the UTC. Generally, all NTS-treated plants showed greater plant growth properties compared to UTC. All NTS systems showed improved corn dry shoot weight compared to that of UTC (FIG. 60) as well as improved corn dry root weight (FIG. 61).

Example 15: Analysis of Base Products from NTS Systems for Presence of Corn Root Colonizers and MS3900 and MS3907 in a Sterile System The end product (e.g., reactor base product, BP) from four different NTS versions were tested to determine which version(s) resulted in higher abundances of root colonizing microbes. Four different NTS systems were tested: NTS-1.1, NTS-1.2, NTS-1.3, and NTS-1.4. End products from NTS-1 and NTS-3 were prepared in Packed-Bed Reactor systems and end products from NTS-2 and NTS-4 were prepared in Fluidized-Bed Reactor systems. Corn seeds were surface sterilized in 70% ethanol for 1 minute, 5% (v/v) household bleach for 5 minutes, rinsed 3 times with sterile RO water for 1 minute each and air dried overnight. NTS BP solutions were diluted 1:10 ($10^{-1}$), 1:100 ($10^{-2}$) and 1:1000 ($10^{-3}$) and sterile corn seeds were soaking in these diluted solutions for 2 hours at room temperature and 200 rpm. For the untreated, negative control, seeds were soaked in sterile water in the same conditions. After soaking, seeds were aseptically moved to a sterile petri dish to completely dry. Seeds were placed in a sterile 50 mL conical tube with 15 mL 0.4% water agar and placed in a growth chamber with a 16-hr day at 24° C./8-hr night at 22° C. cycle for 11 days. Each treatment and dilution had four replicate corn tubes. After 11 days, the corn plant seedlings were gently pulled from the water agr tubes. Roots of the corn plants were pressed into two ¼ TSA plates to create a root stamp and qualitatively determine the abundance of root colonizers. The root-stamped agar plates were then incubated in either aerobic conditions or anaerobic conditions for 5 to 7 days at 30° C. Following incubation, the plates were evaluated for the presence of colonies, which indicated that the corn roots contained root-colonizing microbes.

Analysis of this experiment showed that roots from corn seeds inoculated with BP from Fluidized-Bed Reactor systems (NTS-2 and NTS-4) had a higher abundance of root colonizing-microbes compared to roots from corn seeds inoculated with BP from Packed-Bed Reactor systems (NTS-1 and NTS-3). Specifically, there was a higher percentage of plates with colonies present that were stamped with roots from corn seeds inoculated with BP from NTS-2 or NTS-4 compared to plates stamped with roots from corn seeds inoculated with BP from NTS-1 or NTS-3. This finding was confirmed across all BP dilutions tested. Table 22 shows the percentage of plates with colonies present for the different BPs tested at the three dilutions.

TABLE 22

Percentage of colonies present on Root-Stamped Agar Plates

| | Reactor base product (BP) Sample | | | | | |
|---|---|---|---|---|---|---|
| | Percent of plates with root colonizers (aerobically incubated) | | | Percent of plates with root colonizers (anaaerobically incubated) | | |
| | Dilution of BP used to inoculate | | | | | |
| | $10^{-1}$ | $10^{-2}$ | $10^{-3}$ | $10^{-4}$ | $10^{-5}$ | $10^{-6}$ |
| NTS-1 | 100% | 100% | 0% | 100% | 25% | 0% |
| NTS-2 | 100% | 100% | 75% | 100% | 75% | 75% |
| NTS-3 | 75% | 0% | 0% | 25% | 0% | 0% |
| NTS-4 | 100% | 25% | 50% | 100% | 25% | 25% |

Figure 64:
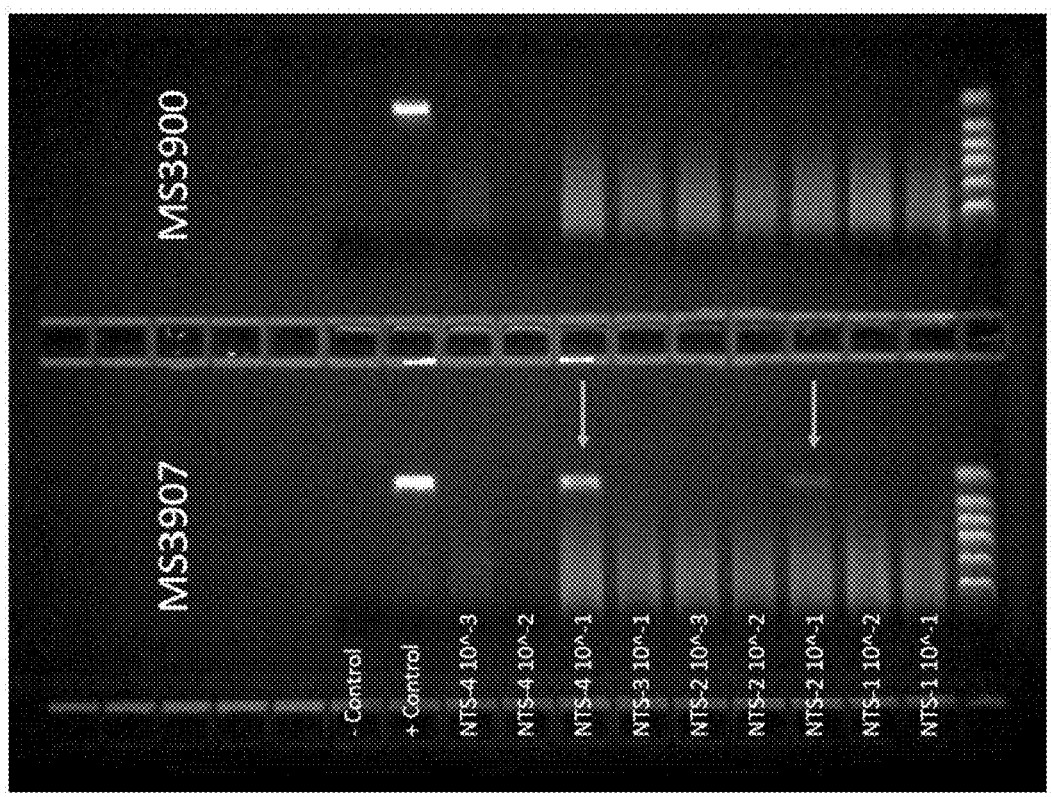
FIG. 64 shows testing for DNA markers of MS3907 and MS3900 in NTS 1.0 treated plant roots. MS3907 was identified by MS3907-specific DNA markers in the microbial populations colonizing the plant roots of NTS-1.2 and NTS-1.4 treated seedlings.

Additionally, the colonies from the root-stamped plates were evaluated for the presence of MS3907 or MS3900 in the corn roots. The presence of MS3907 or MS3900 was determined by DNA analysis of the colonies on the root-stamped plates. The DNA analysis specifically looked for DNA markers specific for MS3907 or MS3900. For this analysis, the colonies grown in aerobic and anaerobic conditions were combined. Root stamp plates were flooded with 4 mL sterile water and pushed around the plate with a sterile hockey stick to create a plate wash. Plate wash solution from each replicate plant for that dilution and NTS treatment (n=4) and each incubation condition (aerobic and anaerobic) were pooled into one 960 uL plate wash solution. DNA was extracted using the MP Biomedical FAST Spin DNA kit for soil with some modification. After bead beating and removing the solution for protein precipitation, the debris in the bead beating tube was treated with 250 μL of lysozyme (18 mg/mL) and incubated at 37° C. for 10 min to further release any DNA bound within the cell debris. Then, 750 uL sodium phosphate buffer was added and the bead tube centrifuged to pellet the debris. This new solution was then added to the same protein precipitation step and merged with the first extract. Then, the DNA extraction was completed per manufacturer's instructions. This plate wash DNA was used in PCR to detect MS3900 (YinC gene) and MS3907 (cynS gene) as described previously. MS3900 was not found in the roots of any of the corn plants tested, however MS3907 was found in the roots of corn seeds that were inoculated with the $10^{-1}$ dilution of BP NTS-2 or the 10-dilution of the BP NTS-4 (FIG. 64). Table 23 shows the NTS BP solutions tested that contained MS3907 in the roots of the corn plants.

TABLE 23

Presence or Absence of MS3907 in corn roots

Reactor base product (BP) sample
Aerobic and anaerobic culture combined
Dilution of original inoculating solution

|  | $10^{-1}$ | $10^{-2}$ | $10^{-3}$ |
|---|---|---|---|
| NTS-1 | — | — | — |
| NTS-2 | X | — | — |
| NTS-3 | — | — | — |
| NTS-4 | X | — | — |

Example 16: Characterization of Microbial Community of Water-Based Phosphate Solubilizing Technology (PwST)

Figure 72:
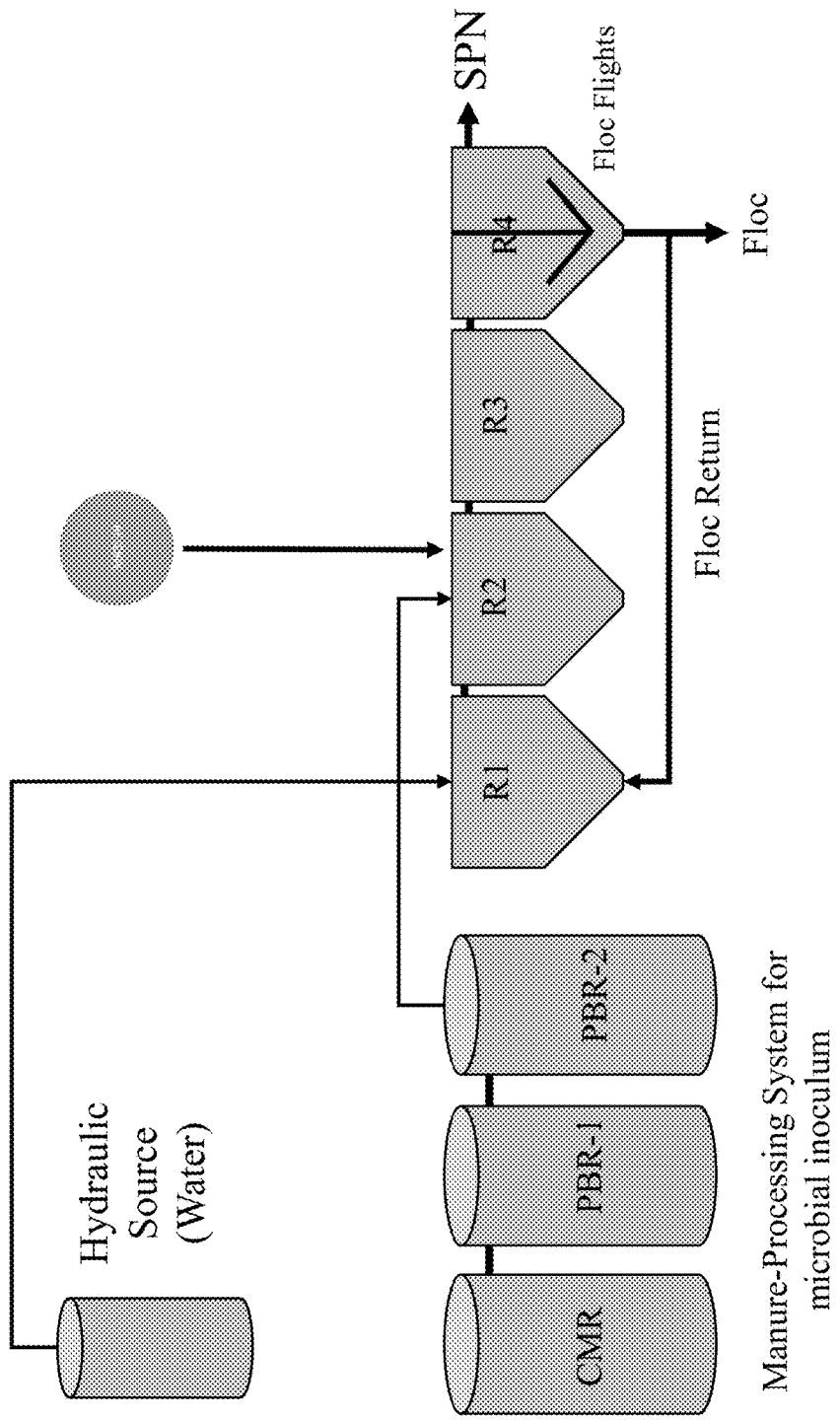
FIG. 72 is an exemplary schematic depicting the $P_wST$ system. Water is the hydraulic source.

In this example, an aerobic fluidized bed digestion system (referred to herein as the PwST system) was used to produce a biostimulant. Aerobic conditions are defined as DO>2 mg/L. An overview of the PwST system is shown in FIG. 72. The core of the system included four reactor containers (R1 to R4) arranged in series, each one flowing into the next in a hydraulically balanced fashion. The input into the first reactor was water, 200 mesh rock phosphate particles, and a return feed of floc from a later reactor in the system. This mixture was incubated in the first reactor and continuously flowed at a constant rate into the second reactor. In addition to the inflow from the first container, a fluid feed mixture containing a microbial consortium, filtered cow manure (at one liter/day), and *Saccharomyces cerevisiae* yeast (at 2 g/day), was introduced into the second container. The microbial consortium was prepared by an anaerobic packed bed reactor system (referred to herein as the "PBR2 system"), which is a shortened version the digestion system depicted in FIG. 5 of US2013/03244061 in which only two packed bed reactors are used, with the outflow of the second packed bed reactor (PBR2) serving as the source of the microbial consortium introduced into R2 in the PwST system, as depicted in FIG. 72. The feedstock for the PBR2 system was a mixture of filtered cow manure (at 5 liter/day with a range Chemical Oxygen Demand of 1200-3000 mg/L), *Saccharomyces cerevisiae* yeast (at 1.3 g/day), and water, mixed together in a complete mix reactor (CMR in FIG. 72) flowing into a packed bed reactor ("PBR") container that included a scaffold of solid supports on which microbes can grow in biofilms. The fluid was incubated in the first packed bed reactor (PBR-1 in FIG. 72) as a continuous flow of the fluid from the top of the first PBR flowed into a second PBR in a hydraulically balanced fashion (i.e., the rate of outflow matched the rate of inflow of feedstock). The fluid from the first PBR was incubated in the second PBR (PBR-2 in FIG. 72) in the same fashion as in the first PBR, with the rate of outflow from the top of the second PBR matching the rate of inflow from the top of the first PBR. The outflow from the top of the second PBR (the "PBR2 product") was used as the microbial inoculum provided to the second fluidized bed reactor ("FBR") of the PwST system. The FBRs of the PwST system did not include solid scaffold supports. The fluid within the reactors was circulated at a rate that kept the rock phosphate particles suspended and that aerated the fluid by either strong continuous mixing or air sparging, thereby establishing conditions for aerobic (dissolved oxygen content of 7.47-8.17_mg/L) digestion of the digestible substrates (i.e., rock phosphate, manure, yeast, other microbes from the inoculum coming from the PBR2 system, and organic substances present in the inoculum coming from the PBR2 system). The outflow from the top of the second FBR of the PwST system (R2 in FIG. 72) flowed into a third FBR (R3) in a hydraulically balanced fashion, and the outflow from the top of the third FBR flowed into a fourth FBR (R4) in a hydraulically balanced fashion. The outflow from the top of the fourth FBR is referred to herein as the PwST supernatant ("SUP" or "SPN"). The outflow from the bottom of the fourth FBR, referred to as floc, was flowed back to the first FBR. The floc is primarily biosolids, containing high microbial content, that is generated throughout the fermentation that settle out in the clarification stage of the process. Different ratios of supernatant and floc can be adjusted to produce the Whole Broth "WB" for specific purposes. The PwST system operated continuously, and microbial consortia from four PwST WB (1:1 ratio of PwST floc to PwST supernatant) monthly batches and a composite sample of the four batches, were characterized (FIG. 73). A total of $10^5$ microbial species common to all five batches were identified using culture-independent DNA analysis using similar methods and analysis in Hugerth 2017. The five most abundant species found in all four batches and composite samples included *Lewinella coharens*, *Thauera phenylacetica*, *Thauera mechernichensis*, *Solitalea canadensis*, and *Nitrospira moscoviensis* (FIG. 74).

Example 17: PGP Capacity and Nitrogen-Fixation Capacity of PwST

Figure 75:
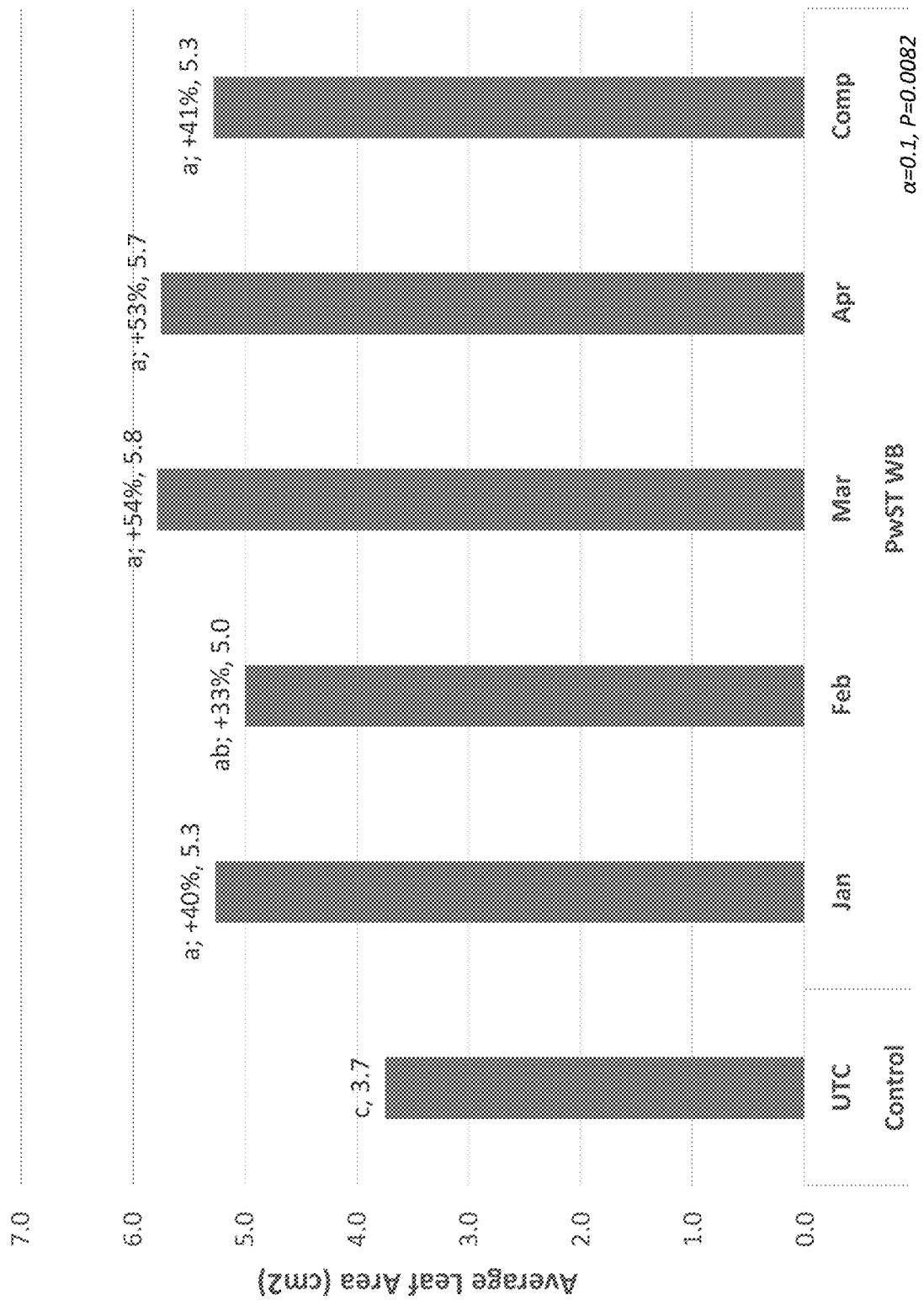
FIG. 75 is a graph showing the plant growth production of *Arabidopsis* (measured in average leaf area, cm2) for UTC and PwST samples from across four months.

PwST WB samples were tested in *Arabidopsis* for plant growth promoting ability, using average leaf area (in cm$^2$) as the primary metric. *Arabidopsis thaliana* (genotype Col-0) seedlings were germinated and grown for 7 days on 2 strength MS media (Murashige & Skoog Basal Medium with Vitamins, M519) plates in the growth chamber before transplanting into rockwool cubes for plant growth assays. Rockwool was used as an inert substrate for growing *Arabidopsis* in a hydroponic-like system. The rockwool cubes are fitted into a 6-well tray and each treatment consisted of three replicate well trays. Eight 1 L ½ strength MS media (Murashige & Skoog Basal Medium with Vitamins, M519) solutions were made. The test substance was then added at the rate given below in Table 25 and the pH of the solution was raised to 5.7. Forty mL of each 1 L treatment solution was dispensed to each rockwool cube. Then, each wetted cube received one *Arabidopsis* seedling. *Arabidopsis* plants grew on an LED light cart for 12 days. Leaf area was determined using the ImageJ software package. All the data collected were put through JMP for ANOVA analysis. Across four monthly batches, and a composite sample made up of equal amounts of the four monthly batches, PwST WB showed consistent PGP activity (FIG. 75) and showed significantly greater average leaf area than that measured from UTC (p=0.0082).

TABLE 25

Treatments for testing plates.

1. ½MS Media+ UTC
2. ½MS Media+ 0.8% PwST WB Jan. Batch (v/v) (8 mL/L)
3. ½MS Media+ 0.8% PwST WB Feb. Batch (v/v) (8 mL/L)

TABLE 25-continued

Treatments for testing plates.

4. ½MS Media+ 0.8% PwST WB Mar. Batch (v/v) (8 mL/L)
5. ½MS Media+ 0.8% PwST WB Apr. Batch (v/v) (8 mL/L)
6. ½MS Media+ 0.8% PwST WB Composite Batch (v/v) (8 mL/L)

Figure 76:
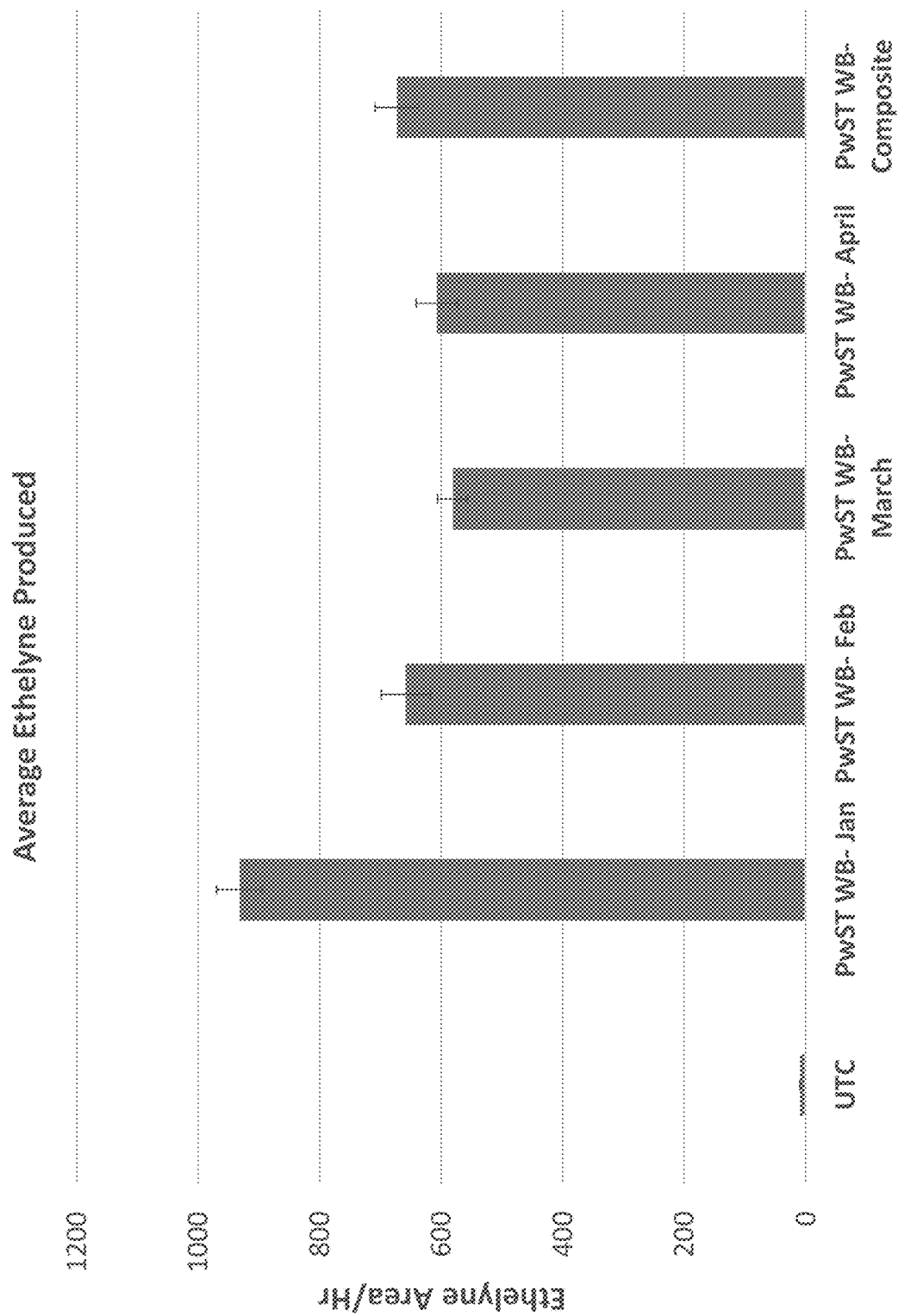
FIG. 76 is a graph showing average ethylene produced (in area/hr) for PwST samples across four months. Average ethylene produced was compared to UTC.

An acetylene reduction assay was performed to assess nitrogen-fixation capacity of PwST WB samples. Acetylene reduction measures the activity of nitrogenase which are the enzymes responsible for the reduction of nitrogen to ammonia and are the same involved in reduction of acetylene to ethylene. Three 4-mL replicate samples were incubated in 21 mL vials with 12% acetylene of the headspace (v/v) under air on a rotary shaker at 30° C. and 60 rpm for 168 hours. PwST WB samples showed consistent acetylene reduction capacity and superior ethylene production compared to UTC (FIG. 76).

Example 18: Exemplary Enzymes in PwST WB

Using the predictive bioinformatics tool, PICRUSt (Hugerth 2017), metagenome functional content was used to screen for functional enzymes in PwST WB samples. Enzyme content with function in nitrogen fixation, phosphate-solubilization, and zinc-solubilization were identified (FIG. 77). Nitrogenase, quinoprotein glucose dehydrogenase (PQQ), and gluconate 2-dehydrogenase were identified as key functional enzymes for nitrogen fixation and phosphate solubilization, respectively. The average abundance of these enzymes was measured in PwST WB. PwST WB showed an average abundance of PQQ, nitrogenase, and gluconate 2-dehydrogenase as set forth in FIG. 78.

Example 19: Effects of PwST Supernatant on Plant Growth Promotion

Figure 79:
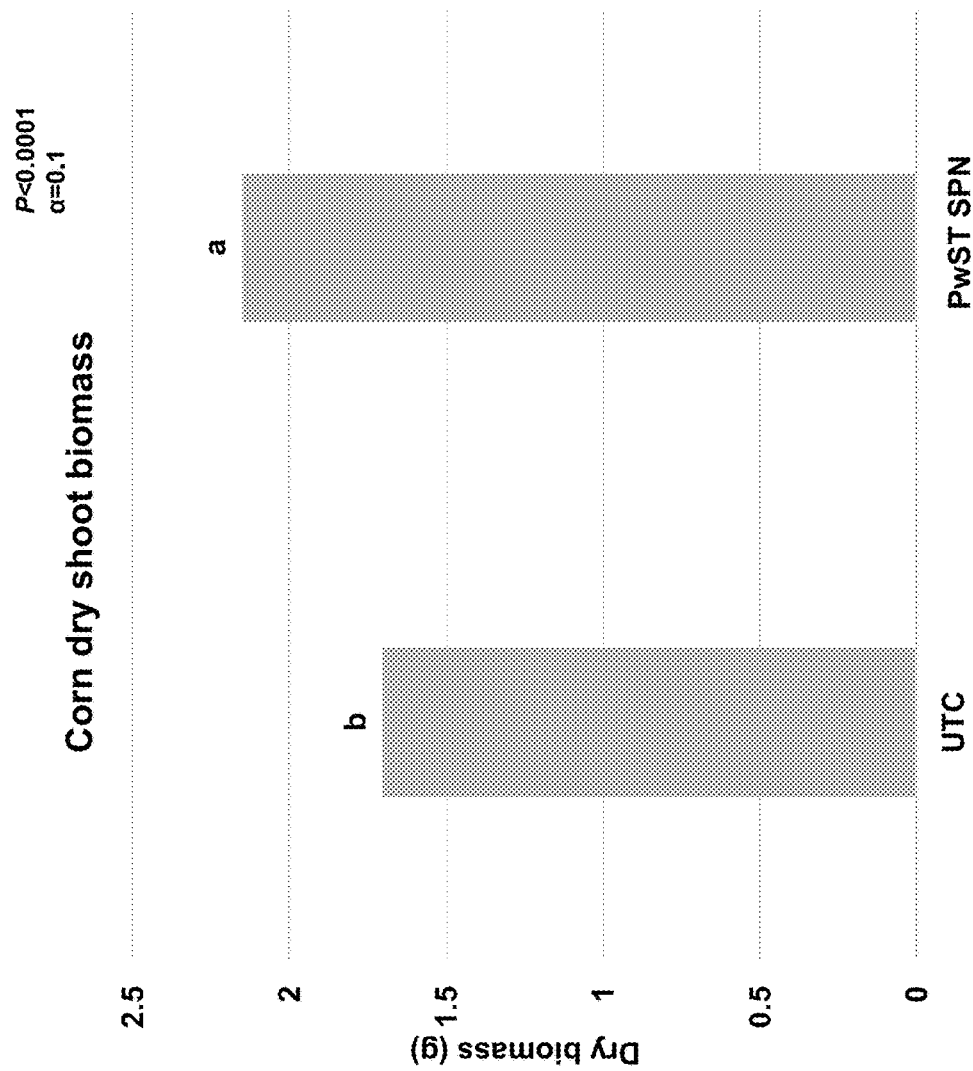
FIG. 79 is a graph showing dry shoot biomass (g) between corn treated with monoammonium phosphate (MAP) fertilizer coated with water (UTC) or with PwST supernatant (SPN).
Figure 80:
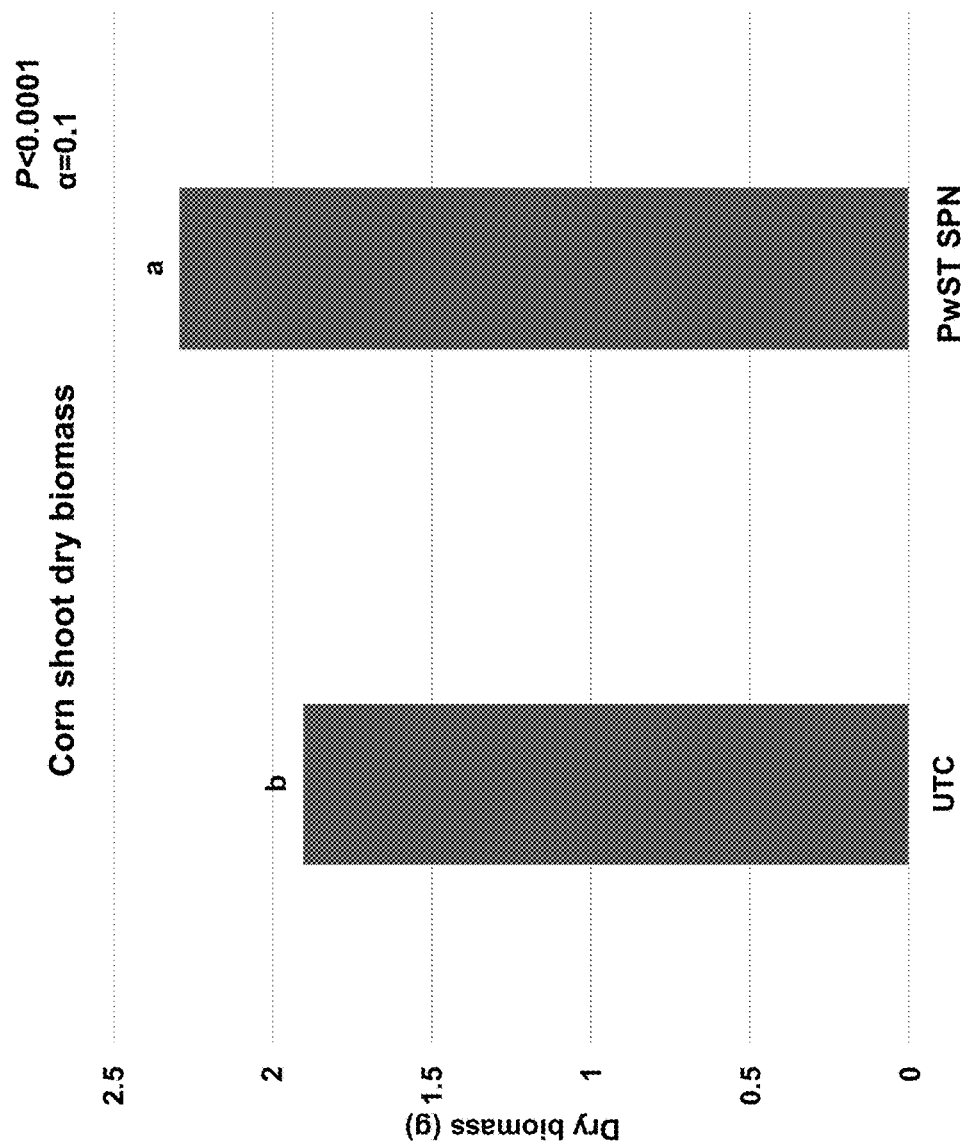
FIG. 80 is a graph showing dry shoot biomass (g) between corn treated with an in-furrow application of water (UTC) or PWST supernatant at planting.

PGP of PwST supernatant was evaluated by measuring dry biomass of corn plants in untreated controls (UTC) and PwST SPN-treated plants. For coated MAP treatments, shoot dry biomass of PWST-treated corn was significantly greater than that of UTC plants at a rate of 2 qt./t (FIG. 79). For corn treated in-furrow at a rate of 4 qt./A, shoot dry biomass was significantly greater in plants treated with PwST compared to UTC (FIG. 80).

Figure 81:
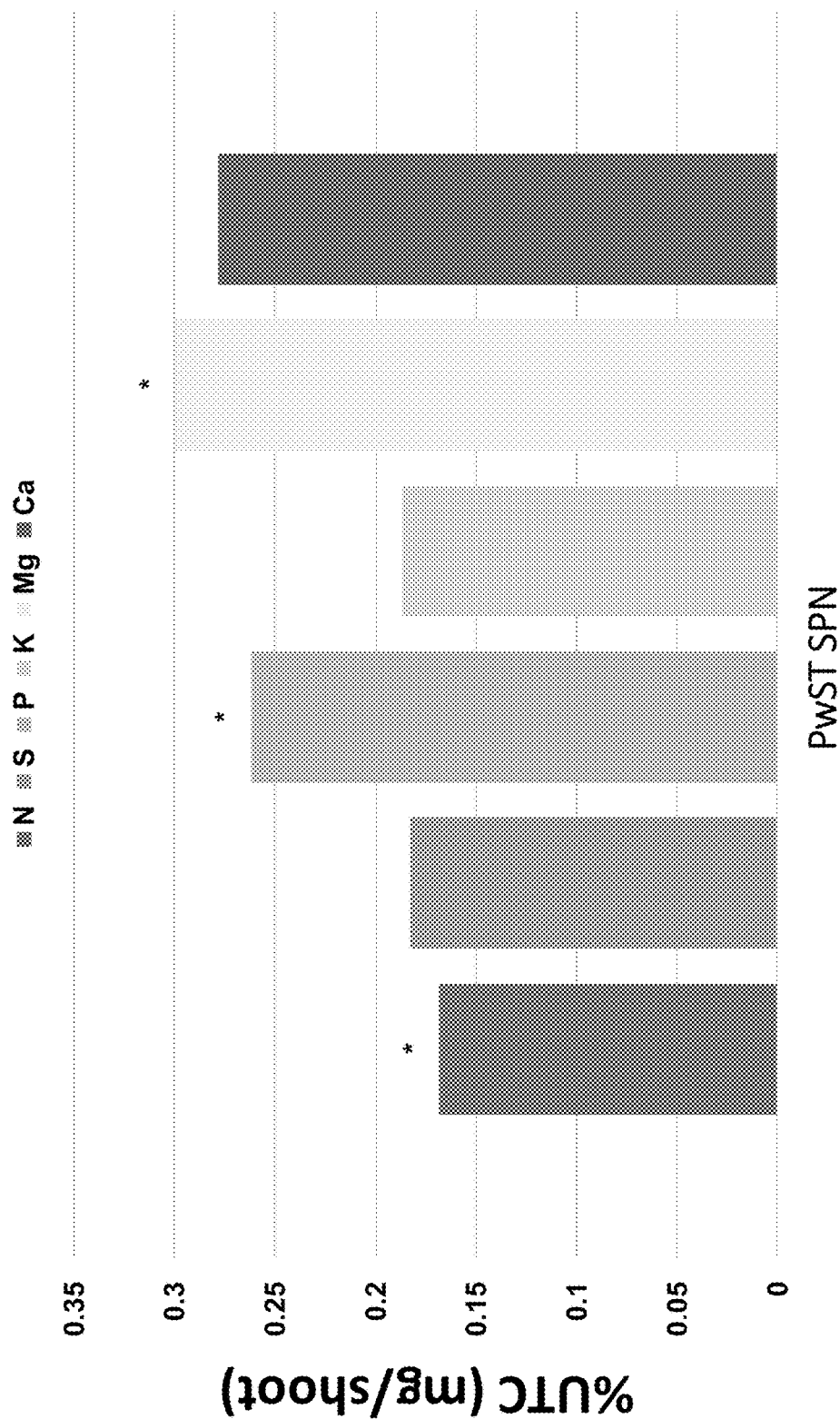
FIG. 81 is a graph showing nutrient uptake (measured as % UTC) across six shoot macronutrients in corn treated with MAP fertilizer coated with $P_wST$ SPN (shown from left to right: nitrogen (N), sulfur (S), phosphorus (P), potassium (K), magnesium (Mg), and calcium (Ca)). An asterisk indicates statistically significantly different from UTC at p=0.1.
Figure 82:
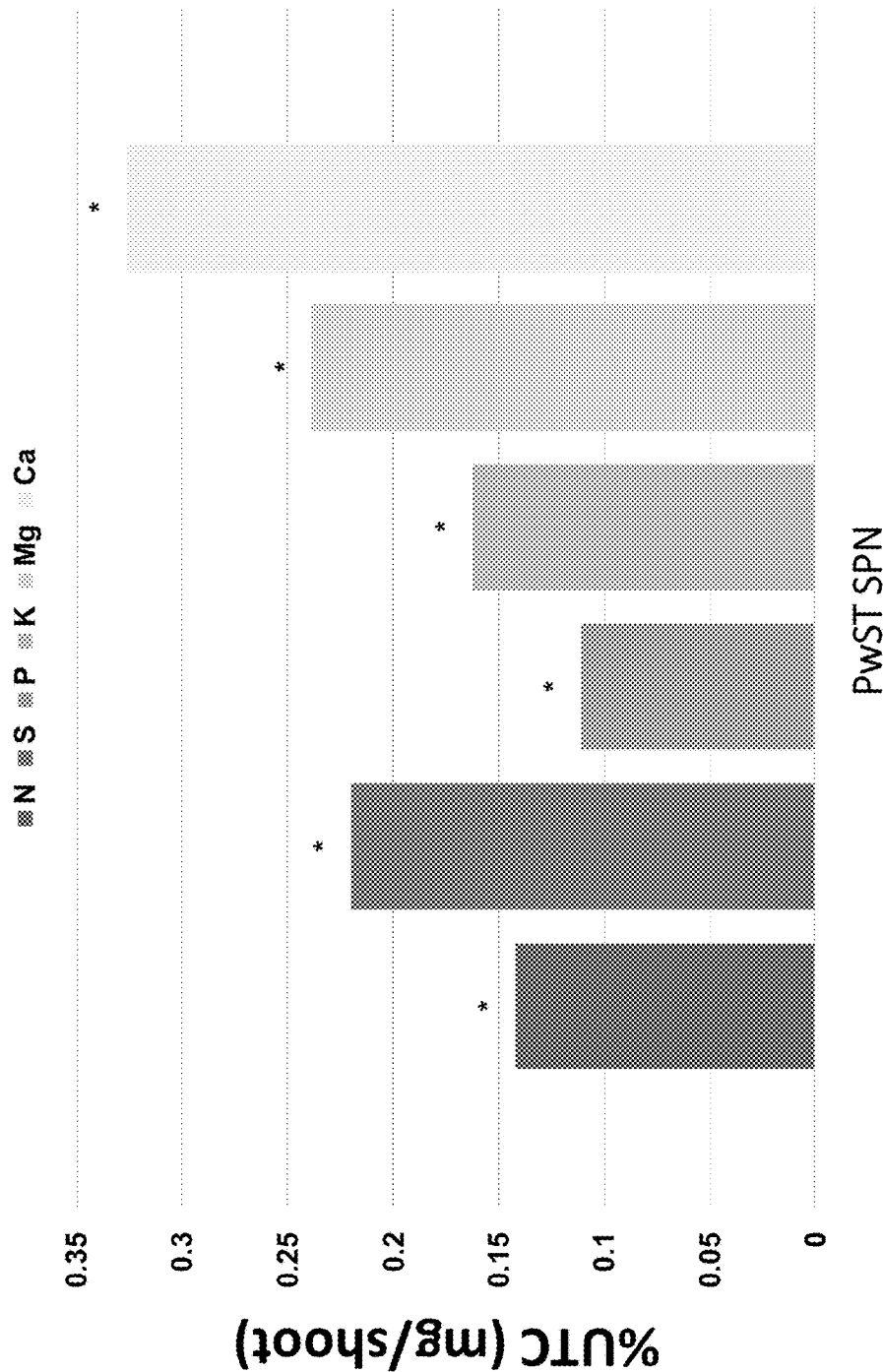
FIG. 82 is a graph showing nutrient uptake in corn treated with in-furrow application of $P_wST$ SPN (measured as % UTC) across six corn shoot macronutrients (shown from left to right: nitrogen (N), sulfur (S), phosphorus (P), potassium (K), magnesium (Mg), and calcium (Ca)). An asterisk indicates statistically significantly different using ANOVA from UTC at p=0.1.
Figure 83:
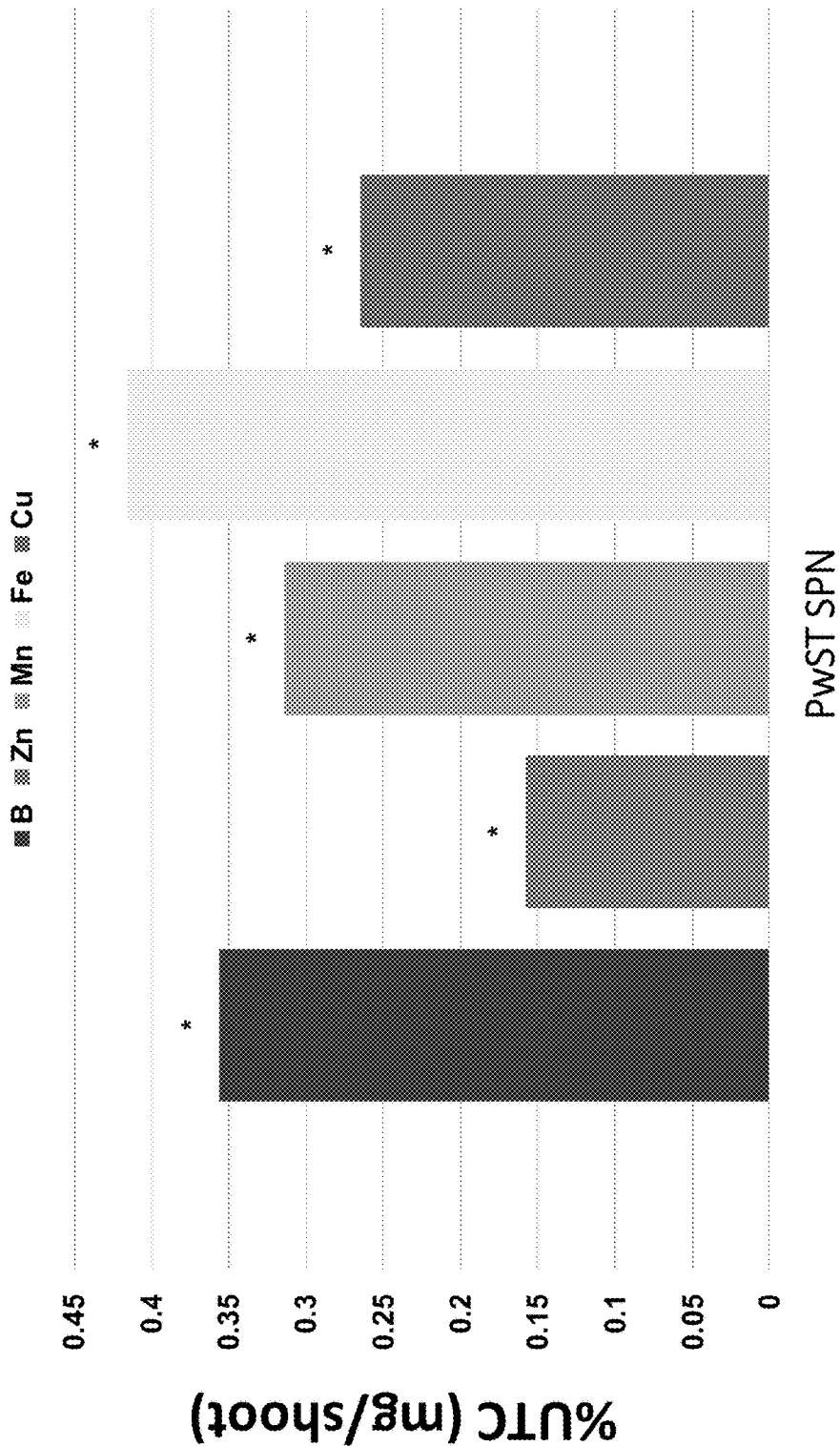
FIG. 83 is a graph showing micronutrient uptake in corn treated with an in-furrow application of $P_wST$ SPN (measured as % UTC) across five shoot micronutrients (shown from left to right: boron (B), zinc (Zn), manganese (Mg), iron (Fe), and copper (Cu)). An asterisk indicates statistically significantly different from UTC at p=0.1.
Figures 84A, 84B, 84C, 84D:
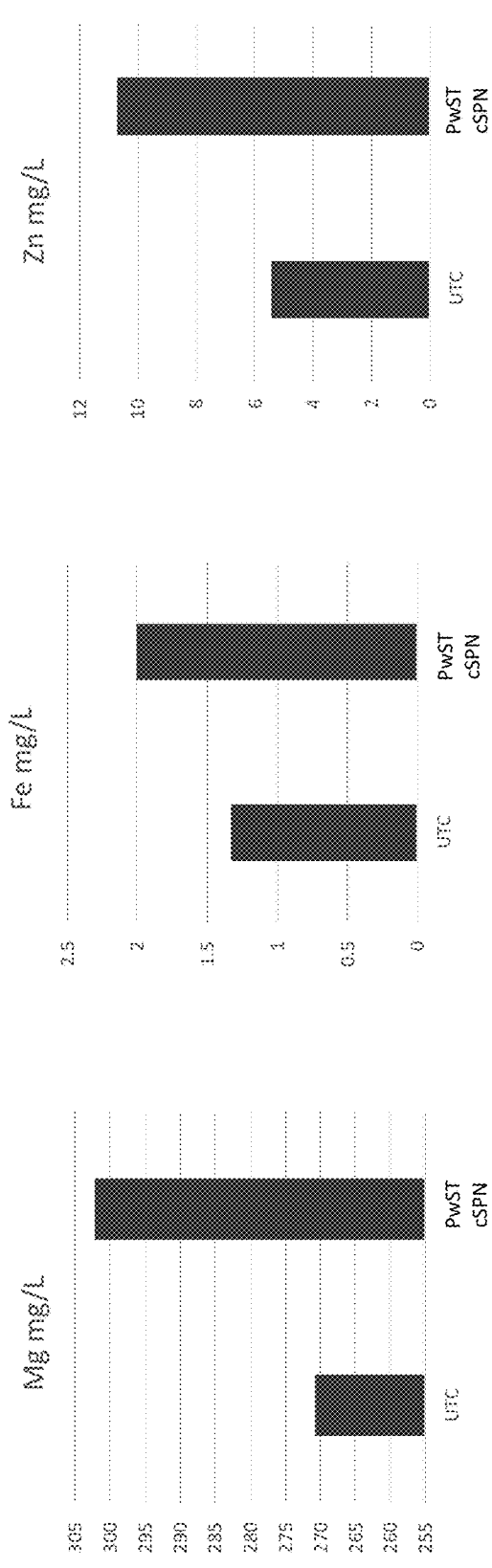
FIGS. 84A-84D are a series of graphs showing the release (in mg/L) of micronutrients such as magnesium (FIG. 84A), iron (FIG. 84B), and zinc (FIG. 84C) from MAP fertilizer coated with P$_w$ST cSPN.

PwST supernatant as a coating on MAP increased phosphate uptake from fertilizers in plants. PwST supernatant also increased macronutrients uptake in plants from the soils and fertilizers. Levels of nitrogen, sulfur, phosphorous, potassium, magnesium, and calcium were tested from the soil or fertilizer of MAP-coated corn shoot plants with PwST SPN technology (FIG. 81). PwST SPN coated on MAP increased uptake of all macronutrients at a rate of 2 qt./t. Nitrogen, phosphorous, and magnesium all showed significant increased levels compared to those from UTC. Similar results were also seen from in-furrow application. PwST supernatant increased uptake of all macronutrients in shoots from corn treated in-furrow at a rate of 4 qt./A (FIG. 82). All five macronutrients showed significantly increased levels compared to those from UTC. PwST supernatant also increased uptake in shoots of all tested micronutrients from corn treated in-furrow at a rate of 4 qt./A (FIG. 83).

PwST supernatant improved release of micronutrients from fertilizer placed in water (FIGS. 84A-84D). Sixty grams of MAP, coated at 2 qt/t with either water (UTC) or with PwST, was added to 200 mls volume water in a beaker, covered for six days. The resulting water was measured for nutrients after 6 days. Manganese (FIG. 84A), iron (FIG. 84B), and zinc (FIG. 84C) showed increased levels (as % UTC) when the MAP was coated with PwST supernatant.

Example 20: Effects of PwST Supernatant on Phosphate Solubilization

Figure 85A:
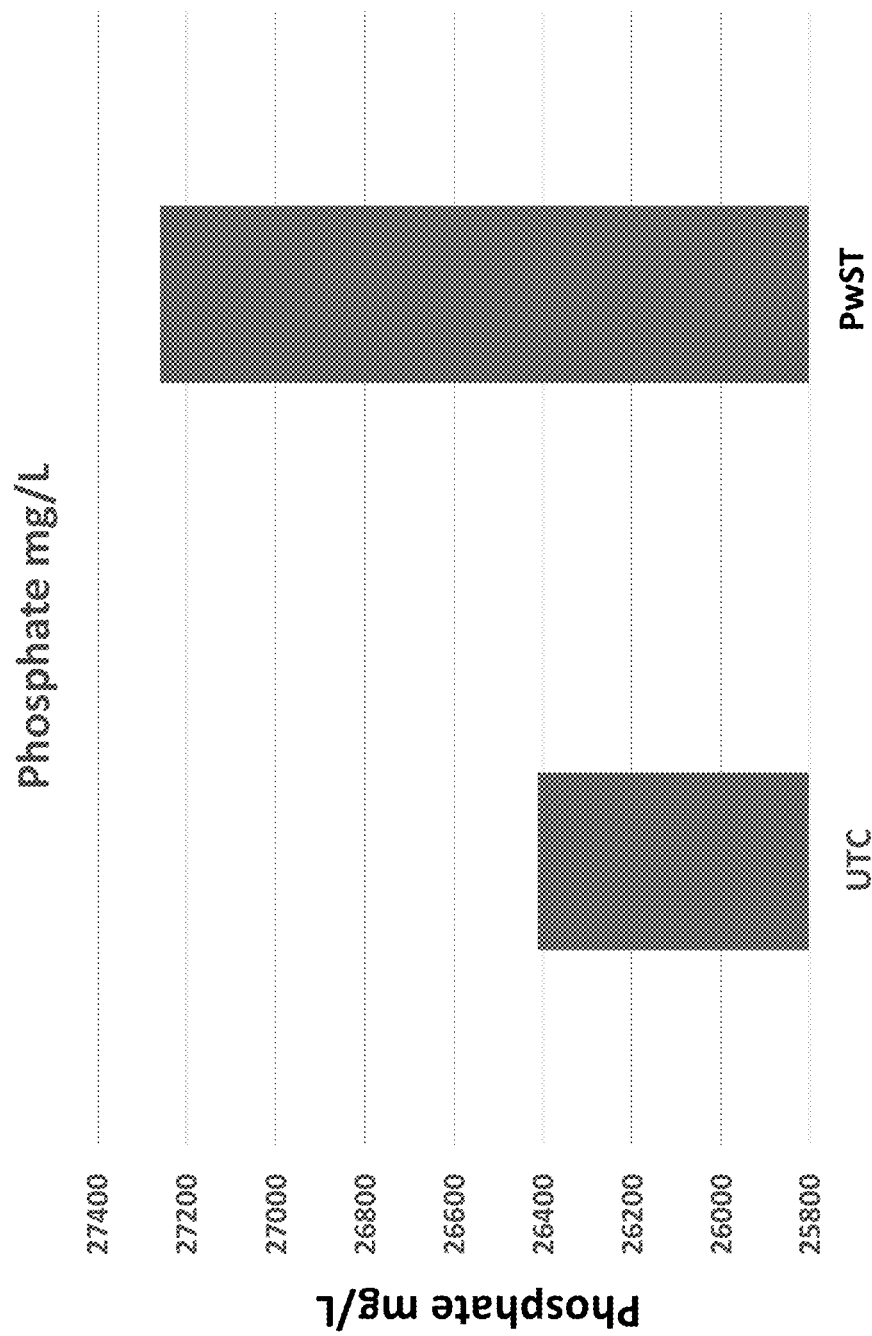
FIGS. 85A-85B show a series of graphs showing phosphate solubilization (in mg/L) between untreated control (UTC) and P$_w$ST cSPN.
Figure 85B:
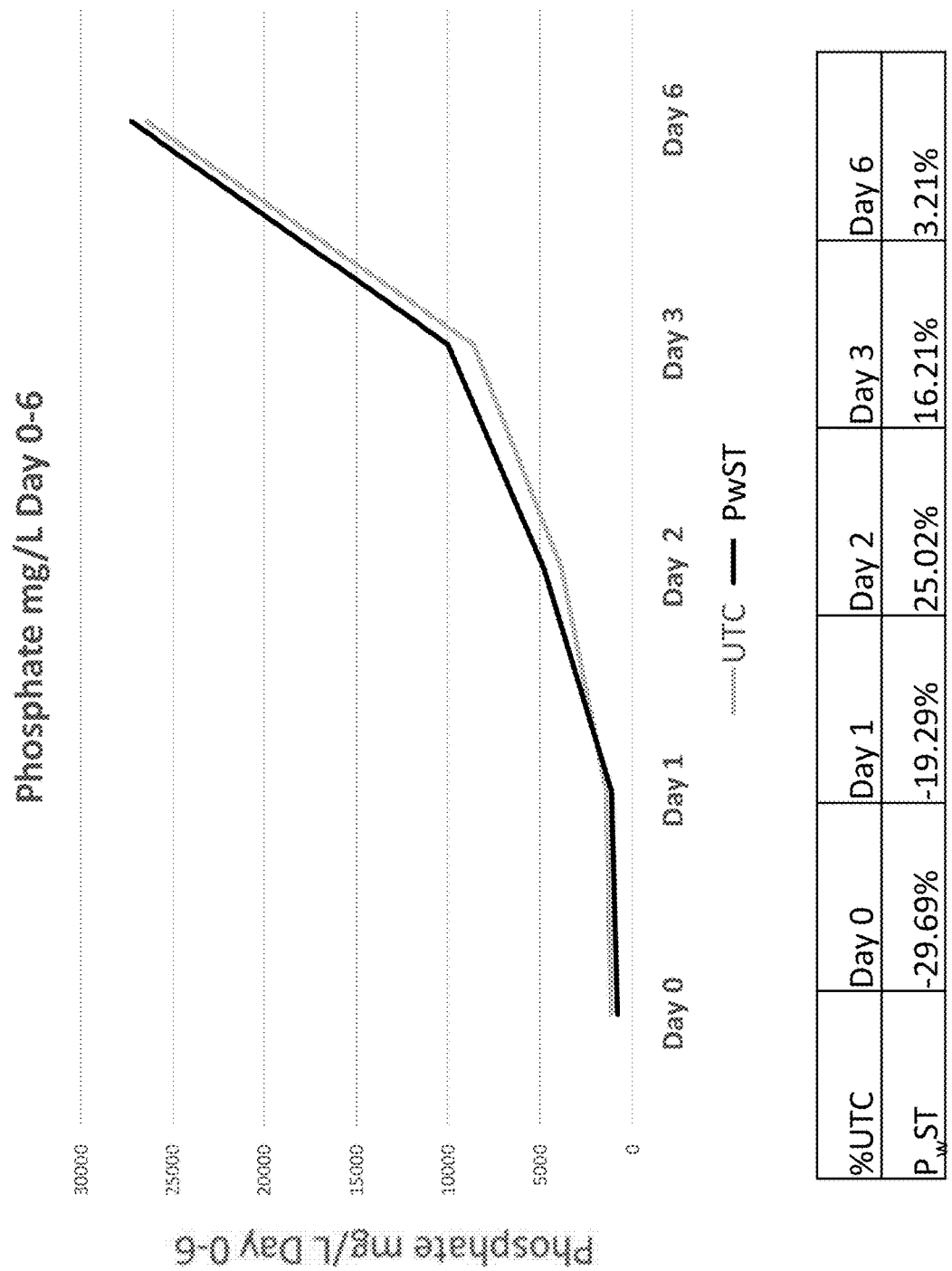

PwST supernatant improved phosphate solubilization from MAP fertilizer. PwST supernatant was coated to MAP fertilizer at an application rate of 2 qt/t. The coated fertilizer was then added to water and the water was measured after 6 days for phosphate solubilization capacity. On average, the fertilizer treated with PwST supernatant showed greater levels of phosphate released into the water compared to those levels from UTC fertilizer (FIG. 85A). Over the six days of testing, PwST supernatant-coated MAP showed increasing levels of phosphate solubilization, surpassing the capacity of UTC fertilizer by Day 2 (FIG. 85B).

Example 21: Differences in Microbial Counts Between Supernatant and WB from PwST System Supernatant and WB from the PwST system both had similar microbial counts for spore-formers and total bacteria. Samples from both the supernatant and WB were plated on quarter-Strength Trypctic Soy Agar (TSA; Difco) and incubated for 7 days at 30 C before reading. For spore-forming bacteria enumeration, samples were heated at 80 C for 15 minutes before plating. Plates were incubated for 7 days at 30 C before counting. Fungi and yeast enumeration was done using Dichloran Rose Bengal Agar (Sigma #17147) and incubated based on manufacturers recommendation. For the quantification of phosphate-solubilizers, the media used to measure the phosphate solubilization capacity was used in agar format (Kim et al. 1998). Different sources of phosphate (Phytate, Hydroxyapatite, and NBRIP) were used using the same base media, swapping out the phosphate source. WB displayed greater counts of yeast and three measured phosphate solubilizers—phytate, hydroxyapatite, and NBRIP. Results are shown in Table 26.

TABLE 26

Microbial counts (in cfu/ml) for PwST SPN and WB

| | SPN | WB |
|---|---|---|
| Total Bacteria | $4.10 \times 10^5$ | $4.2 \times 10^8$ |
| Spore-formers | $2.45 \times 10^4$ | $1.84 \times 10^6$ |
| Fungi | $1.00 \times 10^2$ | $4.15 \times 10^4$ |
| Yeast | <100 | $1.92 \times 10^5$ |
| P-solubilizers Phytate $C_6H_{18}O_{24}P_6$ | <100 | $1.75 \times 10^4$ |
| P-solubilizers Hydroxyapatite $Ca_5(PO_4)_3$ | $3.00 \times 10^2$ | $>1.0 \times 10^4$ |
| P-solubilizers NBRIP $Ca_3(PO_4)_2$ | $3.20 \times 10^3$ | $>1.0 \times 10^4$ |

The characterization of PwST WB used similar culture-dependent methods with the addition of characterizing the solutions in selective agar media such nitrogen-free medium to enumerate potential nitrogen-fixers. Modified N-free medium is described in Mirza 2012.

Example 22: Effects of Intact and NTS Metabolites on Plant Growth Promotion

A version of the product that was filter sterilized to remove the bacteria from the system product also promoted plant growth in experiments with *Arabidopsis*.

Figure 86:
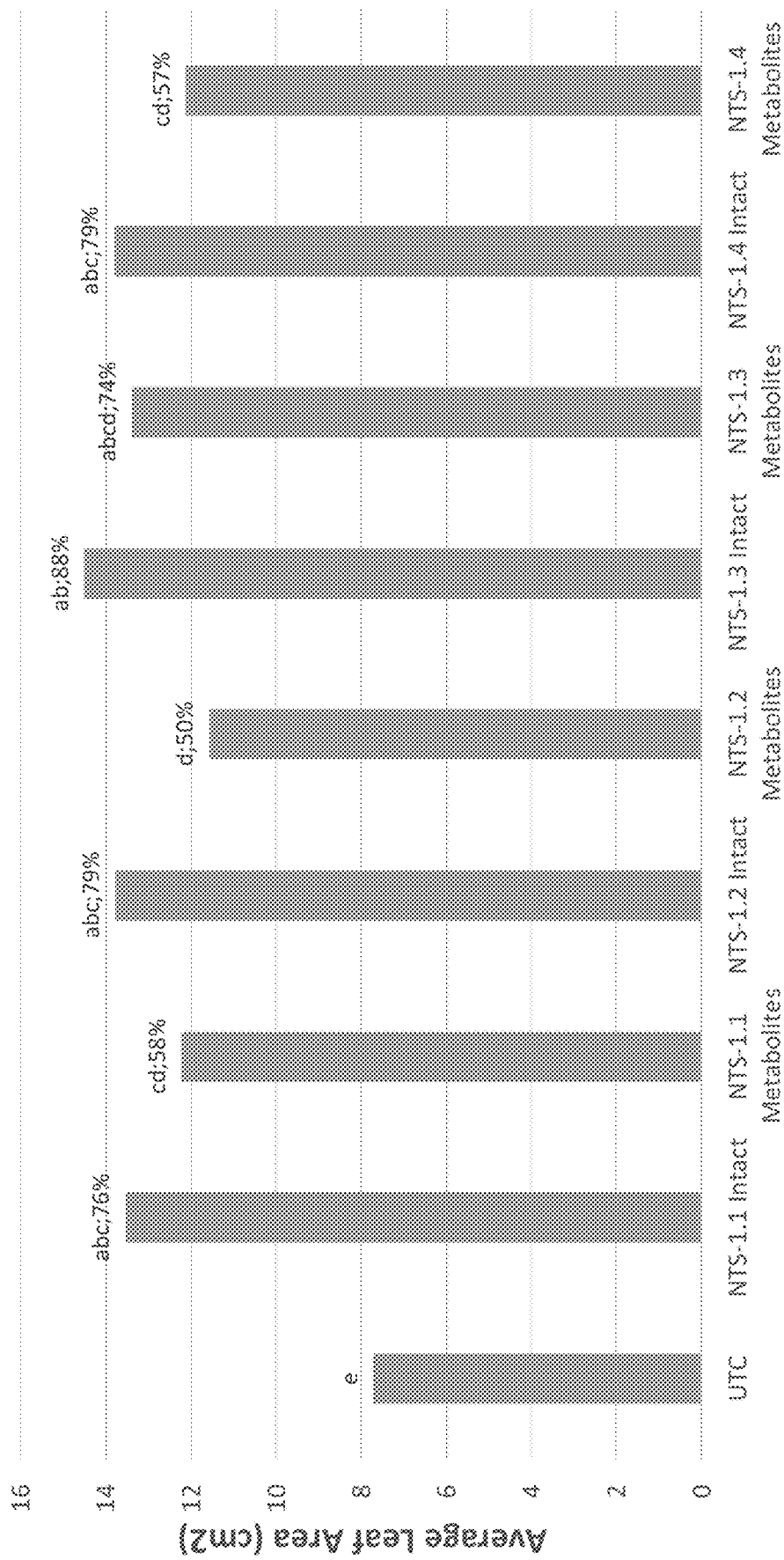
FIG. 86 shows the plant growth promotion of intact NTS solutions and metabolites. Intact NTS 1.0 system solutions and their metabolites showed increased average leaf area compared to that from UTC plants.

NTS-1.0 base product solutions were tested in *Arabidopsis* for plant growth promoting ability, using average leaf area (in cm2) as the primary metric. All systems were tested under 0.8% v/v and intact and filter-sterilized looking at the metabolites of the solutions. Solutions were filter-sterilized using a 0.22-micron filter. *Arabidopsis thaliana* (genotype Col-0) seedlings were germinated and grown for 7 days on 2 strength MS media (Murashige & Skoog Basal Medium with Vitamins, M519) plates in the growth chamber before transplanting into rockwool cubes for plant growth assays. Rockwool cubes were used as an inert substrate for growing *Arabidopsis* in a hydroponic-like system. The rockwool cubes were fitted into a 6-well tray and each treatment consisted of three replicate well trays. Nine, 1 L ½ strength MS media (Murashige & Skoog Basal Medium with Vitamins, M519) solutions were made. The test substance was then added at the rate given below in Table 27, and the pH of the solution was raised to 5.7. Forty mL of each 1 L treatment solution was dispensed to each rockwool cube. Then, each wetted cube received one *Arabidopsis* seedling. *Arabidopsis* plants grew on an LED light cart for 12 days. Leaf area was determined using the ImageJ software package. All the data collected were put through JMP for ANOVA analysis. All treatments showed numerically greater average leaf area measurement from the UTC with NTS-1 having the most significant plant growth promotion ($p<0.0001$) (FIG. 86). All base product solutions across all systems showed consistent PGP activity over the UTC control. The results demonstrated that intact solutions and metabolites alone promoted higher leaf area in *Arabidopsis*.

TABLE 27

Treatment conditions for Arabidopsis metabolite study

| | | |
|---|---|---|
| 1. | ½MS Media+ | UTC |
| 2. | ½MS Media+ | 0.8% NTS-1.1 Base Product Solution Intact (v/v) (8 mL/L) |
| 3. | ½MS Media+ | 0.8% NTS-1.1 Base Product Solution Metabolites (v/v) (8 mL/L) |
| 4. | ½MS Media+ | 0.8% NTS-1.2 Base Product Solution Intact (v/v) (8 mL/L) |
| 5. | ½MS Media+ | 0.8% NTS-1.2 Base Product Solution Metabolites (v/v) (8 mL/L) |
| 6. | ½MS Media+ | 0.8% NTS-1.3 Base Product Solution Intact (v/v) (8 mL/L) |
| 7. | ½MS Media+ | 0.8% NTS-1.3 Base Product Solution Metabolites (v/v) (8 mL/L) |
| 8. | ½MS Media+ | 0.8% NTS-1.4 Base Product Solution Intact (v/v) (8 mL/L) |
| 9. | ½MS Media+ | 0.8% NTS-1.4 Base Product Solution Metabolites (v/v) (8 mL/L) |

Example 23: Phosphate Solubilizing Technology (PST) System

In some digestion systems described in the Examples above, an input into the digestion is indicated as being PST WB, which is a product of a PST digestion system. The PST system was the same as PwST described above except that, in the place of the water, the feed into the first FBR of the PST system includes a product of an anaerobic digestion of cow manure by a packed bed reactor system (referred to herein as the "P2 system") in the place of the water. The P2 system had a similar initial stage as the PBR2 system described above but continued past the second PBR with a series of four additional PBR containers, for a total of six PBRs maintained under anaerobic conditions with continuous, hydraulically balanced flow through each of the PBRs. The outflow from the top of the sixth PBR is referred to herein as the "P2 base product," which was used as the hydraulic input into the PST system. The P2 base product is substantially the ultimate output of a system as depicted in FIG. 5 of US2013/03244061.

Example 24: Assessment of nifH Content Across NTS Systems

Figure 87:
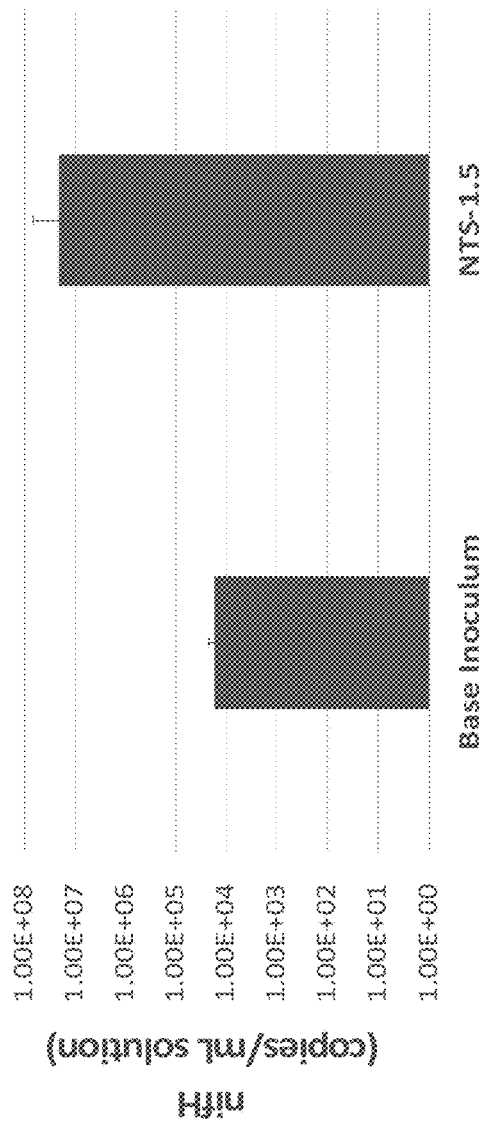
FIG. 87 shows the nitrogen fixation gene (nif) enriched in systems without the addition of nitrogen-fixing isolates.

Methods of quantification of nifH content from NTS products was similar to those described in Example 12. Following process optimization, the base technology represented by the NTS-1.5 system, which does not contain any target isolates, showed that the system design and selected feedstocks enriched for nitrogen fixing capacity over the 1:3 PwST WB base inoculum. Compared to 1:3 PwST WB, the NTS-1.5 product showed superior nitrogen fixation capacity, measured as greater nifH content (FIG. 87).

In an example, the NTS-2.2 and NTS-2.3 provided conditions for enrichment of a nitrogen-fixing microbial community (Table 24) and the base product solutions were tested for nitrogen fixation capacity as measured with the ARA assay (previously described in Example 12). Base products from both NTS-2.2 and NTS-2.3 showed nitrogen fixation capacity. Nitrogen fixation capacity was measured from both scaled-up systems and results showed an increase in nifH content compared to the Reactor 1a Input inoculum (Table 24).

Figure 88:
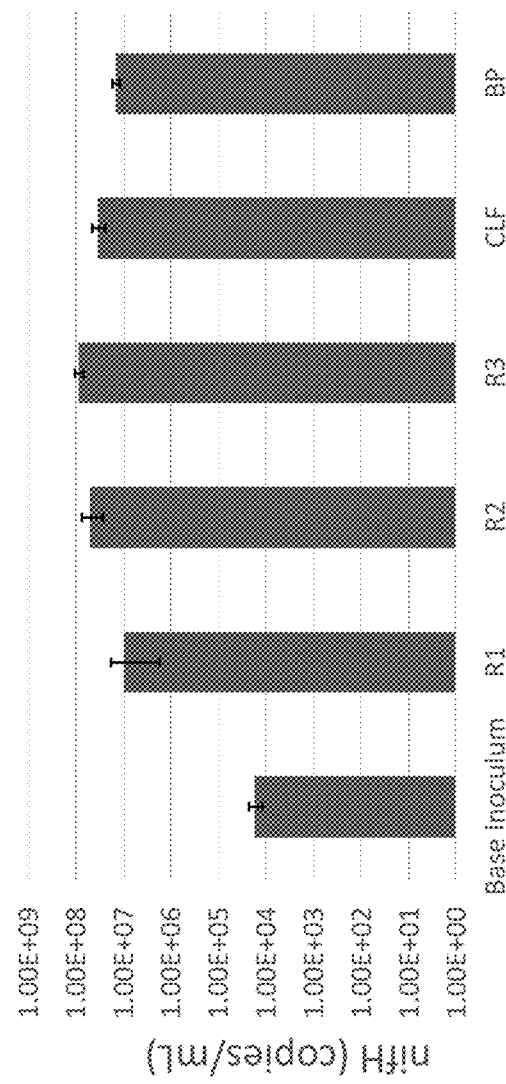
FIG. 88 shows nitrogen-fixer capacity (measured as enrichment of nifH) across reactors of the serialized NTS 2.3 system.

The NTS 2.2 and NTS 2.3 output solutions either intact or filter sterilized (e.g., metabolites only) provide plant growth promotion in high throughput assays with *Arabidopsis* as well as in greenhouse experiments in multiple crops such as corn, sorghum, fescue, wheat, canola, soybean, tomato. There is a positive effect on growth, yield and nitrogen content in crops grown in outdoor pot studies and field trials with crops like corn, sorghum, wheat and soybean. The produced base products of the NTS 2.2 and NTS 2.3 lines have a pH range of 7.8-8.88, electrical conductivity (Cond) range of 1.50-2.8 mS/cm, and a chemical oxygen demand (COD) range of 80-500 mg/L. The nitrogen fixing capacity in the NTS-2.3 system showed an enrichment in nitrogen fixer bacteria over both the base inoculum and the nitrogen-fixing microbial isolates. The base inoculum represented a final 1% inoculum into the system when added to the first reactor. The first reactor working solution was increased 2.7 log fold over the base inoculum. Further increases through the reactors showed the process increases bacteria capable of nitrogen fixation (FIG. 88).

The base (e.g., nitrogen-fixing bacteria) inoculum consisted of PwST WB (1:3) where the inoculum was introduced into reactor 1 at a 1% rate accounting for $1.71 \times 10^4$ nifH copies/mL of reactor 1 solution. Reactors of the NTS-2.3 showed an early enrichment over the base inoculum in the first reactor. Reactor 1 showed an immediate enrichment of nitrogen fixing bacteria within the system (measured as in nifH copies/mL of reactor solution).

Nitrogen-fixing microbial isolates, MS3907 and MS4921, were introduced into Reactor 1 of NTS-2.3 at a final target concentration of $1 \times 10^5$ cfu/mL of reactor 1 solution. Both isolates contained only one copy of the nifH gene in their genome. The nitrogen-fixing microbial isolates were quantified with a semi-quantitative method and the same DNA extractions used for qPCR of the nifH gene. Quantitative assessment of nifH genes, MS3907_cynS genes and MS4921_hyd7 genes, per milliliter of NTS-2.3 reactor solutions showed microbial isolates comprised less than 3% of the total nitrogen-fixers in each reactor, demonstrating the system was amenable to the enrichment of other types of nitrogen-fixing bacterial communities (Table 28).

TABLE 28

Composition of microbial isolates in comparison to all nitrogen fixers

| | nifH (copies/mL) | MS3907_cynS (copies/mL) | MS4921_hyd7 (copies/mL) |
|---|---|---|---|
| PwST WB (1:3) Inoculum | 1.71E+04 | 0.00E+00 | 0.00E+00 |
| Reactor 1 | 1.00E+07 | 2.70E+05 | 2.07E+01 |
| Reactor 2 | 5.13E+07 | 2.70E+05 | 2.07E+01 |
| Reactor 3 | 8.68E+07 | 2.70E+05 | 5.70E+04 |
| Clarifier | 3.49E+07 | 2.70E+05 | 1.09E+05 |
| Base Product | 1.46E+07 | 2.70E+05 | 2.69E+06* |

*Average of two time points months after inoculation

Table 28 provides evidence of the retention and enrichment of the nitrogen-fixing target isolates MS3907 and MS4921 within the reactors. Semi-quantification PCR results showed that both isolates were enriched and retained along the continuous process. Semi-quantification of the cynS gene indicated that MS3907 was present at predicted inoculation rates in Reactor 1. Semi-quantification of the hyd7 gene showed that MS4921 demonstrated growth only in Reactor 3, Clarifier, and in Base Product.

Example 25: Reduced Nitrogen *Arabidopsis* Assay for NTS 1.4 and 1.5 Systems

The purpose of this experiment was to characterize the NTS-1.4, with target isolates MS3900 and MS3907 within the system and compare the efficacy under reduced nitrogen conditions (1 mM N) in *Arabidopsis* to the NTS-1.5 base product (BP), with no target isolates in the system. The experiment evaluated whether the target isolates, when grown outside the NTS system in microbial cultivation media (TSB, Tryptic Soy Broth, Millipore, #22092) and then diluted into the NTS-1.5 BP to the same concentration found in the NTS-1.4, provided a similar benefit as the NTS-1.4 system. For the nitrogen-reduced assay, *Arabidopsis thaliana* (genotype Col-0) seedlings were first germinated and grown for 7 days at 20° C. on 2 strength MS (Murashige & Skoog Basal Medium with Vitamins, M519) media plates in a growth chamber before being transplanted into rockwool cubes for plant growth assays. Rockwool was used as an inert substrate for growing *Arabidopsis* in a hydroponic-like system. Four rockwool cubes, each with one seedling, constituted a replicate. Each treatment had four replicates. 1 L ½ strength solutions formulation of MS media (Murashige & Skoog Basal Medium with Vitamins without nitrogen, MSP07) which is free of nitrate micronutrients (no ammonium nitrate or potassium nitrate) were made and then added different concentrations of the corresponding nitrogen source. The reduced nitrogen concentration tested in the case of an inorganic N source supplemented with addition of $KNO_3$ and $NH_4NO_3$ was 1 mM total Nitrogen. MES was added as a buffer to the solution at 0.5 g/L, and each respective treatment was then added to have a final concentration of 0.8% v/v. The pH of each solution for each treatment solution was finally raised to 5.7. Forty mL of each 1 L treatment solution was dispensed to each rockwool cube. A full nitrogen strength provided with ½ strength solution of the M519 (30 mM N) was included as a control as well as corresponding untreated water controls with the same nitrogen concentrations to compare to each treatment. Target isolates, MS3900 and MS3907, were spiked in NTS-1.5 BP for treatments "NTS-1.5+isos" at similar concentrations found in NTS-1.4 BP (2.00E+04 cfu/ml). Table 29 and Table 30 below detail the list of treatments and application rates used for these experiments.

TABLE 29

Description of treatment for Arabidopsis test at 30 mM N

| | MS Media | N-Concentration | Treatment | Application Rate (v/v) |
|---|---|---|---|---|
| 1 | ½ M519 | 30 mM | UTC (Untreated Control) | |
| 2 | ½ M519 | 30 mM | NTS-1.5 BP | 0.8% |
| 3 | ½ M519 | 30 mM | NTS-1.5 BP + Isos | 0.8% |
| 4 | ½ M519 | 30 mM | NTS-1.4 BP | 0.8% |

The treated plants were placed on LED grow carts in completed randomized block design and grown at approximately 20° C. The cubes were kept moist by adding 8 mL of water every 2 days. After 16 days, the leaf area of each plant was measured using ImageJ software of shoot photographic images. All the data collected were put through JMP for statistical analysis.

TABLE 30

Description of treatment for Arabidopsis test at 1 mM N

| | MS Media | N-Concentration | Treatment | Application Rate (v/v) |
|---|---|---|---|---|
| 1 | ½ MSP07 | 1 mM | UTC (Untreated Control) | |
| 2 | ½ MSP07 | 1 mM | NTS-1.5 BP | 0.8% |
| 3 | ½ MSP07 | 1 mM | NTS-1.5 BP + Isos | 0.8% |
| 4 | ½ MSP07 | 1 mM | NTS-1.4 BP | 0.8% |

Figure 89A:
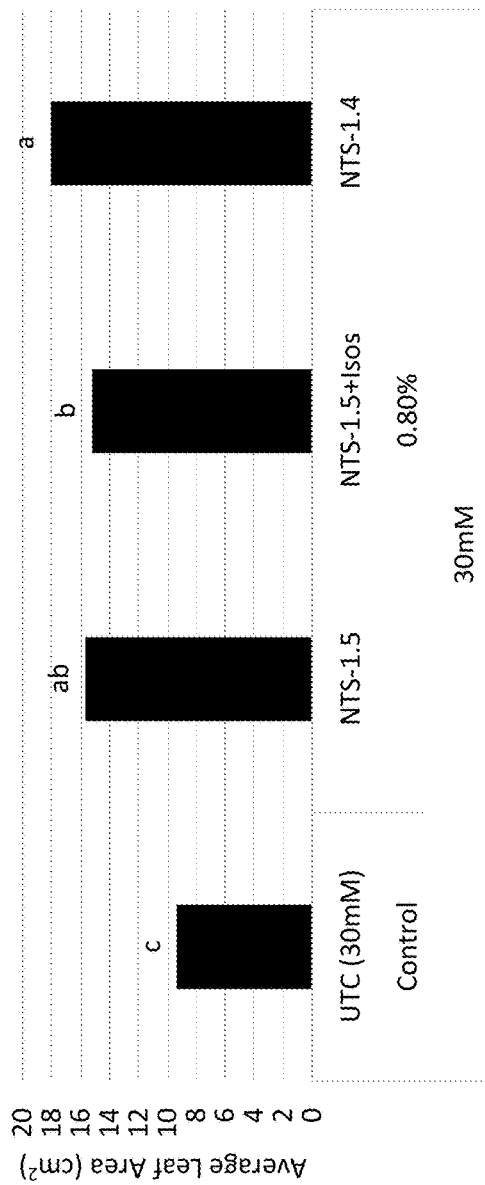
FIGS. 89A-89B show *Arabidopsis* plant growth using only inorganic N as the nitrogen source in NTS 1.4 and NTS 1.5 systems.

Under standard inorganic nitrogen conditions (30 mM) which is sufficient to provide normal growth, all NTS treatments had significantly greater plant growth promotion measured in the form of leaf area than the untreated control (FIG. 89A). In this experiment, when the target isolates (MS3900 and MS3907) were spiked in the base product of NTS-1.5 (base technology, no target isolates in system), the average leaf area of both treatments were similar and not significantly different from each other. However, *Arabidopsis* plants treated with NTS-1.4 (with target isolates in the system) had a significantly higher leaf area than either of the NTS-1.5 treatments. These results showed that the system in which the target isolates were grown as resident microbes performed significantly better than when the same isolates were added to the end product of the NTS 1.5 system in which they were not resident.

Figure 89B:

Under low inorganic N conditions (1 mM) which limits *Arabidopsis* growth, all NTS treatments had significantly improved *Arabidopsis* growth as measured in the form of leaf area than the untreated control (FIG. 89B). In this experiment, when the target isolates (MS3900 and MS3907) were spiked in the base product of NTS-1.5 (no target isolates resident in system), the average leaf area of both treatments were similar and not significantly different from each other. However, *Arabidopsis* plants treated with NTS-1.4 (with target isolates resident in the system) had a significantly higher leaf area than NTS-1.5 treatments. These results showed that when the target isolates were grown within the NTS process (NTS-1.4), the base product had a greater plant growth promotion and nitrogen use efficiency effect than the base technology alone (NTS-1.5, no target isolates within the system), or when the target isolates were spiked in the base product (NTS-1.5+Isos).

Example 26: Reduced Nitrogen *Arabidopsis* Assay for NTS 2.2 and 2.3 Systems The effect of the output solution from the NTS 2.0 lines (e.g., NTS-2.2 and NTS-2.3 base product, BP), on nitrogen use efficiency was tested in an *Arabidopsis* platform under reduced nitrogen conditions. The experimental methods were similar to those used in Example 25. Table 31 and Table 32 below detail the list of treatments and application rates used for these experiments.

TABLE 31

Description of treatments for Arabidopsis test at 30 mM N

| | MS Media | N-Concentration | Treatment | Application Rate (v/v) |
|---|---|---|---|---|
| 1 | ½ M519 | 30 mM | UTC (Untreated Control) | |
| 2 | ½ M519 | 30 mM | NTS-2.2 | 0.2% |
| 3 | ½ M519 | 30 mM | NTS-2.3 | 0.2% |
| 4 | ½ M519 | 30 mM | NTS-2.2 | 0.8% |
| 5 | ½ M519 | 30 mM | NTS-2.3 | 0.8% |

The treated plants were placed on LED grow carts in completed randomized block design and grown at approximately 20° C. The cubes were kept moist by adding 8 mL of water every 2 days. After 16 days, the leaf area of each plant was measured using ImageJ software of shoot photographic images. All the data collected were put through JMP for statistical analysis.

TABLE 32

Description of treatments for Arabidopsis test at 1 mM N

| | MS Media | N-Concentration | Treatment | Application Rate (v/v) |
|---|---|---|---|---|
| 1 | ½ MSP07 | 1 mM | UTC (Untreated Control) | |
| 2 | ½ MSP07 | 1 mM | NTS-2.2 | 0.2% |
| 3 | ½ MSP07 | 1 mM | NTS-2.3 | 0.2% |
| 4 | ½ MSP07 | 1 mM | NTS-2.2 | 0.8% |
| 5 | ½ MSP07 | 1 mM | NTS-2.3 | 0.8% |

Using an inorganic N source at the standard rate (30 mM N) which supports normal growth, the product of both NTS lines 2.2 and 2.3 resulted in significantly improved growth (FIG. 90A). NTS-2.3 at 0.8% showed the greatest plant growth promotion capacity. At reduced N concentrations of 1 mM N, which limits *Arabidopsis* growth, the plants treated with NTS outputs showed significantly improved growth when compared to the growth of the water control (untreated) at the same conditions (FIG. 90B). Similarly to the standard rate results, NTS-2.3 at 0.8% showed the greatest growth capacity at a nitrogen concentration of 1 mM N.

Example 27: Reduced Nitrogen *Arabidopsis* Assay for NTS 2.2 and 2.3 Systems with Inorganic and Organic Nitrogen Sources The effect of the output solution from the NTS 2.0 lines (e.g, NTS-2.2 and NTS2.3 base product, BP) on nitrogen use efficiency was tested in an *Arabidopsis* platform under reduced N conditions with either an inorganic nitrogen source ($KNO_3$ and $NH_4NO_3$) or an organic nitrogen source (Ferticell-Explorer 16-0-0). The experimental methods were similar to those used in Example 25.

The reduced nitrogen concentration tested when using an organic soy nitrogen source was 1 mM. Likewise, the reduced nitrogen concentrations tested in the case of an inorganic nitrogen source supplemented with addition of $KNO_3$ and $NH_4NO_3$ were 10, 1, and 0.1 mM. MES was added as a buffer to the solution at 0.5 g/L, and each respective treatment was then added to have a final concentration of 0.2% v/v. The pH of each solution was finally raised to 5.7. Forty mL of each 1 L treatment solution was dispensed to each rockwool cube. A full nitrogen strength provided with ½ strength solution of the M519 (30 mM N) was included as a control as well as corresponding untreated water controls with the same nitrogen concentrations to compare to each treatment. The treated plants were placed on LED grow carts in completed randomized block design and grown at approximately 20° C. The cubes were kept moist by adding 8 mL of water every 2 days. After 16 days, the leaf area of each plant was measured using ImageJ software of shoot photographic images. All the data collected were put through JMP for statistical analysis.

Figure 91A:
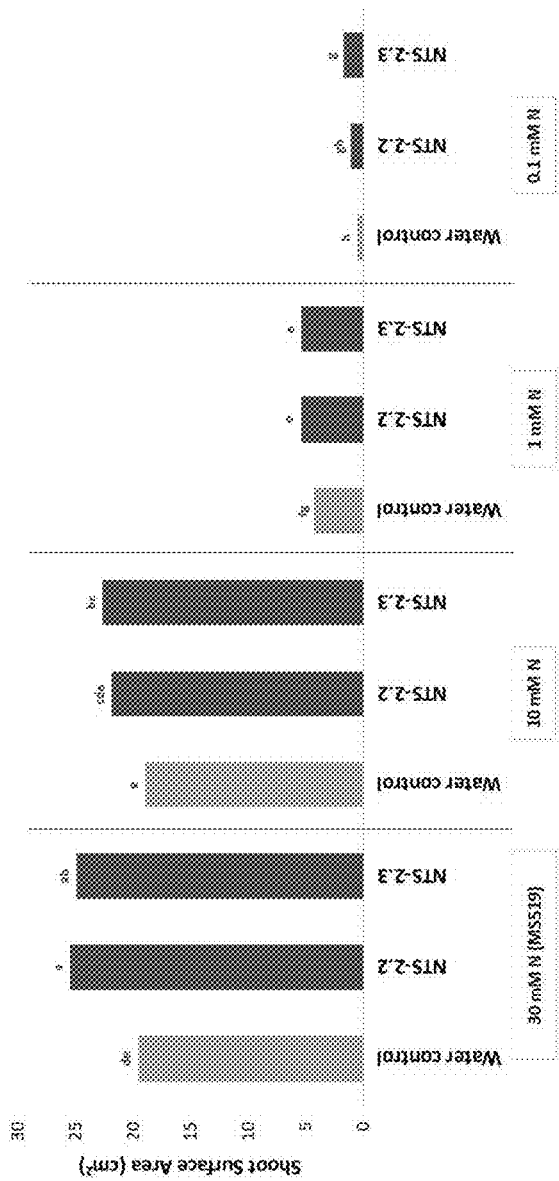
FIGS. 91A-91B show *Arabidopsis* plant growth using inorganic N and organic N as the nitrogen source in NTS 2.2 and NTS 2.3 systems.
Figure 91B:
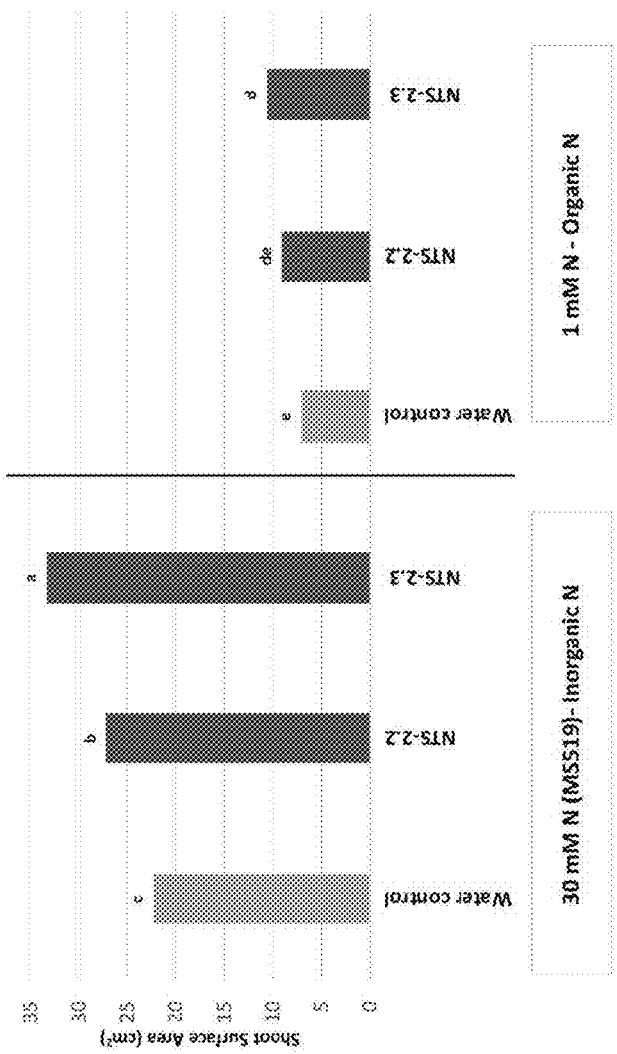

Using an inorganic N source, the product of both NTS lines 2.2 and 2.3 resulted in improved growth even under reduced nitrogen conditions (FIG. 91A). At reduced nitrogen concentrations of 10, 1, and 0.1 mM N, the growth of treated plants with NTS outputs continued to improve significantly when compared to the water control (untreated) at the same conditions. These results showed a more efficient use of nutrients and nitrogen under stress conditions. A similar result was obtained under reduced nitrogen conditions when an only organic N source at 1 mM was used (FIG. 91B). Treated plants with NTS products used organic N more efficiently resulting in improved and better growth than when using inorganic nitrogen at a similar concentration. FIGS. 91A and 91B both show the the NTS products improved plant growth compared to the control even under optimal inorganic nitrogen conditions (30 mM N).

Example 28: Plant Growth Promotion Capacity in NTS Systems as Intact Solution or as Metabolites Plant growth promotion was tested in *Arabidopsis* for the NTS 2.0 lines as both intact and filter-sterilized (F/S; e.g., metabolite) solutions. *Arabidopsis thaliana* (genotype Col-0) seedlings were germinated and grown for 7 days on 1 strength MS media (Murashige & Skoog Basal Medium with Vitamins, M519) plates in the growth chamber before transplanting into rockwool cubes for plant growth assays. Rockwool was used as an inert substrate for growing *Arabidopsis* in a hydroponic-like system. The rockwool cubes may be fitted into a 6-well tray and each treatment consisted of three replicate well trays. Thirteen, 1 L ½ strength MS media (Murashige & Skoog Basal Medium with Vitamins, M519) solutions were made. The test substance was then added at the rate as shown below in Table 33 and the pH of the solution was raised to 5.7. Forty mL of each 1 L treatment solution was dispensed to each rockwool cube. Each wetted cube then received one *Arabidopsis* seedling.

TABLE 33

Treatment conditions for testing plates

| | Treatment | Application Rate (v/v) | Type of Solution |
|---|---|---|---|
| 1 | ½MS Media+ | UTC | |
| 2 | ½MS Media+ | NTS-2.2 BP | 0.05% | Intact |
| 3 | ½MS Media+ | | | Metabolites |
| 4 | ½MS Media+ | | 0.2% | Intact |
| 5 | ½MS Media+ | | | Metabolites |
| 6 | ½MS Media+ | | 0.8% | Intact |
| 7 | ½MS Media+ | | | Metabolites |
| 8 | ½MS Media+ | NTS-2.3 BP | 0.05% | Intact |
| 9 | ½MS Media+ | | | Metabolites |
| 10 | ½MS Media+ | | 0.2% | Intact |
| 11 | ½MS Media+ | | | Metabolites |
| 12 | ½MS Media+ | | 0.8% | Intact |
| 13 | ½MS Media+ | | | Metabolites |

Figure 92:
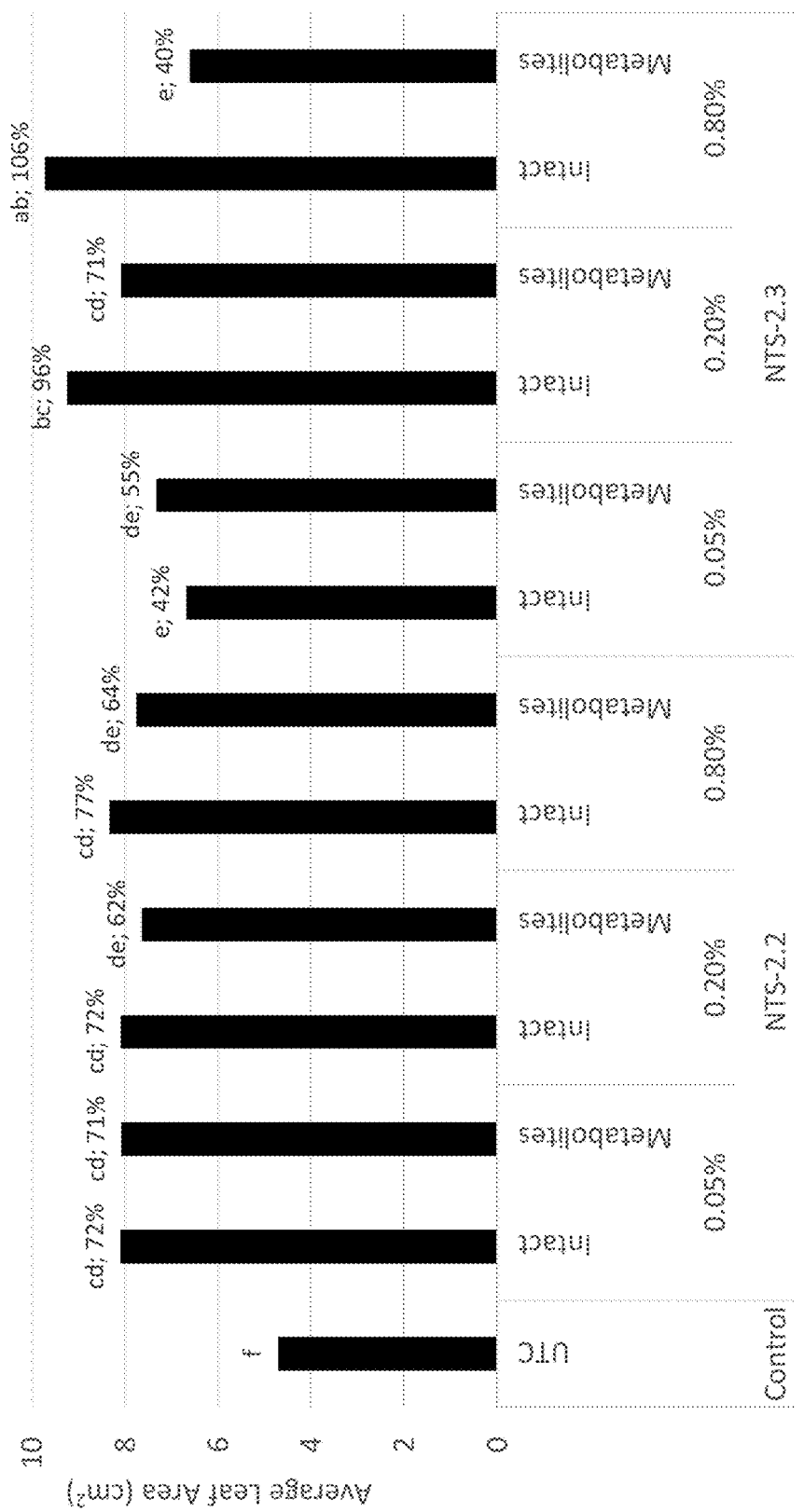
FIG. 92 shows *Arabidopsis* plant growth in NTS 2.2 and NTS 2.3 systems with intact solution or metabolites. All NTS 2.0 system treatments showed greater average leaf area than untreated control.

*Arabidopsis* plants grew on an LED light cart for 12 days. Leaf area was determined using the ImageJ software package. All the data collected were put through JMP for ANOVA analysis (a=0.1, p<0.0001). Results show that at all application rates, both NTS 2.0 lines have significantly improved the *Arabidopsis* leaf area over the untreated control when the solutions are intact (FIG. 92). Additionally, the metabolites produced along the process and that remained in the base product also had a significant effect on plant growth.

Plant growth promotion was also tested in *Arabidopsis* for the NTS 1.4 and NTS 1.5 systems as both intact and filter-sterilized (F/S; i.e., metabolite) solutions. The experimental methods were similar to those above for the NTS 2.0 systems. Seven 1 L ½ strength MS media (Murashige & Skoog Basal Medium with Vitamins, M519) solutions were made. The test substance was then added at the rate as shown below in Table 34, and the pH of the solution was raised to 5.7. Leaf area was determined using the ImageJ software package. All the data collected were put through JMP for ANOVA analysis with a=0.01 and p value=0.0025.

TABLE 34

Treatment conditions for testing plates

| 1 | ½MS Media+ UTC (untreated control) |
|---|---|
| 2 | ½MS Media+ 0.2% NTS-1.5 BP (v/V) |
| 3 | ½MS Media+ 0.2% NTS-1.5 BP + Isolates (v/v) |
| 4 | ½MS Media+ 0.2% NTS-1.4 BP (v/v) |
| 5 | ½MS Media+ 0.8% NTS-1.5 BP Metabolites (v/v) |
| 6 | ½MS Media+ 0.8% NTS-1.5 BP + Isolates Metabolites (v/v) |
| 7 | ½MS Media+ 0.8% NTS-1.4 BP Metabolites (v/v) |

Figure 93A:
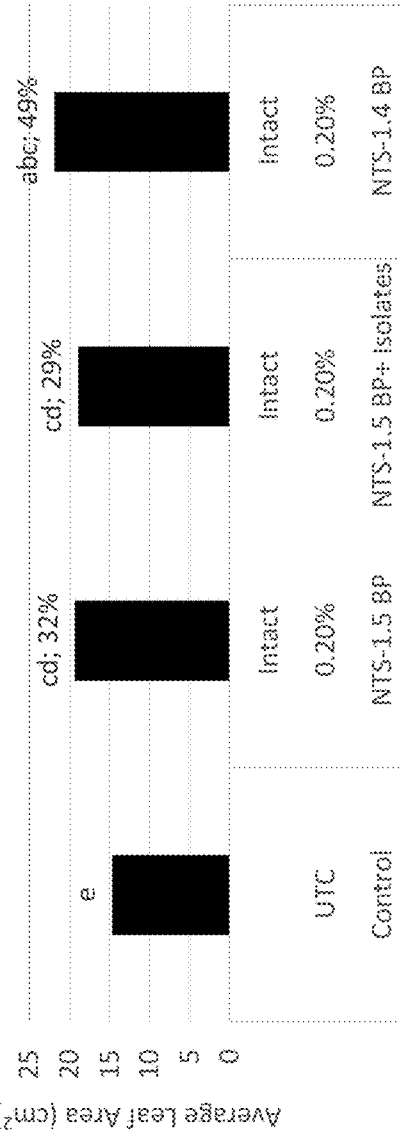
FIGS. 93A-93B show *Arabidopsis* plant growth in NTS 1.4 and NTS 1.5 systems with intact solution or metabolites.
Figure 93B:

In this experiment NTS 1.5 (no isolates) was evaluated to compare the metabolites of the base product (BP) to the metabolites of the NTS-1.4 (inoculated with target isolates within the reactor system, MS3900 and MS3907), as well as NTS-1.5 base product with the target isolates spiked at the end to the final base product (NTS-1.5 BP+Isolates). When the intact solutions were evaluated for plant growth promotion in *Arabidopsis*, there was a numerical increase in average leaf area of plants treated with NTS-1.4 BP over the NTS-1.5 BP and NTS-1.5 BP+Isolates treatments (FIG. 93A). All treatments had significantly greater leaf area than the untreated control (UTC). The metabolites of these solutions tested at 0.8%, showed a greater effect in increase leaf area in *Arabidopsis* with the NTS-1.4 metabolites being significantly different with greater leaf area than the NTS-1.5 metabolite-treated plants (FIG. 93B). These results demonstrated that the metabolites generated in the process by the target isolates or under the presence of the target isolate had plant growth promotion properties.

Example 29: Effects of Foliar Application of NTS 1.4 System on Plant Growth Promotion and Nitrogen Use Efficiency in Corn A corn experiment was conducted using Denton, Texas sandy-loam soil with turface and peat mix (1:1:1) for corn growth in a greenhouse experiment. All the treatments were applied as a foliar spray after thinning the plants. Hybrid GMO corn (Dyna-Grow seed) seed variety was used for this test. The 15 cm round pot was used, and the experimental design was four stacked 4×4 Latin squares. The growing medium was 1:1:1 Turface-peat-Denton sandy loam soil mix. The urea ammonium nitrate (UAN) 32 at 15 lbs./A, potash at 200 lbs./A, Jackpot micronutrient, and sodium molybdate fertilizer were mixed together and applied after thinning the plant. Six treatments and twelve replicates were used for this greenhouse test. Three seeds were planted in a 2-inch-deep hole in the center of each pot and the pot was covered with the growing medium and 1 week after planting thinned to 1 plant per pot. 50 mL fertilizer was applied to each pot after thinning. Treatment conditions are shown in Table 35. Pots were arranged in a replicated Latin square design. The data for all metrics were analyzed using JMP 17 software (SAS Institute, Cary, NC, USA) using the Fit Model procedure and mean separation at alpha=0.1 level of significance.

TABLE 35

Treatment conditions for foliar experiment

| Treatment | A.I. µL/15 cm pot |
|---|---|
| RO water only | 0 |
| NTS-1.4 + MS3900 - 2 qt./A | 36 |
| NTS-1.4 + MS3900 + MS4921 - 2 qt./A | 36 |
| High N fertilization (+10 lbs. N/A) | 0 |

Figure 94:
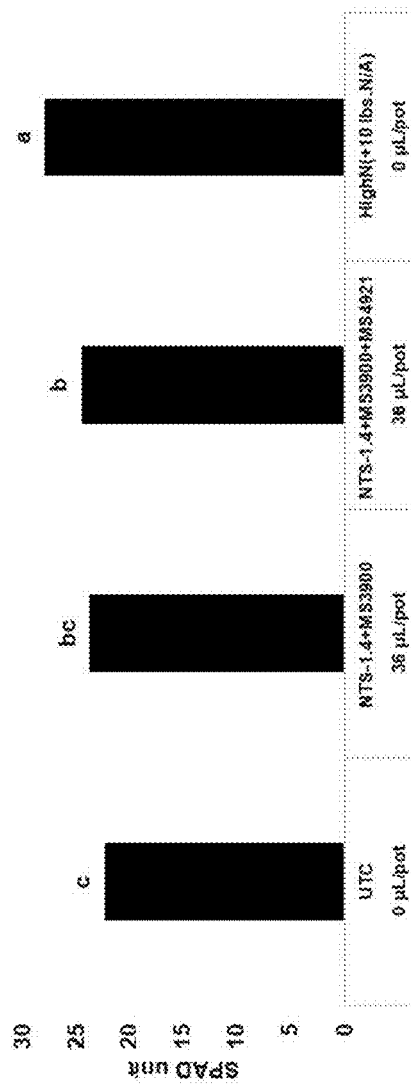
FIG. 94 shows corn leaf chlorophyll contents 10 days after foliar treatment application.

The leaf chlorophyll contents were measured from the topmost fully expanded leaf using a Chlorophyll Meter, SPAD (Soil Plant Analysis Development-502, Konica Minolta, Tokyo, Japan). The middle leaf position of leaf was selected for measuring the leaf chlorophyll contents to prevent the variation and three measurements were taken for each leaf. Corn leaf chlorophyll contents of foliar treated plants significantly increased 10 days after planting (FIG. 94). The nitrogen trifecta system (NTS)-1.4 spiked with MS3900 and MS4921 at 36 µL/pot had significantly greater leaf chlorophyll contents when applied as foliar treatment application. As chlorophyll molecules are rich in nitrogen, these results indicated that NTS treatments promoted greater chlorophyll content, possibly through greater nitrogen uptake from either the soil and fertilizer, nitrogen-fixation in or around the plant, or both.

Figure 95:
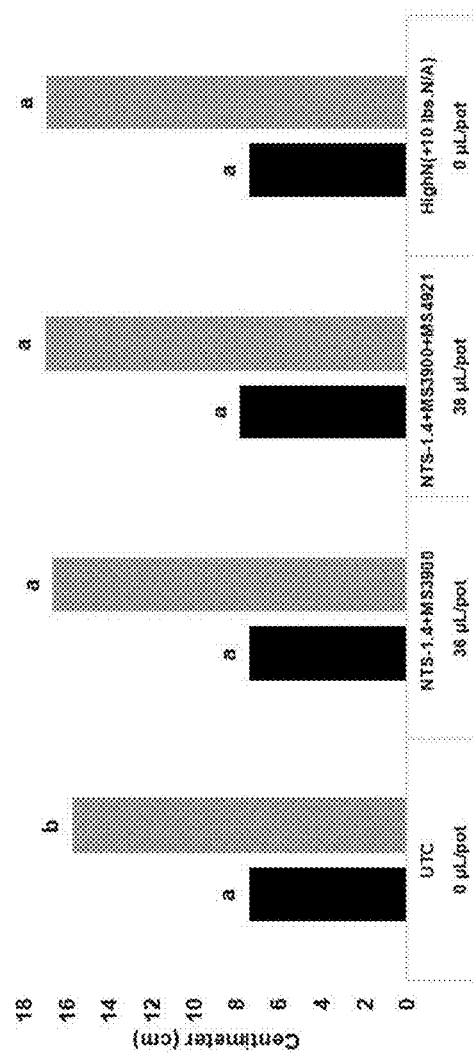
FIG. 95 shows corn plant height before and after foliar treatment. Black bars indicate plant height pre-treatment and gray bars indicate plant height ten days post-foliar treatment.
Figure 96:
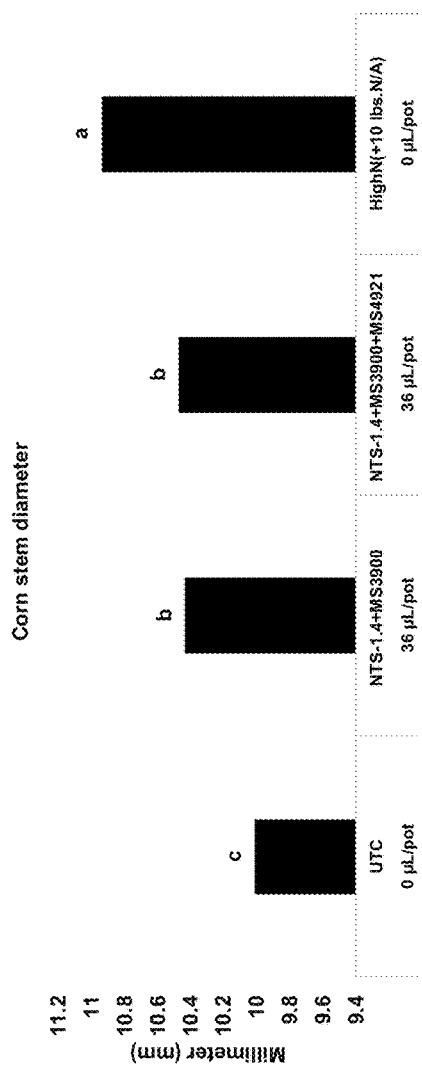
FIG. 96 shows corn stem diameter measured prior to harvest. Both NTS 1.4 treatment conditions showed greater stem diameter compared to that of untreated control plants.

The plant height was measured from the bottom of the plant at the soil surface to the fully developed leaf collar for corn plants in centimeter (cm). The stem diameter was measured using 0-40"/1000 mm Xtra-Range Electronic Caliper (Fowler high precision, Valencia, Ca, USA) in millimeter (mm). Plant height during early growth stages is an indicator of plant nutrition status. Corn plant height and stem diameter of foliar treated plants significantly increased 10 days after planting. The NTS-1.4 spiked with MS3900 and MS4921 significantly enhanced plant height and stem diameter at 36 μL/plant when applied as foliar treatment application (FIG. 95 and FIG. 96). The plant height and stem diameter for NTS-1.4 spiked with MS3900 and MS4921 were 17 cm and 10 mm, respectively. These results indicated that the plant growth promotion by the NTS solutions was a result of increased uptake of nutrients or nitrogen-fixation within or around the plant roots that provided the plants with extra nitrogen. The 36 μL/pot foliar application rate with NTS-1.4 spiked with MS3900 and MS4921 increased plant height by 8% over the control (FIG. 95).

Figure 97:
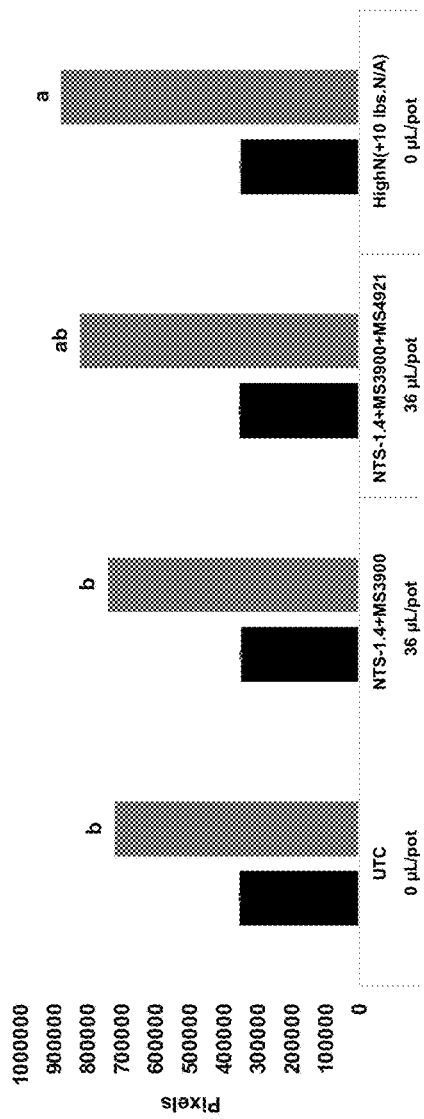
FIG. 97 shows corn leaf area measured before and after foliar treatment. Black bars indicate leaf area pre-treatment and gray bars indicate leaf area ten days post-foliar treatment.

Plant leaf area was recorded using the PlantGazer phenotyping system (Confluence Research & Development, LLC). The NTS-1.4 spiked with MS3900 or MS3900 and MS4921 enhanced leaf area at 36 μL/pot when applied as foliar treatment application, but not significantly (FIG. 97).

Example 30: Effects of In-Furrow and Foliar Application of NTS 1.4 Isolate-Spiked Treatments on Plant Growth Promotion and Nitrogen Use Efficiency in Sorghum A sorghum experiment was conducted, in a 48 ft.×48. ft. square poly-covered rainout shelter. The growing medium consisted of Denton, Texas sandy-loam soil with turface and peat mix (1:1:1). The pot size the 10 gallons and 30 cm diameter at top. The pots were watered every day using an automatic sprinkler (10 minutes and twice a day in the morning and afternoon). The experimental unit was one sorghum plant in each pot. For 80% grower standard practice (GSP)—MESZ (12-40-0-10S-1Zn) at 81.6 lbs. nitrogen at pre-planting fertilizer was used for this test. For 100% grower standard practice (GSP)-MESZ (12-40-0-10S-1Zn) at 102 lbs. nitrogen at pre-planting fertilizer was used for this test. Treatments were applied in-furrow over sorghum seed or sorghum plant in each pot was sprayed with foliar treatments containing 36 μL of treatment using a 50-gallon/A carrier volume during the late boot stage. A surfactant (0.25%) was included in each foliar spray to improve spread, wetting, and absorption of the treatments on the foliage. Metrics collected included leaf chlorophyll content and plant physiological traits, such as stomatal conductance, transpiration rate, quantum yield, and electron transport rate, and were recorded at vegetative growth stage (V6) after foliar treatment application. Treatment conditions are shown in Table 36.

TABLE 36

Treatment conditions for in-furrow and foliar conditions

| Treatments | A.I. μL/30 cm pot |
| --- | --- |
| UTC100% GSP | 18 |
| UTC80% GSP | 18 |
| NTS-1.4 + MS3900-80% GSP | 18 |
| NTS-1.4 + MS3900 + MS4921-80% GSP | 18 |
| NTS-1.4 + MS3900-80% GSP | 36 |
| NTS-1.4 + MS3900 + MS4921-80% GSP | 36 |
| NTS-1.4 + MS3900-80% GSP (Foliar) | 36 |
| NTS-1.4 + MS3900 + MS4921-80% GSP (Foliar) | 36 |

Figure 98:
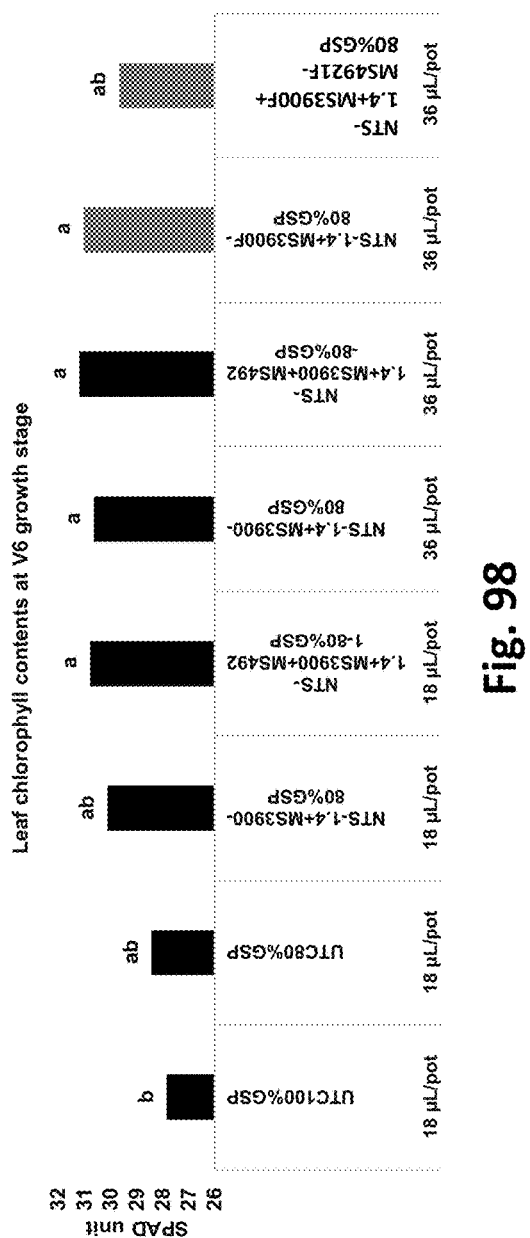
FIG. 98 shows sorghum leaf chlorophyll contents at vegetative growth stage V6 following in-furrow or foliar treatment application of NTS 1.4 with MS3900 or MS3900 and MS4921 (gray bars indicate foliar treatment application).
Figure 99:
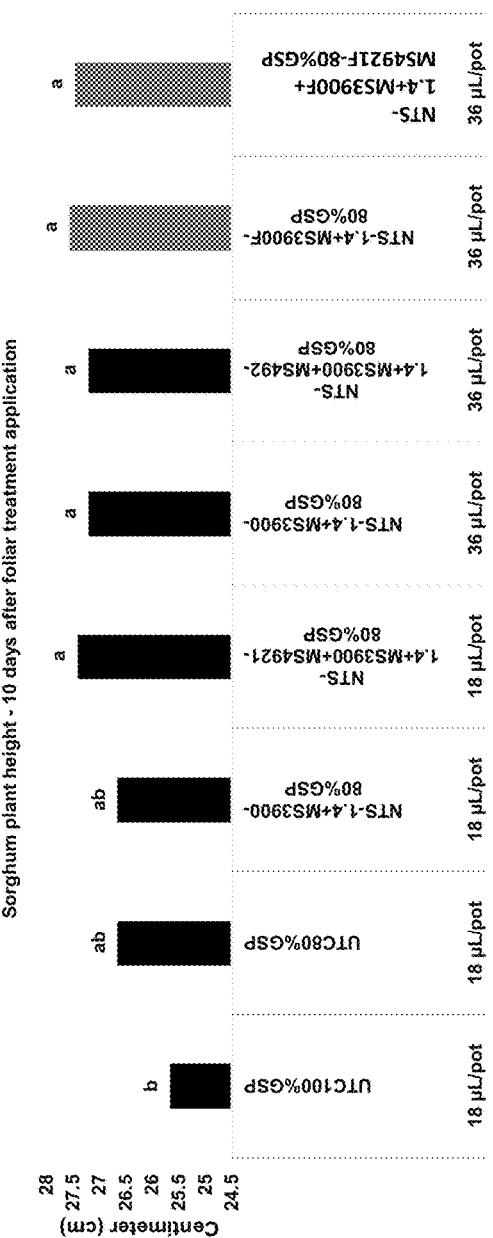
FIG. 99 shows sorghum plant height 10 days following in-furrow or foliar treatment application of NTS 1.4 with MS3900 or MS3900 and MS4921 (gray bars indicate foliar treatment application).

Methods for quantifying leaf chlorophyll content, plant height, and stem diameter are similar to those in Example 29. Sorghum leaf chlorophyll contents of foliar treatment (gray color bars) and in-furrow treated plants were increased compared to that of untreated control plants (FIG. 98). NTS-1.4 spiked with MS3900 alone or with MS3900 and MS4921 had greater sorghum leaf chlorophyll contents at 18 and 36 μL/pot when applied as in-furrow and foliar treatment application (FIG. 98). The 36 μL/pot foliar application rate with NTS-1.4 spiked with MS3900 and MS4921 increased sorghum plant height by 3% over the untreated control (FIG. 99). All NTS 1.4 treated plants showed greater plant height than that of untreated controls.

Figure 100C:
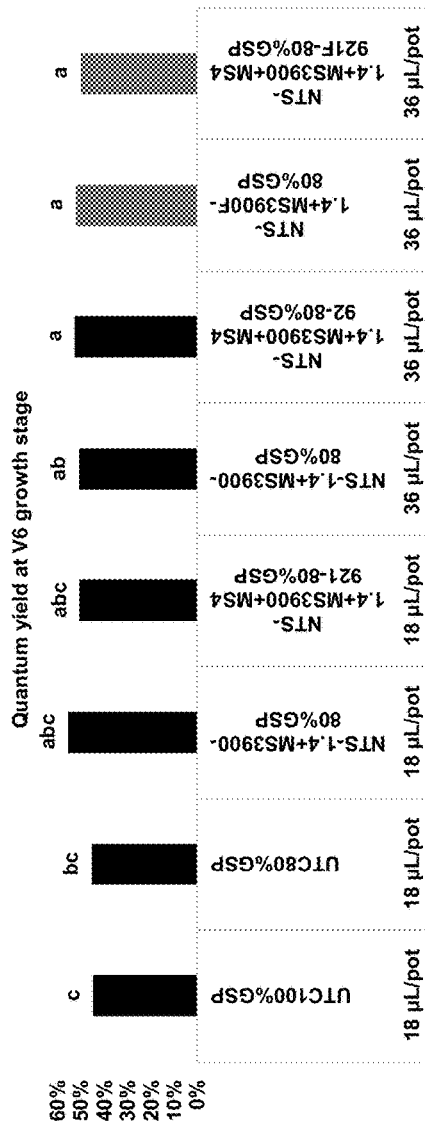
Figure 100D:
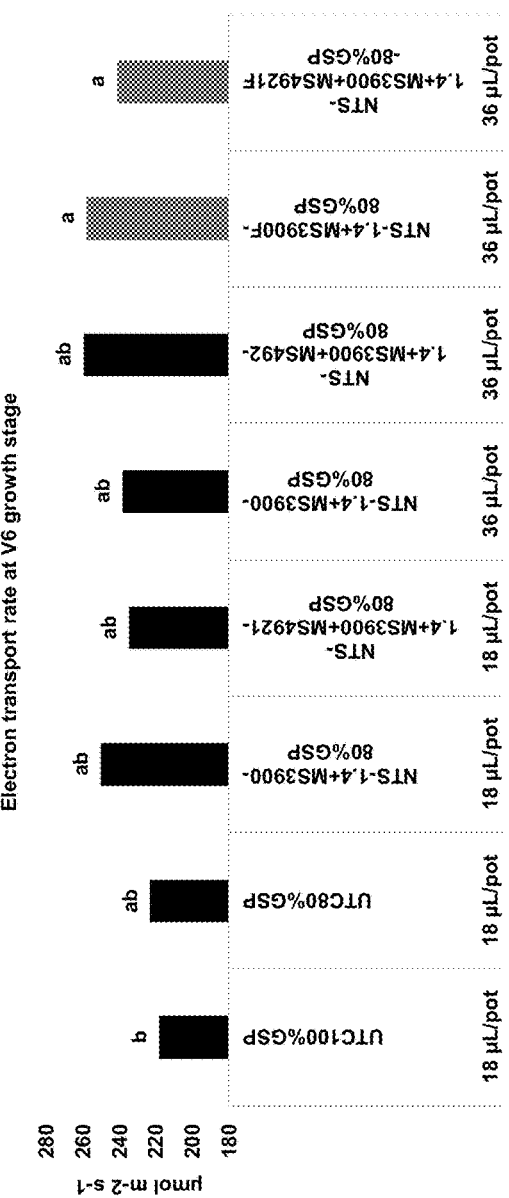
Figure 101:
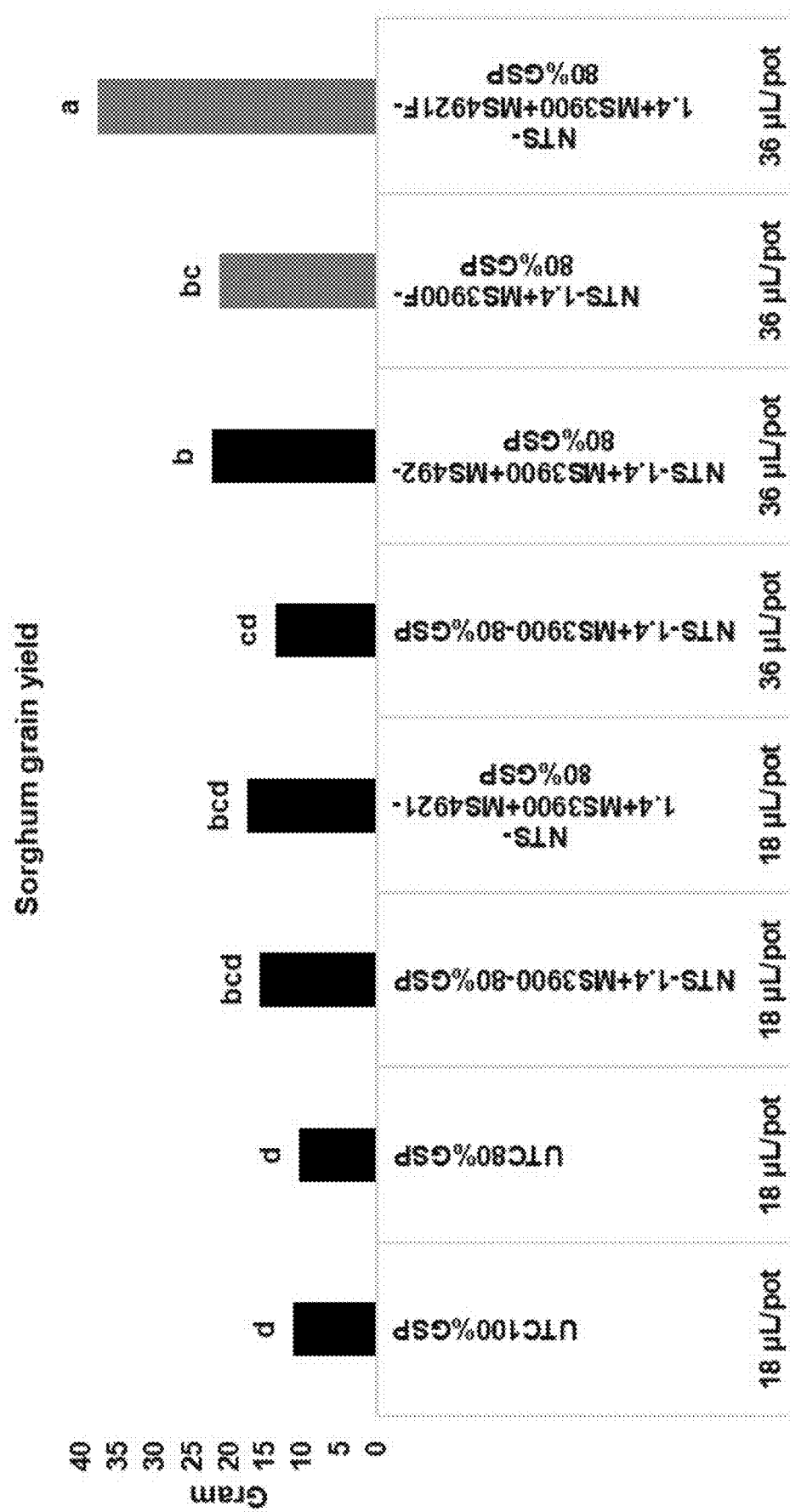
FIG. 101 shows sorghum grain yield following in-furrow or foliar treatment application of NTS 1.4 with MS3900 or MS3900 and MS4921 (gray bars indicate foliar treatment application).

Plant physiological traits, such as the gas-exchange metrics, stomatal conductance (gsw), and transpiration rate (E), chlorophyll fluorescence/quantum yield (QY), and electron transport rate (ETR) were measured using a LICOR 600PF Porometer/Fluorometer Portable Photosynthesis System (Li-Cor, Inc. Lincoln, NE, USA) after the treatment application. Plant physiological parameters were measured between 11:00 am and 15:00 pm on the topmost fully expanded leaf of each plant. Sorghum stomatal conductance, transpiration rate, and quantum yield of NTS-1.4 spiked with MS3900 alone or with MS3900 and MS4921 treated plants were significantly increased at 36 μL/pot when applied as foliar treatment application (FIGS. 100A-C). Electron transport rate of sorghum plants treated with NTS 1.4 with MS3900 alone or with MS3900 and MS4921 was increased compared to that of the untreated control with 100% GSP (FIG. 100D). The sorghum grain yields were measured using an electric balance after drying in a mechanical convection oven at 70° C. for 48 hr. Foliar treatment application significantly increased sorghum grain yields. NTS-1.4 spiked with MS3900 and MS4921 produced significantly greater sorghum grain yields (FIG. 101). The 36 μL/pot foliar application rate with NTS-1.4 spiked with MS3900 and MS4921 increased sorghum grain yield by 258% over the control.

Example 31: Effects of Foliar Application of NTS 2.2 and 2.3 Isolate-Spiked Treatments on Plant Growth Promotion and Nitrogen Use Efficiency in Soybeans A soybean experiment was conducted, in a 48 ft.×48. ft. square poly-covered rainout shelter. The growing medium consisted of Denton, Texas sandy-loam soil with turface and peat mix (1:1:1). The pot volume was 10 gallon with a 36 cm diameter. The pots were watered everyday using an automatic sprinkler (2 minutes and twice a day in the morning and afternoon). The experimental unit was four soybean plants in each pot. Fertilizer was not applied as there was sufficient nutrient levels already present in the soil mix from a previous wheat experiment in which the soybean was planted using the no-till method. Soybean plants in each pot were sprayed with foliar treatments containing 36 μl of treatment using a 50-gallon/A carrier volume during vegetative growth stage (V4). A surfactant (0.25%) was included in each foliar spray to improve spread, wetting, and absorption of the treatments on the foliage. Metrics collected included leaf chlorophyll content and plant physiological traits, such as stomatal conductance, transpiration rate, quantum yield, and electron transport rate, which were recorded 8 and 9 days after foliar treatment application. The number of pods that had developed at R3 in each pot was recorded. The treatment conditions and rates of application are shown in Table 37.

TABLE 37

Conditions and rates of application for foliar treatments

| Treatment | Rate |
| --- | --- |
| UTC (untreated control) | |
| NTS-1.4 + MS3900 + MS4921 | 36 μL/pot |
| NTS-2.2 | 36 μL/pot |
| NTS-2.3 | 36 μL/pot |

TABLE 37-continued

Conditions and rates of application for foliar treatments

| Treatment | Rate |
|---|---|
| NTS-2.2 + MS4921 | 36 µL/pot |
| NTS-2.3 + MS4921 | 36 µL/pot |

Experimental methods for evaluating leaf chlorophyll content, plant height, stem diameter, stromal conductance, transpiration rate, quantum yield, and electron transport rate were described in Example 30. The normalized difference vegetation index (NDVI) was measured using CI-710 Miniature Leaf Spectrometer (CID-Bioscience, USA). Three leaves and replications were used for measuring the NDVI. NDVI measurement indirectly measured leaf chlorophyll contents, similar to SPAD measurement, but using different spectral wave bands.

Figure 102:
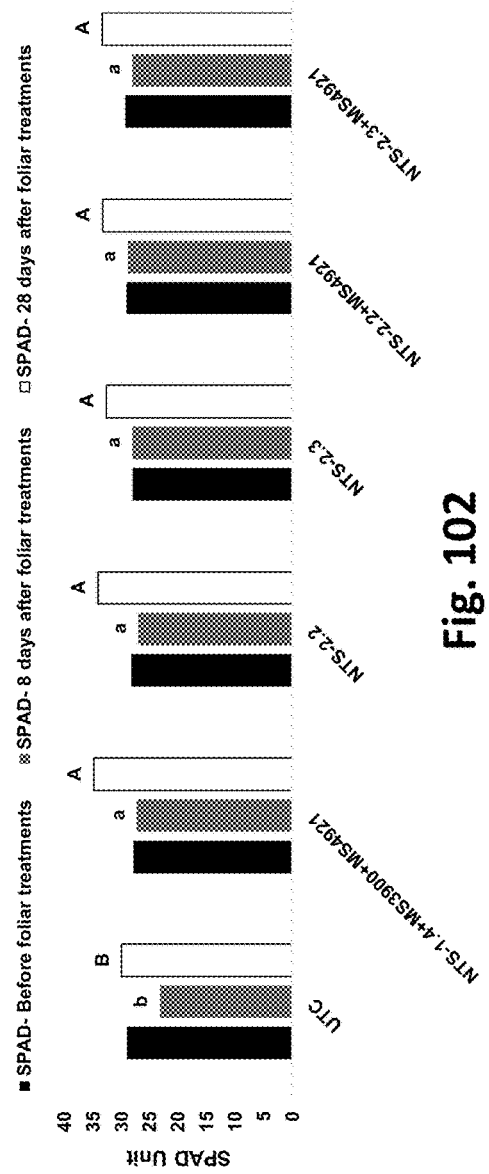
FIG. 102 shows leaf chlorophyll content before and after soybean foliar treatment application across NTS 2.0 systems.
Figure 103:
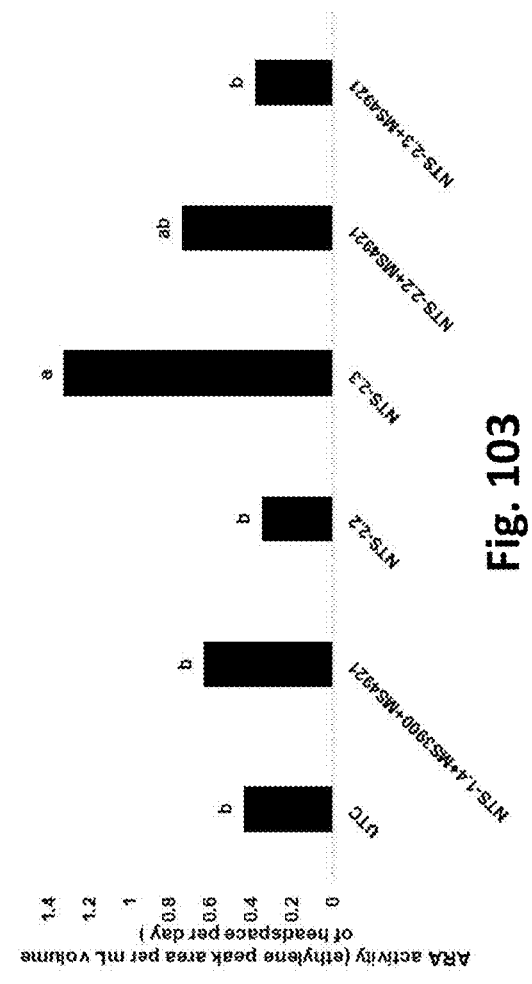
FIG. 103 shows acetylene reduction activity in soybean following treatment with NTS 2.0 systems alone or spiked with isolate.
Figure 104A:
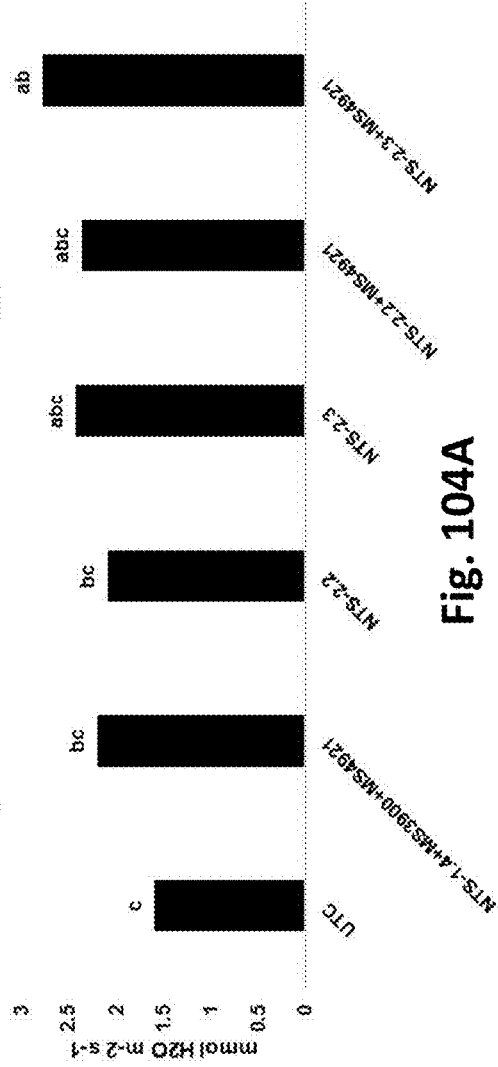
FIGS. 104A-104C show results of plant physiological trait tests following soybean foliar treatment application of NTS 2.0 solutions with MS4921 or MS3900 and MS4921.
Figure 104B:
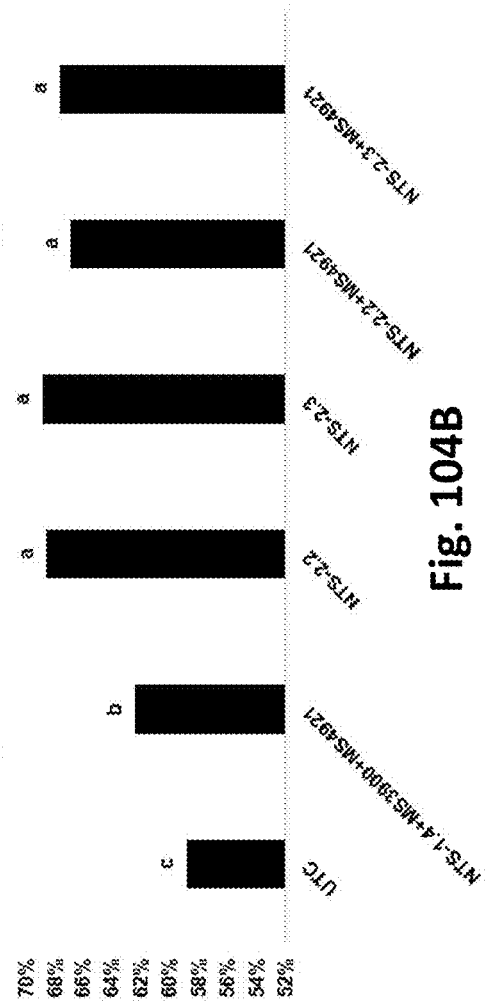
Figure 104C:
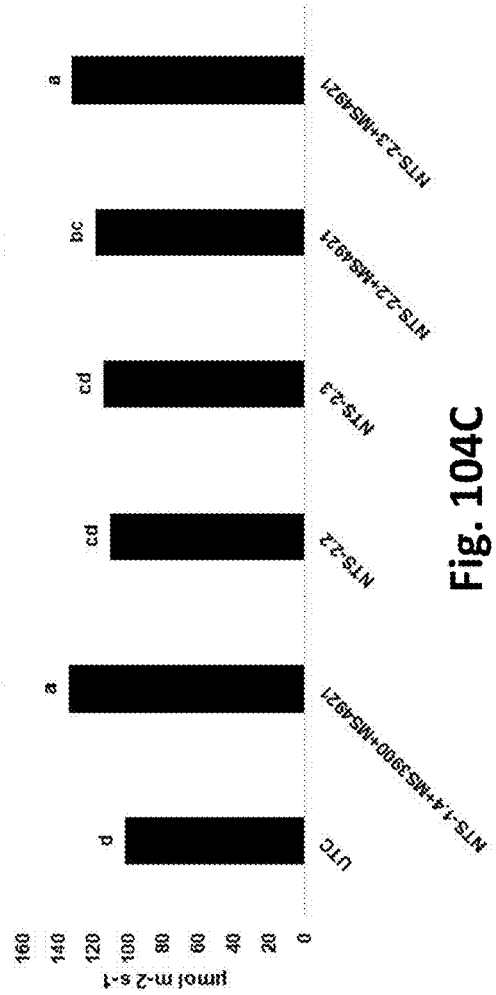
Figure 105:
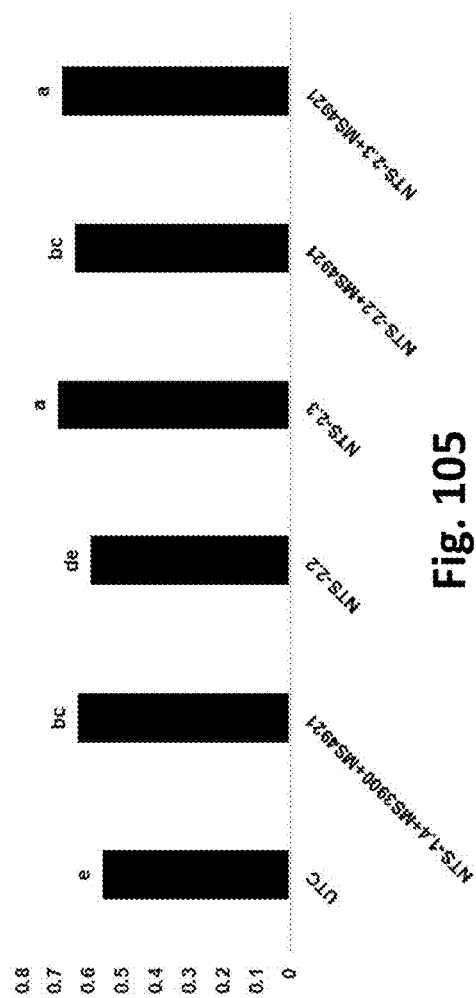
FIG. 105 shows results of normalized difference vegetation index (NDVI) measurements following soybean foliar treatment application of NTS 2.0 solutions with MS4921 or MS3900 and MS4921.

For the whole root acetylene reduction assay, plants were gently removed from the pots and processed. Roots were washed to remove soil and then cut. Root crowns were cut to fit, weighed, and placed into 250 mL plastic jars with septa inserted into the lids. Hoagland's+Carbon solution (10 mL) was added to the jars to keep roots moist and then jars were closed. The Hoagland's+Carbon solution was prepared by dissolving 0.268 g of Hoagland No. 2 Basal Salt Mixture Without Nitrogen (Caisson Labs, Smithfield, UT) into 150 mL of Type I water and adding 0.4 g each of D-Glucose, di-Sodium DL-Malate, soluble starch, and D-Mannitol, adjusting the final volume to 200 mL and mixing until dissolved. Headspace gas was removed from each jar (25 mL) through the septa and then 25 mL of pre-warmed acetylene was injected into each jar. Jars incubated at 28° C. with shaking at 50 rpm for 48-96 hours. On the day of sampling, 10 mL of root container headspace gas was transferred to 21 mL screw-top GC vials before loading onto the GC/MS for analysis. Soybean root nodules were used as a positive control. The instrument used for analysis was an Agilent 8890 GC/MS with an $Al_2O_3$ column ($Na_2SO_4$ deactivated) with Helium as carrier gas (2 ml/min). The injector was set at 200 C and 0.5 mL of sample was injected for analysis. The FID detector was set at 250° C. and the oven at 40° C. for 2 minutes, followed by 40-140° C. at 40° C./minute. Data was presented as ethylene peak area per ml volume of headspace per day ($C_2H_4$/mL HS/day). Pots were arranged in a randomized complete block design (RCBD). Experimental unit for this soybean experiment was four plants per pot. The data for all metrics were analyzed using JMP 17 software (SAS Institute, Cary, NC, USA) using the Fit Model procedure and mean separation at alpha=0.1 level of significance. N-fixer abundance data was analyzed by a Kruskal-Wallis T-test in the statistical platform R Soybean leaf chlorophyll contents of foliar treated plants were significantly increased. All the NTS treatments had significantly greater leaf chlorophyll contents than the untreated control. NTS-1.4 spiked with MS3900 and MS4921 had significantly higher leaf chlorophyll contents at 36 µL/pot and increased by 16% over the control (FIG. 102). NTS-2.3 treated soybean roots had double the ethylene output compared to the untreated control (FIG. 103). The ethylene output of NTS-2.3 significantly increased by 210% nmol/10 mL over the untreated control. Root crown N-fixing activity was higher in plants treated with NTS-1.4 solution iterations. The N-fixing activity was highest in the NTS-1.4 with MS3900 and MS4921 at 36 µL and the High N fertilization (+10 lbs N/A) positive control. Increased N-fixing activity in the roots of treated plants provided evidence of recruitment of beneficial N-fixing organisms into the root zone with the NTS treatments, especially those with MS4921 either added to the system or spiked in the output product. Plant physiological parameters such as transpiration rate, quantum yield, and electron transport rate were increased by treating soybean plants with NTS spiked with MS3900 and MS4921 at 36 µL/pot as a foliar spray (FIGS. 104A-C). All the treated plants had greater transpiration rate, quantum yield, and electron transport rate than the untreated control at 36 µL/pot. NTS-2.3 treated plants had significantly greater NDVI and increased by 23% over the control (FIG. 105).

Figure 106:
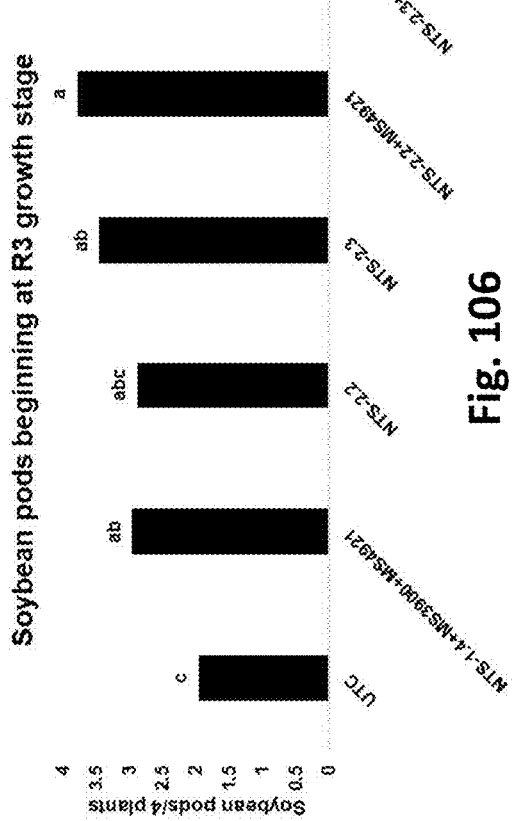
FIG. 106 shows the number of soybean pods per four plants across conditions with foliar treatment application of NTS 2.0 solutions with MS4921 or MS3900 and MS4921.
Figure 107:
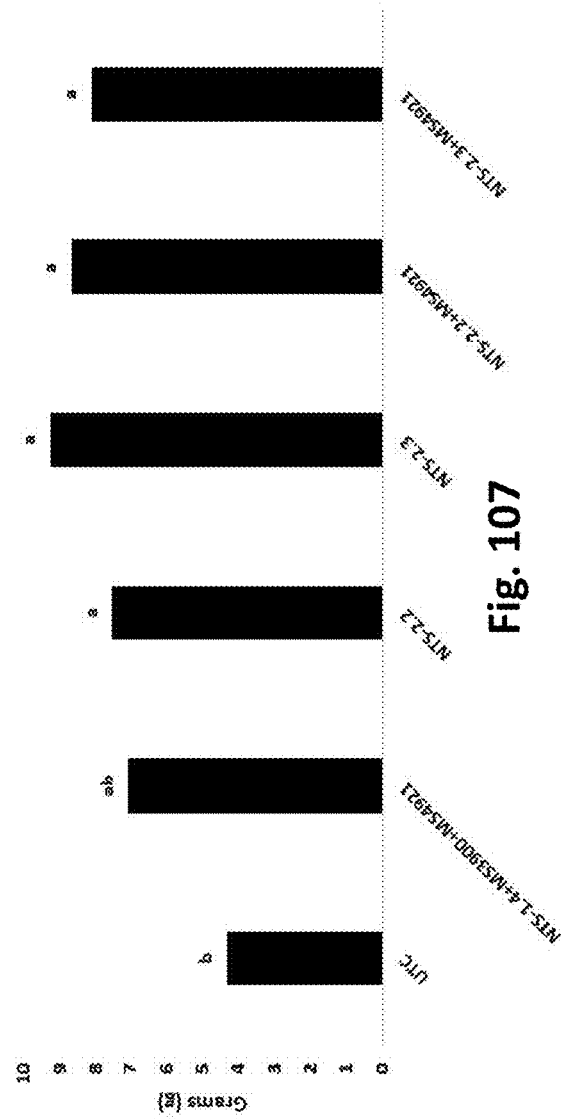
FIG. 107 shows soybean grain yield (in grams) across conditions following foliar treatment application of NTS 2.0 solutions with MS4921 or MS3900 and MS4921.

Soybean pod set (e.g., number of pods in each experimental unit of four plants) was evaluated during the R3 growth stage. The soybean plants were treated with a foliar spray at the V4 growth stage and pod sets were recorded 28 days after treatment application. NTS-2.2 spiked with MS4921 produced a significantly greater number of pods and increased by 94% over the untreated control (FIG. 106). Soybean grain was weighed out at the end of harvest from each treatment which was 115 days after planting and 81 days after foliar application (V4 growth stage). All NTS solutions improved grain yield with NTS-2.3 increasing yield by over 114% (FIG. 107).

Example 32: Plant Growth Promotion and Recruitment Effects of NTS 1.4 System Isolate-Spiked Treatments in Corn This corn experiment was conducted following a similar experimental protocol as described in Example 29. All of the treatments were applied as an in-furrow on the corn seed surface. Treatment conditions are shown in Table 38.

TABLE 38

Treatment conditions for NTS 1.4 nitrogen recruitment

| Treatment | A.I. µL/15 cm pot |
|---|---|
| RO water only | 0 |
| NTS1.4 + MS3900 - 1 qt./A | 18 |
| NTS1.4 + MS3900 + MS4921 1 qt./A | 18 |
| NTS1.4 + MS3900 - 2 qt./A | 36 |
| NTS1.4 + MS3900 + MS4921 - 2 qt./A | 36 |
| High N fertilization (+10 lbs. N/A) | 0 |

Methods for quantifying leaf chlorophyll content, plant height, stem diameter, and leaf area, were described in Examples 29-30. To measure acetylene reduction of whole root, plant root systems including the crown were washed, cut from the stem in the crown region, blotted on a paper towel to remove excess water, weighed (fresh weight), and put into 250 ml jars. The whole root crown including all the root mass was used from each plant. Then, 10 mL of Hoagland's solution (without Nitrogen; 1.34 g/L) supplemented with D-Glucose, di-Sodium DL-Malate, soluble starch, and D-Mannitol (each 2 g/L) was pipetted into the container and the lids fitted with rubber gaskets were closed tightly. 25 ml of headspace air from each airtight 250 ml container was replaced with 25 ml acetylene. The acetylene injected containers with plant tissues were incubated in shakers (50 rpm; 28° C.). The ethylene content in the headspace of each container was measured after 72 hours of incubation using an Agilent GC-8890 equipped with an FID detector.

Plants also underwent a microbial community analysis. At harvest, the rhizospheres were removed from the bulk soil and immediately weighed out for DNA extractions and stored at −20 C. DNA from rhizosphere soil from plants was extracted using the MP Biomedical, FastDNA SPIN kit for soil (Solon, Ohio), as directed with n=4 replicates for each treatment. DNA was quantified using Quibit™ ds DNA BR Assay kit, as directed. All rhizosphere DNA samples were normalized to the same concentration. Normalized DNAs were then sent out for next generation DNA sequencing by Molecular Research Labs (MR DNA, Shallowater, TX) using their standard protocols including the Illumina platform, 20K reads and amplification and sequencing of the total bacterial population. Visualization and analyses of the total bacterial community composition was completed using the metaMDS and adonis functions in the vegan package in R. The same data generated to compare whole community differences was also used to calculate the total bacterial diversity in each rhizosphere soil DNA sample. Shannon's diversity index was calculated for each sample using R. Normalized DNA from the rhizosphere were also used in quantitative PCR (qPCR) to determine the abundance of N-fixing bacteria. The isolated DNA was analyzed via qPCR using SYBR Green. Degenerate PCR primers, PolF/PolR, were picked to capture a wide number of expected nitrogen-fixing microbes (Gabby and Buckley, 2017). The qPCR output values were normalized to the DNA concentrations and presented as nifH gene copy number per ng DNA extracted. Pots were arranged in a replicated Latin square design. The data for all metrics were analyzed using JMP 17 software (SAS Institute, Cary, NC, USA) using the Fit Model procedure and mean separation at alpha=0.1 level of significance.

Figure 108:
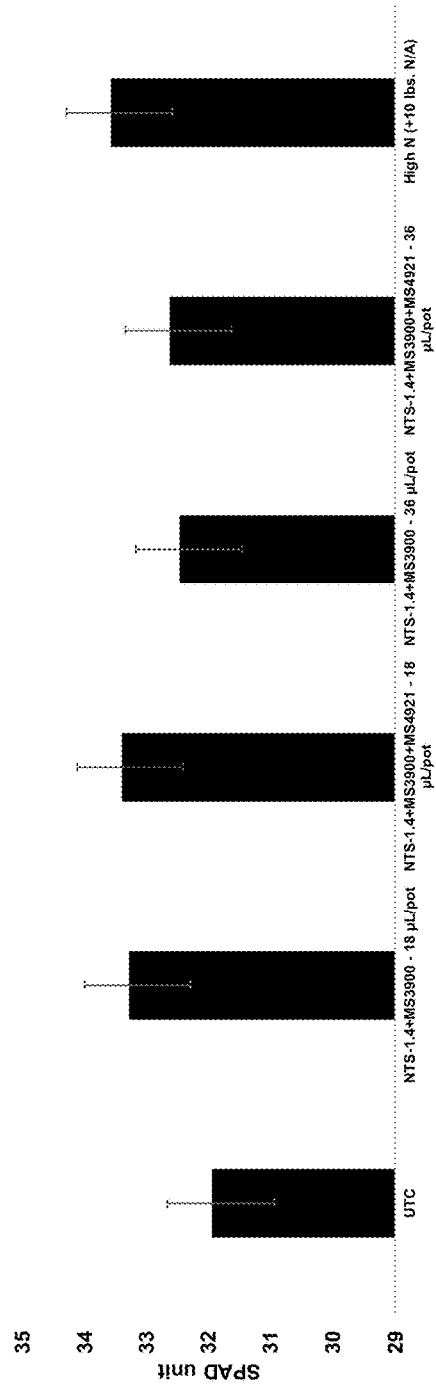
FIG. 108 shows average corn leaf chlorophyll contents measured prior to harvest following in-furrow treatment application of NTS 1.4 solutions with MS3900 or MS3900 and MS4921.
Figure 109:
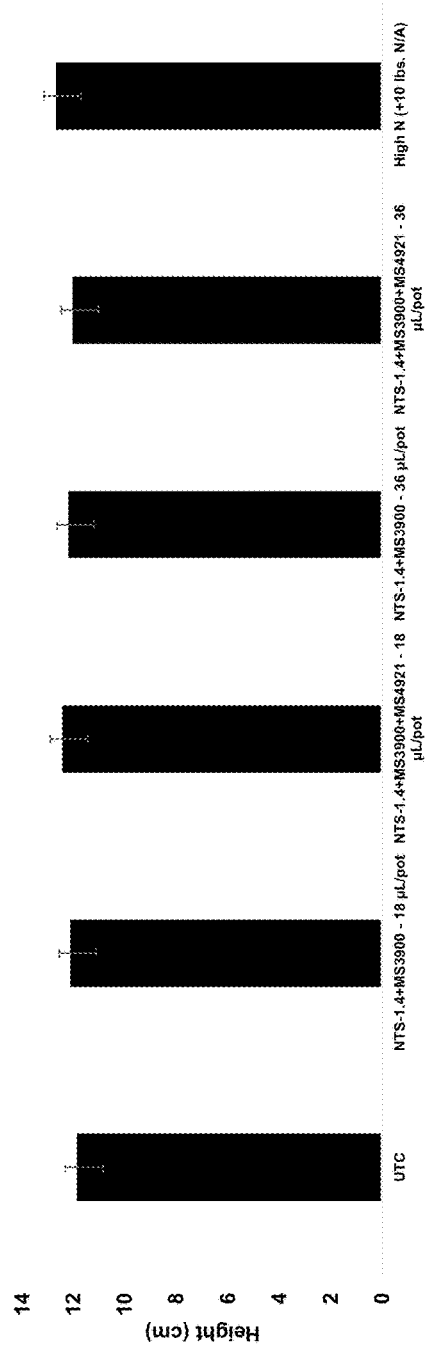
FIG. 109 shows average corn plant height (in centimeters) measured prior to harvest following in-furrow treatment application of NTS 1.4 solutions with MS3900 or MS3900 and MS4921.
Figure 110:
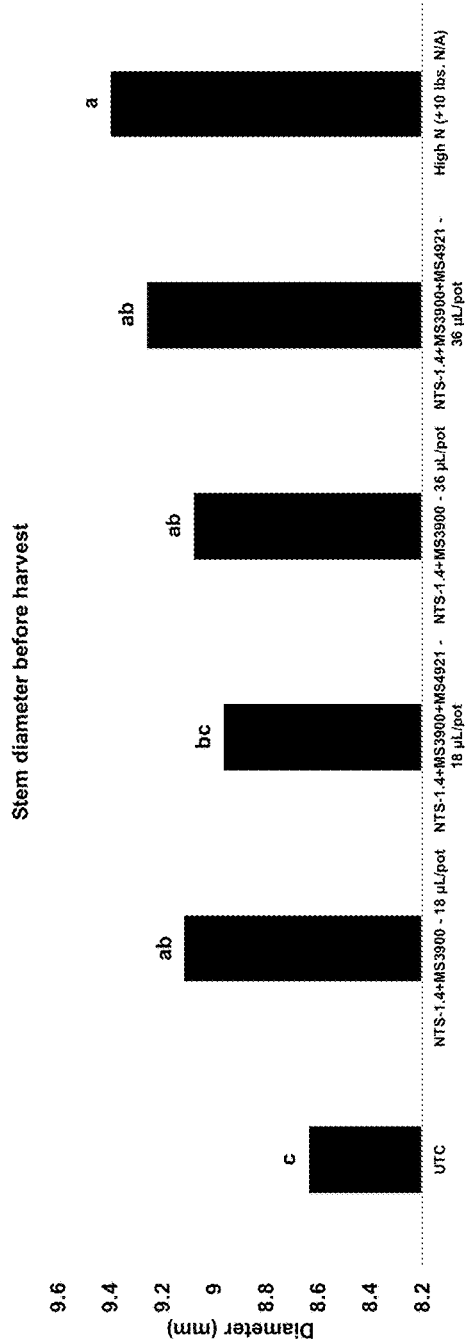
FIG. 110 shows stem diameter (in millimeters) measured prior to harvest following in-furrow treatment application of NTS 1.4 solutions with MS3900 or MS3900 and MS4921.
Figure 111:
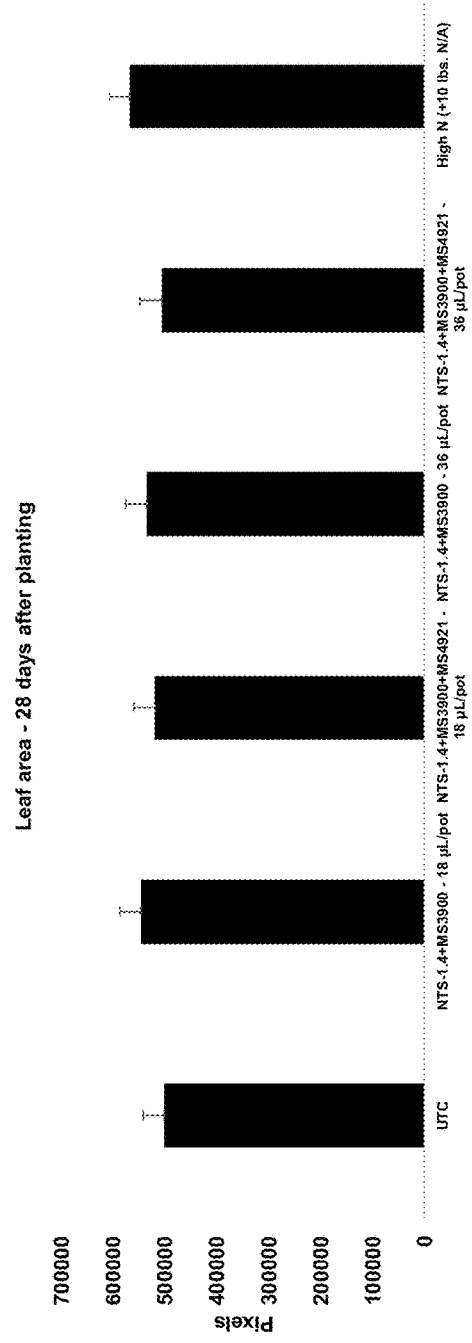
FIG. 111 shows corn leaf area measured 28 days after in-furrow treatment application of NTS 1.4 solutions with MS3900 or MS3900 and MS4921.
Figure 112:
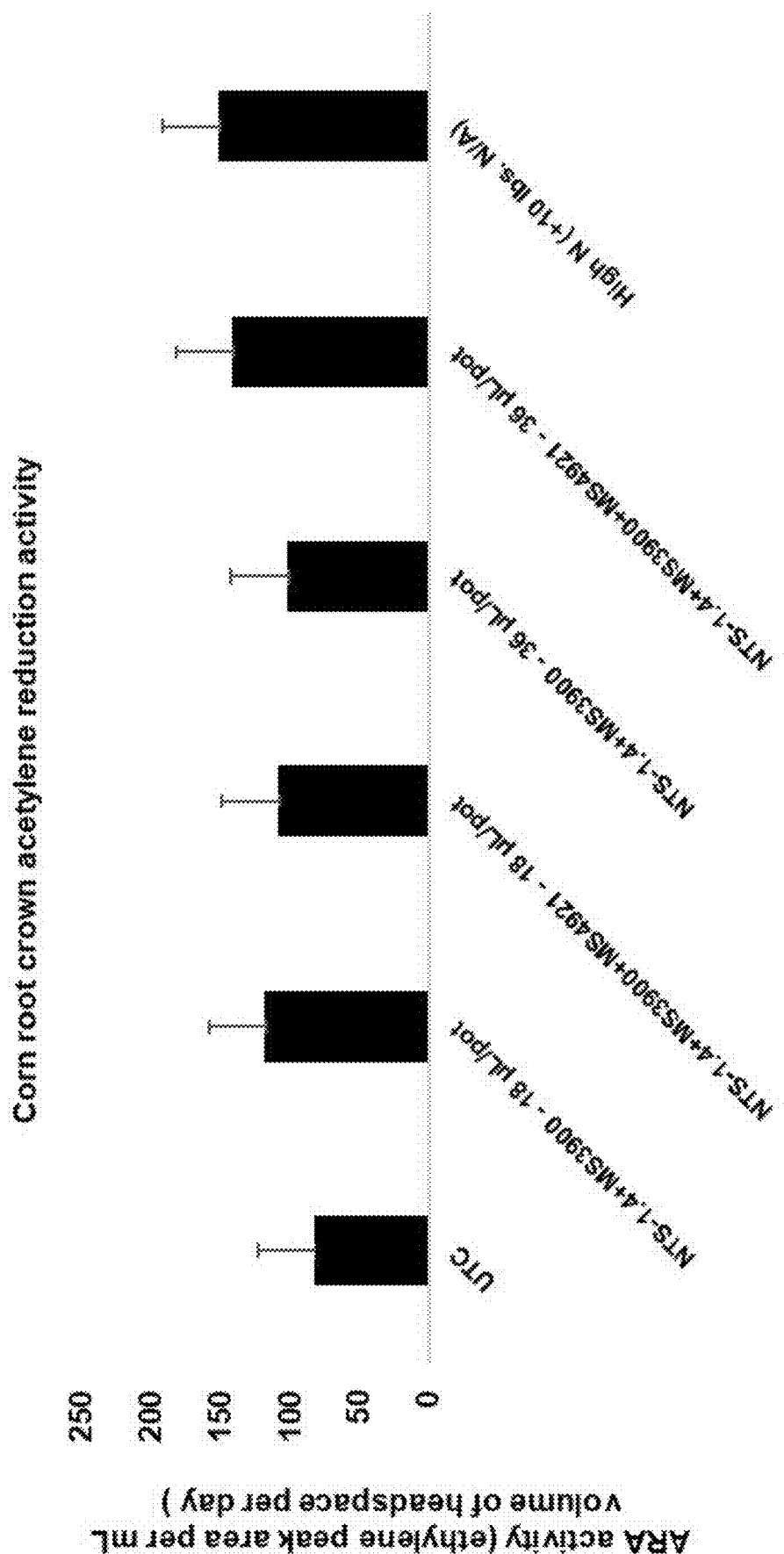
FIG. 112 shows corn root ethylene output from acetylene reduction assay (ARA) increased by broadcast treatment application (NTS 1.4 with MS3900 and MS4921 at 36 uL/pot).

Leaf chlorophyll content increased in all treated plants compared with that of untreated control. NTS-1.4 spiked with MS3900 and MS4921 showed greatest leaf chlorophyll contents at 18 µL/pot of 5% over the control (FIG. 108). Corn plant height and stem diameter of in-furrow treated plants increased when compared to the untreated control (UTC). The plant height for NTS-1.4 spiked with MS3900 and MS4921 was 12 cm and increased by 5% over the untreated control at 18 µL/pot (FIG. 109). The stem diameters for NTS-1.4 spiked with MS3900 and MS4921 significantly increased and was 9 mm (FIG. 110), respectively. There was no change in leaf area following in-furrow treatment with the NTS 1.4 solutions with spiked isolates compared to leaf area of untreated control (FIG. 111). NTS-1.4 spiked with MS3900 and MS4921 treated corn roots had double the ethylene output compared to the untreated control at 36 µL/pot. The ethylene output of NTS-1.4 spiked with MS3900 and MS4921 increased by 70% nmol/10 mL over the untreated control at 36 µL/pot. Root crown N-fixing activity was higher in plants treated with NTS-1.4 solution iterations. The N-fixing activity was highest in the NTS-1.4 with MS3900 and MS4921 at 36 µL and the High N fertilization (+10 lbs N/A) positive control (FIG. 112). Increased acetylene reduction activity in the roots of treated plants provided evidence of a N-fixation associated mode of action within the root zone as a result of treatment with NTS solutions.

Figure 113:
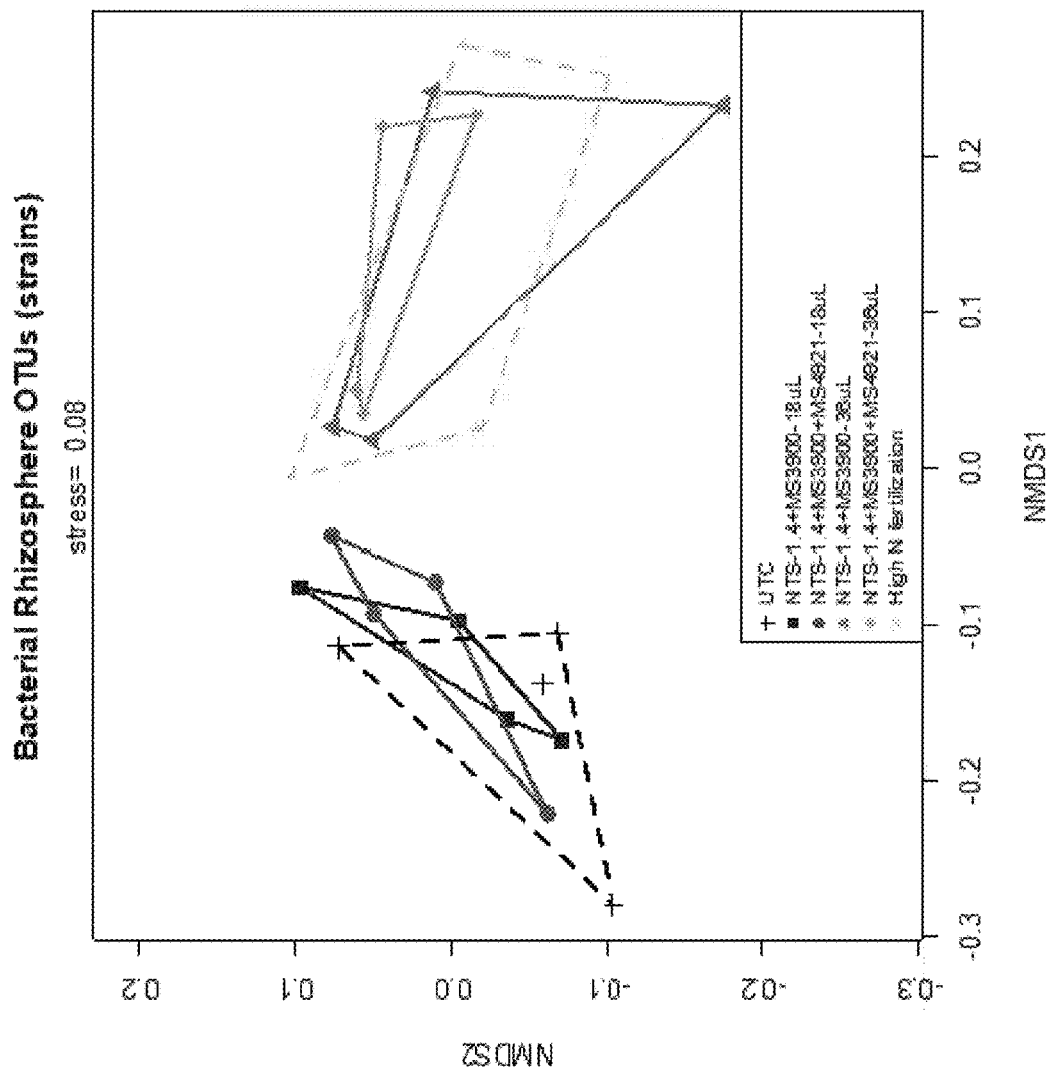
FIG. 113 shows non-metric dimensional scaling (NMDS) display of whole bacterial community compositions for rhizosphere communities of plants treated with NTS 1.4 with isolates solutions and controls. Each symbol represents one DNA extraction (e.g., one rhizosphere soil community).

For the rhizosphere bacterial communities, there were significant differences at the whole community level with treatment (p=0.005). The rhizosphere bacterial communities of the UTC, NTS-1.4+MS3900-18 uL and NTS-1.4+MS3900+MS4921-18 uL are completely different (do not overlap) from the rhizosphere communities of the NTS-1.4+MS3900-36 uL, NTS-1.4+MS3900+MS4921-36 uL and High N fertilization. The rhizosphere bacterial communities of plants treated at 18 uL per pot were not different from the UTC, but the rhizospheres of plants treated at 36 uL pot were significantly different from the UTC (FIG. 113). Differences in whole community composition in the roots of treated plants provided evidence of recruitment into the root zone with NTS-1.4 treatment.

Figures 114A, 114B:
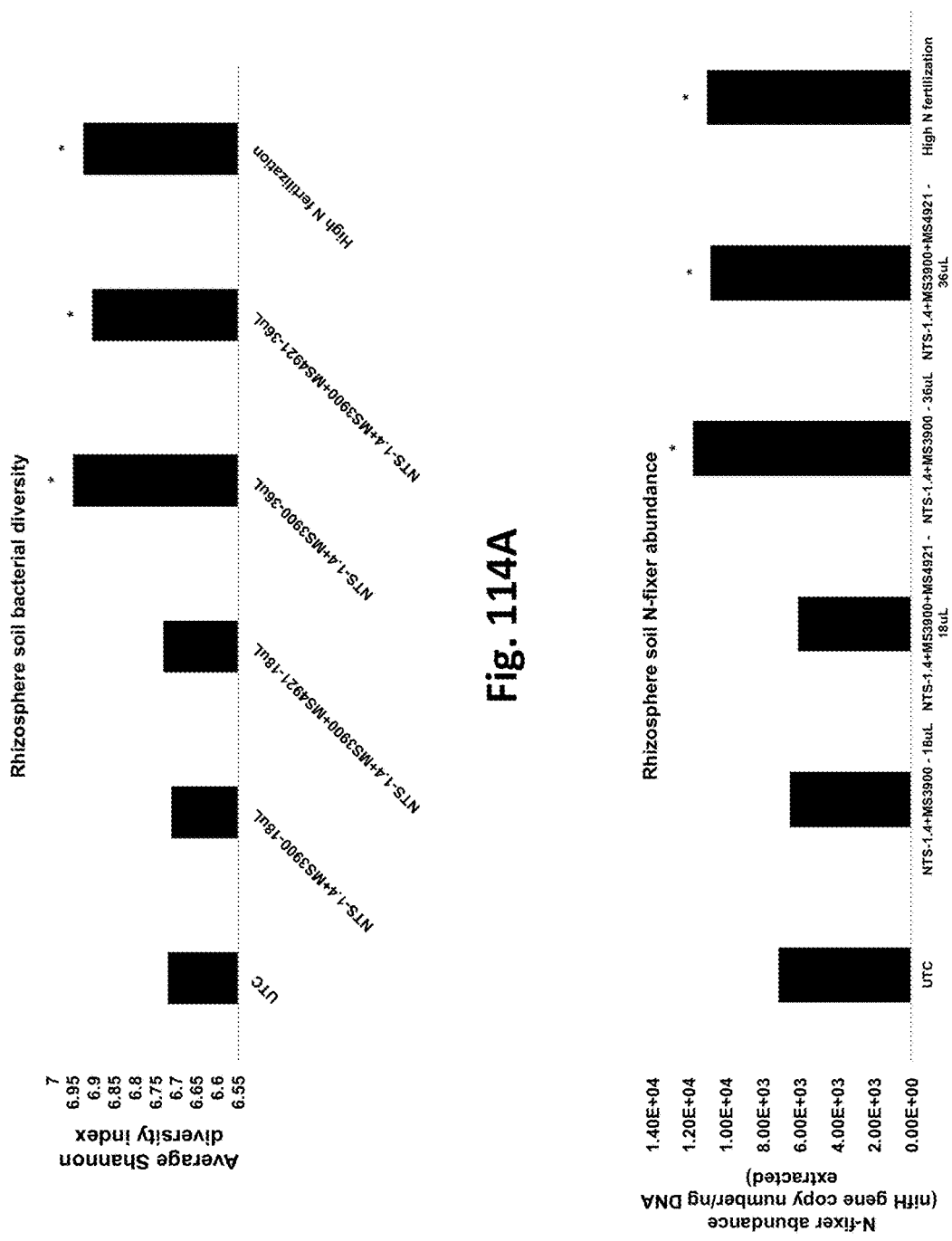
FIGS. 114A-114B show rhizosphere soil quantifications.

For the rhizosphere soil bacterial communities, the NTS-1.4+MS3900-36 uL/pot, NTS-1.4+MS3900+MS4921-36 uL/pot and High N fertilization samples had significantly greater diversity of total bacteria than the UTC rhizosphere communities (FIG. 114A). As in the whole community analyses, these differences in diversity with treatment trended to a dose-dependent pattern. Increased diversity in the rhizospheres of NTS treated plants provided evidence of recruitment into the root zone. For the rhizosphere nitrogen-fixers, the NTS-1.4+MS3900-36 uL/pot, NTS-1.4+MS3900+MS4921-36 uL/pot and High N fertilization had significantly more N-fixing bacteria than the rhizospheres of the UTC or the 18 uL/pot treatments (FIG. 114B). These data supported a dose response with treatment as the 18 uL/pot condition had less response and 36 uL condition had more response. The increase in N-fixing bacteria with the 36 uL application rate provided evidence of recruitment of N-fixers into the root zone with NTS treatments.

Example 33: Effects of NTS 1.4 Solution with Isolates on Plant Growth Promotion, Nitrogen Fixation, and Recruitment of N-Fixer Bacteria This experiment evaluated efficacy of NTS 1.4 product, spiked with MS3900 alone or with MS3900 and MS4921, on early corn growth and nitrogen use efficiency (NUE) at 18 µL/pot and 36 µL/pot in-furrow application rates. Treatment conditions are shown in Table 39.

TABLE 39

Treatment conditions for NTS 1.4 plant growth promotion and NUE experiment

| Treatment | Application Rate µL/40 cm pot |
|---|---|
| UTC - 100% GSP | 0 |
| UTC - 80% GSP | 0 |
| NTS-1.4 + MS3900 - 80% GSP | 18 |
| NTS-1.4 + MS3900 + MS4921 - 80% GSP | 18 |
| NTS-1.4 + MS3900 - 80% GSP - 2 qt./A | 36 |
| NTS-1.4 + MS3900 + MS4921 - 80% GSP | 36 |

Experimental methods for quantifying leaf chlorophyll content, plant height, stem diameter, stomatal conductance, transpiration rate, quantum yield, electron transport rate, ARA of root crowns, and leaf area, were described in Examples 29-32. Statistical analyses were similar as those described in Examples 29-32. Corn grain yields were measured using an electronic balance after drying in a mechanical convection oven at 70° C. for 48 hours. Quantitative PCR (qPCR) was conducted for enumeration of nitrogen-fixing bacteria. At harvest, the rhizospheres were removed from the bulk soil and immediately weighed out for DNA extractions and stored at −20° C. DNA from rhizosphere soil from plants was extracted using the MP Biomedical, FastDNA SPIN kit for soil (Solon, Ohio), as directed. For the rhizosphere soils, there were 4 replicates for each treatment. DNA concentrations were quantified using Quibit™ ds DNA BR Assay kit, as directed. All rhizosphere DNA samples were normalized to the same concentration. Normalized DNA from the rhizosphere were used in quantitative PCR (qPCR) to determine the abundance of N-fixing bacteria. The isolated DNA was analyzed via qPCR using SYBR Green. Degenerate PCR primers, PolF/PolR, were picked to capture a wide number of expected nitrogen-fixing microbes. The qPCR output values were normalized to the DNA concentrations and presented as nifH gene copy number per ng DNA extracted.

Figure 115:
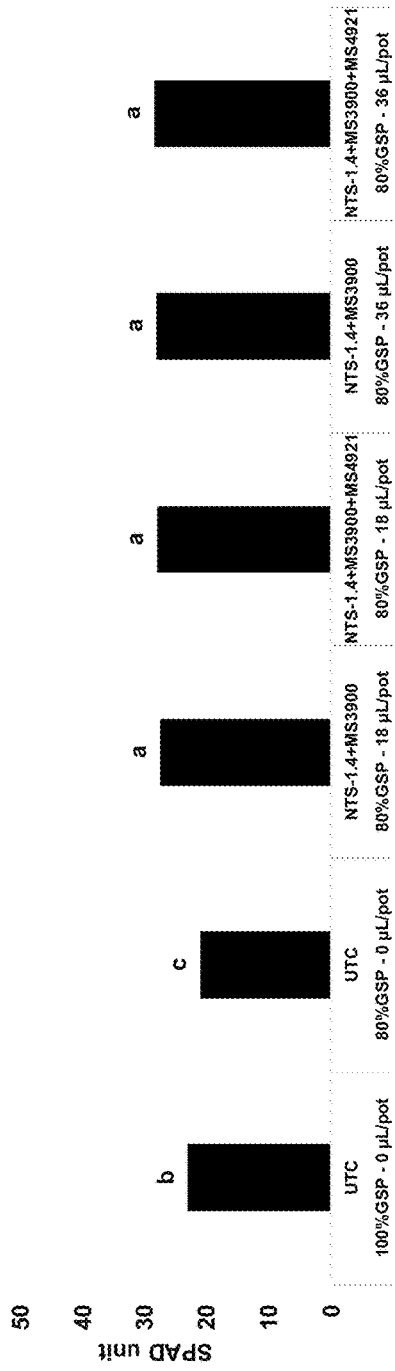
FIG. 115 shows corn leaf chlorophyll contents at vegetative growth (V8) stage for untreated controls or following in-furrow treatment application of NTS 1.4 solutions with MS3900 or MS3900 and MS4921.
Figure 116:
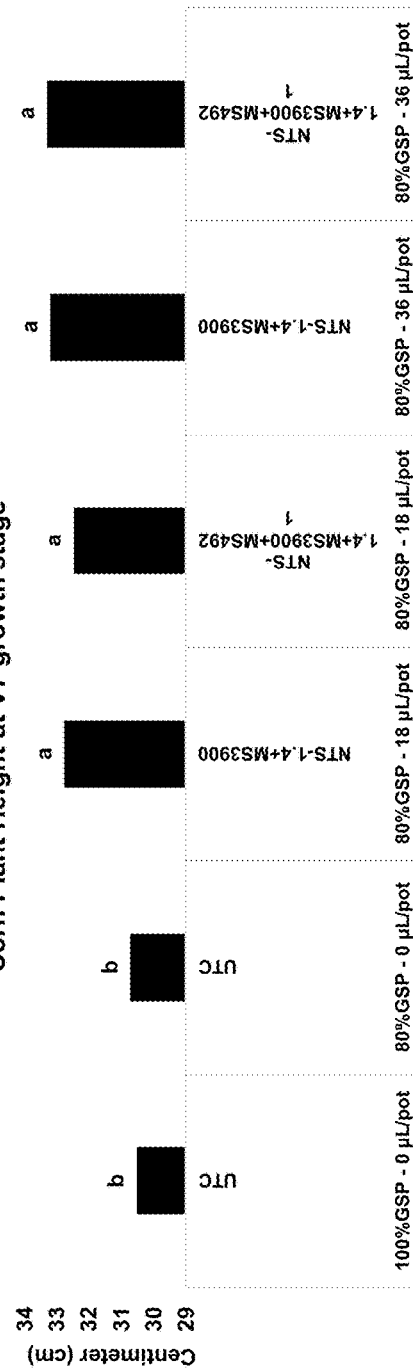
FIG. 116 shows corn plant height at vegetative growth stage (V7) for untreated controls or following in-furrow treatment application of NTS 1.4 solutions with MS3900 or MS3900 and MS4921.
Figure 117:
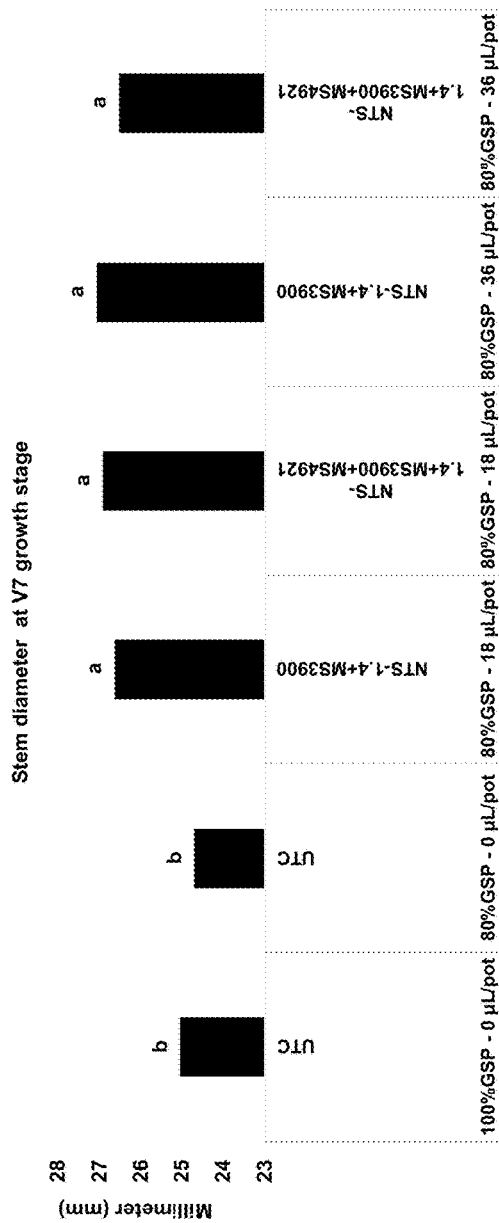
FIG. 117 shows corn stem diameter at V7 growth stage for untreated controls or following in-furrow treatment application of NTS 1.4 solutions with MS3900 or MS3900 and MS4921.

Corn leaf chlorophyll contents of in-furrow treated plants were significantly increased. NTS-1.4 spiked with MS3900 alone or with MS3900 and MS4921 at 18 and 36 µL/pot, applied as in-furrow treatment had significantly greater corn leaf chlorophyll contents than the water control (FIG. 115). The leaf chlorophyll contents of NTS-1.4 spiked with MS3900 alone or with MS3900 and MS4921 at 18 and 38 µL/plant were 27.48, 28.01, 28.11, and 28.48, respectively. The 18 and 36 µL/pot in-furrow application rates had significantly greater plant height and stem diameter than the untreated control. The 36 µL/pot in-furrow application rate with NTS-1.4 spiked with MS3900 and MS4921 increased corn plant height and stem diameter by 8 and 13%, respectively, over the control (FIG. 116 and FIG. 117).

Figure 118:
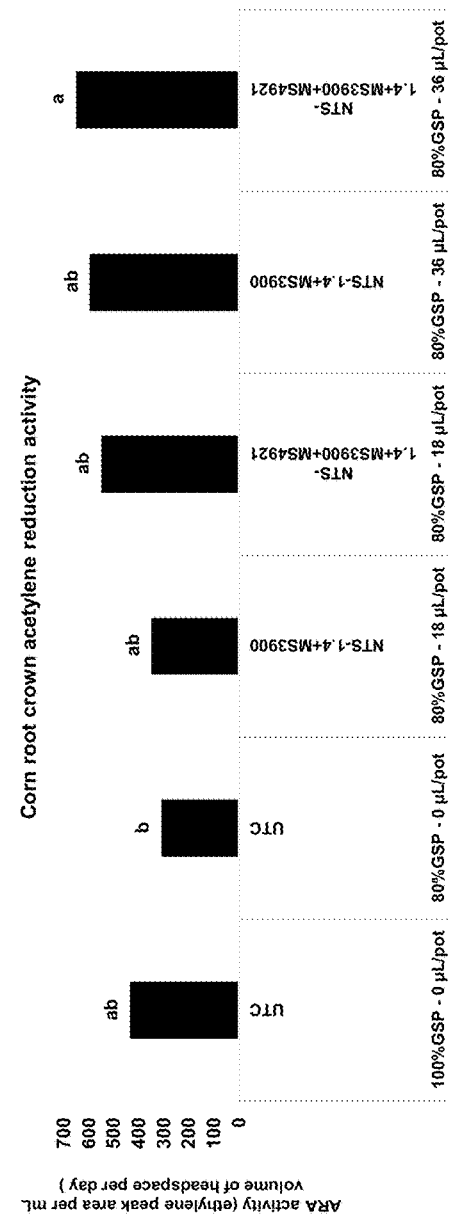
FIG. 118 shows that corn root crown ethylene output from an acetylene reduction assay (ARA) increased by in-furrow treatment application compared to that of untreated control plant.

The 18 and 36 µL/pot in-furrow application rates, both had greater ethylene production than the untreated control. NTS-1.4 spiked with MS3900 and MS4921 had significantly greater ethylene output in corn roots with 36 µL/pot application rate when applied as in-furrow treatment application (FIG. 118). Ethylene output measured by gas chromatography in acetylene reduction assays indirectly indicates potential N-fixing activity. Corn root crown N-fixing activity was higher in plants treated with NTS-1.4 solution iterations. The N-fixing activity was lower with treatments at 18 µL and higher with treatments at 36 uL, providing some evidence for a positive dose response with NTS treatment. Only NTS-1.4 with MS3900 and MS4921 at 36 uL had significantly greater N-fixing activity than the 80% GSP-N alone control treatment. Differences in root crown N-fixing activity in treated plants was strong evidence in support of recruitment.

In addition to the enhancement of plant growth metrics, plant physiological parameters, such as stomatal conductance, transpiration rate, quantum yield, and electron transport rate were also significantly increased by treating plants in-furrow with NTS-1.4 spiked with MS3900 alone or with MS3900 and MS4921 at 18 and 36 µL/pot (FIGS. 119A-D).

In-furrow treatment application significantly increased the corn ear length, corn dry weights, and grain yields. Corn ear length and dry weight of NTS-1.4 spiked with MS3900 alone or with MS3900 and MS4921 treated plants were significantly increased using either 18 or 36 µL/pot (FIGS. 120A-D). The number of the kernel rows around the ears of NTS-1.4 spiked with MS3900 alone or with MS3900 and MS4921 isolates only treated plants also significantly increased using either 18 or 36 µL/pot (FIG. 120C). NTS-1.4 spiked with MS3900 and MS4921 produced the longest corn ears (FIG. 120A), greater ear dry weights (FIG. 120B), and the highest number of kernel rows around the ear. All treatments produced greater corn grain yields than the untreated control (FIG. 120D). The NTS-1.4 spiked with MS3900 at 18 µL/pot and the NTS-1.4 spiked with MS3900 and MS4921 at 36 µL/pot significantly increased corn grain yields.

For the rhizosphere soil N-fixers, all NTS-1.4 with isolates treatments had more N-fixers than the GSP-80% N control. The NTS-1.4+3900-36 uL and NTS-1.4+MS3900+ MS4921-36 uL conditions had the highest N-fixer abundance, but only the treatment with both MS3900 and MS4921 was significantly higher than the GSP-80% N control (FIG. 121). Increased abundance of N-fixing bacteria in the root zone of NTS treated plants provided evidence of recruitment of N-fixers into the root zone.

Example 34: Effects of NTS 1.4 Solution with Spiked Isolates on Plant Growth Promotion Corn variety WS095 (Certified organic corn from Welter Seed & Honey Co., Lot #18-W4-92-SF) was planted (3 seeds per pot) into 6" pots filled with moist sandy loam, sand, and peat mixture (1:1:1 v/v). Pots were placed in a greenhouse set at 24° C. with 16 hours of light and 8 hours of darkness. The pots were watered with RO water as necessary. The seedlings were thinned to one per pot one week after planting and fertilized one time with 15 lbs N, 30 lbs P, 20 lbs S, 75 lbs K, and 0.2 lbs Mo. All nutrients were applied in solution at per acre rates. The micronutrients were provided by Jackpot™ micronutrient fertilizer (0.195 ml/pot). Treatment conditions and application rates are shown in Table 40.

TABLE 40

Treatment conditions and application rate
Treatment & Rate

NTS-1.4-63 µL/pot
NTS-1.4-63 µL/pot and
MS4921 + MS3900-32 µL/pot
NTS-1.4-63 µL/pot and
MS3907 + MS3900-32 µL/pot
NTS-1.4-63 µL/pot and MS4921 + MS3907 + MS3900-32 µL/pot For treatment of NTS 1.4 with isolates, 63 µL of NST-1.4 and 32 µL of MS3900+MS4921 isolate mix (each isolate at $10^4$ cfu/ml) or MS3900+MS3907 isolate mix (each isolate at $10^4$ cfu/ml) were diluted to 0.5 ml with RO water and pipetted over the seeds. The plants were harvested 31 days after planting.

Experimental methods for quantifying leaf chlorophyll content, plant height, stem diameter, and dry weights, were similar as those described in Examples 29-32. Pots were arranged in a Latin square design with one plant per pot. The data for all metrics were analyzed using JMP 17 software (SAS Institute, Cary, NC, USA) using the Fit Model procedure and mean separation at alpha=0.1 level of significance.

Measurements of the collar height after treatment revealed that plants treated with NTS-1.4 spiked with MS4921+MS3900 and NTS 1.4 spiked with MS3907+ MS3900 were significantly taller than those plants that only received NTS 1.4 (FIG. 122). Plants treated with NTS-1.4 spiked with MS4921+MS3900 shows the greatest collar height. Stem diameters showed the greatest increase when NTS-1.4 was spiked with MS4921+3900, and diameters also increased in plants that were exposed to MS3907+MS3900 compared to treatments that only received NTS-1.4 (FIG. 123). Treatments with added MS3907+MS3900 had higher leaf chlorophyll content compared to that of NTS-1.4 alone and NTS-1.4+MS4921+MS3900 treatments (FIG. 124). Plants treated with NTS-1.4 spiked with MS4921+MS3900 showed greater shoot biomass compared with shoot biomass of those plants treated with NTS 1.4 alone. increased significantly when NTS-1.4 is spiked with MS4921+MS3900 (FIG. 125). Treatment with NTS 1.4 spiked with MS3907+ MS3900 also led to an increase in shoot biomass. Plants had a significantly higher root biomass when MS3907+MS3900 was added to NTS-1.4 (FIG. 126).

Example 35: Evaluation of Nitrogen Use Efficiency in NTS 2.0 Systems

This experiment analyzed plant growth promotion and nitrogen use efficiency in products from NTS 2.2 and NTS 2.3 systems on early growth of corn. Experimental setup and planting was similar to that described in Example 29. Six treatments and twelve replicates were used for this greenhouse test. the experimental design was two stacked 6×6 Latin squares. The negative control was fertilizer only, and the positive control had an additional 10 lbs/A provided by urea ammonium nitrate (UAN) 32. Treatment conditions are shown in Table 41.

TABLE 41

Treatment conditions for NUE experiments in NTS 2.0 systems

| Treatment | A.I. μL/15 cm pot |
|---|---|
| RO water only | 0 |
| NTS-2.2 base product | 36 |
| NTS-2.3 base product | 36 |
| High N fertilization (+10 lbs. N/A) | 0 |

Methods for quantifying leaf chlorophyll content, plant height, stem diameter, leaf area, root ARA, and dry biomass are similar to those described in Examples 29-31. For nitrogen content analysis, all the shoot samples were sent to Waypoint Analytical for macro and micronutrients uptake test (Waypoint Analytical, LLC) and analyzed in milligram per shoot.

Corn leaf chlorophyll contents of in-furrow treated plants significantly increased 17 days after planting. The NTS-2.3 treatment condition showed significantly greater leaf chlorophyll contents at 36 μL/pot (FIG. 127). The leaf chlorophyll content of NTS-2.3 alone was 36.99 at 36 μL/plant. Chlorophyll molecules are rich in nitrogen. Corn plant height and stem diameter of in-furrow treated plants significantly increased 17 days after planting using 36 μL/plant in-furrow application rate (FIGS. 128A-B). The plant height and stem diameter for NTS-2.2 and NTS-2.3 solutions were 12 and 12 cm, and 9 and 9 mm, respectively. These results provided evidence of improved plant growth at reduced nitrogen levels by the NTS solutions which were similar to that of the high nitrogen positive control. Corn leaf area significantly increased 17 days after in-furrow treatment application (FIG. 129). All NTS-treated plants showed greater leaf area compared to that of untreated control.

Greater ethylene output from acetylene reduction assay was observed in corn roots of plants treated with NTS-2.2 (FIG. 130). The plants treated with NTS-2.2 showed both greater ethylene output and had greater leaf chlorophyll contents at 36 μL/pot in greenhouse test, which showed good correspondence between the two metrics. SPAD chlorophyll measurements indirectly assess the plant nitrogen status and ARA results show potential nitrogen fixation within the plant. These results indicated that the NTS treatments increased plant nitrogen status through nitrogen-fixation, resulting in greater chlorophyll contents. Plants treated with NTS-2.2 or NTS-2.3 showed enhanced shoot nitrogen uptake compared to that of untreated control (FIG. 131). NTS-2.2 and NTS-2.3 significantly increased corn dry biomass. NTS-2.2 and NTS-2.3 treated plants had significantly greater dry shoot biomass and increased by 91 and 87% over the untreated control (FIGS. 132A-B). NTS-2.2 and NTS-2.3 treated plants had significantly greater dry root biomass and increased by 77 and 111% over the untreated control.

Example 35: Effects of In-Furrow and Foliar Application of Isolates MS4921 and MS3900 on Plant Growth Promotion in Corn A greenhouse experiment was conducted with corn to evaluate the effect of nitrogen fixing isolates on plant growth (24° C., 16 hours light, and 8 hours darkness). Corn variety WS095 (certified organic corn from Welter Seed & Honey Co., Lot #18-W4-92-SF) was planted into 6" diameter pots containing a soil mix of Denton, Texas sandy-loam soil with sand and peat mix (1:1:1). Treatments were applied as an in-furrow application over the corn seeds at planting, or as a foliar treatment three weeks after planting. For in-furrow isolate treatment, 32 μL spore suspensions of MS4921 (at $10^4$ cfu/ml) or MS4921 with MS3900 (MS4921+MS3900; each at $10^4$ cfu/ml) were diluted to 0.5 ml with RO water and pipetted over the seeds. For foliar application, 1280 μl of MS4921 spore suspension (at $10^4$ cfu/ml) and 12.5 μl of Liberate™ were diluted to 20 ml with RO water. Top three leaves of two weeks old plants were sprayed with 0.5 ml of diluted isolate+Liberate™ surfactant mixture on both sides. Plants were harvested 37 days after planting. Methods for quantifying the dry weights and acetylene reduction assays of whole root were similar to those described in Examples 29-32. Pots were arranged in a randomized design. The data for all metrics were analyzed using JMP 17 software (SAS Institute, Cary, NC, USA) using the Fit Model procedure and mean separation at alpha=0.1 level of significance for dry weights and at alpha=0.05 for acetylene reduction results.

In-furrow treatment with isolate MS4921 or isolates MS4921+MS3900 resulted in greater total dry weights over that measured in the UTC (FIG. 133). Foliar treatment with isolate MS4921 resulted in roots with greater acetylene reduction activity compared to that from in-furrow treatments with isolate MS4921 or isolates MS4921+MS3900, or untreated control (FIG. 134). These results demonstrated the plant growth promotion capacity of the isolates as well as their nitrogen-fixation mode of action associated with roots and root/crown tissues.

Example 36: Effects of NTS Treatment as Additive with UAN32 on Plant Growth Promotion and Nitrogen Use Efficiency in Corn A corn experiment was conducted using Denton, Texas sandy-loam soil with turface and peat mix (1:1:1) for corn growth in a greenhouse. All the treatments were applied as broadcast of a tank mix with urea ammonium nitrate (UAN32) on the pot after thinning the plants. Hybrid GMO corn (Dyna-Grow seed) seed variety was used for this test. The 15 cm round pot was used, and the experimental design was two stacked 6×6 Latin squares. The growing medium was 1:1:1 Turface-peat-Denton sandy loam soil mix. The urea ammonium nitrate (UAN) 32 at 15 lbs./A, potash at 200 lbs./A, Jackpot micronutrient, and sodium molybdate fertilizer were mixed together and applied after thinning the plant. Six treatments and twelve replicates were used for this greenhouse test. Planted 3 seeds in a 2-inch-deep hole in the center of each pot and covered the pot with the growing medium and 1 week after planting thinned to 1 plant per pot. 50 mL fertilizer was applied to each pot after thinning. Treatment conditions and rates are shown in Table 42.

TABLE 42

Treatment conditions for NTS system product with UAN32

| Treatment | A.I. µL/pot |
|---|---|
| UAN alone | 0 |
| UAN + NTS-1.4 + MS3900 | 18 |
| UAN + NTS-1.4 + MS3900 + MS4921 | 18 |
| UAN + NTS-1.4 + MS3900 | 36 |
| UAN + NTS-1.4 + MS3900 + MS4921 | 36 |
| Positive N control | 0 |

Experimental methods for quantifying chlorophyll content, plant height, stem diameter, leaf area, and root crown ARA were similar to those described in Examples 29-33. Pots were arranged in a replicated Latin square design. The data for all metrics were analyzed using JMP 17 software (SAS Institute, Cary, NC, USA) using the Fit Model procedure and mean separation at alpha=0.1 level of significance.

Corn leaf chlorophyll contents of broadcast treated plants significantly increased 7 days after planting. NTS-1.4 spiked with MS3900 alone or with MS3900 and MS4921 at 18 µL/pot had significantly greater leaf chlorophyll contents when applied as broadcast treatment application with urea ammonium nitrate (UAN32) (FIG. 135). Plant height during early growth stages is an indicator of plant nutrition status. Corn plant height and stem diameter of broadcast treated plants significantly increased 7 days after planting (FIG. 136 and FIG. 137). The plant height for NTS-1.4 spiked with MS3900 alone or MS3900 and MS4921 were 11, 12, 11, and 12 cm (FIG. 136), respectively. The 36 µL/pot broadcast application rate with NTS-1.4 spiked with MS3900 and MS4921 increased plant height by 16% over the control. The stem diameters for NTS-1.4 spiked with MS3900 alone or MS3900 and MS4921 were 9, 9, 9, and 10 mm (FIG. 137), respectively. Corn leaf area significantly increased 8 days after broadcast treatment application (FIG. 138). Greater ethylene output from acetylene reduction assays (ARA) was observed in corn roots of plants treated with NTS-1.4 spiked with MS3900 alone, or with MS3900 and MS4921, as an additive to UAN32 liquid fertilizer, at 36 µL/pot, which also had significantly greater leaf chlorophyll contents in greenhouse test (FIG. 139). These results indicated that the NTS treatments increased plant N status through N-fixation, resulting in greater chlorophyll contents and plant growth.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the present disclosure may be employed in practicing the present disclosure. It is intended that the following claims define the scope of the present disclosure and that methods and structures within the scope of these claims and their equivalents be covered thereby.

What is claimed is:

1. A bioreactor system comprising:
(a) a conduit comprising a stream of an aqueous feedstock in fluid communication with a first container comprising a volume of a first working fluid and a first container outflow port in fluid communication with the first working fluid and located below the top of the first working fluid, wherein the aqueous feedstock comprises a microbial consortium, wherein the first working fluid comprises an established population of a nitrogen use efficiency-promoting microbial strain;
(b) a second container in fluid communication with the first container, wherein the second container comprises a second working fluid and a second container inflow port in fluid communication with the first container outflow port and arranged to allow hydraulically balanced continuous flow of the first working fluid from the first container outflow port to the second container inflow port driven by gravity, and wherein the second container comprises a second container outflow port located below the top of the second working fluid, and wherein the second container is configured to maintain a population of the nitrogen use efficiency-promoting microbial strain;
(c) one or more additional containers arranged in series with the first container and the second container, wherein each of the one or more additional containers comprises a volume of a working fluid and is in fluid communication with at least one other container in the series, wherein either the second container or at least one of the one or more additional containers comprises a product outflow stream port, wherein at least two of the first container, the second container, or the one or more additional containers are fluidized bed reactors, and wherein the one or more additional containers are configured to maintain a population of the nitrogen use efficiency-promoting microbial strain; and
(d) a product outflow stream in fluid communication with the product outflow stream port, wherein the product outflow stream port is configured to allow hydraulically balanced continuous flow of the product outflow stream driven by gravity.

2. The bioreactor system of claim 1, wherein the nitrogen use efficiency-promoting microbial strain is one that performs nitrogen fixation, promotes nitrogen fixation in the tissues of plants, recruits nitrogen fixers to the root zones or other tissues of plants, or increases organic nitrogen content and/or mineralization of organic nitrogen in soil.

3. The bioreactor system of claim 1, wherein the nitrogen use efficiency-promoting microbial strain is positive for a nifH gene.

4. The bioreactor system of claim 1, wherein the nitrogen use efficiency-promoting microbial strain is one that promotes plant growth in a nitrogen-poor growth medium.

5. The bioreactor system of claim 1, wherein the nitrogen use efficiency-promoting microbial strain is of the genus *Kosakonia, Klebsiella, Rahnella, Kluyvera, Enterobacter, Achromobacter, Microbacterium, Gluconobacter, Methylobacterium, Pseudomonas, Pantoea, Azospirillum, Azocarus, Herbaspirillum, Burkholderia, Cyanobacteria, Bacillus*, or *Paenibacillus*.

6. The bioreactor system of claim 1, wherein the nitrogen use efficiency-promoting microbial strain is of the species *Kosakonia sacchari, Klebsiella variicola, Rahnella aquatilis, Kluyvera intermedia, Kosakonia pseusosacchari, Enterobacter* spp., *Achromobacter marplatensis, Azopirillum lipoferum, Microbacterium murale, Gluconobacter diazotrophicus, Methylobacterium symbioticum, Paenibacillus borealis, Bacillus megaterium (Priestia megaterium)*, or *Paenibacillus sonchi*.

7. The bioreactor system of claim 1, wherein the bioreactor system is a continuous flow bioreactor system and the stream of the aqueous feedstock is a continuous stream.

8. The bioreactor system of claim 1, wherein each of the first container and the one or more additional containers comprises a concentration of the nitrogen use efficiency-promoting microbial strain that remains at least $1\times10^2$ CFU/ml during operation of the bioreactor system.

9. The bioreactor system of claim 1, wherein the microbial consortium comprises at least $1\times10^5$ CFU/ml of microbes.

10. The bioreactor system of claim 1, wherein the aqueous feedstock further comprises an organic material digestible by microbes present in the first container, the second container, and the one or more additional containers.

11. The bioreactor system of claim 10, wherein the organic material comprises manure or material derived from manure.

12. The bioreactor system of claim 1, wherein the aqueous feedstock further comprises rock phosphate particles.

13. The bioreactor system of claim 1, wherein the microbial consortium comprises microbes derived from manure and rock phosphate particles.

14. The bioreactor system of claim 1, wherein the container comprising the product outflow stream port is a clarifier container configured to separate a portion of a working fluid in the clarifier container into a supernatant portion and a floc portion.

15. The bioreactor system of claim 14, wherein the clarifier container comprises one or more floc folding flights configured to agitate settled floc in the clarifier container without resuspending solids in the floc portion into the supernatant portion.

16. The bioreactor system of claim 14, further comprising a floc return stream that flows from the clarifier to an earlier container in the series.

17. The bioreactor system of claim 14, wherein the product outflow stream comprises the supernatant portion.

18. The bioreactor system of claim 17, wherein the product outflow stream comprises at least $1\times10^4$ CFU/ml of the nitrogen use efficiency-promoting microbial strain.

19. The bioreactor system of claim 17, wherein the product outflow stream comprises at least $1\times10^2$ CFU/ml of a sporulated form of the nitrogen use efficiency-promoting microbial strain.

20. The bioreactor system of claim 17, wherein the product outflow stream comprises a total dry weight of 0.2 to 2.5 mg/ml.

21. The bioreactor system of claim 17, wherein the product outflow stream has a chemical oxygen demand of 80 to 500 mg/L.

22. The bioreactor system of claim 17, wherein the product outflow stream has an electrical conductivity between 1.3 and 3.0 mS/cm.

23. The bioreactor system of claim 1, wherein the first working fluid comprises malate at a concentration of at least 0.2% w/v.

24. The bioreactor system of claim 1, wherein the first working fluid comprises soy flour at a concentration of at least 0.2% w/v.

25. The bioreactor system of claim 1, wherein the first working fluid comprises microaerobic conditions.

26. The bioreactor system of claim 25, wherein the working fluid in at least one of the one or more additional containers comprises microaerobic conditions.

27. The bioreactor system of claim 1, wherein the system has a hydraulic retention time of at least 5 days.

28. The bioreactor system of claim 1, wherein the first working fluid further comprises an established population of a second nitrogen use efficiency-promoting microbial strain.

29. The bioreactor system of claim 28, wherein the second nitrogen use efficiency-promoting microbial strain is of the species *Kosakonia sacchari, Klebsiella variicola, Rahnella aquatilis, Kluyvera intermedia, Kosakonia pseusosacchari, Enterobacter* spp., *Achromobacter marplatensis, Azopirillum lipoferum, Microbacterium murale, Gluconobacter diazotrophicus, Methylobacterium symbioticum, Paenibacillus borealis, Bacillus megaterium (Priestia megaterium),* or *Paenibacillus sonchi*.

30. The bioreactor system of claim 1, wherein the first working fluid comprises a total population of microbes positive for a nifH gene of at least $1\times10^5$ CFU/ml.

31. The bioreactor system of claim 1, wherein the fluidized bed reactors are configured to maintain a higher concentration of the nitrogen use efficiency-promoting microbial strain in the bioreactor system as compared to packed bed reactors.

32. The bioreactor system of claim 1, wherein the second container is configured to maintain a concentration of the nitrogen use efficiency-promoting microbial strain at at least the concentration of the nitrogen use efficiency-promoting microbial strain in the first working fluid in the first container.

33. The bioreactor system of claim 1, wherein the fluidized bed reactors comprise particles of an inorganic substrate.

34. The bioreactor system of claim 33, wherein the particles of the inorganic substrate are rock phosphate particles.

35. The bioreactor system of claim 28, wherein the nitrogen use efficiency-promoting microbial strain is of the genus *Paenibacillus*, and the second nitrogen use efficiency-promoting microbial strain is of the genus *Bacillus*.

36. The bioreactor system of claim 35, wherein the nitrogen use efficiency-promoting microbial strain is of the species *Paenibacillus borealis* and the second nitrogen use efficiency-promoting microbial strain is of the species *Bacillus megaterium*.

37. The bioreactor system of claim 36, wherein the *Paenibacillus borealis* comprises the *Paenibacillus borealis* strain deposited under ATCC Accession No. PTA-127654 and the *Bacillus megaterium* comprises the *Bacillus megaterium* strain deposited under ATCC Accession No. PTA-127653.

38. The bioreactor system of claim 37, wherein the first working fluid further comprises a *Paenibacillus sonchi* strain deposited under ATCC Accession No. PTA-127655.

39. The bioreactor system of claim 17, wherein the product outflow stream comprises at least $1\times10^2$ CFU/ml of the nitrogen use efficiency-promoting microbial strain.

40. The bioreactor system of claim 1, wherein the second container is configured to maintain the population of the nitrogen use efficiency-promoting microbial strain for at least 5 days.

41. The bioreactor system of claim 40, wherein the one or more additional containers are configured to maintain the population of the nitrogen use efficiency-promoting microbial strain for at least 5 days.

42. The bioreactor system of claim 1, wherein the second container is configured to maintain the population of the nitrogen use efficiency-promoting microbial strain for at least 2 months.

43. The bioreactor system of claim 42, wherein the one or more additional containers are configured to maintain the population of the nitrogen use efficiency-promoting microbial strain for at least 2 months.

* * * * *